US012559464B2

(12) United States Patent
Hawryluk et al.

(10) Patent No.: US 12,559,464 B2
(45) Date of Patent: Feb. 24, 2026

(54) QUINAZOLINONE DIONE COMPOUNDS AND USES THEREOF

(71) Applicant: Edgewise Therapeutics, Inc., Boulder, CO (US)

(72) Inventors: Natalie Anne Hawryluk, Nederland, CO (US); Stephen Thomas Schlachter, Boulder, CO (US); Kevin Koch, Niwot, CO (US); Michael Joseph Luzzio, Groton, CT (US); Michael Mark Duvall, Vancouver, WA (US); Alan James Russell, Boulder, CO (US); Marc Justin Evanchik, Boulder, CO (US); Kevin Hunt, Boulder, CO (US)

(73) Assignee: EDGEWISE THERAPEUTICS, INC., Boulder, CO (US)

( * ) Notice: Subject to any disclaimer, the term of this patent is extended or adjusted under 35 U.S.C. 154(b) by 0 days.

(21) Appl. No.: 18/882,652

(22) Filed: Sep. 11, 2024

(65) Prior Publication Data

US 2025/0026726 A1 Jan. 23, 2025

Related U.S. Application Data

(63) Continuation of application No. PCT/US2024/021537, filed on Mar. 26, 2024.

(60) Provisional application No. 63/513,844, filed on Jul. 14, 2023, provisional application No. 63/492,439, filed on Mar. 27, 2023.

(51) Int. Cl.

| | |
|---|---|
| ***C07D 239/96*** | (2006.01) |
| ***A61K 31/517*** | (2006.01) |
| ***A61K 31/519*** | (2006.01) |
| ***A61K 31/5377*** | (2006.01) |
| ***C07D 401/06*** | (2006.01) |
| ***C07D 401/12*** | (2006.01) |
| ***C07D 403/12*** | (2006.01) |
| ***C07D 405/12*** | (2006.01) |
| ***C07D 409/12*** | (2006.01) |
| ***C07D 413/12*** | (2006.01) |
| ***C07D 417/12*** | (2006.01) |
| ***C07D 471/04*** | (2006.01) |
| ***C07D 487/04*** | (2006.01) |
| ***C07D 491/048*** | (2006.01) |

(52) U.S. Cl.

CPC .......... *C07D 239/96* (2013.01); *A61K 31/517* (2013.01); *A61K 31/519* (2013.01); *A61K 31/5377* (2013.01); *C07D 401/06* (2013.01); *C07D 401/12* (2013.01); *C07D 403/12* (2013.01); *C07D 405/12* (2013.01); *C07D 409/12* (2013.01); *C07D 413/12* (2013.01); *C07D 417/12* (2013.01); *C07D 471/04* (2013.01); *C07D 487/04* (2013.01); *C07D 491/048* (2013.01)

(58) Field of Classification Search

CPC .. C07D 239/96; C07D 401/06; C07D 401/12; C07D 403/12; C07D 405/12; C07D 409/12; C07D 413/12; C07D 417/12; C07D 471/04; C07D 487/04; C07D 491/048; A61K 31/517; A61K 31/519; A61K 31/5377

See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 7,429,604 | B2 | 9/2008 | Corte et al. |
| 7,875,636 | B2 | 1/2011 | Barrow et al. |
| 9,464,065 | B2 | 10/2016 | Schultz et al. |
| 9,522,140 | B2 | 12/2016 | Inoue et al. |
| 9,585,883 | B2 | 3/2017 | Oslob et al. |
| 11,052,092 | B2 | 7/2021 | Delhomel et al. |
| 11,306,098 | B2 | 4/2022 | Letourneau et al. |
| 11,931,358 | B2 | 3/2024 | Honarpour et al. |
| 11,945,803 | B2 | 4/2024 | Lennek et al. |
| 2007/0148185 | A1 | 6/2007 | Rathore et al. |
| 2009/0023169 | A1 | 1/2009 | Hartman et al. |
| 2010/0113391 | A1 | 5/2010 | Koga et al. |
| 2012/0108597 | A1 | 5/2012 | Guo et al. |
| 2016/0176868 | A1 | 6/2016 | Oslob et al. |
| 2019/0077793 | A1 | 3/2019 | Ashcraft et al. |
| 2020/0369626 | A1 | 11/2020 | Tu et al. |
| 2021/0276991 | A1 | 9/2021 | Morgan et al. |
| 2022/0106265 | A1 | 4/2022 | Thiele et al. |

(Continued)

FOREIGN PATENT DOCUMENTS

| | | | |
|---|---|---|---|
| CN | 1521171 | A | 8/2004 |
| CN | 109836477 | A | 6/2019 |

(Continued)

OTHER PUBLICATIONS

Arranz, Esther. et al. Synthesis And Pharmacological Evaluationof 2,3-dihydro-3-oxo-4h-thieno[3,4-e][1,2,4]Thiadiazine 1,1-Dioxidesas Voltage-Dependent Calcium Channel Blockers. European Journal of Medicinal Chemistry 35(7-8):751-759 (2000).

(Continued)

*Primary Examiner* — James H Alstrum-Acevedo

*Assistant Examiner* — Manahil Mirghani Ali Abdalhameed

(74) *Attorney, Agent, or Firm* — WILSON SONSINI GOODRICH & ROSATI

(57) ABSTRACT

Provided are quinazolinone dione compounds for treating cardiac indications such as hypertrophic cardiomyopathy and diastolic dysfunction.

30 Claims, No Drawings

(56) References Cited

U.S. PATENT DOCUMENTS

| | | | |
|---|---|---|---|
| 2023/0012449 A1 | 1/2023 | Bondy et al. | |
| 2023/0149394 A1 | 5/2023 | Honarpour et al. | |
| 2024/0164138 A1 | 5/2024 | Ham et al. | |
| 2024/0279206 A1 | 8/2024 | Lennek et al. | |
| 2025/0154111 A1 | 5/2025 | Hawryluk et al. | |

FOREIGN PATENT DOCUMENTS

| | | | | |
|---|---|---|---|---|
| CN | 114149423 A | 3/2022 | | |
| EP | 0561252 A1 | 9/1993 | | |
| EP | 0585913 A2 | 3/1994 | | |
| EP | 1724264 A1 | 11/2006 | | |
| EP | 2010493 A2 | 1/2009 | | |
| EP | 2729448 B1 | 9/2015 | | |
| EP | 3573960 B1 | 8/2023 | | |
| JP | S6463518 A | 3/1989 | | |
| JP | H01125369 A | 5/1989 | | |
| MA | 30462 B1 | 6/2009 | | |
| WO | WO-0032587 A1 | 6/2000 | | |
| WO | WO-0142216 A2 | 6/2001 | | |
| WO | WO-0206264 A1 | 1/2002 | | |
| WO | WO-02064578 A1 | 8/2002 | | |
| WO | WO-2005085210 A1 | 9/2005 | | |
| WO | WO-2007078839 A2 | 7/2007 | | |
| WO | WO-2007120729 A2 | 10/2007 | | |
| WO | WO-2007124617 A1 | 11/2007 | | |
| WO | WO-2008010964 A1 | 1/2008 | | |
| WO | WO-2008016648 A2 | 2/2008 | | |
| WO | WO-2008016669 A2 | 2/2008 | | |
| WO | WO-2008076225 A2 | 6/2008 | | |
| WO | WO-2008107436 A1 | 9/2008 | | |
| WO | WO-2009023655 A1 | 2/2009 | | |
| WO | WO-2009054983 A1 | 4/2009 | | |
| WO | WO-2010002779 A2 | 1/2010 | | |
| WO | WO-2010056549 A1 | 5/2010 | | |
| WO | WO-2010137351 A1 | 12/2010 | | |
| WO | WO-2013006738 A1 | 1/2013 | | |
| WO | WO-2014205223 A1 | 12/2014 | | |
| WO | WO-2016004417 A1 | 1/2016 | | |
| WO | WO-2016162390 A1 | 10/2016 | | |
| WO | WO-2017161119 A1 | 9/2017 | | |
| WO | WO-2019028360 A1 | 2/2019 | | |
| WO | WO-2020005888 A1 | 1/2020 | | |
| WO | WO-2020033413 A2 | 2/2020 | | |
| WO | WO-2020097265 A1 | 5/2020 | | |
| WO | WO-2020123675 A1 | 6/2020 | | |
| WO | WO-2020172565 A1 | 8/2020 | | |
| WO | WO-2020210032 A1 | 10/2020 | | |
| WO | WO-2020221376 A1 * | 11/2020 | .............. | A61P 35/00 |
| WO | WO-2021092598 A1 | 5/2021 | | |
| WO | WO-2021231546 A1 | 11/2021 | | |
| WO | WO-2021231565 A1 | 11/2021 | | |
| WO | WO-2022212902 A1 | 10/2022 | | |
| WO | WO-2023277605 A1 | 1/2023 | | |
| WO | WO-2023159234 A2 | 8/2023 | | |
| WO | WO-2023208165 A1 | 11/2023 | | |
| WO | WO-2023240134 A1 | 12/2023 | | |
| WO | WO-2024050139 A1 | 3/2024 | | |
| WO | WO-2024073426 A1 | 4/2024 | | |
| WO | WO-2024138042 A1 | 6/2024 | | |
| WO | WO-2024182469 A1 | 9/2024 | | |
| WO | WO-2024206339 A1 | 10/2024 | | |
| WO | WO-2024206345 A1 | 10/2024 | | |
| WO | WO-2024206347 A1 | 10/2024 | | |

OTHER PUBLICATIONS

Awinda et al., Mavacamten decreases maximal force and $Ca^{2+}$ sensitivity in the N47K-myosin regulatory light chain mouse model of hypertrophic cardiomyopathy. Am J. Physio. Heart Cir. Physiol., 320(2): Feb. 1, 2021;H881-H890.

Chatterjee, Tanmay. et al. Base-Promoted Synthesis of 2-Aryl Quinazolines from 2-Aminobenzylamines in Water. The Journal of Organic Chemistry 83(14):7423-7430 (2018).

Chem, Ji-Wang. et al. Studies on 1, 2, 4-Benzothiadiazine 1, 1-Dioxide IX.1 Synthesis and Pharmacological Evaluation of 1, 2, 4-Benzothiadiazine 1, 1-Dioxide Biphenyl Tetrazoles as Angiotensin II Antagonists. Journal of the Chinese Chemical Society 45(6):805-810 (1998).

Davis, J. S. et al., The Overall pattern of Cardiac contraction depends on a spatial gradient of Myosin Regulatory Light Chain Phosphorylation. Cell, vol. 107, 631-641, Nov. 30, 2001.

Engler, Thomas A. et al. Substituted 3-imidazo[1,2-a]pyridin-3-yl-4-(1,2,3,4-tetrahydro-[1,4]diazepino-[6,7,1-hi]indol-7-yl)pyrrole-2,5-diones as highly selective and potent inhibitors of glycogen synthase kinase-3. Journal of Medicinal Chemistry 47(16):3934-3937 (2004).

Evans, Anthony E. Synthesis of Radiolabeled Compounds. Journal of Radioanalytical and Nuclear Chemistry 64(1-2):9-32 (1981).

Fedorak, Richard N. et al. A novel colon-specific steroid prodrug enhances sodium chloride absorption in rat colitis. American Journal of Physiology 269(2 Pt 1):G210-G218 (1995).

Fieser, Louis. F, and Mary Fieser. Reagents for Organic Synthesis. John Wiley and Sons:119-121 (1994).

Highlights of Prescribing Information These highlights do not include all the information needed to use CAMZYOS safely and effectively. Apr. 2022, 27 Pages.

Higuchi, T, and V. Stella. Pro-Drugs as Novel Delivery Systems, vol. 14 of the A.C.S. Symposium Series. American Chemical Society (1975).

Hochhaus, Gunther. et al. A Selective HPLC/RIA for Dexamethasone and its Prodrug Dexamethasone-21-sulphobenzoate Sodium in Biological Fluids. Biomedical Chromatography 6(6):283-286 (1992).

Kabalka, George W. et al. The Synthesis of Radiolabeled Compounds via Organometallic Intermediates. Tetrahedron 45(21):6601-6621 (1989).

Larsen, Jorn Drustrup, and Hans Bundgaard. Prodrug forms for the sulfonamide group. I. Evaluation of N-acyl derivatives, N-sulfonylamidines, N-sulfonylsulfilimines and sulfonylureas as possible prodrug derivatives. International Journal of pharmaceutics 37(1-2):87-95 (1987).

Larsen, Jorn Drustrup. et al. Prodrug forms for the Sulfonamide Group. II. Water-soluble Amino Acid Derivatives of N-methylsulfonamides as Possible Prodrugs. International Journal of Pharmaceutics 47:103-110 (1988).

Liu, Dazhi. et al. Design, synthesis and evaluation of 1, 2-benzisothiazol-3-one derivatives as potent caspase-3 inhibitors. Bioorganic & medicinal chemistry 21(11):2960-2967 (2013).

Mcleod, Andrew D. et al. A glucocorticoid prodrug facilitates normal mucosal function in rat colitis without adrenal suppression. Gastroenterology 106(2):405-413 (1994).

PCT/US2023/075138 International Search Report and Written Opinion dated Nov. 28, 2023.

PCT/US2024/021528 International Search Report and Written Opinion dated Aug. 6, 2024.

PCT/US2024/021537 International Search Report and Written Opinion dated Jul. 18, 2024.

PCT/US2024/021539 International Search Report and Written Opinion dated Aug. 12, 2024.

Ro, R. et al., Vector Flow Mapping in Obstructive Hypertrophic Cardiomyopathy to Assess the Relationship of Early Systolic Left Ventricular Flow and the Mitral Valve. Journal of the American College of Cardiology, 2014, vol. 64. No. 19; 1984-95.

Sinkula, A A, and Samuel H. Yalkowsky. Rationale for design of biologically reversible drug derivatives: prodrugs. Journal of pharmaceutical sciences 64(2):181-210 (1975).

Smith, Joshua D. Isoform selectivities of novel 4-hydroxycoumarin imines as inhibitors of myosin II. European journal of medicinal chemistry 247:115008, 1-38 (2023).

Sun, Lin. et al. Design, Synthesis, and Mechanism Study of Benzenesulfonamide-Containing Phenylalanine Derivatives as Novel HIV-1 Capsid Inhibitors with Improved Antiviral Activities. Journal of Medicinal Chemistry 63(9):4790-4810 (2020).

Wang, Min. et al. [11C]GSK2126458 and [18F]GSK2126458, The First Radiosynthesis of New Potential PET Agents for Imaging of PI3K and mTOR in Cancers. Bioorganic & Medicinal Chemistry Letters 22(4):1569-1574 (2012).

(56) References Cited

OTHER PUBLICATIONS

Zhang, J. et al., Hypertrophic cardiomyopathy associated E22K mutation in myosin regulatory light chain decreases calcium-activated tension and stiffness and reduces myofilament Ca2+ sensitivity. FEBS J. Aug. 2021 ; 288(15): 4596-4613. doi:10.1111/febs.15753.
Ukrainets, I. V. et al. 4-Hydroxyquinolin-2-ones. 45. Synthesis, Structure, and Biological Activity of N-Substituted 1H-4-Hydroxy-2-oxoquinoline-3-acetic Acid Amides. Chemistry of Heterocyclic Compounds 36:1319-1325 (2000).
Database CaPlus [Online] ChemicA1 Abstracts Service, Jan. 1, 1990 (Jan. 1, 1990). Chen Qingping et a1: Proton NMR spectra of 7[beta]-(6-substituted-2-quinolone-3-aceta mido)- and 7[beta]-(6-substituted-4-hydroxyquinoline-3-formamido)-cephA1osporins. XP093279164, Database accession No. 1991:631920.
Database Registry, ChemicA1 Abstracts Service; (Nov. 9, 2021), Database accession No. 2727956-55-8, XP093279204.
Database Registry, Chemical Abstracts Service (Aug. 2, 2012), Database accession No. 1385267-38-8, XP093279922.
Database Registry, Chemical Abstracts Service (Jun. 18, 2015), Database accession No. 1783105-24-7, XP093279920.
Database Registry, Chemical Abstracts Service; (Dec. 16, 2015), Database accession No. 1831179-14-6, XP093277426.
Database Registry, Chemical Abstracts Service; (Dec. 8, 2015), Database accession No. 1832193-03-9, XP093277424.
Database Registry, Chemical Abstracts Service; (Jul. 6, 2016), Database accession No. 1946404-58-5, XP093277421.
Database Registry, Chemical Abstracts Service; (Jul. 10, 2016), Database accession No. 1948573-95-2, XP093277416.
Database Registry, Chemical Abstracts Service (Jan. 25, 2017), Database accession No. 2058772-64-6, XP093279919.
Database Registry, Chemical Abstracts Service; (Jan. 27, 2017), Database accession No. 2060133-05-1, XP093277413.
Database Registry, Chemical Abstracts Service; (Jul. 26, 2017), Database accession No. 2103065-64-9, XP093277409.
Database Registry, Chemical Abstracts Service; (Feb. 15, 2018), Database accession No. 2173908-64-8, XP093277398.
Database Registry, Chemical Abstracts Service; (Mar. 12, 2018), Database accession No. 2189172-68-5, XP093277394.
Database Registry, Chemical Abstracts Service; (Jul. 28, 2019), Database accession No. 2361760-55-4, XP093277429.
Database Registry, Chemical Abstracts Service; (Jul. 28, 2019), Database accession No. 2361838-41-5, XP093277392.
Database Registry, Chemical Abstracts Service; (Jul. 28, 2019), Database accession No. 2361907-19-7, XP093277513.
Database Registry, Chemical Abstracts Service (Aug. 29, 2019), Database accession No. 2369930-64-1, XP093279918.
Database Registry, Chemical Abstracts Service (Jan. 1, 2020), Database accession No. 2398077-26-2, XP093279916.
Database Registry, Chemical Abstracts Service (Jan. 2, 2020), Database accession No. 2398164-43-5, XP093279914.
Database Registry, Chemical Abstracts Service (Jan. 8, 2020), Database accession No. 2402509-76-4, XP093279912.
Database Registry, Chemical Abstracts Service (Jan. 10, 2020), Database accession No. 2404419-52-7, XP093279910.
Database Registry, Chemical Abstracts Service (Jan. 13, 2020), Database accession No. 2405463-55-8, XP093279908.
Database Registry, Chemical Abstracts Service (Jun. 8, 2020), Database accession No. 2420362-92-9, XP093279906.
Database Registry, Chemical Abstracts Service (Jun. 9, 2020), Database accession No. 2421242-17-1, XP093279905.
Database Registry, Chemical Abstracts Service (Jun. 22, 2020), Database accession No. 2431889-47-1, XP093279901.
Database Registry, Chemical Abstracts Service (Jun. 23, 2020), Database accession No. 2432461-84-0, XP093279900.
Database Registry, Chemical Abstracts Service (Aug. 31, 2020), Database accession No. 2468117-82-8, XP093279897.
Database Registry, Chemical Abstracts Service; (Sep. 23, 2021), Database accession No. 2699886-11-6, XP093277387.
Database Registry, Chemical Abstracts Service; (Oct. 14, 2021), Database accession No. 2712289-98-8, XP093277386.
Database Registry, Chemical Abstracts Service; (Oct. 15, 2021), Database accession No. 2712788-51-5, XP093277508.
Database Registry, Chemical Abstracts Service; (Oct. 17, 2021), Database accession No. 2713664-04-9, XP093277384.
Database Registry, Chemical Abstracts Service (Jul. 26, 2022), Database accession No. 2797160-72-4, XP093279894.
Database Registry, Chemical Abstracts Service; (Sep. 1, 2022), Database accession No. 2816805-43-1, X P093277382.
Database Registry, Chemical Abstracts Service; (Jun. 23, 2023), Database accession No. 2935080-68-3, XP093277525.
Database Registry, Chemical Abstracts Service; (Aug. 29, 2023), Database accession No. 2966899-34-1, XP093277520.
Database Registry, Chemical Abstracts Service; (Aug. 31, 2023), Database accession No. 2968160-16-7, XP093277515.
Database Registry, Chemical Abstracts Service; (Oct. 18, 2023), Database accession No. 2990803-91-1, XP093277379.
Database Registry, Chemical Abstracts Service; (Dec. 1, 2023), Database accession No. 3009361-40-1, XP093277454.
Madhu, Desagoni. et al. 3-Trifluoroacetyl-quinolin-2(1 H)-ones as Carbonyl and Acid Surrogates in the Passerini-/Ugi-Type Reaction. The Journal of Organic Chemistry 87(5):2301-2314 (2022).
Okuzumi, Tatsuya. et al. Efficient solid-phase synthesis of quinazoline-2, 4-diones with various substituents on aromatic rings. Tetrahedron 59(29):5603-5608 (2003).
PCT/US2025/021324 International Search Report and Written Opinion dated Jun. 13, 2025.
PCT/US2025/021387 International Search Report and Written Opinion dated Jun. 13, 2025.
PCT/US2025/021402 International Search Report and Written Opinion dated Jun. 13, 2025.
PCT/US2025/021405 International Search Report and Written Opinion dated Jun. 16, 2025.
Sivakamasundari, S. et al. Pyrroloquinolines: Part IV—Synthesis of 1-Aryl-1H-pyrrolo [2,3-b]quinolines. Indian Journal of Chemistry XP002950352, 26B 744-747 (1987).
Ukrainets, I. et al. 4 Hydroxy-2-quinolones. 35. Synthesis and Study of Antithyroid Properties of 1H-2-OxO-3-(coumarin-3-yl)-4-hydroxyquinolines. Chemistry of Heterocyclic Compounds, Xp093278695 33(8):959-963 (1999).
Ukrainets I. V. et al. 4-Hydroxyquinolin-2-ones. 45. Synthesis, Structure, and Biological Activity of N-Substituted 1H-4-Hydroxy-2-oxoquinoline-3-acetic Acid Amides. Chemistry of Heterocyclic Compounds XP093278700, 36(11):1319-1325 (2000).

* cited by examiner

QUINAZOLINONE DIONE COMPOUNDS AND USES THEREOF

CROSS-REFERENCE

This application is a continuation application of International Patent Application No. PCT/US2024/021537, filed Mar. 26, 2024, which claims the benefit of U.S. Provisional Patent Application No. 63/492,439, filed Mar. 27, 2023, and claims the benefit of U.S. Provisional Patent Application No. 63/513,844, filed Jul. 14, 2023, each of which is incorporated herein by reference in its entirety.

BACKGROUND OF THE INVENTION

Hypertrophic cardiomyopathy HCM is a chronic, progressive disease of the cardiac sarcomere. The etiology of HCM is multifactorial; a significant portion of affected people have at least one mutation in the genes that encode cardiac sarcomere proteins. Regardless of the cause of HCM, in many cases, excess myosin-actin crossbridge formation in systole and diastole leads to hyperdynamic contraction and impaired relaxation. Over time this excess stress leads to tissue remodeling characterized histologically by myocyte hypertrophy, myofilament disarray, microvascular remodeling, and fibrosis. HCM may be genetic (e.g., heritable) or not genetic. HCM includes a group of highly penetrant, monogenic, autosomal dominant myocardial diseases. Such HCM may be caused by one or more of over 1,000 known point mutations in any one of the proteins contributing to the functional unit of myocardium, the sarcomere. About 1 in 500 individuals in the general population are found to have left ventricular hypertrophy unexplained by other known causes (e.g., hypertension or valvular disease), and many of these can be shown to have HCM, e.g., once other heritable (e.g., lysosomal storage diseases), metabolic, or infiltrative causes have been excluded.

Medical therapy for HCM is limited and many patients' symptoms are empirically managed with beta-blockers, non-dihydropyridine calcium channel blockers, and/or disopyramide. None of these agents carry labeled indications for treating HCM, and essentially no rigorous clinical trial evidence is available to guide their use. In approximately 60% of patients with HCM, the left ventricular outflow tract becomes obstructed, impeding the flow of blood and creating a pressure gradient between the LV cavity and the aorta. For patients with hemodynamically significant outflow tract obstruction (gradient >50 mmHg), surgical myectomy or alcohol septal ablation can be utilized to alleviate the hemodynamic obstruction albeit with significant clinical morbidity and mortality. Provided herein are new therapeutic agents and methods that remedy the long-felt need for improved treatment of HCM and related cardiac disorders.

SUMMARY OF THE INVENTION

The disclosure provides compound and salts thereof for use in treating disease. In certain aspects, the disclosure provides compounds of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep), as well as salts and pharmaceutical compositions thereof, as well as methods of use in the treatment of disease.

INCORPORATION BY REFERENCE

All publications, patents, and patent applications mentioned in this specification are herein incorporated by reference to the same extent as if each individual publication, patent, or patent application was specifically and individually indicated to be incorporated by reference. U.S. Provisional Application 63/492,439 (filed Mar. 27, 2023) is incorporated by reference herein in its entirety. U.S. Provisional Application 63/513,844 (filed Jul. 14, 2023) is incorporated by reference herein in its entirety.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In certain aspects, the disclosure provides methods for treating a cardiac disease in an individual in need thereof, the method comprising administering a therapeutically effective amount of a compound of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep), or salts thereof, N-oxides thereof, or pharmaceutical compositions thereof.

Diseases treated by the methods described herein include, but are not limited to, cardiac diseases. Cardiac diseases treated by the method described herein include, but are not limited to, heart muscle disease (cardiomyopathy), hypertrophic cardiomyopathy (HCM), abnormal heart rhythms, aorta disease, Marfan syndrome, coronary artery disease, heart attack, heart failure, rhematic heart disease, peripheral vascular disease, stroke, deep vein thrombosis and pulmonary embolism.

Cardiomyopathy is a heart disease wherein the heart may be abnormally enlarged, thicked, and/or stiffened and may have few or no symptoms early on. As the disease gets worse, symptoms include, but are not limited to, shortness of breath, feeling tired, irregular heartbeat, fainting, and onset of heart failure. Types of cardiomyopathy include, but are not limited to arrhythmogenic right ventricular dysplasia, dilated cardiomyopathy, hypertrophic cardiomyopathy, restrictive cardiomyopathy, and Takotsubo cardiomyopathy.

Hypertrophic cardiomyopathy (HCM) may be genetic (e.g., heritable) or not genetic (e.g., not heritable). HCM may be obstructive or nonobstructive. Genetic hypertrophic cardiomyopathy (HCM) comprises a group of highly penetrant, monogenic, autosomal dominant myocardial diseases. HCM may be caused by one or more of over 1,000 known point mutations in any one of the proteins contributing to the functional unit of myocardium, the sarcomere.

In approximately two-thirds of HCM subjects, the path followed by blood exiting the heart, known as the left ventricular outflow tract (LVOT), becomes obstructed by the enlarged and diseased muscle, restricting the flow of blood from the heart to the rest of the body (obstructive HCM). In other subjects, the thickened heart muscle does not block the LVOT, and their disease is driven by diastolic impairment due to the enlarged and stiffened heart muscle (non-obstructive HCM). In either obstructive or non-obstructive HCM subjects, exertion can result in fatigue or shortness of breath, interfering with a subject's ability to participate in activities of daily living. HCM has also been associated with increased risks of atrial fibrillation, stroke, heart failure and sudden cardiac death.

Currently available therapies for HCM may be variably effective in alleviating symptoms but may show decreased efficacy with increasing disease duration. Patients may be thus empirically managed with beta-blockers, non-dihydropyridine calcium channel blockers, and/or disopyramide. Mavacamten may also be used. In approximately 60% of patients with HCM, the left ventricular outflow tract becomes obstructed, impeding the flow of blood and creating a pressure gradient between the LV cavity and the aorta. For patients with hemodynamically significant outflow tract obstruction (gradient >50 mmHg), surgical myectomy or alcohol septal ablation can be utilized to alleviate the hemodynamic obstruction albeit with significant clinical morbidity and mortality. Provided are new therapeutic agents and methods that remedy the long-felt need for improved treatment of HCM and related cardiac disorders.

The compounds of the invention or their pharmaceutically acceptable salts can alter the natural history of HCM and other diseases rather than merely palliating symptoms. The mechanisms conferring clinical benefit to HCM patients can extend to patients with other forms of heart disease sharing similar pathophysiology, with or without demonstrable genetic influence. For example, an effective treatment for HCM, by improving ventricular relaxation during diastole, can also be effective in a broader population characterized by diastolic dysfunction. The compounds of the invention or their pharmaceutically acceptable salts can specifically target the root causes of the conditions or act upon other downstream pathways. Accordingly, the compounds of the invention or their pharmaceutically acceptable salts can also confer benefit to patients suffering from diastolic heart failure with preserved ejection fraction, ischemic heart disease, angina pectoris, or restrictive cardiomyopathy. Compounds of the invention or their pharmaceutically acceptable salts can also promote salutary ventricular remodeling of left ventricular hypertrophy due to volume or pressure overload; e.g., chronic mitral regurgitation, chronic aortic stenosis, or chronic systemic hypertension; in conjunction with therapies aimed at correcting or alleviating the primary cause of volume or pressure overload (valve repair/replacement, effective antihypertensive therapy). By reducing left ventricular filling pressures the compounds could reduce the risk of pulmonary edema and respiratory failure. Reducing or eliminating functional mitral regurgitation and/or lowering left atrial pressures may reduce the risk of paroxysmal or permanent atrial fibrillation, and with it reduce the attendant risk of arterial thromboembolic complications including but not limited to cerebral arterial embolic stroke. Reducing or eliminating either dynamic and/or static left ventricular outflow obstruction may reduce the likelihood of requiring septal reduction therapy, either surgical or percutaneous, with their attendant risks of short- and long term complications. The compounds or their pharmaceutically acceptable salts may reduce the severity of the chronic ischemic state associated with HCM and may thereby reduce the risk of Sudden Cardiac Death (SCD) or its equivalent in patients with implantable cardioverter-defibrillators (frequent and/or repeated ICD discharges) and/or the need for potentially toxic antiarrhythmic medications. The compounds or their pharmaceutically acceptable salts could be valuable in reducing or eliminating the need for concomitant medications with their attendant potential toxicities, drug-drug interactions, and/or side effects. The compounds or their pharmaceutically acceptable salts may reduce interstitial myocardial fibrosis and/or slow the progression, arrest, or reverse left ventricular hypertrophy.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

The term "$C_{x-y}$" or "$C_x$-$C_y$" (e.g., when used in conjunction with a chemical moiety, such as alkyl, alkenyl, or alkynyl) is meant to include groups that comprise a number of carbon atoms greater than or equal to x carbon atoms and less than or equal to y carbon atoms in the chemical moiety, subject to the following. The term "$C_{x-y}$" or "$C_x$-$C_y$" is not meant to limit the number of carbon atoms which may be attached to the chemical moiety when the chemical moiety is substituted with a second chemical moiety. For example, the term "$C_{1-6}$ alkyl" or "$C_1$ to $C_6$ alkyl" refers to saturated, substituted or unsubstituted, hydrocarbon groups, including straight-chain alkyl groups (e.g., linear alkyl groups) and branched alkyl groups that contain 1, 2, 3, 4, 5, or 6 carbon atoms, plus however many carbon atoms may be present in any substituents of the $C_{1-6}$ alkyl. For example, if a $C_{1-6}$ alkyl is optionally substituted with a second chemical moiety comprising two carbon atoms, then it will be understood that the $C_{1-6}$ alkyl can include between 1 and 8 carbon atoms.

The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond, respectively.

"Amino" refers to the $—NH_2$ moiety.

"Cyano" refers to the —CN moiety.

"Nitro" refers to the $—NO_2$ moiety.

"Oxa" refers to the —O— moiety.

"Oxo" refers to the =O moiety.

"Thioxo" refers to the =S moiety.

"Imino" refers to the =N—H moiety.

"Oximo" refers to the =N—OH moiety.

"Hydrazino" refers to the $=N—NH_2$ moiety.

"Alkyl" refers to a straight (e.g., linear) or branched (e.g., nonlinear) hydrocarbon moiety consisting solely of carbon and hydrogen atoms, fully saturated. In certain embodiments, "alkyl" comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl, e.g., methyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (2-propyl, iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond.

"Aminoalkyl" refers to a moiety boded through a nitrogen atom of the form —N(H)(alkyl) or N(alkyl)(alkyl), wherein when the moiety is N(alkyl)(alkyl), the two alkyl groups bonded to nitrogen can be the same alkyl groups or different alkyl groups.

"Alkoxy" refers to a moiety bonded through an oxygen atom of the formula —O-alkyl, where alkyl is an alkyl chain as defined above.

"Alkenyl" refers to a straight (e.g., linear) or branched (e.g., nonlinear) hydrocarbon moiety consisting solely of carbon and hydrogen atoms, the moiety comprising at least one carbon-carbon double bond. In certain embodiments, an alkenyl comprises two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (e.g., vinyl), prop-1-enyl (e.g., allyl), but-1-enyl, pent-1-enyl, penta-1,4-dienyl, and the like.

"Alkynyl" refers to a straight (e.g., linear) or branched (e.g., nonlinear) hydrocarbon moiety consisting solely of carbon and hydrogen atoms, the moiety comprising at least one carbon-carbon triple bond. In some embodiments, an alkynyl comprises from two to twelve carbon atoms. In some embodiments, an alkynyl optionally further comprises at least one carbon-carbon double bond. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like.

"Alkylene" or "alkylene chain" refers to a linear (e.g., straight), or branched (e.g., nonlinear), divalent, hydrocarbon moiety. An "alkylene" or "alkylene chain" can link a portion of the molecule to a second moiety. An "alkylene" or "alkylene chain" consists solely of carbon and hydrogen atoms (substitution of an alkylene with one or more substituents comprising atoms other than hydrogen, such as N, O, and S, may be specified). An "alkylene" or "alkylene chain" can contain no unsaturation (notwithstanding the points of attachment of an alkylene to the rest of the molecule). In certain embodiments, the "alkylene" or "alkylene chain" and comprises one to twelve carbon atoms, for example, methylene, ethylene, propylene, n-butylene, and the like. The alkylene chain can be attached to the portion of the molecule through a single bond and to the second moiety through a single bond. The points of attachment of an alkylene chain to the rest of the molecule and to the second moiety can be through one carbon atom in the alkylene chain or can be through any two carbon atoms within the alkylene. In certain embodiments, an alkylene comprises one to eight carbon atoms (e.g., $C_1$-$C_5$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene).

"Alkenylene" or "alkenylene chain" refers to a linear (e.g., straight), or branched, divalent, hydrocarbon moiety. An "alkenylene" or "alkenylene chain" can link a portion of the molecule to a second moiety. An "alkenylene" or "alkenylene chain" consists solely of carbon and hydrogen atoms (substitution of an alkenylene with one or more substituents comprising atoms other than hydrogen, such as N, O, and S, may be specified). An "alkenylene" or "alkenylene chain" comprises at least one carbon-carbon double bond. In certain embodiments, an "alkenylene" or "alkenylene chain" comprises from two to twelve carbon atoms. The alkenylene chain can be attached to the portion of the molecule through a single bond and to the second moiety through a single bond. The points of attachment of an alkenylene chain to the rest of the molecule and to the second moiety can be through one carbon atom in the alkenylene chain or through any two carbon atoms within the alkenylene chain. In certain embodiments, an alkenylene comprises two to eight carbon atoms (e.g., $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e.g., $C_2$-$C_3$ alkenylene). In other embodiments, an alkenylene comprises five to eight carbon atoms (e.g., $C_5$-$C_5$ alkenylene). In other embodiments, an alkenylene comprises two to five carbon atoms (e.g. $C_2$-$C_5$ alkenylene). In other embodiments, an alkenylene comprises three to five carbon atoms (e.g., $C_3$-$C_5$ alkenylene).

"Alkynylene" or "alkynylene chain" refers to a linear (e.g., straight), or branched, divalent, hydrocarbon moiety. An "alkynylene" or "alkynylene chain" can link a portion of the molecule to a second moiety. An "alkynylene" or "alkynylene chain" consists solely of carbon and hydrogen (substitution of an alkynylene with one or more substituents comprising atoms other than hydrogen, such as N, O, and S, may be specified). An "alkynylene" or "alkynylene chain" comprises at least one carbon-carbon triple bond. In certain embodiments, an "alkynylene" or "alkynylene chain" comprises from two to twelve carbon atoms. An alkynylene chain can be attached to the portion of the molecule through a single bond and to the second moiety through a single bond. The points of attachment of an alkynylene chain to the rest of the molecule and to the second moiety can be through one carbon atom in the alkynylene chain or through any two carbon atoms within the alkynylene chain. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atoms (e.g., $C_2$ alkynylene). In other embodiments, an alkynylene comprises five to eight carbon atoms (e.g., $C_5$-$C_5$ alkynylene). In other embodiments, an alkynylene comprises three to five carbon atoms (e.g., $C_3$-$C_5$ alkynylene).

The term "carbocycle" as used herein refers to a saturated or unsaturated (e.g., aromatic or nonaromatic unsaturated) ring or ring system in which each atom of the ring is carbon. The term "carbocycle" comprises "aryls," "cycloalkenyls," and "cycloalkyls." For example, the term "carbocycle" includes 3- to 12-membered monocyclic rings (e.g., 3- to 10-membered monocyclic rings) and 4- to 20-membered polycyclic ring systems (e.g., 5- to 15-membered spiro polycyclic ring systems, 5- to 15-membered bridged polycyclic ring systems, or 4- to 15-membered fused polycyclic ring systems). For example, carbocycle includes 4- to 15-membered bicyclic rings (e.g., 5- to 15-membered spiro bicycles, 5- to 15-membered bridged bicyclic ring systems, or 4- to 15-membered fused bicyclic ring systems). For example, carbocycle includes tricyclic ring systems, which may be bridged, fused, spiro, or a combination thereof. For example, carbocycle includes tetracyclic ring systems, which may be bridged, fused, spiro, or a combination thereof. For example, carbocycle includes ring systems that are both fused and bridged; ring systems that are both fused and spiro; ring systems that are both bridged and spiro; and ring systems that are both fused and bridged and are also spiro. Each ring of a polycyclic carbocycle may be selected from saturated and unsaturated (e.g., aromatic or nonaromatic unsaturated) rings. In an exemplary embodiment, an aromatic ring (e.g., phenyl) of a polycyclic carbocycle may be fused to a saturated or unsaturated ring (e.g., cyclohexane, cyclopentane, cyclohexene, or phenyl). A polycyclic carbocycle includes any combination of saturated and unsaturated (e.g., aromatic or nonaromatic unsaturated) rings, as valence permits. For example, polycyclic carbocycles can be spiro bicyclic rings, such as spiropentane. For example, a polycyclic carbocycle includes any combination of ring sizes such as 2-2 spiro ring systems (e.g., spiro[2.2]pentane), 3-3 spiro ring systems, 4-4 spiro ring systems, 4-5 fused ring systems (e.g., bicyclo[4.5.0] fused ring systems), 5-5 fused ring systems, 5-6 fused ring systems, 6-6 fused ring systems (e.g., naphthalene), 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, trans-bicyclo[4.4.0]decane, cis-bicylo[4.4.0]decane, spiro[3.4]octane, fluoranthene, and bicyclo[1.1.1]pentanyl.

The term "aryl" refers to an aromatic monocyclic or aromatic polycyclic hydrocarbon ring system comprising at least one cyclic, delocalized (4n+2) π-electronic system, wherein n is an integer greater than or equal to 0, in accordance with Hückel theory. In some embodiments, the aromatic monocyclic or aromatic polycyclic hydrocarbon ring system comprises only hydrogen atoms and carbon atoms. In some embodiments, the aromatic monocyclic or polycyclic system contains from three to twenty carbon atoms. In some embodiments, at least one of the rings in the polycyclic aromatic ring system is aromatic. In some embodiments, the aromatic monocyclic or aromatic polycyclic hydrocarbon ring system comprises a cyclic, delocalized (4n+2) π-electronic system in accordance with Hückel theory. In some embodiments, the ring system from which aryl groups are derived include, but are not limited to, groups such as benzene, fluorene, indane, indene, anthracene, tetralin, and naphthalene. In some embodiments, the aryl substituent is not charged (e.g., neutral). In some embodiments, the aryl substituent bears no charges. In some embodiments, the aryl substituent bears no net charge. In some embodiments, the aryl substituent bears no net charge and is not zwitterionic. In some embodiments, none of the carbon atoms of the aryl substituent are charged. In some embodiments, none of the carbon atoms of the aryl substituent are charged.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises three to seven carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Examples of polycyclic cycloalkyls include, but are not limited to, adamantyl, spiropentane, norbornyl (e.g., bicyclo[2.2.1]heptanyl), decalinyl, 7,7 dimethyl bicyclo[2.2.1]heptanyl, bicyclo[1.1.1]pentanyl, spiropentane, and the like.

The term "cycloalkenyl" refers to a saturated ring in which each atom of the ring is carbon and there is at least one double bond between two ring carbon atoms. Cycloalkenyl may include monocyclic and polycyclic rings, such as 3- to 10-membered monocyclic rings and 4- to 12-membered bicyclic rings (e.g., 5- to 12-membered bridged bicyclic rings, fused 4- to 12-membered bicyclic rings, and spiro 5- to 12-membered bicyclic rings). In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, a halo is fluoro, chloro, or bromo. In some embodiments, a halo is a fluoro or a chloro. In some embodiments, a halo is a fluoro. In some embodiments, a halo is a chloro.

The term "haloalkyl" refers to an alkyl, as defined above, that is substituted by one or more halogens, for example, trifluoromethyl, dichloromethyl, bromomethyl, 2,2,2-trifluoroethyl, 1-chloromethyl-2-fluoroethyl, and the like. In some embodiments, the alkyl part of the haloalkyl is optionally further substituted as described herein.

The term "heterocycle" as used herein refers to a saturated or unsaturated (e.g., aromatic or nonaromatic unsaturated) ring or ring system in which one or more heteroatom(s) is(are) member(s) of the ring or ring system. Exemplary heteroatoms include N, O, Si, P, B, and S atoms. For example, heterocycles include 3- to 12-membered monocyclic rings (e.g., 3- to 10-membered monocyclic rings) and 4- to 20-membered polycyclic ring systems (e.g., 4- to 15-membered fused poly ring systems, 5- to 15-membered spiro polycyclic ring systems, and 5- to 15-membered bridged polycyclic ring systems). For example, heterocycles include 4- to 20-membered bicyclic ring systems (e.g., 4- to 15-membered fused bicyclic ring systems, 5- to 15-membered spiro bicyclic ring systems, and 5- to 15-membered bridged bicyclic ring systems). For example, heterocycle includes tricyclic ring systems, which may be bridged, fused, spiro, or a combination thereof. For example, heterocycle includes tetracyclic ring systems, which may be bridged, fused, spiro, or a combination thereof. For example, heterocycle includes ring systems that are both fused and bridged; ring systems that are both fused and spiro; ring systems that are both bridged and spiro; and ring systems that are both fused and bridged and are also spiro. Each ring of a polycyclic heterocycle may be selected from saturated and unsaturated (e.g., aromatic or nonaromatic unsaturated) rings. A polycyclic heterocycle includes any combination of saturated, and unsaturated (e.g., aromatic or nonaromatic unsaturated) rings, as valence permits. In an exemplary embodiment, an aromatic ring, e.g., pyridyl or phenyl, may be fused to a saturated or unsaturated ring, e.g., cyclohexane, cyclopentane, morpholine, piperidine or cyclohexene, in a heterocycle, as long as at least one atom in the resulting fused ring system is a heteroatom. A polycyclic heterocycle includes any combination of ring sizes such as 3-3 spiro, 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered spiro bicycles, such as 2-oxa-6-azaspiro[3.3]heptane. In some embodiments, a heterocycle comprises multiple heteroatoms. In some embodiments, a heterocycle comprises an atom selected from nitrogen, oxygen, and sulfur. In some embodiments, a heterocycle comprises multiple atoms selected from nitrogen, oxygen, and sulfur. In some embodiments, a heterocycle comprises one or more atom(s) selected from nitrogen, oxygen, and sulfur. In some embodiments, a heterocycle comprises one or more atom(s) selected from nitrogen and oxygen. In some embodiments, a heterocycle comprises one or more atom(s) selected from nitrogen and sulfur. In some embodiments, a heterocycle comprises one or more atom(s) selected from oxygen and sulfur. In some embodiments, a heterocycle comprises one or more atom(s) selected from nitrogen. In some embodiments, a heterocycle comprises one or more atom(s) selected from oxygen. In some embodiments, a heterocycle comprises one or more atom(s) selected from sulfur. Nonlimiting examples of heterocycles include pyridine, pyrrole, indole, carbazole, piperidine, oxazole, morpholine, thiophene, benzothiophene, furan, tetrahydrofuran, and pyran. Nonlimiting examples of heterocycles include azepinyl, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (e.g., thienyl).

In some embodiments, a heterocycle is attached to the molecule by a carbon atom. In some embodiments, the heterocycle is attached to the molecule by a nitrogen atom.

In some embodiments, a heterocycle comprises a moiety selected from a heteroaryl, a heterocycloalkyl, and a heterocycloalkenyl. In some embodiments, the heterocycle is a heteroaryl. In some embodiments, the heterocycle is a heterocycloalkyl. In some embodiments, the heterocycle is a heterocycloalkenyl.

In some embodiments, a heterocycle comprises an atom selected from nitrogen and oxygen. In some embodiments, a heterocycle comprises an atom selected from nitrogen and sulfur. In some embodiments, a heterocycle comprises an atom selected from oxygen and sulfur. In some embodiments, a heterocycle comprises an atom selected from nitrogen. In some embodiments, a heterocycle comprises an atom selected from oxygen. In some embodiments, a heterocycle comprises an atom selected from sulfur.

In some embodiments, a heterocycle comprises 1 to 8 heteroatoms. In some embodiments, the heterocycle comprises 1 to 5 heteroatoms. In some embodiments, the heterocycle comprises 1 to 3 heteroatoms. In some embodiments, the heterocycle comprises 1 to 2 heteroatoms. In some embodiments, the heterocycle comprises 1 heteroatom. In some embodiments, the heterocycle comprises 2 heteroatoms. In some embodiments, the heterocycle comprises 3 heteroatoms. In some embodiments, the heterocycle comprises 4 heteroatoms. In some embodiments, the heterocycle comprises 5 heteroatoms. In some embodiments, the heterocycle comprises 6 heteroatoms.

In some embodiments, a heterocycle comprises a 3-membered ring, 4-membered ring, 5-membered ring, 6-membered ring, 7-membered ring, 8-membered ring, 9-membered ring, 10-membered ring, 11-membered ring, 12-membered ring, 13-membered ring, 14-membered ring, or 15-20 membered ring. In some embodiments, a heterocycle is 3- to 10-membered. In some embodiments, a heterocycle is 3- to 6-membered. In some embodiments, a heterocycle is 5- to 6-membered. In some embodiments, a heterocycle is 9- to 10-membered. In some embodiments, a heterocycle is 9- to 11-membered. In some embodiments, a heterocycle is 9- to 15-membered.

In some embodiments, the heterocycle is monosubstituted, disubstituted, trisubstituted, tetrasubstituted, or pentasubstituted (e.g., with further substituents in addition to the point of attachment). In some embodiments, the total number of substituents (e.g., atoms other than hydrogen) on the heterocycle (e.g., bonded to the ring of the heterocycle) is 1, 2, 3, 4, 5, 6, 7, 8, 9, 10, or more.

In some embodiments, in the molecule or moiety (e.g., in a heterocycle), one or more nitrogen atoms, if present, can be optionally quaternized. In some embodiments, the heterocycle substituent is positively charged. In some embodiments, the heterocycle moiety is neutral. In some embodiments, the heterocycle substituent is zwitterionic. Alternatively, or in addition, in some embodiments, the heterocycle substituent is not charged. In some embodiments, the heterocycle substituent bears no charges. In some embodiments, the heterocycle substituent bears no net charge. In some embodiments, no atoms within the heterocycle substituent bear any net charge. In some embodiments, the heterocycle substituent bears no net charge and is not zwitterionic. The term "heteroaryl" refers to a moiety derived from an aromatic monocyclic or aromatic polycyclic ring system, in which one or more heteroatom(s) is(are) member(s) of the ring system, and the ring system comprises at least one cyclic, delocalized (4n+2) π-electronic system, wherein n is an integer greater than or equal to 0, in accordance with Hackel theory. In some embodiments, one or more heteroatom(s) is(are) member(s) of the ring system comprising the cyclic, delocalized (4n+2) π-electronic system (e.g., the ring with aromaticity). Exemplary heteroatoms include N, O, Si, P, B, and S atoms. In some embodiments, a heteroaryl comprises an aromatic ring, in which one or more heteroatom(s) is(are) member(s) of the ring system, to which one or more nonaromatic rings, each of which may or may not comprise one or more heteroatom(s), may be fused. In some embodiments, a heteroaryl includes one or more heteroatoms selected from nitrogen, oxygen, and sulfur. In some embodiments, a heteroaryl includes multiple heteroatoms selected from nitrogen, oxygen, and sulfur. In certain embodiments, "heteroaryl" includes rings and ring systems comprising 3 to 20 atoms. In some embodiments, "heteroaryl" includes rings and ring systems that comprise two to seventeen carbon atoms and from one to six heteroatoms selected from nitrogen, oxygen and sulfur. As used herein, the heteroaryl moiety is a monocyclic or polycyclic (e.g., bicyclic, tricyclic or tetracyclic) ring system, wherein at least one of the rings in the ring system is aromatic, e.g., it contains a cyclic, delocalized (4n+2) π-electron system in accordance with the Hückel theory. Heteroaryl includes fused, bridged, and spiro ring systems. The heteroatom(s) in the heteroaryl moiety is(are) optionally oxidized. One or more nitrogen atom(s), if present, is(are) optionally quaternized. The heteroaryl is attached to the rest of the molecule through any atom of the ring(s). Examples of heteroaryls include, but are not limited to, acridinyl, benzimidazolyl, benzindolyl, 1,3-benzodioxolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, oxazolyl, 5,6,6a,7,8,9,10,10a-octahydrobenzo[h]quinazolinyl, 1-phenyl-TH-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (e.g., thienyl). In some embodiments, further examples of "heteroaryl" include 5,6,7,8-tetrahydroquinoline; 1,2,3,4-tetrahydro-1,8-naphthyridine; 6,7-dihydro-5H-cyclopenta[b]pyridine; 2,3-dihydro-1H-pyrrolo[2,3-b]pyridine; 4,5,6,7-tetrahydrobenzofuran; 4,5,6,7-tetrahydrofuro[2,3-b]pyridine; 5,6-dihydro-4H-cyclopenta[b]furan; 4,5-dihydrothieno[2,3-b]furan. In some embodiments, the heteroaryl substituent is positively or negatively charged. In some embodiments, the heteroaryl substituent is neutral. In some embodiments, the heteroaryl substituent is zwitterionic; alternatively, or in addition, in some embodiments, the heteroaryl substituent is not charged. In some embodiments, the heteroaryl substituent bears no charges. In some embodiments, the heteroaryl substituent bears no net charge. In some embodiments, the heteroaryl substituent bears no net charge and is not zwitterionic.

The term "heterocycle" comprises "heteroaryls," "heterocycloalkenyls," and "heterocycloalkyls."

The term "heterocycloalkyl" refers to a moiety comprising a saturated ring (e.g., a ring with only single bonds connecting the members of the ring), wherein the saturated ring comprises carbon atom(s) and one or more heteroatom(s) as member(s) of the saturated ring, and wherein the saturated ring may be optionally fused, bridged with, or spiro to an additional ring, wherein the additional ring may comprise only carbon atoms as members of the additional ring or wherein the additional ring may comprise one or more heteroatom(s) as member(s) of the additional ring. In some embodiments, a heterocycloalkyl may be covalently bound to one or more carbocycle(s) or heterocycle(s). Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, 5- to 12-membered spiro bicycles, or 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 2-oxa-6-azaspiro[3.3]heptane, and 1,1-dioxo-thiomorpholinyl. In some embodiments, a heterocycloalkyl comprises one heteroatom. In some embodiments, a heterocycloalkyl comprises one heteroatom selected from N, O, and S. In some embodiments, a heterocycloalkyl comprises multiple heteroatoms. In some embodiments, a heterocycloalkyl comprises multiple heteroatoms selected from N, O, and S.

The term "heterocycloalkenyl" refers to a moiety comprising an unsaturated ring (e.g., a nng with either single bonds or double bonds connecting the members of the ring): wherein the unsaturated ring comprises carbon atoms and one or more heteroatom(s); wherein the unsaturated ring may be optionally fused, bridged with, or spiro to an additional ring, wherein the additional ring may comprise only carbon atoms as members of the additional ring or wherein the additional ring may comprise one or more heteroatom(s) as member(s) of the additional ring; and wherein there is at least one double bond between two ringcarbon atoms (e.g., carbon atoms that are members of the unsaturated ring). Heterocycloalkenyl does not include heteroaryl rings. Exemplary heteroatoms include N, O, Si, P, B, and S atoms. Heterocycloalkenyl may include monocyclic and polycyclic rings such as 3- to 10-membered monocyclic rings, 6- to 12-membered bicyclic rings, and 5- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine.

A "spirocyclic" moiety (e.g., a "spiro" moiety) (e.g., a spirocyclic heterocycle, a spirocyclic heterocycloalkenyl, a spirocyclic carbocycle, a spirocyclic heterocycloalkyl, a spirocyclic cycloalkenyl, or a spirocyclic cycloalkyl) is a polycyclic system (e.g., bicyclic, tricyclic, tetracyclic) system wherein two rings share exactly one atom. Examples of spirocyclic moieties include, but are not limited to:

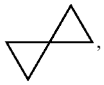, 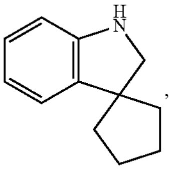, 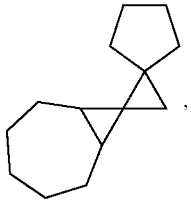,

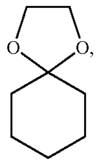 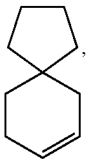, 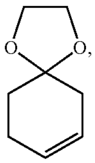 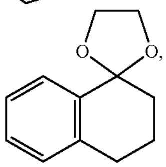

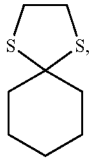 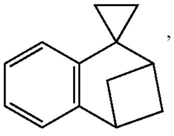, 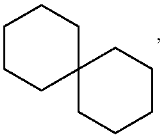,

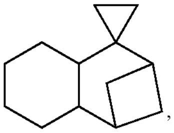, 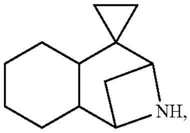 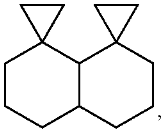,

-continued

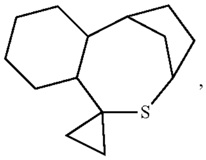, and 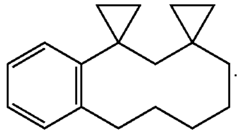.

A spirocyclic heterocycle comprises a spirocyclic moiety that comprises at least one heteroatom in the ring system of the spirocyclic moiety. Examples of spirocyclic heterocycles include, but are not limited to:

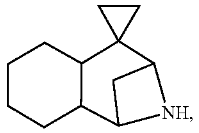 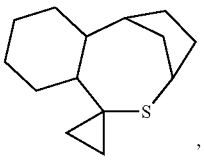, 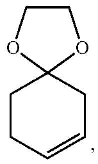,

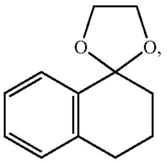 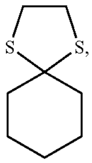 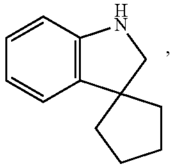, 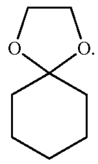

A spirocyclic carbocycle comprises a spirocyclic moiety that comprises only carbon atoms in the ring system of the spirocyclic moiety. Examples of spirocyclic carbocycles include, but are not limited to:

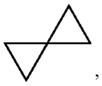, 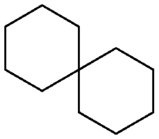 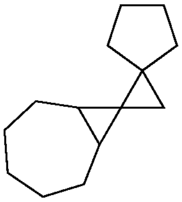,

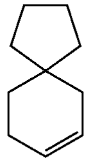, 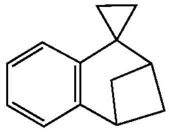, 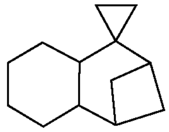,

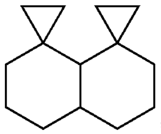, and 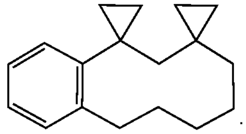.

A "fused" moiety (e.g., a fused heterocycle, a fused carbocycle, a fused heterocycloalkyl, or a fused cycloalkyl) is a polycyclic system (e.g., bicyclic, tricyclic, tetracyclic) wherein two rings share exactly two atoms. Examples of fused moieties include, but are not limited to:

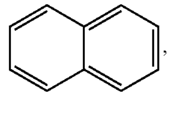, 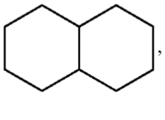, 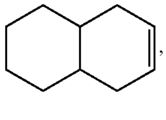,

-continued

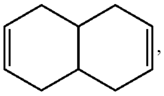,
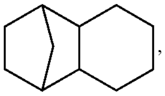,
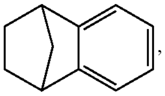,
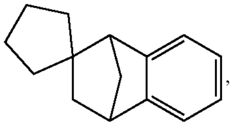,
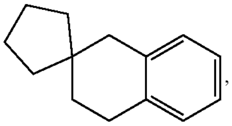,
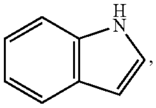,
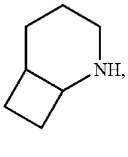,
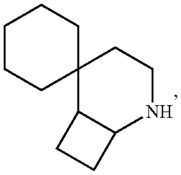,
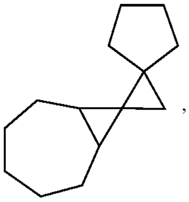,
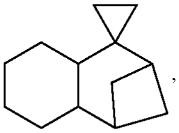,
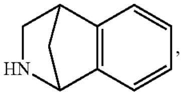, and
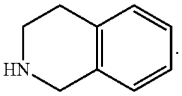.

A "fused" heterocycle comprises a fused moiety that comprises at least one heteroatom in the ring system of the fused moiety. Examples of fused heterocycles include, but are not limited to:

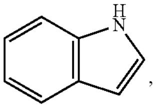,
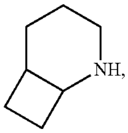,
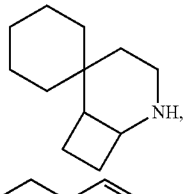,
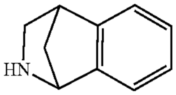, and
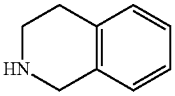.

A "fused" carbocycle comprises a fused moiety that comprises only carbon atoms in the ring system of the fused moiety. Examples of fused carbocycles include, but are not limited to:

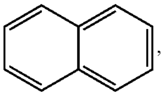,
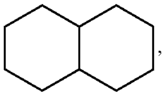,
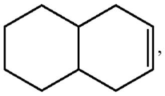,
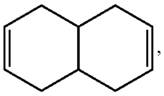,
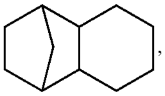,
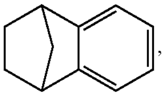,
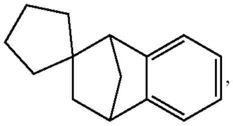,
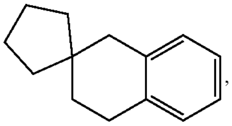, -continued

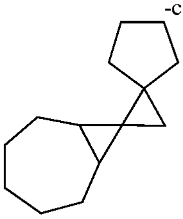, and
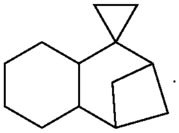.

A "bridged" moiety (e.g., a bridged heterocycle, a bridged carbocycle, a bridged heterocycloalkyl, a bridged heterocycloalkenyl, or a bridged cycloalkyl) is a polycyclic system (e.g., bicyclic, tricyclic, tetracyclic) which comprises two or more bridgeheads, wherein in at least one combination of two bridgeheads, each bridgehead in the combination of two bridgeheads is separated from the other bridgehead in the combination of two bridgeheads by three bridges, each bridge comprising at least one atom, wherein each of the three bridges does not contain any of the same atoms as either of the other two bridges.

In some embodiments, a "bridged" moiety (e.g., a bridged heterocycle, a bridged carbocycle, a bridged heterocycloalkyl, a bridged heterocycloalkenyl, or a bridged cycloalkyl) is a polycyclic system (e.g., bicyclic, tricyclic, tetracyclic) which comprises two or more bridgeheads, wherein in at least one pair of bridgeheads, each bridgehead in the pair is separated from the other bridgehead in the pair by three bridges, each bridge comprising at least one atom, wherein each of the three bridges does not contain any of the same atoms as either of the other two bridges.

In some embodiments, a bridgehead atom is a $sp^3$-hybridized carbon or nitrogen atom that forms a *nexus* between two or more rings. In some embodiments, a bridge comprises one or more atom(s) connecting two bridgehead atoms.

Examples of bridged moieties include, but are not limited to:

bicyclo[1.1.1]pentane),

(bicyclo[2.1.1]hexane), norbomane (  ), norbomene (  ),
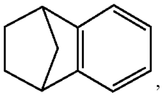,
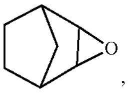,
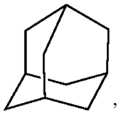, -continued

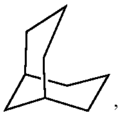, 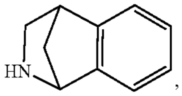, 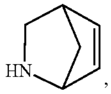,

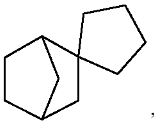, 2-oxa-S-azabicyclo[2.2.1]heptane (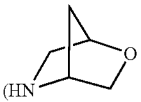), 7-oxabicyclo[2.2.1]heptane (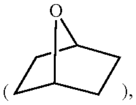), 7-azabicyclo[2.2.1]heptane (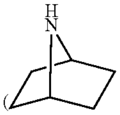), bicyclo[3.1.1]heptane

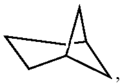, bicyclo[2.2.2]octane, twistane

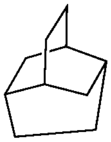, isotwistane

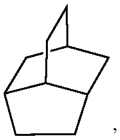, 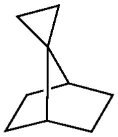

spiro[bicyclo[2.2.1]heptane-7,1'-cyclopropane],

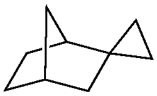

spiro[bicyclo[2.2.1]heptane-2,1'-cyclopropane],

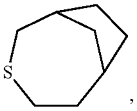, 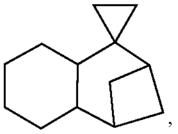, and 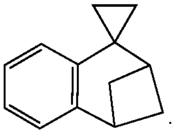.

A “bridged” carbocycle comprises a bridged moiety that comprises only carbon atoms in the ring system of the bridged moiety. Examples of bridged carbocycles include, but are not limited to:

(bicyclo[1.1.1]pentane),

(bicyclo[2.1.1]hexane), norbornane (), norbornene (), 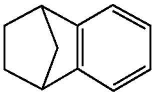 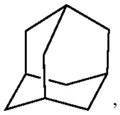,

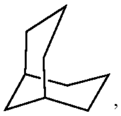, 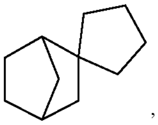, bicyclo[3.1.1]heptane

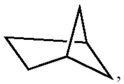, bicyclo[2.2.2]octane, twistane

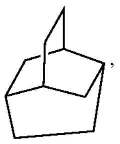

isotwistane

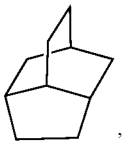

,

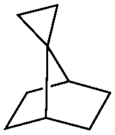

spiro[bicyclo[2.2.1]heptane-7,1'-cyclopropane], and

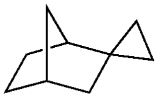

spiro [bicyclo[2.2.1]heptane-2,1'-cyclopropane].

A “bridged” heterocycle comprises a bridged moiety that comprises at least one heteroatom in the ring system of the bridged moiety. Examples of bridged heterocycles include, but are not limited to:

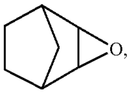

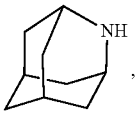

,

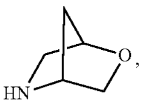

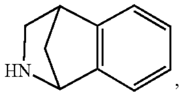

,

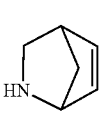

,

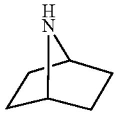

, or

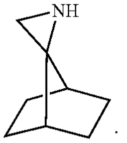

.

The term “substituted” refers to moieties having substituents replacing a hydrogen on one or more carbon atom(s) or substitutable heteroatoms, e.g., an NH or $NH_2$ of a compound. It will be understood that “substitution” or “substituted with” includes the implicit proviso that such substitution is in accordance with permitted valence of the substituted atom and the substituent and further includes the proviso that the substitution results in a stable compound, e.g., a compound which does not rapidly undergo rearrangement, cyclization, elimination, etc. In certain embodiments, substituted refers to moieties having substituents replacing two hydrogen atoms on the same carbon atom, such as substituting the two hydrogen atoms on a single carbon atom with an oxo, imino, oxime, hydrazone, or thioxo group. As used herein, the term “substituted” is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, the term “one or more substituents” may refer to one substituent, or two substituents, or three substituents, or four substituents, or five substituents, or six substituents, or more than six substituents. In some embodiments, the term “one or more substituents” may refer to one substituent. In some embodiments, the term “one or more substituents” may refer to two substituents. In some embodiments, the term “one or more substituents” may refer to three substituents. In some embodiments, the term “one or more substituents” may refer to four substituents. In some embodiments, the term “one or more substituents” may refer to five substituents. In some embodiments, the term “one or more substituents” may refer to more than five substituents. In some embodiments, the term “one or more substituents” may refer to 1 substituent to 10 substituents. In some embodiments, the term “one or more substituents” may refer to at least 1 substituent. In some embodiments, the term “one or more substituents” may refer to at most 10 substituents. In some embodiments, the term “one or more substituents” may refer to at most 5 substituents. In some embodiments, the term “one or more substituents” may refer to at most 2 substituents. In some embodiments, the term “one or more substituents” may refer to 1 substituent to 2 substituents. In some embodiments, the term “one or more substituents” may refer to 1 substituent to 1 substituent. 1 substituent to 3 substituents, 1 substituent to 4 substituents, 1 substituent to 5 substituents, 1 substituent to 6 substituents, 1 substituent to 7 substituents, 1 substituent to 10 substituents, 2 substituents to 3 substituents, 2 substituents to 4 substituents, 2 substituents to 5 substituents, 2 substituents to 6 substituents, 2 substituents to 7 substituents, 2 substituents to 10 substituents, 3 substituents to 4 substituents, 3 substituents to 5 substituents, 3 substituents to 6 substituents, 3 substituents to 7 substituents, 3 substituents to 10 substituents, 4 substituents to 5 substituents, 4 substituents to 6 substituents, 4 substituents to 7 substituents, 4 substituents to 10 substituents, 5 substituents to 6 substituents, 5 substituents to 7 substituents, 5 substituents to 10 substituents, 6 substituents to 7 substituents, 6 substituents to 10 substituents, or 7 substituents to 10 substituents. In some embodiments, the term “one or more substituents” may refer to 1 substituent, 2 substituents, 3 substituents, 4 substituents, 5 substituents, 6 substituents, 7 substituents, or 10 substituents.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2), and —$R^b$—$S(O)_tN(R^a)_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C (O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (═O), thioxo (═S), cyano (—CN), nitro (—$NO_2$), imino (═N—H), oximo (═N—OH), hydrazine (═N—$NH_2$), —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "═S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and/or organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and/or organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is selected from ammonium, potassium, sodium, calcium, and magnesium salts.

As used herein, "treatment" or "treating" refers to an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated. Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not require the involvement of a medical professional.

Chemical entities having carbon-carbon double bonds or carbon-nitrogen double bonds may exist in Z- or E- form (or cis- or trans- form). Furthermore, some chemical entities may exist in various tautomeric forms. Unless otherwise specified, all structures described herein are intended to disclose, implicitly or explicitly, all Z-, E-, and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibria include, but are not limited to:

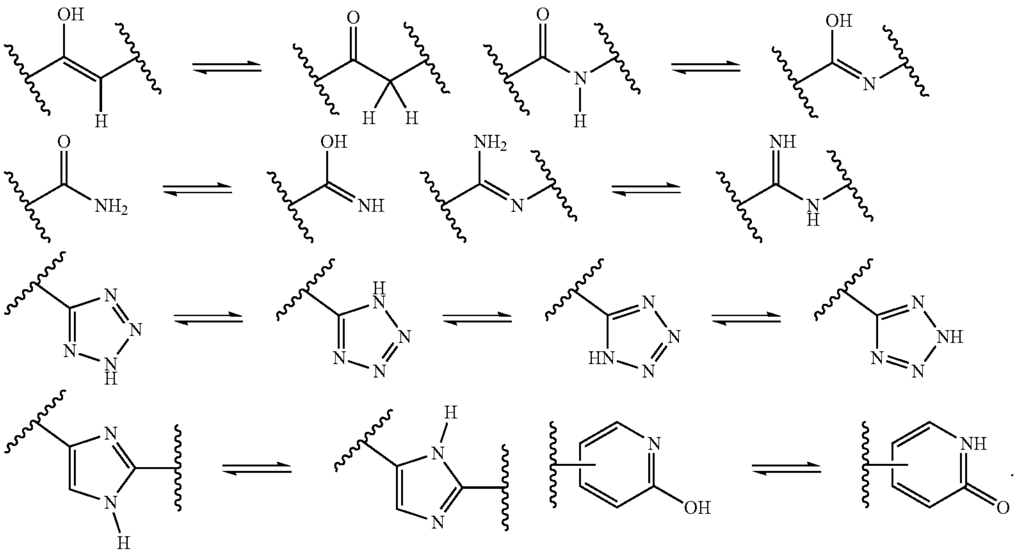

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy of drugs, thus increasing the duration of action of drugs.

Unless otherwise stated, compounds described herein are intended to include compounds which differ only in the presence of one or more isotopically enriched atoms. For example, compounds having the present structures except for the replacement of one or more proton(s) by one or more deuterium(deuteria) or tritium(tritia), or combinations thereof, or except for the replacement of one or more $^{12}C$ atom(s) in the structure by one or more $^{13}C$ atom(s), one or more $^{14}C$ atom(s), or combinations thereof, in the structure are within the scope of the present disclosure.

The compounds of the present disclosure optionally comprise unnatural proportions of atomic isotopes at one or more atom(s) that constitute such compounds. For example, the compounds may be labeled with one or more isotope(s), such as for example, deuterium ($^{2}H$), tritium ($^{3}H$), iodine-125 ($^{125}I$) or carbon-14 ($^{14}C$). Isotopic substitution with $^{2}H$, $^{3}H$, $^{11}C$, $^{13}C$, $^{14}C$, $^{15}C$, $^{12}N$, $^{13}N$, $^{15}N$, $^{16}N$, $^{17}O$, $^{18}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, and $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium-substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as MilliporeSigma.

Included in the present disclosure are salts, particularly pharmaceutically acceptable salts, of the compounds described herein. The compounds of the present disclosure that comprise one or more sufficiently acidic functional group(s), one or more sufficiently basic functional group(s), or both one or more sufficiently acidic functional group(s) and one or more sufficiently basic functional group(s) to form a salt (particularly a pharmaceutically acceptable salt), can react with any of a number of inorganic organic bases or inorganic or organic acids, to form a salt; combinations thereof); or combinations thereof. Alternatively, compounds that are inherently charged, such as those with a quaternary nitrogen, can form a salt with an appropriate counterion.

The compounds and salts described herein may in some cases exist as diastereomers, enantiomers, or other stereoisomeric forms. Unless otherwise specified (e.g., in tables of biological data), the structures disclosed herein are intended to include, explicitly or implicitly, disclosure of all diastereomeric (e.g., epimeric) and enantiomeric forms as well as mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In certain embodiments, the compounds or salts of the compounds may be prodrugs. For example, in some embodiments, a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) may be prodrugs of the present disclosure. In some embodiments, a prodrug for an amine might rely on enzymatic activation. In some embodiments, a prodrug for an amine might rely on physiological chemical conditions for release of the drugs. In some embodiments, a prodrug for an amine may be selected from an amide, a carbonate, an N-acyloxy alkyl derivative, an N-acyloxy carbonyl derivative, a beta-aminoketone, an (oxodioxolenyl)methyl derivative, an N-Mannich base, an imine (e.g., a Schiff base), an enamine, an enaminone, an azo compound, a system capable of undergoing lactonization, a tetrahydrothiadiazine-2-thione, a redox system, or a PEG.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.,* 269:G210-218 (1995); McLoed et al., *Gastroenterol,* 106: 405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al., *J. Pharm. Sci.,* 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Compounds

The following comprises a discussion of compounds and salts thereof that may be used in the methods of the disclosure. In certain embodiments, the compounds and salts are described in Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), and Formula (IIIa-ep)

In one aspect, disclosed herein is a compound represented by Formula (Ia):

(Ia)

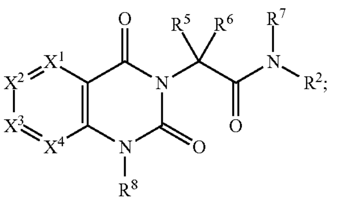

or a salt thereof, wherein: $R^2$ is selected from:

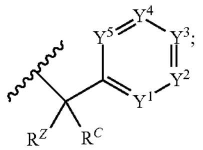

$X^1$ is selected from $C(R^{1a})$, N, and $N^+(—O^-)$;
$X^2$ is selected from $C(R^{1b})$, N, and $N^+(—O^-)$;
$X^3$ is selected from $C(R^{1c})$, N, and $N^+(—O^-)$;
$X^4$ is selected from $C(R^{1d})$, N, and $N^+(—O^-)$;
wherein no more than two of $X^1$, $X^2$, $X^3$, and $X^4$ are N or $N^+(—O^-)$;
$Y^1$ is selected from $C(R^{9bA})$, N, and $N^+(—O^-)$;
$Y^2$ is selected from $C(R^{9bB})$, N, and $N^+(—O^-)$;
$Y^3$ is selected from $C(R^{9bC})$, N, and $N^+(—O^-)$;
$Y^4$ is selected from $C(R^{9bD})$, N, and $N^+(—O^-)$;
$Y^5$ is selected from $C(R^{9bE})$, N, and $N^+(—O^-)$;
wherein at least one of $Y^1$, $Y^2$, $Y^3$, $Y^4$, and $Y^5$ is N or $N^+(—O^-)$;
wherein no more than three of $Y^1$, $Y^2$, $Y^3$, $Y^4$, and $Y^5$ are N or $N^+(—O^-)$;
$R^{1a}$, $R^{1b}$, $R^{1c}$, and $R^{1d}$, are each independently selected from:
hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;
$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$;

$R^Z$ is selected from:

—CN, —$C(O)R^{10z}$, —$C(O)N(R^{10z})_2$, and —$C(O)OR^{10z}$;

$C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9z}$;

$R^C$ is selected from:

hydrogen; —CN, —$C(O)R^{10c}$, —$C(O)N(R^{10c})_2$, —$C(O)OR^{10c}$;

$C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9c}$; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{90}$; or $R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9c}$;

$R^5$ is selected from:

hydrogen;

halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, —$N_3$, and —CN;

$C_{1-6}$ alkyl, $C_{2-6}$ alkenyl, and $C_{2-6}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, =O, =S, =$N(R^{10d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)$Rod, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10a}$, —$NO_2$, =O, =S, =$N(R^{10d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9d}$; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9d}$;

$R^6$ is selected from:

hydrogen;

halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, —$N_3$, and —CN;

$C_{1-6}$ alkyl, $C_{2-6}$ alkenyl, and $C_{2-6}$ alkynyl, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, =O, =S, =$N(R^{10e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9e}$; and $C_{3-10}$ carbocycle and 3- to 10-membered heterocycle, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$N(R^{10e})C(O)N(R^{10e})_2$, —$OC(O)N(R^{10e})_2$, —$N(R^{10e})C(O)OR^{10e}$, —$C(O)OR^{10e}$, —$OC(O)R^{10e}$, —$S(O)R^{10e}$, —$S(O)_2R^{10e}$, —$NO_2$, =O, =S, =$N(R^{10e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9e}$; or $R^6$ together with $R^5$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9e}$;

$R^7$ is selected from:

hydrogen; —$C(O)R^{10f}$, —$C(O)N(R^{10f})_2$, —$C(O)OR^{10f}$, —$S(O)R^{10f}$, and —$S(O)_2R^{10f}$;

$C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{f}$, —$S(O)R^{10f}$, —$S(O)_2R^{f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$;

$R^8$ is selected from:

hydrogen; —$C(O)R^{10g}$, —$C(O)N(R^{10g})_2$, —$C(O)OR^{10g}$, —$S(O)R^{10g}$, and —$S(O)_2R^{10g}$;

$C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =O, =S, =$N(R^{10g})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9g}$; and $C_{3-10}$ carbocycle and 3- to 10-membered heterocycle, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9g}$;

each $R^{9a}$ is independently selected from:

halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, and —CN;

$R^{9bA}$, $R^{9bB}$, $R^{9bC}$, $R^{9bD}$, and $R^{9bE}$ are each independently selected from:

hydrogen; halogen, —$NO_2$, —$N_3$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —$N_3$, —CN, $C_{1-6}$ alkyl, $C_{2-6}$ alkenyl, and $C_{2-6}$ alkynyl;

each $R^{9z}$ is independently selected from:

halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C (O)N($R^{10c}$)$_2$, —OC(O)N($R^{10c}$)$_2$, —N($R^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N($R^{10c}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —OR$^{10c}$, —SR$^{10c}$, —N($R^{10c}$)$_2$, —C(O)R$^{10c}$, —C(O)N($R^{10c}$)$_2$, —N($R^{10c}$)C(O)R$^{10c}$, —N($R^{10c}$)C(O)N($R^{10c}$)$_2$, —OC(O)N($R^{10c}$)$_2$, —N($R^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N($R^{10c}$), —N$_3$, and —CN;

each $R^{9d}$ is independently selected from:

halogen, —OR$^{10d}$, —SR$^{10d}$, —N($R^{10d}$)$_2$, —C(O)R$^{10d}$, —C(O)N($R^{10d}$)$_2$, —N($R^{10d}$)C(O)R$^{10d}$, —N($R^{10d}$)C(O)N($R^{10d}$)$_2$, —OC(O)N($R^{10d}$)$_2$, —N($R^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, =O, =S, =N($R^{10d}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —OR$^{10d}$, —SR$^{10d}$, —N($R^{10d}$)$_2$, —C(O)R$^{10d}$, —C(O)N($R^{10d}$)$_2$, —N($R^{10d}$)C(O)R$^{10d}$, —N($R^{10d}$)C(O)N($R^{10d}$)$_2$, —OC(O)N($R^{10d}$)$_2$, —N($R^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, =O, =S, =N($R^{10d}$), —N$_3$, and —CN;

each $R^{9e}$ is independently selected from:

halogen, —OR$^{10e}$, —SR$^{10e}$, —N($R^{10e}$)$_2$, —C(O)R$^{10e}$, —C(O)N($R^{10e}$)$_2$, —N($R^{10e}$)C(O)R$^{10e}$, —N($R^{10e}$)C(O)N($R^{10e}$)$_2$, —OC(O)N($R^{10e}$)$_2$, —N($R^{10e}$)C(O)OR$^{10e}$, —C(O)OR$^{10e}$, —OC(O)R$^{10e}$, —S(O)R$^{10e}$, —S(O)$_2$R$^{10e}$, —NO$_2$, =O, =S, =N($R^{10e}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —OR$^{10e}$, —SR$^{10e}$, —N($R^{10e}$)$_2$, —C(O)R$^{10e}$, —C(O)N($R^{10e}$)$_2$, —N($R^{10e}$)C(O)R$^{10e}$, —N($R^{10e}$)C(O)N($R^{10e}$)$_2$, —OC(O)N($R^{10e}$)$_2$, —N($R^{10e}$)C(O)OR$^{10e}$, —C(O)OR$^{10e}$, —OC(O)R$^{10e}$, —S(O)R$^{10e}$, —S(O)$_2$R$^{10e}$, —NO$_2$, =O, =S, =N($R^{10e}$), —N$_3$, and —CN;

each $R^{9f}$ is independently selected from:

halogen, —OR$^{10f}$, —SR$^{10f}$, —N($R^{10f}$)$_2$, —C(O)R$^{10f}$, —C(O)N($R^{10f}$)$_2$, —N($R^{10f}$)C(O)R$^{10f}$, —N($R^{10f}$)C(O)N($R^{10f}$)$_2$, —OC(O)N($R^{10f}$)$_2$, —N($R^{10f}$)C(O)OR$^{10f}$, —C(O)OR$^{10f}$, —OC(O)R$^{10f}$, —S(O)R$^{10f}$, —S(O)$_2$R$^{10f}$, —NO$_2$, =O, =S, =N($R^{10f}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —OR$^{10f}$, —SR$^{10f}$, —N($R^{10f}$)$_2$, —C(O)R$^{10f}$, —C(O)N($R^{10f}$)$_2$, —N($R^{10f}$)C(O)R$^{10f}$, —N($R^{10f}$)C(O)N($R^{10f}$)$_2$, —OC(O)N($R^{10f}$)$_2$, —N($R^{10f}$)C(O)OR$^{10f}$, —C(O)OR$^{10f}$, —OC(O)R$^{10f}$, —S(O)R$^{10f}$, —S(O)$_2$R$^{10f}$, —NO$_2$, =O, =S, =N($R^{10f}$), —N$_3$, and —CN;

each $R^{9g}$ is independently selected from:

halogen, —OR$^{10g}$, —SR$^{10g}$, —N($R^{10g}$)$_2$, —C(O)R$^{10g}$, —C(O)N($R^{10g}$)$_2$, —N($R^{10g}$)C(O)R$^{10g}$, —N($R^{10g}$)C(O)N($R^{10g}$)$_2$, —OC(O)N($R^{10g}$)$_2$, —N($R^{10g}$)C(O)OR$^{10g}$, —C(O)OR$^{10g}$, —OC(O)R$^{10g}$, —S(O)R$^{10g}$, —S(O)$_2$R$^{10g}$, —NO$_2$, =O, =S, =N($R^{10g}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —OR$^{10g}$, —SR$^{10g}$, —N($R^{10g}$)$_2$, —C(O)R$^{10g}$, —C(O)N($R^{10g}$)$_2$, —N($R^{10g}$)C(O)R$^{10g}$, —N($R^{10g}$)C(O)N($R^{10g}$)$_2$, —OC(O)N($R^{10g}$)$_2$, —N($R^{10g}$)C(O)OR$^{10g}$, —C(O)OR$^{10g}$, —OC(O)R$^{10g}$, —S(O)R$^{10g}$, —S(O)$_2$R$^{10g}$, —NO$_2$, =O, =S, =N($R^{10g}$), —N$_3$, and —CN; and each $R^{10a}$, $R^{10b}$, $R^{10z}$, $R^{10c}$, $R^{10d}$, $R^{10e}$, $R^{10f}$, and $R^{10g}$ is independently selected from:

hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —NO$_2$, —NH$_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl;

wherein when $Y^1$ is N or N$^+$(—O$^-$), $Y^2$ is C(H), $Y^3$ is C(H), $Y^4$ is C(H), and $Y^5$ is C(H); then $R^7$ is selected from:

hydrogen; —C(O)R$^{10f}$, —C(O)N($R^{10f}$)$_2$, —C(O)OR$^{10f}$, —S(O)R$^{10f}$, and —S(O)$_2$R$^{10f}$;

$C_1$ alkyl substituted with one or more substituents independently selected from halogen, —OR$^{10f}$, —SR$^{10f}$, —N($R^{10f}$)$_2$, —C(O)R$^{10f}$, —C(O)N($R^{10f}$)$_2$, —N($R^{10f}$)C(O)R$^{10f}$, —C(O)OR$^{10f}$, —OC(O)R$^{10f}$, —N($R^{10f}$)C(O)N($R^{10f}$)$_2$, —OC(O)N($R^{10f}$)$_2$, —N($R^{10f}$)C(O)OR$^{10f}$, —S(O)R$^{10f}$, —S(O)$_2$R$^{10f}$, —NO$_2$, =O, =S, =N($R^{10f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$;

$C_{2-6}$ alkyl optionally substituted with one or more substituents independently selected from halogen, —OR$^{10f}$, —SR$^{10f}$, —N($R^{10f}$)$_2$, —C(O)R$^{10f}$, —C(O)N($R^{10f}$)$_2$, —N($R^{10f}$)C(O)R$^{10f}$, —C(O)OR$^{10f}$, —OC(O)R$^{10f}$, —N($R^{10f}$)C(O)N($R^{10f}$)$_2$, —OC(O)N($R^{10f}$)$_2$, —N($R^{10f}$)C(O)OR$^{10f}$, —S(O)R$^{10f}$, —S(O)$_2$R$^{10f}$, —NO$_2$, =O, =S, =N($R^{10f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, —OR$^{10f}$, —SR$^{10f}$, —N($R^{10f}$)$_2$, —C(O)R$^{10f}$, —C(O)N($R^{10f}$)$_2$, —N($R^{10f}$)C(O)R$^{10f}$, —N($R^{10f}$)C(O)N($R^{10f}$)$_2$, —OC(O)N($R^{10f}$)$_2$, —N($R^{10f}$)C(O)OR$^{10f}$, —C(O)OR$^{10f}$, —OC(O)R$^{10f}$, —S(O)R$^{10f}$, —S(O)$_2$R$^{10f}$, —NO$_2$, =O, =S, =N($R^{10f}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$;

wherein when $Y^1$ is C(H), $Y^2$ is C(H), $Y^3$ is C(H), $Y^4$ is C(H), and $Y^5$ is N or $N^+(—O^-)$; then $R^7$ is selected from:

hydrogen; $—C(O)R^{10f}$, $—C(O)N(R^{10f})_2$, $—C(O)OR^{10f}$, $—S(O)R^{10f}$, and $—S(O)_2R^{10f}$;

$C_1$ alkyl substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$;

$C_{2-6}$ alkyl optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—N(R^{10f})C(O)N(R^{10f})_2$, $—OC(O)N(R^{10f})_2$, $—N(R^{10f})C(O)OR^{10f}$, $—C(O)OR^{10f}$, $—OC(O)R^{10f}$, $—S(O)R^{10f}$, $—S(O)_2R^{10f}$, $—NO_2$, =O, =S, $=N(R^{10f})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$;

wherein when $Y^1$ is C(H), $Y^2$ is C(H), $Y^3$ is N or $N^+(—O^-)$, $Y^4$ is C(H), and $Y^5$ is C(H); then $R^C$ is selected from:

hydrogen; —CN, $—C(O)R^{10c}$, $—C(O)N(R^{10c})_2$, $—C(O)OR^{10c}$;

$C_{1-6}$ alkyl, $C_{2-6}$ alkenyl, and $C_{2-6}$ alkynyl, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—C(O)OR^{10c}$, $—OC(O)R^{10c}$, $—N(R^{10c})C(O)N(R^{10c})_2$, $—OC(O)N(R^{10c})_2$, $—N(R^{10c})C(O)OR^{10c}$, $—S(O)R^{10c}$, $—S(O)_2R^{10c}$, $—NO_2$, =O, =S, $=N(R^{10c})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9c}$; and $C_{3-10}$ cycloalkyl and 3- to 10-membered heterocycle, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, $—S(O)R^{10c}$, $—S(O)_2R^{10c}$, $—NO_2$, =O, =S, $=N(R^{10c})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9c}$; and wherein when $Y^1$ is C(H), $Y^2$ is C(H), $Y^3$ is N or $N^+(—O^-)$, $Y^4$ is C(H), and $Y^5$ is C(H); then $R^7$ is selected from:

hydrogen; $—C(O)R^{10f}$, $—C(O)N(R^{10f})_2$, $—C(O)OR^{10f}$, $—S(O)R^{10f}$, and $—S(O)_2R^{10f}$;

$C_1$ alkyl substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$;

$C_{2-6}$ alkyl, $C_{2-6}$ alkenyl, and $C_{2-6}$ alkynyl, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—N(R^{10f})C(O)N(R^{10f})_2$, $—OC(O)N(R^{10f})_2$, $—N(R^{10f})C(O)OR^{10f}$, $—C(O)OR^{10f}$, $—OC(O)R^{10f}$, $—S(O)R^{10f}$, $—S(O)_2R^{10f}$, $—NO_2$, =O, =S, $=N(R^{10f})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$.

In one aspect, disclosed herein is a compound of Formula (Ia) that is represented by Formula (Ia-ep):

(Ia-ep)

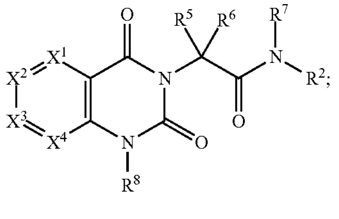

or a salt thereof, wherein: $R^2$ is selected from:

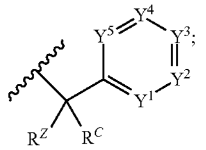

$X^1$ is selected from $C(R^{1a})$ and N; $X^2$ is selected from $C(R^{1b})$ and N; $X^3$ is selected from $C(R^{1c})$ and N; $X^4$ is selected from $C(R^{1d})$ and N; wherein no more than two of $X^1$, $X^2$, $X^3$, and $X^4$ are N; $Y^1$ is selected from $C(R^{9bA})$ and N; $Y^2$ is selected from $C(R^{9bB})$ and N; $Y^3$ is selected from $C(R^{9bC})$ and N; $Y^4$ is selected from $C(R^{9bD})$ and N; $Y^5$ is selected from $C(R^{9bE})$ and N; wherein at least one of $Y^1$, $Y^2$, $Y^3$, $Y^4$, and $Y^5$ is N; wherein no more than two of $Y^1$, $Y^2$, $Y^3$, $Y^4$, and $Y^5$ are N; $R^{1a}$, $R^{1b}$, $R^{1c}$, and $R^{1d}$, are each independently selected from: hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{1-6}$ haloalkyl, and $C_{1-6}$ alkyl; $R^Z$ is selected from: $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; $R^C$ is selected from: hydrogen; $R^5$ and $R^6$ are each independently selected from: hydrogen; halogen; and $C_{1-6}$ alkyl, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; or $R^5$ together with $R^6$ form a $C_{3-10}$ carbocycle or 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; $R^7$ is selected from: hydrogen; $R^8$ is selected from: hydrogen; and $R^{9bA}$, $R^{9b}$B $R^{9bC}$, $R^{9bD}$, and $R^{9bE}$ are each independently selected from: hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$.

In some embodiments, for a compound or salt of Formula (Ia), no more than three of $X^1$, $X^2$, $X^3$, and $X^4$ are C(H). In some embodiments, no more than three of $X^1$, $X^2$, and $X^3$, are C(H). In some embodiments, no more than three of $X^1$, $X^2$, and $X^4$, are C(H). In some embodiments, no more than three of $X^2$, $X^3$, and $X^4$, are C(H). In some embodiments, $X^1$ and $X^2$ are not C(H). In some embodiments, $X^3$ and $X^4$ are C(H).

In some embodiments, for a compound or salt of Formula (Ia), no more than one of $X^1$, $X^2$, $X^3$, and $X^4$ is N. In some embodiments, wherein no more than two of $Y^1$, $Y^2$, $Y^3$, $Y^4$, and $Y^5$ are N. In some embodiments, no more than one of $Y^1$, $Y^2$, $Y^3$, $Y^4$, and $Y^5$ are N. In some embodiments, at least two of $Y^1$, $Y^2$, $Y^3$, $Y^4$, and $Y^5$ are N. In some embodiments, no more than one of $X^1$, $X^2$, $X^3$, and $X^4$ is N or $N^+$(—$O^-$). In some embodiments, no more than two of $Y^1$, $Y^2$, $Y^3$, $Y^4$, and $Y^5$ are N or $N^+$(—$O^-$). In some embodiments, no more than one of $Y^1$, $Y^2$, $Y^3$, $Y^4$, and $Y^5$ are N or $N^+$(—$O^-$). In some embodiments, at least two of $Y^1$, $Y^2$, $Y^3$, $Y^4$, and $Y^5$ are N or $N^+$(—$O^-$). In some embodiments, at least three of $Y^1$, $Y^2$, $Y^3$, $Y^4$, and $Y^5$ are N or $N^+$(—$O^-$). In some embodiments, no more than three of $X^1$, $X^2$, $X^3$, and $X^4$ is N or $N^+$(—$O^-$). In some embodiments, no more than three of $Y^1$, $Y^2$, $Y^3$, $Y^4$, and $Y^5$ are N or $N^+$(—$O^-$). In some embodiments, no more than three of $Y^1$, $Y^2$, $Y^3Y^4$, and $Y^5$ are N or $N^+$(—$O^-$). In some embodiments, for a compound or salt of Formula (Ia), $X^1$ is selected from $C(R^{1a})$ and N. In some embodiments, $X^1$ is selected from $C(R^{1a})$. In some embodiments, $X^1$ is selected from C(H), C(F), C(CN), and $C(CH_3)$. In some embodiments, $X^1$ is selected from C(CN), C(H) and C(F). In some embodiments, $X^1$ is selected from C(H) and C(F). In some embodiments, $X^1$ is selected from C(H) and C(F). In some embodiments, $X^1$ is selected from C(H). In some embodiments, $X^1$ is selected from C(F).

In some embodiments, for a compound or salt of Formula (Ia), $X^2$ is selected from $C(R^{1b})$ and N. In some embodiments, $X^2$ is selected from N, C(H), C(F), and C(CN). In some embodiments, $X^2$ is selected from C(H) and C(F). In some embodiments, $X^2$ is selected from C(H). In some embodiments, $X^2$ is selected from C(F). In some embodiments, for a compound or salt of Formula (Ia), $X^3$ is selected from $C(R^{1c})$ and N. In some embodiments, $X^3$ is selected from $C(R^{1c})$. In some embodiments, $X^3$ is selected from C(H). In some embodiments, for a compound or salt of Formula (Ia), $X^4$ is selected from $C(R^{1d})$ and N. In some embodiments, $X^4$ is selected from $C(R^{1d})$. In some embodiments, $X^4$ is selected from C(H). In some embodiments, for a compound or salt of Formula (Ia), $X^3$ and $X^4$ are C(H). In some embodiments, $X^1$ is C(H), and $X^2$ is C(F); or $X^1$ is C(F), and $X^2$ is C(F); or $X^1$ is C(H), and $X^2$ is C(H); or $X^1$ is C(H), and $X^2$ is C(CN); or $X^1$ is $C(CH_3)$, and $X^2$ is N.

In some embodiments, for a compound or salt of Formula (Ia), $R^{1a}$, $R^{1b}$, $R^{1c}$, and $R^{1d}$, are each independently selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —C(O)OR$^{10a}$, —OC(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —S(O)R$^{10a}$, —S(O)$_2$R$^{10a}$, —NO$_2$, =O, =S, =N(R$^{10a}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$; and C$_{3-10}$ carbocycle and 3- to 10-membered heterocycle, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —S(O)R$^{10a}$, —S(O)$_2$R$^{10a}$, —NO$_2$, =O, —N$_3$, —CN, and C$_{1-6}$ alkyl. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; C$_{1-6}$ alkyl, C$_{2-6}$ alkenyl, and C$_{2-6}$ alkynyl, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —S(O)R$^{10a}$, —S(O)$_2$R$^{10a}$, —NO$_2$, =O, =S, =N(R$^{10a}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$; and C$_{3-10}$ carbocycle and 3- to 10-membered heterocycle, each of which is optionally substituted with one or more substituents independently selected from halogen, —CN, and C$_{1-6}$ alkyl. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; C$_{1-6}$ alkyl, C$_{2-6}$ alkenyl, and C$_{2-6}$ alkynyl, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —S(O)R$^{10a}$, —S(O)$_2$R$^{10a}$, —NO$_2$, =O, =S, =N(R$^{10a}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$; and C$_{3-10}$ carbocycle and 3- to 10-membered heterocycle. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; and C$_{1-6}$ alkyl, C$_{2-6}$ alkenyl, and C$_{2-6}$ alkynyl, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —S(O)R$^{10a}$, —S(O)$_2$R$^{10a}$, —NO$_2$, =O, =S, =N(R$^{10a}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; and C$_{1-6}$ alkyl, C$_{2-6}$ alkenyl, and C$_{2-6}$ alkynyl, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —S(O)R$^{10a}$, —S(O)$_2$R$^{10a}$, —NO$_2$, =O, =S, =N(R$^{10a}$), —N$_3$, —CN, C$_{3-10}$ carbocycle and 3- to 10-membered heterocycle. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; and C$_{1-6}$ alkyl, C$_{2-6}$ alkenyl, and C$_{2-6}$ alkynyl, each of which is optionally substituted with one or more substituents independently selected from halogen, —OR$^{10a}$, —SR$^{10a}$, —N(R$^{10a}$)$_2$, —NO$_2$, =O, —N$_3$, —CN, C$_{3-10}$ carbocycle and 3- to 10-membered heterocycle. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; and C$_{1-6}$ alkyl optionally substituted with one or more substituents independently selected from halogen, —OR$^{10a}$, —SR$^{10a}$, —N(R$^{10a}$)$_2$, —NO$_2$, =O, —N$_3$, —CN, C$_{3-10}$ carbocycle and 3- to 10-membered heterocycle. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; and C$_{1-6}$ alkyl optionally substituted with one or more substituents independently selected from halogen, —OR$^{10a}$, —SR$^{10a}$, —N(R$^{10a}$)$_2$, —NO$_2$, =O, —N$_3$, and —CN. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —S(O)R$^{10a}$, and —S(O)$_2$R$^{10a}$; and C$_{1-6}$ alkyl optionally substituted with one or more substituents independently selected from halogen, —OR$^{10a}$, —SR$^{10a}$, —N(R$^{10a}$)$_2$, —NO$_2$, =O, —N$_3$, and —CN. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, and —OC(O)R$^{10a}$; and C$_{1-6}$ alkyl optionally substituted with one or more substituents independently selected from halogen, —OR$^{10a}$, —SR$^{10a}$, —N(R$^{10a}$)$_2$, —NO$_2$, =O, —N$_3$, and —CN. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, and —N(R$^{10a}$)$_2$; C$_{1-6}$ alkyl optionally substituted with one or more substituents independently selected from halogen, —OR$^{10a}$, —SR$^{10a}$, —N(R$^{10a}$)$_2$, —NO$_2$, =O, —N$_3$, and —CN. In some embodiments, R$^{1a}$, R$^{1b}$, R$^{1c}$, and R$^{1d}$, are each independently selected from: hydrogen; halogen, —NO$_2$, —N$_3$, —CN, —OR$^{10a}$, —SR$^{10a}$, and —N(R$^{10a}$)$_2$; and C$_{1-6}$ alkyl optionally substituted with one or more substituents independently selected from halogen, =O, —$N_3$, and —CN. In some embodiments, $R^{1a}$, $R^{1b}$, $R^{1c}$, and $R^{1d}$, are each independently selected from: hydrogen; halogen, —$NO_2$, —$N_3$, —CN, —$OR^{10a}$, —$SR^{10a}$, and —$N(R^{10a})_2$; and $C_{1-6}$ alkyl optionally substituted with one or more substituents independently selected from halogen and —CN. In some embodiments, $R^{1a}$, $R^{1b}$, $R^{1c}$, and $R^{1d}$, are each independently selected from: hydrogen; halogen, —$NO_2$, —$N_3$, —CN, —$OR^{10a}$, —$SR^{10a}$, and —$N(R^{10a})_2$; and $C_{1-6}$ alkyl optionally substituted with one or more substituents independently selected from fluoro and —CN. In some embodiments, $R^{1a}$, $R^{1b}R^{1c}$, and $R^{1d}$, are each independently selected from: hydrogen; halogen, —$NO_2$, —$N_3$, and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; halogen and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; fluoro, chloro and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; fluoro and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen, fluoro, —CN, and $C_{1-6}$ alkyl. In some embodiments, $R^{1a}$, $R^{1b}$, $R^{1c}$, and $R^{1d}$, are each independently selected from: hydrogen, fluoro, —CN, and $C_{1-3}$ alkyl. In some embodiments, $R^{1a}$, $R^{1b}$, $R^{1c}$, and $R^{1d}$, are each independently selected from: hydrogen, fluoro, —CN, and $C_1$ alkyl. In some embodiments, $R^{1a}$, $R^{1b}$, $R^{1c}$, and $R^{1d}$, are each independently selected from: hydrogen, fluoro, and —CN. In some embodiments, $R^{1a}$, $R^{1b}$, $R^{1c}$, and $R^{1d}$, are each independently selected from: hydrogen and fluoro. In some embodiments, $R^{1a}$, $R^{1b}$, $R^{1c}$, and $R^{1d}$, are each independently selected from: hydrogen.

In some embodiments, for a compound or salt of Formula (Ia), $R^{1a}$ is selected from: hydrogen, fluoro, —CN, and $C_1$ alkyl. In some embodiments, $R^{1a}$ is selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$S(O)R^{10a}$, —$S(O)_2R^{10a}$, —$NO_2$, =O, —$N_3$, —CN, and $C_{1-6}$ alkyl. In some embodiments, $R^{1a}$ is selected from: hydrogen, fluoro, and —CN. In some embodiments, $R^{1a}$ is selected from: hydrogen and fluoro. In some embodiments, $R^{1a}$ is selected from: hydrogen. In some embodiments, $R^{1a}$ is selected from: fluoro.

In some embodiments, for a compound or salt of Formula (Ia), $R^{1b}$ is selected from: hydrogen, fluoro, —CN, and $C_1$ alkyl. In some embodiments, $R^{1b}$ is selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$S(O)R^{10a}$, —$S(O)_2R^{10a}$, —$NO_2$, =O, —$N_3$, —CN, and $C_{1-6}$ alkyl. In some embodiments, $R^{1b}$ is selected from: hydrogen, fluoro, and —CN. In some embodiments, $R^{1b}$ is selected from: hydrogen and fluoro. In some embodiments, $R^{1b}$ is selected from: hydrogen. In some embodiments, $R^{1b}$ is selected from: fluoro.

In some embodiments, for a compound or salt of Formula (Ia), $R^{1c}$ is selected from: hydrogen, fluoro, —CN, and $C_1$ alkyl. In some embodiments, $R^{1c}$ is selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$S(O)R^{10a}$, —$S(O)_2R^{10a}$, —$NO_2$, =O, —$N_3$, —CN, and $C_{1-6}$ alkyl. In some embodiments, $R^{1c}$ is selected from: hydrogen, fluoro, and —CN. In some embodiments, $R^{1c}$ is selected from: hydrogen and fluoro. In some embodiments, $R^{1c}$ is selected from: hydrogen. In some embodiments, $R^{1c}$ is selected from: fluoro.

In some embodiments, for a compound or salt of Formula (Ia), $R^{1d}$ is selected from: hydrogen, fluoro, —CN, and $C_1$ alkyl. In some embodiments, $R^{1d}$ is selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —C(O)

$N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$S(O)R^{10a}$, —$S(O)_2R^{10a}$, —$NO_2$, =O, —$N_3$, —CN, and $C_{1-6}$ alkyl. In some embodiments, $R^{1d}$ is selected from: hydrogen, fluoro, and —CN. In some embodiments, $R^{1d}$ is selected from: hydrogen and fluoro. In some embodiments, $R^{1d}$ is selected from: hydrogen. In some embodiments, $R^{1d}$ is selected from: fluoro.

In some embodiments, for a compound or salt of Formula (Ia), $R^Z$ is selected from: —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, —CN, and $C_{1-6}$ alkyl. In some embodiments, $R^Z$ is selected from: —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$N_3$, —CN, and $C_{1-6}$ alkyl. In some embodiments, $R^Z$ is selected from: —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen and —CN. In some embodiments, $R^Z$ is selected from: —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle. In some embodiments, $R^Z$ is selected from: —CN, —$C(O)R^{10z}$, —$C(O)N(R^{10z})_2$, and —$C(O)OR^{10z}$; and $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$. In some embodiments, $R^Z$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$In some embodiments, $R^Z$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, —$N_3$, —CN, $C_{3-10}$ carbocycle and 3- to 10-membered heterocycle. In some embodiments, $R^Z$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$=0, —$N_3$, —CN, $C_{3-10}$ carbocycle and 3- to 10-membered heterocycle. In some embodiments, $R^Z$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, =O, —$N_3$, —CN. In some embodiments, $R^Z$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, =O, —$N_3$, —CN.

In some embodiments, $R^Z$ is selected from $C_{1-6}$ alkyl optionally substituted with one or more substituents independently selected from halogen, —$OR^{10z}$, —$SR^{10z}$, —$N(R^{10z})_2$, =O, —$N_3$, —CN. In some embodiments, $R^Z$ is selected from $C_{1-6}$ alkyl optionally substituted with one or more substituents independently selected from halogen, —$OR^{10z}$, and —CN. In some embodiments, $R^Z$ is selected from $C_{1-6}$ alkyl optionally substituted with one or more substituents independently selected from fluoro, —$OR^{10z}$, and —CN. In some embodiments, $R^Z$ is selected from $C_{1-6}$ alkyl optionally substituted with one or more substituents independently selected from fluoro and —CN. In some embodiments, $R^Z$ is selected from $C_{1-6}$ alkyl optionally substituted with one or more substituents independently selected from fluoro. In some embodiments, $R^Z$ is selected from $C_{1-6}$ alkyl. In some embodiments, $R^Z$ is selected from $C_{1-3}$ alkyl. In some embodiments, $R^Z$ is selected from $C_{1-2}$ alkyl. In some embodiments, $R^Z$ is selected from $C_1$ alkyl. In some embodiments, $R^Z$ is selected from hydrogen. In some embodiments, $R^Z$ is not selected from hydrogen. In some embodiments, $R^Z$ is selected from —$CF_3$. In some embodiments, $R^Z$ is selected from —$CH_2OH$. In some embodiments, $R^Z$ is selected from halogen. In some embodiments, $R^Z$ is selected from fluorine.

In some embodiments, for a compound or salt of Formula (Ia), $R^C$ is selected from: hydrogen; —CN, —$C(O)R^{10c}$, —$C(O)N(R^{10c})_2$, —$C(O)OR^{10c}$; $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9c}$; and $C_{3-10}$ carbocycle and 3- to 10-membered heterocycle. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9c}$. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{9c}$. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, —$OR^{10c}$, —$SR^{10c}$, —$N(R^{10c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{9c}$. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, —$OR^{10c}$, —$SR^{10c}$, —$N(R^{10c})_2$, =O, —$N_3$, and —CN, $C_{3-10}$ carbocycle and 3- to 10-membered heterocycle. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, —$OR^{10c}$, —$SR^{10c}$, —$N(R^{10c})_2$, =O, —$N_3$, and —CN. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, and —CN. In some embodiments, $R^C$ is selected from: hydrogen; —CN; and $C_{1-6}$ alkyl optionally substituted with one or more substituents independently selected from halogen, and —CN. In some embodiments, $R^C$ is selected from: hydrogen, —CN, and $C_{1-6}$ alkyl. In some embodiments, $R^C$ is selected from: hydrogen and $C_{1-6}$ alkyl. In some embodiments, $R^C$ is selected from: hydrogen and $C_1$ alkyl. In some embodiments, $R^C$ is selected from: hydrogen. In some embodiments, $R^C$ is selected from fluoro. In some embodiments, $R^C$ is selected from halogen.

In some embodiments, for a compound or salt of Formula (Ia), $R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9c}$. In some embodiments, $R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9c}$; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9c}$. In some embodiments, $R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from halogen, —$OR^{10c}$, —$SR^{10c}$, —$N(R^{10c})_2$, and —CN; $C_{1-6}$ alkyl, optionally substituted with one or more substituents independently selected from halogen, —OH, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10c}$, =O, —CN, and $C_{1-6}$ alkyl. In some embodiments, $R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from —F, —Cl, —OH, —$OCH_3$, and —$CH_3$. In some embodiments, $R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from —F.

In some embodiments, for a compound or salt of Formula (Ia), $R^5$ is selected from: hydrogen; halogen, —C(O)$R^{10d}$, —C(O)N($R^{10d}$)$_2$, —C(O)O$R^{10d}$, —S(O)$R^{10d}$, —S(O)$_2R^{10a}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{10d}$, —S$R^{10d}$, —N($R^{10d}$)$_2$, —C(O)$R^{10a}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10a}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10}$a and —CN; $C_{1-6}$ alkyl, $C_{2-6}$ alkenyl, and $C_{2-6}$ alkynyl, each of which is optionally substituted with one or more substituents independently selected from halogen, —O$R^{10}$, —S$R^{10d}$, —N($R^{10d}$)$_2$, —C(O)$R^{10a}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —O$R^{10a}$, —S$R^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, and $C_{1-6}$ alkyl. In some embodiments, $R^5$ is selected from: hydrogen; halogen, —C(O)$R^{10a}$, —C(O)N($R^{10d}$)$_2$, —C(O)O$R^{10a}$, and —CN; $C_{1-6}$ alkyl, optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, —O$R^{10d}$, —S$R^{10a}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —$NO_2$, =O, —CN, $C_{3-10}$ carbocycle and 3- to 10-membered heterocycle. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, —O$R^{10d}$, —S$R^{10d}$, —N($R^{10d}$)$_2$, =O, —CN, $C_{3-10}$ carbocycle and 3- to 10-membered heterocycle. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, —CN, $C_{3-10}$ carbocycle and 3- to 10-membered heterocycle. In some embodiments, $R^5$ is selected from: hydrogen; halogen and —CN; and $C_{1-6}$ alkyl, optionally substituted with one or more substituents independently selected from halogen, —CN, $C_{3-10}$ carbocycle and 3- to 10-membered heterocycle. In some embodiments, $R^5$ is selected from: hydrogen; halogen and —CN; and $C_{1-6}$ alkyl, optionally substituted with one or more substituents independently selected from halogen, —CN, and $C_{3-10}$ carbocycle. In some embodiments, $R^5$ is selected from: hydrogen; fluoro and —CN; and $C_{1-6}$ alkyl, optionally substituted with one or more substituents independently selected from fluoro, —CN, and cyclopropyl. In some embodiments, $R^5$ is selected from: hydrogen; fluoro and —CN; and $C_{1-6}$ alkyl, optionally substituted with one or more substituents independently selected from fluoro, —CN; and $C_1$ alkyl optionally substituted with cyclopropyl. In some embodiments, $R^5$ is selected from: hydrogen; fluoro; and $C_{1-6}$ alkyl, optionally substituted with one or more substituents independently selected from fluoro. In some embodiments, $R^5$ is selected from: hydrogen; and $C_{1-6}$ alkyl, optionally substituted with one or more substituents independently selected from fluoro. In some embodiments, $R^5$ is selected from —$CH_2$(cyclopropyl). In some embodiments, $R^5$ is selected from: hydrogen and $C_{1-6}$ alkyl. In some embodiments, $R^5$ is selected from: hydrogen and $C_{1-4}$ alkyl. In some embodiments, $R^5$ is selected from: hydrogen, methyl, and isobutyl. In some embodiments, $R^5$ is selected from: hydrogen, and isobutyl. In some embodiments, $R^5$ is selected from: hydrogen. In some embodiments, $R^5$ is selected from: fluoro. In some embodiments, $R^5$ together with $R^6$ form a $C_{3-10}$ carbocycle or 3- to 10-membered heterocycle optionally substituted with one or more $R^{9d}$. In some embodiments, $R^5$ together with $R^6$ form a cyclopropyl optionally substituted with one or more $R^{9d}$. In some embodiments, $R^5$ together with $R^6$ form a cyclopropyl optionally substituted with one or more F. In some embodiments, $R^5$ together with $R^6$ form a cyclopropyl.

In some embodiments, for a compound or salt of Formula (Ia), $R^6$ is selected from: hydrogen; halogen, —C(O)$R^{10e}$, —C(O)N($R^{10e}$)$_2$, —C(O)O$R^{10e}$, —S(O)$R^{10e}$, —S(O)$_2R^{10e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, =O, =S, =N($R^{10e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —$NO_2$, =O, =S, =N($R^{10e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$ and —CN; $C_{1-6}$ alkyl, $C_{2-6}$ alkenyl, and $C_{2-6}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, =O, =S, =N($R^{10e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —$NO_2$, =O, =S, =N($R^{10e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$, and —CN; $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, =O, =S, =N($R^{10e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —$NO_2$, =O, =S, =N($R^{10e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$, and —CN; $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, =O, =S, =N($R^{10e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$N(R^{10e})C(O)N(R^{10e})_2$, —$OC(O)N(R^{10e})_2$, —$N(R^{10e})C(O)OR^{10e}$, —$C(O)OR^{10e}$, —$OC(O)R^{10e}$, —$S(O)R^{10e}$, —$S(O)_2R^{10e}$, —$NO_2$, =O, =S, =$N(R^{10e})$, —$N_3$, —CN, and $C_{1-6}$ alkyl. In some embodiments, $R^6$ is selected from: hydrogen; halogen, —$C(O)R^{10e}$, —$C(O)N(R^{10e})_2$, —$C(O)OR^{10e}$, and —CN; $C_{1-6}$ alkyl, optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, =O, =S, =$N(R^{10e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^6$ is selected from: hydrogen; halogen, —$C(O)R^{10e}$, —$C(O)N(R^{10e})_2$, —$C(O)OR^{10e}$, and —CN; $C_{1-6}$ alkyl, optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, =O, =S, =$N(R^{10e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle. In some embodiments, $R^6$ is selected from: hydrogen; halogen, —$C(O)R^{10e}$, —$C(O)N(R^{10e})_2$, —$C(O)OR^{10e}$, and —CN; and $C_{1-6}$ alkyl, optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, =O, =S, =$N(R^{10e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$. In some embodiments, $R^6$ is selected from: hydrogen; halogen, —$C(O)R^{10e}$, —$C(O)N(R^{10e})_2$, —$C(O)OR^{10e}$, and —CN; and $C_{1-6}$ alkyl, optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$NO_2$, =O, —CN, $C_{3-10}$ carbocycle and 3- to 10-membered heterocycle. In some embodiments, $R^6$ is selected from: hydrogen; halogen, —$C(O)R^{10e}$, —$C(O)N(R^{10e})_2$, —$C(O)OR^{10e}$, and —CN; and $C_{1-6}$ alkyl, optionally substituted with one or more substituents independently selected from halogen, —$OR^{10e}$, —$SR^{10e}$, —$N(R^{10e})_2$, =O, —CN, $C_{3-10}$ carbocycle and 3- to 10-membered heterocycle. In some embodiments, $R^6$ is selected from: hydrogen; halogen, —$C(O)R^{10e}$, —$C(O)N(R^{10e})_2$, —$C(O)OR^{10e}$, and —CN; and $C_{1-6}$ alkyl, optionally substituted with one or more substituents independently selected from halogen, —CN, $C_{3-10}$ carbocycle and 3- to 10-membered heterocycle. In some embodiments, $R^6$ is selected from: hydrogen; halogen and —CN; and $C_{1-6}$ alkyl, optionally substituted with one or more substituents independently selected from halogen, —CN, $C_{3-10}$ carbocycle and 3- to 10-membered heterocycle. In some embodiments, $R^6$ is selected from: hydrogen; halogen and —CN; and $C_{1-6}$ alkyl, optionally substituted with one or more substituents independently selected from halogen, —CN, and $C_{3-10}$ carbocycle. In some embodiments, $R^6$ is selected from: hydrogen; fluoro and —CN; and $C_{1-6}$ alkyl, optionally substituted with one or more substituents independently selected from fluoro, —CN, and cyclopropyl. In some embodiments, $R^6$ is selected from: hydrogen; fluoro and —CN; and $C_{1-6}$ alkyl, optionally substituted with one or more substituents independently selected from fluoro, —CN; and $C_1$ alkyl optionally substituted with cyclopropyl. In some embodiments, $R^6$ is selected from: hydrogen; fluoro; and $C_{1-6}$ alkyl, optionally substituted with one or more substituents independently selected from fluoro. In some embodiments, $R^6$ is selected from —$CH_2$(cyclopropyl). In some embodiments, $R^6$ is selected from: hydrogen; and $C_{1-6}$ alkyl, optionally substituted with one or more substituents independently selected from fluoro. In some embodiments, $R^6$ is selected from: hydrogen and $C_{1-6}$ alkyl. In some embodiments, $R^6$ is selected from: hydrogen and $C_{1-4}$ alkyl. In some embodiments, $R^6$ is selected from: hydrogen, methyl, and isobutyl. In some embodiments, $R^6$ is selected from: hydrogen, and isobutyl. In some embodiments, $R^6$ is selected from: hydrogen. In some embodiments, $R^6$ is selected from: fluoro. In some embodiments, $R^5$ together with $R^6$ form a $C_{3-10}$ carbocycle or 3- to 10-membered heterocycle optionally substituted with one or more $R^{9d}$. In some embodiments, $R^5$ together with $R^6$ form a cyclopropyl optionally substituted with one or more $R^{9e}$. In some embodiments, $R^5$ together with $R^6$ form a cyclopropyl.

In some embodiments, for a compound or salt of Formula (Ia), $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. In some embodiments, $R^5$ together with $R^6$ form a 3- to 10-membered heterocycle or $C_{3-10}$ carbocycle. In some embodiments, $R^5$ together with $R^6$ form a $C_{3-10}$ carbocycle. In some embodiments, $R^5$ together with $R^6$ form a $C_{3-7}$ carbocycle. In some embodiments, $R^5$ together with $R^6$ form a $C_{3-6}$ carbocycle. In some embodiments, $R^5$ together with $R^6$ form a cyclopropyl optionally substituted with one or more substitutents independently selected from —F, —Cl, and —OH. In some embodiments, $R^5$ together with $R^6$ form a cyclopropyl optionally substituted with one or more substituents independently selected from —F. In some embodiments, $R^5$ together with $R^6$ form a cyclopropyl optionally substituted with two substituents selected from —F. In some embodiments, $R^5$ together with $R^6$ form a moiety selected from =O, =S, =$N(O)(R^{10e})$, =$C(R^{10e})_2$ and =$N(R^{10d})$. In some embodiments, $R^5$ together with $R^6$ form a moiety selected from =O, =S, =$N(O)(R^{10e})$, and =$N(R^{10d})$. In some embodiments, $R^5$ together with $R^6$ form a moiety selected from =O, =S, =$N(O)(R^{10e})$, and =$N(R^{10d})$. In some embodiments, $R^5$ together with $R^6$ form a moiety selected from =O and =$N(R^{10a})$. In some embodiments, $R^5$ together with $R^6$ form a moiety selected from =O.

In some embodiments, for a compound or salt of Formula (Ia), $R^5$ is hydrogen, and $R^6$ is hydrogen. In some embodiments, $R^5$ is hydrogen, and $R^6$ is isobutyl. In some embodiments, $R^5$ is —F, and $R^6$ is —F. In some embodiments, $R^5$ is halogen, and $R^6$ is halogen.

In some embodiments, for a compound or salt of Formula (Ia), $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{f}$, —$S(O)R^{10f}$, —$S(O)_2R^{f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, and $C_{1-6}$ alkyl. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^f$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, and $C_{1-6}$ alkyl. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, =O, —CN, and $C_{1-6}$ alkyl. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; and $C_{3-10}$ carbocycle and 3- to 10-membered heterocycle. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, =O, —CN, $C_{3-10}$ carbocycle and 3- to 10-membered heterocycle. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, =O, and —CN. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen and —CN. In some embodiments, $R^7$ is selected from: hydrogen; —$C(O)R^{10f}$, —$C(O)N(R^{10f})_2$, —$C(O)OR^{10f}$; $C_{1-6}$ alkyl optionally substituted with one or more substituents independently selected from halogen and —CN. In some embodiments, $R^7$ is selected from: hydrogen; and $C_{1-6}$ alkyl optionally substituted with one or more substituents independently selected from halogen and —CN. In some embodiments, $R^7$ is selected from: hydrogen; and $C_{1-6}$ alkyl optionally substituted with one or more substituents independently selected from fluoro and —CN. In some embodiments, $R^7$ is selected from hydrogen and $C_{1-6}$ alkyl. In some embodiments, $R^7$ is selected from hydrogen and $C_{1-4}$ alkyl. In some embodiments, $R^7$ is selected from hydrogen and $C_1$ alkyl. In some embodiments, $R^7$ is selected from hydrogen.

In some embodiments, for a compound or salt of Formula (Ia), $Y^1$ is selected from $C(R^{9bA})$ and N. In some embodiments, $Y^1$ is selected from C(H), C(F), $C(CH_3)$, and N. In some embodiments, $Y^1$ is selected from C(H) and N. In some embodiments, $Y^1$ is selected from C(H). In some embodiments, $Y^1$ is selected from N. In some embodiments, $Y^1$ is selected from $C(R^{9bA})$. In some embodiments, $Y^1$ is selected from $N^+(—O^-)$. In some embodiments, for a compound or salt of Formula (Ia), $Y^2$ is selected from $C(R^{9bB})$ and N. In some embodiments, $Y^2$ is selected from C(H), C(F), $C(CH_3)$, and N. In some embodiments, $Y^2$ is selected from C(H) and N. In some embodiments, $Y^2$ is selected from C(H). In some embodiments, $Y^2$ is selected from N. In some embodiments, $Y^2$ is selected from $C(R^{9bB})$. In some embodiments, $Y^2$ is selected from $N^+(—O^-)$. In some embodiments, for a compound or salt of Formula (Ia), $Y^3$ is selected from $C(R^{9bC})$ and N. In some embodiments, $Y^3$ is selected from N, C(H), C(CN), C(F), C(Cl), and C(OH). In some embodiments, $Y^3$ is selected from N, C(CN), C(F), C(Cl), and C(OH). In some embodiments, $Y^3$ is selected from N, C(CN), and C(F). In some embodiments, $Y^3$ is selected from C(CN), and C(F). In some embodiments, $Y^3$ is selected from C(CN), and N. In some embodiments, $Y^3$ is selected from N. In some embodiments, $Y^3$ is selected from C(CN). In some embodiments, $Y^3$ is not selected from C(H). In some embodiments, $Y^3$ is selected from $C(R^{9bC})$. In some embodiments, $Y^3$ is selected from $N^+(—O^-)$. In some embodiments, for a compound or salt of Formula (Ia), $Y^4$ is selected from $C(R^{9bD})$ and N. In some embodiments, $Y^4$ is selected from C(H), C(F), $C(CH_3)$, and N. In some embodiments, $Y^4$ is selected from C(H) and N. In some embodiments, $Y^4$ is selected from C(H). In some embodiments, $Y^4$ is selected from N. In some embodiments, $Y^4$ is selected from $C(R^{9bD})$. In some embodiments, $Y^4$ is selected from $N^+(—O^-)$. In some embodiments, for a compound or salt of Formula (Ia), $Y^5$ is selected from $C(R^{9bE})$ and N. In some embodiments, $Y^5$ is selected from N C(H), C(F), and $C(CH_3)$. In some embodiments, $Y^5$ is selected from N and C(H), and C(F). In some embodiments, $Y^5$ is selected from C(H), and C(F). In some embodiments, $Y^5$ is selected from N. In some embodiments, $Y^5$ is selected from $C(R^{9bE})$ In some embodiments, $Y^5$ is selected from $N^+(—O^-)$. In some embodiments, for a compound or salt of Formula (Ia), $Y^1$ is N, $Y^2$ is C(H), $Y^3$ is C(CN), $Y^4$ is C(H), and $Y^5$ is C(F). In some embodiments, $Y^1$ is N, $Y^2$ is C(H), $Y^3$ is C(CN), $Y^4$ is C(H), and $Y^5$ is $C(CH_3)$. In some embodiments, $Y^1$ is N, $Y^2$ is C(H), $Y^3$ is C(CN), $Y^4$ is C(H), and $Y^5$ is C(H). In some embodiments, $Y^1$ is N, $Y^2$ is C(H), $Y^3$ is C(F), $Y^4$ is C(H), and $Y^5$ is C(F). In some embodiments, $Y^1$ is N, $Y^2$ is C(H), $Y^3$ is C(H), $Y^4$ is C(H), and $Y^5$ is C(Cl). In some embodiments, $Y^1$ is N, $Y^2$ is C(H), $Y^3$ is C(F), $Y^4$ is C(H), and $Y^5$ is C(H). In some embodiments, $Y^1$ is C(H), $Y^2$ is N, $Y^3$ is C(OH), $Y^4$ is C(H), and $Y^5$ is C(H). In some embodiments, $Y^1$ is C(H), $Y^2$ is C(H), $Y^3$ is N, $Y^4$ is C(H), and $Y^5$ is C(F). In some embodiments, $Y^1$ is N, $Y^2$ is C(H), $Y^3$ is C(CN), $Y^4$ is C(H), and $Y^5$ is N. In some embodiments, $Y^1$ is C(H), $Y^2$ is N, $Y^3$ is C(CN), $Y^4$ is N, and $Y^5$ is C(H). In some embodiments, $Y^1$ is N, $Y^2$ is C(H), $Y^3$ is N, $Y^4$ is C(H), and $Y^5$ is C(H). In some embodiments, $Y^1$ is C(H), $Y^2$ is C(H), $Y^3$ is C(CN), $Y^4$ is N, and $Y^5$ is N. In some embodiments, for a compound or salt of Formula (Ia), no more than four of $Y^1$, $Y^2$, $Y^3$, $Y^4$, and $Y^5$ are N. In some embodiments, no more than four of $Y^1$, $Y^2$, $Y^3$, $Y^4$, and $Y^5$ are N or $N^+(—O^-)$. In some embodiments, no more than three of $Y^1$, $Y^2$, $Y^3$, $Y^4$, and $Y^5$ are N. In some embodiments, no more than three of $Y^1$, $Y^2$, $Y^3$, $Y^4$, and $Y^5$ are N or $N^+(—O^-)$. In some embodiments, no more than two of $Y^1$, $Y^2$, $Y^3$, $Y^4$, and $Y^5$ are N. In some embodiments, no more than two of $Y^1$, $Y^2$, $Y^3$, $Y^4$, and $Y^5$ are N or $N^+(—O^-)$. In some embodiments, no more than one of $Y^1$, $Y^2$, $Y^3$, $Y^4$, and $Y^5$ is N. In some embodiments, no more than one of $Y^1$, $Y^2$, $Y^3$, $Y^4$, and $Y^5$ is N or $N^+(—O^-)$. In some embodiments, for a compound or salt of Formula (Ia), at least one of $Y^1$, $Y^2$, $Y^3$, $Y^4$, and $Y^5$ is N or $N^+(—O^-)$. In some embodiments, at least one of $Y^1$, $Y^2$, $Y^3$, $Y^4$, and $Y^5$ is N. In some embodiments, at least one of $Y^1$, $Y^2$, $Y^3$, $Y^4$, and $Y^5$ need not be N. In some embodiments, at least one of $Y^1$, $Y^2$, $Y^3$, $Y^4$, and $Y^5$ need not be N or $N^+(—O^-)$. In some embodiments, $Y^1$ is selected from $C(R^{9bA})$, and $Y^2$ is selected from $C(R^{9bB})$ and $Y^3$ is selected from $C(R^{9bC})$, and $Y^4$ is selected from $C(R^{9bD})$, and $Y^5$ is selected from $C(R^{9bE})$.

In some embodiments, for a compound or salt of Formula (Ia), $R^2$ is selected from

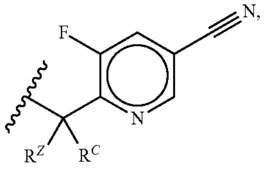
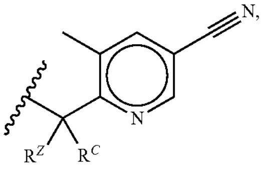
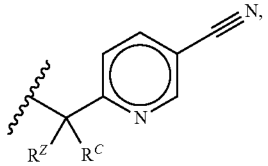
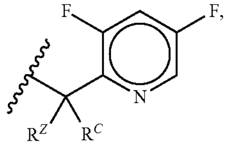
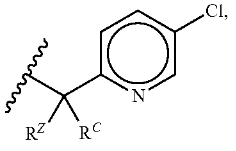
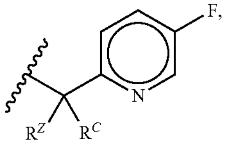
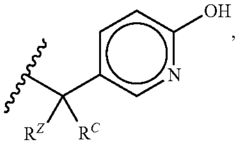
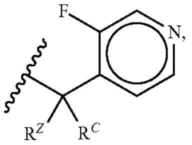
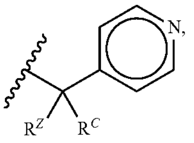
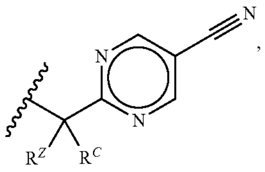
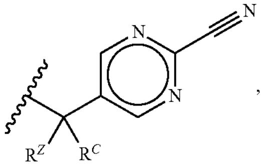
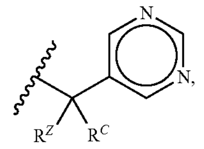
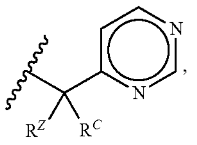
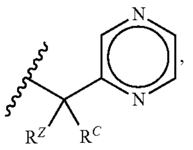
and
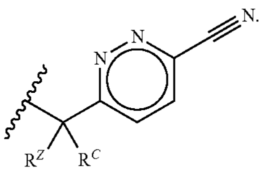

In some embodiments, $R^2$ is selected from
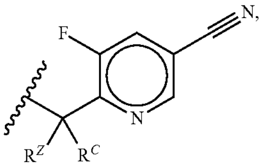
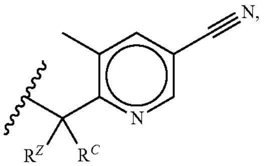
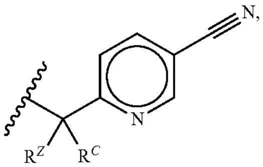
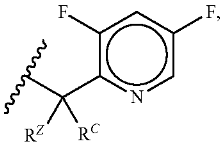
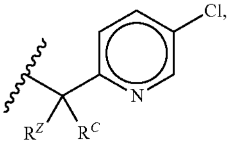
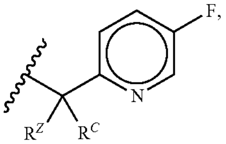
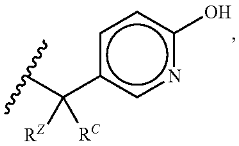
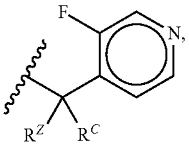
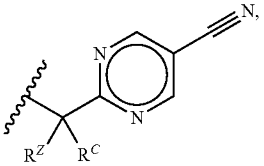
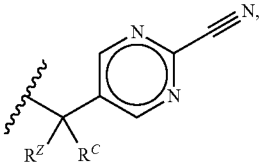
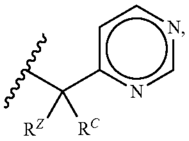 and
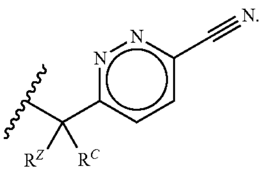
In some embodiments, $R^2$ is selected from
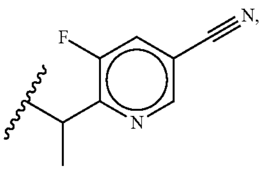
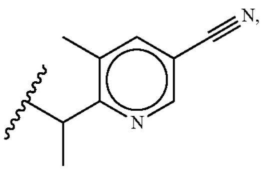
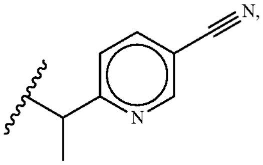
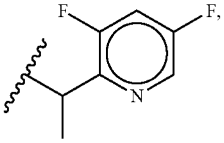
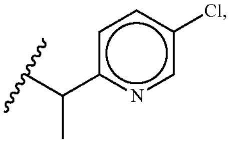
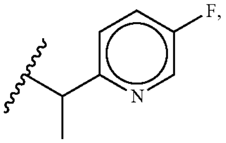
-continued
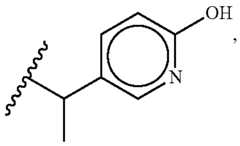
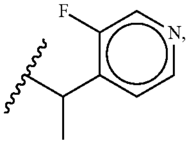
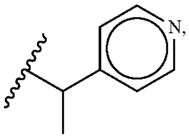
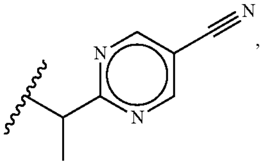
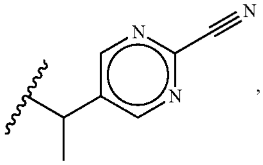 ,
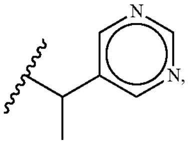
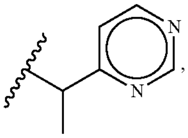
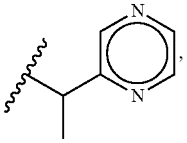 and
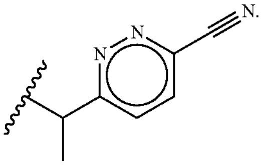
In some embodiments, $R^2$ is selected from
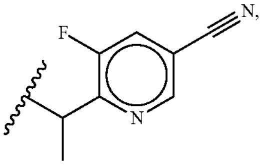
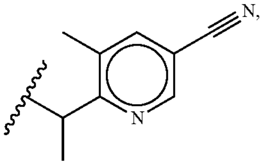
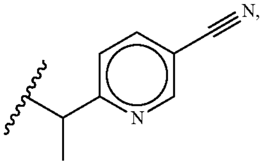
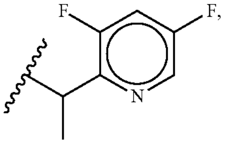
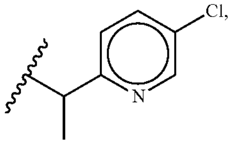
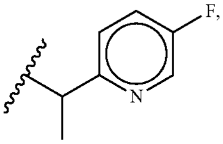
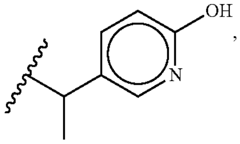
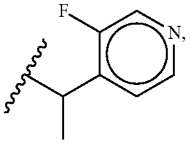
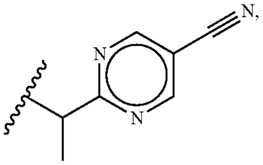
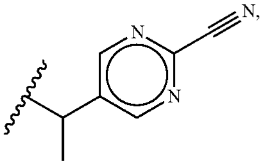

-continued

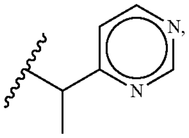

and

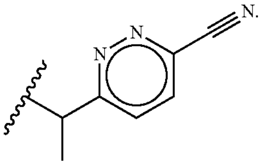

In some embodiments, for a compound or salt of Formula (Ia), $R^8$ is selected from: hydrogen; —$C(O)R^{10g}$, —$C(O)N(R^{10g})_2$, —$C(O)OR^{10g}$, —$S(O)R^{10g}$, and —$S(O)_2R^{10g}$; and $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =O, =S, =$N(R^{10g})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{99}$.

In some embodiments, $R^8$ is selected from: hydrogen; —$C(O)R^{10g}$, —$C(O)N(R^{10g})_2$, —$C(O)OR^{10g}$, —$S(O)R^{10g}$, and —$S(O)_2R^{10g}$; and $C_{1-6}$ alkyl optionally substituted with one or more substituents independently selected from halogen, —$OR^{10g}$, —$SR^{10g}$, —$N(R^{10g})_2$, =O, —CN, $C_{3-10}$ carbocycle and 3- to 10-membered heterocycle. In some embodiments, $R^8$ is selected from: hydrogen; and $C_{1-6}$ alkyl optionally substituted with one or more substituents independently selected from halogen, and —CN. In some embodiments, $R^8$ is selected from: hydrogen; and $C_{1-6}$ alkyl optionally substituted with one or more substituents independently selected from fluoro, and —CN. In some embodiments, $R^8$ is selected from hydrogen; and $C_{1-6}$ alkyl optionally substituted with one or more substituents independently selected from fluoro. In some embodiments, $R^8$ is selected from: hydrogen and $C_{1-6}$ alkyl. In some embodiments, $R^8$ is selected from: hydrogen and $C_{1-3}$ alkyl. In some embodiments, $R^8$ is selected from: hydrogen and $C_1$ alkyl. In some embodiments, $R^8$ is selected from: hydrogen.

In some embodiments, for a compound or salt of Formula (Ia), each $R^{9a}$ is independently selected from: halogen, —$OR^{10a}$, —$SR^{10a}$, —$N(R^{10a})_2$, =O, and —CN; and $C_{1-3}$ alkyl each of which is optionally substituted with one or more substituents independently selected from halogen, —$OR^{10a}$, —$SR^{10a}$, —$N(R^{10a})_2$, =O, and —CN. In some embodiments, each $R^{9a}$ is independently selected from: halogen, —$OR^{10a}$, —$SR^{10a}$, —$N(R^{10a})_2$, =O, and —CN; and $C_{1-3}$ alkyl each of which is optionally substituted with one or more substituents independently selected from halogen and —CN. In some embodiments, each $R^{9a}$ is independently selected from: halogen, —$OR^{10a}$, —$SR^{10a}$, —$N(R^{10a})_2$, =O, —CN, and $C_{1-3}$ alkyl. In some embodiments, each $R^{9a}$ is independently selected from: halogen, —$OR^{10a}$, —CN, and $C_1$ alkyl. In some embodiments, each $R^{9a}$ is independently selected from: fluoro and —CN. In some embodiments, each $R^{9a}$ is independently selected from: fluoro. In some embodiments, each $R^{9a}$ is independently selected from: —CN.

In some embodiments, for a compound or salt of Formula (Ia), $R^{9bA}$, $R^{9bB}$, $R^{9bC}$, $R^{9bD}$ and $R^{9bE}$ are each independently selected from: hydrogen; halogen, —$NO_2$, —$N_3$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$; $C_{1-6}$ alkyl optionally substituted with one or more substituents independently selected from halogen, —$OR^{10b}$, —$SR^{10b}$, —$N(R^{10b})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, =O, —CN, $C_{1-6}$ alkyl. In some embodiments, $R^{9bA}$, $R^{9bB}$, $R^{9bC}$, $R^{9bD}$, and $R^{9bE}$ are each independently selected from: hydrogen; halogen, —$NO_2$, —$N_3$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$; $C_{1-6}$ alkyl optionally substituted with one or more substituents independently selected from halogen, —$OR^{10b}$, —$SR^{10b}$, —$N(R^{10b})_2$, =O, —CN, $C_{3-10}$ carbocycle and 3- to 10-membered heterocycle; and $C_{3-10}$ carbocycle and 3- to 10-membered heterocycle. In some embodiments, $R^{9bA}$, $R^{9bB}$, $R^{9bC}$, $R^{9bD}$, and $R^{9bE}$ are each independently selected from: hydrogen; halogen, —$NO_2$, —$N_3$, —CN, —$OR^{10b}$, —$SR^{10b}$, and —$N(R^{10b})_2$; $C_{1-6}$ alkyl optionally substituted with one or more substituents independently selected from halogen, —$OR^{10b}$, —$SR^{10b}$, —$N(R^{10b})_2$, =O, —CN, $C_{3-10}$ carbocycle and 3- to 10-membered heterocycle; and $C_{3-10}$ carbocycle and 3- to 10-membered heterocycle. In some embodiments, $R^{9bA}$, $R^{9bB}$, $R^{9bC}$, $R^{9bD}$, and $R^{9bE}$ are each independently selected from: hydrogen; halogen, —$NO_2$, —$N_3$, —CN, —$OR^{10b}$, —$SR^{10b}$, and —$N(R^{10b})_2$; and $C_{1-6}$ alkyl optionally substituted with one or more substituents independently selected from halogen, —$OR^{10b}$, —$SR^{10b}$, —$N(R^{10b})_2$, =O, —CN, $C_{3-10}$ carbocycle and 3- to 10-membered heterocycle. In some embodiments, $R^{9bA}$, $R^{9bB}$, $R^{9bC}$, $R^{9bD}$, and $R^{9bE}$ are each independently selected from: hydrogen; halogen, —CN, —$OR^{10b}$, —$SR^{10b}$, and —$N(R^{10b})_2$; and $C_{1-6}$ alkyl optionally substituted with one or more substituents independently selected from halogen, —$OR^{10b}$, —$SR^{10b}$, —$N(R^{10b})_2$, =O, and —CN. In some embodiments, $R^{9bA}$, $R^{9bB}$, $R^{9bC}$, $R^{9bD}$, and $R^{9bE}$ are each independently selected from: hydrogen, halogen, —CN, —$OR^{10b}$, —$SR^{10b}$, and —$N(R^{10b})_2$, and $C_{1-6}$ alkyl. In some embodiments, $R^{9bA}$, $R^{9bB}$, $R^{9bC}$, $R^{9bD}$, and $R^{9bE}$ are each independently selected from: hydrogen, halogen, —CN, —$OR^{10b}$, and $C_{1-6}$ alkyl. In some embodiments, $R^{9bA}$, $R^{9bB}$, $R^{9bC}$, $R^{9bD}$, and $R^{9bE}$ are each independently selected from: hydrogen, fluoro, —CN, —$OR^{10b}$, and $C_{1-6}$ alkyl. In some embodiments, $R^{9bA}$, $R^{9bB}$, $R^{9bC}$, $R^{9bD}$, and $R^{9bE}$ are each independently selected from: hydrogen, fluoro, —CN, —$OR^{10b}$, and $C_1$ alkyl. In some embodiments, $R^{9bA}$, $R^{9bB}$, $R^{9bC}$, $R^{9bD}$, and $R^{9bE}$ are each independently selected from: hydrogen, fluoro, and —CN. In some embodiments, $R^{9bA}$, $R^{9bB}$, $R^{9bC}$, $R^{9bD}$, and $R^{9bE}$ are each independently selected from: hydrogen, and fluoro. In some embodiments, $R^{9bA}$, $R^{9bB}$, $R^{9bC}$, $R^{9bD}$, and $R^{9bE}$ are each independently selected from: hydrogen, and —CN. In some embodiments, for a compound or salt of Formula (Ia), $R^{9b}$A is selected from: hydrogen, fluoro, and —CN. In some embodiments, $R^{9b}$A is selected from: hydrogen. In some embodiments, $R^{9b}$A is selected from: fluoro. In some embodiments, $R^{9b}$A is selected from: —CN. In some embodiments, for a compound or salt of Formula (Ia), $R^{9b}$B is selected from: hydrogen, fluoro, and —CN. In some embodiments, $R^{9b}$B is selected from: hydrogen. In some embodiments, $R^{9b}$B is selected from: fluoro. In some embodiments, $R^{9b}$B is selected from: —CN. In some embodiments, for a compound or salt of Formula (Ia), $R^{9bC}$ is selected from: hydrogen, fluoro, and —CN. In some embodiments, $R^{9bC}$ is selected from: hydrogen. In some embodiments, $R^{9bC}$ is selected from: fluoro. In some embodiments, $R^{9bC}$ is selected from: —CN. In some embodiments, for a compound or salt of Formula (Ia), $R^{9bD}$ is selected from: hydrogen, fluoro, and —CN. In some embodiments, $R^{9bD}$ is selected from: hydrogen. In some embodiments, $R^{9bD}$ is selected from: fluoro. In some embodiments, $R^{9bD}$ is selected from: —CN. In some embodiments, for a compound or salt of Formula (Ia), $R^{9bE}$ is selected from: hydrogen, fluoro, and —CN. In some embodiments, $R^{9bE}$ is selected from: hydrogen. In some embodiments, $R^{9bE}$ is selected from: fluoro. In some embodiments, $R^{9bE}$ is selected from: —CN.

In some embodiments, for a compound or salt of Formula (Ia), each $R^{9z}$ is independently selected from: halogen, —$OR^{10z}$, —$SR^{10z}$, —$N(R^{10z})_2$, =O, and —CN; and $C_{1-3}$ alkyl each of which is optionally substituted with one or more substituents independently selected from halogen, —$OR^{10z}$, —$SR^{10z}$, —$N(R^{10z})_2$, =O, and —CN. In some embodiments, each $R^{9z}$ is independently selected from: halogen, —$OR^{10z}$, —$SR^{10z}$, —$N(R^{10z})_2$, =O, and —CN; and $C_{1-3}$ alkyl each of which is optionally substituted with one or more substituents independently selected from halogen and —CN. In some embodiments, each $R^{9z}$ is independently selected from: halogen, —$OR^{10z}$, —$SR^{10z}$, —$N(R^{10z})_2$, =O, —CN, and $C_{1-3}$ alkyl. In some embodiments, each $R^{9z}$ is independently selected from: halogen, —$OR^{10z}$, —CN, and $C_1$ alkyl. In some embodiments, each $R^{9z}$ is independently selected from: fluoro and —CN. In some embodiments, each $R^{9z}$ is independently selected from: fluoro. In some embodiments, each $R^{9z}$ is independently selected from: —CN. In some embodiments, for a compound or salt of Formula (Ia), each $R^{9c}$ is independently selected from: halogen, —$OR^{10c}$, —$SR^{10c}$, —$N(R^{10c})_2$, =O, and —CN; and $C_{1-3}$ alkyl each of which is optionally substituted with one or more substituents independently selected from halogen, —$OR^{10c}$, —$SR^{10c}$, —$N(R^{10c})_2$, =O, and —CN. In some embodiments, each $R^{9c}$ is independently selected from: halogen, —$OR^{10c}$, —$SR^{10c}$, —$N(R^{10c})_2$, =O, and —CN; and $C_{1-3}$ alkyl each of which is optionally substituted with one or more substituents independently selected from halogen and —CN. In some embodiments, each $R^{9c}$ is independently selected from: halogen, —$OR^{10c}$, —$SR^{10c}$, —$N(R^{10c})_2$, =O, —CN, and $C_{1-3}$ alkyl. In some embodiments, each $R^{9c}$ is independently selected from: halogen, —$OR^{10c}$, —CN, and $C_1$ alkyl. In some embodiments, each $R^{9c}$ is independently selected from: fluoro and —CN. In some embodiments, each $R^{9c}$ is independently selected from: fluoro. In some embodiments, each $R^{9c}$ is independently selected from: —CN. In some embodiments, for a compound or salt of Formula (Ia), each $R^{9d}$ is independently selected from: halogen, —$OR^{10d}$, —$SR^{10d}$, —$N(R^{10d})_2$, =O, and —CN; and $C_{1-3}$ alkyl each of which is optionally substituted with one or more substituents independently selected from halogen, —$OR^{10d}$, —$SR^{10d}$, —$N(R^{10d})_2$, =O, and —CN. In some embodiments, each $R^{9d}$ is independently selected from: halogen, —$OR^{10d}$, —$SR^{10d}$, —$N(R^{10d})_2$, =O, and —CN; and $C_{1-3}$ alkyl each of which is optionally substituted with one or more substituents independently selected from halogen and —CN. In some embodiments, each $R^{9d}$ is independently selected from: halogen, —$OR^{10d}$, —$SR^{10d}$, —$N(R^{10d})_2$, =O, —CN, and $C_{1-3}$ alkyl. In some embodiments, each $R^{9d}$ is independently selected from: halogen, —$OR^{10d}$, —CN, and $C_1$ alkyl. In some embodiments, each $R^{9d}$ is independently selected from: fluoro and —CN. In some embodiments, each $R^{9d}$ is independently selected from: fluoro. In some embodiments, each $R^{9d}$ is independently selected from: —CN. In some embodiments, for a compound or salt of Formula (Ia), each $R^{9e}$ is independently selected from: halogen, —$OR^{10e}$, —$SR^{10e}$, —$N(R^{10e})_2$, =O, and —CN; and $C_{1-3}$ alkyl each of which is optionally substituted with one or more substituents independently selected from halogen, —$OR^{10e}$, —$SR^{10e}$, —$N(R^{10e})_2$, =O, and —CN. In some embodiments, each $R^{9e}$ is independently selected from: halogen, —$OR^{10e}$, —$SR^{10e}$, —$N(R^{10e})_2$, =O and —CN; and $C_{1-3}$ alkyl each of which is optionally substituted with one or more substituents independently selected from halogen and —CN. In some embodiments, each $R^{9e}$ is independently selected from: halogen, —$OR^{10e}$, —$SR^{10e}$, —$N(R^{10e})_2$, =O, —CN, and $C_{1-3}$ alkyl. In some embodiments, each $R^{9e}$ is independently selected from: halogen, —$OR^{10e}$, —CN, and $C_1$ alkyl. In some embodiments, each $R^{9e}$ is independently selected from: fluoro and —CN. In some embodiments, each $R^{9e}$ is independently selected from: fluoro. In some embodiments, each $R^{9e}$ is independently selected from: —CN. In some embodiments, for a compound or salt of Formula (Ia), each $R^{9f}$ is independently selected from: halogen, —$OR^{10f}$, —$SR^{10f}$, —$N(R^{10f})_2$, =O, and —CN; and $C_{1-3}$ alkyl each of which is optionally substituted with one or more substituents independently selected from halogen, —$OR^{10f}$, —$SR^{10f}$, —$N(R^{10f})_2$, =O, and —CN. In some embodiments, each $R^{9f}$ is independently selected from: halogen, —$OR^{10f}$, —$SR^{10f}$, —$N(R^{10f})_2$, =O, and —CN; and $C_{1-3}$ alkyl each of which is optionally substituted with one or more substituents independently selected from halogen and —CN. In some embodiments, each $R^{9f}$ is independently selected from: halogen, —$OR^{10f}$, —$SR^{10f}$, —$N(R^{10f})_2$, =O, —CN, and $C_{1-3}$ alkyl. In some embodiments, each $R^{9f}$ is independently selected from: halogen, —$OR^{10f}$, —CN, and $C_1$ alkyl. In some embodiments, each $R^{9f}$ is independently selected from: fluoro and —CN. In some embodiments, each $R^{9f}$ is independently selected from: fluoro. In some embodiments, each $R^{9f}$ is independently selected from: —CN. In some embodiments, for a compound or salt of Formula (Ia), each $R^{9g}$ is independently selected from: halogen, —$OR^{10g}$, —$SR^{10g}$, —$N(R^{10g})_2$, =O, and —CN; and $C_{1-3}$ alkyl each of which is optionally substituted with one or more substituents independently selected from halogen, —$OR^{10g}$, —$SR^{10g}$, —$N(R^{10g})_2$, =O, and —CN. In some embodiments, each $R^{9g}$ is independently selected from: halogen, —$OR^{10g}$, —$SR^{10g}$, —$N(R^{10g})_2$, =O, and —CN; and $C_{1-3}$ alkyl each of which is optionally substituted with one or more substituents independently selected from halogen and —CN. In some embodiments, each $R^{9g}$ is independently selected from: halogen, —$OR^{10g}$, —$SR^{10g}$, —$N(R^{10g})_2$, =O, —CN, and $C_{1-3}$ alkyl. In some embodiments, each $R^{9g}$ is independently selected from: halogen, —$OR^{10g}$, —CN, and $C_1$ alkyl. In some embodiments, each $R^{9g}$ is independently selected from: fluoro and —CN. In some embodiments, each $R^{9g}$ is independently selected from: fluoro. In some embodiments, each $R^{9g}$ is independently selected from: —CN.

In some embodiments, for a compound or salt of Formula (Ia), each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —$NH_2$, ═O, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, and $C_{1-6}$ haloalkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl optionally substituted with one or more substituents independently selected from halogen, —CN, and —OH; and $C_{3-10}$ carbocycle, and 3- to 10-membered heterocycle, each of which is optionally substituted with one or more substituents independently selected from halogen, —CN, —OH, $C_{1-6}$ alkyl, and $C_{1-6}$ haloalkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl optionally substituted with one or more substituents independently selected from fluoro and CN; and $C_{3-10}$ carbocycle, and 3- to 10-membered heterocycle, each of which is optionally substituted with one or more substituents independently selected from fluoro and —CN. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen; and $C_{1-6}$ alkyl optionally substituted with one or more substituents independently selected from fluoro and CN. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen and $C_{1-6}$ alkyl. In some embodiments, each $R^{10a}$, $R^{10b}$, $R^{10z}R^{10c}$, $R^{10d}$, $R^{10e}$, $R^{10f}$, and $R^{10g}$ is independently selected from: hydrogen and $C_1$ alkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen. In some embodiments, for a compound or salt of Formula (Ia), each $R^{10a}$ is independently selected from: hydrogen. In some embodiments, each $R^{10a}$ is independently selected from: hydrogen and $C_1$ alkyl. In some embodiments, for a compound or salt of Formula (Ia), each $R^{10b}$ is independently selected from: hydrogen. In some embodiments, each $R^{10b}$ is independently selected from: hydrogen and $C_1$ alkyl. In some embodiments, for a compound or salt of Formula (Ia), each $R^{10e}$ is independently selected from: hydrogen. In some embodiments, each $R^{10e}$ is independently selected from: hydrogen and $C_1$ alkyl. In some embodiments, for a compound or salt of Formula (Ia), each $R^{10d}$ is independently selected from: hydrogen. In some embodiments, each $R^{10d}$ is independently selected from: hydrogen and $C_1$ alkyl. In some embodiments, for a compound or salt of Formula (Ia), each $R^{10f}$ is independently selected from: hydrogen. In some embodiments, each $R^{10e}$ is independently selected from: hydrogen and $C_1$ alkyl. In some embodiments, for a compound or salt of Formula (Ia), each $R^{10f}$ is independently selected from: hydrogen. In some embodiments, each $R^{10f}$ is independently selected from: hydrogen and $C_1$ alkyl. In some embodiments, for a compound or salt of Formula (Ia), each $R^{10g}$ is independently selected from: hydrogen. In some embodiments, each $R^{10g}$ is independently selected from: hydrogen and $C_1$ alkyl. In some embodiments, for a compound or salt of Formula (Ia), each $R^{10z}$ is independently selected from: hydrogen. In some embodiments, each $R^{10z}$ is independently selected from: hydrogen and $C_1$ alkyl. In some embodiments, for a compound or salt of Formula (Ia), each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl, optionally substituted with one or more substituents independently selected from halogen, —CN, —OH, —$OCH_3$, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle, wherein each $C_{3-10}$ carbocycle and 3- to 10-membered heterocycle is optionally substituted with one or more substituents independently selected from halogen, —CN, —OH, —$OCH_3$, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —$OCH_3$, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{3-10}$ carbocycle, 3- to 10-membered heterocycle, and $C_{1-6}$ haloalkyl, wherein each $C_{1-6}$ alkyl, $C_{3-10}$ carbocycle, and 3- to 10-membered heterocycle is optionally substituted with one or more substituents independently selected from halogen, —CN, —OH, —$OCH_3$, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl) and $C_{1-6}$ alkyl. In some embodiments, for a compound or salt of Formula (Ia), each each $R^{10a}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, for a compound or salt of Formula (Ia), each each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, for a compound or salt of Formula (Ia), each each $R^{10c}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, for a compound or salt of Formula (Ia), each each $R^{10d}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, for a compound or salt of Formula (Ia), each each $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, for a compound or salt of Formula (Ia), each each $R^{10f}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. In some embodiments, for a compound or salt of Formula (Ia), each each $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, for a compound or salt of Formula (Ia), when $Y^1$ is N, $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N; then $R^7$ is selected from: hydrogen; —C(O)$R^{10f}$, —C(O)N($R^{10f}$)$_2$, —C(O)O$R^{10f}$, —S(O)$R^{10f}$, and —S(O)$_2R^{10f}$; $C_1$ alkyl substituted with one or more substituents independently selected from halogen, —O$R^{10f}$, —S$R^{10f}$, —N($R^{10f}$)$_2$, =O, —CN, $C_{3-10}$ carbocycle and 3- to 10-membered heterocycle; $C_{2-6}$ alkyl optionally substituted with one or more substituents independently selected from halogen, —O$R^{10f}$, —S$R^{10f}$, —N($R^{10f}$)$_2$, =O, —CN; and $C_{3-10}$ carbocycle and 3- to 10-membered heterocycle, each of which is optionally substituted with one or more substituents independently selected from halogen, —O$R^{10f}$, —S$R^{10f}$, —N($R^{10f}$)$_2$, =O, —CN, $C_{1-6}$ alkyl.

In some embodiments, when $Y^1$ is N, $Y^2$ is C($R^{9bB}$), $Y^3$ is C($R^{9bC}$), $Y^4$ is C($R^{9bD}$) and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N; then $R^7$ is selected from: hydrogen; —C(O)$R^{10f}$, —C(O)N($R^{10f}$)$_2$, —C(O)O$R^{10f}$, —S(O)$R^{10f}$, and —S(O)$_2$ $R^{10f}$; $C_1$ alkyl substituted with one or more substituents independently selected from halogen, —O$R^{10f}$, and —CN; $C_{2-6}$ alkyl optionally substituted with one or more substituents independently selected from halogen and —CN; and $C_{3-10}$ carbocycle and 3- to 10-membered heterocycle. In some embodiments, when $Y^1$ is N, $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N; then $R^7$ is selected from: hydrogen; $C_1$ alkyl substituted with one or more substituents independently selected from halogen, —O$R^{10f}$, and —CN; $C_{2-6}$ alkyl optionally substituted with one or more substituents independently selected from halogen and —CN. In some embodiments, when $Y^1$ is N, $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N; then $R^7$ is selected from hydrogen; and $C_{2-6}$ alkyl. In some embodiments, when $Y^1$ is N, $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N; then $R^7$ is selected from hydrogen. In some embodiments, when $Y^1$ is N; or when $Y^5$ is N; then $R^7$ is selected from hydrogen. In some embodiments, when $Y^1$ is N then $R^7$ is selected from hydrogen. In some embodiments, when $Y^5$ is N then $R^7$ is selected from hydrogen.

In some embodiments, for a compound or salt of Formula (Ia), when $Y^1$ is N or $N^+$(—$O^-$), $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N or $N^+$(—$O^-$); then $R^7$ is selected from:

hydrogen;

—C(O)$R^{10f}$, —C(O)N($R^{10f}$)$_2$, —C(O)O$R^{10f}$, —S(O)$R^{10f}$, and —S(O)$_2R^{10f}$;

$C_1$ alkyl substituted with one or more substituents independently selected from halogen, —O$R^{10f}$, —S$R^{10f}$, —N($R^{10f}$)$_2$, =O, —CN, $C_{3-10}$ carbocycle and 3- to 10-membered heterocycle;

$C_{2-6}$ alkyl optionally substituted with one or more substituents independently selected from halogen, —O$R^{10f}$, —S$R^{10f}$, —N($R^{10f}$)$_2$, =O, —CN; and $C_{3-10}$ carbocycle and 3- to 10-membered heterocycle, each of which is optionally substituted with one or more substituents independently selected from halogen, —O$R^{10f}$, —S$R^{10f}$, —N($R^{10f}$)$_2$, =O, —CN, $C_{1-6}$ alkyl.

In some embodiments, when $Y^1$ is N or $N^+$(—$O^-$), $Y^2$ is C($R^{9bB}$), $Y^3$ is C($R^{9bC}$), $Y^4$ is C($R^{9bD}$) and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N or $N^+$(—$O^-$); then $R^7$ is selected from: hydrogen; —C(O)$R^{10f}$, —C(O)N($R^{10f}$)$_2$, —C(O)O$R^{10f}$, —S(O)$R^{10f}$, and —S(O)$_2R^{10f}$; $C_1$ alkyl substituted with one or more substituents independently selected from halogen, —O$R^{10f}$, and —CN; $C_{2-6}$ alkyl optionally substituted with one or more substituents independently selected from halogen and —CN; and $C_{3-10}$ carbocycle and 3- to 10-membered heterocycle. In some embodiments, when $Y^1$ is N or $N^+$(—$O^-$), $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$), $Y^2$ is C($R^{9bB}$), $Y^3$ is C($R^{9bC}$), $Y^4$ is C($R^{9bD}$), and $Y^5$ is N or $N^+$(—$O^-$); then $R^7$ is selected from: hydrogen; $C_1$ alkyl substituted with one or more substituents independently selected from halogen, —O$R^{10f}$, and —CN; $C_{2-6}$ alkyl optionally substituted with one or more substituents independently selected from halogen and —CN. In some embodiments, when $Y^1$ is N or $N^+(—O^-)$, $Y^2$ is $C(R^{9bB})$, $Y^3$ is $C(R^{9bC})$, $Y^4$ is $C(R^{9bD})$, and $Y^5$ is $C(R^{9bE})$; or when $Y^1$ is $C(R^{9bA})$, $Y^2$ is $C(R^{9bB})$, $Y^3$ is $C(R^{9bC})$, $Y^4$ is $C(R^{9bD})$, and $Y^5$ is N or $N^+(—O^-)$; then $R^7$ is selected from hydrogen; and $C_{2-6}$ alkyl. In some embodiments, when $Y^1$ is N or $N^+(—O^-)$, $Y^2$ is $C(R^{9bB})$, $Y^3$ is $C(R^{9bC})$, $Y^4$ is $C(R^{9bD})$, and $Y^5$ is $C(R^{9bE})$; or when $Y^1$ is $C(R^{9bA})$, $Y^2$ is $C(R^{9bB})$, $Y^3$ is $C(R^{9bC})$, $Y^4$ is $C(R^{9bD})$ and $Y^5$ is N or $N^+(—O^-)$; then $R^7$ is selected from hydrogen. In some embodiments, when $Y^1$ is N or $N^+(—O^-)$; or when $Y^5$ is N or $N^+(—O^-)$; then $R^7$ is selected from hydrogen. In some embodiments, when $Y^1$ is N or $N^+(—O^-)$, then $R^7$ is selected from hydrogen. In some embodiments, when $Y^5$ is N or $N^+(—O^-)$, then $R^7$ is selected from hydrogen.

in some embodiments, for a compound or salt of Formula (Ia), when $Y^1$ is N or $N^+(—O^-)$, $Y^2$ is $C(R^{9bB})$, $Y^3$ is $C(R^{9bC})$, $Y^4$ is $C(R^{9bD})$, and $Y^5$ is $C(R^{9bE})$; or when $Y^1$ is $C(R^{9bA})$, $Y^2$ is $C(R^{9bB})$, $Y^3$ is $C(R^{9bC})$, $Y^4$ is $C(R^{9bD})$, and $Y^5$ is N or $N^+(—O^-)$; then $R^7$ is selected from: $—CH_3$. In some embodiments, when $Y^1$ is N or $N^+(—O^-)$, $Y^2$ is $C(R^{9bB})$, $Y^3$ is $C(R^{9bC})$, $Y^4$ is $C(R^{9bD})$, and $Y^5$ is $C(R^{9bE})$; then $R^7$ is selected from: $—CH_3$. In some embodiments, when $Y^1$ is $C(R^{9bA})$, $Y^2$ is $C(R^{9bB})$ $Y^3$ is $C(R^{9bC})$, $Y^4$ is $C(R^{9bD})$, and $Y^5$ is N or $N^+(—O^-)$, then $R^7$ is selected from: $—CH_3$. In some embodiments, for a compound or salt of Formula (Ia), $R^7$ is $—CH_3$. in some embodiments, for a compound or salt of Formula (Ia), when $Y^1$ is N, $Y^2$ is $C(R^{9bB})$, $Y^3$ is $C(R^{9bC})$, $Y^4$ is $C(R^{9bD})$, and $Y^5$ is $C(R^{9bE})$; or when $Y^1$ is $C(R^{9bA})$, $Y^2$ is $C(R^{9bB})$, $Y^3$ is $C(R^{9bC})$, $Y^4$ is $C(R^{9bD})$, and $Y^5$ is N; then $R^7$ is selected from: $—CH_3$. In some embodiments, when $Y^1$ is N, $Y^2$ is $C(R^{9bB})$, $Y^3$ is $C(R^{9bC})$, $Y^4$ is $C(R^{9bD})$, and $Y^5$ is $C(R^{9bE})$; then $R^7$ is selected from: $—CH_3$. In some embodiments, when $Y^1$ is C($R^9$% A) $Y^2$ is $C(R^{9bB})$, $Y^3$ is $C(R^{9bC})$, $Y^4$ is $C(R^{9bD})$, and $Y^5$ is N. then $R^7$ is selected from: $—CH_3$.

In some embodiments, for a compound or salt of Formula (Ia), when $R^C$ is H, and $R^Z$ is phenyl, then $R^7$ is selected from: hydrogen; $—C(O)R^{10f}$, $—C(O)N(R^{10f})_2$, $—C(O)OR^{10f}$, $—S(O)R^{10f}$, and $—S(O)_2R^{10f}$; $C_1$ alkyl substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, $=O$, $=S$, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; $C_{2-6}$ alkyl optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, $=O$, $=S$, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—N(R^{10f})C(O)N(R^{10f})_2$, $—OC(O)N(R^{10f})_2$, $—N(R^{10f})C(O)OR^{10f}$, $—C(O)OR^{10f}$, $—OC(O)R^{10f}$, $—S(O)R^{10f}$, $—S(O)_2R^{10f}$, $—NO_2$, $=O$, $=S$, $=N(R^{10f})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$. In some embodiments, for a compound or salt of Formula (Ia), when $R^C$ is H, and $R^Z$ is phenyl, then $R^7$ is selected from: hydrogen; $—C(O)R^{10f}$, $—C(O)N(R^{10f})_2$, $—C(O)OR^{10f}$, $—S(O)R^{10f}$, and $—S(O)_2R^{10f}$; $C_{2-6}$ alkyl optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, $=O$, $=S$, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—N(R^{10f})C(O)N(R^{10f})_2$, $—OC(O)N(R^{10f})_2$, $—N(R^{10f})C(O)OR^{10f}$, $—C(O)OR^{10f}$, $—OC(O)R^{10f}$, $—S(O)R^{10f}$, $—S(O)_2R^{10f}$, $—NO_2$, $=O$, $=S$, $=N(R^{10f})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$. In some embodiments, when $R^C$ is H, and $R^Z$ is phenyl, then $R^7$ is selected from: hydrogen; $C_{2-6}$ alkyl optionally substituted with one or more substituents independently selected from —F, and —OH, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $=O$, —CN, and $C_{1-6}$ alkyl, optionally substituted with one or more substituents independently selected from $R^{9f}$. In some embodiments, when $R^C$ is H, and $R^Z$ is phenyl, then $R^7$ is selected from: hydrogen. In some embodiments, when $R^c$ is H, and when $R^Z$ is phenyl, and when either: (i) $Y^1$ is N or $N^+(—O^-)$, $Y^2$ is $C(R^{9bB})$ $Y^3$ is $C(R^{9bC})$ $Y^4$ is $C(R^{9bD})$, and $Y^5$ is $C(R^{9bE})$; or (ii), $Y^1$ is $C(R^{9bA})$, $Y^2$ is $C(R^{9bB})$, $Y^3$ is $C(R^{9bC})$, $Y^4$ is $C(R^{9bD})$ and $Y^5$ is N or $N^+(—O^-)$; then $R^7$ is selected from: hydrogen; $—C(O)R^{10f}$, $—C(O)N(R^{10f})_2$, $—C(O)OR^{10f}$, $—S(O)R^{10f}$, and $—S(O)_2R^{10f}$; $C_1$ alkyl substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, $=O$, $=S$, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; $C_{2-6}$ alkyl optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, $=O$, $=S$, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, $—OR^{10f}$, $—SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$. In some embodiments, when $R^C$ is H, and $R^Z$ is phenyl, and when either: (i) $Y^1$ is N or $N^+$(—$O^-$), $Y^2$ is $C(R^{9bB})$, $Y^3$ is $C(R^{9bC})$, $Y^4$ is $C(R^{9bD})$, and $Y^5$ is $C(R^{9bE})$; or (ii), $Y^1$ is $C(R^{9bA})$, $Y^2$ is $C(R^{9bB})$, $Y^3$ is $C(R^{9bC})$, $Y^4$ is $C(R^{9bD})$, and $Y^5$ is N or $N^+$(—$O^-$); then $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{2-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$. In some embodiments, when $R^C$ is H, and $R^Z$ is phenyl, and when either: (i) $Y^1$ is N or $N^+$(—$O^-$), $Y^2$ is $C(R^{9bB})$, $Y^3$ is $C(R^{9bC})$, $Y^4$ is $C(R^{9bD})$, and $Y^5$ is $C(R^{9bE})$; or (11), $Y^1$ is $C(R^{9bA})$, $Y^2$ is $C(R^{9bB})$, $Y^3$ is $C(R^{9bC})$, $Y^4$ is $C(R^{9bD})$, and $Y^5$ is N or $N^+$(—$O^-$); then $R^7$ is selected from: hydrogen; $C_{2-6}$ alkyl optionally substituted with one or more substituents independently selected from —F, and —OH, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, =O, —CN, and $C_{1-6}$ alkyl, optionally substituted with one or more substituents independently selected from $R^{9f}$. In some embodiments, when $R^C$ is H, and $R^Z$ is phenyl, then $R^7$ is selected from: hydrogen.

In some embodiments, for a compound or salt of Formula (Ia), when $Y^1$ is N or $N^+$(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen; —CN, —$C(O)R^{10c}$, —$C(O)N(R^{10c})_2$, —$C(O)OR^{10c}$; $C_{1-6}$ alkyl, optionally substituted with one or more substituents independently selected from halogen, —$OR^{10c}$, —$SR^{10c}$, —$N(R^{10c})_2$, =O, —CN, $C_{3-10}$ carbocycle and 3- to 10-membered heterocycle; and $C_{3-10}$ cycloalkyl and 3- to 10-membered heterocycle, each of which is optionally substituted with one or more substituents. In some embodiments, when $Y^1$ is N or $N^+$(—O—), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen; $C_{1-6}$ alkyl, optionally substituted with one or more substituents independently selected from halogen, —$OR^{10c}$, —$SR^{10c}$, —$N(R^{10c})_2$, =O, and —CN; and $C_{3-10}$ cycloalkyl and 3- to 10-membered heterocycle. In some embodiments, when $Y^1$ is N or $N^+$(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen; and $C_{1-6}$ alkyl, optionally substituted with one or more substituents independently selected from halogen, —$OR^{10c}$, —$SR^{10c}$, —$N(R^{10c})_2$, =O, and —CN. In some embodiments, when $Y^1$ is N or $N^+$(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen; and $C_{1-6}$ alkyl, optionally substituted with one or more substituents independently selected from halogen and —CN. In some embodiments, when $Y^1$ is N or N+(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen and $C_{1-6}$ alkyl, optionally substituted with one or more substituents independently selected from halogen and —CN. In some embodiments, when $Y^1$ is N or $N^+$(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen and $C_{1-6}$ alkyl. In some embodiments, when $Y^1$ is N or $N^+$(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or $N^+$(—$O^-$); then $R^C$ is selected from: hydrogen and $C_1$ alkyl. In some embodiments, when $Y^1$ is N or $N^+$(—$O^-$), $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or N+(—O–); then $R^C$ is selected from: hydrogen. In some embodiments, when $Y^3$ is N or $N^+$(—$O^-$); then $R^C$ is selected from: hydrogen. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^C$ is selected from: hydrogen; —CN, —$C(O)R^{10c}$, —$C(O)N(R^{10c})_2$, —$C(O)OR^{10c}$; $C_{1-6}$ alkyl, optionally substituted with one or more substituents independently selected from halogen, —$OR^{10c}$, —$SR^{10c}$, —$N(R^{10c})_2$, =O, —CN, $C_{3-10}$ carbocycle and 3- to 10-membered heterocycle; and $C_{3-10}$ cycloalkyl and 3- to 10-membered heterocycle, each of which is optionally substituted with one or more substituents. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N or N; then $R^C$ is selected from: hydrogen; $C_{1-6}$ alkyl, optionally substituted with one or more substituents independently selected from halogen, —$OR^{10c}$, —$SR^{10c}$, —$N(R^{10c})_2$, =O, and —CN; and $C_{3-10}$ cycloalkyl and 3- to 10-membered heterocycle. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^C$ is selected from: hydrogen; and $C_{1-6}$ alkyl, optionally substituted with one or more substituents independently selected from halogen, —$OR^{10}$, —$SR^{10c}$, —$N(R^{10c})_2$, =O, and —CN. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^C$ is selected from: hydrogen; and $C_{1-6}$ alkyl, optionally substituted with one or more substituents independently selected from halogen and —CN. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^C$ is selected from: hydrogen and $C_{1-6}$ alkyl, optionally substituted with one or more substituents independently selected from halogen and —CN. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^c$ is selected from: hydrogen and $C_{1-6}$ alkyl. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^C$ is selected from: hydrogen and $C_1$ alkyl. In some embodiments, when $Y^1$ is N, $Y^2$ is C(H), $Y^3$ is C(H), $Y^4$ is C(H), and $Y^5$ is C(H); or when $Y^1$ is C(H), $Y^2$ is C(H), $Y^3$ is C(H), $Y^4$ is C(H), and $Y^5$ is N; then $R^C$ is selected from: hydrogen. In some embodiments, when $Y^3$ is N; then $R^C$ is selected from: hydrogen. In some embodiments, $R^C$ is a $C_{3-10}$ carbocycle optionally substituted with one or more substituents independently selected from halogen, —$OR^{10}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9c}$. In some embodiments, $R^C$ is a $C_{3-5}$ carbocycle or $C_{7-10}$ carbocycle optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9c}$. In some embodiments, $R^C$ is a $C_6$ carbocycle optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9c}$. In some embodiments, $R^C$ is a $C_6$ carbocycle substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9c}$.

In some embodiments, for a compound or salt of Formula (Ia), when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen; —CN, —$C(O)R^{10c}$, —$C(O)N(R^{10c})_2$, —$C(O)OR^{10c}$; $C_{1-6}$ alkyl, optionally substituted with one or more substituents independently selected from halogen, —$OR^{10c}$, —$SR^{10c}$, —$N(R^{10c})_2$, =O, —CN, $C_{3-10}$ carbocycle and 3- to 10-membered heterocycle; and $C_{3-10}$ cycloalkyl and 3- to 10-membered heterocycle, each of which is optionally substituted with one or more substituents independently selected from halogen, —$OR^{10c}$, —$SR^{10c}$, —$N(R^{10c})_2$, =O, —CN, and $C_{1-6}$ alkyl.

In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen; $C_{1-6}$ alkyl, optionally substituted with one or more substituents independently selected from halogen, —$OR^{10c}$, —$SR^{10c}$, —$N(R^{10c})_2$, =O, and —CN; and $C_{3-10}$ cycloalkyl and 3- to 10-membered heterocycle. In some embodiments, when $Y^1$ is $C(R^{9bA})$, $Y^2$ is $C(R^{9bB})$ $Y^3$ is N, $Y^4$ is $C(R^{9bD})$, and $Y^5$ is $C(R^{9bE})$; then $R^C$ is selected from: hydrogen; and $C_{1-6}$ alkyl, optionally substituted with one or more substituents independently selected from halogen, —$OR^{10c}$, —$SR^{10c}$, —$N(R^{10c})_2$, =O, and —CN. In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen; and $C_{1-6}$ alkyl, optionally substituted with one or more substituents independently selected from halogen and —CN. In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^c$ is selected from: hydrogen and $C_{1-6}$ alkyl, optionally substituted with one or more substituents independently selected from halogen and —CN. In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen and $C_{1-6}$ alkyl. In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen and $C_1$. In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen. In some embodiments, when $Y^3$ is N; then $R^C$ is selected from: hydrogen.

In some embodiments, for a compound or salt of Formula (Ia), when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^7$ is selected from: hydrogen; $C_1$ alkyl substituted with one or more substituents independently selected from halogen, —$OR^{10f}$, and —CN; $C_{2-6}$ alkyl, optionally substituted with one or more substituents independently selected from halogen, —$OR^{10f}$, —$SR^{10f}$, —$N(R^{10f})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$NO_2$, =O, —CN, and $C_{1-6}$ alkyl. In some embodiments, for a compound or salt of Formula (Ia), when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^7$ is selected from: hydrogen; $C_{2-6}$ alkyl, optionally substituted with one or more substituents independently selected from halogen, and —CN; and $C_{3-10}$ carbocycle and 3- to 10-membered heterocycle. In some embodiments, when $Y^1$ is $C(R^{9bA})$ $Y^2$ is $C(R^{9bB})$, $Y^3$ is N, $Y^4$ is $C(R^{9bD})$, and $Y^5$ is $C(R^{9bE})$; then $R^7$ is selected from: hydrogen and $C_{2-6}$ alkyl. In some embodiments, when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^7$ is selected from: hydrogen. In some embodiments, when $Y^3$ is N; then $R^7$ is selected from: hydrogen.

In some embodiments, for a compound or salt of Formula (Ia), when $Y^3$ is N, then no more than three of $X^1$, $X^2$, $X^3$, and $X^4$ are C(H). In some embodiments, for a compound or salt of Formula (Ia), when $Y^1$ and $Y^4$ are both N, then no more than three of $X^1$, $X^2$, $X^3$, and $X^4$ are C(H). In some embodiments, when $Y^1$ is N, then no more than three of $X^1$, $X^2$, $X^3$, and $X^4$ are C(H). In some embodiments, when $Y^2$ is N, then no more than three of $X^1$, $X^2$, $X^3$, and $X^4$ are C(H). In some embodiments, when $Y^3$ is N, then no more than three of $X^1$, $X^2$, $X^3$, and $X^4$ are C(H). In some embodiments, when $Y^4$ is N, then no more than three of $X^1$, $X^2$, $X^3$, and $X^4$ are C(H). In some embodiments, when $Y^5$ is N, then no more than three of $X^1$, $X^2$, $X^3$, and $X^4$ are C(H). In some embodiments, when two of $Y^1$, $Y^2$, $Y^3$, $Y^4$, and $Y^5$ are N, then no more than three of $X^1$, $X^2$, $X^3$, and $X^4$ are C(H).

In some embodiments, the compound or salt of Formula (Ia) is selected from: compound 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, 213, 214, 215, 3001, 3002, 3003, 3004, 3005, 3006, 3007, 3008, 3009, 3010, 3011, 3013, 3014, and 3015, or a salt thereof. In some embodiments, the compound or salt of Formula (Ia) is selected from: compound 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, 213, 214, and 215 or a salt thereof. In some embodiments, the compound or salt of Formula (Ia) is selected from: compound 3008, 13, 22, 3002, 3009, 208, 8, 3004, 210, 21, 3006, 6, 3007, 206, 3013, 7, 3010, 30, 12, 4, 18, 20, 3011, 17, 3015, 3005, 16, 203, 1, 14,29, 3003, 204, 2, 11, 5, 3, 15, 19, 27, 28, 47, 106, 201, 202, 205, 207, 209, 211, 212, 3001, and 3014, or a salt thereof. In some embodiments, the compound or salt of Formula (Ia) is selected from: compound 3008, 13, 22, 3002, 3009, 208, 8, 3004, 210, 21, 3006, 6, 3007, 206, 3013, 7, 3010, 30, 12, 4, 18, 20, 3011, 17, 3015, 3005, 16, 203, 1, 14, 29, 3003, and 204, or a salt thereof. In some embodiments, the compound or salt of Formula (Ia) is selected from: compound 3008, 13, 22, 3002, 3009, 208, 8, 3004, 210, 21, 3006,6, 3007, 206, 3013, 7, 3010, 30, 12, 4, 18, 20, and 3011, or a salt thereof. In some embodiments, the compound or salt of Formula (Ia) is selected from: compound 3008, 13, 22, 3002, 3009, 208, 8, 3004, 210, 21, 3006, 6, and 3007, or a salt thereof. In some embodiments, the compound or salt of Formula (Ia) is selected from: compound 3008, or a salt thereof. In some embodiments, the compound or salt of Formula (Ia) is selected from: compound, 97, 105, 98, 99, 100, 213, 214, 215, 13, 3008, 22, 208, 8, 3009, 3002, 6, 210, 4, 3004, 3013, 5, 3006, 206, 3007, 7, 18, 17, 16, 1, 3, 12, 3011, 3003, 47, 29, 21, 3015, 3010, 20, 203, 3005, 15, 3001, 205, 14, 11, 202, 19, 2, 201, and 28, or a salt thereof. In some embodiments, the compound or salt of Formula (Ia) is selected from: compound, 97, 105, 98, 99, 100, 213, 214, 215, 13, 3008, 22, 208, 8, 3009, 3002, 6, 210, 4, 3004, 3013, 5, 3006, 206, 3007, 7, 18, 17, 16, 1, 3, 12, 3011, 3003, 47, 29, 21, 3015, 3010, 20, 203, 3005, 15, 3001, 205, 14, and 11, or a salt thereof. In some embodiments, the compound or salt of Formula (Ia) is selected from: compound, 97, 105, 98, 99, 100, 213, 214, 215, 13, 3008, 22, 208, 8, 3009, 3002, 6, 210, 4, 3004, 3013, 5, 3006, 206, 3007, 7, 18, 17, 16, and 1, or a salt thereof. In some embodiments, the compound or salt of Formula (Ia) is selected from: compound, 97, 105, 98, 99, 100, 213, 214, 215, 13, 3008, 22, 208, and 8, or a salt thereof. In some embodiments, the compound or salt of Formula (Ia) is selected from: compound 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, 214, 3001, 3002, 3003, 3004, 3005, 3006, 3007, 3008, 3009, 3010, 3011, 3013, 3014, and 3015, or a salt thereof. In some embodiments, the compound or salt of Formula (Ia) is selected from: compound 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, and 214, or a salt thereof. In some embodiments, the compound or salt of Formula (Ia) is selected from: compound 3008, 13, 22, 3002, 3009, 208, 8, 3004, 210, 21, 3006, 6, 3007, 206, 3013, 7, 3010, 30, 12, 4, 18, 20, 3011, 17, 3015, 3005, 16, 203, 1, 14,29, 3003, 204, 2, 11, 5, 3, 15, 19, 27, 28, 47, 106, 201, 202, 205, 207, 209, 211, 212, 3001, and 3014, or a salt thereof. In some embodiments, the compound or salt of Formula (Ia) is selected from: compound 3008, 13, 22, 3002, 3009, 208, 8, 3004, 210, 21, 3006, 6, 3007, 206, 3013, 7, 3010, 30, 12, 4, 18, 20, 3011, 17, 3015, 3005, 16, 203, 1, 14, 29, 3003, and 204, or a salt thereof. In some embodiments, the compound or salt of Formula (Ia) is selected from: compound 3008, 13, 22, 3002, 3009, 208, 8, 3004, 210, 21, 3006, 6, 3007, 206, 3013, 7, 3010, 30, 12, 4, 18, 20, and 3011, or a salt thereof. In some embodiments, the compound or salt of Formula (Ia) is selected from: compound 3008, 13, 22, 3002, 3009, 208, 8, 3004, 210, 21, 3006, 6, and 3007, or a salt thereof. In some embodiments, the compound or salt of Formula (Ia) is selected from: compound 3008, or a salt thereof. In some embodiments, the compound or salt of Formula (Ia) is selected from: compound, 97, 105, 98, 99, 100, 214, 13, 3008, 22, 208, 8, 3009, 3002, 6, 210, 4, 3004, 3013, 5, 3006, 206, 3007, 7, 18, 17, 16, 1, 3, 12, 3011, 3003, 47, 29, 21, 3015, 3010, 20, 203, 3005, 15, 3001, 205, 14, 11, 202, 19, 2, 201, and 28, or a salt thereof. In some embodiments, the compound or salt of Formula (Ia) is selected from: compound, 97, 105, 98, 99, 100, 214, 13, 3008, 22, 208, 8, 3009, 3002, 6, 210, 4, 3004, 3013, 5, 3006, 206, 3007, 7, 18, 17, 16, 1, 3, 12, 3011, 3003, 47, 29, 21, 3015, 3010, 20, 203, 3005, 15, 3001, 205, 14, and 11, or a salt thereof. In some embodiments, the compound or salt of Formula (Ia) is selected from: compound, 97, 105, 98, 99, 100, 214, 13, 3008, 22, 208, 8, 3009, 3002, 6, 210, 4, 3004, 3013, 5, 3006, 206, 3007, 7, 18, 17, 16, and 1, or a salt thereof. In some embodiments, the compound or salt of Formula (Ia) is selected from: compound, 97, 105, 98, 99, 100, 214, 13, 3008, 22, 208, and 8, or a salt thereof.

In one aspect, disclosed herein is a compound represented by Formula (Ib):

(Ib)

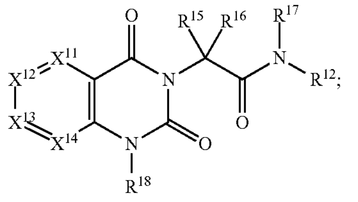

or a salt thereof, wherein: $R^2$ is selected from

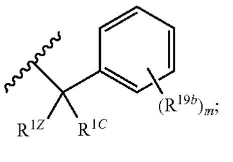

m is an integer selected from 1, 2, 3, 4, and 5; $X^{11}$ is selected from $C(R^{11a})$, N, and $N^+(—O^-)$; $X^{12}$ is selected from $C(R^{11b})$ N, and $N^+(—O^-)$; $X^{13}$ is selected from $C(R^{1a})$, N, and $N^+(—O^-)$; $X^{14}$ is selected from $C(R^{10d})$, N, and $N^+(—O^-)$; wherein at least one of $X^{11}$, $X^{12}$, $X^{13}$, and $X^{14}$ is N or $N^+(—O^-)$; wherein no more than two of $X^{11}$, $X^{12}$, $X^{13}$, and $X^{14}$ are N or $N^+(—O^-)$; $R^{11a}$, $R^{11b}$, $R^{11c}$, and $R^{11d}$ are each independently selected from: hydrogen; halogen, $—NO_2$, $—N_3$, —CN, $—OR^{110a}$, $—SR^{110a}$, $—N(R^{110a})_2$, $—C(O)R^{110a}$, $—C(O)N(R^{110a})_2$, $—N(R^{110a})C(O)R^{110a}$, $—N(R^{110a})C(O)N(R^{110a})_2$, $—OC(O)N(R^{110a})_2$, $—N(R^{110a})C(O)$ OR$^{110a}$, —C(O)OR$^{110a}$, —OC(O)R$^{110a}$, —S(O)R$^{110a}$, and —S(O)$_2$R$^{110a}$; C$_{1-6}$ alkyl, C$_{2-6}$ alkenyl, and C$_{2-6}$ alkynyl, each of which is optionally substituted with one or more substituents independently selected from halogen, —OR$^{110a}$, —SR$^{110a}$, —N(R$^{110a}$)$_2$, —C(O)R$^{110a}$, —C(O)N(R$^{110a}$)$_2$, —N(R$^{110a}$)C(O)R$^{110a}$, —C(O)OR$^{110a}$, —OC(O)R$^{110a}$, —N(R$^{110a}$)C(O)N(R$^{110a}$)$_2$, —OC(O)N(R$^{110a}$)$_2$, —N(R$^{110a}$)C(O)OR$^{110a}$, —S(O)R$^{110a}$, —S(O)$_2$R$^{110a}$, —NO$_2$, =O, =S, =N(R$^{110a}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19a}$; and C$_{3-10}$ carbocycle and 3- to 10-membered heterocycle, each of which is optionally substituted with one or more substituents independently selected from halogen, —OR$^{110a}$, —SR$^{110a}$, —N(R$^{110a}$)$_2$, —C(O)R$^{110a}$, —C(O)N(R$^{110a}$)$_2$, —N(R$^{110a}$)C(O)R$^{110a}$, —N(R$^{110a}$)C(O)N(R$^{110a}$)$_2$, —OC(O)N(R$^{110a}$)$_2$, —N(R$^{110a}$)C(O)OR$^{110a}$, —C(O)OR$^{110a}$, —OC(O)R$^{110a}$, —S(O)R$^{110a}$, —S(O)$_2$R$^{110a}$, —NO$_2$, =O, =S, =N(R$^{110a}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19a}$; R$^{1Z}$ is selected from: —C(O)R$^{110z}$, —C(O)N(R$^{110z}$)$_2$, —C(O)OR$^{110z}$, and —CN; C$_{1-6}$ alkyl, C$_{2-6}$ alkenyl, and C$_{2-6}$ alkynyl, each of which is optionally substituted with one or more substituents independently selected from halogen, —OR$^{110z}$, —SR$^{110z}$, —N(R$^{110z}$)$_2$, —C(O)R$^{110z}$, —C(O)N(R$^{110z}$)$_2$, —N(R$^{110z}$)C(O)R$^{110z}$, —C(O)OR$^{110z}$, —OC(O)R$^{110z}$, —N(R$^{110z}$)C(O)N(R$^{110z}$)$_2$, —OC(O)N(R$^{110z}$)$_2$, —N(R$^{110z}$)C(O)OR$^{110z}$, —S(O)R$^{110z}$, —S(O)$_2$R$^{110z}$, —NO$_2$, =O, =S, =N(R$^{110z}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19z}$; and C$_{3-10}$ carbocycle and 3- to 10-membered heterocycle, each of which is optionally substituted with one or more substituents independently selected from halogen, —OR$^{110z}$, —SR$^{110z}$, —N(R$^{110z}$)$_2$, —C(O)R$^{110z}$, —C(O)N(R$^{110z}$)$_2$, —N(R$^{110z}$)C(O)R$^{110z}$, —N(R$^{110z}$)C(O)N(R$^{110z}$)$_2$, —OC(O)N(R$^{110z}$)$_2$, —N(R$^{110z}$)C(O)OR$^{110z}$, —C(O)OR$^{110z}$, —OC(O)R$^{110z}$, —S(O)R$^{110z}$, —S(O)$_2$R$^{110z}$, —NO$_2$, =O, =S, =N(R$^{110z}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19z}$; R$^{1C}$ is selected from: hydrogen; —C(O)R$^{110c}$, —C(O)N(R$^{110c}$)$_2$, —C(O)OR$^{110c}$, and —CN; C$_{1-6}$ alkyl, C$_{2-6}$ alkenyl, and C$_{2-6}$ alkynyl, each of which is optionally substituted with one or more substituents independently selected from halogen, —OR$^{110c}$, —SR$^{110c}$, —N(R$^{110c}$)$_2$, —C(O)R$^{110c}$, —C(O)N(R$^{110c}$)$_2$, —N(R$^{110c}$)C(O)R$^{110c}$, —C(O)OR$^{110c}$, —OC(O)R$^{110c}$, —N(R$^{110c}$)C(O)N(R$^{110c}$)$_2$, —OC(O)N(R$^{110c}$)$_2$, —N(R$^{110c}$)C(O)OR$^{110c}$, —S(O)R$^{110c}$, —S(O)$_2$R$^{110c}$, —NO$_2$, =O, =S, =N(R$^{110c}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19c}$; and C$_{3-10}$ carbocycle and 3- to 10-membered heterocycle, each of which is optionally substituted with one or more substituents independently selected from halogen, —OR$^{110c}$, —SR$^{110c}$, —N(R$^{110c}$)$_2$, —C(O)R$^{110c}$, —C(O)N(R$^{110c}$)$_2$, —N(R$^{110c}$)C(O)R$^{110c}$, —N(R$^{110c}$)C(O)N(R$^{110c}$)$_2$, —OC(O)N(R$^{110c}$)$_2$, —N(R$^{110c}$)C(O)OR$^{110c}$, —C(O)OR$^{110c}$, —OC(O)R$^{110c}$, —S(O)R$^{110c}$, —S(O)$_2$R$^{110c}$, —NO$_2$, =O, =S, =N(R$^{110c}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19c}$; R$^{15}$ is selected from: hydrogen; halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —C(O)OR$^{110d}$, —OC(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —S(O)R$^{110d}$, —S(O)$_2$R$^{110d}$, —NO$_2$, —N$_3$, and —CN; C$_{1-6}$ alkyl, C$_{2-6}$ alkenyl, and C$_{2-6}$ alkynyl, each of which is optionally substituted with one or more substituents independently selected from halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —C(O)OR$^{110d}$, —OC(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —S(O)R$^{110d}$, —S(O)$_2$R$^{110d}$, —NO$_2$, =O, =S, =N(R$^{110d}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19d}$; and C$_{3-10}$ carbocycle and 3- to 10-membered heterocycle, each of which is optionally substituted with one or more substituents independently selected from halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —C(O)OR$^{110d}$, —OC(O)R$^{110d}$, —S(O)R$^{110d}$, —S(O)$_2$R$^{110d}$, —NO$_2$, =O, =S, =N(R$^{110d}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19d}$; or R$^{15}$ together with R$^{16}$ form a 3- to 10-membered heterocycle or C$_{3-10}$ carbocycle, wherein the 3- to 10-membered heterocycle or C$_{3-10}$ carbocycle is optionally substituted with one or more R$^{19d}$; R$^{16}$ is selected from: hydrogen; halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —C(O)OR$^{110e}$, —OC(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —S(O)R$^{110e}$, —S(O)$_2$R$^{110e}$, —NO$_2$, —N$_3$, and —CN; C$_{1-6}$ alkyl, C$_{2-6}$ alkenyl, and C$_{2-6}$ alkynyl, each of which is optionally substituted with one or more substituents independently selected from halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —C(O)OR$^{110e}$, —OC(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —S(O)R$^{110e}$, —S(O)$_2$R$^{110e}$, —NO$_2$, =O, =S, =N(R$^{110e}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19e}$; and C$_{3-10}$ carbocycle and 3- to 10-membered heterocycle, each of which is optionally substituted with one or more substituents independently selected from halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —C(O)OR$^{110e}$, —OC(O)R$^{110e}$, —S(O)R$^{110e}$, —S(O)$_2$R$^{110e}$, —NO$_2$, =O, =S, =N(R$^{110e}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19e}$; or R$^{16}$ together with R$^{15}$ form a 3- to 10-membered heterocycle or C$_{3-10}$ carbocycle, wherein the 3- to 10-membered heterocycle or C$_{3-10}$ carbocycle is optionally substituted with one or more R$^{19e}$; R$^{17}$ is selected from: hydrogen; —C(O)R$^{110f}$, —C(O)N(R$^{110f}$)$_2$, —C(O)OR$^{110f}$, —S(O)R$^{110f}$, and —S(O)$_2$R$^{110f}$; C$_{1-6}$ alkyl optionally substituted with one or more substituents independently selected from halogen, —OR$^{110f}$, —SR$^{110f}$, —N(R$^{110f}$)$_2$, —C(O)R$^{110f}$, —C(O)N(R$^{110f}$)$_2$, —N(R$^{110f}$)C(O)R$^{110f}$, —C(O)OR$^{110f}$, —OC(O)R$^{110f}$, —N(R$^{110f}$)C(O)N(R$^{110f}$)$_2$, —OC(O)N(R$^{110f}$)$_2$, —N(R$^{110f}$)C(O)OR$^{110f}$, —S(O)R$^{110f}$, —S(O)$_2$R$^{110f}$, —NO$_2$, =O, =S, =N(R$^{110f}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19f}$; and C$_{3-10}$ carbocycle and 3- to 10-membered heterocycle, each of which is optionally substituted with one or more substituents independently selected from halogen, —OR$^{110f}$, —SR$^{110f}$, —N(R$^{110f}$)$_2$, —C(O)R$^{110f}$, —C(O)N(R$^{110f}$)$_2$, —N(R$^{110f}$)C(O)R$^{110f}$, —N(R$^{110f}$)C(O)N(R$^{110f}$)$_2$, —OC(O)N(R$^{110f}$)$_2$, —N(R$^{110f}$)C(O)OR$^{110f}$, —C(O)OR$^{110f}$, —OC(O)R$^{110f}$, —S(O)R$^{110f}$, —S(O)$_2$R$^{110f}$, —NO$_2$, ═O, ═S, ═N(R$^{110f}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19f}$; R$^{18}$ is selected from: hydrogen; —C(O)R$^{110g}$, —C(O)N(R$^{110g}$)$_2$, —C(O)OR$^{110g}$, —S(O)R$^{110g}$, and —S(O)$_2$R$^{110g}$; C$_{1-6}$ alkyl optionally substituted with one or more substituents independently selected from halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —C(O)OR$^{110g}$, —OC(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —S(O)R$^{110g}$, —S(O)$_2$R$^{110g}$, —NO$_2$, ═O, ═S, ═N(R$^{110g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19g}$; and C$_{3-10}$ carbocycle and 3- to 10-membered heterocycle, each of which is optionally substituted with one or more substituents independently selected from halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —C(O)OR$^{110g}$, —OC(O)R$^{110g}$, —S(O)R$^{110g}$, —S(O)$_2$R$^{110g}$, —NO$_2$, ═O, ═S, ═N(R$^{110g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19g}$; each R$^{19a}$ is independently selected from: halogen, —OR$^{110a}$, —SR$^{10a}$, —N(R$^{110a}$)$_2$, —C(O)R$^{110a}$, —C(O)N(R$^{110a}$)$_2$, —N(R$^{110a}$)C(O)R$^{110a}$, —N(R$^{110a}$)C(O)N(R$^{110a}$)$_2$, —OC(O)N(R$^{110a}$)$_2$, —N(R$^{110a}$)C(O)OR$^{110a}$, —C(O)OR$^{110a}$, —OC(O)R$^{110a}$, —S(O)R$^{110a}$, —S(O)$_2$R$^{110a}$, —NO$_2$, ═O, ═S, ═N(R$^{110a}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110a}$, —SR$^{110a}$, —N(R$^{110a}$)$_2$, —C(O)R$^{110a}$, —C(O)N(R$^{110a}$)$_2$, —N(R$^{110a}$)C(O)R$^{110a}$, —N(R$^{110a}$)C(O)N(R$^{110a}$)$_2$, —OC(O)N(R$^{110a}$)$_2$, —N(R$^{110a}$)C(O)OR$^{110a}$, —C(O)OR$^{110a}$, —OC(O)R$^{110a}$, —S(O)R$^{110a}$, —S(O)$_2$R$^{110a}$, —NO$_2$, ═O, ═S, ═N(R$^{110a}$), —N$_3$, and —CN; each R$^{19b}$ is independently selected from: halogen, —NO$_2$, —N$_3$, —CN, —OR$^{110b}$, —SR$^{110b}$, —N(R$^{110b}$)$_2$, —C(O)R$^{110b}$, —C(O)N(R$^{110b}$)$_2$, —N(R$^{110b}$)C(O)R$^{110b}$, —N(R$^{110b}$)C(O)N(R$^{110b}$)$_2$, —OC(O)N(R$^{110b}$)$_2$, —N(R$^{110b}$)C(O)OR$^{110b}$, —C(O)OR$^{110b}$, —OC(O)R$^{110b}$, —S(O)R$^{110b}$, and —S(O)$_2$R$^{110b}$; C$_{1-6}$ alkyl, C$_{2-6}$ alkenyl, and C$_{2-6}$ alkynyl, each of which is optionally substituted with one or more substituents independently selected from halogen, —OR$^{110b}$, —SR$^{110b}$, —N(R$^{110b}$)$_2$, —C(O)R$^{110b}$, —C(O)N(R$^{110b}$)$_2$, —N(R$^{110b}$)C(O)R$^{110b}$, —C(O)OR$^{110b}$, —OC(O)R$^{110b}$, —N(R$^{110b}$)C(O)N(R$^{110b}$)$_2$, —OC(O)N(R$^{110b}$)$_2$, —N(R$^{110b}$)C(O)OR$^{110b}$, —S(O)R$^{110b}$, —S(O)$_2$R$^{110b}$, —NO$_2$, ═O, ═S, ═N(R$^{110b}$), —N$_3$, —CN, C$_{3-10}$ carbocycle and 3- to 10-membered heterocycle, wherein the C$_{3-10}$ carbocycle and 3- to 10-membered heterocycle; and C$_{3-10}$ carbocycle and 3- to 10-membered heterocycle, each of which is optionally substituted with one or more substituents independently selected from halogen, —OR$^{110b}$, —SR$^{110b}$, —N(R$^{110b}$)$_2$, —C(O)R$^{110b}$, —C(O)N(R$^{110b}$)$_2$, —N(R$^{110b}$)C(O)R$^{110b}$, —N(R$^{110b}$)C(O)N(R$^{110b}$)$_2$, —OC(O)N(R$^{110b}$)$_2$, —N(R$^{110b}$)C(O)OR$^{110b}$, —C(O)OR$^{110b}$, —OC(O)R$^{110b}$, —S(O)R$^{110b}$, —S(O)$_2$R$^{110b}$, —NO$_2$, ═O, ═S, ═N(R$^{110b}$), —N$_3$, —CN, C$_{1-6}$ alkyl, C$_{2-6}$ alkenyl, and C$_{2-6}$ alkynyl; each R$^{19z}$ is independently selected from: halogen, —OR$^{110z}$, —SR$^{110z}$, —N(R$^{110z}$)$_2$, —C(O)R$^{110z}$, —C(O)N(R$^{110z}$)$_2$, —N(R$^{110z}$)C(O)R$^{110z}$, —N(R$^{110z}$)C(O)N(R$^{110z}$)$_2$, —OC(O)N(R$^{110z}$)$_2$, —N(R$^{110z}$)C(O)OR$^{110z}$, —C(O)OR$^{110z}$, —OC(O)R$^{110z}$, —S(O)R$^{110z}$, —S(O)$_2$R$^{110z}$, —NO$_2$, ═O, ═S, ═N(R$^{110z}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110z}$, —SR$^{110z}$, —N(R$^{110z}$)$_2$, —C(O)R$^{110z}$, —C(O)N(R$^{110z}$)$_2$, —N(R$^{110z}$)C(O)R$^{110z}$, —N(R$^{110z}$)C(O)N(R$^{110z}$)$_2$, —OC(O)N(R$^{110z}$)$_2$, —N(R$^{110z}$)C(O)OR$^{110z}$, —C(O)OR$^{110z}$, —OC(O)R$^{110z}$, —S(O)R$^{110z}$, —S(O)$_2$R$^{110z}$, —NO$_2$, ═O, ═S, ═N(R$^{110z}$), —N$_3$, and —CN; each R$^{19c}$ is independently selected from: halogen, —OR$^{110c}$, —SR$^{110c}$, —N(R$^{110c}$)$_2$, —C(O)R$^{110c}$, —C(O)N(R$^{110c}$)$_2$, —N(R$^{110c}$)C(O)R$^{110c}$, —N(R$^{110c}$)C(O)N(R$^{110c}$)$_2$, —OC(O)N(R$^{110c}$)$_2$, —N(R$^{110c}$)C(O)OR$^{110c}$, —C(O)OR$^{110c}$, —OC(O)R$^{110c}$, —S(O)R$^{110c}$, —S(O)$_2$R$^{110c}$, —NO$_2$, ═O, ═S, ═N(R$^{110c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110c}$, —SR$^{110c}$, —N(R$^{110c}$)$_2$, —C(O)R$^{110c}$, —C(O)N(R$^{110c}$)$_2$, —N(R$^{110c}$)C(O)R$^{110c}$, —N(R$^{110c}$)C(O)N(R$^{110c}$)$_2$, —OC(O)N(R$^{110c}$)$_2$, —N(R$^{110c}$)C(O)OR$^{110c}$, —C(O)OR$^{110c}$, —OC(O)R$^{110c}$, —S(O)R$^{110c}$, —S(O)$_2$R$^{110c}$, —NO$_2$, ═O, ═S, ═N(R$^{110c}$), —N$_3$, and —CN; each R$^{19d}$ is independently selected from: halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —C(O)OR$^{110d}$, —OC(O)R$^{110d}$, —S(O)R$^{110d}$, —S(O)$_2$R$^{110d}$, —NO$_2$, ═O, ═S, ═N(R$^{110d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —C(O)OR$^{110d}$, —OC(O)R$^{110d}$, —S(O)R$^{110d}$, —S(O)$_2$R$^{110d}$, —NO$_2$, ═O, ═S, ═N(R$^{110d}$), —N$_3$, and —CN; each R$^{19e}$ is independently selected from: halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —C(O)OR$^{110e}$, —OC(O)R$^{110e}$, —S(O)R$^{110e}$, —S(O)$_2$R$^{110e}$, —NO$_2$, ═O, ═S, ═N(R$^{110e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —C(O)OR$^{110e}$, —OC(O)R$^{110e}$, —S(O)R$^{110e}$, —S(O)$_2$R$^{110e}$, —NO$_2$, ═O, ═S, ═N(R$^{110e}$), —N$_3$, and —CN; each R$^{19f}$ is independently selected from: halogen, —OR$^{110f}$, —SR$^{110f}$, —N(R$^{110f}$)$_2$, —C(O)R$^{110f}$, —C(O)N(R$^{110f}$)$_2$, —N(R$^{110f}$)C(O)R$^{110f}$, —N(R$^{110f}$)C(O)N(R$^{110f}$)$_2$, —OC(O)N(R$^{110f}$)$_2$, —N(R$^{110f}$)C(O)OR$^{110f}$, —C(O)OR$^{110f}$, —OC(O)R$^{110f}$, —S(O)R$^{110f}$, —S(O)$_2$R$^{110f}$, —NO$_2$, ═O, ═S, ═N(R$^{110f}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110f}$, —SR$^{110f}$, —N(R$^{110f}$)$_2$, —C(O)R$^{110f}$, —C(O)N(R$^{110f}$)$_2$, —N(R$^{110f}$)C(O)R$^{110f}$, —N(R$^{110f}$)C(O)N(R$^{110f}$)$_2$, —OC(O)N(R$^{110f}$)$_2$, —N(R$^{110f}$)C(O)OR$^{110f}$, —C(O)OR$^{110f}$, —OC(O)R$^{110f}$, —S(O)R$^{110f}$, —S(O)$_2$R$^{110f}$, —NO$_2$, ═O, ═S, ═N(R$^{110f}$), —N$_3$, and —CN; each R$^{19g}$ is independently selected from:

halogen, $—OR^{110g}$, $—SR^{110g}$, $—N(R^{110g})_2$, $—C(O)R^{110g}$, $—C(O)N(R^{110g})_2$, $—N(R^{110g})C(O)R^{110g}$, $—N(R^{110g})C(O)N(R^{110g})_2$, $—OC(O)N(R^{110g})_2$, $—N(R^{110g})C(O)OR^{110g}$, $—C(O)OR^{110g}$, $—OC(O)R^{110g}$, $—S(O)R^{110g}$, $—S(O)_2R^{110g}$, $—NO_2$, ═O, ═S, $═N(R^{110g})$, $—N_3$, and —CN; and $C_{1-3}$ alkyl, $C_{2-3}$ alkenyl, and $C_{2-3}$ alkynyl, each of which is optionally substituted with one or more substituents independently selected from halogen, $—OR^{110g}$, $—SR^{110g}$, $—N(R^{110g})_2$, $—C(O)R^{110g}$, $—C(O)N(R^{110g})_2$, $—N(R^{110g})C(O)R^{110g}$, $—N(R^{110g})C(O)N(R^{110g})_2$, $—OC(O)N(R^{110g})_2$, $—N(R^{110g})C(O)OR^{110g}$, $—C(O)OR^{110g}$, $—OC(O)R^{110g}$, $—S(O)R^{110g}$, $—S(O)_2R^{110g}$, $—NO_2$, ═O, ═S, $═N(R^{110g})$, $—N_3$, and —CN; and each $R^{110a}$, $R^{110b}$, $R^{110b}$, $R^{110d}$, $R^{110e}$, $R^{110f}$, $R^{110g}$, $R^{110z}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, ═O, ═S, $—O—C_{1-6}$ alkyl, $—S—C_{1-6}$ alkyl, $—N(C_{1-6}\text{ alkyl})_2$, $—NH(C_{1-6}\text{ alkyl})$, $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, ═O, ═S, $—O—C_{1-6}$ alkyl, $—S—C_{1-6}$ alkyl, $—N(C_{1-6}\text{ alkyl})_2$, $—NH(C_{1-6}\text{ alkyl})$, $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; and wherein when $X^{14}$ is N or $N^+(—O^-)$, then $R^{18}$ is selected from: hydrogen; $—C(O)R^{110g}$, $—C(O)N(R^{110g})_2$, $—C(O)OR^{110g}$, $—S(O)R^{110g}$, and $—S(O)_2R^{110g}$; $C_1$ alkyl substituted with one or more substituents independently selected from halogen, $—OR^{110g}$, $—SR^{110g}$, $—N(R^{110g})_2$, $—C(O)R^{110g}$, $—C(O)N(R^{110g})_2$, $—N(R^{110g})C(O)R^{110g}$, $—C(O)OR^{110g}$, $—OC(O)R^{110g}$, $—N(R^{110g})C(O)N(R^{110g})_2$, $—OC(O)N(R^{110g})_2$, $—N(R^{110g})C(O)OR^{110g}$, $—S(O)R^{110g}$, $—S(O)_2R^{110g}$, $—NO_2$, ═O, ═S, $═N(R^{110g})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19g}$; $C_{2-6}$ alkyl optionally substituted with one or more substituents independently selected from halogen, $—OR^{110g}$, $—SR^{110g}$, $—N(R^{110g})_2$, $—C(O)R^{110g}$, $—C(O)N(R^{110g})_2$, $—N(R^{110g})C(O)R^{110g}$, $—C(O)OR^{110g}$, $—OC(O)R^{110g}$, $—N(R^{110g})C(O)N(R^{110g})_2$, $—OC(O)N(R^{110g})_2$, $—N(R^{110g})C(O)OR^{110g}$, $—S(O)R^{110g}$, $—S(O)_2R^{110g}$, $—NO_2$, ═O, ═S, $═N(R^{110g})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19g}$; and $C_{3-10}$ carbocycle and 3- to 10-membered heterocycle, each of which is optionally substituted with one or more substituents independently selected from halogen, $—OR^{110g}$, $—SR^{110g}$, $—N(R^{110g})_2$, $—C(O)R^{110g}$, $—C(O)N(R^{110g})_2$, $—N(R^{110g})C(O)R^{110g}$, $—N(R^{110g})C(O)N(R^{110g})_2$, $—OC(O)N(R^{110g})_2$, $—N(R^{110g})C(O)OR^{110g}$, $—C(O)OR^{110g}$, $—OC(O)R^{110g}$, $—S(O)R^{110g}$, $—S(O)_2R^{110g}$, $—NO_2$, ═O, ═S, $═N(R^{110g})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19g}$.

In one aspect, disclosed herein is a compound of Formula (Ib) that is represented by Formula (Ib-ep):

(Ib-ep)

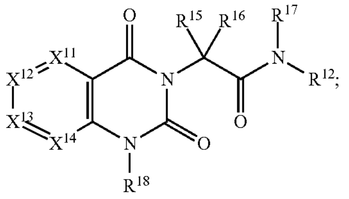

or a salt thereof, wherein: $R^{12}$ is selected from

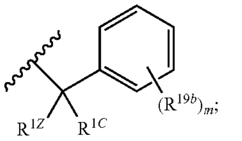

m is an integer selected from 1, 2, and 3; $X^{11}$ is selected from $C(R^{11a})$, and N; $X^{12}$ is selected from $C(R^{11b})$, and N; $X^{13}$ is selected from $C(R^{11c})$, and N; $X^{14}$ is selected from $C(R^{11d})$, and N; wherein at least one of $X^{11}$, $X^{12}$, $X^{13}$, and $X^{14}$ is N; wherein no more than two of $X^{11}$, $X^{12}$, $X^{13}$, and $X^{14}$ are N; $R^{11a}$, $R^{11b}$, $R^{11c}$, and $R^{11d}$ are each independently selected from: hydrogen; halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$; $C_{1-6}$ alkyl, optionally substituted with one or more substituents independently selected from halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, $—N(C_{1-6}\text{ alkyl})_2$, $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$, and $C_{1-6}$ alkyl; $R^{1Z}$ is selected from: $C_{1-6}$ alkyl, optionally substituted with one or more substituents independently selected from halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$, $C_{3-10}$ carbocycle and 3- to 10-membered heterocycle; $R^{1C}$ is selected from: hydrogen; $R^{15}$ and $R^{16}$ are each independently selected from: hydrogen; halogen; and $C_{1-6}$ alkyl, optionally substituted with one or more substituents independently selected from halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$, $C_{3-10}$ carbocycle, and 3- to 10-membered heterocycle; and $R^{17}$ is selected from: hydrogen; $R^{18}$ is selected from: hydrogen; and each $R^{19b}$ is independently selected from: halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$; $C_{1-6}$ alkyl, optionally substituted with one or more substituents independently selected from halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$; and $C_{3-10}$ carbocycle and 3- to 10-membered heterocycle, each of which is optionally substituted with one or more substituents independently selected from halogen, $—NO_2$, —CN, —OH, $—O(C_{1-6}\text{ alkyl})$, $—O(C_{1-6}\text{ haloalkyl})$, —SH, $—S(C_{1-6}\text{ alkyl})$, $—NH_2$, $—NH(C_{1-6}\text{ alkyl})$, and $—N(C_{1-6}\text{ alkyl})_2$.

In some embodiments, for a compound or salt of Formula (Ib), m is an integer selected from 1, 2, 3, and 4. In some embodiments, m is an integer selected from 1, 2, and 3. In some embodiments, m is an integer selected from 1 and 2. In some embodiments, m is an integer selected from 2. In some embodiments, m is an integer selected from 1. In some embodiments, m is an integer selected from 0.

In some embodiments, for a compound or salt of Formula (Ib), no more than two of $X^{11}$ $X^{12}$ $X^{13}$, and $X^{14}$ is N or $N^+(—O^-)$. In some embodiments, no more than one of $X^{11}$ $X^{12}$, $X^{13}$, and $X^{14}$ is N or $N^+(—O^-)$. In some embodiments, no more than two of $X^{11}$, $X^{12}$, $X^{13}$, and $X^{14}$ is N. In some embodiments, no more than one of $X^{11}$ $X^{12}$, $X^{13}$, and $X^{14}$ is N. In some embodiments, no more than three of $X^{11}$ $X^{12}$, $X^{13}$, and $X^{14}$ is N or $N^+(—O^-)$. In some embodiments, at least one of $X^{11}$, $X^{12}$, $X^{13}$ and $X^{14}$ is N or $N^+(—O^-)$. In some embodiments, at least one of $X^1$, $X^{12}$, $X^{13}$, and $X^{14}$ is N. In some embodiments, none of $X^{11}$, $X^{12}$, $X^{13}$, and $X^{14}$ need be N nor $N^+(—O^-)$. In some embodiments, $X^{11}$ is selected from $C(R^{11a})$, and $X^{12}$ is selected from $C(R^{11b})$, and $X^{13}$ is selected from $C(R^{11c})$, and $X^{14}$ is selected from $C(R^{11d})$, N, and $N^+(—O^-)$. In some embodiments, $X^{11}$ is selected from $C(R^{11a})$ and N, In some embodiments, $X^{11}$ is selected from $C(R^{11a})$, In some embodiments, $X^{11}$ is selected from C(H), C(OH), $C(OCH_3)$, and N. In some embodiments, $X^{11}$ is selected from C(H) and N. In some embodiments, $X^{11}$ is selected from N. In some embodiments, $X^{11}$ is selected from C(H). In some embodiments, $X^{12}$ is selected from $C(R^{11b})$ and N, In some embodiments, $X^{12}$ is selected from N, and C(H). In some embodiments, $X^{12}$ is selected from N. In some embodiments, $X^{13}$ is selected from $C(R^{11c})$ and N, In some embodiments, $X^{13}$ is selected from C(H) and N, In some embodiments, $X^{13}$ is selected from $C(R^{11c})$, In some embodiments, $X^{13}$ is selected from C(H). In some embodiments, $X^{13}$ is selected from $C(R^{11d})$ and N, In some embodiments, $X^{13}$ is selected from C(H) and N, In some embodiments, $X^{13}$ is selected from $C(R^{11d})$, In some embodiments, $X^{13}$ is selected from C(H). In some embodiments, $X^{13}$ and $X^{14}$ are C(H). In some embodiments, $X^{12}$ and $X^{14}$ are N; or $X^{11}$ and $X^{13}$ are N.

In some embodiments, for a compound or salt of Formula (Ib), $R^{11a}$, $R^{11b}$, $R^{11c}$, and $R^{11d}$, are each independently selected from: hydrogen; halogen, $—NO_2$, $—N_3$, —CN, $—OR^{110a}$, $—SR^{110a}$, $—N(R^{110a})_2$; $C_{1-6}$ alkyl optionally substituted with one or more substituents independently selected from halogen, $—OR^{110a}$, $—SR^{110a}$, $—N(R^{110a})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, $—OR^{110a}$, $—SR^{110a}$, $—N(R^{110a})_2$, =O, —CN, $C_{1-6}$ alkyl. In some embodiments, $R^{11a}$, $R^{11b}$, $R^{11c}$, and $R^{11d}$, are each independently selected from: hydrogen; halogen, $—NO_2$, $—N_3$, —CN, $—OR^{110a}$, $—SR^{110a}$, $—N(R^{110a})_2$; $C_{1-6}$ alkyl optionally substituted with one or more substituents independently selected from halogen, $—OR^{110a}$, $—SR^{110a}$, $—N(R^{110a})_2$, =O, —CN, $C_{3-10}$ carbocycle and 3- to 10-membered heterocycle; and $C_{3-10}$ carbocycle and 3- to 10-membered heterocycle. In some embodiments, $R^{11a}$, $R^{11b}$, $R^{11c}$, and $R^{11d}$, are each independently selected from: hydrogen; halogen, $—NO_2$, $—N_3$, —CN, $—OR^{110a}$, $—SR^{110a}$, $—N(R^{110a})_2$; and $C_{1-6}$ alkyl optionally substituted with one or more substituents independently selected from halogen, $—OR^{110a}$, $—SR^{110a}$, $—N(R^{110a})_2$, =O, —CN, $C_{3-10}$ carbocycle and 3- to 10-membered heterocycle. In some embodiments, $R^{11a}$, $R^{11b}$, $R^{11c}$, and $R^{11d}$, are each independently selected from: hydrogen; halogen, —CN, $—OR^{110a}$, $—N(R^{110a})_2$; and $C_{1-6}$ alkyl optionally substituted with one or more substituents independently selected from halogen, $—OR^{110a}$, and —CN. In some embodiments, $R^{11a}$, $R^{11b}$, $R^{11c}$, and $R^{11d}$, are each independently selected from: hydrogen, halogen, —CN, $—OR^{110a}$, $—N(R^{110a})_2$, and $C_{1-6}$ alkyl. In some embodiments, $R^{11a}$, $R^{11b}$, $R^{11c}$, and $R^{11d}$, are each independently selected from: hydrogen, halogen, —CN, and $—OR^{110a}$. In some embodiments, $R^{11a}$, $R^{11b}$, $R^{11c}$, and $R^{11d}$, are each independently selected from: hydrogen, fluoro, —CN, and $—OR^{110a}$. In some embodiments, $R^{11a}$, $R^{11b}$, $R^{11c}$, and $R^{11d}$, are each independently selected from: hydrogen and $—OR^{110a}$. In some embodiments, $R^{11a}$, $R^{11b}$, $R^{11c}$, and $R^{11d}$, are each independently selected from: hydrogen, —OH, and $—OCH_3$. In some embodiments, $R^{11a}$, $R^{11b}$, $R^{11c}$, and $R^{11d}$, are each independently selected from: hydrogen.

In some embodiments, for a compound or salt of Formula (Ib), $R^{1Z}$ is selected from: —CN, $—C(O)R^{10z}$, $—C(O)N(R^{10z})_2$, and $—C(O)OR^{10z}$; $C_{1-6}$ alkyl, $C_{2-6}$ alkenyl, and $C_{2-6}$ alkynyl, each of which is optionally substituted with one or more substituents independently selected from halogen, $—OR^{10z}$, $—SR^{10z}$, $—N(R^{10z})_2$, $—C(O)R^{10z}$, $—C(O)N(R^{10z})_2$, $—N(R^{10z})C(O)R^{10z}$, $—C(O)OR^{10z}$, $—OC(O)R^{10z}$, $—N(R^{10z})C(O)N(R^{10z})_2$, $—OC(O)N(R^{10z})_2$, $—N(R^{10z})C(O)OR^{10z}$, $—S(O)R^{10z}$, $—S(O)_2R^{10z}$, $—NO_2$, =O, =S, $=N(R^{10z})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19z}$; and $C_{3-10}$ carbocycle and 3- to 10-membered heterocycle, each of which is optionally substituted with one or more substituents independently selected from halogen, $—OR^{10z}$, $—SR^{10z}$, $—N(R^{10z})_2$, $—C(O)R^{10z}$, $—C(O)N(R^{10z})_2$, $—N(R^{10z})C(O)R^{10z}$, $—N(R^{10z})C(O)N(R^{10z})_2$, $—OC(O)N(R^{10z})_2$, $—N(R^{10z})C(O)OR^{10z}$, $—C(O)OR^{10z}$, $—OC(O)R^{10z}$, $—S(O)R^{10z}$, $—S(O)_2R^{10z}$, $—NO_2$, =O, =S, $=N(R^{10z})$, $—N_3$, —CN, and $C_{1-6}$ alkyl. In some embodiments, $R^{1Z}$ is selected from: —CN, $—C(O)R^{10z}$, $—C(O)N(R^{10z})_2$, and $—C(O)OR^{10z}$; $C_{1-6}$ alkyl, $C_{2-6}$ alkenyl, and $C_{2-6}$ alkynyl, each of which is optionally substituted with one or more substituents independently selected from halogen, $—OR^{10z}$, $—SR^{10z}$, $—N(R^{10z})_2$, $—C(O)R^{10z}$, $—C(O)N(R^{10z})_2$, $—N(R^{10z})C(O)R^{10z}$, $—C(O)OR^{10z}$, $—OC(O)R^{10z}$, $—N(R^{10z})C(O)N(R^{10z})_2$, $—OC(O)N(R^{10z})_2$, $—N(R^{10z})C(O)OR^{10z}$, $—S(O)R^{10z}$, $—S(O)_2R^{10z}$, $—NO_2$, =O, =S, $=N(R^{10z})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19z}$; and $C_{3-10}$ carbocycle and 3- to 10-membered heterocycle, each of which is optionally substituted with one or more substituents independently selected from halogen, $—OR^{10z}$, $—SR^{10z}$, $—N(R^{10z})_2$, $—N_3$, —CN, and $C_{1-6}$ alkyl. In some embodiments, $R^{1Z}$ is selected from: —CN, $—C(O)R^{10z}$, $—C(O)N(R^{10z})_2$, and $—C(O)OR^{10z}$; $C_{1-6}$ alkyl, $C_{2-6}$ alkenyl, and $C_{2-6}$ alkynyl, each of which is optionally substituted with one or more substituents independently selected from halogen, $—OR^{10z}$, $—SR^{10z}$, $—N(R^{10z})_2$, $—C(O)R^{10z}$, $—C(O)N(R^{10z})_2$, $—N(R^{10z})C(O)R^{10z}$, $—C(O)OR^{10z}$, $—OC(O)R^{10z}$, $—N(R^{10z})C(O)N(R^{10z})_2$, $—OC(O)N(R^{10z})_2$, $—N(R^{10z})C(O)OR^{10z}$, $—S(O)R^{10z}$, $—S(O)_2R^{10z}$, $—NO_2$, =O, =S, $=N(R^{10z})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19z}$; and $C_{3-10}$ carbocycle and 3- to 10-membered heterocycle, each of which is optionally substituted with one or more substituents independently selected from halogen and —CN. In some embodiments, $R^{1Z}$ is selected from: —CN, —C(O)$R^{10z}$, —C(O)N($R^{10z}$)$_2$, and —C(O)O$R^{10z}$; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2$$R^{10z}$, —$NO_2$, ═O, ═S, ═N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19Z}$; and $C_{3-10}$ carbocycle and 3- to 10-membered heterocycle. In some embodiments, $R^{1Z}$ is selected from: —CN, —C(O)$R^{10z}$, —C(O)N($R^{10z}$)$_2$, and —C(O)O$R^{10z}$; and $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2$$R^{10z}$, —$NO_2$, ═O, ═S, ═N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19z}$. In some embodiments, $R^{1Z}$ is selected from: —CN, —C(O)$R^{10z}$, —C(O)N($R^{10z}$)$_2$, and —C(O)O$R^{10z}$; and $C_{1-6}$ alkyl optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2$$R^{10z}$, —$NO_2$, ═O, ═S, ═N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19z}$. In some embodiments, $R^{1Z}$ is selected from: —CN, —C(O)$R^{10z}$, —C(O)N($R^{10z}$)$_2$, and —C(O)O$R^{10z}$; and $C_{1-6}$ alkyl optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2$$R^{10z}$, —$NO_2$, ═O, —$N_3$, —CN, $C_{3-10}$ carbocycle and 3- to 10-membered heterocycle. In some embodiments, $R^{1Z}$ is selected from: —CN, —C(O)$R^{10z}$, —C(O)N($R^{10z}$)$_2$, and —C(O)O$R^{10z}$; and $C_{1-6}$ alkyl optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, ═O, —$N_3$, —CN, $C_{3-10}$ carbocycle and 3- to 10-membered heterocycle. In some embodiments, $R^{1Z}$ is selected from: —CN, —C(O)$R^{10z}$, —C(O)N($R^{10z}$)$_2$, and —C(O)O$R^{10z}$; and $C_{1-6}$ alkyl optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$=0, —$N_3$, —CN. In some embodiments, $R^{1Z}$ is selected from: —CN, —C(O)$R^{10z}$, —C(O)N($R^{10z}$)$_2$, and —C(O)O$R^{10z}$; and $C_{1-6}$ alkyl optionally substituted with one or more substituents independently selected from halogen, —O$R^{10z}$, —S$R^{10z}$, —N($R^{10z}$)$_2$, ═O, —$N_3$, —CN. In some embodiments, $R^{1Z}$ is selected from $C_{1-6}$ alkyl optionally substituted with one or more substituents independently selected from halogen, —O$R^{10z}$, —S$R^{10z}$, —N($R^{10z}$)$_2$, ═O, —$N_3$, —CN. In some embodiments, $R^{1Z}$ is selected from $C_{1-6}$ alkyl optionally substituted with one or more substituents independently selected from halogen, —O$R^{10z}$, and —CN. In some embodiments, $R^{1Z}$ is selected from $C_{1-6}$ alkyl optionally substituted with one or more substituents independently selected from fluoro, —O$R^{10z}$, and —CN. In some embodiments, $R^{1Z}$ is selected from $C_{1-6}$ alkyl optionally substituted with one or more substituents independently selected from fluoro and —CN. In some embodiments, $R^{1Z}$ is selected from $C_{1-6}$ alkyl optionally substituted with one or more substituents independently selected from fluoro. In some embodiments, $R^{1Z}$ is selected from $C_{1-6}$ alkyl. In some embodiments, $R^{1Z}$ is selected from $C_{1-3}$ alkyl. In some embodiments, $R^{1Z}$ is selected from $C_{1-2}$ alkyl. In some embodiments, $R^{1Z}$ is selected from $C_1$ alkyl. In some embodiments, $R^{1Z}$ is selected from hydrogen. In some embodiments, $R^{1Z}$ is selected from —$CF_3$. In some embodiments, $R^{1Z}$ is selected from —$CH_2$OH. In some embodiments, $R^{1Z}$ is selected from halogen. In some embodiments, $R^{1Z}$ is selected from fluorine.

In some embodiments, for a compound or salt of Formula (Ib), $R^{1C}$ is selected from: hydrogen; —CN, —C(O)$R^{110c}$, —C(O)N($R^{110c}$)$_2$, —C(O)O$R^{110c}$; $C_{1-6}$ alkyl, $C_{2-6}$ alkenyl, and $C_{2-6}$ alkynyl, each of which is optionally substituted with one or more substituents independently selected from halogen, —O$R^{110c}$, —S$R^{110c}$, —N($R^{110c}$)$_2$, —C(O)$R^{110c}$, —C(O)N($R^{110c}$)$_2$, —N($R^{110c}$)C(O)$R^{110c}$, —C(O)O$R^{110c}$, —OC(O)$R^{110c}$, —N($R^{110c}$)C(O)N($R^{110c}$)$_2$, —OC(O)N($R^{110c}$)$_2$, —N($R^{110c}$)C(O)O$R^{110c}$, —S(O)$R^{110c}$, —S(O)$_2$$R^{110c}$, —$NO_2$, ═O, ═S, ═N($R^{110c}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19c}$; and $C_{3-10}$ carbocycle and 3- to 10-membered heterocycle. In some embodiments, $R^{1C}$ is selected from: hydrogen; —CN, —C(O)$R^{110c}$, —C(O)N($R^{110c}$)$_2$, —C(O)O$R^{110c}$; and $C_{1-6}$ alkyl, $C_{2-6}$ alkenyl, and $C_{2-6}$ alkynyl, each of which is optionally substituted with one or more substituents independently selected from halogen, —O$R^{110c}$, —S$R^{110c}$, —N($R^{110c}$)$_2$, —C(O)$R^{110c}$, —C(O)N($R^{110c}$)$_2$, —N($R^{110c}$)C(O)$R^{110c}$, —C(O)O$R^{110c}$, —OC(O)$R^{110c}$, —N($R^{110c}$)C(O)N($R^{110c}$)$_2$, —OC(O)N($R^{110c}$)$_2$, —N($R^{110c}$)C(O)O$R^{110c}$, —S(O)$R^{110c}$, —S(O)$_2$$R^{110c}$, —$NO_2$, ═O, ═S, ═N($R^{110c}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19c}$. In some embodiments, $R^{1C}$ is selected from: hydrogen; —CN, —C(O)$R^{110c}$, —C(O)N($R^{110c}$)$_2$, —C(O)O$R^{110c}$; and $C_{1-6}$ alkyl, $C_{2-6}$ alkenyl, and $C_{2-6}$ alkynyl, each of which is optionally substituted with one or more substituents independently selected from halogen, —O$R^{110c}$, —S$R^{110c}$, —N($R^{110c}$)$_2$, ═O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{19c}$. In some embodiments, $R^{1C}$ is selected from: hydrogen; —CN, —C(O)$R^{110c}$, —C(O)N($R^{110c}$)$_2$, —C(O)O$R^{110c}$; and $C_{1-6}$ alkyl optionally substituted with one or more substituents independently selected from halogen, —O$R^{110c}$, —S$R^{110c}$, —N($R^{110c}$)$_2$, ═O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{19c}$. In some embodiments, $R^{1C}$ is selected from: hydrogen; —CN, —C(O)$R^{110c}$, —C(O)N($R^{110c}$)$_2$, —C(O)O$R^{110c}$; and $C_{1-6}$ alkyl optionally substituted with one or more substituents independently selected from halogen, —O$R^{110c}$, —S$R^{110c}$, —N($R^{110c}$)$_2$, ═O, —$N_3$, and —CN, $C_{3-10}$ carbocycle and 3- to 10-membered heterocycle. In some embodiments, $R^{1C}$ is selected from: hydrogen; —CN, —C(O)$R^{110c}$, —C(O)N$(R^{110c})_2$, —C(O)O$R^{110c}$; and $C_{1-6}$ alkyl optionally substituted with one or more substituents independently selected from halogen, —O$R^{110c}$, —S$R^{110c}$, —N$(R^{110c})_2$, =O, —$N_3$, and —CN. In some embodiments, $R^{1C}$ is selected from: hydrogen; —CN, —C(O)$R^{110c}$, —C(O)N$(R^{110c})_2$, —C(O)O$R^{110c}$; and $C_{1-6}$ alkyl optionally substituted with one or more substituents independently selected from halogen, and —CN. In some embodiments, $R^{1C}$ is selected from: hydrogen; —CN; and $C_{1-6}$ alkyl optionally substituted with one or more substituents independently selected from halogen, and —CN. In some embodiments, $R^{1C}$ is selected from: hydrogen, —CN, and $C_{1-6}$ alkyl. In some embodiments, $R^{1C}$ is selected from: hydrogen and $C_{1-6}$ alkyl. In some embodiments, $R^{1C}$ is selected from: hydrogen and $C_1$ alkyl. In some embodiments, $R^{1C}$ is selected from: hydrogen. In some embodiments, $R^{1C}$ is selected from halogen. In some embodiments, $R^{1C}$ is selected from fluoro.

In some embodiments, for a compound or salt of Formula (Ib), $R^{15}$ is selected from: hydrogen; halogen, —C(O)$R^{110d}$, —C(O)N$(R^{110d})_2$, —C(O)O$R^{110d}$, —S(O)$R^{110d}$, —S(O)$_2$$R^{110d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —C(O)O$R^{110d}$, —OC(O)$R^{110d}$, —N$(R^{110d})$C(O)N$(R^{110d})_2$, —OC(O)N$(R^{110d})_2$, —N$(R^{110d})$C(O)O$R^{110d}$, —S(O)$R^{110d}$, —S(O)$_2$$R^{110d}$, —$NO_2$, =O, =S, =N$(R^{110d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$; and $C_{3-10}$ carbocycle and 3- to 10-membered heterocycle, each of which is optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —N$(R^{110d})$C(O)N$(R^{110d})_2$, —OC(O)N$(R^{110d})_2$, —N$(R^{110d})$C(O)O$R^{110d}$, —C(O)O$R^{110d}$, —OC(O)$R^{110d}$, —S(O)$R^{110d}$, —S(O)$_2$$R^{110d}$, —$NO_2$, =O, =S, =N$(R^{110d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19d}$. In some embodiments, $R^{15}$ is selected from: hydrogen; halogen, —C(O)$R^{110d}$, —C(O)N$(R^{110d})_2$, —C(O)O$R^{110d}$, and —CN; $C_{1-6}$ alkyl, $C_{2-6}$ alkenyl, and $C_{2-6}$ alkynyl, each of which is optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —C(O)O$R^{110d}$, —OC(O)$R^{110d}$, —N$(R^{110d})$C(O)N$(R^{110d})_2$, —OC(O)N$(R^{110d})_2$, —N$(R^{110d})$C(O)O$R^{110d}$, —S(O)$R^{110d}$, —S(O)$_2$$R^{110d}$, —$NO_2$, =O, =S, =N$(R^{110a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$; and $C_{3-10}$ carbocycle and 3- to 10-membered heterocycle, each of which is optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —N$(R^{110d})$C(O)N$(R^{110d})_2$, —OC(O)N$(R^{110d})_2$, —N$(R^{110d})$C(O)O$R^{110d}$, —C(O)O$R^{110d}$, —OC(O)$R^{110d}$, —S(O)$R^{110d}$, —S(O)$_2$$R^{110d}$, —$NO_2$, =O, =S, =N$(R^{110d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19d}$. In some embodiments, $R^{15}$ is selected from: hydrogen; halogen, —C(O)$R^{110d}$, —C(O)N$(R^{110d})_2$, —C(O)O$R^{110d}$, and —CN; $C_{1-6}$ alkyl, optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —C(O)O$R^{110d}$, —OC(O)$R^{110d}$, —N$(R^{110d})$C(O)N$(R^{110d})_2$, —OC(O)N$(R^{110d})_2$, —N$(R^{110d})$C(O)O$R^{110d}$, —S(O)$R^{110d}$, —S(O)$_2$$R^{110d}$, —$NO_2$, =O, =S, =N$(R^{110d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$; and $C_{3-10}$ carbocycle and 3- to 10-membered heterocycle, each of which is optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —N$(R^{110d})$C(O)N$(R^{110d})_2$, —OC(O)N$(R^{110d})_2$, —N$(R^{110d})$C(O)O$R^{110d}$, —C(O)O$R^{110d}$, —OC(O)$R^{110d}$, —S(O)$R^{110d}$, —S(O)$_2$$R^{110d}$, —$NO_2$, =O, =S, =N$(R^{110d})$, —$N_3$, —CN, and $C_{1-6}$ alkyl. In some embodiments, $R^{15}$ is selected from: hydrogen; halogen, —C(O)$R^{110d}$, —C(O)N$(R^{110d})_2$, —C(O)O$R^{110d}$, and —CN; $C_{1-6}$ alkyl, optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —C(O)O$R^{110d}$, —OC(O)$R^{110d}$, —N$(R^{110d})$C(O)N$(R^{110d})_2$, —OC(O)N$(R^{110d})_2$, —N$(R^{110c})$C(O)O$R^{110d}$, —S(O)$R^{110d}$, —S(O)$_2$$R^{110d}$, —$NO_2$, =O, =S, =N$(R^{110d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{15}$ is selected from: hydrogen; halogen, —C(O)$R^{110d}$, —C(O)N$(R^{110d})_2$, —C(O)O$R^{110d}$, and —CN; $C_{1-6}$ alkyl, optionally substituted with one or more substituents independently selected from halogen, —O$R^{110d}$, —S$R^{110d}$, —N$(R^{110d})_2$, —C(O)$R^{110d}$, —C(O)N$(R^{110d})_2$, —N$(R^{110d})$C(O)$R^{110d}$, —C(O)O$R^{110d}$, —OC(O)$R^{110d}$, —N$(R^{110d})$C(O)N$(R^{110d})_2$, —OC(O)N$(R^{110d})_2$, —N$(R^{110d})$C(O)O$R^{110d}$, —S(O)$R^{110d}$, —S(O)$_2$$R^{110d}$, —$NO_2$, =O, =S, =N$(R^{110d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$; and $C_{3-10}$ carbocycle and 3- to 10-membered heterocycle. In some embodiments, $R^{15}$ is selected from: hydrogen; halogen, —C(O)$R^{110d}$, —C(O)N($R^{110d}$)$_2$, —C(O)O$R^{110d}$, and —CN; and $C_{1-6}$ alkyl, optionally substituted with one or more substituents independently selected from halogen, —O$R^{110d}$, —S$R^{110d}$, —N($R^{110d}$)$_2$, —C(O)$R^{110d}$, —C(O)N($R^{110d}$)$_2$, —N($R^{110d}$)C(O)$R^{110d}$, —C(O)O$R^{110d}$, —OC(O)$R^{110d}$, —N($R^{110d}$)C(O)N($R^{110d}$)$_2$, —OC(O)N($R^{110d}$)$_2$, —N($R^{110d}$)C(O)O$R^{110d}$, —S(O)$R^{110d}$, —S(O)$_2R^{110d}$, —$NO_2$, ═O, ═S, ═N($R^{110d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$. In some embodiments, $R^{15}$ is selected from: hydrogen; halogen, —C(O)$R^{110d}$, —C(O)N($R^{110d}$)$_2$, —C(O)O$R^{110d}$, and —CN; and $C_{1-6}$ alkyl, optionally substituted with one or more substituents independently selected from halogen, —O$R^{110d}$, —S$R^{110d}$, —N($R^{110d}$)$_2$, —C(O)$R^{110d}$, —C(O)N($R^{110d}$)$_2$, —N($R^{110d}$)C(O)$R^{110d}$, —C(O)O$R^{110d}$, —OC(O)$R^{110d}$, —$NO_2$, ═O, —CN, $C_{3-10}$ carbocycle and 3- to 10-membered heterocycle In some embodiments, $R^{15}$ is selected from: hydrogen; halogen, —C(O)$R^{110d}$, —C(O)N($R^{110d}$)$_2$, —C(O)O$R^{110d}$, and —CN; and $C_{1-6}$ alkyl, optionally substituted with one or more substituents independently selected from halogen, —O$R^{110d}$, —S$R^{110d}$, —N($R^{110d}$)$_2$, ═O, —CN, $C_{3-10}$ carbocycle and 3- to 10-membered heterocycle. In some embodiments, $R^{15}$ is selected from: hydrogen; halogen, —C(O)$R^{110d}$, —C(O)N($R^{110d}$)$_2$, —C(O)O$R^{110d}$, and —CN; and $C_{1-6}$ alkyl, optionally substituted with one or more substituents independently selected from halogen, and —CN. In some embodiments, $R^{15}$ is selected from: hydrogen; halogen and —CN; and $C_{1-6}$ alkyl, optionally substituted with one or more substituents independently selected from halogen, and —CN. In some embodiments, $R^{15}$ is selected from: hydrogen; fluoro and —CN; and $C_{1-6}$ alkyl, optionally substituted with one or more substituents independently selected from fluoro, and —CN. In some embodiments, $R^{15}$ is selected from: hydrogen; fluoro; and $C_{1-6}$ alkyl, optionally substituted with one or more substituents independently selected from fluoro. In some embodiments, $R^{15}$ is selected from: hydrogen; and $C_{1-6}$ alkyl, optionally substituted with one or more substituents independently selected from fluoro. In some embodiments, $R^{15}$ is selected from: hydrogen and $C_{1-6}$ alkyl. In some embodiments, $R^{15}$ is selected from: hydrogen and $C_{1-4}$ alkyl. In some embodiments, $R^{15}$ is selected from: hydrogen and methyl. In some embodiments, $R^{15}$ is selected from: hydrogen. In some embodiments, $R^{15}$ is selected from: halogen. In some embodiments, $R^{15}$ is selected from: fluoro. In some embodiments, $R^{15}$ together with $R^{16}$ form a $C_{3-10}$ carbocycle or 3- to 10-membered heterocycle optionally substituted with one or more $R^{19d}$. In some embodiments, $R^{15}$ together with $R^{16}$ form a cyclopropyl optionally substituted with one or more $R^{19d}$. In some embodiments, $R^{15}$ together with $R^{16}$ form a cyclopropyl optionally substituted with one or more F. In some embodiments, $R^{15}$ together with $R^{16}$ form a cyclopropyl. In some embodiments, for a compound or salt of Formula (Ib), $R^{16}$ is selected from: hydrogen; halogen, —C(O)$R^{110e}$, —C(O)N($R^{110e}$)$_2$, —C(O)O$R^{110e}$, —S(O)$R^{110e}$, —S(O)$_2R^{110e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —C(O)O$R^{110e}$, —OC(O)$R^{110e}$, —N($R^{110e}$)C(O)N($R^{110e}$)$_2$, —OC(O)N($R^{110e}$)$_2$, —N($R^{110e}$)C(O)O$R^{110e}$, —S(O)$R^{110e}$, —S(O)$_2R^{110e}$, —$NO_2$, ═O, ═S, ═N($R^{110e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —N($R^{110e}$)C(O)N($R^{110e}$)$_2$, —OC(O)N($R^{110e}$)$_2$, —N($R^{110e}$)C(O)O$R^{110e}$, —C(O)O$R^{110e}$, —OC(O)$R^{110e}$, —S(O)$R^{110e}$, —S(O)$_2R^{110e}$, —$NO_2$, ═O, ═S, ═N($R^{110e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19c}$. In some embodiments, $R^{16}$ is selected from: hydrogen; halogen, —C(O)$R^{110e}$, —C(O)N($R^{110e}$)$_2$, —C(O)O$R^{110e}$, and —CN; $C_{1-6}$ alkyl, $C_{2-6}$ alkenyl, and $C_{2-6}$ alkynyl, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —C(O)O$R^{110e}$, —OC(O)$R^{110e}$, —N($R^{110e}$)C(O)N($R^{110e}$)$_2$, —OC(O)N($R^{110e}$)$_2$, —N($R^{110e}$)C(O)O$R^{110e}$, —S(O)$R^{110e}$, —S(O)$_2R^{110e}$, —$NO_2$, ═O, ═S, ═N($R^{110e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —N($R^{110e}$)C(O)N($R^{110e}$)$_2$, —OC(O)N($R^{110e}$)$_2$, —N($R^{110e}$)C(O)O$R^{110e}$, —C(O)O$R^{110e}$, —OC(O)$R^{110e}$, —S(O)$R^{110e}$, —S(O)$_2R^{110e}$, —$NO_2$, ═O, ═S, ═N($R^{110e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19c}$. In some embodiments, $R^{16}$ is selected from: hydrogen; halogen, —C(O)$R^{110e}$, —C(O)N($R^{110e}$)$_2$, —C(O)O$R^{110e}$, and —CN; $C_{1-6}$ alkyl, optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —C(O)O$R^{110e}$, —OC(O)$R^{10e}$, —N($R^{110e}$)C(O)N($R^{110e}$)$_2$, —OC(O)N($R^{110e}$)$_2$, —N($R^{110e}$)C(O)O$R^{110e}$, —S(O)$R^{110e}$, —S(O)$_2R^{110e}$, —$NO_2$, ═O, ═S, ═N($R^{110e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{10e}$, —N($R^{110e}$)C(O)N($R^{110e}$)$_2$, —OC(O)N($R^{10e}$)$_2$, —N($R^{110e}$)C(O)O$R^{110e}$, —C(O)O$R^{110e}$, —OC(O)$R^{110e}$, —S(O)$R^{110e}$, —S(O)$_2R^{110e}$, —$NO_2$, ═O, ═S, ═N($R^{110e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19c}$. In some embodiments, $R^{16}$ is selected from: hydrogen; halogen, —C(O)$R^{110e}$, —C(O)N($R^{110e}$)$_2$, —C(O)O$R^{110e}$, and —CN; $C_{1-6}$ alkyl, optionally substituted with one or more substituents independently selected from halogen, —O$R^{110e}$, —S$R^{110e}$, —N($R^{110e}$)$_2$, —C(O)$R^{110e}$, —C(O)N($R^{10e}$)$_2$, —N($R^{110e}$)C(O)$R^{110e}$, —C(O)O$R^{110e}$, —OC(O)$R^{110e}$, —N($R^{110e}$)C(O)N($R^{110e}$)$_2$, —OC(O)N($R^{110e}$)$_2$, —N($R^{110e}$)C(O)O$R^{110e}$, —S(O)$R^{110e}$, —S(O)$_2R^{110e}$, —$NO_2$, ═O, ═S, ═N($R^{110e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle, each of which is optionally substituted with one or more substituents independently selected from halogen, —$OR^{110e}$, —$SR^{110e}$, —$N(R^{110e})_2$, —$C(O)R^{110e}$, —$C(O)N(R^{10e})_2$, —$N(R^{110e})C(O)R^{10e}$, —$N(R^{110e})C(O)N(R^{110e})_2$, —$OC(O)N(R^{10e})_2$, —$N(R^{110e})C(O)OR^{110e}$, —$C(O)OR^{110e}$, —$OC(O)R^{110e}$, —$S(O)R^{110e}$, —$S(O)_2R^{110e}$, —$NO_2$, =O, =S, =$N(R^{110e})$, —$N_3$, —CN, and $C_{1-6}$ alkyl. In some embodiments, $R^{16}$ is selected from: hydrogen; halogen, —$C(O)R^{110e}$, —$C(O)N(R^{110e})_2$, —$C(O)OR^{110e}$, and —CN; $C_{1-6}$ alkyl, optionally substituted with one or more substituents independently selected from halogen, —$OR^{110e}$, —$SR^{110e}$, —$N(R^{110e})_2$, —$C(O)R^{110e}$, —$C(O)N(R^{10e})_2$, —$N(R^{110e})C(O)R^{110e}$, —$C(O)OR^{110e}$, —$OC(O)R^{110e}$, —$N(R^{110e})C(O)N(R^{110e})_2$, —$OC(O)N(R^{110e})_2$, —$N(R^{110e})C(O)OR^{110e}$, —$S(O)R^{110e}$, —$S(O)_2R^{110e}$, —$NO_2$, =O, =S, =$N(R^{110e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{16}$ is selected from: hydrogen; halogen, —$C(O)R^{110e}$, —$C(O)N(R^{110e})_2$, —$C(O)OR^{110e}$, and —CN; $C_{1-6}$ alkyl, optionally substituted with one or more substituents independently selected from halogen, —$OR^{110e}$, —$SR^{110e}$, —$N(R^{110e})_2$, —$C(O)R^{110e}$, —$C(O)N(R^{110e})_2$, —$N(R^{110e})C(O)R^{110e}$, —$C(O)OR^{110e}$, —$OC(O)R^{110e}$, —$N(R^{110e})C(O)N(R^{110e})_2$, —$OC(O)N(R^{110e})_2$, —$N(R^{110e})C(O)OR^{110e}$, —$S(O)R^{110e}$, —$S(O)_2R^{110e}$, —$NO_2$, =O, =S, =$N(R^{110e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle. In some embodiments, $R^{16}$ is selected from: hydrogen; halogen, —$C(O)R^{110e}$, —$C(O)N(R^{110e})_2$, —$C(O)OR^{110e}$, and —CN; and $C_{1-6}$ alkyl, optionally substituted with one or more substituents independently selected from halogen, —$OR^{110e}$, —$SR^{110e}$, —$N(R^{110e})_2$, —$C(O)R^{110e}$, —$C(O)N(R^{110e})_2$, —$N(R^{110e})C(O)R^{110e}$, —$C(O)OR^{110e}$, —$OC(O)R^{110e}$, —$N(R^{110e})C(O)N(R^{110e})_2$, —$OC(O)N(R^{110e})_2$, —$N(R^{110e})C(O)OR^{110e}$, —$S(O)R^{110e}$, —$S(O)_2R^{110e}$, —$NO_2$, =O, =S, =$N(R^{110e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$. In some embodiments, $R^{16}$ is selected from: hydrogen; halogen, —$C(O)R^{110e}$, —$C(O)N(R^{110e})_2$, —$C(O)OR^{110e}$, and —CN; and $C_{1-6}$ alkyl, optionally substituted with one or more substituents independently selected from halogen, —$OR^{110e}$, —$SR^{110e}$, —$N(R^{110e})_2$, —$C(O)R^{110e}$, —$C(O)N(R^{110e})_2$, —$N(R^{110e})C(O)R^{110e}$, —$C(O)OR^{110e}$, —$OC(O)R^{110e}$e, —$NO_2$, =O, —CN, $C_{3-10}$ carbocycle and 3- to 10-membered heterocycle In some embodiments, $R^{16}$ is selected from: hydrogen; halogen, —$C(O)R^{110e}$, —$C(O)N(R^{110e})_2$, —$C(O)OR^{110e}$, and —CN; and $C_{1-6}$ alkyl, optionally substituted with one or more substituents independently selected from halogen, —$OR^{110e}$, —$SR^{110e}$, —$N(R^{110e})_2$, =O, —CN, $C_{3-10}$ carbocycle and 3- to 10-membered heterocycle. In some embodiments, $R^{16}$ is selected from: hydrogen; halogen, —$C(O)R^{110e}$, —$C(O)N(R^{110e})_2$, —$C(O)OR^{110e}$, and —CN; and $C_{1-6}$ alkyl, optionally substituted with one or more substituents independently selected from halogen, and —CN. In some embodiments, $R^{16}$ is selected from: hydrogen; halogen and —CN; and $C_{1-6}$ alkyl, optionally substituted with one or more substituents independently selected from halogen, and —CN. In some embodiments, $R^{16}$ is selected from: hydrogen; fluoro and —CN; and $C_{1-6}$ alkyl, optionally substituted with one or more substituents independently selected from fluoro, and —CN. In some embodiments, $R^{16}$ is selected from: hydrogen; fluoro; and $C_{1-6}$ alkyl, optionally substituted with one or more substituents independently selected from fluoro. In some embodiments, $R^{16}$ is selected from: hydrogen; and $C_{1-6}$ alkyl, optionally substituted with one or more substituents independently selected from fluoro. In some embodiments, $R^{16}$ is selected from: hydrogen and $C_{1-6}$ alkyl. In some embodiments, $R^{16}$ is selected from: hydrogen and $C_{1-4}$ alkyl. In some embodiments, $R^{16}$ is selected from: hydrogen, and methyl. In some embodiments, $R^{16}$ is selected from: hydrogen. In some embodiments, $R^{16}$ is selected from: halogen. In some embodiments, $R^{16}$ is selected from: fluoro. In some embodiments, $R^{15}$ together with $R^{16}$ form a $C_{3-10}$ carbocycle or 3- to 10-membered heterocycle optionally substituted with one or more $R^{19e}$. In some embodiments, $R^{15}$ together with $R^{16}$ form a cyclopropyl optionally substituted with one or more $R^{19e}$. In some embodiments, $R^{15}$ together with $R^{16}$ form a cyclopropyl optionally substituted with one or more F. In some embodiments, $R^{15}$ together with $R^{16}$ form a cyclopropyl.

In some embodiments, for a compound or salt of Formula (Ib), $R^{15}$ together with $R^{16}$ form a 3- to 10-membered heterocycle or $C_{3-10}$ carbocycle, wherein the 3- to 10-membered heterocycle or $C_{3-10}$ carbocycle is optionally substituted with one or more $R^{19d}$. In some embodiments, $R^{15}$ together with $R^{16}$ form a 3- to 10-membered heterocycle or $C_{3-10}$ carbocycle. In some embodiments, $R^{15}$ together with $R^{16}$ form a $C_{3-10}$ carbocycle. In some embodiments, $R^{15}$ is hydrogen, and $R^{16}$ is hydrogen. In some embodiments, $R^{15}$ is hydrogen, and $R^{16}$ is $C_{1-6}$ alkyl. In some embodiments, $R^{15}$ together with $R^6$ form a moiety selected from =O, =S, =$N(O)(R^{110e})$, and =$N(R^{110d})$. In some embodiments, $R^{15}$ together with $R^{16}$ form a moiety selected from =O.

In some embodiments, for a compound or salt of Formula (Ib), $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, —$N(R^{110f})C(O)N(R^{110f})_2$, —$OC(O)N(R^{110f})_2$, —$N(R^{110f})C(O)OR^{110f}$, —$S(O)R^{110f}$, —$S(O)_2R^{110f}$, —$NO_2$, =O, =S, =$N(R^{110f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$; and $C_{3-10}$ carbocycle and 3- to 10-membered heterocycle, each of which is optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$N(R^{110f})C(O)N(R^{110f})_2$, —$OC(O)N(R^{110f})_2$, —$N(R^{110f})C(O)OR^{110f}$, —$C(O)OR^{110f}$, —$OC(O)R^{110f}$, —$S(O)R^{110f}$, —$S(O)_2R^{110f}$, —$NO_2$, =O, =S, =$N(R^{110f})$, —$N_3$, —CN, and $C_{1-6}$ alkyl. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl each of which is optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, —$N(R^{110f})C(O)N(R^{110f})_2$, —$OC(O)N(R^{110f})_2$, —$N(R^{110f})C(O)OR^{110f}$, —$S(O)R^{110f}$, —$S(O)_2R^{110f}$, —$NO_2$, =O, =S, =$N(R^{110f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$; and $C_{3-10}$ carbocycle and 3- to 10-membered heterocycle, each of which is optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$N(R^{110f})C(O)N(R^{110f})_2$, —$OC(O)N(R^{110f})_2$, —$N(R^{110f})C(O)OR^{110f}$, —$C(O)OR^{110f}$, —$OC(O)R^{110f}$, —$S(O)R^{110f}$, —$S(O)_2R^{110f}$, —$NO_2$, =O, =S, =$N(R^{110f})$, —$N_3$, —CN, and $C_{1-6}$ alkyl. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, —$N(R^{110f})C(O)N(R^{110f})_2$, —$OC(O)N(R^{110f})_2$, —$N(R^{110f})C(O)OR^{110f}$, —$S(O)R^{110f}$, —$S(O)_2R^{110f}$, —$NO_2$, =O, =S, =$N(R^{110f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$; and $C_{3-10}$ carbocycle and 3- to 10-membered heterocycle, each of which is optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, =O, —CN, and $C_{1-6}$ alkyl. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, —$N(R^{110f})C(O)N(R^{110f})_2$, —$OC(O)N(R^{110f})_2$, —$N(R^{110f})C(O)OR^{110f}$, —$S(O)R^{110f}$, —$S(O)_2R^{110f}$, —$NO_2$, =O, =S, =$N(R^{110f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$; and $C_{3-10}$ carbocycle and 3- to 10-membered heterocycle. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, —$N(R^{110f})C(O)N(R^{110f})_2$, —$OC(O)N(R^{110f})_2$, —$N(R^{110f})C(O)OR^{110f}$, —$S(O)R^{110f}$, —$S(O)_2R^{110f}$, —$NO_2$, =O, =S, =$N(R^{110f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, —$N(R^{110f})C(O)N(R^{110f})_2$, —$OC(O)N(R^{110f})_2$, —$N(R^{110f})C(O)OR^{110f}$, —$S(O)R^{110f}$, —$S(O)_2R^{110f}$, —$NO_2$, =O, =S, =$N(R^{110f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, =O, —CN, $C_{3-10}$ carbocycle and 3- to 10-membered heterocycle. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen, —$OR^{110f}$, —$SR^{110f}$, —$N(R^{110f})_2$, —$C(O)R^{110f}$, —$C(O)N(R^{110f})_2$, —$N(R^{110f})C(O)R^{110f}$, —$C(O)OR^{110f}$, —$OC(O)R^{110f}$, =O, and —CN. In some embodiments, $R^{17}$ is selected from: hydrogen; —$C(O)R^{110f}$, —$C(O)N(R^{110f})_2$, —$C(O)OR^{110f}$, —$S(O)R^{110f}$, and —$S(O)_2R^{110f}$; $C_{1-6}$ alkyl optionally substituted with one or more substituents independently selected from halogen and —CN. In some embodiments, $R^{17}$ is selected from: hydrogen; —$C(O)R^{110f}$, —$C(O)N(R^{110f})_2$, —$C(O)OR^{110f}$; $C_{1-6}$ alkyl optionally substituted with one or more substituents independently selected from halogen and —CN. In some embodiments, $R^{17}$ is selected from: hydrogen; and $C_{1-6}$ alkyl optionally substituted with one or more substituents independently selected from halogen and —CN. In some embodiments, $R^{17}$ is selected from: hydrogen; and $C_{1-6}$ alkyl optionally substituted with one or more substituents independently selected from fluoro and —CN. In some embodiments, $R^{17}$ is selected from hydrogen and $C_{1-6}$ alkyl. In some embodiments, $R^{17}$ is selected from hydrogen and $C_{1-4}$ alkyl. In some embodiments, $R^{17}$ is selected from hydrogen and $C_1$ alkyl. In some embodiments, $R^{17}$ is selected from hydrogen.

In some embodiments, for a compound or salt of Formula (Ib), $R^{18}$ is selected from: hydrogen; —$C(O)R^{110g}$, —$C(O)N(R^{110g})_2$, —$C(O)OR^{110g}$, —$S(O)R^{110g}$, and —$S(O)_2R^{110g}$; and $C_{1-6}$ alkyl optionally substituted with one or more substituents independently selected from halogen, —$OR^{110g}$, —$SR^{110g}$, —$N(R^{110g})_2$, —$C(O)R^{110g}$, —$C(O)N(R^{110g})_2$, —$N(R^{110g})C(O)R^{110g}$, —$C(O)OR^{110g}$, —$OC(O)R^{110g}$, —$N(R^{110g})C(O)N(R^{110g})_2$, —$OC(O)N(R^{110g})_2$, —$N(R^{110g})C(O)OR^{110g}$, —$S(O)R^{110g}$, —$S(O)_2R^{110g}$, —$NO_2$, =O, =S, =$N(R^{110g})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19g}$. In some embodiments, $R^{18}$ is selected from: hydrogen; —$C(O)R^{110g}$, —$C(O)N(R^{110g})_2$, —$C(O)OR^{110g}$, —$S(O)R^{110g}$, and —$S(O)_2R^{110g}$; and $C_{1-6}$ alkyl optionally substituted with one or more substituents independently selected from halogen, —$OR^{110g}$, —$SR^{110g}$, —$N(R^{110g})_2$, =O, —CN, $C_{3-10}$ carbocycle and 3- to 10-membered heterocycle. In some embodiments, $R^{18}$ is selected from: hydrogen; and $C_{1-6}$ alkyl optionally substituted with one or more substituents independently selected from halogen, and —CN. In some embodiments, $R^{18}$ is selected from: hydrogen; and $C_{1-6}$ alkyl optionally substituted with one or more substituents independently selected from fluoro, and —CN. In some embodiments, $R^{18}$ is selected from: hydrogen; and $C_{1-6}$ alkyl optionally substituted with one or more substituents independently selected from fluoro. In some embodiments, $R^{18}$ is selected from: hydrogen and $C_{1-6}$ alkyl. In some embodiments, $R^{18}$ is selected from: hydrogen and $C_{1-3}$ alkyl. In some embodiments, $R^{18}$ is selected from: hydrogen and $C_1$ alkyl. In some embodiments, $R^{18}$ is selected from: hydrogen.

In some embodiments, for a compound or salt of Formula (Ib), each $R^{19a}$ is independently selected from: halogen, $—OR^{110a}$, $—SR^{110a}$, $—N(R^{110a})_2$, =O, and —CN; and $C_{1-3}$ alkyl each of which is optionally substituted with one or more substituents independently selected from halogen, $—OR^{110a}$, $—SR^{110a}$, $—N(R^{110a})_2$, =O, and —CN. In some embodiments, each $R^{19a}$ is independently selected from: halogen, $—OR^{110a}$, $—SR^{110a}$, $—N(R^{110a})_2$, =O, and —CN; and $C_{1-3}$ alkyl each of which is optionally substituted with one or more substituents independently selected from halogen and —CN. In some embodiments, each $R^{19a}$ is independently selected from: halogen, $—OR^{110a}$, $—SR^{110a}$, $—N(R^{110a})_2$, =O, —CN, and $C_{1-3}$ alkyl. In some embodiments, each $R^{19a}$ is independently selected from: halogen, $—OR^{110a}$, —CN, and $C_1$ alkyl. In some embodiments, each $R^{19a}$ is independently selected from: fluoro and —CN.

In some embodiments, for a compound or salt of Formula (Ib), each $R^{19b}$ is independently selected from: halogen, $—NO_2$, $—N_3$, —CN, $—OR^{110b}$, $—SR^{110b}$, $—N(R^{110b})_2$, $—C(O)R^{110b}$, $—C(O)N(R^{110b})_2$, $—N(R^{110b})C(O)R^{110b}$, $—N(R^{110b})C(O)N(R^{110b})_2$, $—OC(O)N(R^{110b})_2$, $—N(R^{110b})C(O)OR^{110b}$, $—C(O)OR^{110b}$, $—OC(O)R^{110b}$, $—S(O)R^{110b}$, and $—S(O)_2R^{110b}$; $C_{1-6}$ alkyl optionally substituted with one or more substituents independently selected from halogen, $—OR^{110b}$, $—SR^{110b}$, $—N(R^{110b})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, $—OR^{110b}$, $—SR^{110b}$, $—N(R^{110b})_2$, =O, —CN, $C_{1-6}$ alkyl. In some embodiments, each $R^{19b}$ is independently selected from: halogen, $—NO_2$, $—N_3$, —CN, $—OR^{110b}$, $—SR^{110b}$, $—N(R^{110b})_2$, $—C(O)R^{110b}$, $—C(O)N(R^{110b})_2$, $—N(R^{110b})C(O)R^{110b}$, $—N(R^{110b})C(O)N(R^{110b})_2$, $—OC(O)N(R^{110b})_2$, $—N(R^{110b})C(O)OR^{110b}$, $—C(O)OR^{110b}$, $—OC(O)R^{110b}$, $—S(O)R^{110b}$, and $—S(O)_2R^{110b}$; $C_{1-6}$ alkyl optionally substituted with one or more substituents independently selected from halogen, $—OR^{110b}$, $—SR^{110b}$, $—N(R^{110b})_2$, =O, —CN, $C_{3-10}$ carbocycle and 3- to 10-membered heterocycle; and $C_{3-10}$ carbocycle and 3- to 10-membered heterocycle. In some embodiments, each $R^{19b}$ is independently selected from: halogen, $—NO_2$, $—N_3$, —CN, $—OR^{110b}$, $—SR^{110b}$, and $—N(R^{110b})_2$; $C_{1-6}$ alkyl optionally substituted with one or more substituents independently selected from halogen, $—OR^{110b}$, $—SR^{110b}$, $—N(R^{110b})_2$, =O, —CN, $C_{3-10}$ carbocycle and 3- to 10-membered heterocycle; and $C_{3-10}$ carbocycle and 3- to 10-membered heterocycle. In some embodiments, each $R^{19b}$ is independently selected from: halogen, $—NO_2$, $—N_3$, —CN, $—OR^{110b}$, $—SR^{110b}$, and $—N(R^{110b})_2$; and $C_{1-6}$ alkyl optionally substituted with one or more substituents independently selected from halogen, $—OR^{110b}$, $—SR^{110b}$, $—N(R^{110b})_2$, =O, —CN, $C_{3-10}$ carbocycle and 3- to 10-membered heterocycle. In some embodiments, each $R^{19b}$ is independently selected from: halogen, —CN, $—OR^{110b}$, $—SR^{110b}$, and $—N(R^{110b})_2$; and $C_{1-6}$ alkyl optionally substituted with one or more substituents independently selected from halogen, $—OR^{110b}$, $—SR^{110b}$, $—N(R^{110b})_2$, =O, and —CN. In some embodiments, each $R^{19b}$ is independently selected from: halogen, —CN, $—OR^{110b}$, $—SR^{110b}$, and $—N(R^{110b})_2$, and $C_{1-6}$ alkyl. In some embodiments, each $R^{19b}$ is independently selected from: halogen, —CN, $—OR^{110b}$, and $C_{1-6}$ alkyl. In some embodiments, each $R^{19b}$ is independently selected from m: hydrogen, fluoro, —CN, $—OR^{110b}$, and $C_{1-6}$ alkyl. In some embodiments, each $R^{19b}$ is independently selected from: fluoro, —CN, $—OR^{110b}$, and $C_1$ alkyl. In some embodiments, each $R^{19b}$ is independently selected from fluoro, and —CN. In some embodiments, each $R^{19b}$ is independently selected from: halogen. In some embodiments, each $R^{19b}$ is independently selected from: fluoro.

In some embodiments, for a compound or salt of Formula (Ib), each $R^{19z}$ is independently selected from: halogen, $—OR^{110z}$, $—SR^{110z}$, $—N(R^{110z})_2$, =O, and —CN; and $C_{1-3}$ alkyl each of which is optionally substituted with one or more substituents independently selected from halogen, $—OR^{110z}$, $—SR^{110z}$, $—N(R^{110z})_2$, =O, and —CN. In some embodiments, each $R^{19z}$ is independently selected from: halogen, $—OR^{110z}$, $—SR^{110z}$, $—N(R^{110z})_2$, =O, and —CN; and $C_{1-3}$ alkyl each of which is optionally substituted with one or more substituents independently selected from halogen and —CN. In some embodiments, each $R^{19z}$ is independently selected from: halogen, $—OR^{110z}$, $—SR^{110z}$, $—N(R^{110z})_2$, =O, —CN, and $C_{1-3}$ alkyl. In some embodiments, each $R^{19z}$ is independently selected from: halogen, $—OR^{110z}$, —CN, and $C_1$ alkyl. In some embodiments, each $R^{19z}$ is independently selected from: fluoro and —CN. In some embodiments, for a compound or salt of Formula (Ib), each $R^{19c}$ is independently selected from: halogen, $—OR^{110c}$, $—SR^{110c}$, $—N(R^{110c})_2$, =O, and —CN; and $C_{1-3}$ alkyl each of which is optionally substituted with one or more substituents independently selected from halogen, $—OR^{110c}$, $—SR^{110c}$, $—N(R^{110c})_2$, =O, and —CN. In some embodiments, each $R^{19c}$ is independently selected from: halogen, $—OR^{110c}$, $—SR^{110c}$, $—N(R^{110c})_2$, =O, and —CN; and $C_{1-3}$ alkyl each of which is optionally substituted with one or more substituents independently selected from halogen and —CN. In some embodiments, each $R^{19c}$ is independently selected from: halogen, $—OR^{110c}$, $—SR^{110c}$, $—N(R^{110c})_2$, =O, —CN, and $C_{1-3}$ alkyl. In some embodiments, each $R^{19c}$ is independently selected from: halogen, $—OR^{110c}$, —CN, and $C_1$ alkyl. In some embodiments, each $R^{19c}$ is independently selected from: fluoro and —CN. In some embodiments, for a compound or salt of Formula (Ib), each $R^{19d}$ is independently selected from: halogen, $—OR^{110d}$, $—SR^{110d}$, $—N(R^{110d})_2$, =O, and —CN; and $C_{1-3}$ alkyl each of which is optionally substituted with one or more substituents independently selected from halogen, $—OR^{110a}$, $—SR^{110d}$, $—N(R^{110d})_2$, =O, and —CN. In some embodiments, each $R^{19d}$ is independently selected from: halogen, $—OR^{110d}$, $—SR^{110d}$, $—N(R^{110d})_2$, =O, and —CN; and $C_{1-3}$ alkyl each of which is optionally substituted with one or more substituents independently selected from halogen and —CN. In some embodiments, each $R^{19d}$ is independently selected from: halogen, $—OR^{110d}$, $—SR^{110d}$, $—N(R^{110d})_2$, =O, —CN, and $C_{1-3}$ alkyl. In some embodiments, each $R^{19d}$ is independently selected from: halogen, $—OR^{110d}$, —CN, and $C_1$ alkyl. In some embodiments, each $R^{19d}$ is independently selected from: fluoro and —CN. In some embodiments, for a compound or salt of Formula (Ib), each $R^{19e}$ is independently selected from: halogen, $—OR^{110e}$, $—SR^{110e}$, $—N(R^{110e})_2$, =O, and —CN; and $C_{1-3}$ alkyl each of which is optionally substituted with one or more substituents independently selected from halogen, $—OR^{110e}$, $—SR^{110e}$, $—N(R^{110e})_2$, =O, and —CN. In some embodiments, each $R^{19e}$ is independently selected from: halogen, $—OR^{110e}$, $—SR^{110e}$, $—N(R^{110e})_2$, =O, and —CN; and $C_{1-3}$ alkyl each of which is optionally substituted with one or more substituents independently selected from halogen and —CN. In some embodiments, each $R^{19e}$ is independently selected from: halogen, $—OR^{110e}$, $—SR^{110e}$, $—N(R^{110e})_2$, =O, —CN, and $C_{1-3}$ alkyl. In some embodiments, each $R^{19e}$ is independently selected from: halogen, —$OR^{110e}$, —CN, and $C_1$ alkyl. In some embodiments, each $R^{19e}$ is independently selected from: fluoro and —CN. In some embodiments, for a compound or salt of Formula (Ib), each $R^{19f}$ is independently selected from: halogen, —$OR^{110f}$, —$SR^{110f}$, —$N(R^{110f})_2$, =O, and —CN; and $C_{1-3}$ alkyl each of which is optionally substituted with one or more substituents independently selected from halogen, —$OR^{110f}$, —$SR^{110f}$, —$N(R^{110f})_2$, =O, and —CN. In some embodiments, each $R^{19f}$ is independently selected from: halogen, —$OR^{110f}$, —$SR^{110f}$, —$N(R^{110f})_2$, =O, and —CN; and $C_{1-3}$ alkyl each of which is optionally substituted with one or more substituents independently selected from halogen and —CN. In some embodiments, each $R^{19f}$ is independently selected from: halogen, —$OR^{110f}$, —$SR^{110f}$, —$N(R^{110f})_2$, =O, —CN, and $C_{1-3}$ alkyl. In some embodiments, each $R^{19f}$ is independently selected from: halogen, —$OR^{110f}$, —CN, and $C_1$ alkyl. In some embodiments, each $R^{19f}$ is independently selected from: fluoro and —CN. In some embodiments, for a compound or salt of Formula (Ib), each $R^{19g}$ is independently selected from: halogen, —$OR^{110g}$, —$SR^{110g}$, —$N(R^{110g})_2$, =O, and —CN; and $C_{1-3}$ alkyl each of which is optionally substituted with one or more substituents independently selected from halogen, —$OR^{110g}$, —$SR^{110g}$, —$N(R^{110g})_2$, =O, and —CN. In some embodiments, each $R^{19g}$ is independently selected from: halogen, —$OR^{110g}$, —$SR^{110g}$, —$N(R^{110g})_2$, =O, and —CN; and $C_{1-3}$ alkyl each of which is optionally substituted with one or more substituents independently selected from halogen and —CN. In some embodiments, each $R^{19g}$ is independently selected from: halogen, —$OR^{110g}$, —$SR^{110g}$, —$N(R^{110g})_2$, =O, —CN, and $C_{1-3}$ alkyl. In some embodiments, each $R^{19g}$ is independently selected from: halogen, —$OR^{10g}$, —CN, and $C_1$ alkyl. In some embodiments, each $R^{19g}$ is independently selected from: fluoro and —CN.

In some embodiments, for a compound or salt of Formula (Ib), each $R^{110a}$, $R^{110b}$, $R^{110z}$, $R^{110c}$, $R^{110d}$, $R^{110e}$, $R^{110f}$, and $R^{110g}$ is independently selected from: hydrogen; $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NH_2$, =O, —O—$C_{1-6}$ alkyl, —S—$C_{1-6}$ alkyl, —N($C_{1-6}$ alkyl)$_2$, —NH ($C_{1-6}$ alkyl), $C_{1-6}$ alkyl, and $C_{1-6}$ haloalkyl. In some embodiments, each $R^{110a}$, $R^{110b}$, $R^{110z}$, $R^{110c}$, $R^{110d}$, $R^{110e}$, $R^{110f}$, and $R^{110g}$ is independently selected from: hydrogen; $C_{1-6}$ alkyl optionally substituted with one or more substituents independently selected from halogen, —CN, and —OH; and $C_{3-10}$ carbocycle, and 3- to 10-membered heterocycle, each of which is optionally substituted with one or more substituents independently selected from halogen, —CN, —OH, $C_{1-6}$ alkyl, and $C_{1-6}$ haloalkyl. In some embodiments, each $R^{110a}$, $R^{110b}$, $R^{110z}$, $R^{110c}$, $R^{110d}$, $R^{110e}$, $R^{110f}$, and $R^{110g}$ is independently selected from: hydrogen; $C_{1-6}$ alkyl optionally substituted with one or more substituents independently selected from fluoro and CN; and $C_{3-10}$ carbocycle, and 3- to 10-membered heterocycle, each of which is optionally substituted with one or more substituents independently selected from fluoro and —CN. In some embodiments, each $R^{110a}$, $R^{110b}$, $R^{110z}$, $R^{110c}$, $R^{110d}$, $R^{110e}$, $R^{110f}$, and $R^{110g}$ is independently selected from: hydrogen; and $C_{1-6}$ alkyl optionally substituted with one or more substituents independently selected from fluoro and CN. In some embodiments, each $R^{110a}$, $R^{110b}$, $R^{110z}$, $R^{110c}$, $R^{110d}$, $R^{110e}$, $R^{110f}$, and $R^{110g}$ is independently selected from: hydrogen and $C_{1-6}$ alkyl. In some embodiments, each $R^{110a}$, $R^{110b}$, $R^{110z}$, $R^{110c}$, $R^{110d}$, $R^{110e}$, $R^{110f}$, and $R^{110g}$ is independently selected from: hydrogen and $C_1$ alkyl. In some embodiments, each $R^{110a}$, $R^{110b}$, $R^{110z}$, $R^{110c}$, $R^{110d}$, $R^{110e}$, $R^{110f}$, and $R^{110g}$ is independently selected from: hydrogen. In some embodiments, each $R^{110a}$ is independently selected from: hydrogen. In some embodiments, each $R^{110b}$ is independently selected from: hydrogen. In some embodiments, each $R^{110c}$ is independently selected from: hydrogen. In some embodiments, each $R^{110d}$ is independently selected from: hydrogen. In some embodiments, each $R^{110e}$ is independently selected from: hydrogen. In some embodiments, each $R^{110f}$ is independently selected from: hydrogen. In some embodiments, each $R^{110g}$ is independently selected from: hydrogen. In some embodiments, each $R^{110z}$ is independently selected from: hydrogen.

In some embodiments, for a compound or salt of Formula (Ib), when $X^{14}$ is N or $N^+$(—$O^-$), then $R^{18}$ is selected from: hydrogen; $C_{2-6}$ alkyl, optionally substituted with one or more substituents independently selected from halogen, —$OR^{110g}$, —$SR^{110g}$, —$N(R^{110g})_2$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{110g}$, —$SR^{110g}$, —$N(R^{110g})_2$, —CN, and $C_{1-6}$ alkyl. In some embodiments, when $X^{14}$ is N, then $R^{18}$ is selected from: hydrogen; —C(O)$R^{110g}$, —C(O)$N(R^{110g})_2$, —C(O)$OR^{110g}$, —S(O)$R^{110g}$, and —$S(O)_2R^{110g}$; $C_1$ alkyl substituted with one or more substituents independently selected from halogen, —$OR^{110g}$, —$SR^{110g}$, —$N(R^{110g})_2$, —CN, $C_{3-10}$ carbocycle and 3- to 10-membered heterocycle; $C_{2-6}$ alkyl, optionally substituted with one or more substituents independently selected from halogen, —$OR^{110g}$, —$SR^{110g}$, —$N(R^{110g})_2$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{110g}$, —$SR^{110g}$, —$N(R^{110g})_2$, —CN, and $C_{1-6}$ alkyl. In some embodiments, when $X^{14}$ is N, then $R^{18}$ is selected from: hydrogen; —C(O)$R^{110g}$, —C(O)$N(R^{110g})_2$, —C(O)$OR^{110g}$; $C_{2-6}$ alkyl optionally substituted with one or more substituents independently selected from fluoro and —CN; and $C_{3-10}$ carbocycle and 3- to 10-membered heterocycle, each of which is optionally substituted with one or more substituents independently selected from fluoro and —CN. In some embodiments, when $X^{14}$ is N, then $R^{18}$ is selected from: hydrogen; $C_{2-6}$ alkyl optionally substituted with one or more substituents independently selected from fluoro and —CN; and $C_{3-10}$ carbocycle and 3- to 10-membered heterocycle, each of which is optionally substituted with one or more substituents independently selected from fluoro and —CN. In some embodiments, when $X^{14}$ is N, then $R^{18}$ is selected from: hydrogen; $C_{2-6}$ alkyl; and $C_{3-10}$ carbocycle and 3- to 10-membered heterocycle. In some embodiments, when $X^{14}$ is N, then $R^{18}$ is selected from: hydrogen. In some embodiments, when $X^{14}$ is N or $N^+$(—$O^-$), then $R^{18}$ is selected from: hydrogen. In some embodiments, when $X^{14}$ is N, then $R^{18}$ is selected from: $C_{2-6}$ alkyl. In some embodiments, when $X^{14}$ is N, $X^{11}$ is $C(R^{11a})$, $X^{12}$ is $C(R^{11b})$, and $X^{13}$ is $C(R^{11c})$; then $R^{18}$ is selected from: hydrogen. In some embodiments, when $X^{14}$ is N, $X^{11}$ is $C(R^{11a})$, $X^{12}$ is N, and $X^{13}$ is $C(R^{11c})$; then $R^{18}$ is selected from: hydrogen.

In some embodiments, for a compound or salt of Formula (Ib), $R^{12}$ is

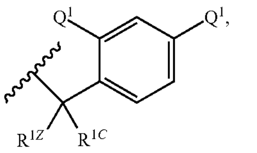

wherein each $Q^1$ is independently selected from halogen, —CN, —OH, —O($C_{1-6}$ alkyl), and —OH. In some embodiments, $Q^1$ is selected from halogen, —CN, —OH, —O($C_{1-6}$ alkyl), and —OH. In some embodiments, $R^{12}$ is

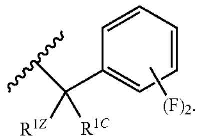

In some embodiments, $R^{12}$ from

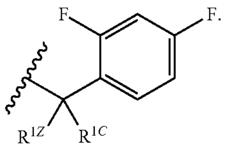

In some embodiments, $R^{12}$ is

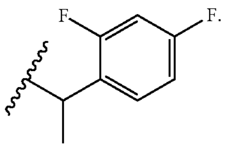 [SMILES: *C(C)c1ccc(F)cc1F]

In some embodiments, the compound or salt of Formula (Ib) is not: 1,4-Dihydro-1-methyl-N-[1-[4-(2-methylpropyl)phenyl]ethyl]-2,4-dioxo-7-(trifluoromethyl)pyrido[2,3-d]pyrimidine-3(2H)-acetamide; or N-[1-(4-Chlorophenyl)ethyl]-1,4-dihydro-1-methyl-2,4-dioxo-7-(trifluoromethyl)pyrido[2,3-d]pyrimidine-3(2H)-acetamide; or N-[1-(3,4-Dimethylphenyl)ethyl]-1,4-dihydro-1-methyl-2,4-dioxo-7-(trifluoromethyl)pyrido[2,3-d]pyrimidine-3(2H)-acetamide; or 3-[2-[4,5-Dihydro-5-(4-methylphenyl)-3-(2-thienyl)-1H-pyrazol-1-yl]-2-oxoethyl]-S-methoxy-1-methylpyrido[2,3-d]pyrimidine-2,4(1H,3H)-dione; or 3-[2-[5-(4-Fluorophenyl)-4,5-dihydro-3-(2-thienyl)-1H-pyrazol-1-yl]-2-oxoethyl]-S-methoxy-1-ethylpyrido[2,3-d]pyrimidine-2,4(1H,3H)-dione.

In some embodiments, the compound or salt of Formula (Ib) is selected from: compound 59, 95, 96, and 141, or a salt thereof. In some embodiments, the compound or salt of Formula (Ib) is selected from 65, or a salt thereof. In some embodiments, the compound or salt of formula (Ib) is selected from 301, 302, and 303, or a salt thereof. In some embodiments, the compound or salt of Formula (Ib) is selected from: compound 141, 59, 65, and 302, or a salt thereof. In some embodiments, the compound or salt of Formula (Ib) is selected from: compound 141, or a salt thereof. In some embodiments, the compound or salt of Formula (Ib) is selected from: compound 141, 65, and 302, or a salt thereof. In some embodiments, the compound or salt of Formula (Ib) is selected from: compound 141 and 65, or a salt thereof. In some embodiments, the compound or salt of Formula (Ib) is not compound 301 or compound 302 or compound 303. In some embodiments, the compound or salt of Formula (Ib) is not compound 65.

In one aspect, disclosed herein is a compound represented by Formula (IIa):

(IIa)

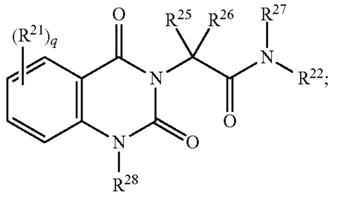

or a salt thereof, wherein $R^{22}$ is selected from:

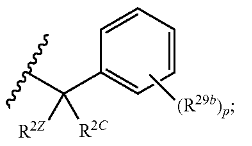

p is an integer selected from 1, 2, 3, 4, and 5; q is an integer selected from 1, 2, 3, and 4; each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$N(R^{210a})C(O)N(R^{210a})_2$, —$OC(O)N(R^{210a})_2$, —$N(R^{210a})C(O)OR^{210a}$, —$S(O)R^{210a}$, —$S(O)_2R^{210a}$, —$NO_2$, =O, =S, =$N(R^{210a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; and $C_{3-10}$ carbocycle and 3- to 10-membered heterocycle, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, —$S(O)_2R^{210a}$, —$NO_2$, =O, =S, =$N(R^{210a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29a}$; $R^{2Z}$ is selected from: —$C(O)R^{210z}$, —$C(O)N(R^{210z})_2$, —$C(O)OR^{210z}$, and —CN; $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the C$_{3-10}$ carbocycle and 3- to 10-membered heterocycle are each optionally substituted with one or more R$^{29z}$; and C$_{3-10}$ carbocycle and 3- to 10-membered heterocycle, each of which is optionally substituted with one or more substituents independently selected from halogen, —OR$^{210z}$, —SR$^{210z}$, —N(R$^{210z}$)$_2$, —C(O)R$^{210z}$, —C(O)N(R$^{210z}$)$_2$, —N(R$^{210z}$)C(O)R$^{210z}$, —N(R$^{210z}$)C(O)N(R$^{210z}$)$_2$, —OC(O)N(R$^{210z}$)$_2$, —N(R$^{210z}$)C(O)OR$^{210z}$, —C(O)OR$^{210z}$, —OC(O)R$^{210z}$, —S(O)R$^{210z}$, —S(O)$_2$R$^{210z}$, —NO$_2$, =O, =S, =N(R$^{210z}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{29z}$; R$^{2C}$ is selected from: hydrogen; —C(O)R$^{210c}$, —C(O)N(R$^{210c}$)$_2$, —C(O)OR$^{210c}$, and —CN; C$_{1-6}$ alkyl, C$_{2-6}$ alkenyl, and C$_{2-6}$ alkynyl, each of which is optionally substituted with one or more substituents independently selected from halogen, —OR$^{210c}$, —SR$^{210c}$, —N(R$^{210c}$)$_2$, —C(O)R$^{210c}$, —C(O)N(R$^{210c}$)$_2$, —N(R$^{210c}$)C(O)R$^{210c}$, —C(O)OR$^{210c}$, —OC(O)R$^{210c}$, —N(R$^{210c}$)C(O)N(R$^{210c}$)$_2$, —OC(O)N(R$^{210c}$)$_2$, —N(R$^{210c}$)C(O)OR$^{210c}$, —S(O)R$^{210c}$, —S(O)$_2$R$^{210c}$, —NO$_2$, =O, =S, =N(R$^{210c}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{29c}$; and C$_{3-10}$ carbocycle and 3- to 10-membered heterocycle, each of which is optionally substituted with one or more substituents independently selected from halogen, —OR$^{210c}$, —SR$^{210c}$, —N(R$^{210c}$)$_2$, —C(O)R$^{210c}$, —C(O)N(R$^{210c}$)$_2$, —N(R$^{210c}$)C(O)R$^{210c}$, —N(R$^{210c}$)C(O)N(R$^{210c}$)$_2$, —OC(O)N(R$^{210c}$)$_2$, —N(R$^{210c}$)C(O)OR$^{210c}$, —C(O)OR$^{210c}$, —OC(O)R$^{210c}$, —S(O)R$^{210c}$, —S(O)$_2$R$^{210c}$, —NO$_2$, =O, =S, =N(R$^{210c}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{29c}$; R$^{25}$ is selected from: hydrogen; halogen, —OR$^{210d}$, —SR$^{210d}$, —N(R$^{210d}$)$_2$, —C(O)R$^{210d}$, —C(O)N(R$^{210d}$)$_2$, —N(R$^{210d}$)C(O)R$^{210d}$, —C(O)OR$^{210d}$, —OC(O)R$^{210d}$, —N(R$^{210d}$)C(O)N(R$^{210d}$)$_2$, —OC(O)N(R$^{210d}$)$_2$, —N(R$^{210d}$)C(O)OR$^{210d}$, —S(O)R$^{210d}$, —S(O)$_2$R$^{210d}$, —NO$_2$, —N$_3$, and —CN; C$_{1-6}$ alkyl, C$_{2-6}$ alkenyl, and C$_{2-6}$ alkynyl, each of which is optionally substituted with one or more substituents independently selected from halogen, —OR$^{210d}$, —SR$^{210d}$, —N(R$^{210d}$)$_2$, —C(O)R$^{210d}$, —C(O)N(R$^{210d}$)$_2$, —N(R$^{210d}$)C(O)R$^{210d}$, —C(O)OR$^{210d}$, —OC(O)R$^{210d}$, —N(R$^{210d}$)C(O)N(R$^{210d}$)$_2$, —OC(O)N(R$^{210d}$)$_2$, —N(R$^{210d}$)C(O)OR$^{210d}$, —S(O)R$^{210d}$, —S(O)$_2$R$^{210d}$, —NO$_2$, =O, =S, =N(R$^{210d}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{29d}$; and C$_{3-10}$ carbocycle and 3- to 10-membered heterocycle, each of which is optionally substituted with one or more substituents independently selected from halogen, —OR$^{210d}$, —SR$^{210d}$, —N(R$^{210d}$)$_2$, —C(O)R$^{210d}$, —C(O)N(R$^{210d}$)$_2$, —N(R$^{210d}$)C(O)R$^{210d}$, —N(R$^{210d}$)C(O)N(R$^{210d}$)$_2$, —OC(O)N(R$^{210d}$)$_2$, —N(R$^{210d}$)C(O)OR$^{210d}$, —C(O)OR$^{210d}$, —OC(O)R$^{210d}$, —S(O)R$^{210d}$, —S(O)$_2$R$^{210d}$, —NO$_2$, =O, =S, =N(R$^{210d}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{29d}$; or R$^{25}$ together with R$^{26}$ form a 3- to 10-membered heterocycle or C$_{3-10}$ carbocycle, wherein the 3- to 10-membered heterocycle or C$_{3-10}$ carbocycle is optionally substituted with one or more R$^{29d}$; R$^{26}$ is selected from: hydrogen; halogen, —OR$^{210e}$, —SR$^{210e}$, —N(R$^{210e}$)$_2$, —C(O)R$^{210e}$, —C(O)N(R$^{210e}$)$_2$, —N(R$^{210e}$)C(O)R$^{210e}$, —C(O)OR$^{210e}$, —OC(O)R$^{210e}$, —N(R$^{210e}$)C(O)N(R$^{210e}$)$_2$, —OC(O)N(R$^{210e}$)$_2$, —N(R$^{210e}$)C(O)OR$^{210e}$, —S(O)R$^{210e}$, —S(O)$_2$R$^{210e}$, —NO$_2$, —N$_3$, and —CN; C$_{1-6}$ alkyl, C$_{2-6}$ alkenyl, and C$_{2-6}$ alkynyl, each of which is optionally substituted with one or more substituents independently selected from halogen, —OR$^{210e}$, —SR$^{210e}$, —N(R$^{210e}$)$_2$, —C(O)R$^{210e}$, —C(O)N(R$^{210e}$)$_2$, —N(R$^{210e}$)C(O)R$^{210e}$, —C(O)OR$^{210e}$, —OC(O)R$^{210e}$, —N(R$^{210e}$)C(O)N(R$^{210e}$)$_2$, —OC(O)N(R$^{210e}$)$_2$, —N(R$^{210e}$)C(O)OR$^{210e}$, —S(O)R$^{210e}$, —S(O)$_2$R$^{210e}$, —NO$_2$, =O, =S, =N(R$^{210e}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{29e}$; and C$_{3-10}$ carbocycle and 3- to 10-membered heterocycle, each of which is optionally substituted with one or more substituents independently selected from halogen, —OR$^{210e}$, —SR$^{210e}$, —N(R$^{210e}$)$_2$, —C(O)R$^{210e}$, —C(O)N(R$^{210e}$)$_2$, —N(R$^{210e}$)C(O)R$^{210e}$, —N(R$^{210e}$)C(O)N(R$^{210e}$)$_2$, —OC(O)N(R$^{210e}$)$_2$, —N(R$^{210e}$)C(O)OR$^{210e}$, —C(O)OR$^{210e}$, —OC(O)R$^{210e}$, —S(O)R$^{210e}$, —S(O)$_2$R$^{210e}$, —NO$_2$, =O, =S, =N(R$^{210e}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{29e}$; or R$^{26}$ together with R$^{25}$ form a 3- to 10-membered heterocycle or C$_{3-10}$ carbocycle, wherein the 3- to 10-membered heterocycle or C$_{3-10}$ carbocycle is optionally substituted with one or more R$^{29e}$; R$^{27}$ is selected from: hydrogen; —C(O)R$^{210f}$, —C(O)N(R$^{210f}$)$_2$, —C(O)OR$^{210f}$, —S(O)R$^{210f}$, and —S(O)$_2$R$^{210f}$; C$_{1-6}$ alkyl optionally substituted with one or more substituents independently selected from halogen, —OR$^{210f}$, —SR$^{210f}$, —N(R$^{210f}$)$_2$, —C(O)R$^{210f}$, —C(O)N(R$^{210f}$)$_2$, —N(R$^{210f}$)C(O)R$^{210f}$, —C(O)OR$^{210f}$, —OC(O)R$^{210f}$, —N(R$^{210f}$)C(O)N(R$^{210f}$)$_2$, —OC(O)N(R$^{210f}$)$_2$, —N(R$^{210f}$)C(O)OR$^{210f}$, —S(O)R$^{210f}$, —S(O)$_2$R$^{210f}$, —NO$_2$, =O, =S, =N(R$^{210f}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{29f}$; and C$_{3-10}$ carbocycle and 3- to 10-membered heterocycle, each of which is optionally substituted with one or more substituents independently selected from halogen, —OR$^{210f}$, —SR$^{210f}$, —N(R$^{210f}$)$_2$, —C(O)R$^{210f}$, —C(O)N(R$^{210f}$)$_2$, —N(R$^{210f}$)C(O)R$^{210f}$, —N(R$^{210f}$)C(O)N(R$^{210f}$)$_2$, —OC(O)N(R$^{210f}$)$_2$, —N(R$^{210f}$)C(O)OR$^{210f}$, —C(O)OR$^{210f}$, —OC(O)R$^{210f}$, —S(O)R$^{210f}$, —S(O)$_2$R$^{210f}$, —NO$_2$, =O, =S, =N(R$^{210f}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{29f}$; R$^{28}$ is selected from: hydrogen; —C(O)R$^{210g}$, —C(O)N(R$^{210g}$)$_2$, —C(O)OR$^{210g}$, —S(O)R$^{210g}$, and —S(O)$_2$R$^{210g}$; C$_{1-6}$ alkyl optionally substituted with one or more substituents independently selected from halogen, —OR$^{210g}$, —SR$^{210g}$, —N(R$^{210g}$)$_2$, —C(O)R$^{210g}$, —C(O)N(R$^{210g}$)$_2$, —N(R$^{210g}$)C(O)R$^{210g}$, —C(O)OR$^{210g}$, —OC(O)R$^{210g}$, —N(R$^{210g}$)C(O)N(R$^{210g}$)$_2$, —OC(O)N(R$^{210g}$)$_2$, —N(R$^{210g}$)C(O)OR$^{210g}$, —S(O)R$^{210g}$, —S(O)$_2$R$^{210g}$, —NO$_2$, =O, =S, =N(R$^{210g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{29g}$; and C$_{3-10}$ carbocycle and 3- to 10-membered heterocycle, each of which is optionally substituted with one or more substituents independently selected from halogen, —OR$^{210g}$, —SR$^{210g}$, —N(R$^{210g}$)$_2$, —C(O)R$^{210g}$, —C(O)N(R$^{210g}$)$_2$, —N(R$^{210g}$)C(O)R$^{210g}$, —N(R$^{210g}$)C(O)N(R$^{210g}$)$_2$, —OC(O)N(R$^{210g}$)$_2$, —N(R$^{210g}$)C(O)OR$^{210g}$, —C(O)OR$^{210g}$, —OC(O)R$^{210g}$, —S(O)R$^{210g}$, —S(O)$_2$R$^{210g}$, —NO$_2$, =O, =S, =N(R$^{210g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more $R^{29g}$; each $R^{29a}$ is independently selected from: halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, —$S(O)_2R^{210a}$, —$NO_2$, =O, =S, =$N(R^{210a})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, —$S(O)_2R^{210a}$, —$NO_2$, =O, =S, =$N(R^{210a})$, —$N_3$, and —CN; each $R^{29b}$ is independently selected from: halogen, —$NO_2$, —$N_3$, —CN, —$OR^{210b}$, —$SR^{210b}$, —$N(R^{210b})_2$, —$C(O)R^{210b}$, —$C(O)N(R^{210b})_2$, —$N(R^{210b})C(O)R^{210b}$, —$N(R^{210b})C(O)N(R^{210b})_2$, —$OC(O)N(R^{210b})_2$, —$N(R^{210b})C(O)OR^{210b}$, —$C(O)OR^{210b}$, —$OC(O)R^{210b}$, —$S(O)R^{210b}$, and —$S(O)_2R^{210b}$; $C_{1-6}$ alkyl, $C_{2-6}$ alkenyl, and $C_{2-6}$ alkynyl, each of which is optionally substituted with one or more substituents independently selected from halogen, —$OR^{210b}$, —$SR^{210b}$, —$N(R^{210b})_2$, —$C(O)R^{210b}$, —$C(O)N(R^{210b})_2$, —$N(R^{210b})C(O)R^{210b}$, —$C(O)OR^{210b}$, —$OC(O)R^{210b}$, —$N(R^{210b})C(O)N(R^{210b})_2$, —$OC(O)N(R^{210b})_2$, —$N(R^{210b})C(O)OR^{210b}$, —$S(O)R^{210b}$, —$S(O)_2R^{210b}$, —$NO_2$, =O, =S, =$N(R^{210b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{210b}$, —$SR^{210b}$, —$N(R^{210b})_2$, —$C(O)R^{210b}$, —$C(O)N(R^{210b})_2$, —$N(R^{210b})C(O)R^{210b}$, —$N(R^{210b})C(O)N(R^{210b})_2$, —$OC(O)N(R^{210b})_2$, —$N(R^{210b})C(O)OR^{210b}$, —$C(O)OR^{210b}$, —$OC(O)R^{210b}$, —$S(O)R^{210b}$, —$S(O)_2R^{210b}$, —$NO_2$, =O, =S, =$N(R^{210b})$, —$N_3$, —CN, $C_{1-6}$ alkyl, $C_{2-6}$ alkenyl, and $C_{2-6}$ alkynyl; each $R^{29c}$ is independently selected from: halogen, —$OR^{210c}$, —$SR^{210c}$, —$N(R^{210e})_2$, —$C(O)R^{210c}$, —$C(O)N(R^{210c})_2$, —$N(R^{210c})C(O)R^{210c}$, —$N(R^{210c})C(O)N(R^{210c})_2$, —$OC(O)N(R^{210c})_2$, —$N(R^{210c})C(O)OR^{210c}$, —$C(O)OR^{210c}$, —$OC(O)R^{210c}$, —$S(O)R^{210c}$, —$S(O)_2R^{210c}$, —$NO_2$, =O, =S, =$N(R^{210c})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210c}$, —$SR^{210c}$, —$N(R^{210c})_2$, —$C(O)R^{210c}$, —$C(O)N(R^{210c})_2$, —$N(R^{210c})C(O)R^{210c}$, —$N(R^{210c})C(O)N(R^{210c})_2$, —$OC(O)N(R^{210c})_2$, —$N(R^{210c})C(O)OR^{210c}$, —$C(O)OR^{210c}$, —$OC(O)R^{210c}$, —$S(O)R^{210c}$, —$S(O)_2R^{210c}$, —$NO_2$, =O, =S, =$N(R^{210e})$, —$N_3$, and —CN; each $R^{29d}$ is independently selected from: halogen, —$OR^{210d}$, —$SR^{210d}N(R^{210d})_2$, —$C(O)R^{210d}$, —$C(O)N(R^{210d})_2$, —$N(R^{210d})C(O)R^{210d}$, —$N(R^{210d})C(O)N(R^{210d})_2$, —$OC(O)N(R^{210d})_2$, —$N(R^{210d})C(O)OR^{210d}$, —$C(O)OR^{210d}$, —$OC(O)R^{210d}$, —$S(O)R^{210d}$, —$S(O)_2R^{210d}$, —$NO_2$, =O, =S, =$N(R^{210d})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210d}$, —$SR^{210d}$, —$N(R^{210d})_2$, —$C(O)R^{210d}$, —$C(O)N(R^{210d})_2$, —$N(R^{210d})C(O)R^{210d}$, —$N(R^{210d})C(O)N(R^{210d})_2$, —$OC(O)N(R^{210d})_2$, —$N(R^{210d})C(O)OR^{210d}$, —$C(O)OR^{210d}$, —$OC(O)R^{210d}$, —$S(O)R^{210d}$, —$S(O)_2R^{210d}$, —$NO_2$, =O, =S, =$N(R^{210d})$, —$N_3$, and —CN; each $R^{29e}$ is independently selected from: halogen, —$OR^{210e}$, —$SR^{210e}$, —$N(R^{210e})_2$, —$C(O)R^{210e}$, —$C(O)N(R^{210e})_2$, —$N(R^{210e})C(O)R^{210e}$, —$N(R^{210e})C(O)N(R^{210e})_2$, —$OC(O)N(R^{210e})_2$, —$N(R^{210e})C(O)OR^{210e}$, —$C(O)OR^{210e}$, —$OC(O)R^{210e}$, —$S(O)R^{210e}$, —$S(O)_2R^{210e}$, —$NO_2$, =O, =S, =$N(R^{210e})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210e}$, —$SR^{210e}$, —$N(R^{210e})_2$, —$C(O)R^{210e}$, —$C(O)N(R^{210e})_2$, —$N(R^{210e})C(O)R^{210e}$, —$N(R^{210e})C(O)N(R^{210e})_2$, —$OC(O)N(R^{210e})_2$, —$N(R^{210e})C(O)OR^{210e}$, —$C(O)OR^{210e}$, —$OC(O)R^{210e}$, —$S(O)R^{210e}$, —$S(O)_2R^{210e}$, —$NO_2$, =O, =S, =$N(R^{210e})$, —$N_3$, and —CN; each $R^{29f}$ is independently selected from: halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$N(R^{210f})C(O)N(R^{210f})_2$, —$OC(O)N(R^{210f})_2$, —$N(R^{210f})C(O)OR^{210f}$, —$C(O)OR^{210f}$, —$OC(O)R^{210f}$, —$S(O)R^{210f}$, —$S(O)_2R^{210f}$, —$NO_2$, =O, =S, =$N(R^{210f})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$N(R^{210f})C(O)N(R^{210f})_2$, —$OC(O)N(R^{210f})_2$, —$N(R^{210f})C(O)OR^{210f}$, —$C(O)OR^{210f}$, —$OC(O)R^{210f}$, —$S(O)R^{210f}$, —$S(O)_2R^{210f}$, —$NO_2$, =O, =S, =$N(R^{210f})$, —$N_3$, and —CN; each $R^{29g}$ is independently selected from: halogen, —$OR^{210g}$, —$SR^{210g}$, —$N(R^{210g})_2$, —$C(O)R^{210g}$, —$C(O)N(R^{210g})_2$, —$N(R^{210g})C(O)R^{210g}$, —$N(R^{210g})C(O)N(R^{210g})_2$, —$OC(O)N(R^{210g})_2$, —$N(R^{210g})C(O)OR^{210g}$, —$C(O)OR^{210g}$, —$OC(O)R^{210g}$, —$S(O)R^{210g}$, —$S(O)_2R^{210g}$, —$NO_2$, =O, =S, =$N(R^{210g})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210g}$, —$SR^{210g}$, —$N(R^{210g})_2$, —$C(O)R^{210g}$, —$C(O)N(R^{210g})_2$, —$N(R^{210g})C(O)R^{210g}$, —$N(R^{210g})C(O)N(R^{210g})_2$, —$OC(O)N(R^{210g})_2$, —$N(R^{210g})C(O)OR^{210g}$, —$C(O)OR^{210g}$, —$OC(O)R^{210g}$, —$S(O)R^{210g}$, —$S(O)_2R^{210g}$, —$NO_2$, =O, =S, =$N(R^{210g})$, —$N_3$, and —CN; each $R^{29z}$ is independently selected from: halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$N(R^{210z})C(O)N(R^{210z})_2$, —$OC(O)N(R^{210z})_2$, —$N(R^{210z})C(O)OR^{210z}$, —$C(O)OR^{210z}$, —$OC(O)R^{210z}$, —$S(O)R^{210z}$, —$S(O)_2R^{210z}$, —$NO_2$, =O, =S, =$N(R^{210z})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$N(R^{210z})C(O)N(R^{210z})_2$, —$OC(O)N(R^{210z})_2$, —$N(R^{210z})C(O)OR^{210z}$, —$C(O)OR^{210z}$, —$OC(O)R^{210z}$, —$S(O)R^{210z}$, —$S(O)_2R^{210z}$, —$NO_2$, =O, =S, =$N(R^{210z})$, —$N_3$, and —CN; and each $R^{210a}$, $R^{210b}$, $R^{210c}$, $R^{210d}$, $R^{210e}$, $R^{210f}$, $R^{210g}$ and $R^{210z}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In one aspect, disclosed herein is a compound of Formula (IIa) that is represented by Formula (IIa-ep):

(IIa-ep)

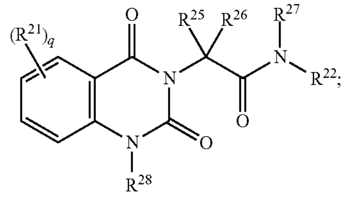

or a salt thereof, wherein $R^{22}$ is selected from:

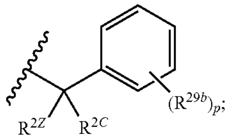

p is an integer selected from 1, 2, and 3; q is an integer selected from 1, 2, and 3; each $R^{21}$ is independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; $R^{2Z}$ is selected from: $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; $R^{2c}$ is selected from: hydrogen; $R^{25}$ and $R^{26}$ are each independently selected from: hydrogen; halogen; and $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; or $R^{25}$ together with $R^{26}$ form a 3- to 10-membered heterocycle or $C_{3-10}$ carbocycle; $R^{27}$ is selected from: hydrogen; $R^{28}$ is selected from: hydrogen; and each $R^{29b}$ is independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$.

In some embodiments, for a compound or salt of Formula (IIa), p is an integer selected from 1, 2, 3, and 4. In some embodiments, p is an integer selected from 1, 2 and 3. In some embodiments, p is an integer selected from 1 and 2. In some embodiments, p is an integer selected from 2, 3, and 4. In some embodiments, p is an integer selected from 2 and 3. In some embodiments, p is an integer selected from 2. In some embodiments, p is an integer selected from 1. In some embodiments, p is an integer selected from 3. In some embodiments, p is an integer selected from 4. In some embodiments, p is an integer selected from 5. In some embodiments, q is an integer selected from 1, 2, 3, and 4. In some embodiments, q is an integer selected from 1, 2 and 3. In some embodiments, q is an integer selected from 1 and 2. In some embodiments, q is an integer selected from 2, 3, and 4. In some embodiments, q is an integer selected from 2 and 3. In some embodiments, q is an integer selected from 2. In some embodiments, q is an integer selected from 1. In some embodiments, q is an integer selected from 3. In some embodiments, q is an integer selected from 4. In some embodiments, q is 5. In some embodiments, p is 0. In some embodiments, q is 0.

In some embodiments, for a compound or salt of Formula (IIa), each $R^{21}$ is independently selected from: halogen, —$NO_2$, —$N_3$, —CN, —$OR^{210a}$, —$SR^{210a}$, —N($R^{210a}$)$_2$, —C(O)$R^{210a}$, —C(O)N($R^{210a}$)$_2$, —N($R^{210a}$)C(O)$R^{210a}$, —N($R^{210a}$)C(O)N($R^{210a}$)$_2$, —OC(O)N($R^{210a}$)$_2$, —N($R^{210a}$)C(O)O$R^{210a}$, —C(O)O$R^{210a}$, —OC(O)$R^{210a}$, —S(O)$R^{210a}$, and —S(O)$_2R^{210a}$; $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —N($R^{210a}$)$_2$, —C(O)$R^{210a}$, —C(O)N($R^{210a}$)$_2$, —N($R^{210a}$)C(O)$R^{210a}$, —C(O)O$R^{210a}$, —OC(O)$R^{210a}$, —N($R^{210a}$)C(O)N($R^{210a}$)$_2$, —OC(O)N($R^{210a}$)$_2$, —N($R^{210a}$)C(O)O$R^{210a}$, —S(O)$R^{210a}$, —S(O)$_2R^{210a}$, —$NO_2$, =O, =S, =N($R^{210a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; and $C_{3-10}$ carbocycle and 3- to 10-membered heterocycle, each of which is optionally substituted with one or more substituents independently selected from halogen, —$OR^{210a}$, —$SR^{210a}$, —N($R^{210a}$)$_2$, —C(O)$R^{210a}$, —C(O)N($R^{210a}$)$_2$, —N($R^{210a}$)C(O)$R^{210a}$, —C(O)O$R^{210a}$, —OC(O)$R^{210a}$, —S(O)$R^{210a}$, —S(O)$_2R^{210a}$, —$NO_2$, =O, —$N_3$, —CN, and $C_{1-6}$ alkyl. In some embodiments, each $R^{21}$ is independently selected from: halogen, —$NO_2$, —$N_3$, —CN, —$OR^{210a}$, —$SR^{210a}$, —N($R^{210a}$)$_2$, —C(O)$R^{210a}$, —C(O)N($R^{210a}$)$_2$, —N($R^{210a}$)C(O)$R^{210a}$, —N($R^{210a}$)C(O)N($R^{210a}$)$_2$, —OC(O)N($R^{210a}$)$_2$, —N($R^{210a}$)C(O)O$R^{210a}$, —C(O)O$R^{210a}$, —OC(O)$R^{210a}$, —S(O)$R^{210a}$, and —S(O)$_2R^{210a}$; $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —N($R^{210a}$)$_2$, —C(O)$R^{210a}$, —C(O)N($R^{210a}$)$_2$, —N($R^{210a}$)C(O)$R^{210a}$, —C(O)O$R^{210a}$, —OC(O)$R^{210a}$, —N($R^{210a}$)C(O)N($R^{210a}$)$_2$, —OC(O)N($R^{210a}$)$_2$, —N($R^{210a}$)C(O)O$R^{210a}$, —S(O)$R^{210a}$, —S(O)$_2R^{210a}$, —$NO_2$, =O, =S, =N($R^{210a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; and $C_{3-10}$ carbocycle and 3- to 10-membered heterocycle, each of which is optionally substituted with one or more substituents independently selected from halogen, —CN, and $C_{1-6}$ alkyl. In some embodiments, each $R^{21}$ is independently selected from: halogen, —$NO_2$, —$N_3$, —CN, —$OR^{210a}$, —$SR^{210a}$, —N($R^{210a}$)$_2$, —C(O)$R^{210a}$, —C(O)N($R^{210a}$)$_2$, —N($R^{210a}$)C(O)$R^{210a}$, —N($R^{210a}$)C(O)N($R^{210a}$)$_2$, —OC(O)N($R^{210a}$)$_2$, —N($R^{210a}$)C(O)O$R^{210a}$, —C(O)O$R^{210a}$, —OC(O)$R^{210a}$, —S(O)$R^{210a}$, and —S(O)$_2R^{210a}$; $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$N(R^{210a})C(O)N(R^{210a})_2$, —$OC(O)N(R^{210a})_2$, —$N(R^{210a})C(O)OR^{210a}$, —$S(O)R^{210a}$, —$S(O)_2R^{210a}$, —$NO_2$, =O, =S, =$N(R^{210a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; and $C_{3-10}$ carbocycle and 3- to 10-membered heterocycle. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; and $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$N(R^{210a})C(O)N(R^{210a})_2$, —$OC(O)N(R^{210a})_2$, —$N(R^{210a})C(O)OR^{210a}$, —$S(O)R^{210a}$, —$S(O)_2R^{210a}$, —$NO_2$, =O, =S, =$N(R^{210a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; and $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$N(R^{210a})C(O)N(R^{210a})_2$, —$OC(O)N(R^{210a})_2$, —$N(R^{210a})C(O)OR^{210a}$, —$S(O)R^{210a}$, —$S(O)_2R^{210a}$, —$NO_2$, =O, =S, =$N(R^{210a})$, —$N_3$, —CN, $C_{3-10}$ carbocycle and 3- to 10-membered heterocycle. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; and $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$NO_2$, =O, —$N_3$, —CN, $C_{3-10}$ carbocycle and 3- to 10-membered heterocycle. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; and $C_{1-6}$ alkyl optionally substituted with one or more substituents independently selected from halogen, —$OR^{210a}$, —$SR^{210a}$, —$N(R^{210a})_2$, —$NO_2$, =O, —$N_3$, —CN, $C_{3-10}$ carbocycle and 3- to 10-membered heterocycle. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; and $C_{1-6}$ alkyl optionally substituted with one or more substituents independently selected from halogen, —$OR^{210a}$, —$SR^{210a}$, —$N(R^{210a})_2$, —$NO_2$, =O, —$N_3$, and —CN. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$S(O)R^{210a}$, and —$S(O)_2R^{210a}$; and $C_{1-6}$ alkyl optionally substituted with one or more substituents independently selected from halogen, —$OR^{210a}$, —$SR^{210a}$, —$N(R^{210a})_2$, —$NO_2$, =O, —$N_3$, and —CN. In some embodiments, each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, and —$OC(O)R^{210a}$; and $C_{1-6}$ alkyl optionally substituted with one or more substituents independently selected from halogen, —$OR^{210a}$, —$SR^{210a}$, —$N(R^{210a})_2$, —$NO_2$, =O, —$N_3$, and —CN. In some embodiments, each $R^{21}$ is independently selected from: halogen, —$NO_2$, —$N_3$, —CN, —$OR^{210a}$, —$SR^{210a}$, and —$N(R^{210a})_2$; $C_{1-6}$ alkyl optionally substituted with one or more substituents independently selected from halogen, —$OR^{210a}$, —$SR^{210a}$, —$N(R^{210a})_2$, —$NO_2$, =O, —$N_3$, and —CN. In some embodiments, each $R^{21}$ is independently selected from: halogen, —$NO_2$, —$N_3$, —CN, —$OR^{210a}$, —$SR^{210a}$, and —$N(R^{210a})_2$; and $C_{1-6}$ alkyl optionally substituted with one or more substituents independently selected from halogen, =O, —$N_3$, and —CN. In some embodiments, each $R^{21}$ is independently selected from: halogen, —$NO_2$, —$N_3$, —CN, —$OR^{210a}$, —$SR^{210a}$, and —$N(R^{210a})_2$; and $C_{1-6}$ alkyl optionally substituted with one or more substituents independently selected from halogen and —CN. In some embodiments, each $R^{21}$ is independently selected from: halogen, —$NO_2$, —$N_3$, —CN, —$OR^{210a}$, —$SR^{210a}$, and —$N(R^{210a})_2$; and $C_{1-6}$ alkyl optionally substituted with one or more substituents independently selected from fluoro and —CN. In some embodiments, each $R^{21}$ is independently selected from: halogen, —CN, —$OR^{210a}$, and $C_{1-6}$ alkyl optionally substituted with one or more substituents independently selected from fluoro and —CN. In some embodiments, each $R^{21}$ is independently selected from: fluoro, chloro, —OH, and $C_{1-6}$ alkyl optionally substituted with one or more fluoro. In some embodiments, each $R^{21}$ is independently selected from: fluoro, chloro, —OH, and $C_1$ alkyl optionally substituted with one or more fluoro. In some embodiments, each $R^{21}$ is independently selected from: fluoro, chloro, —OH, and —$CF_3$. In some embodiments, each $R^{21}$ is independently selected from: halogen, —CN, —$OR^{210a}$ and $C_{1-6}$ alkyl. In some embodiments, each $R^{21}$ is independently selected from: halogen, —CN, —$OR^{210a}$, and $C_1$ alkyl. In some embodiments, each $R^{21}$ is independently selected from: fluoro, chloro, —CN, —$OR^{210a}$, and $C_1$ alkyl. In some embodiments, each $R^{21}$ is independently selected from: fluoro, chloro, —CN, —OH, —$O(CH_3)$, and $C_1$ alkyl. In some embodiments, each $R^{21}$ is independently selected from: fluoro, chloro, —OH, —$O(CH_3)$, and $C_1$ alkyl. In some embodiments, each $R^{21}$ is independently selected from: fluoro, chloro, and —OH. In some embodiments, each $R^{21}$ is independently selected from: fluoro, and —OH.

In some embodiments, for a compound or salt of Formula (IIa), $R^{2Z}$ is selected from: —CN, —$C(O)R^{210z}$, —$C(O)N(R^{210z})_2$, and —$C(O)OR^{210z}$; $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —OC(O)N $(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$; and $C_{3-10}$ carbocycle and 3- to 10-membered heterocycle, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$N(R^{210z})C(O)N(R^{210z})_2$, —$OC(O)N(R^{210z})_2$, —$N(R^{210z})C(O)OR^{210z}$, —$C(O)OR^{210z}$, —$OC(O)R^{210z}$, —$S(O)R^{210z}$, —$S(O)_2R^{210z}$, —$NO_2$, =O, =S, =$N(R^{210z})$, —$N_3$, —CN, and $C_{1-6}$ alkyl. In some embodiments, $R^{2Z}$ is selected from: —CN, —$C(O)R^{210z}$, —$C(O)N(R^{210z})_2$, and —$C(O)OR^{210z}$; $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$; and $C_{3-10}$ carbocycle and 3- to 10-membered heterocycle, each of which is optionally substituted with one or more substituents independently selected from halogen, —$OR^{210z}$, —$SR^{210z}$, —$N(R^{210z})_2$, —$N_3$, —CN, and $C_{1-6}$ alkyl. In some embodiments, $R^{2Z}$ is selected from: —CN, —$C(O)R^{210z}$, —$C(O)N(R^{210z})_2$, and —$C(O)OR^{210z}$; $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$; and $C_{3-10}$ carbocycle and 3- to 10-membered heterocycle, each of which is optionally substituted with one or more substituents independently selected from halogen and —CN. In some embodiments, $R^{2Z}$ is selected from: —CN, —$C(O)R^{210z}$, —$C(O)N(R^{210z})_2$, and —$C(O)OR^{210z}$; $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$; and $C_{3-10}$ carbocycle and 3- to 10-membered heterocycle. In some embodiments, $R^{2Z}$ is selected from: —CN, —$C(O)R^{210z}$, —$C(O)N(R^{210z})_2$, and —$C(O)OR^{210z}$; and $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$In some embodiments, $R^{2Z}$ is selected from: —CN, —$C(O)R^{210z}$, —$C(O)N(R^{210z})_2$, and —$C(O)OR^{210z}$; and $C_{1-6}$ alkyl optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, =S, =$N(R^{210z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$. In some embodiments, $R^{2Z}$ is selected from: —CN, —$C(O)R^{210z}$, —$C(O)N(R^{210z})_2$, and —$C(O)OR^{210z}$; and $C_{1-6}$ alkyl optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, —$N(R^{210z})C(O)N(R^{210z})_2$, —$OC(O)N(R^{210z})_2$, —$N(R^{210z})C(O)OR^{210z}$, —$S(O)R^{210z}$, —$S(O)_2R^{210z}$, —$NO_2$, =O, —$N_3$, —CN, $C_{3-10}$ carbocycle and 3- to 10-membered heterocycle. In some embodiments, $R^{2Z}$ is selected from: —CN, —$C(O)R^{210z}$, —$C(O)N(R^{210z})_2$, and —$C(O)OR^{210z}$; and $C_{1-6}$ alkyl optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, =O, —$N_3$, —CN, $C_{3-10}$ carbocycle and 3- to 10-membered heterocycle. In some embodiments, $R^{2Z}$ is selected from: —CN, —$C(O)R^{210z}$, —$C(O)N(R^{210z})_2$, and —$C(O)OR^{210z}$; and $C_{1-6}$ alkyl optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —$OC(O)R^{210z}$, =O, —$N_3$, —CN. In some embodiments, $R^{2Z}$ is selected from: —CN, —$C(O)R^{210z}$, —$C(O)N(R^{210z})_2$, and —$C(O)OR^{210z}$; and $C_{1-6}$ alkyl optionally substituted with one or more substituents independently selected from halogen, —$OR^{210z}$, —$SR^{210z}$, —$N(R^{210z})_2$, =O, —$N_3$, —CN. In some embodiments, $R^{2Z}$ is selected from $C_{1-6}$ alkyl optionally substituted with one or more substituents independently selected from halogen, —$OR^{210z}$, —$SR^{210z}$, —$N(R^{210z})_2$, =O, —$N_3$, —CN. In some embodiments, $R^{2Z}$ is selected from $C_{1-6}$ alkyl optionally substituted with one or more substituents independently selected from halogen, —$OR^{210z}$, and —CN. In some embodiments, $R^{2Z}$ is selected from $C_{1-6}$ alkyl optionally substituted with one or more substituents independently selected from fluoro, —$OR^{210z}$, and —CN. In some embodiments, $R^{2Z}$ is selected from $C_{1-6}$ alkyl optionally substituted with one or more substituents independently selected from fluoro and —CN. In some embodiments, $R^{2Z}$ is selected from $C_{1-6}$ alkyl optionally substituted with one or more substituents independently selected from fluoro. In some embodiments, $R^{2Z}$ is selected from $C_{1-6}$ alkyl. In some embodiments, $R^{2Z}$ is selected from $C_{1-3}$ alkyl. In some embodiments, $R^{2Z}$ is selected from $C_{1-2}$ alkyl. In some embodiments, $R^{2Z}$ is selected from $C_1$ alkyl. In some embodiments, $R^{2Z}$ is selected from hydrogen. In some embodiments, $R^{2Z}$ is selected from —$CF_3$. In some embodiments, $R^{2Z}$ is selected from —$CH_2OH$. In some embodiments, $R^{2Z}$ is selected from halogen. In some embodiments, $R^{2Z}$ is selected from fluorine.

In some embodiments, for a compound or salt of Formula (IIa), when $R^{2Z}$ is selected from hydrogen, then $R^{21}$ is selected from halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$N(R^{210a})C(O)N(R^{210a})_2$, —$OC(O)N(R^{210a})_2$, —$N(R^{210a})C(O)OR^{210a}$, —$S(O)R^{210a}$, —$S(O)_2R^{210a}$, —$NO_2$, =O, =S, =$N(R^{210a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; $C_{3-10}$ carbocycle optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, —$S(O)_2R^{210a}$, —$NO_2$, =O, =S, =$N(R^{210a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29a}$; and 3- to 10-membered heterocycle, optionally substituted with one or more substituents independently selected from halogen, —$OR^{210a}$, —$SR^{210a}$, —$N(R^{210a})_2$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, —$S(O)_2R^{210a}$, —$NO_2$, =S, =$N(R^{210a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29a}$. In some embodiments, when $R^{2Z}$ is selected from hydrogen, then $R^{21}$ is selected from halogen, —$NO_2$, —CN, —$OR^{210a}$, —$SR^{210a}$, —$N(R^{210a})_2$; $C_{1-6}$ alkyl, optionally substituted with one or more substituents independently selected from halogen, —$OR^{210a}$, —$SR^{210a}$, —$N(R^{210a})_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; $C_{3-10}$ carbocycle optionally substituted with one or more substituents independently selected from halogen, —$OR^{210a}$, —$SR^{210a}$, —$N(R^{210a})_2$, =O, —CN, and $C_{1-6}$ alkyl, wherein each $C_{1-6}$ alkyl is optionally substituted with one or more $R^{29a}$; and 3- to 10-membered heterocycle, optionally substituted with one or more substituents independently selected from halogen, —$OR^{210a}$, —CN, and $C_{1-6}$ alkyl. In some embodiments, when $R^{2Z}$ is selected from hydrogen, then $R^{21}$ is selected from halogen, —$NO_2$, —CN, —$OR^{210a}$, —$SR^{210a}$, —$N(R^{210a})_2$; $C_{1-6}$ alkyl, optionally substituted with one or more substituents independently selected from halogen, —$OR^{210a}$, —$SR^{210a}$, —$N(R^{210a})_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; $C_{3-10}$ carbocycle optionally substituted with one or more substituents independently selected from halogen, —$OR^{210a}$, —$SR^{210a}$, —$N(R^{210a})_2$, =O, —CN, and $C_{1-6}$ alkyl, wherein each $C_{1-6}$ alkyl is optionally substituted with one or more $R^{29a}$; and 3- to 10-membered heterocycle. In some embodiments, when $R^{2Z}$ is selected from hydrogen, then $R^{21}$ is selected from halogen, —$NO_2$, —CN, —$OR^{210a}$, —$SR^{210a}$, —$N(R^{210a})_2$; $C_{1-6}$ alkyl, optionally substituted with one or more substituents independently selected from halogen and —$OR^{210a}$; and $C_{3-10}$ carbocycle optionally substituted with one or more substituents independently selected from halogen, —$OR^{210a}$, —CN, and $C_{1-6}$ alkyl. In some embodiments, when $R^{2Z}$ is selected from hydrogen, then $R^{21}$ is selected from halogen, —CN, and $C_{1-6}$ alky. In some embodiments, when $R^{2Z}$ is selected from hydrogen, then $R^{21}$ is selected from fluoro and —CN, and —$CH_3$. In some embodiments, when $R^{2Z}$ is selected from hydrogen, then $R^{21}$ is selected from fluoro.

In some embodiments, the compound or salt of Formula (IIa) is not 3(2H)-Quinazolineacetamide, 6-(4-acetyl-1-piperazinyl)-N-[(3,4-dichlorophenyl)methyl]-1,4-dihydro-2,4-dioxo-. In some embodiments, the compound or salt of Formula (IIa) is not 2023028-08-0, wherein said number is a CAS registry number.

In some embodiments, for a compound or salt of Formula (IIa), $R^{2C}$ is selected from: hydrogen; —CN, —$C(O)R^{210c}$, —$C(O)N(R^{210c})_2$, —$C(O)OR^{210c}$; $C_{1-6}$ alkyl, $C_{2-6}$ alkenyl, and $C_{2-6}$ alkynyl, each of which is optionally substituted with one or more substituents independently selected from halogen, —$OR^{210c}$, —$SR^{210c}$, —$N(R^{210c})_2$, —$C(O)R^{210c}$, —$C(O)N(R^{210c})_2$, —$N(R^{210c})C(O)R^{210c}$, —$C(O)OR^{210c}$, —$OC(O)R^{210c}$, —$N(R^{210c})C(O)N(R^{210c})_2$, —$OC(O)N(R^{210c})_2$, —$N(R^{210c})C(O)OR^{210c}$, —$S(O)R^{210c}$, —$S(O)_2R^{210c}$, —$NO_2$, =O, =S, =$N(R^{210c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29c}$; and $C_{3-10}$ carbocycle and 3- to 10-membered heterocycle. In some embodiments, $R^{2C}$ is selected from: hydrogen; —CN, —$C(O)R^{210c}$, —$C(O)N(R^{210c})_2$, —$C(O)OR^{210c}$; and $C_{1-6}$ alkyl, $C_{2-6}$ alkenyl, and $C_{2-6}$ alkynyl, each of which is optionally substituted with one or more substituents independently selected from halogen, —$OR^{210c}$, —$SR^{210c}$, —$N(R^{210c})_2$, —$C(O)R^{210c}$, —$C(O)N(R^{210c})_2$, —$N(R^{210c})C(O)R^{210c}$, —$C(O)OR^{210c}$, —$OC(O)R^{210c}$, —$N(R^{210c})C(O)N(R^{210c})_2$, —$OC(O)N(R^{210c})_2$, —$N(R^{210c})C(O)OR^{210c}$, —$S(O)R^{210c}$, —$S(O)_2R^{210c}$, —$NO_2$, =O, =S, =$N(R^{210c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29c}$. In some embodiments, $R^{2C}$ is selected from: hydrogen; —CN, —$C(O)R^{210c}$, —$C(O)N(R^{210c})_2$, —$C(O)OR^{210c}$; and $C_{1-6}$ alkyl, $C_{2-6}$ alkenyl, and $C_{2-6}$ alkynyl, each of which is optionally substituted with one or more substituents independently selected from halogen, —$OR^{210c}$, —$SR^{210c}$, —$N(R^{210c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{29c}$. In some embodiments, $R^{2C}$ is selected from: hydrogen; —CN, —$C(O)R^{210c}$, —$C(O)N(R^{210c})_2$, —$C(O)OR^{210c}$; and $C_{1-6}$ alkyl optionally substituted with one or more substituents independently selected from halogen, —$OR^{210c}$, —$SR^{210c}$, —$N(R^{210c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{29c}$. In some embodiments, $R^{2C}$ is selected from: hydrogen; —CN, —$C(O)R^{210c}$, —$C(O)N(R^{210c})_2$, —$C(O)OR^{210c}$; and $C_{1-6}$ alkyl optionally substituted with one or more substituents independently selected from halogen, —$OR^{210c}$, —$SR^{210c}$, —$N(R^{210c})_2$, =O, —$N_3$, and —CN, $C_{3-10}$ carbocycle and 3- to 10-membered heterocycle. In some embodiments, $R^{2C}$ is selected from: hydrogen; —CN, —$C(O)R^{210c}$, —$C(O)N(R^{210c})_2$, —$C(O)OR^{210c}$; and $C_{1-6}$ alkyl optionally substituted with one or more substituents independently selected from halogen, —$OR^{210c}$, —$SR^{210c}$, —$N(R^{210c})_2$, =O, —$N_3$, and —CN. In some embodiments, $R^{2C}$ is selected from: hydrogen; —CN, —C(O)$R^{210c}$, —C(O)N($R^{210c}$)$_2$, —C(O)O$R^{210c}$; and $C_{1-6}$ alkyl optionally substituted with one or more substituents independently selected from halogen, and —CN. In some embodiments, $R^{2C}$ is selected from: hydrogen; —CN; and $C_{1-6}$ alkyl optionally substituted with one or more substituents independently selected from halogen, and —CN. In some embodiments, $R^{2C}$ is selected from: hydrogen, —CN, and $C_{1-6}$ alkyl. In some embodiments, $R^{2C}$ is selected from: hydrogen and $C_{1-6}$ alkyl. In some embodiments, $R^{2C}$ is selected from: hydrogen and $C_1$ alkyl. In some embodiments, $R^{2C}$ is selected from: hydrogen. In some embodiments, $R^{2C}$ is selected from halogen. In some embodiments, $R^{2C}$ is selected from fluoro.

In some embodiments, for a compound or salt of Formula (IIa), $R^{25}$ is selected from: hydrogen; halogen, —C(O)$R^{210d}$, —C(O)N($R^{210d}$)$_2$, —C(O)O$R^{210d}$, —S(O)$R^{210d}$, —S(O)$_2$$R^{210d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —$NO_2$, =O, =S, =N($R^{210d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —N($R^{210d}$)C(O)N($R^{210d}$)$_2$, —OC(O)N($R^{210d}$)$_2$, —N($R^{210d}$)C(O)O$R^{210d}$, —C(O)O$R^{210d}$, —OC(O)$R^{210d}$, —S(O)$R^{210d}$, —S(O)$_2$$R^{210d}$, —$NO_2$, =O, =S, =N($R^{210d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29d}$. In some embodiments, $R^{25}$ is selected from: hydrogen; halogen, —C(O)$R^{210d}$, —C(O)N($R^{210d}$)$_2$, —C(O)O$R^{210d}$, and —CN; $C_{1-6}$ alkyl, $C_{2-6}$ alkenyl, and $C_{2-6}$ alkynyl, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —$NO_2$, =O, =S, =N($R^{210d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —N($R^{210d}$)C(O)N($R^{210d}$)$_2$, —OC(O)N($R^{210d}$)$_2$, —N($R^{210d}$)C(O)O$R^{210d}$, —C(O)O$R^{210d}$, —OC(O)$R^{210d}$, —S(O)$R^{210d}$, —S(O)$_2$$R^{210d}$, —$NO_2$, =O, =S, =N($R^{210d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29d}$. In some embodiments, $R^{25}$ is selected from: hydrogen; halogen, —C(O)$R^{210d}$, —C(O)N($R^{210d}$)$_2$, —C(O)O$R^{210d}$, and —CN; $C_{1-6}$ alkyl, optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —$NO_2$, =O, =S, =N($R^{210d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —N($R^{210d}$)C(O)N($R^{210d}$)$_2$, —OC(O)N($R^{210d}$)$_2$, —N($R^{210d}$)C(O)O$R^{210d}$, —C(O)O$R^{210d}$, —OC(O)$R^{210d}$, —S(O)$R^{210d}$, —S(O)$_2$$R^{210d}$, —$NO_2$, =O, =S, =N($R^{210d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29d}$. In some embodiments, $R^{25}$ is selected from: hydrogen; halogen, —C(O)$R^{210d}$, —C(O)N($R^{210d}$)$_2$, —C(O)O$R^{210d}$, and —CN; $C_{1-6}$ alkyl, optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —$NO_2$, =O, =S, =N($R^{210d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle, each of which is optionally substituted with one or more substituents independently selected from halogen, —O$R^{210a}$, —S$R^{210d}$, —N($R^{210d}$)$_2$, —C(O)$R^{210d}$, —C(O)N($R^{210d}$)$_2$, —N($R^{210d}$)C(O)$R^{210d}$, —N($R^{210d}$)C(O)N($R^{210d}$)$_2$, —OC(O)N($R^{210d}$)$_2$, —N($R^{210d}$)C(O)O$R^{210d}$, —C(O)O$R^{210d}$, —OC(O)$R^{210d}$, —S(O)$R^{210d}$, —S(O)$_2$$R^{210d}$, —$NO_2$, =O, =S, =N($R^{210d}$), —$N_3$, —CN, and $C_{1-6}$ alkyl. In some embodiments, $R^{25}$ is selected from: hydrogen; halogen, —C(O)$R^{210d}$, —C(O)N($R^{210d}$)$_2$, —C(O)O$R^{210a}$, and —CN; $C_{1-6}$ alkyl, optionally substituted with one or more substituents independently selected from halogen, —O$R^{210a}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —$NO_2$, =O, =S, =N($R^{210d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{25}$ is selected from: hydrogen; halogen, —C(O)$R^{210d}$, —C(O)N($R^{210d}$)$_2$, —C(O)O$R^{210d}$, and —CN; $C_{1-6}$ alkyl, optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —$NO_2$, =O, =S, =N($R^{210d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle. In some embodiments, $R^{25}$ is selected from: hydrogen; halogen, —C(O)$R^{210d}$, —C(O)N($R^{210d}$)$_2$, —C(O)O$R^{210d}$, and —CN; and $C_{1-6}$ alkyl, optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)

$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2R^{210d}$, —NO$_2$, ═O, ═S, ═N($R^{210d}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$. In some embodiments, $R^{25}$ is selected from: hydrogen; halogen, —C(O)$R^{210d}$, —C(O)N($R^{210d}$)$_2$, —C(O)O$R^{210d}$, and —CN; and $C_{1-6}$ alkyl, optionally substituted with one or more substituents independently selected from halogen, —O$R^{210d}$, —S$R^{210d}$, —N($R^{210d}$)$_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$. In some embodiments, $R^{25}$ is selected from: hydrogen; and $C_{1-6}$ alkyl, optionally substituted with one or more substituents independently selected from halogen, —O$R^{210d}$, —S$R^{210d}$, —N($R^{210d}$)$_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$. In some embodiments, $R^{25}$ is selected from: hydrogen; and $C_{1-6}$ alkyl, optionally substituted with one or more substituents independently selected from halogen, —O$R^{210d}$, —S$R^{210d}$, —N($R^{210d}$)$_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$. In some embodiments, $R^{25}$ is selected from: hydrogen; and $C_{1-6}$ alkyl, optionally substituted with one or more substituents independently selected from halogen, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$. In some embodiments, $R^{25}$ is selected from: hydrogen; and $C_{1-6}$ alkyl, optionally substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more $R^{29d}$. In some embodiments, $R^{25}$ is selected from: hydrogen; and $C_{1-6}$ alkyl, optionally substituted with one or more substituents independently selected from $C_{3-10}$ carbocycle optionally substituted with one or more $R^{29d}$. In some embodiments, $R^{25}$ is selected from: hydrogen; and $C_{1-6}$ alkyl, optionally substituted with one or more substituents independently selected from $C_{3-10}$ carbocycle. In some embodiments, $R^{25}$ is selected from: hydrogen; and $C_1$ alkyl, optionally substituted with one or more substituents independently selected from $C_{3-10}$ carbocycle. In some embodiments, $R^{25}$ is selected from hydrogen, methyl, and benzyl. In some embodiments, $R^{25}$ is selected from hydrogen and methyl. In some embodiments, $R^{25}$ is selected from hydrogen. In some embodiments, $R^{25}$ is selected from: halogen. In some embodiments, $R^{25}$ is selected from: fluoro. In some embodiments, $R^{25}$ together with $R^{26}$ form a $C_{3-10}$ carbocycle or 3- to 10-membered heterocycle optionally substituted with one or more $R^{29d}$. In some embodiments, $R^{25}$ together with $R^{26}$ form a cyclopropyl optionally substituted with one or more $R^{29d}$. In some embodiments, $R^{25}$ together with $R^{26}$ form a cyclopropyl. In some embodiments, $R^{25}$ is —F, and $R^{26}$ is —F.

In some embodiments, for a compound or salt of Formula (IIa), $R^{26}$ is selected from: hydrogen; halogen, —C(O)$R^{210e}$, —C(O)N($R^{210e}$)$_2$, —C(O)O$R^{210e}$, —S(O)$R^{210e}$, —S(O)$_2$ $R^{210e}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2$ $R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —N($R^{210e}$)C(O)N($R^{210e}$)$_2$, —OC(O)N($R^{210e}$)$_2$, —N($R^{210e}$)C(O)O$R^{210e}$, —C(O)O$R^{210e}$, —OC(O)$R^{210e}$, —S(O)$R^{210e}$, —S(O)$_2R^{210e}$, —NO$_2$, ═O, ═S, ═N($R^{210e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; $C_{1-6}$ alkyl, $C_{2-6}$ alkenyl, and $C_{2-6}$ alkynyl, each of which is optionally substituted with one or more substituents independently selected from halogen, —O$R^{210e}$, —S$R^{210e}$, —N($R^{210e}$)$_2$, —C(O)$R^{210e}$, C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2R^{210e}$, —NO$_2$, ═O, ═S, ═N($R^{21e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —N($R^{210e}$)C(O)N($R^{210e}$)$_2$, —OC(O)N($R^{210e}$)$_2$, —N($R^{210e}$)C(O)O$R^{210e}$, —C(O)O$R^{210e}$, —OC(O)$R^{210e}$, —S(O)$R^{210e}$, —S(O)$_2R^{210e}$, —NO$_2$, ═O, ═S, ═N($R^{210e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; $C_{1-6}$ alkyl, optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2$ $R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —N($R^{210e}$)C(O)N($R^{210e}$)$_2$, —OC(O)N($R^{210e}$)$_2$, —N($R^{210e}$)C(O)O$R^{210e}$, —C(O)O$R^{210e}$, —OC(O)$R^{210e}$, —S(O)$R^{210e}$, —S(O)$_2R^{210e}$, —NO$_2$, ═O, ═S, ═N($R^{210e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; $C_{1-6}$ alkyl, optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —N($R^{210e}$)C(O)N($R^{210e}$)$_2$, —OC(O)N($R^{210e}$)$_2$, —N($R^{210e}$)C(O)O$R^{210e}$, —C(O)O$R^{210e}$, —OC(O)$R^{210e}$, —S(O)$R^{210e}$, —S(O)$_2R^{210e}$, —NO$_2$, ═O, ═S, ═N($R^{210e}$), —N$_3$, —CN, and $C_{1-6}$ alkyl. In some embodiments, $R^{26}$ is selected from: hydrogen; halogen, —C(O)$R^{210e}$, —C(O)N($R^{210e}$)$_2$, —C(O)O$R^{210e}$, and —CN; $C_{1-6}$ alkyl, optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{26}$ is selected from: hydrogen; halogen, —C(O)$R^{210e}$, —C(O)N($R^{210e}$)$_2$, —C(O)O$R^{210e}$ and —CN; $C_{1-6}$ alkyl, optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle. In some embodiments, $R^{26}$ is selected from: hydrogen; halogen, —C(O)$R^{210e}$, —C(O)N($R^{210e}$)$_2$, —C(O)O$R^{210e}$, and —CN; and $C_{1-6}$ alkyl, optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; and $C_{1-6}$ alkyl, optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2R^{210e}$, —NO$_2$, ═O, ═S, ═N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; and $C_{1-6}$ alkyl, optionally substituted with one or more substituents independently selected from halogen, —O$R^{210e}$, —S$R^{210e}$, —N($R^{210e}$)$_2$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; and $C_{1-6}$ alkyl, optionally substituted with one or more substituents independently selected from halogen, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; and $C_{1-6}$ alkyl, optionally substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more $R^{29e}$. In some embodiments, $R^{26}$ is selected from: hydrogen; halogen, —C(O)$R^{210e}$, —C(O)N($R^{210e}$)$_2$, —C(O)O$R^{210e}$, and —CN; and $C_{1-6}$ alkyl, optionally substituted with one or more substituents independently selected from $C_{3-10}$ carbocycle optionally substituted with one or more $R^{29e}$. In some embodiments, $R^{26}$ is selected from: hydrogen; and $C_{1-6}$ alkyl, optionally substituted with one or more substituents independently selected from $C_{3-10}$ carbocycle. In some embodiments, $R^{26}$ is selected from: hydrogen; and $C_{1-6}$ alkyl, optionally substituted with one or more phenyl. In some embodiments, $R^{26}$ is selected from: hydrogen, methyl, and benzyl. In some embodiments, $R^{26}$ is selected from: hydrogen, and methyl. In some embodiments, $R^{26}$ is selected from: hydrogen. In some embodiments, $R^{26}$ is selected from: halogen. In some embodiments, $R^{26}$ is selected from: fluoro. In some embodiments, $R^{25}$ together with $R^{26}$ form a $C_{3-10}$ carbocycle or 3- to 10-membered heterocycle optionally substituted with one or more $R^{29e}$. In some embodiments, $R^{25}$ together with $R^{26}$ form a cyclopropyl optionally substituted with one or more $R^{29e}$. In some embodiments, $R^{25}$ together with $R^{26}$ form a cyclopropyl. In some embodiments, $R^{25}$ is —F, and $R^{26}$ is —F.

In some embodiments, for a compound or salt of Formula (IIa), $R^{25}$ together with $R^{26}$ form a 3- to 10-membered heterocycle or $C_{3-10}$ carbocycle, wherein the 3- to 10-membered heterocycle or $C_{3-10}$ carbocycle is optionally substituted with one or more $R^{29d}$. In some embodiments, $R^{25}$ together with $R^{26}$ form a 3- to 10-membered heterocycle or $C_{3-10}$ carbocycle. In some embodiments, $R^{25}$ together with $R^{26}$ form a $C_{3-10}$ carbocycle. In some embodiments, $R^5$ together with $R^6$ form a moiety selected from ═O, ═S, ═N(O)($R^{210e}$), and =N($R^{210d}$). In some embodiments, $R^5$ together with $R^6$ form a moiety selected from ═O. In some embodiments, $R^{25}$ is hydrogen, and $R^{26}$ is hydrogen. In some embodiments, $R^{25}$ is hydrogen, and $R^{26}$ is isobutyl.

In some embodiments, for a compound or salt of Formula (IIa), $R^{27}$ is selected from: hydrogen; —C(O)$R^{210f}$, —C(O)N($R^{210f}$)$_2$, —C(O)O$R^{210f}$, —S(O)$R^{210f}$, and —S(O)$_2R^{210f}$; $C_{1-6}$ alkyl optionally substituted with one or more substituents independently selected from halogen, —O$R^{210f}$, —S$R^{210f}$, —N($R^{210f}$)$_2$, —C(O)$R^{210f}$, —C(O)N($R^{210f}$)$_2$, —N($R^{210f}$)C(O)$R^{210f}$, —C(O)O$R^{210f}$, —OC(O)$R^{210f}$, —N($R^{210f}$)C(O)N($R^{210f}$)$_2$, —OC(O)N($R^{210f}$)$_2$, —N($R^{210f}$)C(O)O$R^{210f}$, —S(O)$R^{210f}$, —S(O)$_2R^{210f}$, —NO$_2$, ═O, ═S, ═N($R^{210f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$; and $C_{3-10}$ carbocycle and 3- to 10-membered heterocycle, each of which is optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$N(R^{210f})C(O)N(R^{210f})_2$, —$OC(O)N(R^{210f})_2$, —$N(R^{210f})C(O)OR^{210f}$, —$C(O)OR^{210f}$, —$OC(O)R^{210f}$, —$S(O)R^{210f}$, —$S(O)_2R^{210f}$, —$NO_2$, =O, =S, =$N(R^{210f})$, —$N_3$, —CN, and $C_{1-6}$ alkyl. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2R^{210f}$; $C_{1-6}$ alkyl each of which is optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, —$N(R^{210f})C(O)N(R^{210f})_2$, —$OC(O)N(R^{210f})_2$, —$N(R^{210f})C(O)OR^{210f}$, —$S(O)R^{210f}$, —$S(O)_2R^{210f}$, —$NO_2$, =O, =S, =$N(R^{210f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$; and $C_{3-10}$ carbocycle and 3- to 10-membered heterocycle, each of which is optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$N(R^{210f})C(O)N(R^{210f})_2$, —$OC(O)N(R^{210f})_2$, —$N(R^{210f})C(O)OR^{210f}$, —$C(O)OR^{210f}$, —$OC(O)R^{210f}$, —$S(O)R^{210f}$, —$S(O)_2R^{210f}$, —$NO_2$, =O, =S, =$N(R^{210f})$, —$N_3$, —CN, and $C_{1-6}$ alkyl. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2$ $R^{210f}$; $C_{1-6}$ alkyl optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, —$N(R^{210f})C(O)N(R^{210f})_2$, —$OC(O)N(R^{210f})_2$, —$N(R^{210f})C(O)OR^{210f}$, —$S(O)R^{210f}$, —$S(O)_2R^{210f}$, —$NO_2$, =O, =S, =$N(R^{210f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$; and $C_{3-10}$ carbocycle and 3- to 10-membered heterocycle, each of which is optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, =O, —CN, and $C_{1-6}$ alkyl. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2R^{210f}$; $C_{1-6}$ alkyl optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, —$N(R^{210f})C(O)N(R^{210f})_2$, —$OC(O)N(R^{210f})_2$, —$N(R^{210f})C(O)OR^{210f}$, —$S(O)R^{210f}$, —$S(O)_2R^{210f}$, —$NO_2$, =O, =S, =$N(R^{210f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$; and $C_{3-10}$ carbocycle and 3- to 10-membered heterocycle. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2R^{210f}$; $C_{1-6}$ alkyl optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, —$N(R^{210f})C(O)N(R^{210f})_2$, —$OC(O)N(R^{210f})_2$, —$N(R^{210f})C(O)OR^{210f}$, —$S(O)R^{210f}$, —$S(O)_2R^{210f}$, —$NO_2$, =O, =S, =$N(R^{210f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2R^{210f}$; $C_{1-6}$ alkyl optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2R^{210f}$; $C_{1-6}$ alkyl optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, =O, —CN, $C_{3-10}$ carbocycle and 3- to 10-membered heterocycle. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2$ $R^{210f}$; $C_{1-6}$ alkyl optionally substituted with one or more substituents independently selected from halogen, —$OR^{210f}$, —$SR^{210f}$, —$N(R^{210f})_2$, —$C(O)R^{210f}$, —$C(O)N(R^{210f})_2$, —$N(R^{210f})C(O)R^{210f}$, —$C(O)OR^{210f}$, —$OC(O)R^{210f}$, =O, and —CN. In some embodiments, $R^{27}$ is selected from: hydrogen; —$C(O)R^{210f}$, —$C(O)N(R^{210f})_2$, —$C(O)OR^{210f}$, —$S(O)R^{210f}$, and —$S(O)_2R^{210f}$; $C_{1-6}$ alkyl optionally substituted with one or more substituents independently selected from halogen and —CN. In some embodiments, $R^{27}$ is selected from: hydrogen; —$C(O)R^{210f}$, —$C(O)N(R^{210f})_2$, —$C(O)OR^{210f}$; $C_{1-6}$ alkyl optionally substituted with one or more substituents independently selected from halogen and —CN. In some embodiments, $R^{27}$ is selected from: hydrogen; and $C_{1-6}$ alkyl optionally substituted with one or more substituents independently selected from halogen and —CN. In some embodiments, $R^{27}$ is selected from: hydrogen; and $C_{1-6}$ alkyl optionally substituted with one or more substituents independently selected from fluoro and —CN. In some embodiments, $R^{27}$ is selected from hydrogen and $C_{1-6}$ alkyl. In some embodiments, $R^{27}$ is selected from hydrogen and $C_{1-4}$ alkyl. In some embodiments, $R^{27}$ is selected from hydrogen and $C_1$ alkyl. In some embodiments, $R^{27}$ is selected from hydrogen.

In some embodiments, for a compound or salt of Formula (IIa), $R^{22}$ is

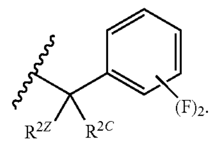

In some embodiments, $R^{22}$ is

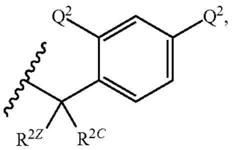

wherein each $Q^2$ is independently selected from halogen, —CN, —OH, —O($C_{1-6}$ alkyl), and —OH. In some embodiments, $R^{22}$ is

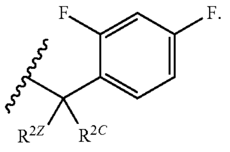

In some embodiments, $R^{22}$ is selected from

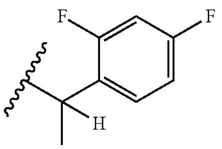

and

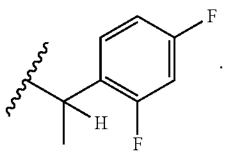

.

In some embodiments, $R^{22}$ is

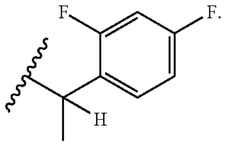 [SMILES: *C(C)c1ccc(F)cc1F]

In some embodiments, for a compound or salt of Formula (IIa), $R^{28}$ is selected from: hydrogen; —C(O)$R^{210g}$, —C(O)N($R^{210g}$)$_2$, —C(O)O$R^{210g}$, —S(O)$R^{210g}$, and —S(O)$_2$$R^{210g}$; and $C_{1-6}$ alkyl optionally substituted with one or more substituents independently selected from halogen, —O$R^{210g}$, —S$R^{210g}$, —N($R^{210g}$)$_2$, —C(O)$R^{210g}$, —C(O)N($R^{210g}$)$_2$, —N($R^{210g}$)C(O)$R^{210g}$, —C(O)O$R^{210g}$, —OC(O)$R^{210g}$, —N($R^{210g}$)C(O)N($R^{210g}$)$_2$, —OC(O)N($R^{210g}$)$_2$, —N($R^{210g}$)C(O)O$R^{210g}$, —S(O)$R^{210g}$, —S(O)$_2$$R^{210g}$, —$NO_2$, =O, =S, =N($R^{210g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29g}$. In some embodiments, $R^{28}$ is selected from: hydrogen; —C(O)$R^{210g}$, —C(O)N($R^{210g}$)$_2$, —C(O)O$R^{210g}$, —S(O)$R^{210g}$, and —S(O)$_2$$R^{210g}$; and $C_{1-6}$ alkyl optionally substituted with one or more substituents independently selected from halogen, —O$R^{210g}$, —S$R^{210g}$, —N($R^{210g}$)$_2$, =O, —CN, $C_{3-10}$ carbocycle and 3- to 10-membered heterocycle. In some embodiments, $R^{28}$ is selected from: hydrogen; and $C_{1-6}$ alkyl optionally substituted with one or more substituents independently selected from halogen, and —CN. In some embodiments, $R^{28}$ is selected from: hydrogen; and $C_{1-6}$ alkyl optionally substituted with one or more substituents independently selected from fluoro, and —CN. In some embodiments, $R^{28}$ is selected from: hydrogen; and $C_{1-6}$ alkyl optionally substituted with one or more substituents independently selected from fluoro. In some embodiments, $R^{28}$ is selected from: hydrogen; and $C_{1-6}$ alkyl optionally substituted with one or more substituents independently selected from —O$R^{210g}$ and —OC(O)$R^{210g}$. In some embodiments, $R^{28}$ is selected from: hydrogen; and $C_1$ alkyl optionally substituted with one or more substituents independently selected from —O$R^{210g}$ and —OC(O)$R^{210g}$. In some embodiments, $R^{28}$ is selected from: hydrogen, —$CH_3$,

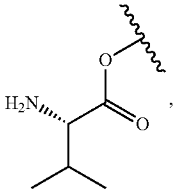

,

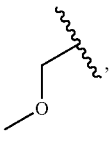

, and

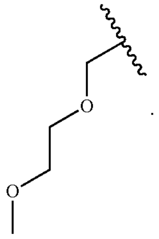

.

In some embodiments, $R^{28}$ is selected from: hydrogen and $C_{1-6}$ alkyl. In some embodiments, $R^{28}$ is selected from: hydrogen and $C_{1-3}$ alkyl. In some embodiments, $R^{28}$ is selected from: hydrogen and $C_1$ alkyl. In some embodiments, $R^{28}$ is selected from: hydrogen.

In some embodiments, for a compound or salt of Formula (IIa), each $R^{29a}$ is independently selected from: halogen, —O$R^{210a}$, —S$R^{210a}$, —N($R^{210a}$)$_2$, =O, and —CN; and $C_{1-3}$ alkyl each of which is optionally substituted with one or more substituents independently selected from halogen, —O$R^{210a}$, —S$R^{210a}$, —N($R^{210a}$)$_2$, =O, and —CN. In some embodiments, each $R^{29a}$ is independently selected from: halogen, —O$R^{210a}$, —S$R^{210a}$, —N($R^{210a}$)$_2$, =O, and —CN; and $C_{1-3}$ alkyl each of which is optionally substituted with one or more substituents independently selected from halogen and —CN. In some embodiments, each $R^{29a}$ is independently selected from: halogen, —O$R^{210a}$, —S$R^{210a}$, —N($R^{210a}$)$_2$, =O, —CN, and $C_{1-3}$ alkyl. In some embodiments, each $R^{29a}$ is independently selected from: halogen, —O$R^{210a}$, —CN, and $C_1$ alkyl. In some embodiments, each $R^{29a}$ is independently selected from: fluoro and —CN.

In some embodiments, for a compound or salt of Formula (IIa), each $R^{29b}$ is independently selected from: halogen, —$NO_2$, —$N_3$, —CN, —O$R^{210b}$, —S$R^{210b}$, —N($R^{210b}$)$_2$, —C(O)$R^{210b}$, —C(O)N($R^{210b}$)$_2$, —N($R^{210b}$)C(O)$R^{210b}$, —N($R^{210b}$)C(O)N($R^{210b}$)$_2$, —OC(O)N($R^{210b}$)$_2$, —N($R^{210b}$)C(O)O$R^{210b}$, —C(O)O$R^{210b}$, —OC(O)$R^{210b}$, —S(O)$R^{210b}$, and —S(O)$_2$$R^{210b}$; $C_{1-6}$ alkyl optionally substituted with one or more substituents independently selected from halogen, —O$R^{210b}$, —S$R^{210b}$, —N($R^{210b}$)$_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{210b}$, —S$R^{210b}$, —N($R^{210b}$)$_2$, =O, —CN, $C_{1-6}$ alkyl. In some embodiments, each $R^{29b}$ is independently selected from: halogen, —$NO_2$, —$N_3$, —CN, —O$R^{210b}$, —S$R^{210b}$, —N($R^{210b}$)$_2$, —C(O)$R^{210b}$, —C(O)N($R^{210b}$)$_2$, —N($R^{210b}$)C(O)$R^{210b}$, —N($R^{210b}$)C(O)N($R^{210b}$)$_2$, —OC(O)N($R^{210b}$)$_2$, —N($R^{210b}$)C(O)O$R^{210b}$, —C(O)O$R^{210b}$, —OC(O)$R^{210b}$, —S(O)$R^{210b}$, and —S(O)$_2$$R^{210b}$; $C_{1-6}$ alkyl optionally substituted with one or more substituents independently selected from halogen, —O$R^{210b}$, —S$R^{210b}$, —N($R^{210b}$)$_2$, =O, —CN, $C_{3-10}$ carbocycle and 3- to 10-membered heterocycle; and $C_{3-10}$ carbocycle and 3- to 10-membered heterocycle. In some embodiments, each $R^{29b}$ is independently selected from: halogen, —$NO_2$, —$N_3$, —CN, —$OR^{210b}$, —$SR^{210b}$, and —$N(R^{210b})_2$; $C_{1-6}$ alkyl optionally substituted with one or more substituents independently selected from halogen, —$OR^{210b}$, —$SR^{210b}$, —$N(R^{210b})_2$, =O, —CN, $C_{3-10}$ carbocycle and 3- to 10-membered heterocycle; and $C_{3-10}$ carbocycle and 3- to 10-membered heterocycle. In some embodiments, each $R^{29b}$ is independently selected from: halogen, —$NO_2$, —$N_3$, —CN, —$OR^{210b}$, —$SR^{210b}$, and —$N(R^{210b})_2$; and $C_{1-6}$ alkyl optionally substituted with one or more substituents independently selected from halogen, —$OR^{210b}$, —$SR^{210b}$, —$N(R^{210b})_2$, =O, —CN, $C_{3-10}$ carbocycle and 3- to 10-membered heterocycle. In some embodiments, each $R^{29b}$ is independently selected from: halogen, —CN, —$OR^{210b}$, —$SR^{210b}$, and —$N(R^{210b})_2$; and $C_{1-6}$ alkyl optionally substituted with one or more substituents independently selected from halogen, —$OR^{210b}$, —$SR^{210b}$, —$N(R^{210b})_2$, =O, and —CN. In some embodiments, each $R^{29b}$ is independently selected from: halogen, —CN, —$OR^{210b}$, —$SR^{210b}$, and —$N(R^{210b})_2$, and $C_{1-6}$ alkyl. In some embodiments, each $R^{29b}$ is independently selected from: halogen, —CN, —$OR^{210b}$, and $C_{1-6}$ alkyl. In some embodiments, each $R^{29b}$ is independently selected from: fluoro, chloro, —CN, —$OR^{210b}$, and $C_{1-6}$ alkyl. In some embodiments, each $R^{29b}$ is independently selected from: fluoro, chloro, —CN, —$OR^{210b}$, and $C_1$ alkyl. In some embodiments, each $R^{29b}$ is independently selected from: fluoro, and —CN. In some embodiments, each $R^{29b}$ is independently selected from; and fluoro. In some embodiments, each $R^{29b}$ is independently selected from: CN.

In some embodiments, for a compound or salt of Formula (IIa), each $R^{29z}$ is independently selected from: halogen, —$OR^{210z}$, —$SR^{210z}$, —$N(R^{210z})_2$, =O, and —CN; and $C_{1-3}$ alkyl each of which is optionally substituted with one or more substituents independently selected from halogen, —$OR^{210z}$, —$SR^{210z}$, —$N(R^{210z})_2$, =O, and —CN. In some embodiments, each $R^{29z}$ is independently selected from: halogen, —$OR^{210z}$, —$SR^{210z}$, —$N(R^{210z})_2$, =O, and —CN; and $C_{1-3}$ alkyl each of which is optionally substituted with one or more substituents independently selected from halogen and —CN. In some embodiments, each $R^{29z}$ is independently selected from: halogen, —$OR^{210z}$, —$SR^{210z}$, —$N(R^{210z})_2$, =O, —CN, and $C_{1-3}$ alkyl. In some embodiments, each $R^{29z}$ is independently selected from: halogen, —$OR^{210z}$, —CN, and $C_1$ alkyl. In some embodiments, each $R^{29z}$ is independently selected from: fluoro and —CN. In some embodiments, for a compound or salt of Formula (IIa), each $R^{29c}$ is independently selected from: halogen, —$OR^{210c}$, —$SR^{210c}$, —$N(R^{210c})_2$, =O, and —CN; and $C_{1-3}$ alkyl each of which is optionally substituted with one or more substituents independently selected from halogen, —$OR^{210c}$, —$SR^{210c}$, —$N(R^{210c})_2$, =O, and —CN. In some embodiments, each $R^{29c}$ is independently selected from: halogen, —$OR^{210c}$, —$SR^{210c}$, —$N(R^{210c})_2$, =O, and —CN; and $C_{1-3}$ alkyl each of which is optionally substituted with one or more substituents independently selected from halogen and —CN. In some embodiments, each $R^{29c}$ is independently selected from: halogen, —$OR^{210c}$, —$SR^{210c}$, —$N(R^{210c})_2$, =O, —CN, and $C_{1-3}$ alkyl. In some embodiments, each $R^{29c}$ is independently selected from: halogen, —$OR^{210c}$, —CN, and $C_1$ alkyl. In some embodiments, each $R^{29c}$ is independently selected from: fluoro and —CN. In some embodiments, for a compound or salt of Formula (IIa), each $R^{29d}$ is independently selected from: halogen, —$OR^{210d}$, —$SR^{210d}$, —$N(R^{210d})_2$, =O, and —CN; and $C_{1-3}$ alkyl each of which is optionally substituted with one or more substituents independently selected from halogen, —$OR^{210d}$, —$SR^{210d}$, —$N(R^{210d})_2$, =O, and —CN. In some embodiments, each $R^{29d}$ is independently selected from: halogen, —$OR^{210d}$, —$SR^{210d}$, —$N(R^{210d})_2$, =O, and —CN; and $C_{1-3}$ alkyl each of which is optionally substituted with one or more substituents independently selected from halogen and —CN. In some embodiments, each $R^{29d}$ is independently selected from: halogen, —$OR^{210d}$, —$SR^{210d}$, —$N(R^{210d})_2$, =O, —CN, and $C_{1-3}$ alkyl. In some embodiments, each $R^{29d}$ is independently selected from: halogen, —$OR^{210d}$, —CN, and $C_1$ alkyl. In some embodiments, each $R^{29d}$ is independently selected from: fluoro and —CN. In some embodiments, for a compound or salt of Formula (IIa), each $R^{29e}$ is independently selected from: halogen, —$OR^{210e}$, —$SR^{210e}$, —$N(R^{210e})_2$, =O, and —CN; and $C_{1-3}$ alkyl each of which is optionally substituted with one or more substituents independently selected from halogen, —$OR^{210e}$, —$SR^{210e}$, —$N(R^{210e})_2$, =O, and —CN. In some embodiments, each $R^{29e}$ is independently selected from: halogen, —$OR^{210e}$, —$SR^{210e}$, —$N(R^{210e})_2$, =O, and —CN; and $C_{1-3}$ alkyl each of which is optionally substituted with one or more substituents independently selected from halogen and —CN. In some embodiments, each $R^{29e}$ is independently selected from: halogen, —$OR^{210e}$, —$SR^{210e}$, —$N(R^{210e})_2$, =O, —CN, and $C_{1-3}$ alkyl. In some embodiments, each $R^{29e}$ is independently selected from: halogen, —$OR^{210e}$, —CN, and $C_1$ alkyl. In some embodiments, each $R^{29e}$ is independently selected from: fluoro and —CN. In some embodiments, for a compound or salt of Formula (IIa), each $R^{29f}$ is independently selected from: halogen, —$OR^{210f}$, —$SR^{210f}$, —$N(R^{210f})_2$, =O, and —CN; and $C_{1-3}$ alkyl each of which is optionally substituted with one or more substituents independently selected from halogen, —$OR^{210f}$, —$SR^{210f}$, —$N(R^{210f})_2$, =O, and —CN. In some embodiments, each $R^{29f}$ is independently selected from: halogen, —$OR^{210f}$, —$SR^{210f}$, —$N(R^{210f})_2$, =O, and —CN; and $C_{1-3}$ alkyl each of which is optionally substituted with one or more substituents independently selected from halogen and —CN. In some embodiments, each $R^{29f}$ is independently selected from: halogen, —$OR^{210f}$, —$SR^{210f}$, —$N(R^{210f})_2$, =O, —CN, and $C_{1-3}$ alkyl. In some embodiments, each $R^{29f}$ is independently selected from: halogen, —$OR^{210f}$, —CN, and $C_1$ alkyl. In some embodiments, each $R^{29f}$ is independently selected from: fluoro and —CN. In some embodiments, for a compound or salt of Formula (IIa), each $R^{29g}$ is independently selected from: halogen, —$OR^{210g}$, —$SR^{210g}$, —$N(R^{210g})_2$, =O, and —CN; and $C_{1-3}$ alkyl each of which is optionally substituted with one or more substituents independently selected from halogen, —$OR^{210g}$, —$SR^{210g}$, —$N(R^{210g})_2$, =O, and —CN. In some embodiments, each $R^{29g}$ is independently selected from: halogen, —$OR^{210g}$, —$SR^{210g}$, —$N(R^{210g})_2$, =O, and —CN; and $C_{1-3}$ alkyl each of which is optionally substituted with one or more substituents independently selected from halogen and —CN. In some embodiments, each $R^{29g}$ is independently selected from: halogen, —$OR^{210g}$, —$SR^{210g}$, —$N(R^{210g})_2$, =O, —CN, and $C_{1-3}$ alkyl. In some embodiments, each $R^{29g}$ is independently selected from: halogen, —$OR^{210g}$, —CN, and $C_1$ alkyl. In some embodiments, each $R^{29g}$ is independently selected from: fluoro and —CN.

In some embodiments, for a compound or salt of Formula (IIa), each $R^{210a}$, $R^{210b}$, $R^{210z}$, $R^{210c}R^{210d}$, $R^{210e}$, $R^{210f}$, and $R^{210g}$ is independently selected from: hydrogen; $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NH_2$, =O, —O—$C_{1-6}$ alkyl, —S—$C_{1-6}$ alkyl, —N($C_{1-6}$ alkyl)$_2$, —NH ($C_{1-6}$ alkyl), $C_{1-6}$ alkyl, and $C_{1-6}$ haloalkyl. In some embodiments, each $R^{210a}$, $R^{210b}$, $R^{210z}$, $R^{210c}$, $R^{210a}$, $R^{210e}$, $R^{210f}$ and $R^{210g}$ is independently selected from: hydrogen; $C_{1-6}$ alkyl optionally substituted with one or more substituents independently selected from halogen, —CN, and —OH; and $C_{3-10}$ carbocycle, and 3- to 10-membered heterocycle, each of which is optionally substituted with one or more substituents independently selected from halogen, —CN, —OH, $C_{1-6}$ alkyl, and $C_{1-6}$ haloalkyl. In some embodiments, each $R^{210a}$, $R^{210b}$, $R^{210z}$, $R^{210c}$, $R^{210d}$, $R^{210e}$, $R^{210f}$ and $R^{210g}$ is independently selected from: hydrogen; $C_{1-6}$ alkyl optionally substituted with one or more substituents independently selected from fluoro and CN; and $C_{3-10}$ carbocycle, and 3- to 10-membered heterocycle, each of which is optionally substituted with one or more substituents independently selected from fluoro and —CN. In some embodiments, each $R^{210a}$, $R^{210b}$, $R^{210z}$, $R^{210c}$, $R^{210d}$, $R^{210e}$, $R^{210f}$ and $R^{210g}$ is independently selected from: hydrogen; and $C_{1-6}$ alkyl optionally substituted with one or more substituents independently selected from fluoro and CN. In some embodiments, each $R^{210a}$, $R^{210b}$, $R^{210z}$, $R^{210c}$, $R^{210d}$, $R^{210e}$, $R^{210e}$, and $R^{210g}$ is independently selected from: hydrogen and $C_{1-6}$ alkyl. In some embodiments, each $R^{210a}$, $R^{210b}$, $R^{210z}$, $R^{210c}$, $R^{210d}$, $R^{210e}$, $R^{210f}$, and $R^{210g}$ is independently selected from: hydrogen and $C_1$ alkyl. In some embodiments, each $R^{210a}$, $R^{210b}$, $R^{210z}$, $R^{210c}$, $R^{210d}$, $R^{210e}$, $R^{210f}$, and $R^{210g}$ is independently selected from: hydrogen. In some embodiments, each $R^{210a}$ is independently selected from: hydrogen. In some embodiments, each $R^{210b}$ is independently selected from: hydrogen. In some embodiments, each $R^{210c}$ is independently selected from: hydrogen. In some embodiments, each $R^{210d}$ is independently selected from: hydrogen. In some embodiments, each $R^{210e}$ is independently selected from: hydrogen. In some embodiments, each $R^{210f}$ is independently selected from: hydrogen. In some embodiments, each $R^{210g}$ is independently selected from: hydrogen. In some embodiments, each $R^{210z}$ is independently selected from: hydrogen.

In some embodiments, the compound or salt of Formula (IIa) is selected from: 142, 405, 406, 408, 155, 72, 136, 39, 73, 104, 154, 36, 35, 38, 40, 51, 37, 41, 34, 33, 69, 143, 401, 402, 403, 404, and 407, or a salt thereof. In some embodiments, the compound or salt of Formula (IIa) is selected from: 142, 405, 406, 408, 155, 72, 136, 39, 104, 154, 36, 35, 38, 40, 51, 37, 41, 34, 33, 143, 402, 403, 404, and 407, or a salt thereof. In some embodiments, the compound or salt of Formula (IIa) is selected from: 155, 72, 136, 39, 73, 104, 154, 36, 35, 38, 40, 51, 37, 41, 34, 33, 69, 143, 402, 403, 404, and 407, or a salt thereof. In some embodiments, the compound or salt of Formula (IIa) is selected from: 155, 72, 136, 39, 73, 104, 154, 36, 35, 38, 40, 51, 37, 41, and 34, or a salt thereof. In some embodiments, the compound or salt of Formula (IIa) is selected from: 155, 72, 136, 39, 73, 104, 154, 36, 35, 38, and 40, or a salt thereof. In some embodiments, the compound or salt of Formula (IIa) is selected from: 155, 72, 136, 39, 73, 104, or a salt thereof. In some embodiments, the compound or salt of Formula (IIa) is selected from: 104, 39, 155, 36, 35, 40, 73, 72, 154, 38, 51, 407, 37, 41, 143, 34, and 402, or a salt thereof. In some embodiments, the compound or salt of Formula (IIa) is selected from: 104, 39, 155, 36, 35, 40, 73, 72, 154, 38, 51, 407, 37, 41, and 143, or a salt thereof. In some embodiments, the compound or salt of Formula (IIa) is selected from: 104, 39, 155, 36, 35, 40, 73, 72, 154, 38, 51, 407, and 37, or a salt thereof. In some embodiments, the compound or salt of Formula (IIa) is selected from: 104, 39, 155, 36, and 35, or a salt thereof.

In some embodiments, the compound or salt of Formula (IIa) is selected from: 72, 39, 73, 104, 36, 35, 38, 40, 51, 37, 41, 34, 33, 69, 402, 403, and 404, or a salt thereof. In some embodiments, the compound or salt of Formula (IIa) is selected from: 72, 39, 104, 36, 35, 38, 40, 51, 37, 41, 34, 33, 402, 403, and 404, or a salt thereof. In some embodiments, the compound or salt of Formula (IIa) is selected from: 72, 39, 73, 104, 36, 35, 38, 40, 51, 37, 41, 34, 33, 69, 402, 403, and 404, or a salt thereof. In some embodiments, the compound or salt of Formula (IIa) is selected from: 72, 39, 73, 104, 36, 35, 38, 40, 51, 37, 41, and 34, or a salt thereof. In some embodiments, the compound or salt of Formula (IIa) is selected from: 72, 39, 73, 104, 36, 35, 38, and 40, or a salt thereof. In some embodiments, the compound or salt of Formula (IIa) is selected from: 72, 39, 73, 104, or a salt thereof. In some embodiments, the compound or salt of Formula (IIa) is selected from: 104, 39, 36, 35, 40, 73, 72, 38, 51, 407, 37, 41, 143, 34, and 402, or a salt thereof. In some embodiments, the compound or salt of Formula (IIa) is selected from: 104, 39, 36, 35, 40, 73, 72, 38, 51, 407, 37, 41, and 143, or a salt thereof. In some embodiments, the compound or salt of Formula (IIa) is selected from: 104, 39, 36, 35, 40, 73, 72, 38, 51, 407, and 37, or a salt thereof. In some embodiments, the compound or salt of Formula (IIa) is selected from: 104, 39, 36, and 35, or a salt thereof.

In some embodiments, the compound or salt of formula (IIa) is not: 136, 142, 143, 154, 155, 401, 405, 406, 407, or 408, or a salt of any thereof.

In some embodiments, the compound or salt of formula (IIa) is selected from compound 69, or a salt thereof. In some embodiments, the compound or salt of Formula (IIa) is selected from compound 72, or a salt thereof. In some embodiments, the compound or salt of Formula (IIa) is selected from compound 401, or a salt thereof. In some embodiments, the compound or salt of formula (IIa) is selected from: compound 73, or a salt thereof. In some embodiments, the compound or salt of Formula (IIa) is not compound 69, 73, 401, or 73, or a salt of any of these.

In one aspect, disclosed herein is a compound represented by Formula (IIb):

(IIb)

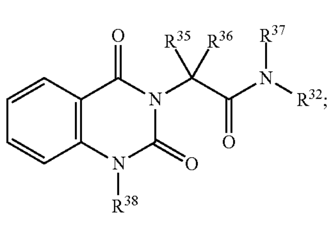

or a salt thereof, wherein: $R^{32}$ is selected from

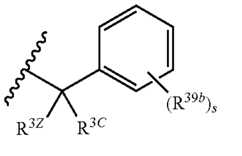

s is an integer selected from 2, 3, 4, and 5; $R^{3Z}$ is selected from: —C(O)$R^{310z}$, —C(O)N($R^{310z}$)$_2$, —C(O)O$R^{310z}$, and —CN; $C_{1-6}$ alkyl, $C_{2-6}$ alkenyl, and $C_{2-6}$ alkynyl, each of which is optionally substituted with one or more substituents independently selected from halogen, —O$R^{310z}$, —S$R^{310z}$, —N($R^{310z}$)$_2$, —C(O)$R^{310z}$, —C(O)N($R^{310z}$)$_2$, —N($R^{310z}$)C(O)$R^{310z}$, —C(O)O$R^{310z}$, —OC(O)$R^{310z}$, —N($R^{310z}$)C(O)N($R^{310z}$)$_2$, —OC(O)N($R^{310z}$)$_2$, —N($R^{310z}$)C(O)O$R^{310z}$, —S(O)$R^{310z}$, —S(O)$_2R^{310z}$, —NO$_2$, =O, =S, =N($R^{310z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{39z}$; and $C_{3-10}$ carbocycle and 3- to 10-membered heterocycle, each of which is optionally substituted with one or more substituents independently selected from halogen, —O$R^{310z}$, —S$R^{310z}$, —N($R^{310z}$)$_2$, —C(O)$R^{310z}$, —C(O)N($R^{310z}$)$_2$, —N($R^{310z}$)C(O)$R^{310z}$, —N($R^{310z}$)C(O)N($R^{310z}$)$_2$, —OC(O)N($R^{310z}$)$_2$, —N($R^{310z}$)C(O)O$R^{310z}$, —C(O)O$R^{310z}$, —OC(O)$R^{310z}$, —S(O)$R^{310z}$, —S(O)$_2R^{310z}$, —NO$_2$, =S, =N($R^{310z}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{39z}$; $R^{3C}$ is selected from: hydrogen; —C(O)$R^{310c}$, —C(O)N($R^{310c}$)$_2$, —C(O)O$R^{310c}$, and —CN; $C_{1-2}$ alkyl optionally substituted with one or more substituents independently selected from halogen, —O$R^{310c}$, —S$R^{310c}$, —N($R^{310c}$)$_2$, —C(O)$R^{310c}$, —C(O)N($R^{310c}$)$_2$, —N($R^{310c}$)C(O)$R^{310c}$, —C(O)O$R^{310c}$, —OC(O)$R^{310c}$, —N($R^{310c}$)C(O)N($R^{310c}$)$_2$, —OC(O)N($R^{310c}$)$_2$, —N($R^{310c}$)C(O)O$R^{310c}$, —S(O)$R^{310c}$, —S(O)$_2R^{310c}$, —NO$_2$, =S, =N($R^{310c}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{39c}$; $C_{3-6}$ alkyl, $C_{2-6}$ alkenyl, and $C_{2-6}$ alkynyl, each of which is optionally substituted with one or more substituents independently selected from halogen, —O$R^{310c}$, —S$R^{310c}$, —N($R^{310c}$)$_2$, —C(O)$R^{310c}$, —C(O)N($R^{310c}$)$_2$, —N($R^{310c}$)C(O)$R^{310c}$, —C(O)O$R^{310c}$, —OC(O)$R^{310c}$, —N($R^{310c}$)C(O)N($R^{310c}$)$_2$, —OC(O)N($R^{310c}$)$_2$, —N($R^{310c}$)C(O)O$R^{310c}$, —S(O)$R^{310c}$, —S(O)$_2R^{310c}$, —NO$_2$, =O, =S, =N($R^{310c}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39c}$; and $C_{3-10}$ carbocycle and 3- to 10-membered heterocycle, each of which is optionally substituted with one or more substituents independently selected from halogen, —O$R^{310c}$, —S$R^{310c}$, —N($R^{310c}$)$_2$, —C(O)$R^{310c}$, —C(O)N($R^{310c}$)$_2$, —N($R^{310c}$)C(O)$R^{310c}$, —N($R^{310c}$)C(O)N($R^{310c}$)$_2$, —OC(O)N($R^{310c}$)$_2$, —N($R^{310c}$)C(O)O$R^{310c}$, —C(O)O$R^{310c}$, —OC(O)$R^{310c}$, —S(O)$R^{310c}$, —S(O)$_2R^{310c}$, —NO$_2$, =O, =S, =N($R^{310c}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{39d}$; $R^{35}$ is selected from: hydrogen; halogen, —O$R^{310d}$, —S$R^{310d}$, —N($R^{310d}$)$_2$, —C(O)$R^{310d}$, —C(O)N($R^{310d}$)$_2$, —N($R^{310d}$)C(O)$R^{310d}$, —C(O)O$R^{310d}$, —OC(O)$R^{310d}$, —N($R^{310d}$)C(O)N($R^{310d}$)$_2$, —OC(O)N($R^{310d}$)$_2$, —N($R^{310d}$)C(O)O$R^{310d}$, —S(O)$R^{310d}$, —S(O)$_2R^{310d}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —O$R^{310d}$, —S$R^{310d}$, —N($R^{310d}$)$_2$, —C(O)$R^{310d}$, —C(O)N($R^{310d}$)$_2$, —N($R^{310d}$)C(O)$R^{310d}$, —C(O)O$R^{310d}$, —C(O)$R^{310d}$, —N($R^{310d}$)C(O)N($R^{310d}$)$_2$, —OC(O)N($R^{310d}$)$_2$, —N($R^{310d}$)C(O)O$R^{310d}$, —S(O)$R^{310d}$, —S(O)$_2R^{310d}$, —NO$_2$, =O, =S, =N($R^{310d}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{39d}$; and $C_{3-10}$ carbocycle and 3- to 10-membered heterocycle, each of which is optionally substituted with one or more substituents independently selected from halogen, —O$R^{310d}$, —S$R^{310d}$, —N($R^{310d}$)$_2$, —C(O)$R^{310d}$, —C(O)N($R^{310d}$)$_2$, —N($R^{310d}$)C(O)$R^{310d}$, —N($R^{310d}$)C(O)N($R^{310d}$)$_2$, —OC(O)N($R^{310d}$)$_2$, —N($R^{310d}$)C(O)O$R^{310d}$, —C(O)O$R^{310d}$, —OC(O)$R^{310d}$, —S(O)$R^{310d}$, —S(O)$_2R^{310d}$, —NO$_2$, =O, =S, =N($R^{310d}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{39d}$; or $R^{35}$ together with $R^{36}$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{39d}$; $R^{36}$ is selected from: hydrogen; halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2R^{310e}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2R^{310e}$, —NO$_2$, =O, =S, =N($R^{310e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{39e}$; and $C_{3-10}$ carbocycle and 3- to 10-membered heterocycle, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —N($R^{310e}$)C(O)N($R^{310e}$)$_2$, —OC(O)N($R^{310e}$)$_2$, —N($R^{310e}$)C(O)O$R^{310e}$, —C(O)O$R^{310e}$, —OC(O)$R^{310e}$, S(O)$R^{310e}$, —S(O)$_2R^{310e}$, —NO$_2$, =O, =S, =N($R^{310e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{39e}$; or $R^{36}$ together with $R^{35}$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{39e}$; $R^{37}$ is selected from: hydrogen; —C(O)$R^{310f}$, —C(O)N($R^{310f}$)$_2$, —C(O)O$R^{310f}$, —S(O)$R^{310f}$, and —S(O)$_2R^{310f}$; $C_{1-6}$ alkyl optionally substituted with one or more substituents independently selected from halogen, —O$R^{310f}$, —S$R^{310f}$, —N($R^{310f}$)$_2$, —C(O)$R^{310f}$, —C(O)N($R^{310f}$)$_2$, —N($R^{310f}$)C(O)$R^{310f}$, —C(O)O$R^{310f}$, —OC(O)$R^{310f}$, —N($R^{310f}$)C(O)N($R^{310f}$)$_2$, —OC(O)N($R^{310f}$)$_2$, —N($R^{310f}$)C(O)O$R^{310f}$, —S(O)$R^{310f}$, —S(O)$_2R^{310f}$, —NO$_2$, =O, =S, =N($R^{310f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{39f}$; and $C_{3-10}$ carbocycle and 3- to 10-membered heterocycle, each of which is optionally substituted with one or more substituents independently selected from halogen, —O$R^{310f}$, —S$R^{310f}$, —N(R$^{310f}$)$_2$, —C(O)R$^{310f}$, —C(O)N(R$^{310f}$)$_2$, —N(R$^{310f}$)C(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —C(O)OR$^{310f}$, —OC(O)R$^{310f}$, —S(O)R$^{310f}$, —S(O)$_2$R$^{310f}$, —NO$_2$, =O, =S, =N(R$^{310f}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more substituents independently selected from R$^{39f}$; R$^{38}$ is selected from: hydrogen; —C(O)R$^{310g}$, —C(O)N(R$^{310g}$)$_2$, —C(O)OR$^{310g}$, —S(O)R$^{310g}$, and —S(O)$_2$R$^{310g}$; C$_{1-6}$ alkyl optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —C(O)OR$^{310g}$, —OC(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —S(O)R$^{310g}$, —S(O)$_2$R$^{310g}$, —NO$_2$, =O, =S, =N(R$^{310g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more substituents independently selected from R$^{39g}$; and C$_{3-10}$ carbocycle and 3- to 10-membered heterocycle, each of which is optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —C(O)OR$^{310g}$, —OC(O)R$^{310g}$, —S(O)R$^{310g}$, —S(O)$_2$R$^{310g}$, —NO$_2$, =O, =S, =N(R$^{310g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more substituents independently selected from R$^{39g}$; each R$^{39z}$ is independently selected from: halogen, —OR$^{310z}$, —SR$^{310z}$, —N(R$^{310z}$)$_2$, —C(O)R$^{310z}$, —C(O)N(R$^{310z}$)$_2$, —N(R$^{310z}$)C(O)R$^{310z}$, —N(R$^{310z}$)C(O)N(R$^{310z}$)$_2$, —OC(O)N(R$^{310z}$)$_2$, —N(R$^{310z}$)C(O)OR$^{310z}$, —C(O)OR$^{310z}$, —OC(O)R$^{310z}$, —S(O)R$^{310z}$, —S(O)$_2$R$^{310z}$, —NO$_2$, =O, =S, =N(R$^{310z}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310z}$, —SR$^{310z}$, —N(R$^{310z}$)$_2$, —C(O)R$^{310z}$, —C(O)N(R$^{310z}$)$_2$, —N(R$^{310z}$)C(O)R$^{310z}$, —N(R$^{310z}$)C(O)N(R$^{310z}$)$_2$, —OC(O)N(R$^{310z}$)$_2$, —N(R$^{310z}$)C(O)OR$^{310z}$, —C(O)OR$^{310z}$, —OC(O)R$^{310z}$, —S(O)R$^{310z}$, —S(O)$_2$R$^{310z}$, —NO$_2$, =O, =S, =N(R$^{310z}$), —N$_3$, and —CN; each R$^{39b}$ is independently selected from: halogen, —NO$_2$, —N$_3$, —CN, —O(C$_{4-6}$ alkyl), —O(C$_{1-6}$ haloalkyl), —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, and —S(O)$_2$R$^{310b}$; C$_1$ alkyl substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, —CN, and C$_{3-10}$ carbocycle and 3- to 10-membered heterocycle; C$_{2-6}$ alkyl, C$_{2-6}$ alkenyl, and C$_{2-6}$ alkynyl, each of which is optionally substituted with one or more substituents independently selected from halogen, —OR$^{310b}$, —SR$^{310b}$, —N(R$^{310b}$)$_2$, —C(O)R$^{310b}$ C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, and —CN; and C$_{3-10}$ carbocycle and 3- to 10-membered heterocycle, each of which is optionally substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, —S(O)$_2$R$^{310b}$, —NO$_2$, =O, =S, =N(R$^{310b}$), —N$_3$, —CN, C$_{1-6}$ alkyl, C$_{2-6}$ alkenyl, and C$_{2-6}$ alkynyl; each R$^{39c}$ is independently selected from: halogen, —OR$^{310c}$, —SR$^{310c}$, —N(R$^{310c}$)$_2$, —C(O)R$^{310c}$, —C(O)N(R$^{310c}$)$_2$, —N(R$^{310c}$)C(O)R$^{310c}$, —N(R$^{310c}$)C(O)N(R$^{310c}$)$_2$, —OC(O)N(R$^{310c}$)$_2$, —N(R$^{310c}$)C(O)OR$^{310c}$, —C(O)OR$^{310c}$, —OC(O)R$^{310c}$, —S(O)R$^{310c}$, —S(O)$_2$R$^{310c}$, —NO$_2$, =O, =S, =N(R$^{310c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310c}$, —SR$^{310c}$, —N(R$^{310c}$)$_2$, —C(O)R$^{310c}$, —C(O)N(R$^{310c}$)$_2$, —N(R$^{310c}$)C(O)R$^{310c}$, —N(R$^{310c}$)C(O)N(R$^{310c}$)$_2$, —OC(O)N(R$^{310c}$)$_2$, —N(R$^{310c}$)C(O)OR$^{310c}$, —C(O)OR$^{310c}$, —OC(O)R$^{310c}$, —S(O)R$^{310c}$, —S(O)$_2$R$^{310c}$, —NO$_2$, =O, =S, =N(R$^{310c}$), —N$_3$, and —CN; each R$^{39d}$ is independently selected from: halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —C(O)OR$^{310d}$, OC(O)R$^{310d}$, —S(O)R$^{310d}$, —S(O)$_2$R$^{310d}$, —NO$_2$, =O, =S, =N(R$^{310d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —C(O)OR$^{310d}$, OC(O)R$^{310d}$, —S(O)R$^{310d}$, —S(O)$_2$R$^{310d}$, —NO$_2$, =O, =S, =N(R$^{310d}$), —N$_3$, and —CN; each R$^{39e}$ is independently selected from: halogen, —OR$^{310e}$, SR$^{310e}$, —N(R$^{310e}$)$_2$, —C(O)R$^{310e}$, —C(O)N(R$^{310e}$)$_2$, —N(R$^{310e}$)C(O)R$^{310e}$, —N(R$^{310e}$)C(O)N(R$^{310e}$)$_2$, —OC(O)N(R$^{310e}$)$_2$, —N(R$^{310e}$)C(O)OR$^{310e}$, —C(O)OR$^{310e}$, —OC(O)R$^{310e}$, —S(O)R$^{310e}$, —S(O)$_2$R$^{310e}$, —NO$_2$, =O, =S, =N(R$^{310e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310e}$, —SR$^{310e}$, —N(R$^{310e}$)$_2$, —C(O)R$^{310e}$, —C(O)N(R$^{310e}$)$_2$, —N(R$^{310e}$)C(O)R$^{310e}$, —N(R$^{310e}$)C(O)N(R$^{310e}$)$_2$, —OC(O)N(R$^{310e}$)$_2$, —N(R$^{310e}$)C(O)OR$^{310e}$, —C(O)OR$^{310e}$, —OC(O)R$^{310e}$, —S(O)R$^{310e}$, —S(O)$_2$R$^{310e}$, —NO$_2$, =O, =S, =N(R$^{310e}$), —N$_3$, and —CN; each R$^{39f}$ is independently selected from: halogen, —OR$^{310f}$, —SR$^{310f}$, —N(R$^{310f}$)$_2$, —C(O)R$^{310f}$, —C(O)N(R$^{310f}$)$_2$, —N(R$^{310f}$)C(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —C(O)OR$^{310f}$, —OC(O)R$^{310f}$, —S(O)R$^{310f}$, —S(O)$_2$R$^{310f}$, —NO$_2$, =O, =S, =N(R$^{310f}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310f}$, —SR$^{310f}$, —N(R$^{310f}$)$_2$, —C(O)R$^{310f}$, —C(O)N(R$^{310f}$)$_2$, —N(R$^{310f}$)C(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —C(O)OR$^{310f}$, —OC(O)R$^{310f}$, —S(O)R$^{310f}$, —S(O)$_2$R$^{310f}$, —NO$_2$, =O, =S, =N(R$^{310f}$), —N$_3$, and —CN; each R$^{39g}$ is independently selected from: halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —C(O)OR$^{310g}$, —OC(O)R$^{310g}$, —S(O)R$^{310g}$, —S(O)$_2$R$^{310g}$, —NO$_2$, =O, =S, =N(R$^{310g}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)

C(O)$R^{310g}$, —N($R^{310g}$)C(O)N($R^{310g}$)$_2$, —OC(O)N($R^{310g}$)$_2$, —N($R^{310g}$)C(O)O$R^{310g}$, —C(O)O$R^{310g}$, —OC(O)$R^{310g}$, —S(O)$R^{310g}$, —S(O)$_2R^{310g}$, —$NO_2$, =O, =S, =N($R^{310g}$), —$N_3$, and —CN; and each $R^{310z}$, $R^{310b}$, $R^{310c}$, $R^{310d}$, $R^{310e}$, $R^{310f}$ and $R^{310g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein when s is 3, then each $R^{39b}$ is independently selected from: fluoro, bromo, iodo, —$NO_2$, —$N_3$, —CN, —O($C_{4-6}$ alkyl), —O($C_{1-6}$ haloalkyl), —S$R^{310b}$, —N($R^{310b}$)$_2$, —C(O)$R^{310b}$, —C(O)N($R^{310b}$)$_2$, —N($R^{310b}$)C(O)$R^{310b}$, —N($R^{310b}$)C(O)N($R^{310b}$)$_2$, —OC(O)N($R^{310b}$)$_2$, —N($R^{310b}$)C(O)O$R^{310b}$, —C(O)O$R^{310b}$, —OC(O)$R^{310b}$, —S(O)$R^{310b}$, and —S(O)$_2R^{310b}$; $C_1$ alkyl substituted with one or more substituents independently selected from halogen, —O$R^{310b}$, —S$R^{310b}$, —N($R^{310b}$)$_2$, —C(O)$R^{310b}$, —C(O)N($R^{310b}$)$_2$, —N($R^{310b}$)C(O)$R^{310b}$, —C(O)O$R^{310b}$ OC(O)$R^{310b}$, —N($R^{310b}$)C(O)N($R^{310b}$)$_2$, —OC(O)N($R^{310b}$)$_2$, —N($R^{310b}$)C(O)O$R^{310b}$, —S(O)$R^{310b}$, —S(O)$_2R^{310b}$, —$NO_2$, =O, =S, =N($R^{310b}$), —$N_3$, —CN, and $C_{3-10}$ carbocycle and 3- to 10-membered heterocycle; $C_{2-6}$ alkyl, $C_{2-6}$ alkenyl, and $C_{2-6}$ alkynyl, each of which is optionally substituted with one or more substituents independently selected from halogen, —O$R^{310b}$, —S$R^{310b}$, —N($R^{310b}$)$_2$, —C(O)$R^{310b}$, —C(O)N($R^{310b}$)$_2$, —N($R^{310b}$)C(O)$R^{310b}$, —C(O)O$R^{310b}$, —OC(O)$R^{310b}$, —N($R^{310b}$)C(O)N($R^{310b}$)$_2$, —OC(O)N($R^{310b}$)$_2$, —N($R^{310b}$)C(O)O$R^{310b}$, —S(O)$R^{310b}$, —S(O)$_2R^{310b}$, —$NO_2$, =O, =S, =N($R^{310b}$), —$N_3$, and —CN; and $C_{3-10}$ carbocycle and 3- to 10-membered heterocycle, each of which is optionally substituted with one or more substituents independently selected from halogen, —O$R^{310b}$, —S$R^{310b}$, —N($R^{310b}$)$_2$, —C(O)$R^{310b}$, —C(O)N($R^{310b}$)$_2$, —N($R^{310b}$)C(O)$R^{310b}$, —N($R^{310b}$)C(O)N($R^{310b}$)$_2$, —OC(O)N($R^{310b}$)$_2$, —N($R^{310b}$)C(O)O$R^{310b}$, —C(O)O$R^{310b}$, —OC(O)$R^{310b}$, —S(O)$R^{310b}$, —S(O)$_2$ $R^{310b}$, —$NO_2$, =O, =S, =N($R^{310b}$), —$N_3$, —CN, $C_{1-6}$ alkyl, $C_{2-6}$ alkenyl, and $C_{2-6}$ alkynyl; wherein when $R^{37}$ is —$CH_3$, then $R^{32}$ is selected from

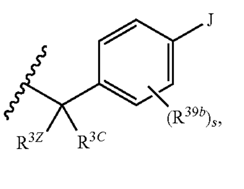

wherein J is selected from halogen, —$NO_2$, —$N_3$, —CN, —O($C_{4-6}$ alkyl), —O($C_{1-6}$ haloalkyl), —S$R^{310b}$, —N($R^{310b}$)$_2$, —C(O)$R^{310b}$, —C(O)N($R^{310b}$)$_2$, —N($R^{310b}$)C(O)$R^{310b}$, —N($R^{310b}$)C(O)N($R^{310b}$)$_2$, —OC(O)N($R^{310b}$)$_2$, —N($R^{310b}$)C(O)O$R^{310b}$, —C(O)O$R^{310b}$, —OC(O)$R^{310b}$, —S(O)$R^{310b}$ and —S(O)$_2R^{310b}$; $C_1$ alkyl substituted with one or more substituents independently selected from halogen, —O$R^{310b}$, —S$R^{310b}$, —N($R^{310b}$)$_2$, —C(O)$R^{310b}$, —C(O)N($R^{310b}$)$_2$, —N($R^{310b}$)C(O)$R^{310b}$, —C(O)O$R^{310b}$, —OC(O)$R^{310b}$, —N($R^{310b}$)C(O)N($R^{310b}$)$_2$, —OC(O)N($R^{310b}$)$_2$, —N($R^{310b}$)C(O)O$R^{310b}$, —S(O)$R^{310b}$, S(O)$_2$ $R^{310b}$, —$NO_2$, =O, =S, =N($R^{310b}$), —$N_3$, —CN, and $C_{3-10}$ carbocycle and 3- to 10-membered heterocycle; $C_{2-6}$ alkyl, $C_{2-6}$ alkenyl, and $C_{2-6}$ alkynyl, each of which is optionally substituted with one or more substituents independently selected from halogen, —O$R^{310b}$, —S$R^{310b}$, —N($R^{310b}$)$_2$, —C(O)$R^{310b}$, —C(O)N($R^{310b}$)$_2$, —N($R^{310b}$)C(O)$R^{310b}$, —C(O)O$R^{310b}$, —OC(O)$R^{310b}$, —N($R^{310b}$)C(O)N($R^{310b}$)$_2$, —OC(O)N($R^{310b}$)$_2$, —N($R^{310b}$)C(O)O$R^{310b}$, —S(O)$R^{310b}$, —S(O)$_2$ $R^{310b}$, —$NO_2$, =O, =S, =N($R^{310b}$), —$N_3$, and —CN; and $C_{3-10}$ carbocycle and 3- to 10-membered heterocycle, each of which is optionally substituted with one or more substituents independently selected from halogen, —O$R^{310b}$, —S$R^{310b}$, —N($R^{310b}$)$_2$, —C(O)$R^{310b}$, —C(O)N($R^{310b}$)$_2$, —N($R^{310b}$)C(O)$R^{310b}$, —N($R^{310b}$)C(O)N($R^{310b}$)$_2$, —OC(O)N($R^{310b}$)$_2$, —N($R^{310b}$)C(O)O$R^{310b}$, —C(O)O$R^{310b}$, —OC(O)$R^{310b}$, —S(O)$R^{310b}$, —S(O)$_2R^{310b}$, —$NO_2$, =O, =S, =N($R^{310b}$), —$N_3$, —CN, $C_{1-6}$ alkyl, $C_{2-6}$ alkenyl, and $C_{2-6}$ alkynyl; wherein when $R^{32}$ is

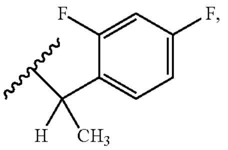 [SMILES: *C(C)c1ccc(F)cc1F]

and $R^{37}$ is H, and $R^{35}$ is H, and $R^{36}$ is H; then $R^{38}$ is selected from: —C(O)$R^{310g}$, —C(O)N($R^{310g}$)$_2$, —C(O)O$R^{310g}$, —S(O)$R^{310g}$, and —S(O)$_2R^{310g}$; $C_{1-6}$ alkyl optionally substituted with one or more substituents independently selected from halogen, —O$R^{310g}$, —S$R^{310g}$, —N($R^{310g}$)$_2$, —C(O)$R^{310g}$, —C(O)N($R^{310g}$)$_2$, —N($R^{310g}$)C(O)$R^{310g}$, —C(O)O$R^{310g}$, —OC(O)$R^{310g}$, —N($R^{310g}$)C(O)N($R^{310g}$)$_2$, —OC(O)N($R^{310g}$)$_2$, —N($R^{310g}$)C(O)O$R^{310g}$, —S(O)$R^{310g}$, —S(O)$_2R^{310g}$, —$NO_2$, =O, =S, =N($R^{310g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{39g}$; and $C_{3-10}$ carbocycle and 3- to 10-membered heterocycle, each of which is optionally substituted with one or more substituents independently selected from halogen, —O$R^{310g}$, —S$R^{310g}$, —N($R^{310g}$)$_2$, —C(O)$R^{310g}$, —C(O)N($R^{310g}$)$_2$, —N($R^{310g}$)C(O)$R^{310g}$, —N($R^{310g}$)C(O)N($R^{310g}$)$_2$, —OC(O)N($R^{310g}$)$_2$, —N($R^{310g}$)C(O)O$R^{310g}$, —C(O)O$R^{310g}$, —OC(O)$R^{310g}$, —S(O)$R^{310g}$, —S(O)$_2R^{310g}$, —$NO_2$, =O, =S, =N($R^{310g}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{39g}$; and wherein when s is 2, and one $R^{39b}$ is

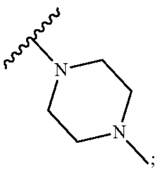 [SMILES: *N1CCN(C)CC1]

then each additional $R^{39b}$ is independently selected from: chloro, bromo, iodo, —$NO_2$, —$N_3$, —CN, —O($C_{4-6}$ alkyl), —O($C_{1-6}$ haloalkyl), —S$R^{310b}$, —N($R^{310b}$)$_2$, —C(O)$R^{310b}$, —C(O)N($R^{310b}$)$_2$, —N($R^{310b}$)C(O)$R^{310b}$, —N($R^{310b}$)C(O)

$N(R^{310b})_2$, —$OC(O)N(R^{310b})_2$, —$N(R^{310b})C(O)OR^{310b}$, —$C(O)OR^{310b}$, —$OC(O)R^{310b}$, —$S(O)R^{310b}$, and —$S(O)_2R^{310b}$; $C_1$ alkyl substituted with one or more substituents independently selected from halogen, —$OR^{310b}$, —$SR^{310b}$, —$N(R^{310b})_2$, —$C(O)R^{310b}$, —$C(O)N(R^{310b})_2$, —$N(R^{310b})C(O)R^{310b}$, —$C(O)OR^{310b}$, —$OC(O)R^{310b}$, —$N(R^{310b})C(O)N(R^{310b})_2$, —$OC(O)N(R^{310b})_2$, —$N(R^{310b})C(O)OR^{310b}$, —$S(O)R^{310b}$, —$S(O)_2R^{310b}$, —$NO_2$, =O, =S, =$N(R^{310b})$, —$N_3$, —CN, and $C_{3-10}$ carbocycle and 3- to 10-membered heterocycle; $C_{2-6}$ alkyl, $C_{2-6}$ alkenyl, and $C_{2-6}$ alkynyl, each of which is optionally substituted with one or more substituents independently selected from halogen, —$OR^{310b}$, —$SR^{310b}$, —$N(R^{310b})_2$, —$C(O)R^{310b}$, —$C(O)N(R^{310b})_2$, —$N(R^{310b})C(O)R^{310b}$, —$C(O)OR^{310b}$, —$OC(O)R^{310b}$, —$N(R^{310b})C(O)N(R^{310b})_2$, —$OC(O)N(R^{310b})_2$, —$N(R^{310b})C(O)OR^{310b}$, —$S(O)R^{310b}$, —$S(O)_2R^{310b}$, —$NO_2$, =O, =S, =$N(R^{310b})$, —$N_3$, and —CN; and $C_{3-10}$ carbocycle and 3- to 10-membered heterocycle, each of which is optionally substituted with one or more substituents independently selected from halogen, —$OR^{310b}$, —$SR^{310b}$, —$N(R^{310b})_2$, —$C(O)R^{310b}$, —$C(O)N(R^{310b})_2$, —$N(R^{310b})C(O)R^{310b}$, —$N(R^{310b})C(O)N(R^{310b})_2$, —$OC(O)N(R^{310b})_2$, —$N(R^{310b})C(O)OR^{310b}$, —$C(O)OR^{310b}$, —$OC(O)R^{310b}$, —$S(O)R^{310b}$, —$S(O)_2R^{310b}$, —$NO_2$, =O, =S, =$N(R^{310b})$, —$N_3$, —CN, $C_{1-6}$ alkyl, $C_{2-6}$ alkenyl, and $C_{2-6}$ alkynyl.

In one aspect, disclosed herein is a compound of Formula (IIb) that is represented by Formula (IIb-ep):

(IIb-ep)

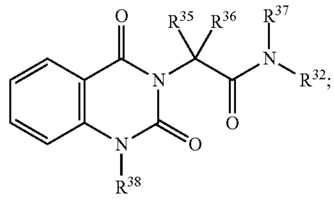

or a salt thereof, wherein: $R^{32}$ is selected from

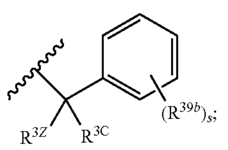

s an integer selected from 2, 3, and 4; $R^{3Z}$ is selected from: $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; $R^{3C}$ is selected from: hydrogen; $R^{35}$ and $R^{36}$ are each independently selected from: hydrogen; halogen; and $C_{1-6}$ alkyl, halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; or $R^{35}$ together with $R^{36}$ form a $C_{3-10}$ carbocycle or 3- to 10-membered heterocycle, each of which is optionally substituted with one or more substituents independently selected from: halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, and $C_{1-6}$ alkyl; $R^{37}$ is selected from: hydrogen; $R^{38}$ is selected from: hydrogen; and each $R^{39b}$ is independently selected from: fluoro and —CN; wherein when $R^{32}$ is

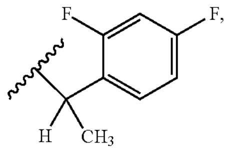

and $R^{37}$ is H, and $R^{35}$ is H, and $R^{36}$ is H; then $R^{38}$ is selected from: $C_{1-6}$ alkyl optionally substituted with one or more substituents independently selected from optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; and $C_{3-10}$ carbocycle and 3- to 10-membered heterocycle, each of which is optionally substituted with one or more substituents independently selected from optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, and $C_{1-6}$ alkyl.

In some embodiments, for a compound or salt of Formula (IIb), the compound is not: N-(1-(2,4-difluorophenyl)ethyl)-2-(2,4-dioxo-1,4-dihydroquinazolin-3(2H)-yl)acetamide; N-(1-(2,6-dichloro-3-fluorophenyl)ethyl)-2-(2,4-dioxo-1,4-dihydroquinazolin-3(2H)-yl)acetamide; N-(1-(2,4-dichloro-S-fluorophenyl)ethyl)-2-(2,4-dioxo-1,4-dihydroquinazolin-3(2H)-yl)acetamide, or N-(1-(2,5-difluorophenyl)ethyl)-2-(2,4-dioxo-1,4-dihydroquinazolin-3(2H)-yl)-N-methylacetamide.

In some embodiments, for a compound or salt of Formula (IIb), when s is 3, then each $R^{39b}$ is independently selected from: fluoro, bromo, iodo, —$NO_2$, —$N_3$, —CN, —$O(C_{4-6}$ alkyl), —$O(C_{1-6}$ haloalkyl), —$SR^{310b}$, —$N(R^{310b})_2$, —$C(O)R^{310b}$, —$C(O)N(R^{310b})_2$, —$N(R^{310b})C(O)R^{310b}$, —$N(R^{310b})C(O)N(R^{310b})_2$, —$OC(O)N(R^{310b})_2$, —$N(R^{310b})C(O)OR^{310b}$, —$C(O)OR^{310b}$, —$OC(O)R^{310b}$, —$S(O)R^{310b}$, and —$S(O)_2R^{310b}$; $C_1$ alkyl substituted with one or more substituents independently selected from halogen, —$OR^{310b}$, —$SR^{310b}$, —$N(R^{310b})_2$, =O, and —CN; $C_{2-6}$ alkyl, optionally substituted with one or more substituents independently selected from halogen, —$OR^{310b}$, —$SR^{310b}$, —$N(R^{310b})_2$, =O, and —CN; and $C_{3-10}$ carbocycle and 3- to 10-membered heterocycle. In some embodiments, when s is 3, then each $R^{39b}$ is independently selected from: fluoro, bromo, iodo, —$NO_2$, —CN; $C_1$ alkyl substituted with one or more substituents independently selected from halogen, - and —CN; $C_{2-6}$ alkyl, optionally substituted with one or more substituents independently selected from halogen, —$OR^{310b}$, and —CN. In some embodiments, when s is 3, then each $R^{39b}$ is independently selected from: fluoro, —CN, and $C_{2-6}$ alkyl, optionally substituted with one or more substituents independently selected from halogen, and —CN. In some embodiments, when s is 3, then each $R^{39b}$ is independently selected from: fluoro, —CN, and $C_{2-6}$ alkyl. In some embodiments, when s is 3, then each $R^{39b}$ is independently selected from: fluoro and —CN. In some embodiments, when s is 3, then each $R^{39b}$ is independently selected from: fluoro.

In some embodiments, for a compound or salt of Formula (IIb), when $R^{37}$ is —$CH_3$, then $R^{32}$ is selected from

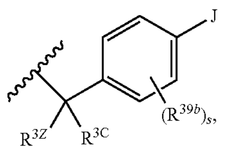

wherein J is selected from halogen, —$NO_2$, —$N_3$, —CN, —$SR^{310b}$, and —$N(R^{310b})_2$; $C_1$ alkyl substituted with one or more substituents independently selected from halogen, —$OR^{310b}$, —$SR^{310b}$, —$N(R^{310b})_2$, —CN, and $C_{3-10}$ carbocycle and 3- to 10-membered heterocycle; $C_{2-6}$ alkyl, optionally substituted with one or more substituents independently selected from halogen, —$OR^{310b}$, —$SR^{310b}$, —$N(R^{310b})_2$, ═O, and —CN; and $C_{3-10}$ carbocycle and 3- to 10-membered heterocycle. In some embodiments, when $R^{37}$ is —$CH_3$, then J is selected from halogen, —$NO_2$, —$N_3$, —CN, —$SR^{310b}$, and —$N(R^{310b})_2$; $C_1$ alkyl substituted with one or more substituents independently selected from halogen and —CN; $C_{2-6}$ alkyl, optionally substituted with one or more substituents independently selected from halogen and —CN. In some embodiments, when $R^{37}$ is —$CH_3$, then J is selected from halogen, —CN; $C_{2-6}$ alkyl, optionally substituted with one or more substituents independently selected from halogen and —CN. In some embodiments, when $R^{37}$ is —$CH_3$, then J is selected from fluoro and —CN. In some embodiments, when $R^{37}$ is —$CH_3$, then J is selected from fluoro.

In some embodiments, for a compound or salt of Formula (IIb), when $R^{32}$ is $R^{32k}$, wherein $R^{32k}$ is

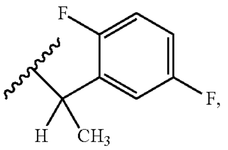 [SMILES: *C(C)c1cc(F)ccc1F]

and $R^{35}$ is H, and $R^{36}$ is H; then $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_1$ alkyl substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, ═O, ═S, ═$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$; $C_{2-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, ═O, ═S, ═$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$; and $C_{3-10}$ carbocycle and 3- to 10-membered heterocycle, each of which is optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$N(R^{310f})C(O)N(R^{310f})_2$, —$OC(O)N(R^{310f})_2$, —$N(R^{310f})C(O)OR^{310f}$, —$C(O)OR^{310f}$, —$OC(O)R^{310f}$, —$S(O)R^{310f}$, —$S(O)_2R^{310f}$, —$NO_2$, ═O, ═S, ═$N(R^{310f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39f}$. In some embodiments, when $R^{32}$ is $R^{32k}$, and $R^{37}$ is —$CH_3$, then $R^{35}$ is selected from: halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, $OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{310d}$, —$SR^{310d}$, —$N(R^{310d})_2$, —$C(O)R^{310d}$, $C(O)N(R^{310d})_2$, —$N(R^{310d})C(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, ═O, ═S, ═$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$N(R^{310d})C(O)N(R^{310d})_2$, —$OC(O)N(R^{310d})_2$, —$N(R^{310d})C(O)OR^{310d}$, —$C(O)OR^{310d}$, —$OC(O)R^{310d}$, —$S(O)R^{310d}$, —$S(O)_2R^{310d}$, —$NO_2$, ═O, ═S, ═$N(R^{310d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39d}$; or $R^{35}$ together with $R^{36}$ form a 3- to 10-membered heterocycle or $C_{3-10}$ carbocycle, wherein the 3- to 10-membered heterocycle or $C_{3-10}$ carbocycle is optionally substituted with one or more $R^{39d}$.

In some embodiments, for a compound or salt of Formula (IIb), when s is 2, and one $R^{39b}$ is $R^{39b-m}$, wherein $R^{39b-m}$ is

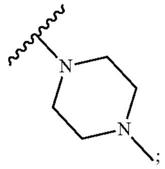 [SMILES: *N1CCN(C)CC1]

then each additional $R^{39b}$ is independently selected from: chloro, bromo, iodo, —$NO_2$, —$N_3$, —CN, —$O(C_{4-6}$ alkyl), —$O(C_{1-6}$ haloalkyl), —$SR^{310b}$, —$N(R^{310b})_2$, —$C(O)R^{310b}$, —$C(O)N(R^{310b})_2$, —$N(R^{310b})C(O)R^{310b}$, —$N(R^{310b})C(O)N(R^{310b})_2$, —$OC(O)N(R^{310b})_2$, —$N(R^{310b})C(O)OR^{310b}$, —$C(O)OR^{310b}$, —$OC(O)R^{310b}$, —$S(O)R^{310b}$, and —$S(O)_2R^{310b}$; $C_1$ alkyl substituted with one or more substituents independently selected from halogen, —$OR^{310b}$, —$SR^{310b}$, —$N(R^{310b})_2$, —$C(O)R^{310b}$, —$C(O)N(R^{310b})_2$, —$N(R^{310b})C(O)R^{310b}$, —$C(O)OR^{310b}$, —$OC(O)R^{310b}$, —$N(R^{310b})C(O)N(R^{310b})_2$, —$OC(O)N(R^{310b})_2$, —$N(R^{310b})C(O)OR^{310b}$, —$S(O)R^{310b}$, —$S(O)_2R^{310b}$, —$NO_2$, ═O, ═S, ═$N(R^{310b})$, —$N_3$, —CN, and $C_{3-10}$ carbocycle and 3- to 10-membered heterocycle; $C_{2-6}$ alkyl, $C_{2-6}$ alkenyl, and $C_{2-6}$ alkynyl, each of which is optionally substituted with one or more substituents independently selected from halogen, —$OR^{310b}$, —$SR^{310b}$, —$N(R^{310b})_2$, —$C(O)R^{310b}$, —$C(O)N(R^{310b})_2$, —$N(R^{310b})C(O)R^{310b}$, —$C(O)OR^{310b}$, —$OC(O)R^{310b}$, —$N(R^{310b})C(O)N(R^{310b})_2$, —$OC(O)N(R^{310b})_2$, —$N(R^{310b})C(O)OR^{310b}$, —$S(O)R^{310b}$, —$S(O)_2R^{310b}$, —$NO_2$, =O, =S, =$N(R^{310b})$, —$N_3$, and —CN; and $C_{3-10}$ carbocycle and 3- to 10-membered heterocycle, each of which is optionally substituted with one or more substituents independently selected from halogen, —$OR^{310b}$, —$SR^{310b}$, —$N(R^{310b})_2$, —$C(O)R^{310b}$, —$C(O)N(R^{310b})_2$, —$N(R^{310b})C(O)R^{310b}$, —$N(R^{310b})C(O)N(R^{310b})_2$, —$OC(O)N(R^{310b})_2$, —$N(R^{310b})C(O)OR^{310b}$, —$C(O)OR^{310b}$, —$OC(O)R^{310b}$, $S(O)R^{310b}$, $S(O)_2R^{310b}$, —$NO_2$, =O, =S, =$N(R^{310b})$, —$N_3$, —CN, $C_{1-6}$ alkyl, $C_{2-6}$ alkenyl, and $C_{2-6}$ alkynyl. In some embodiments, when s is 2, and one $R^{39b}$ is $R^{39b-m}$; then each additional $R^{39b}$ is independently selected from: chloro, bromo, iodo, —CN, —O($C_{4-6}$ alkyl), —O($C_{1-6}$ haloalkyl), —$SR^{310b}$ and —$N(R^{310b})_2$; $C_1$ alkyl substituted with one or more substituents independently selected from halogen, —$OR^{310b}$, —$SR^{310b}$, —$N(R^{310b})_2$, =O, —CN, and $C_{3-10}$ carbocycle and 3- to 10-membered heterocycle; $C_{2-6}$ alkyl, optionally substituted with one or more substituents independently selected from halogen, —$OR^{310b}$, —$SR^{310b}$, —$N(R^{310b})_2$, =O, and —CN; and $C_{3-10}$ carbocycle and 3- to 10-membered heterocycle, each of which is optionally substituted with one or more substituents independently selected from halogen, —$OR^{310b}$, —$SR^{310b}$, —$N(R^{310b})_2$, =O, —CN, and $C_{1-6}$ alkyl. In some embodiments, when s is 2, and one $R^{39b}$ is $R^{39b-m}$; then each additional $R^{39b}$ is independently selected from: chloro, bromo, —CN, —O($C_{1-6}$ haloalkyl), and —$N(R^{310b})_2$; $C_{1-6}$ alkyl optionally substituted with one or more substituents independently selected from halogen; and $C_{3-10}$ carbocycle and 3- to 10-membered heterocycle. In some embodiments, when s is 2, and one $R^{39b}$ is $R^{39b-m}$; then each additional $R^{39b}$ is independently selected from: chloro, bromo, —CN, and $C_1$ alkyl. In some embodiments, when s is 2, and when one $R^{39b}$ comprises

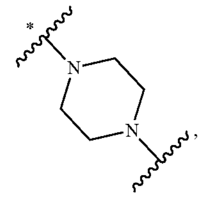 [SMILES: *N1CCN(*)CC1]

wherein * represents the point of attachment to the rest of $R^{32}$; then each additional $R^{39b}$ is independently selected from: chloro, bromo, —CN, and $C_1$ alkyl.

In some embodiments, for a compound or salt of Formula (IIb), when $R^{32}$ is $R^{32-w}$, wherein $R^{32-w}$ is

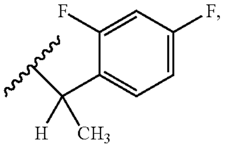 [SMILES: *C(C)c1ccc(F)cc1F]

and when $R^{38}$ is H, and when $R^{35}$ is H, and when $R^{36}$ is H; then $R^{37}$ is selected from $C_{1-6}$ alkyl. In some embodiments, when $R^{32}$ is $R^{32-w}$, and $R^{38}$ is H, and $R^{37}$ is H, then $R^{35}$ is selected from $C_{1-6}$ alkyl optionally substituted with one or more substituents independently selected from halogen, —OH, and $C_{3-10}$ carbocycle and 3- to 10-membered heterocycle, wherein each $C_{3-10}$ carbocycle and 3- to 10-membered heterocycle, is optionally substituted with one or more substituents independently selected from halogen, —OH, —CN, and $C_{1-6}$ alkyl; and $C_{3-10}$ carbocycle and 3- to 10-membered heterocycle optionally substituted with one or more substituents independently selected from halogen, —OH, and —CN. In some embodiments, when $R^{32}$ is $R^{32-w}$, and when $R^{37}$ is H, and $R^{35}$ is H, and $R^{36}$ is H; then $R^{38}$ is selected from $C_{1-6}$ alkyl optionally substituted with one or more substituents independently selected from halogen, —$OR^{310g}$, —$SR^{310g}$, —$N(R^{310g})_2$, =O, =S, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{310g}$, —$SR^{310g}$, —$N(R^{310g})_2$, =O, —CN, and $C_{1-6}$ alkyl. In some embodiments, when $R^{32}$ is $R^{32-w}$, and $R^{37}$ is H, and $R^{35}$ is H, and $R^{36}$ is H; then $R^{38}$ is selected from $C_{1-6}$ alkyl optionally substituted with one or more substituents independently selected from halogen, —$OR^{310g}$, —$SR^{310g}$, —$N(R^{310g})_2$, =O, and —CN; and $C_{3-10}$ carbocycle and 3- to 10-membered heterocycle, each of which is optionally substituted with one or more substituents independently selected from halogen and —CN. In some embodiments, when $R^{32}$ is $R^{32-w}$, and $R^{37}$ is H, and $R^{35}$ is H, and $R^{36}$ is H; then $R^{38}$ is selected from $C_{1-6}$ alkyl optionally substituted with one or more substituents independently selected from halogen and —CN; and $C_{3-10}$ carbocycle and 3- to 10-membered heterocycle. In some embodiments, when $R^{32}$ is $R^{32-w}$, and when $R^{37}$ is H, and $R^{35}$ is H, and $R^{36}$ is H; then $R^{38}$ is selected from $C_{1-6}$ alkyl. In some embodiments, when $R^{32}$ is $R^{32-w}$, and $R^{37}$ is H, and $R^{35}$ is H, and $R^{36}$ is H; then $R^{38}$ is selected from $C_{1-4}$ alkyl. In some embodiments, when $R^{32}$ is $R^{32-w}$, and $R^{37}$ is H, and $R^{35}$ is H, and $R^{36}$ is H; then $R^8$ is selected from $C_1$ alkyl.

In some embodiments, for a compound or salt of Formula (IIb), s is an integer selected from 2, 3, and 4. In some embodiments, s is an integer selected from 2 and 3. In some embodiments, s is an integer selected from 2 and 4. In some embodiments, s is an integer selected from 3 and 4. In some embodiments, s is an integer selected from 2. In some embodiments, s is an integer selected from 3. In some embodiments, s is an integer selected from 4.

In some embodiments, for a compound or salt of Formula (IIb), $R^{3Z}$ is selected from: —$C(O)R^{310z}$, —$C(O)N(R^{310z})_2$, —$C(O)OR^{310z}$, and —CN; $C_{1-6}$ alkyl, $C_{2-6}$ alkenyl, and $C_{2-6}$ alkynyl, each of which is optionally substituted with one or more substituents independently selected from halogen, —$OR^{310z}$, —$SR^{310z}$, —$N(R^{310z})_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{39z}$; and $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, =O, —CN, $C_{1-6}$ alkyl wherein $C_{1-6}$ alkyl optionally substituted with one or more $R^{39z}$. In some embodiments, $R^{3Z}$ is selected from: —$C(O)R^{310z}$, —$C(O)N(R^{310z})_2$, —$C(O)OR^{310z}$, and —CN; $C_{1-6}$ alkyl, $C_{2-6}$ alkenyl, and $C_{2-6}$ alkynyl, each of which is optionally substituted with one or more substituents independently selected from halogen, —$OR^{310z}$, —$SR^{310z}$, —$N(R^{310z})_2$, —CN, $C_{3-10}$ carbocycle and 3- to 10-membered heterocycle, wherein the $C_{3-10}$ carbocycle and 3- to 10-membered heterocycle are each optionally substituted with one or more $R^{39z}$; and $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, —CN, $C_{1-6}$ alkyl wherein $C_{1-6}$ alkyl optionally substituted with one or more $R^{39z}$. In some embodiments, $R^{3Z}$ is selected from: —$C(O)R^{310z}$, —$C(O)N(R^{310z})_2$, —$C(O)OR^{310z}$, and —CN; $C_{1-6}$ alkyl optionally substituted with one or more substituents independently selected from halogen, —$OR^{310z}$, —$SR^{310z}$, —$N(R^{310z})_2$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, —CN, $C_{1-6}$ alkyl wherein $C_{1-6}$ alkyl optionally substituted with one or more $R^{39z}$ In some embodiments, $R^{3Z}$ is selected from: —CN; and $C_{1-6}$ alkyl, optionally substituted with one or more substituents independently selected from halogen, —$OR^{310z}$, —$SR^{310z}$, —$N(R^{310z})_2$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen and —CN. In some embodiments, $R^{3Z}$ is selected from: $C_{1-6}$ alkyl, optionally substituted with one or more substituents independently selected from halogen, —$OR^{310z}$, —$SR^{310z}$, —$N(R^{310z})_2$, —CN, $C_{3-10}$ carbocycle and 3- to 10-membered heterocycle, wherein the $C_{3-10}$ carbocycle and 3- to 10-membered heterocycle are each optionally substituted with one or more $R^{39z}$. In some embodiments, $R^{3Z}$ is selected from: In some embodiments, $R^{3Z}$ is selected from: $C_{1-6}$ alkyl optionally substituted with one or more substituents independently selected from halogen, —$OR^{310z}$, —$SR^{310z}$, —$N(R^{310z})_2$, —CN, $C_{3-10}$ carbocycle and 3- to 10-membered heterocycle; and $C_{3-10}$ carbocycle and 3- to 10-membered heterocycle. In some embodiments, $R^{3Z}$ is selected from: $C_{1-6}$ alkyl, optionally substituted with one or more substituents independently selected from halogen, —$OR^{310z}$, —$SR^{310z}$, —$N(R^{310z})_2$, —CN. In some embodiments, $R^{3Z}$ is selected from: $C_{1-6}$ alkyl, optionally substituted with one or more substituents independently selected from fluoro, —$OR^{310z}$, and —CN. In some embodiments, $R^{3Z}$ is selected from: $C_{1-6}$ alkyl, optionally substituted with one or more substituents independently selected from —$OR^{310z}$. In some embodiments, $R^{3Z}$ is selected from: $C_{1-6}$ alkyl, optionally substituted with one or more substituents independently selected from —OH. In some embodiments, $R^{3Z}$ is selected from: $C_{1-6}$ alkyl, optionally substituted with one or more substituents independently selected from —OH and —F. In some embodiments, $R^{3Z}$ is selected from: $C_{1-4}$ alkyl, optionally substituted with one or more substituents independently selected from —OH. In some embodiments, $R^{3Z}$ is selected from: $C_{1-4}$ alkyl. In some embodiments, $R^{3Z}$ is selected from: methyl, ethyl, isopropyl, isobutyl, and $CH_2OH$. In some embodiments, $R^{3Z}$ is selected from: methyl. In some embodiments, $R^{3Z}$ is selected from $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, —$C(O)R^{310z}$, —$C(O)N(R^{310z})_2$, —$N(R^{310z})C(O)R^{310z}$, —$N(R^{310z})C(O)N(R^{310z})_2$, —$OC(O)N(R^{310z})_2$, —$N(R^{310z})C(O)OR^{310z}$, —$C(O)OR^{310z}$, —$OC(O)R^{310z}$, —$S(O)R^{310z}$, —$S(O)_2R^{310z}$, —$NO_2$, =S, =$N(R^{310z})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39z}$. In some embodiments, $R^{3Z}$ is selected from $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, —CN, and $C_{1-6}$ alkyl, wherein each $C_{1-6}$ alkyl is optionally substituted with one or more $R^{39z}$. In some embodiments, $R^{3Z}$ is selected from $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, —CN, and $C_{1-6}$ alkyl, wherein each $C_{1-6}$ alkyl is optionally substituted with one or more substituents independently selected from —F and —OH. In some embodiments, $R^{3Z}$ is selected from $C_{3-10}$ carbocycle and 3- to 10-membered heterocycle, each of which is optionally substituted with one or more substituents independently selected from halogen, —$OR^{310z}$, —CN, and $C_{1-6}$ alkyl, wherein each $C_{1-6}$ alkyl is optionally substituted with one or more substituents independently selected from —F and —OH. In some embodiments, $R^{3Z}$ is selected from $C_{3-10}$ carbocycle and 3- to 10-membered heterocycle, each of which is optionally substituted with one or more substituents independently selected from fluoro, chloro, —OH, —CN, and —$CH_3$. In some embodiments, $R^{3Z}$ is selected from $C_{3-10}$ carbocycle and 3- to 10-membered heterocycle, each of which is optionally substituted with one or more substituents independently selected from fluoro and —CN. In some embodiments, $R^{3Z}$ is selected from $C_{3-10}$ carbocycle and 3- to 10-membered heterocycle. In some embodiments, $R^{3Z}$ is selected from hydrogen. In some embodiments, $R^{3Z}$ is selected from —$CF_3$. In some embodiments, $R^{3Z}$ is selected from —$CH_2OH$. In some embodiments, $R^{3Z}$ is selected from halogen. In some embodiments, $R^{3Z}$ is selected from fluorine. In some embodiments, $R^{3Z}$ is selected from $C_{3-10}$ carbocycle and 3- to 10-membered heterocycle, each of which is optionally substituted with one or more substituents independently selected from halogen, CN, $C_{1-6}$ alkyl, and —$OR^{310z}$, In some embodiments, $R^{3Z}$ is selected from $C_{3-10}$ carbocycle and 3- to 10-membered heterocycle. In some embodiments, $R^{3Z}$ is selected from

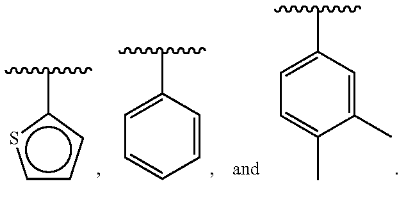

, , and .

In some embodiments, $R^{3Z}$ is selected from hydrogen.

In some embodiments, for a compound or salt of Formula (IIb), $R^{3C}$ is selected from: hydrogen; —CN, —$C(O)R^{310c}$, —$C(O)N(R^{310c})_2$, —$C(O)OR^{310c}$; $C_{1-6}$ alkyl, $C_{2-6}$ alkenyl, and $C_{2-6}$ alkynyl, each of which is optionally substituted with one or more substituents independently selected from halogen, —$OR^{310c}$, —$SR^{310c}$, —$N(R^{310c})_2$, —$C(O)R^{310c}$, —$C(O)N(R^{310c})_2$, —$N(R^{310c})C(O)R^{310c}$, —$C(O)OR^{310c}$, —$OC(O)R^{310c}$, —$N(R^{310c})C(O)N(R^{310c})_2$, —$OC(O)N(R^{310c})_2$, —$N(R^{310c})C(O)OR^{310c}$, —$S(O)R^{310c}$, —$S(O)_2R^{310c}$, —$NO_2$, =O, =S, =$N(R^{310c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39c}$; and $C_{3-10}$ carbocycle and 3- to 10-membered heterocycle. In some embodiments, $R^{3C}$ is selected from: hydrogen; —CN, —$C(O)R^{310c}$, —$C(O)N(R^{310e})_2$, —$C(O)OR^{310c}$; and $C_{1-6}$ alkyl, $C_{2-6}$ alkenyl, and $C_{2-6}$ alkynyl, each of which is optionally substituted with one or more substituents independently selected from halogen, —$OR^{310c}$, —$SR^{310c}$, —$N(R^{310c})_2$, —$C(O)R^{310c}$, —$C(O)N(R^{310c})_2$, —$N(R^{310c})C(O)R^{310c}$, —$C(O)OR^{310c}$, —$OC(O)R^{310c}$, —$N(R^{310c})C(O)N(R^{310c})_2$, —$OC(O)N(R^{310c})_2$, —$N(R^{310c})C(O)OR^{310c}$, —$S(O)R^{310c}$, —$S(O)_2R^{310c}$, —$NO_2$, =O, =S, =$N(R^{310c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39c}$. In some embodiments, $R^{3C}$ is selected from: hydrogen; —CN, —$C(O)R^{310c}$, —$C(O)N(R^{310c})_2$, —$C(O)OR^{310c}$; and $C_{1-6}$ alkyl, $C_{2-6}$ alkenyl, and $C_{2-6}$ alkynyl, each of which is optionally substituted with one or more substituents independently selected from halogen, —$OR^{310c}$, —$SR^{310c}$, —$N(R^{310c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{39c}$. In some embodiments, $R^{3C}$ is selected from: hydrogen; —CN, —$C(O)R^{310c}$, —$C(O)N(R^{310c})_2$, —$C(O)OR^{310c}$; and $C_{1-6}$ alkyl optionally substituted with one or more substituents independently selected from halogen, —$OR^{310c}$, —$SR^{310c}$, —$N(R^{310c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{39c}$. In some embodiments, $R^{3C}$ is selected from: hydrogen; —CN, —$C(O)R^{310c}$, —$C(O)N(R^{310c})_2$, —$C(O)OR^{310c}$; and $C_{1-6}$ alkyl optionally substituted with one or more substituents independently selected from halogen, —$OR^{310c}$, —$SR^{310c}$, —$N(R^{310c})_2$, =O, —$N_3$, and —CN, $C_{3-10}$ carbocycle and 3- to 10-membered heterocycle. In some embodiments, $R^{3C}$ is selected from: hydrogen; —CN, —$C(O)R^{310c}$, —$C(O)N(R^{310c})_2$, —$C(O)OR^{310c}$; and $C_{1-6}$ alkyl optionally substituted with one or more substituents independently selected from halogen, —$OR^{310c}$, —$SR^{310c}$, —$N(R^{310c})_2$, =O, —$N_3$, and —CN. In some embodiments, $R^{3C}$ is selected from: hydrogen; —CN, —$C(O)R^{310c}$, —$C(O)N(R^{310c})_2$, —$C(O)OR^{310c}$; and $C_{1-6}$ alkyl optionally substituted with one or more substituents independently selected from halogen, and —CN. In some embodiments, $R^{3C}$ is selected from: hydrogen; —CN; and $C_{1-6}$ alkyl optionally substituted with one or more substituents independently selected from halogen, and —CN. In some embodiments, $R^{3C}$ is selected from: hydrogen, —CN, and $C_{1-6}$ alkyl. In some embodiments, $R^{3C}$ is selected from: hydrogen and $C_{1-6}$ alkyl. In some embodiments, $R^{3C}$ is selected from: hydrogen and $C_1$ alkyl. In some embodiments, $R^{3C}$ is selected from: hydrogen. In some embodiments, $R^{3C}$ is selected from halogen. In some embodiments, $R^{3C}$ is selected from fluoro.

In some embodiments, for a compound or salt of Formula (IIb), $R^{35}$ is selected from: hydrogen; halogen, —$C(O)R^{310d}$, —$C(O)N(R^{310d})_2$, —$C(O)OR^{310d}$, —$S(O)R^{310d}$, —$S(O)_2R^{310d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$N(R^{310d})C(O)N(R^{310d})_2$, —$OC(O)N(R^{310d})_2$, —$N(R^{310d})C(O)OR^{310d}$, —$C(O)OR^{310d}$, —$OC(O)R^{310d}$, —$S(O)R^{310d}$, —$S(O)_2R^{310d}$, —$NO_2$, =O, =S, =$N(R^{310d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39d}$. In some embodiments, $R^{35}$ is selected from: hydrogen; halogen, —$C(O)R^{310d}$, —$C(O)N(R^{310d})_2$, —$C(O)OR^{310d}$, and —CN; $C_{1-6}$ alkyl, $C_{2-6}$ alkenyl, and $C_{2-6}$ alkynyl, each of which is optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, $OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —$OR^{310d}$, —$SR^{310d}$, —$N(R^{310d})_2$, —$C(O)R^{310d}$, $C(O)N(R^{310d})_2$, —$N(R^{310d})C(O)R^{310d}$, —$N(R^{310d})C(O)N(R^{310d})_2$, —$OC(O)N(R^{310d})_2$, —$N(R^{310d})C(O)OR^{310d}$, —$C(O)OR^{310d}$, —$OC(O)R^{310d}$, —$S(O)R^{310d}$, —$S(O)_2R^{310d}$, —$NO_2$, =O, =S, =$N(R^{310d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39d}$. In some embodiments, $R^{35}$ is selected from: hydrogen; halogen, —$C(O)R^{310d}$, —$C(O)N(R^{310d})_2$, —$C(O)OR^{310d}$, and —CN; $C_{1-6}$ alkyl, optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C+(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$N(R^{310d})C(O)N(R^{310d})_2$, —$OC(O)N(R^{310d})_2$, —$N(R^{310d})C(O)OR^{310d}$, —$C(O)OR^{310d}$, —$OC(O)R^{310d}$, —$S(O)R^{310d}$, —$S(O)_2R^{310d}$, —$NO_2$, =O, =S, =$N(R^{310d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39d}$. In some embodiments, $R^{35}$ is selected from: hydrogen; halogen, —$C(O)R^{310d}$, —$C(O)N(R^{310d})_2$, —$C(O)OR^{310d}$, and —CN; $C_{1-6}$ alkyl, optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$N(R^{310d})C(O)N(R^{310d})_2$, —$OC(O)N(R^{310d})_2$, —$N(R^{310d})$ $C(O)OR^{310d}$, —$C(O)OR^{310d}$, —$OC(O)R^{310d}$, —$S(O)R^{310d}$, —$S(O)_2R^{310d}$, —$NO_2$, =O, =S, =$N(R^{310d})$, —$N_3$, —CN, and $C_{1-6}$ alkyl. In some embodiments, $R^{35}$ is selected from: hydrogen; halogen, —$C(O)R^{310d}$, —$C(O)N(R^{310d})_2$, —$C(O)OR^{310d}$, and —CN; $C_{1-6}$ alkyl, optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{35}$ is selected from: hydrogen; halogen, —$C(O)R^{310d}$, —$C(O)N(R^{310d})_2$, —$C(O)OR^{310d}$, and —CN; $C_{1-6}$ alkyl, optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle. In some embodiments, $R^{35}$ is selected from: hydrogen; halogen, —$C(O)R^{310d}$, —$C(O)N(R^{310d})_2$, —$C(O)OR^{310d}$, and —CN; and $C_{1-6}$ alkyl, optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, —$OC(O)R^{310d}$, —$N(R^{310d})C(O)N(R^{310d})_2$, —$OC(O)N(R^{310d})_2$, —$N(R^{310d})C(O)OR^{310d}$, —$S(O)R^{310d}$, —$S(O)_2R^{310d}$, —$NO_2$, =O, =S, =$N(R^{310d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$. In some embodiments, $R^{35}$ is selected from: hydrogen; halogen, —$C(O)R^{310d}$, —$C(O)N(R^{310d})_2$, —$C(O)OR^{310d}$, and —CN; and $C_{1-6}$ alkyl, optionally substituted with one or more substituents independently selected from halogen, —$OR^{310d}$, —$SR^{310d}$, —$N(R^{310d})_2$, —$C(O)R^{310d}$, —$C(O)N(R^{310d})_2$, —$N(R^{310d})C(O)R^{310d}$, —$C(O)OR^{310d}$, —$OC(O)R^{310d}$, —$NO_2$, =O, —CN, $C_{3-10}$ carbocycle and 3- to 10-membered heterocycle. In some embodiments, $R^{35}$ is selected from: hydrogen; halogen, —$C(O)R^{310d}$, —$C(O)N(R^{310d})_2$, —$C(O)OR^{310d}$, and —CN; and $C_{1-6}$ alkyl, optionally substituted with one or more substituents independently selected from halogen, —$OR^{310d}$, —$SR^{310d}$, —$N(R^{310d})_2$, =O, —CN, $C_{3-10}$ carbocycle and 3- to 10-membered heterocycle. In some embodiments, $R^{35}$ is selected from: hydrogen; halogen, —$C(O)R^{310d}$, —$C(O)N(R^{310d})_2$, —$C(O)OR^{310d}$, and —CN; and $C_{1-6}$ alkyl, optionally substituted with one or more substituents independently selected from halogen, and —CN. In some embodiments, $R^{35}$ is selected from: hydrogen; halogen and —CN; and $C_{1-6}$ alkyl, optionally substituted with one or more substituents independently selected from halogen, and —CN. In some embodiments, $R^{35}$ is selected from: hydrogen; fluoro and —CN; and $C_{1-6}$ alkyl, optionally substituted with one or more substituents independently selected from fluoro, and —CN. In some embodiments, $R^{35}$ is selected from: hydrogen; fluoro; and $C_{1-6}$ alkyl, optionally substituted with one or more substituents independently selected from fluoro. In some embodiments, $R^{35}$ is selected from: hydrogen; and $C_{1-6}$ alkyl, optionally substituted with one or more substituents independently selected from fluoro. In some embodiments, $R^{35}$ is selected from: hydrogen and $C_{1-6}$ alkyl. In some embodiments, $R^{35}$ is selected from: hydrogen and $C_{1-4}$ alkyl. In some embodiments, $R^{35}$ is selected from: hydrogen, methyl, and isobutyl. In some embodiments, $R^{35}$ is selected from: hydrogen, and methyl. In some embodiments, $R^{35}$ is selected from: hydrogen. In some embodiments, $R^{35}$ is selected from: halogen. In some embodiments, $R^{35}$ is selected from: fluoro. In some embodiments, $R^{35}$ together with $R^{36}$ form a $C_{3-10}$ carbocycle or 3- to 10-membered heterocycle optionally substituted with one or more $R^{39d}$. In some embodiments, $R^{35}$ together with $R^{36}$ form a cyclopropyl optionally substituted with one or more $R^{39d}$. In some embodiments, $R^{35}$ together with $R^{36}$ form a cyclopropyl. In some embodiments, $R^{35}$ is —F, and $R^{36}$ is —F.

In some embodiments, $R^{35}$ is selected from: hydrogen; halogen, and —CN; $C_{1-6}$ alkyl, optionally substituted with one or more substituents independently selected from halogen, —$OR^{310d}$, —$SR^{310d}$, —$N(R^{310d})_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{35}$ is selected from: hydrogen; halogen, and —CN; $C_{1-6}$ alkyl, optionally substituted with one or more substituents independently selected from halogen, —$OR^{310a}$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{35}$ is selected from: hydrogen; $C_{1-6}$ alkyl, optionally substituted with one or more substituents independently selected from —$OR^{310d}$ and $C_{3-10}$ carbocycle; and $C_{3-10}$ carbocycle and 3- to 10-membered heterocycle. In some embodiments, $R^{35}$ is selected from: hydrogen; $C_{1-6}$ alkyl, optionally substituted with one or more substituents independently selected from —$OR^{310d}$ and $C_{3-10}$ carbocycle; and $C_{3-10}$ carbocycle and 3- to 10-membered heterocycle. In some embodiments, $R^{35}$ is selected from: hydrogen; $C_{1-6}$ alkyl, optionally substituted with one or more substituents independently selected from —$OR^{310d}$, cyclopropyl and phenyl; and $C_{3-10}$ carbocycle and 3- to 10-membered heterocycle. In some embodiments, $R^{35}$ is selected from: hydrogen; $C_{1-6}$ alkyl, optionally substituted with one or more substituents independently selected from —OH, cyclopropyl and phenyl; and $C_{3-10}$ carbocycle and 3- to 10-membered heterocycle. In some embodiments, $R^{35}$ is selected from: hydrogen, methyl, ethyl, isobutyl, isopropyl, —$CH_2(OH)$, benzyl, —$CH_2$(cyclopropyl), phenyl, and pyridyl. In some embodiments, $R^{35}$ is selected from: hydrogen, methyl, ethyl, isobutyl, isopropyl, —$CH_2(OH)$, benzyl, —$CH_2$(cyclopropyl), phenyl, and 3-pyridyl. In some embodiments, $R^{35}$ is selected from: hydrogen, methyl, ethyl, isobutyl, isopropyl, —$CH_2(OH)$, benzyl, and —$CH_2$(cyclopropyl). In some embodiments, $R^{35}$ is selected from: hydrogen, methyl, ethyl, isobutyl, and —$CH_2(OH)$. In some embodiments, $R^{35}$ is selected from: hydrogen, methyl, ethyl, and isobutyl. In some embodiments, $R^{35}$ is selected from: hydrogen and methyl. In some embodiments, $R^{35}$ is selected from: hydrogen.

In some embodiments, for a compound or salt of Formula (IIb), $R^{36}$ is selected from: hydrogen; halogen, —C(O)$R^{310e}$, —C(O)N($R^{310e}$)$_2$, —C(O)O$R^{310e}$, —S(O)$R^{310e}$, —S(O)$_2$$R^{310e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$; and $C_{3-10}$ carbocycle and 3- to 10-membered heterocycle, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —N($R^{310e}$)C(O)N($R^{310e}$)$_2$, —OC(O)N($R^{310e}$)$_2$, —N($R^{310e}$)C(O)O$R^{310e}$, —C(O)O$R^{310e}$, —OC(O)$R^{310e}$, —S(O)$R^{310e}$, —S(O)$_2$$R^{310e}$, —$NO_2$, =O, =S, =N($R^{310e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39e}$. In some embodiments, $R^{36}$ is selected from: hydrogen; halogen, —C(O)$R^{310e}$, —C(O)N($R^{310e}$)$_2$, —C(O)O$R^{310e}$, and —CN; $C_{1-6}$ alkyl, $C_{2-6}$ alkenyl, and $C_{2-6}$ alkynyl, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$; and $C_{3-10}$ carbocycle and 3- to 10-membered heterocycle, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —N($R^{310e}$)C(O)N($R^{310e}$)$_2$, —OC(O)N($R^{310e}$)$_2$, —N($R^{310e}$)C(O)O$R^{310e}$, —C(O)O$R^{310e}$, —OC(O)$R^{310e}$, —S(O)$R^{310e}$, —S(O)$_2$$R^{310e}$, —$NO_2$, =O, =S, =N($R^{310e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39e}$. In some embodiments, $R^{36}$ is selected from: hydrogen; halogen, —C(O)$R^{310e}$, —C(O)N($R^{310e}$)$_2$, —C(O)O$R^{310e}$, and —CN; $C_{1-6}$ alkyl, optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$; and $C_{3-10}$ carbocycle and 3- to 10-membered heterocycle, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —N($R^{310e}$)C(O)N($R^{310e}$)$_2$, —OC(O)N($R^{310e}$)$_2$, —N($R^{310e}$)C(O)O$R^{310e}$, —C(O)O$R^{310e}$, —OC(O)$R^{310e}$, —S(O)$R^{310e}$, —S(O)$_2$$R^{310e}$, —$NO_2$, =O, =S, =N($R^{310e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39e}$. In some embodiments, $R^{36}$ is selected from: hydrogen; halogen, —C(O)$R^{310e}$, —C(O)N($R^{310e}$)$_2$, —C(O)O$R^{310e}$, and —CN; $C_{1-6}$ alkyl, optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$; and $C_{3-10}$ carbocycle and 3- to 10-membered heterocycle, each of which is optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —N($R^{310e}$)C(O)N($R^{310e}$)$_2$, —OC(O)N($R^{310e}$)$_2$, —N($R^{310e}$)C(O)O$R^{310e}$, —C(O)O$R^{310e}$, —OC(O)$R^{310e}$, —S(O)$R^{310e}$, —S(O)$_2$$R^{310e}$, —$NO_2$, =O, =S, =N($R^{310e}$), —$N_3$, —CN, and $C_{1-6}$ alkyl. In some embodiments, $R^{36}$ is selected from: hydrogen; halogen, —C(O)$R^{310e}$, —C(O)N($R^{310e}$)$_2$, —C(O)O$R^{310e}$, and —CN; $C_{1-6}$ alkyl, optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{36}$ is selected from: hydrogen; halogen, —C(O)$R^{310e}$, —C(O)N($R^{310e}$)$_2$, —C(O)O$R^{310e}$, and —CN; $C_{1-6}$ alkyl, optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, —S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$; and $C_{3-10}$ carbocycle and 3- to 10-membered heterocycle. In some embodiments, $R^{36}$ is selected from: hydrogen; halogen, —C(O)$R^{310e}$, —C(O)N($R^{310e}$)$_2$, —C(O)O$R^{310e}$, and —CN; and $C_{1-6}$ alkyl, optionally substituted with one or more substituents independently selected from halogen, —O$R^{310e}$, —S$R^{310e}$, —N($R^{310e}$)$_2$, —C(O)$R^{310e}$, —C(O)N($R^{310e}$)$_2$, —N($R^{310e}$)C(O)$R^{310e}$, —C(O)O$R^{310e}$, —OC(O)$R^{310e}$, —N($R^{310e}$)C(O)N($R^{310e}$)$_2$, —OC(O)N($R^{310e}$)$_2$, —N($R^{310e}$)C(O)O$R^{310e}$, S(O)$R^{310e}$, —S(O)$_2$$R^{310e}$, —$NO_2$, =O, =S, =N($R^{310e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39e}$. In some embodiments, $R^{36}$ is selected from: hydrogen; halogen, —C(O)$R^{310e}$, —C(O)N($R^{310e}$)$_2$, —C(O)O$R^{310e}$, and —CN; and $C_{1-6}$ alkyl, optionally substituted with one or more substituents independently selected from halogen, —O$R^{310e}$, —S$R^{310e}$, —$N(R^{310e})_2$, —$C(O)R^{310e}$, —$C(O)N(R^{310e})_2$, —$N(R^{310e})C(O)R^{310e}$, —$C(O)OR^{310e}$, —$OC(O)R^{310e}$, —$NO_2$, =O, —CN, $C_{3-10}$ carbocycle and 3- to 10-membered heterocycle In some embodiments, $R^{36}$ is selected from: hydrogen; halogen, —$C(O)R^{310e}$, —$C(O)N(R^{310e})_2$, —$C(O)OR^{310e}$, and —CN; and $C_{1-6}$ alkyl, optionally substituted with one or more substituents independently selected from halogen, —$OR^{310e}$, —$SR^{310e}$, —$N(R^{310e})_2$, =O, —CN, $C_{3-10}$ carbocycle and 3- to 10-membered heterocycle. In some embodiments, $R^{36}$ is selected from: hydrogen; halogen, —$C(O)R^{310e}$, —$C(O)N(R^{310e})_2$, —$C(O)OR^{310e}$, and —CN; and $C_{1-6}$ alkyl, optionally substituted with one or more substituents independently selected from halogen, and —CN. In some embodiments, $R^{36}$ is selected from: hydrogen; halogen and —CN; and $C_{1-6}$ alkyl, optionally substituted with one or more substituents independently selected from halogen, and —CN. In some embodiments, $R^{36}$ is selected from: hydrogen; fluoro and —CN; and $C_{1-6}$ alkyl, optionally substituted with one or more substituents independently selected from fluoro, and —CN. In some embodiments, $R^{36}$ is selected from: hydrogen; fluoro; and $C_{1-6}$ alkyl, optionally substituted with one or more substituents independently selected from fluoro. In some embodiments, $R^{36}$ is selected from: hydrogen; and $C_{1-6}$ alkyl, optionally substituted with one or more substituents independently selected from fluoro. In some embodiments, $R^{36}$ is selected from: hydrogen and $C_{1-6}$ alkyl. In some embodiments, $R^{36}$ is selected from: hydrogen and $C_{1-4}$ alkyl. In some embodiments, $R^{36}$ is selected from: hydrogen, methyl, and isobutyl. In some embodiments, $R^{36}$ is selected from: hydrogen and methyl. In some embodiments, $R^{36}$ is selected from: hydrogen. In some embodiments, $R^{36}$ is selected from: halogen. In some embodiments, $R^{36}$ is selected from: fluoro. In some embodiments, $R^{35}$ together with $R^{36}$ form a $C_{3-10}$ carbocycle or 3- to 10-membered heterocycle optionally substituted with one or more $R^{39e}$. In some embodiments, $R^{35}$ together with $R^{36}$ form a cyclopropyl optionally substituted with one or more $R^{39e}$. In some embodiments, $R^{35}$ together with $R^{36}$ form a cyclopropyl. In some embodiments, $R^{35}$ is —F, and $R^{36}$ is —F.

In some embodiments, $R^{36}$ is selected from: hydrogen; halogen, and —CN; $C_{1-6}$ alkyl, optionally substituted with one or more substituents independently selected from halogen, —$OR^{310d}$, —$SR^{310d}$, —$N(R^{310d})_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{36}$ is selected from: hydrogen; halogen, and —CN; $C_{1-6}$ alkyl, optionally substituted with one or more substituents independently selected from halogen, —$OR^{310d}$, —CN, $C_{3-10}$ carbocycle and 3- to 10-membered heterocycle, wherein the $C_{3-10}$ carbocycle and 3- to 10-membered heterocycle are each optionally substituted with one or more $R^{39d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{36}$ is selected from: hydrogen; $C_{1-6}$ alkyl, optionally substituted with one or more substituents independently selected from —$OR^{310d}$ and $C_{3-10}$ carbocycle; and $C_{3-10}$ carbocycle and 3- to 10-membered heterocycle. In some embodiments, $R^{36}$ is selected from: hydrogen; $C_{1-6}$ alkyl, optionally substituted with one or more substituents independently selected from —$OR^{310d}$ and $C_{3-10}$ carbocycle; and $C_{3-10}$ carbocycle and 3- to 10-membered heterocycle. In some embodiments, $R^{36}$ is selected from: hydrogen; $C_{1-6}$ alkyl, optionally substituted with one or more substituents independently selected from —$OR^{310}$a cyclopropyl and phenyl; and $C_{3-10}$ carbocycle and 3- to 10-membered heterocycle. In some embodiments, $R^{36}$ is selected from: hydrogen; $C_{1-6}$ alkyl, optionally substituted with one or more substituents independently selected from —OH, cyclopropyl and phenyl; and $C_{3-10}$ carbocycle and 3- to 10-membered heterocycle. In some embodiments, $R^{36}$ is selected from: hydrogen, methyl, ethyl, isobutyl, isopropyl, —$CH_2(OH)$, benzyl, —$CH_2$(cyclopropyl), phenyl, and pyridyl. In some embodiments, $R^{36}$ is selected from: hydrogen, methyl, ethyl, isobutyl, isopropyl, —$CH_2(OH)$, benzyl, —$CH_2$(cyclopropyl), phenyl, and 3-pyridyl. In some embodiments, $R^{36}$ is selected from: hydrogen, methyl, ethyl, isobutyl, isopropyl, —$CH_2(OH)$, benzyl, and —$CH_2$(cyclopropyl). In some embodiments, $R^{36}$ is selected from: hydrogen, methyl, ethyl, isobutyl, and —$CH_2(OH)$. In some embodiments, $R^{36}$ is selected from: hydrogen, methyl, ethyl, and isobutyl. In some embodiments, $R^{36}$ is selected from: hydrogen and methyl. In some embodiments, $R^{36}$ is selected from: hydrogen.

In some embodiments, for a compound or salt of Formula (IIb), $R^{35}$ together with $R^{36}$ form a 3- to 10-membered heterocycle or $C_{3-10}$ carbocycle, wherein the 3- to 10-membered heterocycle or $C_{3-10}$ carbocycle is optionally substituted with one or more $R^{39d}$. In some embodiments, $R^{35}$ together with $R^{36}$ form a 3- to 10-membered heterocycle or $C_{3-10}$ carbocycle. In some embodiments, $R^{35}$ together with $R^{36}$ form a $C_{3-10}$ carbocycle. In some embodiments, $R^{35}$ together with $R^{36}$ form a $C_{3-6}$ carbocycle. In some embodiments, $R^{35}$ together with $R^{36}$ form a $C_7$ carbocycle. In some embodiments, $R^{35}$ together with $R^{36}$ form a moiety selected from =O, =S, =$N(O)(R^{310e})$, and =$N(R^{310d})$. In some embodiments, $R^{35}$ together with $R^{36}$ form a moiety selected from =O.

In some embodiments, $R^{35}$ is hydrogen, and $R^{36}$ is hydrogen. In some embodiments, $R^{35}$ is hydrogen, and $R^{36}$ is methyl. In some embodiments, $R^{35}$ is hydrogen, and $R^{36}$ is isobutyl. In some embodiments, $R^{35}$ is hydrogen, and $R^{36}$ is isopropyl. In some embodiments, $R^{35}$ is hydrogen, and $R^{36}$ is phenyl. In some embodiments, $R^{35}$ is hydrogen, and $R^{36}$ is 3-pyridyl. In some embodiments, $R^{35}$ is hydrogen, and $R^{36}$ is —$CH_2OH$. In some embodiments, $R^{35}$ is hydrogen, and $R^{36}$ is —$CH_2$(cyclopropyl). In some embodiments, $R^{35}$ is hydrogen, and $R^{36}$ is benzyl. In some embodiments, $R^{35}$ is methyl, and $R^{36}$ is methyl.

In some embodiments, for a compound or salt of Formula (IIb), $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, =O, =S, =$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$; and $C_{3-10}$ carbocycle and 3- to 10-membered heterocycle, each of which is optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$N(R^{310f})C(O)N(R^{310f})_2$, —$OC(O)N(R^{310f})_2$, —$N(R^{310f})C(O)OR^{310f}$, —$C(O)OR^{310f}$, —$OC(O)R^{310f}$, —$S(O)R^{310f}$, —$S(O)_2R^{310f}$, —$NO_2$, =O, =S, =$N(R^{310f})$, —$N_3$, —CN, and $C_{1-6}$ alkyl. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl each of which is optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, =O, =S, =$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$; and $C_{3-10}$ carbocycle and 3- to 10-membered heterocycle, each of which is optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$N(R^{310f})C(O)N(R^{310f})_2$, —$OC(O)N(R^{310f})_2$, —$N(R^{310f})C(O)OR^{310f}$, —$C(O)OR^{310f}$, —$OC(O)R^{310f}$, —$S(O)R^{310f}$, —$S(O)_2R^{310f}$, —$NO_2$, =O, =S, =$N(R^{310f})$, —$N_3$, —CN, and $C_{1-6}$ alkyl. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2$ $R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, =O, =S, =$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$; and $C_{3-10}$ carbocycle and 3- to 10-membered heterocycle, each of which is optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, =O, —CN, and $C_{1-6}$ alkyl. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, =O, =S, =$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$; and $C_{3-10}$ carbocycle and 3- to 10-membered heterocycle. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, =O, =S, =$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, —$N(R^{310f})C(O)N(R^{310f})_2$, —$OC(O)N(R^{310f})_2$, —$N(R^{310f})C(O)OR^{310f}$, —$S(O)R^{310f}$, —$S(O)_2R^{310f}$, —$NO_2$, =O, =S, =$N(R^{310f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{39f}$. In some embodiments, $R^{37}$ is selected from: hydrogen; —$C(O)R^{310f}$, —$C(O)N(R^{310f})_2$, —$C(O)OR^{310f}$, —$S(O)R^{310}$, and —$S(O)_2R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, =O, —CN, $C_{3-10}$ carbocycle and 3- to 10-membered heterocycle. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2$ $R^{310f}$; $C_{1-6}$ alkyl optionally substituted with one or more substituents independently selected from halogen, —$OR^{310f}$, —$SR^{310f}$, —$N(R^{310f})_2$, —$C(O)R^{310f}$, —$C(O)N(R^{310f})_2$, —$N(R^{310f})C(O)R^{310f}$, —$C(O)OR^{310f}$, —$OC(O)R^{310f}$, =O, and —CN. In some embodiments, $R^{37}$ is selected from: hydrogen; —$C(O)R^{310f}$, —$C(O)N(R^{310f})_2$, —$C(O)OR^{310f}$, —$S(O)R^{310f}$, and —$S(O)_2R^{310f}$; $C_{1-6}$ alkyl optionally substituted with one or more substituents independently selected from halogen and —CN. In some embodiments, $R^{37}$ is selected from: hydrogen; —$C(O)R^{310f}$, —$C(O)N(R^{310f})_2$, —$C(O)OR^{310f}$; $C_{1-6}$ alkyl optionally substituted with one or more substituents independently selected from halogen and —CN. In some embodiments, $R^{37}$ is selected from: hydrogen; and $C_{1-6}$ alkyl optionally substituted with one or more substituents independently selected from halogen and —CN. In some embodiments, $R^{37}$ is selected from: hydrogen; and $C_{1-6}$ alkyl optionally substituted with one or more substituents independently selected from fluoro and —CN. In some embodiments, $R^{37}$ is selected from hydrogen and $C_{1-6}$ alkyl. In some embodiments, $R^{37}$ is selected from hydrogen and $C_{1-4}$ alkyl. In some embodiments, $R^{37}$ is selected from hydrogen, methyl, isopropyl, and isobutyl. In some embodiments, $R^{37}$ is selected from hydrogen and $C_1$ alkyl. In some embodiments, $R^{37}$ is selected from hydrogen.

In some embodiments, for a compound or salt of Formula (Iib), $R^{32}$ is selected from from

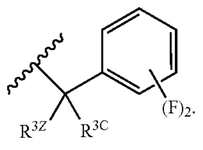

In some embodiments, $R^{32}$ is selected from

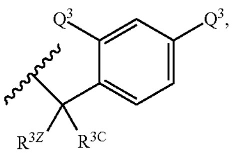

wherein each $Q^3$ is independently selected from halogen, —CN, —OH, —O($C_{1-6}$ alkyl), and —OH. In some embodiments, $R^{32}$ is selected from

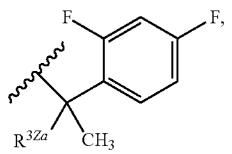

wherein $R^{3Za}$ is selected from methyl, ethyl, isopropyl, isobutyl, and $CH_2OH$. In some embodiments, $R^{32}$ is selected from

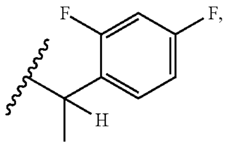
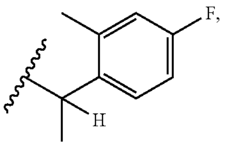
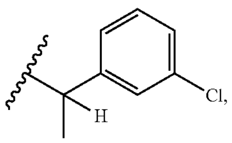
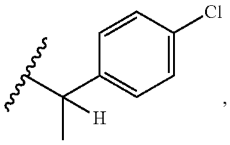
,
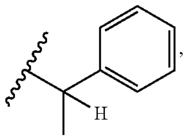
,
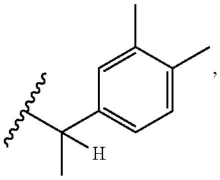
,
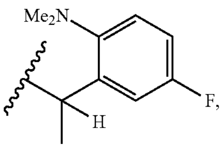
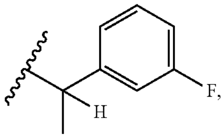
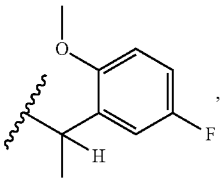
,
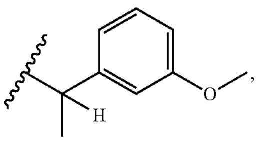
,
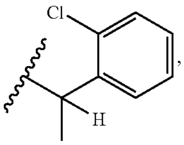
,
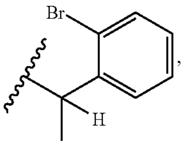
, -continued

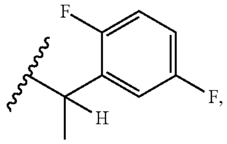
and
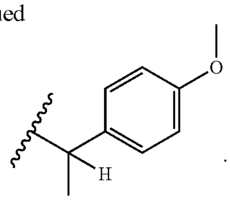
.

In some embodiments, $R^{32}$ is selected from

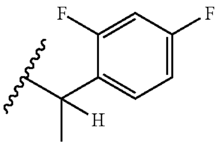
and
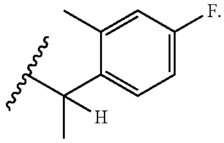

In some embodiments, $R^{32}$ is selected from

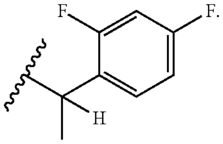 [SMILES: *C(C)c1ccc(F)cc1F]

In some embodiments, for a compound or salt of Formula (IIb), $R^{38}$ is selected from: hydrogen; —C(O)$R^{310g}$, —C(O)N($R^{310g}$)$_2$, —C(O)O$R^{310g}$, —S(O)$R^{310g}$, and —S(O)$_2$$R^{310g}$; and $C_{1-6}$ alkyl optionally substituted with one or more substituents independently selected from halogen, —O$R^{310g}$, —S$R^{310g}$, —N($R^{310g}$)$_2$, —C(O)$R^{310g}$, —C(O)N($R^{310g}$)$_2$, —N($R^{310g}$)C(O)$R^{310g}$, —C(O)O$R^{310g}$, —OC(O)$R^{310g}$, —N($R^{310g}$)C(O)N($R^{310g}$)$_2$, —OC(O)N($R^{310g}$)$_2$, —N($R^{310g}$)C(O)O$R^{310g}$, —S(O)$R^{310g}$, —S(O)$_2$$R^{310g}$, —$NO_2$, =O, =S, =N($R^{310g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39g}$. In some embodiments, $R^{38}$ is selected from: hydrogen; —C(O)$R^{310g}$, —C(O)N($R^{310g}$)$_2$, —C(O)O$R^{310g}$, —S(O)$R^{310g}$, and —S(O)$_2$$R^{310g}$; and $C_{1-6}$ alkyl optionally substituted with one or more substituents independently selected from halogen, —O$R^{310g}$, —S$R^{310g}$, —N($R^{310g}$)$_2$, =O, —CN, $C_{3-10}$ carbocycle and 3- to 10-membered heterocycle. In some embodiments, $R^{38}$ is selected from: hydrogen; and $C_{1-6}$ alkyl optionally substituted with one or more substituents independently selected from halogen, and —CN. In some embodiments, $R^{38}$ is selected from: hydrogen; and $C_{1-6}$ alkyl optionally substituted with one or more substituents independently selected from fluoro, and —CN. In some embodiments, $R^{38}$ is selected from: hydrogen; and $C_{1-6}$ alkyl optionally substituted with one or more substituents independently selected from fluoro. In some embodiments, $R^{38}$ is selected from: hydrogen and $C_{1-6}$ alkyl. In some embodiments, $R^{38}$ is selected from: hydrogen and $C_{1-3}$ alkyl. In some embodiments, $R^{38}$ is selected from: hydrogen and $C_1$ alkyl. In some embodiments, $R^{38}$ is selected from: hydrogen.

In some embodiments, for a compound or salt of Formula (IIb), each $R^{39a}$ is independently selected from: halogen, —O$R^{310a}$, —S$R^{310a}$, —N($R^{310a}$)$_2$, =O, and —CN; and $C_{1-3}$ alkyl each of which is optionally substituted with one or more substituents independently selected from halogen, —O$R^{310a}$, —S$R^{310a}$, —N($R^{310a}$)$_2$, =O, and —CN. In some embodiments, each $R^{39a}$ is independently selected from: halogen, —$OR^{310a}$, —$SR^{310a}$, —$N(R^{310a})_2$, =O, and —CN; and $C_{1-3}$ alkyl each of which is optionally substituted with one or more substituents independently selected from halogen and —CN. In some embodiments, each $R^{39a}$ is independently selected from: halogen, —$OR^{310a}$, —$SR^{310a}$, —$N(R^{310a})_2$, =O, —CN, and $C_{1-3}$ alkyl. In some embodiments, each $R^{39a}$ is independently selected from: halogen, —$OR^{310a}$, —CN, and $C_1$ alkyl. In some embodiments, each $R^{39a}$ is independently selected from: fluoro and —CN. In some embodiments, for a compound or salt of Formula (IIb), each $R^{39b}$ is independently selected from: halogen, —$NO_2$, —$N_3$, —CN, —O($C_{4-6}$ alkyl), —O($C_{1-6}$ haloalkyl), —$SR^{310b}$, and —$N(R^{310b})_2$; $C_1$ alkyl substituted with one or more substituents independently selected from halogen, —$OR^{310b}$, —$SR^{310b}$, —$N(R^{310b})_2$, =O, —CN, and $C_{3-10}$ carbocycle and 3- to 10-membered heterocycle; $C_{2-6}$ alkyl optionally substituted with one or more substituents independently selected from halogen, —$OR^{310b}$, —$SR^{310b}$, —$N(R^{310b})_2$, =O, and —CN; and $C_{3-10}$ carbocycle and 3- to 10-membered heterocycle, each of which is optionally substituted with one or more substituents independently selected from halogen, —$OR^{310b}$, —$SR^{310b}$, —$N(R^{310b})_2$, =O, —CN, and $C_{1-6}$ alkyl. In some embodiments, each $R^{39b}$ is independently selected from: halogen, —$NO_2$, —CN, —O($C_{1-6}$ haloalkyl), —$SR^{310b}$, and —$N(R^{310b})_2$; $C_1$ alkyl substituted with one or more substituents independently selected from halogen, —$OR^{310b}$, —$SR^{310b}$, —$N(R^{310b})_2$, =O, —CN; $C_{2-6}$ alkyl optionally substituted with one or more substituents independently selected from halogen, —$OR^{310b}$, —$SR^{310b}$, —$N(R^{310b})_2$, =O, and —CN. In some embodiments, each $R^{39b}$ is independently selected from: halogen, —$NO_2$, —CN, —O($C_{1-6}$ haloalkyl), —$SR^{310b}$, and —$N(R^{310b})_2$; $C_1$ alkyl substituted with one or more substituents independently selected from halogen, -and —CN; $C_{2-6}$ alkyl optionally substituted with one or more substituents independently selected from halogen, —$OR^{310b}$, and —CN. In some embodiments, each $R^{39b}$ is independently selected from: halogen, —$NO_2$, —CN, —$SR^{310b}$, and —$N(R^{310b})_2$; $C_{2-6}$ alkyl optionally substituted with one or more substituents independently selected from halogen, —$OR^{310b}$, and —CN. In some embodiments, each $R^{39b}$ is independently selected from: halogen, —$NO_2$, —CN, —$SR^{310b}$, and —$N(R^{310b})_2$. In some embodiments, each $R^{39b}$ is independently selected from: —F, —Cl, —Br, —$CH_3$, —$CF_3$, —$N(CH_3)_2$, and —$O(CH_3)$. In some embodiments, each $R^{39b}$ is independently selected from: halogen, and —CN. In some embodiments, each $R^{39b}$ is independently selected from: fluoro, and —CN. In some embodiments, each $R^{39b}$ is independently selected from: fluoro. In some embodiments, each $R^{39b}$ is independently selected from: —CN.

In some embodiments, for a compound or salt of Formula (IIb), each $R^{39z}$ is independently selected from: halogen, —$OR^{310z}$, —$SR^{310z}$, —$N(R^{310z})_2$, =O, and —CN; and $C_{1-3}$ alkyl each of which is optionally substituted with one or more substituents independently selected from halogen, —$OR^{310z}$, —$SR^{310z}$, —$N(R^{310z})_2$, =O, and —CN. In some embodiments, each $R^{39z}$ is independently selected from: halogen, —$OR^{310z}$, —$SR^{310z}$, —$N(R^{310z})_2$, =O, and —CN; and $C_{1-3}$ alkyl each of which is optionally substituted with one or more substituents independently selected from halogen and —CN. In some embodiments, each $R^{39z}$ is independently selected from: halogen, —$OR^{310z}$, —$SR^{310z}$, —$N(R^{310z})_2$, =O, —CN, and $C_{1-3}$ alkyl. In some embodiments, each $R^{39z}$ is independently selected from: halogen, —$OR^{310z}$, —CN, and $C_1$ alkyl. In some embodiments, each $R^{39z}$ is independently selected from: fluoro and —CN. In some embodiments, for a compound or salt of Formula (IIb), each $R^{39c}$ is independently selected from: halogen, —$OR^{310c}$, —$SR^{310c}$, —$N(R^{310c})_2$, =O, and —CN; and $C_{1-3}$ alkyl each of which is optionally substituted with one or more substituents independently selected from halogen, —$OR^{310c}$, —$SR^{310c}$, —$N(R^{310c})_2$, =O, and —CN. In some embodiments, each $R^{39c}$ is independently selected from: halogen, —$OR^{310c}$, —$SR^{310c}$, —$N(R^{310c})_2$, =O, and —CN; and $C_{1-3}$ alkyl each of which is optionally substituted with one or more substituents independently selected from halogen and —CN. In some embodiments, each $R^{39c}$ is independently selected from: halogen, —$OR^{310c}$, —$SR^{310c}$, —$N(R^{310c})_2$, =O, —CN, and $C_{1-3}$ alkyl. In some embodiments, each $R^{39c}$ is independently selected from: halogen, —$OR^{310c}$, —CN, and $C_1$ alkyl. In some embodiments, each $R^{39c}$ is independently selected from: fluoro and —CN. In some embodiments, for a compound or salt of Formula (IIb), each $R^{39d}$ is independently selected from: halogen, —$OR^{310d}$, —$SR^{310d}$, —$N(R^{310d})_2$, =O, and —CN; and $C_{1-3}$ alkyl each of which is optionally substituted with one or more substituents independently selected from halogen, —$OR^{310d}$, —$SR^{310d}$, —$N(R^{310d})_2$, =O, and —CN. In some embodiments, each $R^{39d}$ is independently selected from: halogen, —$OR^{310d}$, —$SR^{310d}$, —$N(R^{310d})_2$, =O, and —CN; and $C_{1-3}$ alkyl each of which is optionally substituted with one or more substituents independently selected from halogen and —CN. In some embodiments, each $R^{39d}$ is independently selected from: halogen, —$OR^{310d}$, —$SR^{310d}$, —$N(R^{310d})_2$, =O, —CN, and $C_{1-3}$ alkyl. In some embodiments, each $R^{39d}$ is independently selected from: halogen, —$OR^{310d}$, —CN, and $C_1$ alkyl. In some embodiments, each $R^{39d}$ is independently selected from: fluoro and —CN. In some embodiments, for a compound or salt of Formula (IIb), each $R^{39e}$ is independently selected from: halogen, —$OR^{310e}$, —$SR^{310e}$, —$N(R^{310e})_2$, =O, and —CN; and $C_{1-3}$ alkyl each of which is optionally substituted with one or more substituents independently selected from halogen, —$OR^{310e}$, —$SR^{310e}$, —$N(R^{310e})_2$, =O, and —CN. In some embodiments, each $R^{39e}$ is independently selected from: halogen, —$OR^{310e}$, —$SR^{310e}$, —$N(R^{310e})_2$, =O, and —CN; and $C_{1-3}$ alkyl each of which is optionally substituted with one or more substituents independently selected from halogen and —CN. In some embodiments, each $R^{39e}$ is independently selected from: halogen, —$OR^{310e}$, —$SR^{310e}$, —$N(R^{310e})_2$, =O, —CN, and $C_{1-3}$ alkyl. In some embodiments, each $R^{39e}$ is independently selected from: halogen, —$OR^{310e}$, —CN, and $C_1$ alkyl. In some embodiments, each $R^{39e}$ is independently selected from: fluoro and —CN. In some embodiments, for a compound or salt of Formula (IIb), each $R^{39f}$ is independently selected from: halogen, —$OR^{310f}$, —$SR^{310f}$, —$N(R^{310f})_2$, =O, and —CN; and $C_{1-3}$ alkyl each of which is optionally substituted with one or more substituents independently selected from halogen, —$OR^{310f}$, —$SR^{310f}$, —$N(R^{310f})_2$, =O, and —CN. In some embodiments, each $R^{39f}$ is independently selected from: halogen, —$OR^{310f}$, —$SR^{310f}$, —$N(R^{310f})_2$, =O, and —CN; and $C_{1-3}$ alkyl each of which is optionally substituted with one or more substituents independently selected from halogen and —CN. In some embodiments, each $R^{39f}$ is independently selected from: halogen, —$OR^{310f}$, —$SR^{310f}$, —$N(R^{310f})_2$, =O, —CN, and $C_{1-3}$ alkyl. In some embodiments, each $R^{39f}$ is independently selected from: halogen, —$OR^{310f}$, —CN, and $C_1$ alkyl. In some embodiments, each $R^{39f}$ is independently selected from: fluoro and —CN. In some embodiments, for a compound or salt of Formula (IIb), each $R^{39g}$ is independently selected from: halogen, —$OR^{310g}$, —$SR^{310g}$, —$N(R^{310g})_2$, =O, and —CN; and $C_{1-3}$ alkyl each of which is optionally substituted with one or more substituents independently selected from halogen, —$OR^{310g}$, —$SR^{310g}$, —$N(R^{310g})_2$, =O, and —CN. In some embodiments, each $R^{39g}$ is independently selected from: halogen, —$OR^{310g}$, —$SR^{310g}$, —$N(R^{310g})_2$, =O, and —CN; and $C_{1-3}$ alkyl each of which is optionally substituted with one or more substituents independently selected from halogen and —CN. In some embodiments, each $R^{39g}$ is independently selected from: halogen, —$OR^{310g}$, —$SR^{310g}$, —$N(R^{310g})_2$, =O, —CN, and $C_{1-3}$ alkyl. In some embodiments, each $R^{39g}$ is independently selected from: halogen, —$OR^{310g}$, —CN, and $C_1$ alkyl. In some embodiments, each $R^{39g}$ is independently selected from: fluoro and —CN.

In some embodiments, for a compound or salt of Formula (IIb), each $R^{310a}$, $R^{310b}$, $R^{310z}$, $R^{310c}$, $R^{310d}$, $R^{310e}$, $R^{310f}$, and $R^{310g}$ is independently selected from: hydrogen; $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NH_2$, =O, —O—$C_{1-6}$ alkyl, —S—$C_{1-6}$ alkyl, —N($C_{1-6}$ alkyl)$_2$, —NH ($C_{1-6}$ alkyl), $C_{1-6}$ alkyl, and $C_{1-6}$ haloalkyl. In some embodiments, each $R^{310a}$, $R^{310b}$, $R^{310z}$, $R^{310c}$, $R^{310d}$, $R^{310e}$, $R^{310f}$, and $R^{310g}$ is independently selected from: hydrogen; $C_{1-6}$ alkyl optionally substituted with one or more substituents independently selected from halogen, —CN, and —OH; and $C_{3-10}$ carbocycle, and 3- to 10-membered heterocycle, each of which is optionally substituted with one or more substituents independently selected from halogen, —CN, —OH, $C_{1-6}$ alkyl, and $C_{1-6}$ haloalkyl. In some embodiments, each $R^{310a}$, $R^{310b}$, $R^{310z}$, $R^{310c}$, $R^{310d}$, $R^{310e}$, $R^{310f}$ and $R^{310g}$ is independently selected from: hydrogen; $C_{1-6}$ alkyl optionally substituted with one or more substituents independently selected from fluoro and CN; and $C_{3-10}$ carbocycle, and 3- to 10-membered heterocycle, each of which is optionally substituted with one or more substituents independently selected from fluoro and —CN. In some embodiments, each $R^{310a}$, $R^{310b}$, $R^{310z}$, $R^{310c}$, $R^{310d}$, $R^{310e}$, $R^{310f}$, and $R^{310g}$ is independently selected from: hydrogen; and $C_{1-6}$ alkyl optionally substituted with one or more substituents independently selected from fluoro and CN. In some embodiments, each $R^{310a}$, $R^{310b}$, $R^{310z}$, $R^{310c}$, $R^{310d}$, $R^{310e}$, $R^{310f}$, and $R^{310g}$ is independently selected from: hydrogen and $C_{1-6}$ alkyl. In some embodiments, each $R^{310a}$, $R^{310b}$, $R^{310z}$, $R^{310c}$, $R^{310d}$, $R^{310e}$, $R^{310f}$ and $R^{310g}$ is independently selected from: hydrogen and $C_1$ alkyl. In some embodiments, each $R^{310a}$, $R^{310b}$, $R^{310z}$, $R^{310c}$, $R^{310d}R^{310e}$, $R^{310f}$, and $R^{310g}$ is independently selected from: hydrogen. In some embodiments, each $R^{310a}$ is independently selected from: hydrogen. In some embodiments, each $R^{310b}$ is independently selected from: hydrogen. In some embodiments, each $R^{310c}$ is independently selected from: hydrogen. In some embodiments, each $R^{310d}$ is independently selected from: hydrogen. In some embodiments, each $R^{310e}$ is independently selected from: hydrogen. In some embodiments, each $R^{310f}$ is independently selected from: hydrogen. In some embodiments, each $R^{310g}$ is independently selected from: hydrogen. In some embodiments, each $R^{310z}$ is independently selected from: hydrogen.

In some embodiments, the compound or salt of Formula (IIb) is selected from: Compound 31, 32, 42, 49, 50, 70, 71, 87, 101, 102, 166, 167, 169, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, and 535, or a salt thereof. In some embodiments, the compound or salt of Formula (IIb) is selected from compound 31, 32, 42, 50, 87, 101, 102, 501, 502, 504, 506, 507, 508, 509, 510, 511, 512, 513, 514, 517, 518, 519, 520, 521, 522, 523, 524, 525, 526, 527, 528, 529, 530, 531, 532, 533, 534, and 535, or a salt thereof. In some embodiments, the compound or salt of Formula (IIb) is selected from compound 31, 32, 42, 50, 87, 101, 102, 501, 502, 504, 506, 507, 508, 509, 510, 511, 512, 513, 514, 517, 518, 519, 520, 521, 522, 523, 524, 525, 526, 527, 528, 529, 530, 533, and 534, or a salt thereof. In some embodiments, the compound or salt of Formula (IIb) is selected from: compound 31, 32, 42, 50, 87, 101, 102, 166, 167, 169, 501, 502, 504, 506, 507, 508, 509, 510, 511, 512, 513, 514, 517, 518, 519, 520, 521, 522, 523, 524, 525, 526, 527, 528, 529, 530, 531, 532, 533, 534, and 535. In some embodiments, the compound or salt of Formula (IIb) is selected from compound 503. In some embodiments, the compound or salt of Formula (IIb) is selected from compound 505. In some embodiments, the compound or salt of Formula (IIb) is selected from compound 515, and compound 516. In some embodiments, the compound or salt of Formula (IIb) is selected from compound 70. In some embodiments, the compound or salt of formula (IIb) is selected from compound 49 and compound 71.

In some embodiments, the compound or salt of Formula (IIb) is selected from: Compound 31, 32, 42, 49, 50, 70, 71, 87, 101, 102, 501, 502, 504, 506, 507, 508, 509, 510, 511, 512, 513, and 535, or a salt thereof. In some embodiments, the compound or salt of Formula (IIb) is selected from compound 31, 32, 42, 50, 87, 101, 102, 501, 502, 504, 506, 507, 508, 509, 510, 511, 512, 513, and 535, or a salt thereof. In some embodiments, the compound or salt of Formula (IIb) is selected from compound 31, 32, 42, 50, 87, 101, 102, 501, 502, 504, 506, 507, 508, 509, 510, 511, 512, or a salt thereof. In some embodiments, the compound or salt of Formula (IIb) is selected from: compound 31, 32, 42, 50, 87, 101, 102, 501, 502, 504, 506, 507, 508, 509, 510, 511, 512, 513, and 535. In some embodiments, the compound or salt of Formula (IIb) is not selected from compound 503. In some embodiments, the compound or salt of Formula (IIb) is not selected from compound 505. In some embodiments, the compound or salt of Formula (IIb) is not selected from compound 515, and compound 516. In some embodiments, the compound or salt of Formula (IIb) is selected from compound 70. In some embodiments, the compound or salt of formula (IIb) is selected from compound 49 and compound 71.

In some embodiments, the compound or salt of Formula (IIb) is not: 166, 167, 169, 503, 505, 514, 517, 518, 519, 520, 521, 522, 523, 524, 525, 526, 527, 528, 529, 530, 531, 532, 533, 534, In an aspect, the present disclosure provides the following compounds and salts thereof: compound 531, and compound 532, and. In an aspect, the present disclosure provides a pharmaceutical composition comprising any of the following compounds or salts thereof and a pharmaceutically acceptable excipient: thereof: In some embodiments, the compound or salt of Formula (IIb) is selected from: compound 531, compound 532, and compound 535. In some embodiments, the compound or salt of Formula (IIb) is selected from: compound 501, 101, 102, 31, 32, 50, 87, 502, 504, 506, 507, 511, 512, 521, and 524, or a salt thereof. In some embodiments, the compound or salt of Formula (IIb) is selected from: compound 501, 101, and 102, or a salt thereof. In some embodiments, the compound or salt of Formula (IIb) is selected from: compound 501 and 101. In some embodiments, the compound or salt of Formula (IIb) is selected from: compound 501. In some embodiments, the compound or salt of Formula (IIb) is selected from: compound 101, 102, 511, 87, 502, 32, 524, 504, 501, and 521, or a salt thereof. In some embodiments, the compound or salt of Formula (IIb) is selected from: compound 101, 102, 511, 87, 502, 32, 524, and 504, or a salt thereof. In some embodiments, the compound or salt of Formula (IIb) is selected from: compound 101, 102, 511, and 87, or a salt thereof.

In an aspect, the present disclosure provides methods of treating a cardiovascular condition (e.g., cardiovascular disease or a related condition) (e.g., HCM), the method comprising administering to a subject in need thereof a compound selected from: compound 531, compound 532, and compound 535., or a salt thereof. In some embodiments, the cardiovascular condition is selected from a cardiovascular condition otherwise disclosed herein. In some embodiments, the compound or salt of Formula (IIb) is not: 3(2H)-Quinazolineacetamide, N-[1-(3,4-dimethoxyphenyl)ethyl]-1,4-dihydro-2,4-dioxo-; N-[(3,4-Dimethylphenyl)phenylmethyl]-1,4-dihydro-2,4-dioxo-3(2H)-quinazolineacetamide; N-[1-(2,4-Difluorophenyl)ethyl]-1,4-dihydro-2,4-dioxo-3(2H)-quinazolineacetamide; 1,4-Dihydro-2,4-dioxo-N-[1-(3,4,5-trimethoxyphenyl)ethyl]-3(2H)-quinazolineacetamide; 3(2H)-Quinazolineacetamide, N-[1-(3,4-dimethoxyphenyl)ethyl]-α-ethyl-1,4-dihydro-2,4-dioxo-; N-[1-(3,4-Dimethoxyphenyl)-2-methylpropyl]-1,4-dihydro-2,4-dioxo-3(2H)-quinazolineacetamide; N-[1-(2,6-Dichloro-3-fluorophenyl)ethyl]-1,4-dihydro-2,4-dioxo-3(2H)-quinazolineacetamide; N-[1-(2,4-Dichloro-S-fluorophenyl)ethyl]-1,4-dihydro-2,4-dioxo-3(2H)-quinazolineacetamide; 3(2H)-Quinazolineacetamide, N-[1-(3,4-dimethoxyphenyl)ethyl]-1,4-dihydro-α-(1-methylethyl)-2,4-dioxo-, (αS)—; N-[1-(3,4-Difluorophenyl)-2-(methylamino)-2-oxoethyl]-1,4-dihydro-2,4-dioxo-3(2H)-quinazolineacetamide; N-[1-(3,4-Diethoxyphenyl)-2-methylpropyl]-1,4-dihydro-2,4-dioxo-3(2H)-quinazolineacetamide; 4-Chloro-α-[[2-(1,4-dihydro-2,4-dioxo-3(2H)-quinazolinyl)acetyl]amino]-3-fluorobenzeneacetic acid; N-[Cyano(3,4,5-trimethoxyphenyl)methyl]-1,4-dihydro-2,4-dioxo-3(2H)-quinazolineacetamide; β-[[2-(1,4-Dihydro-2,4-dioxo-3(2H)-quinazolinyl)acetyl]amino]-2,4-dimethoxybenzenepropanoic acid; Benzenepropanoic acid, β-[[2-(1,4-dihydro-2,4-dioxo-3(2H)-quinazolinyl)acetyl]amino]-3,4-dimethoxy- (ZCI); 3(2H)-Quinazolineacetamide, N-[1-(3,4-dimethoxyphenyl)ethyl]-1,4-dihydro-α-[2-(methylthio)ethyl]-2,4-dioxo-; 3(2H)-Quinazolineacetamide, N-[1-(3,4-dimethoxyphenyl)ethyl]-1,4-dihydro-α-[2-(methylthio)ethyl]-2,4-dioxo-, (αS)—; 4-Chloro-3-[[2-(1,4-dihydro-2,4-dioxo-3(2H)-quinazolinyl)acetyl]amino]-3-fluorobenzenepropanoic acid; 3(2H)-Quinazolineacetamide, N-[1-(3,4-dimethoxyphenyl)ethyl]-1,4-dihydro-2,4-dioxo-α-(phenylmethyl)-; N-[1-[5-Fluoro-2-(4-methyl-1-piperazinyl)phenyl]ethyl]-1,4-dihydro-2,4-dioxo-3(2H)-quinazolineacetamide; N-(2,3-Dihydro-5,6-dimethoxy-TH-inden-1-yl)-1,4-dihydro-2,4-dioxo-3(2H)-quinazolineacetamide; N-[1-(2,5-Difluorophenyl)ethyl]-1,4-dihydro-N-methyl-2,4-dioxo-3(2H)-quinazolineacetamide; N-(2,3-Dihydro-5,6-dimethoxy-TH-inden-1-yl)-α-ethyl-1,4-dihydro-2,4-dioxo-3(2H)-quinazolineacetamide; (αS)—N-(2,3-Dihydro-5,6-dimethoxy-1H-inden-1-yl)-1,4-dihydro-α-[2-(methylthio)ethyl]-2,4-dioxo-3(2H)-quinazolineacetamide; 2,4(1H,3H)-Quinazolinedione, 3-[2-[2-(2,3-dimethylphenyl)-1-pyrrolidinyl]-2-oxoethyl]-; 3-[2-[2-(3,4-Dimethylphenyl)-1-pyrrolidinyl]-2-oxoethyl]-2,4(1H,3H)-quinazolinedione; 2,4(1H,3H)-Quinazolinedione, 3-[2-[2-(2,5-dimethylphenyl)-1-pyrrolidinyl]-2-oxoethyl]-; 3-[2-[2-(2,4-Dimethoxyphenyl)-1-pyrrolidinyl]-2-oxoethyl]-2,4(1H,3H)-quinazolinedione; 3-[2-[3,4-Dihydro-6,7-dimethoxy-1-(2-thienyl)-2(1H)-isoquinolinyl]-2-oxoethyl]-2,4(1H,3H)-quinazolinedione; 3(2H)-Quinazolineacetamide, N-[1-(3,4-dimethoxyphenyl)ethyl]-1,4-dihydro-2,4-dioxo-; N-[(3,4-Dimethylphenyl)phenylmethyl]-1,4-dihydro-2,4-dioxo-3(2H)-quinazolineacetamide; N-[1-(2,4-Difluorophenyl)ethyl]-1,4-dihydro-2,4-dioxo-3(2H)-quinazolineacetamide; or 1,4-Dihydro-2,4-dioxo-N-[1-(3,4,5-trimethoxyphenyl)ethyl]-3(2H)-quinazolineacetamide; or 3(2H)-Quinazolineacetamide, N-[1-(3,4-dimethoxyphenyl)ethyl]-α-ethyl-1,4-dihydro-2,4-dioxo-. In some embodiments, the compound or salt of Formula (IIb) is not 2935170-32-2, 1100186-74-0, 1090486-06-8, 1287996-41-1, 2916214-69-0, 2108614-94-2, 1647579-27-8, 1321213-39-1, 2915393-41-6, 1315989-11-7, 1302302-10-8, 1828319-09-0, 1317817-13-2, 1830637-23-4, 895847-47-9, 2934511-66-5, 2915456-05-0, 1836633-67-0, 2935072-11-8, 1317804-78-6, 2108485-31-8, 1624495-47-1, 2701290-29-9, 2700159-15-3, 2984490-85-7, 2726091-50-3, 2985285-62-7, 2108608-36-0, or 1300356-84-6, wherein said numbers are CAS registry numbers.

In one aspect, disclosed herein is a compound represented by Formula (Ic):

(Ic)

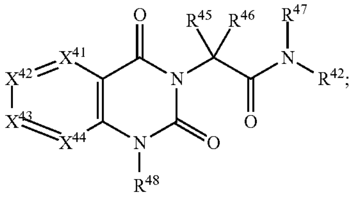

or a salt thereof, wherein: $R^{42}$ is selected from:

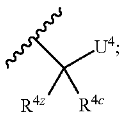

each ---- is independently selected from a single bond and a double bond; $X^{41}$ is selected from $C(R^{41a})$, N, and $N^+(—O^-)$; $X^{42}$ is selected from $C(R^{41b})$, N, and $N^+(—O^-)$; $X^{43}$ is selected from $C(R^{41c})$ N, and $N^+(—O^-)$; $X^{44}$ is selected from $C(R^{41d})$, N, and $N^+(—O^-)$; wherein no more than two of $X^{41}$, $X^{42}$, $X^{43}$, and $X^{44}$ are N or $N^+(—O^-)$; $U^4$ is a $C_5$ carbocycle or 5-membered heterocycle optionally substituted with one or more substituents independently selected from $R^{49bA}$, $R^{49b}$B, $R^{49bC}$, $R^{49bD}$ and $R^{49bE}$; $R^{41a}$, $R^{41b}$, $R^{41c}$, and $R^{41d}$ are each independently selected from: hydrogen; halogen, $—NO_2$, $—N_3$, —CN, $—OR^{410a}$, $—SR^{410a}$, $—N(R^{410a})_2$, $—C(O)R^{410a}$, $—C(O)N(R^{410a})_2$, $—N(R^{410a})C(O)R^{410a}$, $—N(R^{410a})C(O)N(R^{410a})_2$, $—OC(O)N(R^{410a})_2$, $—N(R^{410a})C(O)OR^{410a}$, $—C(O)OR^{410a}$, $—OC(O)R^{410a}$, $—S(O)R^{410a}$, and $—S(O)_2R^{410a}$; $C_{1-6}$ alkyl, $C_{2-6}$ alkenyl, and $C_{2-6}$ alkynyl, each of which is optionally substituted with one or more substituents independently selected from halogen, $—OR^{410a}$, $—SR^{410a}$, $—N(R^{410a})_2$, $—C(O)R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N ($R^{410a}$)$_2$, —N($R^{410a}$)C(O)O$R^{410a}$, —S(O)$R^{410a}$, —S(O)$_2$ $R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49a}$; and $C_{3-10}$ carbocycle and 3- to 10-membered heterocycle, each of which is optionally substituted with one or more substituents independently selected from halogen, —O$R^{410a}$, —S$R^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$) C(O)O$R^{410a}$, —C(O)O$R^{410a}$, —OC(O)$R^{410a}$, —S(O)$R^{410a}$, S(O)$_2R^{410a}$, —$NO_2$, =O, =S, =N($R^{410a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49a}$; wherein when $X^{42}$ is C(H), $X^{43}$ is C(H), and $X^{44}$ is C(H), then $R^{41a}$ is selected from: halogen, —$NO_2$, —$N_3$, —CN, —O$R^{410a}$, —S$R^{410a}$, —N($R^{410a}$)$_2$, —C(O) $R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$) C(O)O$R^{410a}$, —C(O)O$R^{410a}$, —OC(O)$R^{410a}$, —S(O)$R^{410a}$, and —S(O)$_2R^{410a}$; $C_{1-6}$ alkyl, $C_{2-6}$ alkenyl, and $C_{2-6}$ alkynyl, each of which is optionally substituted with one or more substituents independently selected from halogen, —O$R^{410a}$, —S$R^{410a}$, —N($R^{410a}$)$_2$, —C(O)$R^{410a}$, —C(O)N ($R^{410a}$)$_2$, —N($R^{410a}$)C(O)$R^{410a}$, —C(O)O$R^{410a}$, —OC(O) $R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49a}$; and $C_{3-10}$ carbocycle and 3- to 10-membered heterocycle, each of which is optionally substituted with one or more substituents independently selected from halogen, —O$R^{410a}$, —S$R^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$) C(O)O$R^{410a}$, —C(O)O$R^{410a}$, —OC(O)$R^{410a}$, —S(O)$R^{410a}$, —S(O)$_2R^{410a}$, —$NO_2$, =O, =S, =N($R^{410a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49a}$; $R^{4Z}$ is selected from: —C(O)$R^{10z}$, —C(O)N($R^{10z}$)$_2$, —C(O)O$R^{10z}$, and —CN; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O) O$R^{10z}$, —OC(O)$R^{10z}$, —N($R^{10z}$)C(O)N($R^{10z}$)$_2$, —OC(O)N ($R^{10z}$)$_2$, —N($R^{10z}$)C(O)O$R^{10z}$, —S(O)$R^{10z}$, —S(O)$_2R^{10z}$, —$NO_2$, =O, =S, =N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9z}$; and $C_{3-10}$ carbocycle and 3- to 10-membered heterocycle, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C (O)O$R^{10z}$, —C(O)O$R^{10z}$, —OC(O)$R^{10z}$, —S(O)$R^{10z}$, —S(O)$_2R^{10z}$, —$NO_2$, =O, =S, =N($R^{10z}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9z}$; $R^{4C}$ is selected from: hydrogen; —C(O) $R^{410c}$, —C(O)N($R^{410c}$)$_2$, —C(O)O$R^{410c}$, and —CN; $C_{1-6}$ alkyl, $C_{2-6}$ alkenyl, and $C_{2-6}$ alkynyl, each of which is optionally substituted with one or more substituents independently selected from halogen, —O$R^{410c}$, —S$R^{410c}$, —N($R^{410c}$)$_2$, —C(O)$R^{410c}$, —C(O)N($R^{410c}$)$_2$, —N($R^{410c}$)C (O)$R^{410c}$, —C(O)O$R^{410c}$, —OC(O)$R^{410c}$, —N($R^{410c}$)C(O) N($R^{410c}$)$_2$, —OC(O)N($R^{410c}$)$_2$, —N($R^{410c}$)C(O)O$R^{410c}$, —S(O)$R^{410c}$, —S(O)$_2R^{410c}$, —$NO_2$, =O, =S, =N($R^{410c}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49c}$; and $C_{3-10}$ carbocycle and 3- to 10-membered heterocycle, each of which is optionally substituted with one or more substituents independently selected from halogen, —O$R^{410c}$, —S$R^{410c}$, —N($R^{410c}$)$_2$, —C(O)$R^{410c}$, —C(O)N($R^{410c}$)$_2$, —N($R^{410c}$)C(O)$R^{410c}$, —N($R^{410c}$)C(O)N($R^{410c}$)$_2$, —OC (O)N($R^{410c}$)$_2$, —N($R^{410c}$)C(O)O$R^{410c}$, —C(O)O$R^{410c}$, —OC(O)$R^{410c}$, —S(O)$R^{410c}$, —S(O)$_2R^{410c}$, —$NO_2$, =O, =S, =N($R^{410c}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49c}$; $R^{45}$ is selected from: hydrogen; halogen, —O$R^{410d}$, —S$R^{410d}$, —N($R^{410d}$)$_2$, —C(O)$R^{410d}$, —C(O)N($R^{410d}$)$_2$, —N($R^{410d}$) C(O)$R^{410d}$, —C(O)O$R^{410d}$, —OC(O)$R^{410d}$, —N($R^{410d}$)C (O)N($R^{410d}$)$_2$, —OC(O)N($R^{410d}$)$_2$, —N($R^{410d}$)C(O)O$R^{410d}$, —S(O)$R^{410d}$, —S(O)$_2R^{410d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$) C(O)$R^{410d}$, —C(O)O$R^{410d}$, —C(O)$R^{410d}$, —N($R^{410d}$)C(O) N($R^{410d}$)$_2$, —OC(O)N($R^{410d}$)$_2$, —N($R^{410d}$)C(O)O$R^{410d}$, —S(O)$R^{410d}$, —S(O)$_2R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49d}$; and $C_{3-10}$ carbocycle and 3- to 10-membered heterocycle, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —N($R^{410d}$)C(O)N($R^{410d}$)$_2$, —OC (O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2R^{410d}$, —$NO_2$, =O, =S, =N($R^{410d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49d}$; or $R^{45}$ together with $R^{46}$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{49d}$; $R^{46}$ is selected from: hydrogen; halogen, —O$R^{410e}$, —S$R^{410e}$, —N($R^{410e}$)$_2$, —C(O)$R^{410e}$, —C(O)N($R^{410e}$)$_2$, —N($R^{410e}$)C (O)$R^{410e}$, —C(O)O$R^{410e}$, —OC(O)$R^{410e}$, —N($R^{410e}$)C(O) N($R^{410e}$)$_2$, —OC(O)N($R^{410e}$)$_2$, —N($R^{410e}$)C(O)O$R^{410e}$, —S(O)$R^{410e}$, —S(O)$_2R^{410e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{410e}$, —S$R^{410e}$, —N($R^{410e}$)$_2$, —C(O)$R^{410e}$, —C(O)N($R^{410e}$)$_2$, —N($R^{410e}$)C (O)$R^{410e}$, —C(O)O$R^{410e}$, —OC(O)$R^{410e}$, —N($R^{410e}$)C(O)

$N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49e}$; and $C_{3-10}$ carbocycle and 3- to 10-membered heterocycle, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49e}$; or $R^{46}$ together with $R^{45}$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{49e}$; $R^{47}$ is selected from: hydrogen; —$C(O)R^{410f}$, —$C(O)N(R^{410f})_2$, —$C(O)OR^{410f}$, —$S(O)R^{410f}$, and —$S(O)_2R^{410f}$; $C_{1-6}$ alkyl optionally substituted with one or more substituents independently selected from halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$C(O)OR^{410f}$, —$OC(O)R^{410f}$, —$N(R^{410f})C(O)N(R^{410f})_2$, —$OC(O)N(R^{410f})_2$, —$N(R^{410f})C(O)OR^{410f}$, —$S(O)R^{410f}$, —$S(O)_2R^{410f}$, —$NO_2$, =O, =S, =$N(R^{410f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49f}$; and $C_{3-10}$ carbocycle and 3- to 10-membered heterocycle, each of which is optionally substituted with one or more substituents independently selected from halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$N(R^{410f})C(O)N(R^{410f})_2$, —$OC(O)N(R^{410f})_2$, —$N(R^{410f})C(O)OR^{410f}$, —$C(O)OR^{410f}$, —$OC(O)R^{410f}$, —$S(O)R^{410f}$, —$S(O)_2R^{410f}$, —$NO_2$, =O, =S, =$N(R^{410f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49f}$; $R^{48}$ is selected from: hydrogen; —$C(O)R^{410g}$, —$C(O)N(R^{410g})_2$, —$C(O)OR^{410g}$, —$S(O)R^{410g}$, and —$S(O)_2R^{410g}$; $C_{1-6}$ alkyl optionally substituted with one or more substituents independently selected from halogen, —$OR^{410g}$, —$SR^{410g}$, —$N(R^{410g})_2$, —$C(O)R^{410g}$, —$C(O)N(R^{410g})_2$, —$N(R^{410g})C(O)R^{410g}$, —$C(O)OR^{410g}$, —$OC(O)R^{410g}$, —$N(R^{410g})C(O)N(R^{410g})_2$, —$OC(O)N(R^{410g})_2$, —$N(R^{410g})C(O)OR^{410g}$, —$S(O)R^{410g}$, —$S(O)_2R^{410g}$, —$NO_2$, =O, =S, =$N(R^{410g})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49g}$; and $C_{3-10}$ carbocycle and 3- to 10-membered heterocycle, each of which is optionally substituted with one or more substituents independently selected from halogen, —$OR^{410g}$, —$SR^{410g}$, —$N(R^{410g})_2$, —$C(O)R^{410g}$, —$C(O)N(R^{410g})_2$, —$N(R^{410g})C(O)R^{410g}$, —$N(R^{410g})C(O)N(R^{410g})_2$, —$OC(O)N(R^{410g})_2$, —$N(R^{410g})C(O)OR^{410g}$, —$C(O)OR^{410g}$, —$OC(O)R^{410g}$, —$S(O)R^{410g}$, —$S(O)_2R^{410g}$, —$NO_2$, =O, =S, =$N(R^{410g})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49g}$; each $R^{49a}$ is independently selected from: halogen, —$OR^{410a}$, —$SR^{410a}$, —$N(R^{410a})_2$, —$C(O)R^{410a}$, —$C(O)N(R^{410a})_2$, —$N(R^{410a})C(O)R^{410a}$, —$N(R^{410a})C(O)N(R^{410a})_2$, —$OC(O)N(R^{410a})_2$, —$N(R^{410a})C(O)OR^{410a}$, —$C(O)OR^{410a}$, —$OC(O)R^{410a}$, —$S(O)R^{410a}$, —$S(O)_2R^{410a}$, —$NO_2$, =O, =S, =$N(R^{410a})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410a}$, —$SR^{410a}$, —$N(R^{410a})_2$, —$C(O)R^{410a}$, —$C(O)N(R^{410a})_2$, —$N(R^{410a})C(O)R^{410a}$, —$N(R^{410a})C(O)N(R^{410a})_2$, —$OC(O)N(R^{410a})_2$, —$N(R^{410a})C(O)OR^{410a}$, —$C(O)OR^{410a}$, —$OC(O)R^{410a}$, —$S(O)R^{410a}$, —$S(O)_2R^{410a}$, —$NO_2$, =O, =S, =$N(R^{410a})$, —$N_3$, and —CN; each $R^{49bA}$, $R^{49bB}$, $R^{49bC}$, $R^{49bD}$, and $R^{49bE}$ is independently selected from: hydrogen; halogen, —$NO_2$, —$N_3$, —CN, —$OR^{410b}$, —$SR^{410b}$, —$N(R^{410b})_2$, —$C(O)R^{410b}$, —$C(O)N(R^{410b})_2$, —$N(R^{410b})C(O)R^{410b}$, —$N(R^{410b})C(O)N(R^{410b})_2$, —$OC(O)N(R^{410b})_2$, —$N(R^{410b})C(O)OR^{410b}$, —$C(O)OR^{410b}$, —$OC(O)R^{410b}$, —$S(O)R^{410b}$ and —$S(O)_2R^{410b}$; $C_{1-6}$ alkyl, $C_{2-6}$ alkenyl, and $C_{2-6}$ alkynyl, each of which is optionally substituted with one or more substituents independently selected from halogen, —$OR^{410b}$, —$SR^{410b}$, —$N(R^{410b})_2$, —$C(O)R^{410b}$, —$C(O)N(R^{410b})_2$, —$N(R^{410b})C(O)R^{410b}$, —$C(O)OR^{410b}$, —$OC(O)R^{410b}$, —$N(R^{410b})C(O)N(R^{410b})_2$, —$OC(O)N(R^{410b})_2$, —$N(R^{410b})C(O)OR^{410b}$, —$S(O)R^{410b}$, —$S(O)_2R^{410b}$, —$NO_2$, =O, =S, =$N(R^{410b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{410b}$, —$SR^{410b}$, —$N(R^{410b})_2$, —$C(O)R^{410b}$, —$C(O)N(R^{410b})_2$, —$N(R^{410b})C(O)R^{410b}$, —$N(R^{410b})C(O)N(R^{410b})_2$, —$OC(O)N(R^{410b})_2$, —$N(R^{410b})C(O)OR^{410b}$, —$C(O)OR^{410b}$, —$OC(O)R^{410b}$, —$S(O)R^{410b}$, —$S(O)_2R^{410b}$, —$NO_2$, =O, =S, =$N(R^{410b})$, —$N_3$, —CN, $C_{1-6}$ alkyl, $C_{2-6}$ alkenyl, and $C_{2-6}$ alkynyl; each $R^{49z}$ is independently selected from: halogen, —$OR^{410z}$, —$SR^{410z}$, —$N(R^{410z})_2$, —$C(O)R^{410z}$, —$C(O)N(R^{410z})_2$, —$N(R^{410z})C(O)R^{410z}$, —$N(R^{410z})C(O)N(R^{410z})_2$—$OC(O)N(R^{410z})_2$, —$N(R^{410z})C(O)OR^{410z}$, —$C(O)OR^{410z}$, —$OC(O)R^{410z}$, —$S(O)R^{410z}$, —$S(O)_2R^{410z}$, —$NO_2$, =O, =S, =$N(R^{410z})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410z}$, —$SR^{410z}$, —$N(R^{410z})_2$, —$C(O)R^{410z}$, —$C(O)N(R^{410z})_2$, —$N(R^{410z})C(O)R^{410z}$, —$N(R^{410z})C(O)N(R^{410z})_2$, —$OC(O)N(R^{410z})_2$, —$N(R^{410z})C(O)OR^{410z}$, —$C(O)OR^{410z}$, —$OC(O)R^{410z}$, —$S(O)R^{410z}$, —$S(O)_2R^{410z}$, —$NO_2$, =O, =S, =$N(R^{410z})$, —$N_3$, and —CN; each $R^{49c}$ is independently selected from: halogen, —$OR^{410c}$, —$SR^{410c}$, —$N(R^{410c})_2$, —$C(O)R^{410c}$, —$C(O)N(R^{410c})_2$, —$N(R^{410c})C(O)R^{410c}$, —$N(R^{410c})C(O)N(R^{410c})_2$, —$OC(O)N(R^{410c})_2$, —$N(R^{410c})C(O)OR^{410c}$, —$C(O)OR^{410c}$, —$OC(O)R^{410c}$, —$S(O)R^{410c}$, —$S(O)_2R^{410c}$, —$NO_2$, =O, =S, =$N(R^{410c})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410c}$, —$SR^{410c}$, —$N(R^{410c})_2$, —$C(O)R^{410c}$, —$C(O)N(R^{410c})_2$, —$N(R^{410c})C(O)R^{410c}$, —$N(R^{410c})C(O)N(R^{410c})_2$, —$OC(O)N(R^{410c})_2$, —$N(R^{410c})C(O)OR^{410c}$, —$C(O)OR^{410c}$, —$OC(O)R^{410c}$, —$S(O)R^{410c}$, —$S(O)_2R^{410c}$, —$NO_2$, =O, =S, =$N(R^{410c})$, —$N_3$, and —CN; each $R^{49d}$ is independently selected from: halogen, —$OR^{410d}$, —$SR^{410d}$, —$N(R^{410d})_2$, —$C(O)R^{410d}$, —$C(O)N(R^{410d})_2$, —$N(R^{410d})C(O)R^{410d}$, —$N(R^{410d})C(O)N(R^{410d})_2$, —$OC(O)N(R^{410d})_2$, —$N(R^{410d})C(O)OR^{410d}$, —$C(O)OR^{410d}$, —$OC(O)R^{410d}$, —$S(O)R^{410d}$, —$S(O)_2R^{410d}$, —$NO_2$, =O, =S, =$N(R^{410d})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410d}$, —$SR^{410d}$, —$N(R^{410d})_2$, —$C(O)R^{410d}$, —$C(O)N(R^{410d})_2$, —$N(R^{410d})C(O)R^{410d}$, —$N(R^{410d})C(O)N(R^{410d})_2$, —$OC(O)N(R^{410d})_2$, —$N(R^{410d})C(O)OR^{410d}$, —$C(O)OR^{410d}$, —$OC(O)R^{410d}$, —$S(O)R^{410d}$, —$S(O)_2R^{410d}$, —$NO_2$, =O, =S, =$N(R^{410d})$, —$N_3$, and —CN; each $R^{49e}$ is independently selected from: halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, and —CN; each $R^{49f}$ is independently selected from: halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$N(R^{410f})C(O)N(R^{410f})_2$, —$OC(O)N(R^{410f})_2$, —$N(R^{410f})C(O)OR^{410f}$, —$C(O)OR^{410f}$, —$OC(O)R^{410f}$, —$S(O)R^{410f}$, —$S(O)_2R^{410f}$, —$NO_2$, =O, =S, =$N(R^{410f})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$N(R^{410f})C(O)N(R^{410f})_2$, —$OC(O)N(R^{410f})_2$, —$N(R^{410f})C(O)OR^{410f}$, —$C(O)OR^{410f}$, —$OC(O)R^{410f}$, —$S(O)R^{410f}$, —$S(O)_2R^{410f}$, —$NO_2$, =O, =S, =$N(R^{410f})$, —$N_3$, and —CN; each $R^{49g}$ is independently selected from: halogen, —$OR^{410g}$, —$SR^{410g}$, —$N(R^{410g})_2$, —$C(O)R^{410g}$, —$C(O)N(R^{410g})_2$, —$N(R^{410g})C(O)R^{410g}$, —$N(R^{410g})C(O)N(R^{410g})_2$, —$OC(O)N(R^{410})_2$, —$N(R^{410g})C(O)OR^{410g}$, —$C(O)OR^{410g}$, —$OC(O)R^{410g}$, —$S(O)R^{410g}$, —$S(O)_2R^{410g}$, —$NO_2$, =O, =S, =$N(R^{410g})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410}$, —$SR^{410g}$, —$N(R^{410g})_2$, —$C(O)R^{410g}$, —$C(O)N(R^{410g})_2$, —$N(R^{410g})C(O)R^{410g}$, —$N(R^{410g})C(O)N(R^{410g})_2$, —$OC(O)N(R^{410g})_2$, —$N(R^{410g})C(O)OR^{410g}$, —$C(O)OR^{410g}$, —$OC(O)R^{410g}$, —$S(O)R^{410g}$, —$S(O)_2R^{410g}$, —$NO_2$, =O, =S, =$N(R^{410g})$, —$N_3$, and —CN; and each $R^{410a}$, $R^{410b}$, $R^{410c}$, $R^{410d}$, $R^{410e}$, $R^{410f}$, $R^{410g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In one aspect, disclosed herein is a compound of Formula (Ic) that is represented by Formula (Ic-ep):

(Ic-ep)

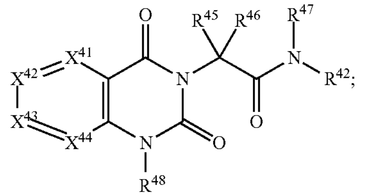

or a salt thereof, wherein: $R^{42}$ is:

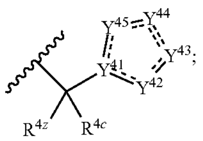

each ---- is independently selected from a single bond and a double bond; $X^{41}$ is selected from $C(R^{41a})$ and N; $X^{42}$ is selected from $C(R^{41b})$, and N; $X^{43}$ is selected from $C(R^{41c})$, and N; $X^{44}$ is selected from $C(R^{41d})$, and N; wherein no more than two of $X^{41}$, $X^{42}$, $X^{43}$, and $X^{44}$ are N; $Y^{41}$ is selected from C, and N; $Y^{42}$ is selected from $C(R^{49bB})$, N, —$N(R^{49bB})$, O, and S; $Y^{43}$ is selected from $C(R^{49bB})$, N, $N(R^{49bB})$, O, and S; $Y^{44}$ is selected from $C(R^{49bB})$ N, —$N(R^{49bB})$, O, and S; $Y^{45}$ is selected from $C(R^{49bB})$, N, —$N(R^{49bB})$, O, and S; wherein no more than two of $Y^{41}$, $Y^{42}$, $Y^{43}$, $Y^{44}$, and $Y^{45}$ are N; $R^{41a}$, $R^{41b}$, $R^{41c}$ and $R^{41d}$ are each independently selected from: hydrogen; halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{1-6}$ haloalkyl, and $C_{1-6}$ alkyl; wherein when $X^{42}$ is C(H), $X^{43}$ is C(H), and $X^{44}$ is C(H), then $R^{41a}$ is selected from: halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{1-6}$ haloalkyl, and $C_{1-6}$ alkyl; $R^{4Z}$ is selected from: $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; $R^{4C}$ is selected from: hydrogen; $R^{45}$ and $R^{46}$ are each independently selected from: hydrogen; halogen; and $C_{1-6}$ alkyl, halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; or $R^5$ together with $R^6$ form a $C_{3-10}$ carbocycle or 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, and $C_{1-6}$ alkyl; $R^{47}$ is selected from: hydrogen; $R^{48}$ is selected from: hydrogen; each $R^{49bA}$, $R^{49bB}$, $R^{49bC}$, $R^{49bD}$, and $R^{49bE}$ is independently selected from: hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$.

In some embodiments, disclosed herein is a compound represented by Formula (Ic-es):

(Ic-es)

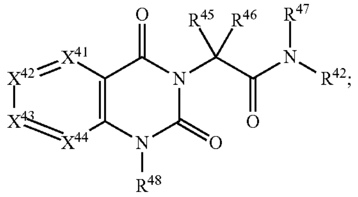

or a salt thereof, wherein: $R^{42}$ is

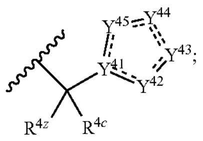

each - - - - is independently selected from a single bond and a double bond; $Y^{41}$ is selected from C, C($R^{49bA}$), N and $N^+$(—$O^-$); $Y^{42}$ is selected from C($R^{49bB}$), C($R^{49bB}$)$_2$, N, $N^+$(—$O^-$), —N($R^{49bB}$), —N($R^{49bB}$)(—$O^-$), and S; $Y^{43}$ is selected from C($R^{49bC}$), C($R^{49bC}$)$_2$, N, $N^+$(—$O^-$), —N($R^{49bC}$), $N^+$($R^{49bC}$)(—$O^-$), O, and S; $Y^{44}$ is selected from C($R^{49bD}$), C($R^{49bD}$)$_2$, N, $N^+$(—$O^-$), —N($R^{49bD}$), $N^+$($R^{49bD}$)(—$O^-$), O, and S; $Y^{45}$ is selected from C($R^{49bE}$), C($R^{49bE}$)$_2$, N, $N^+$(—$O^-$), —N($R^{49bE}$), $N^+$($R^{49bE}$)(—$O^-$), O, and S; wherein at least one of $Y^{41}$, $Y^{42}$, $Y^{43}$, $Y^{44}$, and $Y^{45}$ is N; and no more than three of $Y^{41}$, $Y^{42}$, $Y^{43}$, $Y^{44}$, and $Y^{45}$ are N; and each $R^{49bA}$, $R^{49bB}$, $R^{49bC}$, $R^{49bD}$, and $R^{49bE}$ is independently selected from: hydrogen; halogen, —$NO_2$, —$N_3$, —CN, —$OR^{410b}$, —$SR^{410b}$, —N($R^{410b}$)$_2$, —C(O)$R^{410b}$, —C(O)N($R^{410b}$)$_2$, —N($R^{410b}$)C(O)$R^{410b}$, —N($R^{410b}$)C(O)N($R^{410b}$)$_2$, —OC(O)N($R^{410b}$)$_2$, —N($R^{410b}$)C(O)O$R^{410b}$, —C(O)O$R^{410b}$, —OC(O)$R^{410b}$, —S(O)$R^{410b}$, and —S(O)$_2R^{410b}$; $C_{1-6}$ alkyl, $C_{2-6}$ alkenyl, and $C_{2-6}$ alkynyl, each of which is optionally substituted with one or more substituents independently selected from halogen, —$OR^{410b}$, —$SR^{410b}$, —N($R^{410b}$)$_2$, —C(O)$R^{410b}$, —C(O)N($R^{410b}$)$_2$, —N($R^{410b}$)C(O)$R^{410b}$, —C(O)O$R^{410b}$, —OC(O)$R^{410b}$, —N($R^{410b}$)C(O)N($R^{410b}$)$_2$, —OC(O)N($R^{410b}$)$_2$, —N($R^{410b}$)C(O)O$R^{410b}$, —S(O)$R^{410b}$, —S(O)$_2R^{410b}$, —$NO_2$, =O, =S, =N($R^{410b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{410b}$, —$SR^{410b}$, —N($R^{410b}$)$_2$, —C(O)$R^{410b}$, —C(O)N($R^{410}$)$_2$, —N($R^{410b}$)C(O)$R^{410b}$, —N($R^{410b}$)C(O)N($R^{410b}$)$_2$, —OC(O)N($R^{410b}$)$_2$, —N($R^{410b}$)C(O)O$R^{410b}$, —C(O)O$R^{410b}$, —OC(O)$R^{410b}$, —S(O)$R^{410b}$, —S(O)$_2R^{410b}$, —$NO_2$, =O, =S, =N($R^{410b}$), —$N_3$, —CN, $C_{1-6}$ alkyl, $C_{2-6}$ alkenyl, and $C_{2-6}$ alkynyl.

In some embodiments, for a compound or salt of Formula (Ic), no more than three of $X^{41}$, $X^{42}$, $X^{43}$, and $X^{44}$ is N. In some embodiments, no more than three of $X^{41}$, $X^{42}$, $X^{43}$, and $X^{44}$ is N. In some embodiments, no more than one of $X^{41}$, $X^{42}$, $X^{43}$, and $X^{44}$ is N. In some embodiments, no more than three of $X^{41}$, $X^{42}$, $X^{43}$, and $X^{44}$ is N or $N^+$(—$O^-$). In some embodiments, no more than two of $X^{41}$, $X^{42}$, $X^{43}$, and $X^{44}$ is N or $N^+$(—$O^-$). In some embodiments, no more than one of $X^{41}$, $X^{42}$, $X^{43}$, and $X^{44}$ is N or $N^+$(—$O^-$).

In some embodiments, for a compound or salt of Formula (Ic), no more than three of $Y^{41}$, $Y^{42}$, $Y^{43}Y^{44}$, and $Y^{45}$ are N. In some embodiments, no more than two of $Y^{41}$, $Y^{42}$, $Y^{43}Y^{44}$, and $Y^{45}$ are N. In some embodiments, no more than one of $Y^{41}$, $Y^{42}$, $Y^{43}Y^{44}$, and $Y^{45}$ is N. In some embodiments, no more than three of $Y^4$t, $Y^{42}$, $Y^{43}Y^{44}$, and $Y^{45}$ are N or $N^+$(—$O^-$). In some embodiments, no more than two of $Y^{41}$, $Y^{42}$, $Y^{43}Y^{44}$, and $Y^{45}$ are N or $N^+$(—$O^-$). In some embodiments, no more than one of $Y^{41}$, $Y^{42}Y^{43}Y^{44}$, and $Y^{45}$ is N or $N^+$(—$O^-$). In some embodiments, at least one of $Y^{41}$, $Y^{42}Y^{43}Y^{44}$, and $Y^{45}$ is selected from: N, $N^+$(—$O^-$), O, S, S(O), and S(O)$_2$. Alternatively, In some embodiments, none of $Y^{41}$, $Y^{42}Y^{43}Y^{44}$, and $Y^{45}$ is selected from: N, $N^+$(—$O^-$), O, S, S(O), and S(O)$_2$. In some embodiments, at least one of $Y^{41}$, $Y^{42}Y^{43}Y^{44}$, and $Y^{45}$ is selected from: N, $N^+$(—$O^-$), O, and S. In some embodiments, at least one of $Y^{41}$, $Y^{42}Y^{43}Y^{44}$, and $Y^{45}$ is selected from: N, O, and S. In some embodiments, at least one of $Y^{41}$, $Y^{42}Y^{43}Y^{44}$, and $Y^{45}$ is selected from: N. In some embodiments, at least one of $Y^{41}$, $Y^{42}Y^{43}Y^{44}$, and $Y^{45}$ is selected from: O. In some embodiments, at least one of $Y^{41}Y^{42}Y^{43}Y^{44}$, and $Y^{45}$ is selected from: S. In some embodiments, at least two of $Y^{41}$, $Y^{42}Y^{43}Y^{44}$, and $Y^{45}$ are independently selected from: N, $N^+$(—$O^-$), O, S, S(O), and S(O)$_2$. In some embodiments, at least two of $Y^4$, $Y^{42}$, $Y^{43}$, $Y^{44}$, and $Y^{45}$ are independently selected from: N, N(—$O^-$), O, and S. In some embodiments, at least two of $Y^{41}$, $Y^{42}Y^{43}Y^{44}$, and $Y^{45}$ are independently selected from: N, O, and S. In some embodiments, at least two of $Y^{41}$, $Y^{42}$, $Y^{43}$, $Y^{44}$, and $Y^{45}$ are independently selected from $N^+$(—$O^-$) and N. In some embodiments, at least two of $Y^4$, $Y^{42}Y^{43}Y^{44}$, and $Y^{45}$ are independently selected from N and O. In some embodiments, at least two of $Y^4$, $Y^{42}Y^{43}Y^{44}$, and $Y^{45}$ are independently selected from N and S. In some embodiments, at least two of $Y^4$, $Y^{42}Y^{43}Y^{44}$, and $Y^{45}$ are N. In some embodiments, at least three of $Y^{41}$, $Y^{42}$, $Y^{43}$, $Y^{44}$, and $Y^{45}$ are independently selected from: N, $N^+$(—$O^-$), O, S, S(O), and S(O)$_2$.

In some embodiments, for a compound or salt of Formula (Ic), $X^{41}$ is selected from $C(R^{41a})$ and N, In some embodiments, $X^{41}$ is selected from $C(R^{41a})$, In some embodiments, $X^{41}$ is selected from C(H), C(F), and $C(CH_3)$. In some embodiments, $X^{41}$ is selected from C(H) and C(F). In some embodiments, $X^{41}$ is selected from C(H). In some embodiments, $X^{41}$ is selected from C(F). In some embodiments, $X^{42}$ is selected from $C(R^{41b})$ and N, In some embodiments, $X^{42}$ is selected from N, C(H), C(F), and C(CN). In some embodiments, $X^{42}$ is selected from C(H) and C(F). In some embodiments, $X^{42}$ is selected from C(H). In some embodiments, $X^{42}$ is selected from C(F). In some embodiments, $X^{43}$ is selected from $C(R^{41c})$ and N, In some embodiments, $X^{43}$ is selected from $C(R^{41c})$, In some embodiments, $X^{43}$ is selected from C(H). In some embodiments, $X^{44}$ is selected from $C(R^{41d})$ and N, In some embodiments, $X^{44}$ is selected from $C(R^{41d})$, In some embodiments, $X^{44}$ is selected from C(H). In some embodiments, $X^{43}$ and $X^{44}$ are C(H). In some embodiments, $X^{41}$ is C(H), and $X^{42}$ is C(F); or $X^{41}$ is C(F), and $X^{42}$ is C(F); or $X^{41}$ is C(H), and $X^{42}$ is C(H); or $X^{41}$ is C(H), and $X^{42}$ is C(CN); or $X^{41}$ is $C(CH_3)$, and $X^{42}$ is N. In some embodiments at least one of $X^{41}$, $X^{42}$, $X^{43}$ and $X^{44}$ is not C(H). In some embodiments, $X^{41}$ is $C(R^{41'})$. In some embodiments, $X^{42}$ is $C(R^{41'})$. In some embodiments, $X^{43}$ is $C(R^{41'})$. In some embodiments, $X^{44}$ is $C(R^{41'})$. In some embodiments, when $X^{42}$ is C(H), $X^{43}$ is C(H), and $X^{44}$ is C(H), then $X^{41}$ is selected from N, $N^+(—O^-)$ and $C(R^{41'})$. In some embodiments, when $X^{41}$ is C(H), $X^{43}$ is C(H), and $X^{44}$ is C(H), then $X^{42}$ is selected from N, $N^+(—O^-)$ and $C(R^{41'})$. In some embodiments, when $X^{41}$ is C(H), $X^{42}$ is C(H), and $X^{44}$ is C(H), then $X^{43}$ is selected from N, $N^+(—O^-)$ and $C(R^{41'})$. In some embodiments, when $X^{41}$ is C(H), $X^{42}$ is C(H), and $X^{43}$ is C(H), then $X^{44}$ is selected from N, $N^+(—O^-)$ and $C(R^{41'})$. In some embodiments, when $X^{42}$ is C(H), $X^{43}$ is C(H), and $X^{44}$ is C(H), then $X^{41}$ is selected from N and $C(R^{41'})$. In some embodiments, when $X^{41}$ is C(H), $X^{43}$ is C(H), and $X^{44}$ is C(H), then $X^{42}$ is selected from N and $C(R^{41'})$. In some embodiments, when $X^{41}$ is C(H), $X^{42}$ is C(H), and $X^{44}$ is C(H), then $X^{43}$ is selected from N and $C(R^{41'})$. In some embodiments, when $X^{41}$ is C(H), $X^{42}$ is C(H), and $X^{43}$ is C(H), then $X^{44}$ is selected from N and $C(R^{41'})$. In some embodiments, when $X^{42}$ is C(H), $X^{43}$ is C(H), and $X^{44}$ is C(H), then $X^{41}$ is selected from $C(R^{41'})$. In some embodiments, when $X^{41}$ is C(H), $X^{43}$ is C(H), and $X^{44}$ is C(H), then $X^{42}$ is selected from $C(R^{41'})$. In some embodiments, when $X^{41}$ is C(H), $X^{42}$ is C(H), and $X^{44}$ is C(H), then $X^{43}$ is selected from $C(R^{41'})$. In some embodiments, when $X^{41}$ is C(H), $X^{42}$ is C(H), and $X^{43}$ is C(H), then $X^{44}$ is selected from $C(R^{41'})$.

In some embodiments, for a compound or salt of Formula (Ic), $R^{41'}$ is not hydrogen. In some embodiments, $R^{41'}$ is selected from $R^{41}$, except that $R^{41'}$ is not hydrogen. In some embodiments, $R^{41'}$ is selected from $R^{41b}$, except that $R^{41'}$is not hydrogen. In some embodiments, $R^{41'}$ is selected from $R^{41c}$, except that $R^{41'}$ is not hydrogen. In some embodiments, $R^{41'}$ is selected from $R^{41d}$, except that $R^{41'}$ is not hydrogen. In some embodiments, $R^{41'}$ is selected from: halogen, $—NO_2$, $—N_3$, —CN, $—OR^{410a}$, $—SR^{410a}$, $—N(R^{410a})_2$, $—C(O)R^{410a}$, $—C(O)N(R^{410a})_2$, $—N(R^{410a})C(O)R^{410a}$, $—N(R^{410a})C(O)N(R^{410a})_2$, $—OC(O)N(R^{410a})_2$, $—N(R^{410a})C(O)OR^{410a}$, $—C(O)OR^{410a}$, $—OC(O)R^{410a}$, $—S(O)R^{410a}$, and $—S(O)_2R^{410a}$; $C_{1-6}$ alkyl, $C_{2-6}$ alkenyl, and $C_{2-6}$ alkynyl, each of which is optionally substituted with one or more substituents independently selected from halogen, $—OR^{410a}$, $—SR^{410a}$, $—N(R^{410a})_2$, $—C(O)R^{410a}$, $—C(O)N(R^{410a})_2$, $—N(R^{410a})C(O)R^{410a}$, $—C(O)OR^{410a}$, $—OC(O)R^{410a}$, $—N(R^{410a})C(O)N(R^{410a})_2$, $—OC(O)N(R^{410a})_2$, $—N(R^{410a})C(O)OR^{410a}$, $—S(O)R^{410a}$, $—S(O)_2R^{410a}$, $—NO_2$, =O, =S, $=N(R^{410a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49a}$; and $C_{3-10}$ carbocycle and 3- to 10-membered heterocycle, each of which is optionally substituted with one or more substituents independently selected from halogen, $—OR^{410a}$, $—SR^{410a}$, $—N(R^{410a})_2$, $—C(O)R^{410a}$, $—C(O)N(R^{410a})_2$, $—N(R^{410a})C(O)R^{410a}$, $—N(R^{410a})C(O)N(R^{410a})_2$, $—OC(O)N(R^{410a})_2$, $—N(R^{410a})C(O)OR^{410a}$, $—C(O)OR^{410a}$, $—OC(O)R^{410a}$, $—S(O)R^{410a}$, $—S(O)_2R^{410a}$, $—NO_2$, =O, =S, $=N(R^{410a})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{49a}$. In some embodiments, $R^{41'}$ is selected from: halogen, $—NO_2$, $—N_3$, —CN, $—OR^{410a}$, $—SR^{410a}$, and $—N(R^{410a})_2$; $C_{1-6}$ alkyl, optionally substituted with one or more substituents independently selected from halogen, $—OR^{410a}$, $—SR^{410a}$, $—N(R^{410a})_2$, =O, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49a}$; and $C_{3-10}$ carbocycle and 3- to 10-membered heterocycle, each of which is optionally substituted with one or more substituents independently selected from halogen, $—OR^{410a}$, $—SR^{410a}$, $—N(R^{410a})_2$, $—NO_2$, =O, —CN, and $C_{1-6}$ alkyl, wherein each $C_{1-6}$ alkyl is each optionally substituted with one or more substituents independently selected from $R^{49a}$. In some embodiments, $R^{41'}$ is selected from: halogen, —CN, $—OR^{410a}$, $—SR^{410a}$, and $—N(R^{410a})_2$; $C_{1-6}$ alkyl, optionally substituted with one or more substituents independently selected from halogen, $—OR^{410a}$, $—SR^{410a}$, $—N(R^{410a})_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, $—OR^{410a}$, $—SR^{410a}$, $—N(R^{410a})_2$, $—NO_2$, =O, —CN, and $C_{1-6}$ alkyl, wherein each $C_{1-6}$ alkyl is each optionally substituted with one or more substituents independently selected from $R^{49a}$. In some embodiments, $R^{41'}$ is selected from: halogen, —CN, $—OR^{410a}$, $—SR^{410a}$, and $—N(R^{410a})_2$; $C_{1-6}$ alkyl, optionally substituted with one or more substituents independently selected from halogen, $—OR^{410a}$, $—SR^{410a}$, $—N(R^{410a})_2$; and $C_{3-10}$ carbocycle and 3- to 10-membered heterocycle, each of which is optionally substituted with one or more substituents independently selected from halogen, $—OR^{410a}$, $—SR^{410a}$, $—N(R^{410a})_2$, $—NO_2$, =O, —CN, $C_{1-6}$ alkyl, and $C_{1-6}$ haloalkyl. In some embodiments, $R^{41'}$ is selected from: halogen, —CN, $—OR^{410a}$, $—SR^{410a}$, and $—N(R^{410a})_2$; $C_{1-6}$ alkyl, optionally substituted with one or more substituents independently selected from fluoro and —OH; and $C_{3-10}$ carbocycle and 3- to 10-membered heterocycle, each of which is optionally substituted with one or more substituents independently selected from halogen, $—OR^{410a}$, $—N(R^{410a})_2$, —CN, $C_{1-6}$ alkyl, and $C_{1-6}$ haloalkyl. In some embodiments, $R^{41'}$ is selected from: halogen, —CN, —OH, $—O(CH_3)$; $C_{1-6}$ alkyl, optionally substituted with one or more substituents independently selected from fluoro and —OH; and $C_{3-10}$ carbocycle and 3- to 10-membered heterocycle, each of which is optionally substituted with one or more substituents independently selected from fluoro, —CN, OH, and $—CH_3$. In some embodiments, $R^{41'}$ is selected from: halogen, —CN, —OH, $—O(CH_3)$; $C_{1-6}$ alkyl, optionally substituted with one or more substituents independently selected from fluoro and —OH; and $C_{3-10}$ carbocycle and 3- to 10-membered heterocycle. In some embodiments, $R^{41'}$ is selected from: halogen, —CN, —OH, —O($CH_3$); and $C_{1-6}$ alkyl, optionally substituted with one or more substituents independently selected from fluoro and —OH. In some embodiments, $R^{41'}$ is selected from: halogen, —CN, —OH, —O($CH_3$); and $C_{1-6}$ alkyl. In some embodiments, $R^{41'}$ is selected from: halogen, —CN, —OH, —O($CH_3$); and —$CH_3$. In some embodiments, $R^{41'}$ is selected from: fluoro, chloro, —CN, —OH, —O($CH_3$); and —$CH_3$. In some embodiments, $R^{41'}$ is selected from: fluoro, and —CN, and —$CH_3$. In some embodiments, $R^{41'}$ is selected from: fluoro, and —CN. In some embodiments, $R^{41'}$ is selected from: fluoro. In some embodiments, $R^{41'}$ is selected from —CN. In some embodiments, when $X^{42}$ is C(H), $X^{43}$ is C(H), and $X^{44}$ is C(H), then $R^{41a}$ is selected from: halogen, —CN, —$OR^{410a}$, —$SR^{410a}$, and —N($R^{410a}$)$_2$; $C_{1-6}$ alkyl, optionally substituted with one or more substituents independently selected from halogen, —=O, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{49a}$; and $C_{3-10}$ carbocycle and 3- to 10-membered heterocycle, each of which is optionally substituted with one or more substituents independently selected from halogen, —$OR^{410a}$, —$SR^{410a}$, —N($R^{410a}$)$_2$, —CN, and $C_{1-6}$ alkyl optionally substituted with one or more substituents independently selected from $R^{49a}$. In some embodiments, when $X^{42}$ is C(H), $X^{43}$ is C(H), and $X^{44}$ is C(H), then $R^{41a}$ is selected from: halogen, —CN, —$OR^{410a}$, —$SR^{410a}$, and —N($R^{410a}$)$_2$; and $C_{1-6}$ alkyl, optionally substituted with one or more substituents independently selected from halogen. In some embodiments, when $X^{42}$ is C(H), $X^{43}$ is C(H), and $X^{44}$ is C(H), then $R^{41a}$ is selected from: fluoro, —CN, and —$CH_3$. In some embodiments, when $X^{42}$ is C(H), $X^{43}$ is C(H), and $X^{44}$ is C(H), then $R^{41a}$ is selected from: fluoro, and —$CH_3$. In some embodiments, when $X^{42}$ is C(H), $X^{43}$ is C(H), and $X^{44}$ is C(H), then $R^{41a}$ is selected from: fluoro.

In some embodiments, for a compound or salt of Formula (Ic), $R^{41a}$, $R^{41b}$, $R^{41c}$, and $R^{41d}$, are each independently selected from: hydrogen; halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; $C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49a}$; and $C_{3-10}$ carbocycle and 3- to 10-membered heterocycle, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —S(O)$R^{410a}$, —S(O)$_2R^{410a}$, —$NO_2$, =O, —$N_3$, —CN, and $C_{1-6}$ alkyl. In some embodiments, $R^{41a}$, $R^{41b}$, $R^{41c}$, and $R^{41d}$, are each independently selected from: hydrogen; halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; $C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2$$R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49a}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{41a}$, $R^{41b}$, $R^{41c}$, and $R^{410d}$, are each independently selected from: hydrogen; halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; $C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49a}$; and $C_{3-10}$ carbocycle and 3- to 10-membered heterocycle. In some embodiments, $R^{41a}$, $R^{41b}$, $R^{41c}$, and $R^{41d}$, are each independently selected from: hydrogen; halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; and $C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2R^{410a}$, —$NO_2$, =O, =S, =N($R^{410a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49a}$. In some embodiments, $R^{41a}$, $R^{41b}$, $R^{41c}$, and $R^{410d}$, are each independently selected from: hydrogen; halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; and $C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —N($R^{410a}$)C(O)N($R^{410a}$)$_2$, —OC(O)N($R^{410a}$)$_2$, —N($R^{410a}$)C(O)O$R^{410a}$, —S(O)$R^{410a}$, —S(O)$_2R^{410a}$, —$NO_2$, =O, =S, =N($R^{410a}$), —$N_3$, —CN, $C_{3-10}$ carbocycle and 3- to 10-membered heterocycle. In some embodiments, $R^{41a}$, $R^{41b}$, $R^{41c}$, and $R^{410d}$, are each independently selected from: hydrogen; halogen, —$NO_2$, —$N_3$, —CN, —$OR^{410a}$, —$SR^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; and $C_{1-6}$ alkyl, $C_{2-6}$ alkenyl, and $C_{2-6}$ alkynyl, each of which is optionally substituted with one or more substituents independently selected from halogen, —O$R^{410a}$, —S$R^{410a}$, —N($R^{410a}$)$_2$, —$NO_2$, ═O, —$N_3$, —CN, $C_{3-10}$ carbocycle and 3- to 10-membered heterocycle. In some embodiments, $R^{41a}$, $R^{41b}$, $R^{41c}$, and $R^{410d}$, are each independently selected from: hydrogen; halogen, —$NO_2$, —$N_3$, —CN, —O$R^{410a}$, —S$R^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; and $C_{1-6}$ alkyl optionally substituted with one or more substituents independently selected from halogen, —O$R^{410a}$, —S$R^{410a}$, —N($R^{410a}$)$_2$, —$NO_2$, ═O, —$N_3$, —CN, $C_{3-10}$ carbocycle and 3- to 10-membered heterocycle. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, —N($R^{410a}$)$_2$, —C(O)$R^{410a}$, —C(O)N($R^{410a}$)$_2$, —N($R^{410a}$)C(O)$R^{410a}$, —N($R^{410a}$)C(O)N($R^{410a}$)$_2$, —OC(O)N($R^{410a}$)$_2$, —N($R^{410a}$)C(O)O$R^{410a}$, —C(O)O$R^{410a}$, —OC(O)$R^{410a}$, —S(O)$R^{410a}$, and —S(O)$_2R^{410a}$; and $C_{1-6}$ alkyl optionally substituted with one or more substituents independently selected from halogen, —O$R^{410a}$, —S$R^{410a}$, —N($R^{410a}$)$_2$, —$NO_2$, ═O, —$N_3$, and —CN. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, —OC(O)$R^{410a}$, —S(O)$R^{410a}$, and —S(O)$_2R^{410a}$; and $C_{1-6}$ alkyl optionally substituted with one or more substituents independently selected from halogen, —O$R^{410a}$, —S$R^{410a}$, —N($R^{410a}$)$_2$, —$NO_2$, ═O, —$N_3$, and —CN. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, —N($R^{410a}$)$_2$, —C(O)$R^{410a}$, —C(O)N($R^{410a}$)$_2$, —N($R^{410a}$)C(O)$R^{410a}$, —C(O)O$R^{410a}$, and —OC(O)$R^{410a}$; and $C_{1-6}$ alkyl optionally substituted with one or more substituents independently selected from halogen, —O$R^{410a}$, —S$R^{410a}$, —N($R^{410a}$)$_2$, —$NO_2$, ═O, —$N_3$, and —CN. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, and —N($R^{410a}$)$_2$; $C_{1-6}$ alkyl optionally substituted with one or more substituents independently selected from halogen, —O$R^{410a}$, —S$R^{410a}$, —N($R^{410a}$)$_2$, —$NO_2$, ═O, —$N_3$, and —CN. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, and —N($R^{410a}$)$_2$; and $C_{1-6}$ alkyl optionally substituted with one or more substituents independently selected from halogen, ═O, —$N_3$, and —CN. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, and —N($R^{410a}$)$_2$; and $C_{1-6}$ alkyl optionally substituted with one or more substituents independently selected from halogen and —CN. In some embodiments, $R^{41a}$, $R^{41b}$, $R^{41c}$, and $R^{41d}$, are each independently selected from: hydrogen; halogen, —$NO_2$, —$N_3$, —CN, —O$R^{410a}$, —S$R^{410a}$, and —N($R^{410a}$)$_2$; and $C_{1-6}$ alkyl optionally substituted with one or more substituents independently selected from fluoro and —CN. In some embodiments, $R^{41a}$, $R^{41b}$, $R^{41c}$, and $R^{41d}$, are each independently selected from: hydrogen; halogen, —$NO_2$, —$N_3$, and —CN; and $C_{1-6}$ alkyl optionally substituted with one or more substituents independently selected from fluoro and —CN. In some embodiments, $R^{41a}$, $R^{41b}$, $R^{41c}$, and $R^{41d}$, are each independently selected from: hydrogen; halogen and —CN; and $C_{1-6}$ alkyl optionally substituted with one or more substituents independently selected from fluoro and —CN. In some embodiments, $R^{41a}$, $R^{41b}$, $R^{41c}$, and $R^{41d}$, are each independently selected from: hydrogen; fluoro, chloro and —CN; and $C_{1-6}$ alkyl optionally substituted with one or more substituents independently selected from fluoro and —CN. In some embodiments, $R^{41a}$, $R^{41b}$, $R^{41c}$, and $R^{41d}$, are each independently selected from: hydrogen; fluoro and —CN; and $C_{1-6}$ alkyl optionally substituted with one or more substituents independently selected from fluoro and —CN. In some embodiments, $R^{41a}$, $R^{41b}$, $R^{41c}$, and $R^{41d}$, are each independently selected from: hydrogen, fluoro, —CN, and $C_{1-6}$ alkyl. In some embodiments, $R^{41a}$, $R^{41b}$, $R^{41c}$, and $R^{41d}$, are each independently selected from: hydrogen, fluoro, —CN, and $C_{1-3}$ alkyl. In some embodiments, $R^{41a}$, $R^{41b}$, $R^{41c}$, and $R^{41d}$, are each independently selected from: hydrogen, fluoro, —CN, and $C_1$ alkyl. In some embodiments, $R^{41a}$, $R^{41b}$, $R^{41c}$, and $R^{41d}$, are each independently selected from: hydrogen, fluoro, and —CN. In some embodiments, $R^{41a}$, $R^{41b}$, $R^{41c}$, and $R^{41d}$, are each independently selected from: hydrogen and fluoro. In some embodiments, $R^{41a}$, $R^{41b}$, $R^{41c}$, and $R^{41d}$, are each independently selected from: hydrogen.

In some embodiments, for a compound or salt of Formula (Ic), $R^{4Z}$ is selected from: —CN, —C(O)$R^{10z}$, —C(O)N($R^{10z}$)$_2$, and —C(O)O$R^{10z}$; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2R^{10z}$, —$NO_2$, ═O, ═S, ═N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2R^{10z}$, —$NO_2$, ═O, ═S, ═N($R^{10z}$), —$N_3$, —CN, and $C_{1-6}$ alkyl. In some embodiments, $R^{4Z}$ is selected from: —CN, —C(O)$R^{10z}$, —C(O)N($R^{10z}$)$_2$, and —C(O)O$R^{10z}$; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2R^{10z}$, —$NO_2$, ═O, ═S, ═N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —O$R^{10z}$, —S$R^{10z}$, —N($R^{10z}$)$_2$, —$N_3$, —CN, and $C_{1-6}$ alkyl. In some embodiments, $R^{4Z}$ is selected from: —CN, —C(O)$R^{10z}$, —C(O)N($R^{10z}$)$_2$, and —C(O)O$R^{10z}$; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N $(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen and —CN. In some embodiments, $R^{4Z}$ is selected from: —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle. In some embodiments, $R^{4Z}$ is selected from: —CN, —$C(O)R^{10z}$, —$C(O)N(R^{10z})_2$, and —$C(O)OR^{10z}$; and $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$. In some embodiments, $R^{4Z}$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$. In some embodiments, $R^{4Z}$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, —$N_3$, —CN, $C_{3-10}$ carbocycle and 3- to 10-membered heterocycle. In some embodiments, $R^{4Z}$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, =O, —$N_3$, —CN, $C_{3-10}$ carbocycle and 3- to 10-membered heterocycle. In some embodiments, $R^{4Z}$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, =O, —$N_3$, —CN. In some embodiments, $R^{4Z}$ is selected from: —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, =O, —$N_3$, —CN. In some embodiments, $R^{4Z}$ is selected from $C_{1-6}$ alkyl optionally substituted with one or more substituents independently selected from halogen, —$OR^{10z}$, $SR^{10z}$, —$N(R^{10z})_2$, =O, —$N_3$, —CN. In some embodiments, $R^{4Z}$ is selected from $C_{1-6}$ alkyl optionally substituted with one or more substituents independently selected from halogen, —$OR^{10z}$, and —CN. In some embodiments, $R^{4Z}$ is selected from $C_{1-6}$ alkyl optionally substituted with one or more substituents independently selected from fluoro, —$OR^{10z}$, and —CN. In some embodiments, $R^{4Z}$ is selected from $C_{1-6}$ alkyl optionally substituted with one or more substituents independently selected from fluoro and —CN. In some embodiments, $R^{4Z}$ is selected from $C_{1-6}$ alkyl optionally substituted with one or more substituents independently selected from fluoro. In some embodiments, $R^{4Z}$ is selected from $C_{1-6}$ alkyl. In some embodiments, $R^{4Z}$ is selected from $C_{1-3}$ alkyl. In some embodiments, $R^{4Z}$ is selected from $C_{1-2}$ alkyl. In some embodiments, $R^{4Z}$ is selected from $C_1$ alkyl. In some embodiments, $R^{4Z}$ is selected from hydrogen. In some embodiments, $R^{4Z}$ is selected from —$CF_3$. In some embodiments, $R^{4Z}$ is selected from —$CH_2OH$. In some embodiments, $R^{4Z}$ is selected from halogen. In some embodiments, $R^{4Z}$ is selected from fluorine.

In some embodiments, for a compound or salt of Formula (Ic), $R^{4C}$ is selected from: hydrogen; —CN, —$C(O)R^{410c}$, —$C(O)N(R^{410c})_2$, —$C(O)OR^{410c}$; $C_{1-6}$ alkyl, $C_{2-6}$ alkenyl, and $C_{2-6}$ alkynyl, each of which is optionally substituted with one or more substituents independently selected from halogen, —$OR^{410c}$, —$SR^{410c}$, —$N(R^{410c})_2$, —$C(O)R^{410c}$, —$C(O)N(R^{410c})_2$, —$N(R^{410c})C(O)R^{410c}$, —$C(O)OR^{410c}$, —$OC(O)R^{410c}$, —$N(R^{410c})C(O)N(R^{410c})_2$, —$OC(O)N(R^{410c})_2$, —$N(R^{410c})C(O)OR^{410c}$, —$S(O)R^{410c}$, —$S(O)_2R^{410c}$, —$NO_2$, =O, =S, =$N(R^{410c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49c}$; and $C_{3-10}$ carbocycle and 3- to 10-membered heterocycle. In some embodiments, $R^{4c}$ is selected from: hydrogen; —CN, —$C(O)R^{410c}$, —$C(O)N(R^{410c})_2$, —$C(O)OR^{410c}$; and $C_{1-6}$ alkyl, $C_{2-6}$ alkenyl, and $C_{2-6}$ alkynyl, each of which is optionally substituted with one or more substituents independently selected from halogen, —$OR^{410c}$, —$SR^{410c}$, —$N(R^{410c})_2$, —$C(O)R^{410c}$, —$C(O)N(R^{410c})_2$, —$N(R^{410c})C(O)R^{410c}$, —$C(O)OR^{410c}$, —$OC(O)R^{410c}$, —$N(R^{410c})C(O)N(R^{410c})_2$, —$OC(O)N(R^{410c})_2$, —$N(R^{410c})C(O)OR^{410c}$, —$S(O)R^{410c}$, —$S(O)_2R^{410c}$, —$NO_2$, =O, =S, =$N(R^{410c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49c}$. In some embodiments, $R^{4C}$ is selected from: hydrogen; —CN, —$C(O)R^{410c}$, —$C(O)N(R^{410c})_2$, —$C(O)OR^{410c}$; and $C_{1-6}$ alkyl, $C_{2-6}$ alkenyl, and $C_{2-6}$ alkynyl, each of which is optionally substituted with one or more substituents independently selected from halogen, —$OR^{410c}$, —$SR^{410c}$, —$N(R^{410c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{49c}$. In some embodiments, $R^{4C}$ is selected from: hydrogen; —CN, —$C(O)R^{410c}$, —$C(O)N(R^{410c})_2$, —$C(O)OR^{410c}$; and $C_{1-6}$ alkyl optionally substituted with one or more substituents independently selected from halogen, —$OR^{410c}$, —$SR^{410c}$, —$N(R^{410C})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{49c}$. In some embodiments, $R^{4c}$ is selected from: hydrogen; —CN, —C(O)$R^{410c}$, —C(O)N($R^{410C}$)$_2$, —C(O)O$R^{410c}$; and $C_{1-6}$ alkyl optionally substituted with one or more substituents independently selected from halogen, —O$R^{410c}$, —S$R^{410c}$, —N($R^{410c}$)$_2$, =O, —$N_3$, and —CN, $C_{3-10}$ carbocycle and 3- to 10-membered heterocycle. In some embodiments, $R^{4C}$ is selected from: hydrogen; —CN, —C(O)$R^{410c}$, —C(O)N($R^{410c}$)$_2$, —C(O)O$R^{410c}$; and $C_{1-6}$ alkyl optionally substituted with one or more substituents independently selected from halogen, —O$R^{410c}$, —S$R^{410c}$, —N($R^{410c}$)$_2$, =O, —$N_3$, and —CN. In some embodiments, $R^{4C}$ is selected from: hydrogen; —CN, —C(O)$R^{410c}$, —C(O)N($R^{410c}$)$_2$, —C(O)O$R^{410c}$; and $C_{1-6}$ alkyl optionally substituted with one or more substituents independently selected from halogen, and —CN. In some embodiments, $R^{4C}$ is selected from: hydrogen; —CN; and $C_{1-6}$ alkyl optionally substituted with one or more substituents independently selected from halogen, and —CN. In some embodiments, $R^{4C}$ is selected from: hydrogen, —CN, and $C_{1-6}$ alkyl. In some embodiments, $R^{4C}$ is selected from: hydrogen and $C_{1-6}$ alkyl. In some embodiments, $R^{4C}$ is selected from: hydrogen and $C_1$ alkyl. In some embodiments, $R^{4C}$ is selected from: hydrogen. In some embodiments, $R^{4C}$ is selected from halogen. In some embodiments, $R^{4C}$ is selected from fluoro.

In some embodiments, for a compound or salt of Formula (Ic), $R^{45}$ is selected from: hydrogen; halogen, —C(O)$R^{410d}$, —C(O)N($R^{410d}$)$_2$, —C(O)O$R^{410d}$, —S(O)$R^{410d}$, —S(O)$_2$$R^{410d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2$$R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —N($R^{410d}$)C(O)N($R^{410d}$)$_2$, —OC(O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2$$R^{410d}$, —$NO_2$, =O, =S, =N($R^{410d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49d}$. In some embodiments, $R^{45}$ is selected from: hydrogen; halogen, —C(O)$R^{410d}$, —C(O)N($R^{410d}$)$_2$, —C(O)O$R^{410d}$, and —CN; $C_{1-6}$ alkyl, $C_{2-6}$ alkenyl, and $C_{2-6}$ alkynyl, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2$$R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410}$, —N($R^{410d}$)C(O)N($R^{410d}$)$_2$, —OC(O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2$$R^{410d}$, —$NO_2$, =O, =S, =N($R^{410d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49d}$. In some embodiments, $R^{45}$ is selected from: hydrogen; halogen, —C(O)$R^{410a}$, —C(O)N($R^{410d}$)$_2$, —C(O)O$R^{410}$a and —CN; $C_{1-6}$ alkyl, optionally substituted with one or more substituents independently selected from halogen, —O$R^{410a}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2$$R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —O$R^{410a}$, —S$R^{410d}$, —N($R^{410d}$)$_2$, —C(O)$R^{410d}$, —C(O)N($R^{410d}$)$_2$, —N($R^{410d}$)C(O)$R^{410d}$, —N($R^{410d}$)C(O)N($R^{410d}$)$_2$, —OC(O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2$$R^{410d}$, —$NO_2$, =O, =S, =N($R^{410d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49d}$. In some embodiments, $R^{45}$ is selected from: hydrogen; halogen, —C(O)$R^{410d}$, —C(O)N($R^{410d}$)$_2$, —C(O)O$R^{410}$a and —CN; $C_{1-6}$ alkyl, optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2$$R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —N($R^{410d}$)C(O)N($R^{410d}$)$_2$, —OC(O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2$$R^{410d}$, —$NO_2$, =O, =S, =N($R^{410d}$), —$N_3$, —CN, and $C_{1-6}$ alkyl. In some embodiments, $R^{45}$ is selected from: hydrogen; halogen, —C(O)$R^{410d}$, —C(O)N($R^{410d}$)$_2$, —C(O)O$R^{410}$a and —CN; $C_{1-6}$ alkyl, optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2$$R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{45}$ is selected from: hydrogen; halogen, —C(O)$R^{410d}$, —C(O)N($R^{410d}$)$_2$, —C(O)O$R^{410}$a and —CN; $C_{1-6}$ alkyl, optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —$N(R^{410d})C(O)OR^{410d}$, —$S(O)R^{410d}$, —$S(O)_2R^{410d}$, —$NO_2$, =O, =S, =$N(R^{410d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle. In some embodiments, $R^{45}$ is selected from: hydrogen; halogen, —$C(O)R^{410d}$, —$C(O)N(R^{410d})_2$, —$C(O)OR^{410}$a and —CN; and $C_{1-6}$ alkyl, optionally substituted with one or more substituents independently selected from halogen, —$OR^{410d}$, —$SR^{410d}$, —$N(R^{410d})_2$, —$C(O)R^{410d}$, —$C(O)N(R^{410d})_2$, —$N(R^{410d})C(O)R^{410d}$, —$C(O)OR^{410d}$, —$OC(O)R^{410d}$, —$N(R^{410d})C(O)N(R^{410d})_2$, —$OC(O)N(R^{410d})_2$, —$N(R^{410d})C(O)OR^{410d}$, —$S(O)R^{410d}$, —$S(O)_2R^{410d}$, —$NO_2$, =O, =S, =$N(R^{410d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$. In some embodiments, $R^{45}$ is selected from: hydrogen; halogen, —$C(O)R^{410a}$, —$C(O)N(R^{410d})_2$, —$C(O)OR^{410}$, and —CN; and $C_{1-6}$ alkyl, optionally substituted with one or more substituents independently selected from halogen, —$OR^{410a}$, —$SR^{410d}$, —$N(R^{410d})_2$, —$C(O)R^{410a}$, —$C(O)N(R^{410d})_2$, —$N(R^{410d})C(O)R^{410d}$, —$C(O)OR^{410d}$, —$OC(O)R^{410d}$, —$NO_2$, =O, —CN, $C_{3-10}$ carbocycle and 3- to 10-membered heterocycle In some embodiments, $R^{45}$ is selected from: hydrogen; halogen, —$C(O)R^{410d}$, —$C(O)N(R^{410d})_2$, —$C(O)OR^{410d}$, and —CN; and $C_{1-6}$ alkyl, optionally substituted with one or more substituents independently selected from halogen, —$OR^{410d}$, —$SR^{410d}$, —$N(R^{410d})_2$, =O, —CN, $C_{3-10}$ carbocycle and 3- to 10-membered heterocycle. In some embodiments, $R^{45}$ is selected from: hydrogen; halogen, —$C(O)R^{410d}$, —$C(O)N(R^{410d})_2$, —$C(O)OR^{410d}$, and —CN; and $C_{1-6}$ alkyl, optionally substituted with one or more substituents independently selected from halogen, and —CN. In some embodiments, $R^{45}$ is selected from: hydrogen; halogen and —CN; and $C_{1-6}$ alkyl, optionally substituted with one or more substituents independently selected from halogen, and —CN. In some embodiments, $R^{45}$ is selected from: hydrogen; fluoro and —CN; and $C_{1-6}$ alkyl, optionally substituted with one or more substituents independently selected from fluoro, and —CN. In some embodiments, $R^{45}$ is selected from: hydrogen; fluoro; and $C_{1-6}$ alkyl, optionally substituted with one or more substituents independently selected from fluoro. In some embodiments, $R^{45}$ is selected from: hydrogen; and $C_{1-6}$ alkyl, optionally substituted with one or more substituents independently selected from fluoro. In some embodiments, $R^{45}$ is selected from: hydrogen and $C_{1-6}$ alkyl. In some embodiments, $R^{45}$ is selected from: hydrogen and $C_{1-4}$ alkyl. In some embodiments, $R^{45}$ is selected from: hydrogen, methyl, and isobutyl. In some embodiments, $R^{45}$ is selected from: hydrogen, and isobutyl. In some embodiments, $R^{45}$ is selected from: hydrogen. In some embodiments, $R^{45}$ is selected from: halogen. In some embodiments, $R^{45}$ is selected from: fluoro. In some embodiments, $R^{45}$ together with $R^{46}$ form a $C_{3-10}$ carbocycle or 3- to 10-membered heterocycle optionally substituted with one or more $R^{49d}$. In some embodiments, $R^{45}$ together with $R^{46}$ form a cyclopropyl optionally substituted with one or more $R^{49d}$. In some embodiments, $R^{45}$ together with $R^{46}$ form a cyclopropyl optionally substituted with one or more F. In some embodiments, $R^{45}$ together with $R^{46}$ form a cyclopropyl.

In some embodiments, for a compound or salt of Formula (Ic), $R^{46}$ is selected from: hydrogen; halogen, —$C(O)R^{410e}$, —$C(O)N(R^{410e})_2$, —$C(O)OR^{410e}$, —$S(O)R^{410e}$, —$S(O)_2R^{410e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49e}$. In some embodiments, $R^{46}$ is selected from: hydrogen; halogen, —$C(O)R^{410e}$, —$C(O)N(R^{410e})_2$, —$C(O)OR^{410e}$, and —CN; $C_{1-6}$ alkyl, $C_{2-6}$ alkenyl, and $C_{2-6}$ alkynyl, each of which is optionally substituted with one or more substituents independently selected from halogen, —$OR^{410e}$, —$SR^{410e}$ $N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49e}$. In some embodiments, $R^{46}$ is selected from: hydrogen; halogen, —$C(O)R^{410e}$, —$C(O)N(R^{410e})_2$, —$C(O)OR^{410e}$, and —CN; $C_{1-6}$ alkyl, optionally substituted with one or more substituents independently selected from halogen, —$OR^{410e}$, —$SR^{410e}$ $N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —$OR^{410e}$, —$SR^{410e}$ $N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49e}$. In some embodiments, $R^{46}$ is selected from: hydrogen; halogen, —$C(O)R^{410e}$, —$C(O)N(R^{410e})_2$, —$C(O)OR^{410e}$, and —CN; $C_{1-6}$ alkyl, optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, —CN, and $C_{1-6}$ alkyl. In some embodiments, $R^{46}$ is selected from: hydrogen; halogen, —$C(O)R^{410e}$, —$C(O)N(R^{410e})_2$, —$C(O)OR^{410e}$, and —CN; $C_{1-6}$ alkyl, optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{46}$ is selected from: hydrogen; halogen, —$C(O)R^{410e}$, —$C(O)N(R^{410e})_2$, —$C(O)OR^{410e}$, and —CN; $C_{1-6}$ alkyl, optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle. In some embodiments, $R^{46}$ is selected from: hydrogen; halogen, —$C(O)R^{410e}$, —$C(O)N(R^{410e})_2$, —$C(O)OR^{410e}$, and —CN; and $C_{1-6}$ alkyl, optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$N(R^{410e})C(O)N(R^{410e})_2$, —$OC(O)N(R^{410e})_2$, —$N(R^{410e})C(O)OR^{410e}$, —$S(O)R^{410e}$, —$S(O)_2R^{410e}$, —$NO_2$, =O, =S, =$N(R^{410e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$. In some embodiments, $R^{46}$ is selected from: hydrogen; halogen, —$C(O)R^{410e}$, $C(O)N(R^{410e})_2$, —$C(O)OR^{410e}$, and —CN; and $C_{1-6}$ alkyl, optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$C(O)OR^{410e}$, —$OC(O)R^{410e}$, —$NO_2$, =O, —CN, $C_{3-10}$ carbocycle and 3- to 10-membered heterocycle In some embodiments, $R^{46}$ is selected from: hydrogen; halogen, —$C(O)R^{410e}$, —$C(O)N(R^{410e})_2$, —$C(O)OR^{410e}$, and —CN; and $C_{1-6}$ alkyl, optionally substituted with one or more substituents independently selected from halogen, —$OR^{410e}$, —$SR^{410e}$, —$N(R^{410e})_2$, =O, —CN, $C_{3-10}$ carbocycle and 3- to 10-membered heterocycle. In some embodiments, $R^{46}$ is selected from: hydrogen; halogen, —$C(O)R^{410e}$, —$C(O)N(R^{410e})_2$, —$C(O)OR^{410e}$, and —CN; and $C_{1-6}$ alkyl, optionally substituted with one or more substituents independently selected from halogen, and —CN. In some embodiments, $R^{46}$ is selected from: hydrogen; halogen and —CN; and $C_{1-6}$ alkyl, optionally substituted with one or more substituents independently selected from halogen, and —CN. In some embodiments, $R^{46}$ is selected from: hydrogen; fluoro and —CN; and $C_{1-6}$ alkyl, optionally substituted with one or more substituents independently selected from fluoro, and —CN. In some embodiments, $R^{46}$ is selected from: hydrogen; fluoro; and $C_{1-6}$ alkyl, optionally substituted with one or more substituents independently selected from fluoro. In some embodiments, $R^{46}$ is selected from: hydrogen; and $C_{1-6}$ alkyl, optionally substituted with one or more substituents independently selected from fluoro. In some embodiments, $R^{46}$ is selected from: hydrogen and $C_{1-6}$ alkyl. In some embodiments, $R^{46}$ is selected from: hydrogen and $C_{1-4}$ alkyl. In some embodiments, $R^{46}$ is selected from: hydrogen, methyl, and isobutyl. In some embodiments, $R^{46}$ is selected from: hydrogen, and isobutyl. In some embodiments, $R^{46}$ is selected from: hydrogen. In some embodiments, $R^{46}$ is selected from: halogen. In some embodiments, $R^{46}$ is selected from: fluoro. In some embodiments, $R^{45}$ together with $R^{46}$ form a $C_{3-10}$ carbocycle or 3- to 10-membered heterocycle optionally substituted with one or more $R^{49e}$. In some embodiments, $R^{45}$ together with $R^{46}$ form a cyclopropyl optionally substituted with one or more $R^{49e}$. In some embodiments, $R^{45}$ together with $R^{46}$ form a cyclopropyl optionally substituted with one or more F. In some embodiments, $R^{45}$ together with $R^{46}$ form a cyclopropyl.

In some embodiments, for a compound or salt of Formula (Ic), $R^{45}$ together with $R^{46}$ form a 3- to 10-membered heterocycle or $C_{3-10}$ carbocycle, wherein the 3- to 10-membered heterocycle or $C_{3-10}$ carbocycle is optionally substituted with one or more $R^{49d}$. In some embodiments, $R^{45}$ together with $R^{46}$ form a 3- to 10-membered heterocycle or $C_{3-10}$ carbocycle. In some embodiments, $R^{45}$ together with $R^{46}$ form a $C_{3-10}$ carbocycle. In some embodiments, $R^{45}$ together with $R^{46}$ form a moiety selected from =O, =S, =$N(O)(R^{410e})$, and =$N(R^{410a})$. In some embodiments, $R^{45}$ together with $R^{46}$ form a moiety selected from =O. In some embodiments, $R^{45}$ is hydrogen, and $R^{46}$ is hydrogen. In some embodiments, $R^{45}$ is hydrogen, and $R^{46}$ is isobutyl.

In some embodiments, for a compound or salt of Formula (Ic), $R^{47}$ is selected from: hydrogen; —$C(O)R^{410f}$, —$C(O)N(R^{410f})_2$, —$C(O)OR^{410f}$, —$S(O)R^{410f}$, and —$S(O)_2R^{410f}$; $C_{1-6}$ alkyl optionally substituted with one or more substituents independently selected from halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$C(O)OR^{410f}$, —$OC(O)R^{410f}$, —$N(R^{410f})C(O)N(R^{410f})_2$, —$OC(O)N(R^{410f})_2$, —$N(R^{410f})C(O)OR^{410f}$, —$S(O)R^{410f}$, —$S(O)_2R^{410f}$, —$NO_2$, =O, =S, =$N(R^{410f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$; and $C_{3-10}$ carbocycle and 3- to 10-membered heterocycle, each of which is optionally substituted with one or more substituents independently selected from halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$N(R^{410f})C(O)N(R^{410f})_2$, —$OC(O)N(R^{410f})_2$, —$N(R^{410f})C(O)OR^{410f}$, —$C(O)OR^{410f}$, —$OC(O)R^{410f}$, —$S(O)R^{410f}$, —$S(O)_2R^{410f}$, —$NO_2$, =O, =S, =$N(R^{410f})$, —$N_3$, —CN, and $C_{1-6}$ alkyl. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl each of which is optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —NO$_2$, =O, =S, =N($R^{410}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$; and $C_{3-10}$ carbocycle and 3- to 10-membered heterocycle, each of which is optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —N($R^{410f}$)C(O)N($R^{410f}$)$_2$, —OC(O)N($R^{410f}$)$_2$, —N($R^{410f}$)C(O)O$R^{410f}$, —C(O)O$R^{410f}$, —OC(O)$R^{410f}$, —S(O)$R^{410f}$, —S(O)$_2R^{410f}$, —NO$_2$, =O, =S, =N($R^{410f}$), —N$_3$, —CN, and $C_{1-6}$ alkyl. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2$ $R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —NO$_2$, =O, =S, =N($R^{410f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$; and $C_{3-10}$ carbocycle and 3- to 10-membered heterocycle, each of which is optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, =O, —CN, and $C_{1-6}$ alkyl. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —NO$_2$, =O, =S, =N($R^{410f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$; and $C_{3-10}$ carbocycle and 3- to 10-membered heterocycle. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —NO$_2$, =O, =S, =N($R^{410}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —NO$_2$, =O, =S, =N($R^{410f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, =O, —CN, $C_{3-10}$ carbocycle and 3- to 10-membered heterocycle. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2$ $R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, =O, and —CN. In some embodiments, $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen and —CN. In some embodiments, $R^{47}$ is selected from: hydrogen; —C(O)$R^{410f}$, —C(O)N($R^{410f}$)$_2$, —C(O)O$R^{410f}$; $C_{1-6}$ alkyl optionally substituted with one or more substituents independently selected from halogen and —CN. In some embodiments, $R^{47}$ is selected from: hydrogen; and $C_{1-6}$ alkyl optionally substituted with one or more substituents independently selected from halogen and —CN. In some embodiments, $R^{47}$ is selected from: hydrogen; and $C_{1-6}$ alkyl optionally substituted with one or more substituents independently selected from fluoro and —CN. In some embodiments, $R^{47}$ is selected from hydrogen and $C_{1-6}$ alkyl. In some embodiments, $R^{47}$ is selected from hydrogen and $C_{1-4}$ alkyl. In some embodiments, $R^{47}$ is selected from hydrogen and $C_1$ alkyl. In some embodiments, $R^{47}$ is selected from hydrogen.

In some embodiments, for a compound or salt of Formula (Ic), $Y^{41}$ is selected from C($R^{9bA}$) and N. In some embodiments, $Y^{41}$ is selected from C(H) and N. In some embodiments, $Y^{41}$ is selected from C(H). In some embodiments, $Y^{41}$ is selected from N. In some embodiments, $Y^{41}$ is selected from N and $N^+$(—$O^-$). In some embodiments, $Y^{42}$ is selected from C($R^{9bB}$) and N. In some embodiments, $Y^{42}$ is selected from C(H) and N. In some embodiments, $Y^{42}$ is selected from C(H). In some embodiments, $Y^{42}$ is selected from N. In some embodiments, $Y^{42}$ is selected from N and $N^+$(—$O^-$). In some embodiments, $Y^{42}$ is selected from S. In some embodiments, $Y^{42}$ is selected from O. In some embodiments, $Y^{43}$ is selected from C($R^{9bC}$) and N. In some embodiments, $Y^{43}$ is selected from N, C(H), C(CN), C(F), C(Cl), and C(OH). In some embodiments, $Y^{43}$ is selected from N, C(CN), C(F), C(Cl), and C(OH). In some embodiments, $Y^{43}$ is selected from N, C(CN), and C(F). In some embodiments, $Y^3$ is selected from C(CN), and C(F). In some embodiments, $Y^{43}$ is selected from C(CN), and N. In some embodiments, $Y^{43}$ is selected from C(CN). In some embodiments, $Y^{43}$ is not selected from C(H). In some embodiments, $Y^{43}$ is selected from N and $N^+(—O^-)$. In some embodiments, $Y^{43}$ is selected from S. In some embodiments, $Y^{43}$ is selected from O. In some embodiments, $Y^{44}$ is selected from $C(R^{9bD})$ and N. In some embodiments, $Y^{44}$ is selected from C(H) and N. In some embodiments, $Y^{44}$ is selected from C(H). In some embodiments, $Y^{44}$ is selected from N. In some embodiments, $Y^{44}$ is selected from N and $N^+(—O^-)$. In some embodiments, $Y^{44}$ is selected from S. In some embodiments, $Y^{44}$ is selected from O. In some embodiments, $Y^{45}$ is selected from $C(R^{9bE})$ and N. In some embodiments, $Y^{45}$ is selected from N and C(H), C(F), $C(CH_3)$. In some embodiments, $Y^{45}$ is selected from N and C(H), and C(F). In some embodiments, $Y^{45}$ is selected from C(H), and C(F). In some embodiments, $Y^{45}$ is selected from N. In some embodiments, $Y^{45}$ is selected from N and $N^+(—O^-)$. In some embodiments, $Y^{45}$ is selected from S. In some embodiments, $Y^{45}$ is selected from O. In some embodiments, $Y^{42}$, $Y^{43}$, $Y^{44}$, and $Y^{45}$ are each independently selected from C(H), C(CN), C(F), C(Cl), C(OH), N, O, and S. In some embodiments, $Y^{42}$, $Y^{43}$, $Y^{44}$, and $Y^{45}$ are each independently selected from C(H), C(CN), C(F), N, O, and S. In some embodiments, $Y^{42}$, $Y^{43}$, $Y^{44}$, and $Y^{45}$ are each independently selected from C(H), C(CN), C(F), and N. In some embodiments, $Y^{42}$, $Y^{43}$, $Y^{44}$, and $Y^{45}$ are each independently selected from C(H), C(CN), C(F), and O. In some embodiments, $Y^{42}$, $Y^{43}$, $Y^{44}$, and $Y^{45}$ are each independently selected from C(H), C(CN), C(F), and S.

In some embodiments, for a compound or salt of Formula (Ic), $Y^{41}$ is N, $Y^{42}$ is C(H), $Y^3$ is C(CN), $Y^{44}$ is C(H), and $Y^{45}$ is C(F). In some embodiments, $Y^{41}$ is N, $Y^{42}$ is C(H), $Y^3$ is C(CN), $Y^{44}$ is C(H), and $Y^{45}$ is $C(CH_3)$. In some embodiments, $Y^{41}$ is N, $Y^{42}$ is C(H), $Y^3$ is C(CN), $Y^{44}$ is C(H), and $Y^{45}$ is C(H). In some embodiments, $Y^{41}$ is N, $Y^{42}$ is C(H), $Y^3$ is C(F), $Y^{44}$ is C(H), and $Y^{45}$ is C(F). In some embodiments, $Y^{41}$ is N, $Y^{42}$ is C(H), $Y^3$ is C(H), $Y^{44}$ is C(H), and $Y^{45}$ is C(Cl). In some embodiments, $Y^{41}$ is N, $Y^{42}$ is C(H), $Y^3$ is C(F), $Y^{44}$ is C(H), and $Y^{45}$ is C(H). In some embodiments, $Y^{41}$ is C(H), $Y^{42}$ is N, $Y^3$ is C(OH), $Y^{44}$ is C(H), and $Y^{45}$ is C(H). In some embodiments, $Y^{41}$ is C(H), $Y^{42}$ is C(H), $Y^3$ is N, $Y^{44}$ is C(H), and $Y^{45}$ is C(F). In some embodiments, $Y^{41}$ is N, $Y^{42}$ is C(H), $Y^3$ is C(CN), $Y^{44}$ is C(H), and $Y^{45}$ is N. In some embodiments, $Y^{41}$ is C(H), $Y^{42}$ is N, $Y^3$ is C(CN), $Y^{44}$ is N, and $Y^{45}$ is C(H). In some embodiments, $Y^{41}$ is N, $Y^{42}$ is C(H), $Y^3$ is N, $Y^{44}$ is C(H), and $Y^{45}$ is C(H). In some embodiments, $Y^{41}$ is C(H), $Y^{42}$ is C(H), $Y^3$ is C(CN), $Y^{44}$ is N, and $Y^{45}$ is N.

In some embodiments, for a compound or salt of Formula (Ic), $R^{48}$ is selected from: hydrogen; $—C(O)R^{410g}$, $—C(O)N(R^{410g})_2$, $—C(O)OR^{410g}$, $—S(O)R^{410g}$, and $—S(O)_2R^{4109}$; and $C_{1-6}$ alkyl optionally substituted with one or more substituents independently selected from halogen, $—OR^{410}$, $—SR^{410g}$, $—N(R^{410g})_2$, $—C(O)R^{410g}$, $—C(O)N(R^{410g})_2$, $—N(R^{410g})C(O)R^{410g}$, $—C(O)OR^{410g}$, $—OC(O)R^{410g}$, $—N(R^{410g})C(O)N(R^{410g})_2$, $—OC(O)N(R^{410g})_2$, $—N(R^{410g})C(O)OR^{410g}$, $—S(O)R^{410g}$, $—S(O)_2R^{410g}$, $—NO_2$, =O, =S, $=N(R^{410g})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49g}$In some embodiments, $R^{48}$ is selected from: hydrogen; $—C(O)R^{410g}$, $—C(O)N(R^{410g})_2$, $—C(O)OR^{410g}$, $—S(O)R^{410g}$, and $—S(O)_2R^{410g}$; and $C_{1-6}$ alkyl optionally substituted with one or more substituents independently selected from halogen, $—OR^{410g}$, $—SR^{410g}$, $—N(R^{410g})_2$, =O, —CN, $C_{3-10}$ carbocycle and 3- to 10-membered heterocycle. In some embodiments, $R^{48}$ is selected from: hydrogen; and $C_{1-6}$ alkyl optionally substituted with one or more substituents independently selected from halogen, and —CN. In some embodiments, $R^{48}$ is selected from: hydrogen; and $C_{1-6}$ alkyl optionally substituted with one or more substituents independently selected from fluoro, and —CN. In some embodiments, $R^{48}$ is selected from: hydrogen; and $C_{1-6}$ alkyl optionally substituted with one or more substituents independently selected from fluoro. In some embodiments, $R^{48}$ is selected from: hydrogen and $C_{1-6}$ alkyl. In some embodiments, $R^{48}$ is selected from: hydrogen and $C_{1-3}$ alkyl. In some embodiments, $R^{48}$ is selected from: hydrogen and $C_1$ alkyl. In some embodiments, $R^{48}$ is selected from: hydrogen.

In some embodiments, for a compound or salt of Formula (Ic), each $R^{49a}$ is independently selected from: halogen, $—OR^{410a}$, $—SR^{410a}$, $—N(R^{410a})_2$, =O, and —CN; and $C_{1-3}$ alkyl each of which is optionally substituted with one or more substituents independently selected from halogen, $—OR^{410a}$, $—SR^{410a}$, $—N(R^{410a})_2$, =O, and —CN. In some embodiments, each $R^{49a}$ is independently selected from: halogen, $—OR^{410a}$, $—SR^{410a}$, $—N(R^{410a})_2$, =O, and —CN; and $C_{1-3}$ alkyl each of which is optionally substituted with one or more substituents independently selected from halogen and —CN. In some embodiments, each $R^{49a}$ is independently selected from: halogen, $—OR^{410a}$, $—SR^{410a}$, $—N(R^{410a})_2$, =O, —CN, and $C_{1-3}$ alkyl. In some embodiments, each $R^{49a}$ is independently selected from: halogen, $—OR^{410a}$, —CN, and $C_1$ alkyl. In some embodiments, each $R^{49a}$ is independently selected from: fluoro and —CN. In some embodiments, for a compound or salt of Formula (Ic), each $R^{49bA}$, $R^{49bB}$, $R^{49b}$c $R^{49bD}$, and $R^{49bE}$ is independently selected from: hydrogen; halogen, $—NO_2$, $—N_3$, —CN, $—OR^{410b}$, $—SR^{410b}$, $—N(R^{410b})_2$, $—C(O)R^{410b}$, $—C(O)N(R^{410b})_2$, $—N(R^{410b})C(O)R^{410b}$, $—N(R^{410b})C(O)N(R^{410b})_2$, $—OC(O)N(R^{410b})_2$, $—N(R^{410b})C(O)OR^{410b}$, $—C(O)OR^{410b}$, $—OC(O)R^{410b}$, $—S(O)R^{410b}$, and $—S(O)_2R^{410b}$; $C_{1-6}$ alkyl optionally substituted with one or more substituents independently selected from halogen, $—OR^{410b}$, $—SR^{410b}$, $—N(R^{410b})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, $—OR^{410b}$, $—SR^{410b}$, $—N(R^{410b})_2$, =O, —CN, $C_{1-6}$ alkyl. In some embodiments, each $R^{49bA}$, $R^{49bB}$, $R^{49bC}$, $R^{49bD}$, and $R^{49bE}$ is independently selected from: hydrogen; halogen, $—NO_2$, $—N_3$, —CN, $—OR^{410b}$, $—SR^{410b}$, $—N(R^{410b})_2$, $—C(O)R^{410b}$, $—C(O)N(R^{410b})_2$, $—N(R^{410b})C(O)R^{410b}$, $—N(R^{410b})C(O)N(R^{410b})_2$, $—OC(O)N(R^{410b})_2$, $—N(R^{410b})C(O)OR^{410b}$, $—C(O)OR^{410b}$, $—OC(O)R^{410b}$, $—S(O)R^{410b}$, and $—S(O)_2R^{410b}$; $C_{1-6}$ alkyl optionally substituted with one or more substituents independently selected from halogen, $—OR^{410b}$, $—SR^{410b}$, $—N(R^{410b})_2$, =O, —CN, $C_{3-10}$ carbocycle and 3- to 10-membered heterocycle; and $C_{3-10}$ carbocycle and 3- to 10-membered heterocycle. In some embodiments, each $R^{49bA}$, $R^{49bB}$, $R^{49bC}$, $R^{49bD}$, and $R^{49bE}$ is independently selected from: hydrogen; halogen, $—NO_2$, $—N_3$, —CN, $—OR^{410b}$, $—SR^{410}$, and $—N(R^{410b})_2$; $C_{1-6}$ alkyl optionally substituted with one or more substituents independently selected from halogen, $—OR^{410b}$, $—SR^{410b}$, $—N(R^{410b})_2$, =O, —CN, $C_{3-10}$ carbocycle and 3- to 10-membered heterocycle; and $C_{3-10}$ carbocycle and 3- to 10-membered heterocycle. In some embodiments, each $R^{49bA}$, $R^{49bB}$, $R^{49b}$c $R^{49bD}$, and $R^{49bE}$ is independently selected from: hydrogen; halogen, $—NO_2$, $—N_3$, —CN, $—OR^{410b}$, $—SR^{410b}$, and $—N(R^{410b})_2$; and $C_{1-6}$ alkyl optionally substituted with one or more substituents independently selected from halogen, $—OR^{410b}$, $—SR^{410b}$, $—N(R^{410b})_2$, =O, —CN, $C_{3-10}$ carbocycle and 3- to 10-membered heterocycle. In some embodiments, each $R^{49bA}$, $R^{49bB}$, $R^{49bC}$, $R^{49bD}$, and $R^{49bE}$ is independently selected from: hydrogen; halogen, —CN, —$OR^{410b}$, —$SR^{410b}$, and —$N(R^{410b})_2$; and $C_{1-6}$ alkyl optionally substituted with one or more substituents independently selected from halogen, —$OR^{410b}$, —$SR^{410b}$, —$N(R^{410b})_2$, =O, and —CN. In some embodiments, each $R^{49bA}$, $R^{49bB}$, $R^{49bC}$, $R^{49bD}$ and $R^{49bE}$ is independently selected from: hydrogen, halogen, —CN, —$OR^{410b}$, —$SR^{410b}$, and —$N(R^{410b})_2$, and $C_{1-6}$ alkyl. In some embodiments, each $R^{49bA}$, $R^{49bB}$, $R^{49bC}$, $R^{49bD}$, and $R^{49bE}$ is independently selected from: hydrogen, halogen, —CN, —$OR^{410b}$, and $C_{1-6}$ alkyl. In some embodiments, each $R^{49bA}$, $R^{49bB}$, $R^{49bC}$, $R^{49bD}$, and $R^{49bE}$ is independently selected from: hydrogen, fluoro, —CN, —$OR^{410b}$, and $C_1$i-alkyl. In some embodiments, each $R^{49bA}$, $R^{49bB}$, $R^{49bC}$, $R^{49bD}$, and $R^{49bE}$ is independently selected from: hydrogen, fluoro, —CN, —$OR^{410}$, and $C_1$ alkyl. In some embodiments, each $R^{49bA}$, $R^{49bB}$, $R^{49b}$c $R^{49bD}$, and $R^{49bE}$ is independently selected from: hydrogen and $C_1$ alkyl. In some embodiments, each $R^{49bA}$, $R^{49bB}$, $R^{49bC}$, $R^{49bD}$, and $R^{49bE}$ is independently selected from: hydrogen. In some embodiments, each $R^{49bA}$, $R^{49bB}$, $R^{49bC}$, $R^{49bD}$, and $R^{49bE}$ is independently selected from: $C_1$ alkyl. In some embodiments, for a compound or salt of Formula (Ic), each $R^{49Z}$ is independently selected from: halogen, —$OR^{410z}$, —$SR^{410z}$, —$N(R^{410Z})$, =O, and —CN; and $C_{1-3}$ alkyl each of which is optionally substituted with one or more substituents independently selected from halogen, —$OR^{410z}$, —$SR^{410z}$, —$N(R^{410z})_2$, =O, and —CN. In some embodiments, each $R^{49Z}$ is independently selected from: halogen, —$OR^{410z}$, —$SR^{410z}$, —$N(R^{410Z})$, =O, and —CN; and $C_{1-3}$ alkyl each of which is optionally substituted with one or more substituents independently selected from halogen and —CN. In some embodiments, each $R^{49Z}$ is independently selected from: halogen, —$OR^{410z}$, —$SR^{410z}$, —$N(R^{410Z})$, =O, —CN, and $C_{1-3}$ alkyl. In some embodiments, each $R^{49Z}$ is independently selected from: halogen, —$OR^{410z}$, —CN, and $C_1$ alkyl. In some embodiments, each $R^{49Z}$ is independently selected from: fluoro and —CN. In some embodiments, for a compound or salt of Formula (Ic), each $R^{49c}$ is independently selected from: halogen, —$OR^{410c}$, —$SR^{410c}$, —$N(R^{410c})_2$, =O, and —CN; and $C_{1-3}$ alkyl each of which is optionally substituted with one or more substituents independently selected from halogen, —$OR^{410c}$, —$SR^{410c}$, —$N(R^{410c})_2$, =O, and —CN. In some embodiments, each $R^{49c}$ is independently selected from: halogen, —$OR^{410c}$, —$SR^{410c}$, —$N(R^{410c})_2$, =O, and —CN; and $C_{1-3}$ alkyl each of which is optionally substituted with one or more substituents independently selected from halogen and —CN. In some embodiments, each $R^{49c}$ is independently selected from: halogen, —$OR^{410c}$, —$SR^{410c}$, —$N(R^{410c})_2$, =O, —CN, and $C_{1-3}$ alkyl. In some embodiments, each $R^{49c}$ is independently selected from: halogen, —$OR^{410c}$, —CN, and $C_1$ alkyl. In some embodiments, each $R^{49c}$ is independently selected from: fluoro and —CN. In some embodiments, for a compound or salt of Formula (Ic), each $R^{49d}$ is independently selected from: halogen, —$OR^{410d}$, —$SR^{410d}$, —$N(R^{410d})_2$, =O, and —CN; and $C_{1-3}$ alkyl each of which is optionally substituted with one or more substituents independently selected from halogen, —$OR^{410d}$, —$SR^{410d}$, —$N(R^{410d})_2$, =O, and —CN. In some embodiments, each $R^{49d}$ is independently selected from: halogen, —$OR^{410d}$, —$SR^{410d}$, —$N(R^{410d})_2$, =O, and —CN; and $C_{1-3}$ alkyl each of which is optionally substituted with one or more substituents independently selected from halogen and —CN. In some embodiments, each $R^{49d}$ is independently selected from: halogen, —$OR^{410d}$, —$SR^{410d}$, —$N(R^{410d})_2$, =O, —CN, and $C_{1-3}$ alkyl. In some embodiments, each $R^{49d}$ is independently selected from: halogen, —$OR^{410d}$, —CN, and $C_1$ alkyl. In some embodiments, each $R^{49d}$ is independently selected from: fluoro and —CN. In some embodiments, for a compound or salt of Formula (Ic), each $R^{49e}$ is independently selected from: halogen, —$OR^{410e}$, —$SR^{410e}$, —$N(R^{410e})_2$, =O, and —CN; and $C_{1-3}$ alkyl each of which is optionally substituted with one or more substituents independently selected from halogen, —$OR^{410e}$, —$SR^{410e}$, —$N(R^{410e})_2$, =O, and —CN. In some embodiments, each $R^{49e}$ is independently selected from: halogen, —$OR^{410e}$, —$SR^{410e}$, —$N(R^{410e})_2$, =O, and —CN; and $C_{1-3}$ alkyl each of which is optionally substituted with one or more substituents independently selected from halogen and —CN. In some embodiments, each $R^{49e}$ is independently selected from: halogen, —$OR^{410e}$, —$SR^{410e}$, —$N(R^{410e})_2$, =O, —CN, and $C_{1-3}$ alkyl. In some embodiments, each $R^{49e}$ is independently selected from: halogen, —$OR^{410e}$, —CN, and $C_1$ alkyl. In some embodiments, each $R^{49e}$ is independently selected from: fluoro and —CN. In some embodiments, for a compound or salt of Formula (Ic), each $R^{49f}$ is independently selected from: halogen, —$OR^{410f}$, —$SR^{410f}$, —$N(R^{410f})_2$, =O, and —CN; and $C_{1-3}$ alkyl each of which is optionally substituted with one or more substituents independently selected from halogen, —$OR^{410f}$, —$SR^{410f}$, —$N(R^{410f})_2$, =O, and —CN. In some embodiments, each $R^{49f}$ is independently selected from: halogen, —$OR^{410f}$, —$SR^{410f}$, —$N(R^{410f})_2$, =O, and —CN; and $C_{1-3}$ alkyl each of which is optionally substituted with one or more substituents independently selected from halogen and —CN. In some embodiments, each $R^{49f}$ is independently selected from: halogen, —$OR^{410f}$, —$SR^{410f}$, —$N(R^{410f})_2$, =O, —CN, and $C_{1-3}$ alkyl. In some embodiments, each $R^{49f}$ is independently selected from: halogen, —$OR^{410f}$, —CN, and $C_1$ alkyl. In some embodiments, each $R^{49f}$ is independently selected from: fluoro and —CN. In some embodiments, for a compound or salt of Formula (Ic), each $R^{49g}$ is independently selected from: halogen, —$OR^{410g}$, —$SR^{410g}$, —$N(R^{410g})_2$, =O, and —CN; and $C_{1-3}$ alkyl each of which is optionally substituted with one or more substituents independently selected from halogen, —$OR^{410g}$, —$SR^{410g}$, —$N(R^{410g})_2$, =O, and —CN. In some embodiments, each $R^{49g}$ is independently selected from: halogen, —$OR^{410g}$, —$SR^{410g}$, —$N(R^{410g})_2$, =O, and —CN; and $C_{1-3}$ alkyl each of which is optionally substituted with one or more substituents independently selected from halogen and —CN. In some embodiments, each $R^{49g}$ is independently selected from: halogen, —$OR^{410g}$, —$SR^{410g}$, —$N(R^{410g})_2$, =O, —CN, and $C_{1-3}$ alkyl. In some embodiments, each $R^{49g}$ is independently selected from: halogen, —$OR^{410g}$, —CN, and $C_1$ alkyl. In some embodiments, each $R^{49g}$ is independently selected from: fluoro and —CN.

In some embodiments, for a compound or salt of Formula (Ic), each $R^{410a}$, $R^{410b}$, $R^{410z}$, $R^{410c}$, $R^{410d}$, $R^{410e}$, $R^{410f}$, and $R^{410g}$ is independently selected from: hydrogen; $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NH_2$, =O, —O—$C_{1-6}$ alkyl, —S—$C_{1-6}$ alkyl, —N($C_{1-6}$ alkyl)$_2$, —NH ($C_{1-6}$ alkyl), $C_{1-6}$ alkyl, and $C_{1-6}$ haloalkyl. In some embodiments, each $R^{410a}$, $R^{410b}$, $R^{410z}$, $R^{410c}$, $R^{410d}$, $R^{410e}$, $R^{410f}$ and $R^{410g}$ is independently selected from: hydrogen; $C_{1-6}$ alkyl optionally substituted with one or more substituents independently selected from halogen, —CN, and —OH; and $C_{3-10}$ carbocycle, and 3- to 10-membered heterocycle, each of which is optionally substituted with one or more substituents independently selected from halogen, —CN, —OH, $C_{1-6}$ alkyl, and $C_{1-6}$ haloalkyl. In some embodiments, each $R^{410a}$, $R^{410b}$, $R^{410z}$, $R^{410c}$, $R^{410d}$, $R^{410e}$, $R^{410f}$ and $R^{410g}$ is independently selected from: hydrogen; $C_{1-6}$ alkyl optionally substituted with one or more substituents independently selected from fluoro and CN; and $C_{3-10}$ carbocycle, and 3- to 10-membered heterocycle, each of which is optionally substituted with one or more substituents independently selected from fluoro and —CN. In some embodiments, each $R^{410a}$, $R^{410b}$, $R^{410z}$, $R^{410c}$, $R^{410d}$, $R^{410e}$, $R^{410f}$ and $R^{410g}$ is independently selected from: hydrogen; and $C_{1-6}$ alkyl optionally substituted with one or more substituents independently selected from fluoro and CN. In some embodiments, each $R^{410a}$, $R^{410b}$, $R^{410z}$, $R^{410c}$, $R^{410d}$, $R^{410e}$, $R^{410f}$, and $R^{410g}$ is independently selected from: hydrogen and $C_{1-6}$ alkyl. In some embodiments, each $R^{410a}$, $R^{410b}$, $R^{410z}$, $R^{410c}$, $R^{410d}$, $R^{410e}$, $R^{410f}$ and $R^{410g}$ is independently selected from: hydrogen and $C_1$ alkyl. In some embodiments, each $R^{410a}$, $R^{410b}$, $R^{410z}$, $R^{410c}$, $R^{410d}$, $R^{410e}$, $R^{410f}$, and $R^{410g}$ is independently selected from: hydrogen. In some embodiments, each $R^{410a}$ is independently selected from: hydrogen. In some embodiments, each $R^{410b}$ is independently selected from: hydrogen. In some embodiments, each $R^{410c}$ is independently selected from: hydrogen. In some embodiments, each $R^{410d}$ is independently selected from: hydrogen. In some embodiments, each $R^{410c}$ is independently selected from: hydrogen. In some embodiments, each $R^{410f}$ is independently selected from: hydrogen. In some embodiments, each $R^{410g}$ is independently selected from: hydrogen. In some embodiments, each $R^{410z}$ is independently selected from: hydrogen.

In some embodiments, for a compound or salt of Formula (Ic), when $R^{4Z}$ is hydrogen, and $R^{4C}$ is hydrogen; then: $Y^{42}$ is selected from $C(R^{14b})$, N, and $N(C_{1-6}$ alkyl); and $Y^{45}$ is selected from $C(R^{14b})$, N, and $N(C_{1-6}$ alkyl). In some embodiments, when $R^{4Z}$ is hydrogen, and $R^{4C}$ is hydrogen; then: $Y^{42}$ is selected from $C(R^{14b})$ and N; and $Y^{45}$ is selected from $C(R^{14b})$ and N. In some embodiments, when $R^{4Z}$ is hydrogen, and $R^{4C}$ is hydrogen; then: $Y^{42}$ is selected from C(H), C(F), C(CN) and N; and $Y^{45}$ is selected from C(H), C(F), C(CN), and N. In some embodiments, when $R^{4Z}$ is hydrogen, and $R^{4C}$ is hydrogen; then: $Y^{42}$ is selected from C(F), C(CN) and N; and $Y^{45}$ is selected from C(F), C(CN), and N. In some embodiments, when $R^{4Z}$ is hydrogen, and $R^{4C}$ is hydrogen; then: $Y^{42}$ is selected from N; or $Y^{45}$ is selected from N.

In some embodiments, for a compound or salt of Formula (Ic), $R^{42}$ is selected from

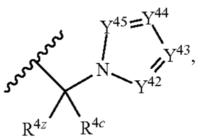

wherein $Y^{42}$ is selected from $C(R^{49bB})$, N, and $N^+(—O^-)$; $Y^{43}$ is selected from $C(R^{49bC})$, N, and $N^+(—O^-)$; $Y^{44}$ is selected from $C(R^{49bD})$, N, and $N^+(—O^-)$; and $Y^{45}$ is selected from $C(R^{49bE})$, N, and $N^+(—O^-)$. In some embodiments, when $R^{42}$ is selected from

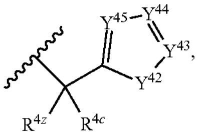

wherein $Y^{42}$ is selected from $C(R^{49bB})_2$, $—N(R^{49bB})$, $N^+(R^{49bB})(—O^-)$, and S; $Y^{43}$ is selected from $C(R^{49bC})$, N, and $N^+(—O^-)$; $Y^{44}$ is selected from $C(R^{49bD})$, N, and $N^+(—O^-)$; and $Y^{45}$ is selected from $C(R^{49bE})$, N, and $N^+(—O^-)$. In some embodiments, $R^{42}$ is selected from

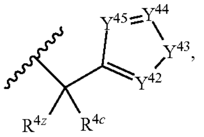

wherein $Y^{42}$ is selected from $C(R^{49bB})$, N, and $N^+(—O^-)$; $Y^{43}$ is selected from $C(R^{49bc})_2$, $—N(R^{49bc})$, $—N(R^{49bC})(—O^-)$, O, and S; $Y^{44}$ is selected from $C(R^{49bD})$, N, and $N^+(—O^-)$; and $Y^{45}$ is selected from $C(R^{49bE})$, N, and $N^+(—O^-)$. In some embodiments, $R^{42}$ is selected fron

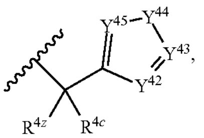

wherein $Y^{42}$ is selected from $C(R^{49bB})$, N, and $N^+(—O^-)$; $Y^{43}$ is selected from $C(R^{49bC})$, N, and $N^+(—O^-)$; $Y^{44}$ is selected from $C(R^{49bD})_2$, $—N(R^{49bD})$, $N^+(R^{49bD})(—O^-)$, O, and S; and $Y^{45}$ is selected from $C(R^{49bE})$, N, and $N^+(—O^-)$. In some embodiments, $R^{42}$ is selected from

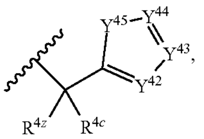

wherein $Y^{42}$ is selected from $C(R^{49bB})$, N, and $N^+(—O^-)$; $Y^{43}$ is selected from $C(R^{49bC})$, N, and $N^+(—O^-)$; $Y^{44}$ is selected from $C(R^{49bD})$, N, and $N^+(—O^-)$; and $Y^{45}$ is selected from $C(R^{49bE})_2$, $—N(R^{49bE})$, $N^+(R^{49bE})(—O^-)$, O, and S. In some embodiments, $R^{42}$ is or

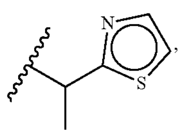,
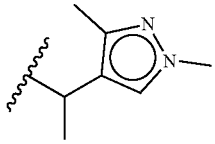,
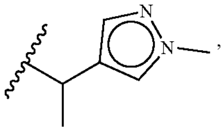,
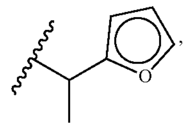, or

-continued

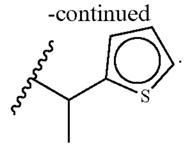

In some embodiments, $R^{42}$ is

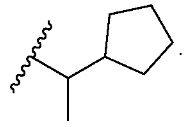 [SMILES: *C(C)C1CCCC1]

In some embodiments, $R^{42}$ is

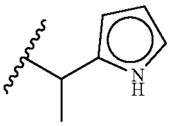

or

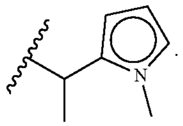

In some embodiments, the compound or salt of Formula (Ic) is selected from: 601, 602, 603, 604, and 606, or a salt thereof. In some embodiments, the compound or salt of Formula (Ic) is selected from 605, or a salt thereof. In some embodiments, the compound or salt of Formula (Ic) is not: 601, 602, 603, 604, or 606, or a salt of any thereof.

In some embodiments, for a compound or salt of Formula (Ic), two of ---- are double bonds. In some embodiments, the ring comprising $Y^{41}$, $Y^{42}Y^{43}Y^{44}$, and $Y^{45}$ is aromatic (e.g., heteroaromatic, or e.g., the ring comprising $Y^{41}$, $Y^{42}Y^{43}Y^{44}$, and $Y^{45}$ is a $C_5$ aryl, or e.g., the ring comprising $Y^{41}$, $Y^{42}$, $Y^{43}$, $Y^{44}$, and $Y^{45}$ is a 5-membered heteroaryl).

In some embodiments, the compound or salt of Formula (Ic) is not: pyrido[2,3-d]pyrimidine-2,4(1H,3H)-dione, 3-[2-(4-ethyl-6,7-dihydrothieno[3,2-c]pyridin-5(4H)-yl)-2-oxoethyl]-1-methyl-7-(trifluoromethyl)-; or pyrido[2,3-d]pyrimidine-2,4(1H,3H)-dione, 3-[2-(3,5-di-2-furanyl-4,5-dihydro-1H-pyrazol-1-yl)-2-oxoethyl]-1-methyl-7-(trifluoromethyl)-. In some embodiments, the compound or salt of Formula (Ic) is not: 1648517-71-8 or 1389444-06-7, wherein said numbers are CAS registry numbers. In some embodiments, the compound or salt of Formula (Ic) is not: N-(2-Furanylmethyl)-1,4-dihydro-S-methoxy-1-methyl-2,4-dioxopyrido[2,3-d]pyrimidine-3(2H)-acetamide; 5-Ethoxy-N-(2-furanylmethyl)-1,4-dihydro-1-methyl-2,4-dioxopyrido[2,3-d]pyrimidine-3(2H)-acetamide; 1,4-Dihydro-S-methoxy-1-methyl-2,4-dioxo-N-[(tetrahydro-2-furanyl)methyl]pyrido[2,3-d]pyrimidine-3(2H)-acetamide; N-(2-Furanylmethyl)-1,4-dihydro-5-methoxy-1,6-dimethyl-2,4-dioxopyrido[2,3-d]pyrimidine-3(2H)-acetamide; N-(2-Furanylmethyl)-1,4-dihydro-1-methyl-2,4-dioxo-S-propoxypyrido[2,3-d]pyrimidine-3(2H)-acetamide; 5-Ethoxy-1,4-dihydro-1-methyl-2,4-dioxo-N-[(tetrahydro-2-furanyl)methyl]pyrido[2,3-d]pyrimidine-3(2H)-acetamide; 1-Ethyl-1,4-dihydro-2,4-dioxo-7-phenyl-N-(2-thienylmethyl)pyrimido[4,5-d]pyrimidine-3(2H)-acetamide; 1-Ethyl-N-(2-furanylmethyl)-1,4-dihydro-2,4-dioxo-7-phenylpyrimido[4,5-d]pyrimidine-3(2H)-acetamide; 6-Ethyl-N-(2-furanylmethyl)-1,4-dihydro-S-methoxy-1-methyl-2,4-dioxopyrido[2,3-d]pyrimidine-3(2H)-acetamide; 5-Ethoxy-N-(2-furanylmethyl)-1,4-dihydro-1,6-dimethyl-2,4-dioxopyrido[2,3-d]pyrimidine-3(2H)-acetamide; 1-Ethyl-1,4-dihydro-N-[(5-methyl-2-furanyl)methyl]-2,4-dioxo-7-phenylpyrimido[4,5-d]pyrimidine-3(2H)-acetamide; N-(2-Furanylmethyl)-1,4-dihydro-1-methyl-2,4-dioxo-7-phenylpyrimido[4,5-d]pyrimidine-3(2H)-acetamide; 1,4-Dihydro-5-methoxy-1,6-dimethyl-2,4-dioxo-N-[(tetrahydro-2-furanyl)methyl]pyrido[2,3-d]pyrimidine-3(2H)-acetamide; N-(2-Furanylmethyl)-1,4-dihydro-5-methoxy-1-methyl-2,4-dioxo-6-propylpyrido[2,3-d]pyrimidine-3(2H)-acetamide; 1,4-Dihydro-1-methyl-2,4-dioxo-5-propoxy-N-[(tetrahydro-2-furanyl)methyl]pyrido[2,3-d]pyrimidine-3(2H)-acetamide; 5-Ethoxy-6-ethyl-N-(2-furanylmethyl)-1,4-dihydro-1-methyl-2,4-dioxopyrido[2,3-d]pyrimidine-3(2H)-acetamide; 1,4-Dihydro-1-methyl-7-(4-methylphenyl)-2,4-dioxo-N-(2-thienylmethyl)pyrimido[4,5-d]pyrimidine-3(2H)-acetamide; N-(2-Furanylmethyl)-1,4-dihydro-1,6-dimethyl-2,4-dioxo-5-propoxypyrido[2,3-d]pyrimidine-3(2H)-acetamide; 5-Ethoxy-N-(2-furanylmethyl)-1,4-dihydro-1-methyl-2,4-dioxo-6-propylpyrido[2,3-d]pyrimidine-3(2H)-acetamide; 1-Ethyl-1,4-dihydro-2,4-dioxo-7-phenyl-N-[(tetrahydro-2-furanyl)methyl]pyrimido[4,5-d]pyrimidine-3(2H)-acetamide; 6-Ethyl-1,4-dihydro-5-methoxy-1-methyl-2,4-dioxo-N-[(tetrahydro-2-furanyl)methyl]pyrido[2,3-d]pyrimidine-3(2H)-acetamide; 5-Ethoxy-1,4-dihydro-1,6-dimethyl-2,4-dioxo-N-[(tetrahydro-2-furanyl)methyl]pyrido[2,3-d]pyrimidine-3(2H)-acetamide; N-(2-Furanylmethyl)-1,4-dihydro-1-methyl-7-(4-methylphenyl)-2,4-dioxopyrimido[4,5-d]pyrimidine-3(2H)-acetamide; 6-Ethyl-N-(2-furanylmethyl)-1,4-dihydro-1-methyl-2,4-dioxo-5-propoxypyrido[2,3-d]pyrimidine-3(2H)-acetamide; 1,4-Dihydro-5-methoxy-1-methyl-2,4-dioxo-6-propyl-N-[(tetrahydro-2-furanyl)methyl]pyrido[2,3-d]pyrimidine-3(2H)-acetamide; 1,4-Dihydro-1-methyl-2,4-dioxo-N-(2-thienylmethyl)-7-(trifluoromethyl)pyrido[2,3-d]pyrimidine-3(2H)-acetamide; 1,4-Dihydro-1-methyl-N-[(5-methyl-2-furanyl)methyl]-7-(4-methylphenyl)-2,4-dioxopyrimido[4,5-d]pyrimidine-3(2H)-acetamide; N-(2-Furanylmethyl)-1,4-dihydro-1-methyl-2,4-dioxo-5-propoxy-6-propylpyrido[2,3-d]pyrimidine-3(2H)-acetamide; 5-Ethoxy-6-ethyl-1,4-dihydro-1-methyl-2,4-dioxo-N-[(tetrahydro-2-furanyl)methyl]pyrido[2,3-d]pyrimidine-3(2H)-acetamide; N-(2-Furanylmethyl)-1,4-dihydro-1-methyl-2,4-dioxo-7-(trifluoromethyl)pyrido[2,3-d]pyrimidine-3(2H)-acetamide; 5-Ethoxy-1,4-dihydro-1-methyl-2,4-dioxo-6-propyl-N-[(tetrahydro-2-furanyl)methyl]pyrido[2,3-d]pyrimidine-3(2H)-acetamide; 1,4-Dihydro-1,6-dimethyl-2,4-dioxo-5-propoxy-N-[(tetrahydro-2-furanyl)methyl]pyrido[2,3-d]pyrimidine-3(2H)-acetamide; N-(2-Furanylmethyl)-1,4-dihydro-7-(4-methoxyphenyl)-1-methyl-2,4-dioxopyrimido[4,5-d]pyrimidine-3(2H)-acetamide; 7-(4-Chlorophenyl)-1-ethyl-1,4-dihydro-2,4-dioxo-N-(2-thienylmethyl)pyrimido[4,5-d]pyrimidine-3(2H)-acetamide; 1,4-Dihydro-1-methyl-7-(4-methylphenyl)-2,4-dioxo-N-[(tetrahydro-2-furanyl)methyl]pyrimido[4,5-d]pyrimidine-3(2H)-acetamide; 7-(4-Chlorophenyl)-1-ethyl-N-(2-furanylmethyl)-1,4-dihydro-2,4-dioxopyrimido[4,5-d]pyrimidine-3(2H)-acetamide; 6-Ethyl-1,4-dihydro-1-methyl-2,4-dioxo-5-propoxy-N-[(tetrahydro-2-furanyl)methyl]pyrido[2,3-d]pyrimidine-3(2H)-acetamide; 1,4-Dihydro-1-methyl-2,4-dioxo-5-propoxy-6-propyl-N-[(tetrahydro-2-furanyl)methyl]pyrido[2,3-d]pyrimidine-3(2H)-acetamide; 7-(4-Chlorophenyl)-1-ethyl-1,4-dihydro-N-[(5-methyl-2-furanyl)methyl]-2,4-dioxopyrimido[4,5-d]pyrimidine-3(2H)-acetamide; 1,4-Dihydro-1-methyl-2,4-dioxo-N-[(tetrahydro-2-furanyl)methyl]-7-(trifluoromethyl)pyrido[2,3-d]pyrimidine-3(2H)-acetamide; 7-(4-Chlorophenyl)-N-(2-furanylmethyl)-1,4- dihydro-1-methyl-2,4-dioxopyrimido[4,5-d]pyrimidine-3(2H)-acetamide; 1,4-Dihydro-7-(4-methoxyphenyl)-1-methyl-2,4-dioxo-N-[(tetrahydro-2-furanyl)methyl]pyrimido[4,5-d]pyrimidine-3(2H)-acetamide; 5-(4-Acetyl-1-piperazinyl)-N-(2-furanylmethyl)-1,4-dihydro-1-methyl-2,4-dioxopyrido[2,3-d]pyrimidine-3(2H)-acetamide; 7-(4-Chlorophenyl)-1-ethyl-1,4-dihydro-2,4-dioxo-N-[(tetrahydro-2-furanyl)methyl]pyrimido[4,5-d]pyrimidine-3(2H)-acetamide; 7-(4-Chlorophenyl)-1,4-dihydro-1-methyl-2,4-dioxo-N-[(tetrahydro-2-furanyl)methyl]pyrimido[4,5-d]pyrimidine-3(2H)-acetamide; 5-(4-Acetyl-1-piperazinyl)-1,4-dihydro-1-methyl-2,4-dioxo-N-[(tetrahydro-2-furanyl)methyl]pyrido[2,3-d]pyrimidine-3(2H)-acetamide; 5-[4-(Cyclopropylcarbonyl)-1-piperazinyl]-N-(2-furanylmethyl)-1,4-dihydro-1-methyl-2,4-dioxopyrido[2,3-d]pyrimidine-3(2H)-acetamide; 5-(4-Acetyl-1-piperazinyl)-1,4-dihydro-1,6-dimethyl-2,4-dioxo-N-[(tetrahydro-2-furanyl)methyl]pyrido[2,3-d]pyrimidine-3(2H)-acetamide; 5-[4-(Cyclopropylcarbonyl)-1-piperazinyl]-1,4-dihydro-1-methyl-2,4-dioxo-N-[(tetrahydro-2-furanyl)methyl]pyrido[2,3-d]pyrimidine-3(2H)-acetamide; 1,4-Dihydro-5,7-dimethyl-N-[(1-methyl-1H-benzimidazol-2-yl)methyl]-2,4-dioxo-1-phenylpyrido[2,3-d]pyrimidine-3(2H)-acetamide; Pyrido[2,3-d]pyrimidine-3(2H)-acetamide, N-[(2,3-dihydro-1-methyl-TH-benzimidazol-2-yl)methyl]-1,4-dihydro-5,7-dimethyl-2,4-dioxo-1-phenyl-; Methyl 1,2,3,4-tetrahydro-7-methyl-2,4-dioxo-3-[2-oxo-2-[[(tetrahydro-2-furanyl)methyl]amino]ethyl]-1-phenylpyrido[2,3-d]pyrimidine-5-carboxylate; 7-(Cyclohexylamino)-1-cyclopentyl-N-[(2,2-dimethyl-1,3-dioxolan-4-yl)methyl]-6-fluoro-1,4-dihydro-2,4-dioxo-3(2H)-quinazolineacetamide; N-(2-Furanylmethyl)-1,4-dihydro-N,1-dimethyl-2,4-dioxo-7-(trifluoromethyl)pyrido[2,3-d]pyrimidine-3(2H)-acetamide; N-[(5-Chloro-2-thienyl)methyl]-1,4-dihydro-N,1-dimethyl-2,4-dioxo-7-(trifluoromethyl)pyrido[2,3-d]pyrimidine-3(2H)-acetamide; N-Cyclopropyl-1,4-dihydro-1-methyl-2,4-dioxo-N-(3-thienylmethyl)-7-(trifluoromethyl)pyrido[2,3-d]pyrimidine-3(2H)-acetamide; 3-[2-(4-Ethyl-6,7-dihydrothieno[3,2-c]pyridin-5(4H)-yl)-2-oxoethyl]-1-methyl-7-(trifluoromethyl)pyrido[2,3-d]pyrimidine-2,4(1H,3H)-dione; or 3-[2-(3,5-Di-2-furanyl-4,5-dihydro-1H-pyrazol-1-yl)-2-oxoethyl]-1-methyl-7-(trifluoromethyl)pyrido[2,3-d]pyrimidine-2,4(1H,3H)-dione. In some embodiments, the compound or salt of Formula (Ic) is not 941898-04-0, 941898-40-4, 941942-43-4, 941984-06-1, 921480-82-2, 941942-73-0, 1358181-82-4, 1358520-91-8, 941942-27-4, 941898-25-5, 1358425-43-0, 1358258-15-7, 921497-26-9, 921468-22-6, 921464-87-1, 1005303-73-0, 1358941-66-8, 921482-53-3, 921460-70-0, 1359488-57-5, 941984-16-3, 941942-57-0, 1359086-75-1, 921478-94-6, 921489-61-4, 2184224-66-4, 1358508-69-6, 921463-87-8, 1005298-34-9, 1385692-05-6, 921501-30-6, 921462-08-0, 1359516-43-0, 1358941-19-1, 1357755-19-1, 1359427-79-4, 921462-99-9, 921479-85-8, 1358673-34-3, 1385692-36-3, 1358449-20-3, 1359427-71-6, 946209-26-3, 1358520-63-4, 1359340-78-5, 1021123-59-0, 1021062-10-1, 1021206-43-8, 1021095-20-4, 1243091-44-2, 3016363-95-1, 933917-41-0, 1075695-69-0, 2180702-48-9, 1089608-56-9, 1318925-81-3, 1648517-71-8, or 1389444-06-7, wherein said numbers are CAS registry numbers.

In one aspect, the present disclosure provides a compound represented by Formula (Id):

(Id)

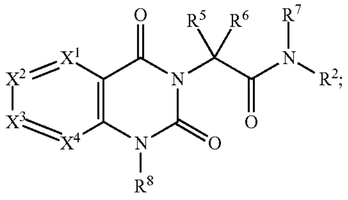

or a salt thereof, wherein: $R^2$ is selected from:

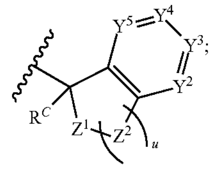

u is an integer selected from 0, 1, 2, and 3; $Z^1$ is selected from: —$C(R^Z)_2$—, —$N(R^Z)$—, —$N^+(—O^-)$, —O—, and —S—; each $Z^2$ is independently selected from: —$C(R^Z)(R^{Z'})$—, —$N(R^Z)$—, —$N^+$(—O—), —O—, and —S—; $X^1$ is selected from $C(R^{1a})$, N, and $N^+(—O^-)$; $X^2$ is selected from $C(R^{1b})$, N, and $N^+(—O^-)$; $X^3$ is selected from $C(R^{1c})$, N, and $N^+(—O^-)$; $X^4$ is selected from $C(R^{1d})$, N, and $N^+(—O^-)$; wherein no more than two of $X^1$, $X^2$, $X^3$, and $X^4$ are N or —$N^+(—O^-)$; $Y^2$ is selected from $C(R^{9bB})$, N, and $N^+(—O^-)$; $Y^3$ is selected from $C(R^{9bC})$, N, and $N^+(—O^-)$; $Y^4$ is selected from $C(R^{9bD})$, N, and $N^+(—O^-)$; $Y^5$ is selected from $C(R^{9bE})$, N, and $N^+(—O^-)$; wherein no more than three of $Y^2$, $Y^3$, $Y^4$, and $Y^5$ are N or —$N^+(—O^-)$; $R^{1a}$, $R^{1b}$, $R^{1c}$, and $R^{1d}$, are each independently selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$; each $R^Z$ is independently selected from: hydrogen; —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —OR$^{10z}$, —SR$^{10z}$, —N(R$^{10z}$)$_2$, —C(O)R$^{10z}$, —C(O)N(R$^{10z}$)$_2$, —N(R$^{10z}$)C(O)R$^{10z}$, —C(O)OR$^{10z}$, —OC(O)R$^{10z}$, —N(R$^{10z}$)C(O)N(R$^{10z}$)$_2$, —OC(O)N(R$^{10z}$)$_2$, —N(R$^{10z}$)C(O)OR$^{10z}$, —S(O)R$^{10z}$, —S(O)$_2$R$^{10z}$, —NO$_2$, ═O, ═S, ═N(R$^{10z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from R$^{9z}$; and $C_{3-10}$ carbocycle and 3- to 10-membered heterocycle, each of which is optionally substituted with one or more substituents independently selected from halogen, —OR$^{10z}$, —SR$^{10z}$, —N(R$^{10z}$)$_2$, —C(O)R$^{10z}$, —C(O)N(R$^{10z}$)$_2$, —N(R$^{10z}$)C(O)R$^{10z}$, —N(R$^{10z}$)C(O)N(R$^{10z}$)$_2$, —OC(O)N(R$^{10z}$)$_2$, —N(R$^{10z}$)C(O)OR$^{10z}$, —C(O)OR$^{10z}$, —OC(O)R$^{10z}$, —S(O)R$^{10z}$, —S(O)$_2$R$^{10z}$, —NO$_2$, ═O, ═S, ═N(R$^{10z}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from R$^{9z}$; each R$^{Z'}$is independently selected from: hydrogen; —CN, —C(O)R$^{10z}$, —C(O)N(R$^{10z}$)$_2$, and —C(O)OR$^{10z}$; $C_1$ alkyl substituted with substituted with one or more substituents independently selected from halogen, —OR$^{10z}$, —SR$^{10z}$, —N(R$^{10z}$)$_2$, —C(O)R$^{10z}$, —C(O)N(R$^{10z}$)$_2$, —N(R$^{10z}$)C(O)R$^{10z}$, —C(O)OR$^{10z}$, —OC(O)R$^{10z}$, —N(R$^{10z}$)C(O)N(R$^{10z}$)$_2$, —OC(O)N(R$^{10z}$)$_2$, —N(R$^{10z}$)C(O)OR$^{10z}$, —S(O)R$^{10z}$, —S(O)$_2$R$^{10z}$, —NO$_2$, ═O, ═S, ═N(R$^{10z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more R$^{9z}$; $C_{2-6}$ alkyl, $C_{2-6}$ alkenyl, and $C_{2-6}$ alkynyl, each of which is optionally substituted with one or more substituents independently selected from halogen, —OR$^{10z}$, —SR$^{10z}$, —N(R$^{10z}$)$_2$, —C(O)R$^{10z}$, —C(O)N(R$^{10z}$)$_2$, —N(R$^{10z}$)C(O)R$^{10z}$, —C(O)OR$^{10z}$, —OC(O)R$^{10z}$, —N(R$^{10z}$)C(O)N(R$^{10z}$)$_2$, —OC(O)N(R$^{10z}$)$_2$, —N(R$^{10z}$)C(O)OR$^{10z}$, —S(O)R$^{10z}$, —S(O)$_2$R$^{10z}$, —NO$_2$, ═O, ═S, ═N(R$^{10z}$), —N$_3$, —CN, $C_{3-10}$ carbocycle and 3-to 10-membered heterocycle, wherein the $C_{3-10}$ carbocycle and 3- to 10-membered heterocycle are each optionally substituted with one or more substituents independently selected from R$^{9z}$; and $C_{3-10}$ carbocycle and 3- to 10-membered heterocycle, each of which is optionally substituted with one or more substituents independently selected from halogen, —OR$^{10z}$, —SR$^{10z}$, —N(R$^{10z}$)$_2$, —C(O)R$^{10z}$, —C(O)N(R$^{10z}$)$_2$, —N(R$^{10z}$)C(O)R$^{10z}$, —N(R$^{10z}$)C(O)N(R$^{10z}$)$_2$, —OC(O)N(R$^{10z}$)$_2$, —N(R$^{10z}$)C(O)OR$^{10z}$, —C(O)OR$^{10z}$, —OC(O)R$^{10z}$, —S(O)R$^{10z}$, —S(O)$_2$R$^{10z}$, —NO$_2$, ═O, ═S, ═N(R$^{10z}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from R$^{9z}$; R$^{C}$ is selected from: hydrogen; —CN, —C(O)R$^{10c}$, —C(O)N(R$^{10c}$)$_2$, —C(O)OR$^{10c}$; $C_{1-6}$ alkyl, $C_{2-6}$ alkenyl, and $C_{2-6}$ alkynyl, each of which is optionally substituted with one or more substituents independently selected from halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —C(O)OR$^{10c}$, —OC(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —S(O)R$^{10c}$, —S(O)$_2$R$^{10c}$, —NO$_2$, ═O, ═S, ═N(R$^{10c}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from R$^{90}$; and $C_{3-10}$ carbocycle and 3- to 10-membered heterocycle, each of which is optionally substituted with one or more substituents independently selected from halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, ═O, ═S, ═N(R$^{10c}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from R$^{9c}$; R$^5$ is selected from: hydrogen; halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —C(O)OR$^{10d}$, —OC(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —S(O)R$^{10d}$, —S(O)$_2$R$^{10d}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —OR$^{10a}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —C(O)OR$^{10d}$, —OC(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —S(O)R$^{10d}$, —S(O)$_2$R$^{10d}$, —NO$_2$, ═O, ═S, ═N(R$^{10d}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from R$^{9d}$; and $C_{3-10}$ carbocycle and 3- to 10-membered heterocycle, each of which is optionally substituted with one or more substituents independently selected from halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10a}$, —N(R$^{10d}$)C(O)N(R$^{10d}$)$_2$, —OC(O)N(R$^{10d}$)$_2$, —N(R$^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, ═O, ═S, ═N(R$^{10d}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from R$^{9d}$; or R$^5$ together with R$^6$ form a 3- to 10-membered heterocycle or $C_{3-10}$ carbocycle, wherein the 3- to 10-membered heterocycle or $C_{3-10}$ carbocycle is optionally substituted with one or more substituents independently selected from R$^{9d}$; R$^6$ is selected from: hydrogen; halogen, —OR$^{10e}$, —SR$^{10e}$, —N(R$^{10e}$)$_2$, —C(O)R$^{10e}$, —C(O)N(R$^{10e}$)$_2$, —N(R$^{10e}$)C(O)R$^{10e}$, —C(O)OR$^{10e}$, —OC(O)R$^{10e}$, —N(R$^{10e}$)C(O)N(R$^{10e}$)$_2$, —OC(O)N(R$^{10e}$)$_2$, —N(R$^{10e}$)C(O)OR$^{10e}$, —S(O)R$^{10e}$, —S(O)$_2$R$^{10e}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —OR$^{10e}$, —SR$^{10e}$, —N(R$^{10e}$)$_2$, —C(O)R$^{10e}$, —C(O)N(R$^{10e}$)$_2$, —N(R$^{10e}$)C(O)R$^{10e}$, —C(O)OR$^{10e}$, —OC(O)R$^{10e}$, —N(R$^{10e}$)C(O)N(R$^{10e}$)$_2$, —OC(O)N(R$^{10e}$)$_2$, —N(R$^{10e}$)C(O)OR$^{10e}$, —S(O)R$^{10e}$, —S(O)$_2$R$^{10e}$, —NO$_2$, ═O, ═S, ═N(R$^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from R$^{9e}$; and $C_{3-10}$ carbocycle and 3- to 10-membered heterocycle, each of which is optionally substituted with one or more substituents independently selected from halogen, —OR$^{10e}$, —SR$^{10e}$, —N(R$^{10e}$)$_2$, —C(O)R$^{10e}$, —C(O)N(R$^{10e}$)$_2$, —N(R$^{10e}$)C(O)R$^{10e}$, —N(R$^{10e}$)C(O)N(R$^{10e}$)$_2$, —OC(O)N(R$^{10e}$)$_2$, —N(R$^{10e}$)C(O)OR$^{10e}$, —C(O)OR$^{10e}$, —OC(O)R$^{10e}$, —S(O)R$^{10e}$, —S(O)$_2$R$^{10e}$, —NO$_2$, ═O, ═S, ═N(R$^{10e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from R$^{9e}$; or R$^6$ together with R$^5$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9e}$; $R^7$ is selected from: hydrogen; —C(O)$R^{10f}$, —C(O)N($R^{10f}$)$_2$, —C(O)O$R^{10f}$, —S(O)$R^{10f}$, and —S(O)$_2R^{10f}$; $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, —N($R^{10f}$)C(O)N($R^{10f}$)$_2$, —OC(O)N($R^{10f}$)$_2$, —N($R^{10f}$)C(O)O$R^{10f}$, —S(O)$R^{10f}$, —S(O)$_2R^{10f}$, —$NO_2$, =O, =S, =N($R^{10f}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —N($R^{10f}$)C(O)N($R^{10f}$)$_2$, —OC(O)N($R^{10f}$)$_2$, —N($R^{10f}$)C(O)O$R^{10f}$, —C(O)O$R^{10f}$, —OC(O)$R^{10f}$, —S(O)$R^{10f}$, —S(O)$_2R^{10f}$, —$NO_2$, =O, =S, =N($R^{10f}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9f}$; $R^8$ is selected from: hydrogen; —C(O)$R^{10g}$, —C(O)N($R^{10g}$)$_2$, —C(O)O$R^{10g}$, —S(O)$R^{10g}$, and —S(O)$_2R^{10g}$; $C_{1-6}$ alkyl optionally substituted with one or more substituents independently selected from halogen, —O$R^{10g}$, —S$R^{10g}$, —N($R^{10g}$)$_2$, —C(O)$R^{10g}$, —N($R^{10g}$)C(O)$R^{10g}$, —C(O)O$R^{10g}$, —OC(O)$R^{10g}$, —N($R^{10g}$)C(O)N($R^{10g}$)$_2$, —OC(O)N($R^{10g}$)$_2$, —N($R^{10g}$)C(O)O$R^{10g}$, —S(O)$R^{10g}$, —S(O)$_2R^{10g}$, —$NO_2$, =O, =S, =N($R^{10g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9g}$; and $C_{3-10}$ carbocycle and 3- to 10-membered heterocycle, each of which is optionally substituted with one or more substituents independently selected from halogen, —O$R^{10g}$, —S$R^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —$NO_2$, =O, =S, =N($R^{10g}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9g}$; each $R^{9a}$ is independently selected from: halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), —$N_3$, and —CN; $R^{9bB}$, $R^{9bC}$, $R^{9bD}$, and $R^{9bE}$ are each independently selected from: hydrogen; halogen, —$NO_2$, —$N_3$, —CN, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —$N_3$, —CN, $C_{1-6}$ alkyl, $C_{2-6}$ alkenyl, and $C_{2-6}$ alkynyl; each $R^{9z}$ is independently selected from: halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2R^{10z}$, —$NO_2$, =O, =S, =N($R^{10z}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2R^{10z}$, —$NO_2$, =O, =S, =N($R^{10z}$), —$N_3$, and —CN; each $R^{90}$ is independently selected from: halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10e}$, —S$R^{10e}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10e}$, —S(O)$R^{10e}$, —S(O)$_2R^{10e}$, —$NO_2$, =O, =S, =N($R^{10c}$), —$N_3$, and —CN; each $R^{9d}$ is independently selected from: halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R_{10d}$, —$NO_2$, =O, =S, =N($R^{10d}$), —$N_3$, and —CN; each $R^{9e}$ is independently selected from: halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10c}$, —$NO_2$, =O, =S, =N($R^{10e}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —$NO_2$, =O, =S, =N($R^{10e}$), —$N_3$, and —CN; each $R^{9f}$ is independently selected from: halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —N($R^{10f}$)C(O)N($R^{10f}$)$_2$, —OC(O)N($R^{10f}$)$_2$, —N($R^{10f}$)C(O)O$R^{10f}$, —C(O)O$R^{10f}$, —OC(O)$R^{10f}$, —S(O)$R^{10f}$, —S(O)$_2R^{10f}$, —$NO_2$, ═O, ═S, ═N($R^{10f}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —N($R^{10f}$)C(O)N($R^{10f}$)$_2$, —OC(O)N($R^{10f}$)$_2$, —N($R^{10f}$)C(O)O$R^{10f}$, —C(O)O$R^{10f}$, —OC(O)$R^{10f}$, —S(O)$R^{10f}$, —S(O)$_2R^{10f}$, —$NO_2$, ═O, ═S, ═N($R^{10f}$), —$N_3$, and —CN; each $R^{9g}$ is independently selected from: halogen, —O$R^{10g}$, —S$R^{10g}$, —N($R^{10c}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —$NO_2$, ═O, ═S, ═N($R^{10g}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10g}$, —S$R^{10g}$, —N($R^{10c}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —$NO_2$, ═O, ═S, ═N($R^{10g}$), —$N_3$, and —CN; and each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein when $X^1$ is C(H), $X^2$ is C(H), $X^3$ is C(H), and $X^4$ is C(H); then $R^{9bC}$ is selected from: halogen, —$NO_2$, —$N_3$, —CN, —OH, —O($C_{2-6}$ alkyl), —O($C_{1-6}$ haloalkyl), —S$R^{10b}$, —NH($C_{1-6}$ alkyl), —N($C_{1-6}$ alkyl)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, ═O, ═S, ═N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, ═O, ═S, ═N($R^{10b}$), —$N_3$, —CN, $C_{1-6}$ alkyl, $C_{2-6}$ alkenyl, and $C_{2-6}$ alkynyl; wherein when $R^7$ is —$CH_3$, and $R^8$ is —$CH_3$, and $X^4$ is N or —$N^+$(—$O^-$), then $R^{1c}$ is selected from hydrogen; halogen, —$NO_2$, —$N_3$, —CN, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2R^{10a}$; $C_{1-6}$ alkyl, $C_{2-6}$ alkenyl, and $C_{2-6}$ alkynyl, each of which is optionally substituted with one or more substituents independently selected from chloro, bromo, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —N($R^{10a}$)C(O)N($R^{10a}$)$_2$, —OC(O)N($R^{10a}$)$_2$, —N($R^{10a}$)C(O)O$R^{10a}$, —S(O)$R^{10a}$, —S(O)$_2R^{10a}$, —$NO_2$, ═O, ═S, ═N($R^{10a}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; $C_1$ alkyl substituted with one —F or two —F; $C_{2-6}$ alkyl substituted with one or more —F; and $C_{3-10}$ carbocycle and 3- to 10-membered heterocycle, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, ═O, ═S, ═N($R^{10a}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$; wherein when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro, chloro, iodo, —$NO_2$, —$N_3$, —CN, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, ═O, ═S, ═N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, ═O, ═S, ═N($R^{10b}$), —$N_3$, —CN, $C_{1-6}$ alkyl, $C_{2-6}$ alkenyl, and $C_{2-6}$ alkynyl; and wherein when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9b}$B is selected from hydrogen; chloro, bromo, iodo, —$NO_2$, —$N_3$, —CN, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, ═O, ═S, ═N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —$N_3$, —CN, $C_{1-6}$ alkyl, $C_{2-6}$ alkenyl, and $C_{2-6}$ alkynyl.

In one aspect, the present disclosure provides a compound of Formula (Id) that is represented by Formula (Id-ep):

(Id-ep)

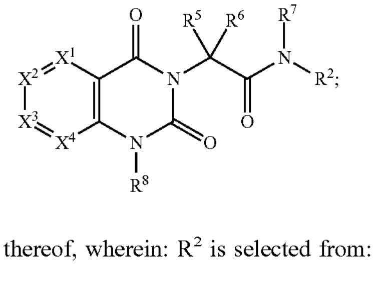

or a salt thereof, wherein: $R^2$ is selected from:

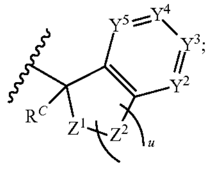

u is an integer selected from 0, 1, and 2; $Z^1$ is selected from: —$C(R^Z)_2$—, —, —$N(R^Z)$—, and —O—; each $Z^2$ is independently selected from: —$C(R^Z)(R^{Z'})$—, —$N(R^Z)$—, and —O—; $X^1$ is selected from $C(R^{1a})$ and N; $X^2$ is selected from $C(R^{1b})$ and N; $X^3$ is selected from $C(R^{10})$ and N; $X^4$ is selected from $C(R^{1d})$ and N; wherein no more than two of $X^1$, $X^2$, $X^3$, and $X^4$ are N; $Y^2$ is selected from $C(R^{9bB})$, and N; $Y^3$ is selected from $C(R^{9bC})$, and N; $Y^4$ is selected from $C(R^{9bD})$ and N; $Y^5$ is selected from $C(R^{9bE})$ and N; Wherein no more than three of $Y^2$, $Y^3$, $Y^4$, and $Y^5$ are N; $R^{1a}$, $R^{1b}$, $R^{1c}$, and $R^{1d}$, are each independently selected from: hydrogen; halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{1-6}$ haloalkyl, and $C_{1-6}$ alkyl; each $R^Z$ is independently selected from: hydrogen; and $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle; —CN, —$C(O)R^{10z}$, —$C(O)N(R^{10z})_2$, and —$C(O)OR^{10z}$; each $R^{Z'}$is independently selected from: hydrogen; $R^C$ is selected from: hydrogen; $R^5$ and $R^6$ are each independently selected from: hydrogen; halogen; and $C_{1-6}$ alkyl, halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, $C_{3-10}$ carbocycle and 3- to 10-membered heterocycle, wherein the $C_{3-10}$ carbocycle and 3- to 10-membered heterocycle are each optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; or $R^5$ together with $R^6$ form a $C_{3-10}$ carbocycle or 3- to 10-membered heterocycle, each of which is optionally substituted with one or more substituents independently selected from: halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$, and $C_{1-6}$ alkyl; $R^7$ is selected from: hydrogen; $R^8$ is selected from: hydrogen; and $R^{9bB}$, $R^{9bC}$, $R^{9bD}$, and $R^{9bE}$ are each independently selected from: hydrogen; halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; $C_{1-6}$ alkyl, optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; and $C_{3-10}$ carbocycle and 3- to 10-membered heterocycle, each of which is optionally substituted with one or more substituents independently selected from halogen, —$NO_2$, —CN, —OH, —$O(C_{1-6}$ alkyl), —$O(C_{1-6}$ haloalkyl), —SH, —$S(C_{1-6}$ alkyl), —$NH_2$, —$NH(C_{1-6}$ alkyl), and —$N(C_{1-6}$ alkyl$)_2$; wherein no more than 3 of $X^1$, $X^2$, $X^3$, and $X^4$ are C(H). In some embodiments, for a compound or salt of Formula (Id-ep), four of $X^1$, $X^2$, $X^3$, and $X^4$ are C(H), and (i) when $X^1$ is C(H), $X^2$ is C(H), $X^3$ is C(H), and $X^4$ is C(H); then $R^{9bC}$ is selected from: hydrogen, -fluuro, -chloro, bromo, —CN, —$CH_3$, and —$CF_3$; and (ii) when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro, —OH, —CN, —$CH_3$, and —$CF_3$; and (iii) when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from: hydrogen, -chloro, bromo, —CN, —OH, —$CH_3$, and —$CF_3$.

In some embodiments, for a compound or salt of Formula (Id), no more than three of $X^1$, $X^2$, $X^3$, and $X^4$ are N. In some embodiments, no more than two of $X^1$, $X^2$, $X^3$, and $X^4$ are N. In some embodiments, no more than one of $X^1$, $X^2$, $X^3$, and $X^4$ is N. In some embodiments, no more than three of $X^1$, $X^2$, $X^3$, and $X^4$ are N or —$N^+$(—$O^-$). In some embodiments, no more than two of $X^1$, $X^2$, $X^3$, and $X^4$ are N or —$N^+$(—$O^-$). In some embodiments, no more than one of $X^1$, $X^2$, $X^3$, and $X^4$ is N or —$N^+$(—$O^-$). In some embodiments, no more than three of $X^1$, $X^2$, $X^3$, and $X^4$ are C(H). In some embodiments, no more than two of $X^1$, $X^2$, $X^3$, and $X^4$ are C(H). In some embodiments, no more than one of $X^1$, $X^2$, $X^3$, and $X^4$ is C(H). In some embodiments, no more than three of $Y^2$, $Y^3$, $Y^4$, and $Y^5$ are N. In some embodiments, no more than two of $Y^2$, $Y^3$, $Y^4$, and $Y^5$ are N. In some embodiments, no more than one of $Y^2$, $Y^3$, $Y^4$, and $Y^5$ is N. In some embodiments, no more than three of $Y^2$, $Y^3$, $Y^4$, and $Y^5$ are N or —$N^+$(—$O^-$). In some embodiments, no more than two of $Y^2$, $Y^3$, $Y^4$, and $Y^5$ are N or —$N^+$(—$O^-$). In some embodiments, no more than one of $Y^2$, $Y^3$, $Y^4$, and $Y^5$ is N or —$N^+$(—$O^-$). In some embodiments, none of $Y^2$, $Y^3$, $Y^4$, and $Y^5$ need be N or $N^+$(—$O^-$). Alternatively, in some embodiments, at least one of $Y^2$, $Y^3$, $Y^4$, and $Y^5$ is N. In some embodiments, at least two of $Y^2$, $Y^3$, $Y^4$, and $Y^5$ are N. In some embodiments, at least one of $Y^2$, $Y^3$, $Y^4$, and $Y^5$ is N or —$N^+$(—$O^-$). In some embodiments, at least two of $Y^2$, $Y^3$, $Y^4$, and $Y^5$ are N or —$N^+$(—$O^-$). In some embodiments, none of $X^1$, $X^2$, $X^3$, and $X^4$, need be N or $N^+(—O^-)$. Alternatively, in some embodiments, at least one of $X^1$, $X^2$, $X^3$, and $X^4$ is N. In some embodiments, at least two of $X^1$, $X^2$, $X^3$, and $X^4$ are N. In some embodiments, at least one of $X^1$, $X^2$, $X^3$, and $X^4$ is N or $—N^+(—O—)$. In some embodiments, at least two of $X^1$, $X^2$, $X^3$, and $X^4$ are N or $—N^+(—O^-)$. In some embodiments, $X^1$ is selected from $C(R^{1a})$ and N. In some embodiments, $X^1$ is selected from $C(R^{1a})$. In some embodiments, $X^1$ is selected from C(H), C(F), and $C(CH_3)$. In some embodiments, $X^1$ is selected from C(H) and C(F). In some embodiments, $X^1$ is selected from C(H). In some embodiments, $X^1$ is selected from C(F). In some embodiments, $X^2$ is selected from $C(R^{1b})$ and N. In some embodiments, $X^2$ is selected from N, C(H), C(F), and C(CN).

In some embodiments, $X^2$ is selected from C(H) and C(F). In some embodiments, $X^2$ is selected from C(H). In some embodiments, $X^2$ is selected from C(F). In some embodiments, $X^3$ is selected from $C(R^{1c})$ and N. In some embodiments, $X^3$ is selected from $C(R^{1c})$. In some embodiments, $X^3$ is selected from C(H). In some embodiments, $X^3$ is selected from C(F). In some embodiments, $X^4$ is selected from $C(R^{1d})$ and N. In some embodiments, $X^4$ is selected from $C(R^{1d})$. In some embodiments, $X^4$ is selected from C(H). In some embodiments, $X^4$ is selected from $C(CH_3)$. In some embodiments, $X^3$ and $X^4$ are C(H). In some embodiments, $X^3$ is C(F), and $X^4$ is $C(CH_3)$. In some embodiments, $X^1$ is C(H), and $X^2$ is C(F); or $X^1$ is C(F), and $X^2$ is C(F); or $X^1$ is C(H), and $X^2$ is C(H); or $X^1$ is C(H), and $X^2$ is C(CN); or $X^1$ is $C(CH_3)$, and $X^2$ is N. In some embodiments, $R^{1a}$, $R^{11}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—S(O)R^{10a}$, $—S(O)_2R^{10a}$, $—NO_2$, =O, $—N_3$, —CN, and $C_{1-6}$ alkyl. In some embodiments, $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle. In some embodiments, $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; and $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$ In some embodiments, $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; and $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle. In some embodiments, $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; and $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—NO_2$, =O, $—N_3$, —CN, $C_{3-10}$ carbocycle and 3- to 10-membered heterocycle. In some embodiments, $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2$$R^{10a}$; and $C_{1-6}$ alkyl optionally substituted with one or more substituents independently selected from halogen, —O$R^{10a}$, —S$R^{10a}$, —N($R^{10a}$)$_2$, —NO$_2$, =O, —N$_3$, —CN, $C_{3-10}$ carbocycle and 3- to 10-membered heterocycle. In some embodiments, $R^{1a}$, $R^{1b}$, $R^{1c}$, and $R^{1d}$, are each independently selected from: hydrogen; halogen, —NO$_2$, —N$_3$, —CN, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2$$R^{10a}$; and $C_{1-6}$ alkyl optionally substituted with one or more substituents independently selected from halogen, —O$R^{10a}$, —S$R^{10a}$, —N($R^{10a}$)$_2$, —NO$_2$, =O, —N$_3$, and —CN. In some embodiments, $R^{1a}$, $R^{11}$, $R^{1c}$, and $R^{1d}$, are each independently selected from: hydrogen; halogen, —NO$_2$, —N$_3$, —CN, —O$R^{10a}$, —S$R^{10aI}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —S(O)$R^{10a}$, and —S(O)$_2$$R^{10a}$; and $C_{1-6}$ alkyl optionally substituted with one or more substituents independently selected from halogen, —O$R^{10a}$, —S$R^{10a}$, —N($R^{10a}$)$_2$, —NO$_2$, =O, —N$_3$, and —CN. In some embodiments, $R^{1a}$, $R^{1b}$, $R^{1c}$, and $R^{1d}$, are each independently selected from: hydrogen; halogen, —NO$_2$, —N$_3$, —CN, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, and —OC(O)$R^{10a}$; and $C_{1-6}$ alkyl optionally substituted with one or more substituents independently selected from halogen, —O$R^{10a}$, —S$R^{10a}$, —N($R^{10a}$)$_2$, —NO$_2$, =O, —N$_3$, and —CN. In some embodiments, $R^{1a}$, $R^{1b}$, $R^{1c}$, and $R^{1d}$, are each independently selected from: hydrogen; halogen, —NO$_2$, —N$_3$, —CN, —O$R^{10a}$, —S$R^{10a}$, and —N($R^{10a}$)$_2$; $C_{1-6}$ alkyl optionally substituted with one or more substituents independently selected from halogen, —O$R^{10a}$, —S$R^{10a}$, —N($R^{10a}$)$_2$, —NO$_2$, =O, —N$_3$, and —CN. In some embodiments, $R^{1a}$, $R^{1b}$, $R^{1c}$, and $R^{1d}$, are each independently selected from: hydrogen; halogen, —NO$_2$, —N$_3$, —CN, —O$R^{10a}$, —S$R^{10a}$ and —N($R^{10a}$)$_2$; and $C_{1-6}$ alkyl optionally substituted with one or more substituents independently selected from halogen, =O, —N$_3$, and —CN. In some embodiments, $R^{1a}$, $R^{1b}$, $R^{1c}$, and $R^{1d}$, are each independently selected from: hydrogen; halogen, —NO$_2$, —N$_3$, —CN, —O$R^{10a}$, —S$R^{10a}$, and —N($R^{10a}$)$_2$; and $C_{1-6}$ alkyl optionally substituted with one or more substituents independently selected from halogen and —CN.

In some embodiments, $R^{1a}$, $R^{1b}$, $R^{1c}$, and $R^{1d}$, are each independently selected from: hydrogen; halogen, —NO$_2$, —N$_3$, —CN, —O$R^{10a}$, —S$R^{10a}$, and —N($R^{10a}$)$_2$; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; halogen, —NO$_2$, —N$_3$, and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; halogen and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; fluoro, chloro and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen; fluoro and —CN; and $C_{1-6}$ alkyl optionally substituted with one or more substituents independently selected from fluoro and —CN. In some embodiments, $R^{1a}$, $R^{1b}$, $R^{1c}$, and $R^{1d}$, are each independently selected from: hydrogen, fluoro, —CN, and $C_{1-6}$ alkyl. In some embodiments, $R^{1a}$, $R^{1b}$, $R^{1c}$, and $R^{1d}$, are each independently selected from: hydrogen, fluoro, —CN, and $C_{1-3}$ alkyl. In some embodiments, $R^{1a}$, $R^{1b}$, $R^{1c}$, and $R^{1d}$, are each independently selected from: hydrogen, fluoro, —CN, and $C_1$ alkyl. In some embodiments, $R^{1a}$, $R^{1b}$, $R^{1c}$, and $R^{1d}$, are each independently selected from: hydrogen, fluoro, and —CN. In some embodiments, $R^{1a}$, $R^{1b}$, $R^{1c}$, and $R^{1d}$, are each independently selected from: hydrogen and fluoro. In some embodiments, $R^{1a}$, $R^{1b}$, $R^{1c}$, and $R^{1d}$, are each independently selected from: hydrogen. In some embodiments, $R^{1a}$, $R^{1b}$, $R^{1c}$, and $R^{1d}$, are each independently selected from: hydrogen, fluoro, and $C_{1-6}$ alkyl. In some embodiments, $R^{1a}$, $R^{1b}$, $R^{1c}$, and $R^{1d}$, are each independently selected from: hydrogen, fluoro, and $C_1$ alkyl. In some embodiments, $R^{1a}$, $R^{1b}$, $R^{11}$, and $R^{1d}$, are each independently selected from: hydrogen.

In some embodiments, for a compound or salt of Formula (Id), $R^{1a}$ is selected from hydrogen, fluoro, and $C_1$ alkyl. In some embodiments, $R^{1a}$ is selected from hydrogen. In some embodiments, $R^{1a}$ is selected from fluoro. In some embodiments, $R^{1a}$ is selected from $C_1$ alkyl. In some embodiments, $R^{1b}$ is selected from hydrogen, fluoro, and $C_1$ alkyl. In some embodiments, $R^{1b}$ is selected from hydrogen. In some embodiments, $R^{1b}$ is selected from fluoro. In some embodiments, $R^{1b}$ is selected from $C_1$ alkyl. In some embodiments, $R^{1c}$ is selected from hydrogen, fluoro, and $C_1$ alkyl. In some embodiments, $R^{1c}$ is selected from hydrogen. In some embodiments, $R^{1c}$ is selected from fluoro. In some embodiments, $R^{1c}$ is selected from $C_1$ alkyl. In some embodiments, $R^{1d}$ is selected from hydrogen, fluoro, and $C_1$ alkyl. In some embodiments, $R^{1d}$ is selected from hydrogen. In some embodiments, $R^{1d}$ is selected from fluoro. In some embodiments, $R^{1d}$ is selected from $C_1$ alkyl.

In some embodiments, for a compound or salt of Formula (Id), each $R^Z$ is independently selected from: hydrogen; —CN, —C(O)$R^{10z}$, —C(O)N($R^{10z}$)$_2$, and —C(O)O$R^{10z}$; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2$$R^{10z}$, —NO$_2$, =O, =S, =N($R^{10z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2$$R^{10z}$, —NO$_2$, =O, =S, =N($R^{10z}$), —N$_3$, —CN, and $C_{1-6}$ alkyl. In some embodiments, each $R^Z$ is independently selected from: hydrogen; —CN, —C(O)$R^{10z}$, —C(O)N($R^{10z}$)$_2$, and —C(O)O$R^{10z}$; $C_{1-6}$ alkyl, $C_{2-6}$ alkenyl, and $C_{2-6}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —C(O)O$R^{10z}$, —OC(O)$R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2$$R^{10z}$, —NO$_2$, =O, =S, =N($R^{10z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$N_3$, —CN, and $C_{1-6}$ alkyl. In some embodiments, each $R^Z$ is independently selected from: hydrogen; —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, ═S, ═$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen and —CN. In some embodiments, each $R^Z$ is independently selected from: hydrogen; —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, ═S, ═$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle. In some embodiments, each $R^Z$ is independently selected from: hydrogen; —CN, —$C(O)R^{10z}$, —$C(O)N(R^{10z})_2$, and —$C(O)OR^{10z}$; and $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, ═S, ═$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$. In some embodiments, each $R^Z$ is independently selected from: hydrogen; —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, ═S, ═$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$In some embodiments, each $R^Z$ is independently selected from: hydrogen; —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, —$N_3$, —CN, $C_{3-10}$ carbocycle and 3- to 10-membered heterocycle. In some embodiments, each $R^Z$ is independently selected from: hydrogen; —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$=0, —$N_3$, —CN, $C_{3-10}$ carbocycle and 3- to 10-membered heterocycle. In some embodiments, each $R^Z$ is independently selected from: hydrogen; —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$=0, —$N_3$, —CN. In some embodiments, each $R^Z$ is independently selected from: hydrogen; —CN, —$C(O)R^{10z}$, —$C(O)N(R^{10z})_2$, and —$C(O)OR^{10z}$; and $C_{1-6}$ alkyl optionally substituted with one or more substituents independently selected from halogen, —$OR^{10z}$, —$SR^{10z}$, —$N(R^{10z})_2$, ═O, —$N_3$, —CN. In some embodiments, each $R^Z$ is independently selected from: hydrogen; and $C_{1-6}$ alkyl optionally substituted with one or more substituents independently selected from halogen, —$OR^{10z}$, —$SR^{10z}$, —$N(R^{10z})_2$, ═O, —$N_3$, —CN. In some embodiments, each $R^Z$ is independently selected from: hydrogen; and $C_{1-6}$ alkyl optionally substituted with one or more substituents independently selected from halogen, —$OR^{10z}$, and —CN. In some embodiments, each $R^Z$ is independently selected from: hydrogen; and $C_{1-6}$ alkyl optionally substituted with one or more substituents independently selected from fluoro, —$OR^{10z}$, and —CN. In some embodiments, each $R^Z$ is independently selected from: hydrogen; and $C_{1-6}$ alkyl optionally substituted with one or more substituents independently selected from fluoro and —CN. In some embodiments, each $R^Z$ is independently selected from: hydrogen; and $C_{1-6}$ alkyl optionally substituted with one or more substituents independently selected from fluoro. In some embodiments, each $R^Z$ is independently selected from: hydrogen; and $C_{1-6}$ alkyl. In some embodiments, each $R^Z$ is independently selected from: hydrogen; and $C_{1-3}$ alkyl. In some embodiments, each $R^Z$ is independently selected from: hydrogen; and $C_{1-2}$ alkyl. In some embodiments, each $R^Z$ is independently selected from: hydrogen; and $C_1$ alkyl. In some embodiments, each $R^Z$ is independently selected from: hydrogen. In some embodiments, one or more $R^Z$ is selected from hydrogen. In some embodiments, one or more $R^Z$ is selected from halogen. In some embodiments, one or more $R^Z$ is selected from fluoro. In some embodiments, for a compound or salt of Formula (Id), each $R^{Z'}$is independently selected from: hydrogen; —CN, —$C(O)R^{10z}$, —$C(O)N(R^{10z})_2$, and —$C(O)OR^{10z}$; $C_1$ alkyl substituted with substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, ═S, ═$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; $C_{2-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, ═O, ═S, ═$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, —CN, and $C_{1-6}$ alkyl. In some embodiments, each $R^{Z'}$ is independently selected from: hydrogen; —CN; $C_1$ alkyl substituted with substituted with one or more substituents independently selected from halogen, —OH, $O(CH_3)$, $C_{3-10}$ carbocycle and 3- to 10-membered heterocycle, wherein the $C_{3-10}$ carbocycle and 3- to 10-membered heterocycle are each optionally substituted with one or more $R^{9z}$; $C_{2-6}$ alkyl optionally substituted with substituted with one or more substituents independently selected from halogen, —OH, —$O(CH_3)$, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$NO_2$, =O, —CN, and $C_{1-6}$ alkyl. In some embodiments, each $R^{Z'}$is independently selected from: hydrogen; —CN; $C_1$ alkyl substituted with substituted with one or more substituents independently selected from fluoro; and $C_{3-10}$ carbocycle and 3- to 10-membered heterocycle, each of which is optionally substituted with one or more substituents independently selected from fluoro, —OH, —CN, and —$CH_3$. In some embodiments, each $R^{Z'}$is independently selected from: hydrogen and —$CH_3$. In some embodiments, each $R^{Z'}$ is independently selected from: hydrogen.

In some embodiments, for a compound or salt of Formula (Id), $R^C$ is selected from: hydrogen; —CN, —$C(O)R^{10c}$, —$C(O)N(R^{10c})_2$, —$C(O)OR^{10c}$; $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{90}$; and $C_{3-10}$ carbocycle and 3- to 10-membered heterocycle. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9C}$. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{9C}$. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, —$OR^{10c}$, —$SR^{10c}$, —$N(R^{10c})_2$, =O, —$N_3$, and —CN, $C_{3-10}$ carbocycle and 3- to 10-membered heterocycle, wherein the $C_{3-10}$ carbocycle and 3- to 10-membered heterocycle are each optionally substituted with one or more $R^{9c}$. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, —$OR^{10c}$, —$SR^{10c}$, —$N(R^{10c})_2$, =O, —$N_3$, and —CN, $C_{3-10}$ carbocycle and 3- to 10-membered heterocycle. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, —$OR^{10c}$, —$SR^{10c}$, —$N(R^{10c})_2$, =O, —$N_3$, and —CN. In some embodiments, $R^C$ is selected from: hydrogen; —CN, —$C(O)R^{10c}$, —$C(O)N(R^{10c})_2$, —$C(O)OR^{10c}$; and $C_{1-6}$ alkyl optionally substituted with one or more substituents independently selected from halogen, and —CN. In some embodiments, $R^C$ is selected from: hydrogen; —CN; and $C_{1-6}$ alkyl optionally substituted with one or more substituents independently selected from halogen, and —CN. In some embodiments, $R^C$ is selected from: hydrogen, —CN, and $C_{1-6}$ alkyl. In some embodiments, $R^C$ is selected from: hydrogen and $C_{1-6}$ alkyl. In some embodiments, $R^C$ is selected from: hydrogen and $C_1$ alkyl. In some embodiments, $R^C$ is selected from: hydrogen. In some embodiments, $R^C$ is selected from halogen. In some embodiments, $R^C$ is selected from fluoro.

In some embodiments, for a compound or salt of Formula (Id), $R^5$ is selected from: hydrogen; halogen, —$C(O)R^{10d}$, —$C(O)N(R^{10d})_2$, —$C(O)OR^{10d}$, —$S(O)R^{10d}$, —$S(O)_2R^{10a}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10a}$, —$NO_2$, =O, =S, =$N(R^{10d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. In some embodiments, $R^5$ is selected from: hydrogen; halogen, —$C(O)R^{10d}$, —$C(O)N(R^{10d})_2$, —$C(O)OR^{10a}$, and —CN; $C_{1-6}$ alkyl, $C_{2-6}$ alkenyl, and $C_{2-6}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10}$a and —CN; $C_{1-6}$ alkyl, optionally substituted with one or more substituents independently selected from halogen, —$OR^{10d}$, —$SR^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —$OR^{10d}$, —$SR^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, and $C_{1-6}$ alkyl. In some embodiments, $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —$OR^{10d}$, —$SR^{10d}$ N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —$OR^{10d}$, —$SR^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle. In some embodiments, $R^5$ is selected from: hydrogen; halogen, —C(O)$R^{10a}$, —C(O)N($R^{10d}$)$_2$, —C(O)O$R^{10d}$, and —CN; and $C_{1-6}$ alkyl, optionally substituted with one or more substituents independently selected from halogen, —$OR^{10a}$, —$SR^{10a}$, —N($R^{10d}$)$_2$, —C(O)$R^{10a}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, —$OR^{10a}$, —$SR^{10a}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —$NO_2$, =O, —CN, $C_{3-10}$ carbocycle and 3- to 10-membered heterocycle. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, —$OR^{10d}$, —$SR^{10d}$, —N($R^{10d}$)$_2$, =O, —CN, $C_{3-10}$ carbocycle and 3- to 10-membered heterocycle. In some embodiments, $R^5$ is selected from: hydrogen; halogen, —C(O)$R^{10d}$, —C(O)N($R^{10d}$)$_2$, —C(O)O$R^{10d}$, and —CN; and $C_{1-6}$ alkyl, optionally substituted with one or more substituents independently selected from halogen, and —CN. In some embodiments, $R^5$ is selected from: hydrogen; halogen and —CN; and $C_{1-6}$ alkyl, optionally substituted with one or more substituents independently selected from halogen, and —CN. In some embodiments, $R^5$ is selected from: hydrogen; fluoro and —CN; and $C_{1-6}$ alkyl, optionally substituted with one or more substituents independently selected from fluoro, and —CN. In some embodiments, $R^5$ is selected from: hydrogen; fluoro; and $C_{1-6}$ alkyl, optionally substituted with one or more substituents independently selected from fluoro. In some embodiments, $R^5$ is selected from: hydrogen; and $C_{1-6}$ alkyl, optionally substituted with one or more substituents independently selected from fluoro. In some embodiments, $R^5$ is selected from: hydrogen and $C_{1-6}$ alkyl. In some embodiments, $R^5$ is selected from: hydrogen and $C_{1-4}$ alkyl. In some embodiments, $R^5$ is selected from: hydrogen, methyl, and isobutyl. In some embodiments, $R^5$ is selected from: hydrogen, and isobutyl. In some embodiments, $R^5$ is selected from: hydrogen. In some embodiments, $R^5$ is selected from: halogen. In some embodiments, $R^5$ is selected from: fluoro. In some embodiments, $R^5$ together with $R^6$ form a $C_{3-10}$ carbocycle or 3- to 10-membered heterocycle optionally substituted with one or more $R^{9d}$. In some embodiments, $R^5$ together with $R^6$ form a cyclopropyl optionally substituted with one or more $R^{9d}$. In some embodiments, $R^5$ together with $R^6$ form a cyclopropyl optionally substituted with one or more F. In some embodiments, $R^5$ together with $R^6$ form a cyclopropyl.

In some embodiments, for a compound or salt of Formula (Id), $R^6$ is selected from: hydrogen; halogen, —C(O)$R^{10c}$, —C(O)N($R^{10e}$)$_2$, —C(O)O$R^{10e}$, —S(O)$R^{10e}$, —S(O)$_2R^{10e}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —NO$_2$, =O, =S, =N($R^{10e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$ and —CN; $C_{1-6}$ alkyl, $C_{2-6}$ alkenyl, and $C_{2-6}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10c}$, —S$R^{10c}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —NO$_2$, =O, =S, =N($R^{10e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$ and —CN; $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10c}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —NO$_2$, =O, =S, =N($R^{10e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$, and —CN; $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10c}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —NO$_2$, =O, =S, =N($R^{10e}$), —N$_3$, —CN, and $C_{1-6}$ alkyl. In some embodiments, $R^6$ is selected from: hydrogen; halogen, —C(O)$R^{10e}$, —C(O)N($R^{10e}$)$_2$, —C(O)O$R^{10e}$, and —CN; $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —CN, and $C_{1-6}$ alkyl. In some embodiments, $R^6$ is selected from: hydrogen; halogen, —C(O)$R^{10e}$, —C(O)N($R^{10e}$)$_2$, —C(O)O$R^{1e}$, and —CN; $C_{1-6}$ alkyl, optionally substituted with one or more substituents independently selected from halogen, —O$R^{10d}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle. In some embodiments, $R^6$ is selected from: hydrogen; halogen, —C(O)$R^{10c}$, —C(O)N($R^{10e}$)$_2$, —C(O)O$R^{10e}$, and —CN; and $C_{1-6}$ alkyl, optionally substituted with one or more substituents independently selected from halogen, —O$R^{10e}$, —S$R^{10e}$, N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —NO$_2$, =O, =S, =N($R^{10e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$. In some embodiments, $R^6$ is selected from: hydrogen; halogen, —C(O)$R^{10e}$, —C(O)N($R^{10e}$)$_2$, —C(O)O$R^{10e}$, and —CN; and $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —$N(R^{10e})C(O)R^{10e}$, —$C(O)OR^{10e}$, —$OC(O)R^{10c}$, —$NO_2$, ═O, —CN, $C_{3-10}$ carbocycle and 3- to 10-membered heterocycle. In some embodiments, $R^6$ is selected from: hydrogen; halogen, —$C(O)R^{10e}$, —$C(O)N(R^{10e})_2$, —$C(O)OR^{10e}$, and —CN; and $C_{1-6}$ alkyl, optionally substituted with one or more substituents independently selected from halogen, —$OR^{10e}$, —$SR^{10e}$, —$N(R^{10e})_2$, ═O, —CN, $C_{3-10}$ carbocycle and 3- to 10-membered heterocycle. In some embodiments, $R^6$ is selected from: hydrogen; halogen, —$C(O)R^{10e}$, —$C(O)N(R^{10e})_2$, —$C(O)OR^{10e}$, and —CN; and $C_{1-6}$ alkyl, optionally substituted with one or more substituents independently selected from halogen, and —CN.

In some embodiments, $R^6$ is selected from: hydrogen; halogen and —CN; and $C_{1-6}$ alkyl, optionally substituted with one or more substituents independently selected from halogen, and —CN. In some embodiments, $R^6$ is selected from: hydrogen; fluoro and —CN; and $C_{1-6}$ alkyl, optionally substituted with one or more substituents independently selected from fluoro, and —CN. In some embodiments, $R^6$ is selected from: hydrogen; fluoro; and $C_{1-6}$ alkyl, optionally substituted with one or more substituents independently selected from fluoro. In some embodiments, $R^6$ is selected from: hydrogen; and $C_{1-6}$ alkyl, optionally substituted with one or more substituents independently selected from fluoro. In some embodiments, $R^6$ is selected from: hydrogen and $C_{1-6}$ alkyl. In some embodiments, $R^6$ is selected from: hydrogen and $C_{1-4}$ alkyl. In some embodiments, $R^6$ is selected from: hydrogen, methyl, and isobutyl. In some embodiments, $R^6$ is selected from: hydrogen, and isobutyl. In some embodiments, $R^6$ is selected from: hydrogen. In some embodiments, $R^6$ is selected from: halogen. In some embodiments, $R^6$ is selected from: fluoro. In some embodiments, $R^5$ together with $R^6$ form a $C_{3-10}$ carbocycle or 3- to 10-membered heterocycle optionally substituted with one or more $R^{9d}$. In some embodiments, $R^5$ together with $R^6$ form a cyclopropyl optionally substituted with one or more $R^{9e}$. In some embodiments, $R^5$ together with $R^6$ form a cyclopropyl.

In some embodiments, for a compound or salt of Formula (Id), $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. In some embodiments, $R^5$ together with $R^6$ form a 3- to 10-membered heterocycle or $C_{3-10}$ carbocycle. In some embodiments, $R^5$ together with $R^6$ form a $C_{3-10}$ carbocycle. In some embodiments, $R^5$ together with $R^6$ form a moiety selected from ═O, ═S, ═$N(O)(R^{10e})$, =$C(R^{10e})_2$ and =$N(R^{10d})$. In some embodiments, $R^5$ together with $R^6$ form a moiety selected from ═O, ═S, ═$N(O)(R^{10e})$, and =$N(R^{10d})$. In some embodiments, $R^5$ together with $R^6$ form a moiety selected from ═O, ═S, ═$N(O)(R^{10e})$, and =$N(R^{10d})$. In some embodiments, $R^5$ together with $R^6$ form a moiety selected from ═O and =$N(R^{10d})$. In some embodiments, $R^5$ together with $R^6$ form a moiety selected from ═O. In some embodiments, $R^5$ is hydrogen, and $R^6$ is hydrogen. In some embodiments, $R^5$ is hydrogen, and $R^6$ is isobutyl.

In some embodiments, for a compound or salt of Formula (Id), $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, ═O, ═S, ═$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, ═O, ═S, ═$N(R^{10f})$, —$N_3$, —CN, and $C_{1-6}$ alkyl. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, ═O, ═S, ═$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{10f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, ═O, ═S, ═$N(R^{10f})$, —$N_3$, —CN, and $C_{1-6}$ alkyl. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, ═O, ═S, ═$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, ═O, —CN, and $C_{1-6}$ alkyl. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, ═O, ═S, ═$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle. In some embodiments, $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, ═O, ═S, ═$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$. In some embodiments, $R^7$ is selected from: hydrogen; —C(O)$R^{10f}$, —C(O)N($R^{10f}$)$_2$, —C(O)O$R^{10f}$, —S(O)$R^{10f}$, and —S(O)$_2$$R^{10f}$; $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, —N($R^{10f}$)C(O)N($R^{10f}$)$_2$, —OC(O)N($R^{10f}$)$_2$, —N($R^{10f}$)C(O)O$R^{10f}$, —S(O)$R^{10f}$, —S(O)$_2$$R^{10f}$, —$NO_2$, ═O, ═S, ═N($R^{10f}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$. In some embodiments, $R^7$ is selected from: hydrogen; —C(O)$R^{10f}$, —C(O)N($R^{10f}$)$_2$, —C(O)O$R^{10f}$, —S(O)$R^{10f}$, and —S(O)$_2$$R^{10f}$; $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, ═O, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$. In some embodiments, $R^7$ is selected from: hydrogen; —C(O)$R^{10f}$, —C(O)N($R^{10f}$)$_2$, —C(O)O$R^{10f}$, —S(O)$R^{10f}$, and —S(O)$_2$$R^{10f}$; $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, ═O, —CN, $C_{3-10}$ carbocycle and 3- to 10-membered heterocycle. In some embodiments, $R^7$ is selected from: hydrogen; —C(O)$R^{10f}$, —C(O)N($R^{10f}$)$_2$, —C(O)O$R^{10f}$, —S(O)$R^{10f}$, and —S(O)$_2$$R^{10f}$; $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, ═O, and —CN. In some embodiments, $R^7$ is selected from: hydrogen; —C(O)$R^{10f}$, —C(O)N($R^{10f}$)$_2$, —C(O)O$R^{10f}$, —S(O)$R^{10f}$, and —S(O)$_2$$R^{10f}$; $C_{1-6}$ alkyl optionally substituted with one or more substituents independently selected from halogen and —CN. In some embodiments, $R^7$ is selected from: hydrogen; —C(O)$R^{10f}$, —C(O)N($R^{10f}$)$_2$, —C(O)O$R^{10f}$; $C_{1-6}$ alkyl optionally substituted with one or more substituents independently selected from halogen and —CN. In some embodiments, $R^7$ is selected from: hydrogen; and $C_{1-6}$ alkyl optionally substituted with one or more substituents independently selected from halogen and —CN. In some embodiments, $R^7$ is selected from: hydrogen; and $C_{1-6}$ alkyl optionally substituted with one or more substituents independently selected from fluoro and —CN. In some embodiments, $R^7$ is selected from hydrogen and $C_{1-6}$ alkyl. In some embodiments, $R^7$ is selected from hydrogen and $C_{1-4}$ alkyl. In some embodiments, $R^7$ is selected from hydrogen and $C_1$ alkyl. In some embodiments, $R^7$ is selected from hydrogen.

In some embodiments, for a compound or salt of Formula (Id), $Y^2$ is selected from C($R^{9bB}$) and N. In some embodiments, $Y^2$ is selected from C(H) and N. In some embodiments, $Y^2$ is selected from C(H). In some embodiments, $Y^2$ is selected from N. In some embodiments, $Y^2$ is selected from C(H). In some embodiments, $Y^3$ is selected from C($R^{9bC}$) and N. In some embodiments, $Y^3$ is selected from N, C(H), C(CN), C(F), C(Cl), and C(OH). In some embodiments, $Y^3$ is selected from N, C(CN), C(F), C(Cl), and C(OH). In some embodiments, $Y^3$ is selected from N, C(CN), and C(F). In some embodiments, $Y^3$ is selected from C(CN), and C(F). In some embodiments, $Y^3$ is selected from C(CN), and N. In some embodiments, $Y^3$ is selected from C(CN). In some embodiments, $Y^3$ is not selected from C(H). In some embodiments, $Y^3$ is selected from N, C(H), C(CN), and C(F). In some embodiments, $Y^2$ is selected from C($R^{9bD}$) and N. In some embodiments, $Y^2$ is selected from C(H) and N. In some embodiments, $Y^2$ is selected from C(H). In some embodiments, $Y^2$ is selected from N. In some embodiments, $Y^5$ is selected from C($R^{9bE}$) and N. In some embodiments, $Y^5$ is selected from N and C(H), C(F), C($CH_3$). In some embodiments, $Y^5$ is selected from N and C(H), and C(F). In some embodiments, $Y^5$ is selected from C(H), and C(F). In some embodiments, $Y^5$ is selected from N. In some embodiments, $Y^5$ is selected from N, C(H), and C(F). In some embodiments, $Y^5$ is selected from C(F).

In some embodiments, for a compound or salt of Formula (Id), $R^2$ is selected from

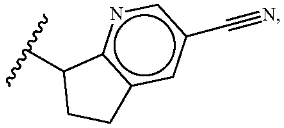
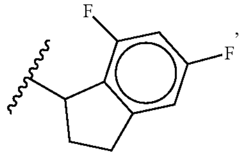
,
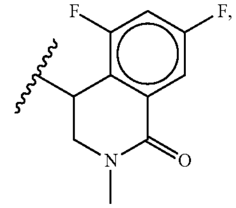
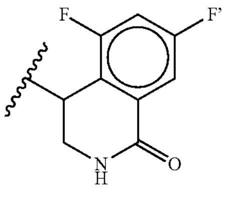
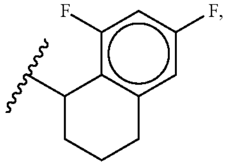
and
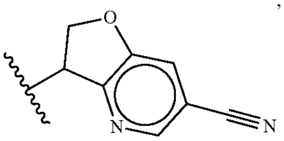
, each of which is optionally substituted with one or more substituents independently selected from —F, —Cl, and —CN. In some embodiments, $R^2$ is selected from

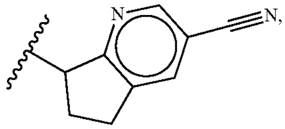
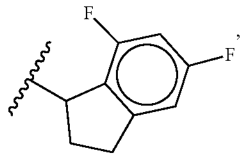
,
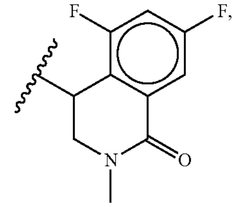
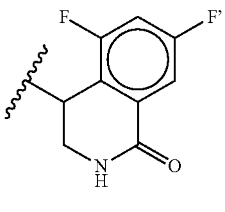
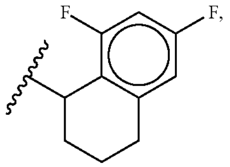
and
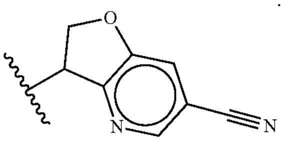
.

In some embodiments, $R^2$ is selected from

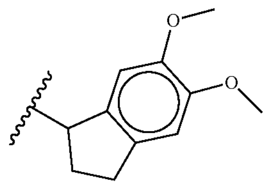

In some embodiments, for a compound or salt of Formula (Id), $R^8$ is selected from: hydrogen; —C(O)$R^{10g}$, —C(O)N($R^{10g}$)$_2$, —C(O)O$R^{10g}$, —S(O)$R^{10g}$, and —S(O)$_2$$R^{10g}$; and $C_{1-6}$ alkyl optionally substituted with one or more substituents independently selected from halogen, —O$R^{10g}$, —S$R^{10g}$, —N($R^{10g}$)$_2$, —C(O)$R^{10g}$, —N($R^{10g}$)C(O)$R^{10g}$, —C(O)O$R^{10g}$, —OC(O)$R^{10g}$, —N($R^{10g}$)C(O)N($R^{10g}$)$_2$, —OC(O)N($R^{10g}$)$_2$, —N($R^{10g}$)C(O)O$R^{10g}$, —S(O)$R^{10g}$, —S(O)$_2$$R^{10g}$, —$NO_2$, =O, =S, =N($R^{10g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{99}$. In some embodiments, $R^8$ is selected from: hydrogen; —C(O)$R^{10g}$, —C(O)N($R^{10g}$)$_2$, —C(O)O$R^{10g}$, —S(O)$R^{10g}$, and —S(O)$_2$$R^{10g}$; and $C_{1-6}$ alkyl optionally substituted with one or more substituents independently selected from halogen, —O$R^{10g}$, —S$R^{10g}$, —N($R^{10g}$)$_2$, =O, —CN, $C_{3-10}$ carbocycle and 3- to 10-membered heterocycle. In some embodiments, $R^8$ is selected from: hydrogen; and $C_{1-6}$ alkyl optionally substituted with one or more substituents independently selected from halogen, and —CN. In some embodiments, $R^8$ is selected from: hydrogen; and $C_{1-6}$ alkyl optionally substituted with one or more substituents independently selected from fluoro, and —CN. In some embodiments, $R^8$ is selected from hydrogen; and $C_{1-6}$ alkyl optionally substituted with one or more substituents independently selected from fluoro. In some embodiments, $R^8$ is selected from: hydrogen and $C_{1-6}$ alkyl. In some embodiments, $R^8$ is selected from: hydrogen and $C_{1-3}$ alkyl. In some embodiments, $R^8$ is selected from: hydrogen and $C_1$ alkyl. In some embodiments, $R^8$ is selected from: hydrogen. In some embodiments, for a compound or salt of Formula (Id), each $R^{9a}$ is independently selected from: halogen, —O$R^{10a}$, —S$R^{10a}$, —N($R^{10a}$)$_2$, =O, and —CN; and $C_{1-3}$ alkyl each of which is optionally substituted with one or more substituents independently selected from halogen, —O$R^{10a}$, —S$R^{10a}$, —N($R^{10a}$)$_2$, =O, and —CN. In some embodiments, each $R^{9a}$ is independently selected from: halogen, —O$R^{10a}$, —S$R^{10a}$, —N($R^{10a}$)$_2$, =O, and —CN; and $C_{1-3}$ alkyl each of which is optionally substituted with one or more substituents independently selected from halogen and —CN. In some embodiments, each $R^{9a}$ is independently selected from: halogen, —O$R^{10a}$, —S$R^{10a}$, —N($R^{10a}$)$_2$, =O, —CN, and $C_{1-3}$ alkyl. In some embodiments, each $R^{9a}$ is independently selected from: halogen, —O$R^{10a}$, —CN, and $C_1$ alkyl. In some embodiments, each $R^{9a}$ is independently selected from: fluoro and —CN. In some embodiments, each $R^{9a}$ is independently selected from: fluoro. In some embodiments, each $R^{9a}$ is independently selected from: —CN. In some embodiments, for a compound or salt of Formula (Id), $R^{9bB}$, $R^{9bC}$, $R^{9bD}$, and $R^{9bE}$ are each independently selected from: hydrogen; halogen, —$NO_2$, —$N_3$, —CN, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2$$R^{10b}$; $C_{1-6}$ alkyl optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, =O, —CN, $C_{1-6}$ alkyl. In some embodiments, $R^{9bB}$, $R^{9bC}$, $R^{9bD}$, and $R^{9bE}$ are each independently selected from: hydrogen; halogen, —$NO_2$, —$N_3$, —CN, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2$$R^{10b}$; $C_{1-6}$ alkyl optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle; and $C_{3-10}$ carbocycle and 3- to 10-membered heterocycle. In some embodiments, $R^{9bB}$, $R^{9bC}$, $R^{9bD}$, and $R^{9bE}$ are each independently selected from: hydrogen; halogen, —$NO_2$, —$N_3$, —CN, —O$R^{10b}$, —S$R^{10b}$, and —N($R^{10b}$)$_2$; $C_{1-6}$ alkyl optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle; and $C_{3-10}$ carbocycle and 3- to 10-membered heterocycle. In some embodiments, $R^{9bB}$, $R^{9bC}$, $R^{9bD}$, and $R^{9bE}$ are each independently selected from: hydrogen; halogen, —$NO_2$, —$N_3$, —CN, —O$R^{10b}$, —S$R^{10}$, and —N($R^{10b}$)$_2$; and $C_{1-6}$ alkyl optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle. In some embodiments, $R^{9bB}$, $R^{9bC}$, $R^{9bD}$, and $R^{9bE}$ are each independently selected from: hydrogen; halogen, —CN, —O$R^{10b}$, —S$R^{10b}$, and —N($R^{10b}$)$_2$; and $C_{1-6}$ alkyl optionally substituted with one or more substituents independently selected from halogen, —O$R^{10b}$, —S$R^{10b}$, —N($R^{10b}$)$_2$, =O, and —CN. In some embodiments, $R^{9bB}$, $R^{9bC}$, $R^{9bD}$, and $R^{9bE}$ are each independently selected from: hydrogen, halogen, —CN, —O$R^{10b}$, —S$R^{10b}$, and —N($R^{10b}$)$_2$, and $C_{1-6}$ alkyl. In some embodiments, $R^{9bB}$, $R^{9bC}$, $R^{9bD}$, and $R^{9bE}$ are each independently selected from: hydrogen, halogen, —CN, —O$R^{10b}$, and $C_{1-6}$ alkyl. In some embodiments, $R^{9bB}$, $R^{9bC}$, $R^{9bD}$, and $R^{9bE}$ are each independently selected from: hydrogen, fluoro, —CN, —O$R^{10b}$, and $C_{1-6}$ alkyl. In some embodiments, $R^{9bB}$, $R^{9bC}$, $R^{9bD}$, and $R^{9bE}$ are each independently selected from: hydrogen, fluoro, —CN, —O$R^{10b}$, and $C_1$ alkyl. In some embodiments, $R^{9bB}$, $R^{9bC}$, $R^{9bD}$ and $R^{9bE}$ are each independently selected from: hydrogen, fluoro, and —CN. In some embodiments, $R^{9bB}$, $R^{9bC}$, $R^{9bD}$, and $R^{9bE}$ are each independently selected from: hydrogen, and fluoro. In some embodiments, $R^{9bB}$, $R^{9bC}$, $R^{9bD}$, and $R^{9bE}$ are each independently selected from: hydrogen, and —CN.

In some embodiments, $R^{9b}$B is selected from: hydrogen, fluoro, and —CN. In some embodiments, $R^{9b}$B is selected from: hydrogen, fluoro, —$CH_3$, and —CN. In some embodiments, $R^{9b}$B is selected from: hydrogen. In some embodiments, $R^{9b}$B is selected from: fluoro. In some embodiments, $R^{9b}$B is selected from: —CN. In some embodiments, $R^{9bC}$ is selected from: hydrogen, fluoro, and —CN. In some embodiments, $R^{9bC}$ is selected from: hydrogen, fluoro, —$CH_3$, and —CN. In some embodiments, $R^{9bC}$ is selected from: hydrogen. In some embodiments, $R^{9bC}$ is selected from: fluoro. In some embodiments, $R^{9bC}$ is selected from: —CN. In some embodiments, $R^{9bD}$ is selected from: hydrogen, fluoro, and —CN. In some embodiments, $R^{9bD}$ is selected from: hydrogen, fluoro, —$CH_3$, and —CN. In some embodiments, $R^{9bD}$ is selected from: hydrogen. In some embodiments, $R^{9bD}$ is selected from: fluoro. In some embodiments, $R^{9bD}$ is selected from: —CN. In some embodiments, $R^{9bE}$ is selected from: hydrogen, fluoro, and —CN. In some embodiments, $R^{9bE}$ is selected from: hydrogen, fluoro, —$CH_3$, and —CN. In some embodiments, $R^{9bE}$ is selected from: hydrogen. In some embodiments, $R^{9bE}$ is selected from: fluoro. In some embodiments, $R^{9bE}$ is selected from: —CN. In some embodiments, for a compound or salt of Formula (Id), each $R^{9z}$ is independently selected from: halogen, —$OR^{10z}$, —$SR^{10z}$, —$N(R^{Oz})_2$, ═O, and —CN; and $C_{1-3}$ alkyl each of which is optionally substituted with one or more substituents independently selected from halogen, —$OR^{10z}$, —$SR^{10z}$, —$N(R^{10z})_2$, ═O, and —CN. In some embodiments, each $R^{9z}$ is independently selected from: halogen, —$OR^{10z}$, —$SR^{10z}$, —$N(R^{10z})_2$, ═O, and —CN; and $C_{1-3}$ alkyl each of which is optionally substituted with one or more substituents independently selected from halogen and —CN. In some embodiments, each $R^{9z}$ is independently selected from: halogen, —$OR^{10z}$, —$SR^{10z}$, —$N(R^{10z})_2$, ═O, —CN, and $C_{1-3}$ alkyl. In some embodiments, each $R^{9z}$ is independently selected from: halogen, —$OR^{10z}$, —CN, and $C_1$ alkyl. In some embodiments, each $R^{9z}$ is independently selected from: fluoro and —CN. In some embodiments, each $R^{9z}$ is independently selected from: fluoro. In some embodiments, each $R^{9z}$ is independently selected from: —CN. In some embodiments, for a compound or salt of Formula (Id), each $R^{90}$ is independently selected from: halogen, —$OR^{10c}$, —$SR^{10c}$, —$N(R^{10c})_2$, ═O, and —CN; and $C_{1-3}$ alkyl each of which is optionally substituted with one or more substituents independently selected from halogen, —$OR^{10c}$, —$SR^{10c}$, —$N(R^{10c})_2$, ═O, and —CN. In some embodiments, each $R^{90}$ is independently selected from: halogen, —$OR^{10c}$, —$SR^{10c}$, —$N(R^{10c})_2$, ═O, and —CN; and $C_{1-3}$ alkyl each of which is optionally substituted with one or more substituents independently selected from halogen and —CN. In some embodiments, each $R^{90}$ is independently selected from: halogen, —$OR^{10c}$, —$SR^{10c}$, —$N(R^{10c})_2$, ═O, —CN, and $C_{1-3}$ alkyl. In some embodiments, each $R^{90}$ is independently selected from: halogen, —$OR^{10c}$, —CN, and $C_1$ alkyl. In some embodiments, each $R^{90}$ is independently selected from: fluoro and —CN. In some embodiments, each $R^{9c}$ is independently selected from: fluoro. In some embodiments, each $R^{9c}$ is independently selected from: —CN. In some embodiments, for a compound or salt of Formula (Id), each $R^{9d}$ is independently selected from: halogen, —$OR^{10d}$, —$SR^{10d}$, —$N(R^{10d})_2$, ═O, and —CN; and $C_{1-3}$ alkyl each of which is optionally substituted with one or more substituents independently selected from halogen, —$OR^{10d}$, —$SR^{10d}$, —$N(R^{10d})_2$, ═O, and —CN. In some embodiments, each $R^{9d}$ is independently selected from: halogen, —$OR^{10d}$, —$SR^{10d}$, —$N(R^{10d})_2$, ═O, and —CN; and $C_{1-3}$ alkyl each of which is optionally substituted with one or more substituents independently selected from halogen and —CN. In some embodiments, each $R^{9d}$ is independently selected from: halogen, —$OR^{10d}$, —$SR^{1d}$, —$N(R^{10d})_2$, ═O, —CN, and $C_{1-3}$ alkyl. In some embodiments, each $R^{9d}$ is independently selected from: halogen, —$OR^{10d}$, —CN, and $C_1$ alkyl. In some embodiments, each $R^{9d}$ is independently selected from: fluoro and —CN. In some embodiments, each $R^{9d}$ is independently selected from: fluoro. In some embodiments, each $R^{9d}$ is independently selected from: —CN. In some embodiments, for a compound or salt of Formula (Id), each $R^{9e}$ is independently selected from: halogen, —$OR^{10e}$, —$SR^{10e}$ $N(R^{10c})_2$, ═O, and —CN; and $C_{1-3}$ alkyl each of which is optionally substituted with one or more substituents independently selected from halogen, —$OR^{10e}$, —$SR^{10e}$, —$N(R^{10e})_2$, ═O, and —CN. In some embodiments, each $R^{9e}$ is independently selected from: halogen, —$OR^{10e}$, —$SR^{10e}$, —$N(R^{10e})_2$, ═O, and —CN; and $C_{1-3}$ alkyl each of which is optionally substituted with one or more substituents independently selected from halogen and —CN. In some embodiments, each $R^{9e}$ is independently selected from: halogen, —$OR^{10e}$, —$SR^{10e}$, —$N(R^{10e})_2$, ═O, —CN, and $C_{1-3}$ alkyl. In some embodiments, each $R^{9e}$ is independently selected from: halogen, —$OR^{10e}$, —CN, and $C_1$ alkyl. In some embodiments, each $R^{9e}$ is independently selected from: fluoro and —CN. In some embodiments, each $R^{9e}$ is independently selected from: fluoro. In some embodiments, each $R^{9e}$ is independently selected from: —CN. In some embodiments, for a compound or salt of Formula (Id), each $R^{9f}$ is independently selected from: halogen, —$OR^{10f}$, —$SR^{10f}$, —$N(R^{10f})_2$, ═O, and —CN; and $C_{1-3}$ alkyl each of which is optionally substituted with one or more substituents independently selected from halogen, —$OR^{10f}$, —$SR^{10f}$, —$N(R^{10f})_2$, ═O, and —CN. In some embodiments, each $R^9$is independently selected from: halogen, —$OR^{10f}$, —$SR^{10f}$, —$N(R^{10f})_2$, ═O, and —CN; and $C_{1-3}$ alkyl each of which is optionally substituted with one or more substituents independently selected from halogen and —CN. In some embodiments, each $R^{9f}$ is independently selected from: halogen, —$OR^{10f}$, —$SR^{10f}$, —$N(R^{10f})_2$, ═O, —CN, and $C_{1-3}$ alkyl. In some embodiments, each $R^{9f}$ is independently selected from: halogen, —$OR^{10f}$, —CN, and $C_1$ alkyl. In some embodiments, each $R^{9f}$ is independently selected from: fluoro and —CN. In some embodiments, each $R^{9f}$ is independently selected from: fluoro. In some embodiments, each $R^{9f}$ is independently selected from: —CN. In some embodiments, for a compound or salt of Formula (Id), each $R^{9g}$ is independently selected from: halogen, —$OR^{10g}$, —$SR^{10g}$, —$N(R^{10g})_2$, ═O, and —CN; and $C_{1-3}$ alkyl each of which is optionally substituted with one or more substituents independently selected from halogen, —$OR^{10g}$, —$SR^{10g}$, —$N(R^{10g})_2$, ═O, and —CN. In some embodiments, each $R^{9g}$ is independently selected from: halogen, —$OR^{10g}$, —$SR^{10g}$, —$N(R^{10g})_2$, ═O, and —CN; and $C_{1-3}$ alkyl each of which is optionally substituted with one or more substituents independently selected from halogen and —CN. In some embodiments, each $R^{9g}$ is independently selected from: halogen, —$OR^{10g}$, —$SR^{10g}$, —$N(R^{10g})_2$, ═O, —CN, and $C_{1-3}$ alkyl. In some embodiments, each $R^{9g}$ is independently selected from: halogen, —$OR^{10}$, —CN, and $C_1$ alkyl. In some embodiments, each $R^{9g}$ is independently selected from: fluoro and —CN. In some embodiments, each $R^{9g}$ is independently selected from: fluoro. In some embodiments, each $R^{9g}$ is independently selected from: —CN. In some embodiments, each $R^{9g}$ is not —$OCH_3$. In some embodiments, each $R^{9g}$ is independently selected from: halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, ═O, ═S, ═$N(R^{10g})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, ═O, ═S, ═$N(R^{10g})$, —$N_3$, and —CN. In some embodiments, each $R^{9g}$ is independently selected from: halogen, —OH, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, and —CN. In some embodiments, each $R^{9g}$ is independently selected from: halogen, —OH, —$SR^{10g}$, —$N(R^{10g})_2$, —$NO_2$, =O, and —CN; and $C_{1-3}$ alkyl, optionally substituted with one or more substituents independently selected from halogen, —$OR^{10g}$, —$SR^{10g}$, —$N(R^{10g})_2$, =O, and —CN. In some embodiments, each $R^{9g}$ is independently selected from: halogen, and —CN; and $C_{1-3}$ alkyl, optionally substituted with one or more substituents independently selected from halogen, —OH=O, and —CN.

In some embodiments, for a compound or salt of Formula (Id), each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, and $C_{1-6}$ haloalkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl optionally substituted with one or more substituents independently selected from halogen, —CN, and —OH; and $C_{3-10}$ carbocycle, and 3- to 10-membered heterocycle, each of which is optionally substituted with one or more substituents independently selected from halogen, —CN, —OH, $C_{1-6}$ alkyl, and $C_{1-6}$ haloalkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl optionally substituted with one or more substituents independently selected from fluoro and CN; and $C_{3-10}$ carbocycle, and 3- to 10-membered heterocycle, each of which is optionally substituted with one or more substituents independently selected from fluoro and —CN. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen; and $C_{1-6}$ alkyl optionally substituted with one or more substituents independently selected from fluoro and CN. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen and $C_{1-6}$ alkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen and $C_1$ alkyl. In some embodiments, each $R^{10a}$, $R^{10b}$, $R^{10z}$, $R^{10c}$, $R^{10d}$, $R^{10e}$, $R^{10f}$, and $R^{10g}$ is independently selected from: hydrogen. In some embodiments, each $R^{10a}$ is independently selected from: hydrogen. In some embodiments, each $R^{10a}$ is independently selected from: hydrogen and $C_1$ alkyl. In some embodiments each $R^{10b}$ is independently selected from: hydrogen. In some embodiments, each $R^{10b}$ is independently selected from: hydrogen and $C_1$ alkyl. In some embodiments, each $R^{10c}$ is independently selected from: hydrogen. In some embodiments, each $R^{10c}$ is independently selected from: hydrogen and $C_1$ alkyl. In some embodiments, each $R^{10d}$ is independently selected from: hydrogen. In some embodiments, each $R^{10d}$ is independently selected from: hydrogen and $C_1$ alkyl. In some embodiments, each $R^{10e}$ is independently selected from: hydrogen. In some embodiments, each $R^{10e}$ is independently selected from: hydrogen and $C_1$ alkyl. In some embodiments, each $R^{10f}$ is independently selected from: hydrogen. In some embodiments, each $R^{10f}$ is independently selected from: hydrogen and $C_1$ alkyl. In some embodiments, each $R^{10g}$ is independently selected from: hydrogen. In some embodiments, each $R^{10g}$ is independently selected from: hydrogen and $C_1$ alkyl. In some embodiments, each $R^{10z}$ is independently selected from: hydrogen. In some embodiments, each $R^{10z}$ is independently selected from: hydrogen and $C_1$ alkyl.

In some embodiments, for a compound or salt of Formula (Id), u is an integer selected from 0, 1, and 2. In some embodiments, u is an integer selected from 0 and 1. In some embodiments, u is an integer selected from 0 and 2. In some embodiments, u is an integer selected from 1 and 2. In some embodiments, u is an integer selected from 0. In some embodiments, u is an integer selected from 1. In some embodiments, u is an integer selected from 2. In some embodiments, u is an integer selected from 3. In some embodiments, u is an integer selected from 4.

In some embodiments, for a compound or salt of Formula (Id), $Z^1$ is selected from: —$C(R^Z)_2$, —, —$N(R^Z)$—, —$N^+(—O^-)$, —O—, and —S—. In some embodiments, $Z^1$ is selected from: —$C(R^Z)_2$, —, —$N(R^Z)$—, and —O—. In some embodiments, $Z^1$ is selected from: —$C(R^Z)_2$, -and —$N(R^Z)$—. In some embodiments, $Z^1$ is selected from: —$C(R^Z)_2$—. In some embodiments, $Z^1$ is selected from: —$CH_2$—. In some embodiments, each $Z^2$ is independently selected from: —$C(R^Z)_2$, —, —$N(R^Z)$—, —$N^+(—O^-)$, —O—, and —S. In some embodiments, $Z^2$ is selected from: —$C(R^Z)_2$, —, —$N(R^Z)$—, and —O—. In some embodiments, $Z^2$ is selected from: —$C(R^Z)_2$— and —$N(R^Z)$—. In some embodiments, $Z^2$ is selected from: —$C(R^Z)_2$—. In some embodiments, $Z^2$ is selected from: —$CH_2$—. In some embodiments, when $Z^1$ is —$N(R^Z)$—, —$N^+(—O^-)$, —O—, or —S—; then the $Z^2$ bound to $Z^1$ is selected from: —$C(R^Z)_2$. In some embodiments, when $Z^1$ is —$N(R^Z)$—, —$N^+(—O^-)$, —O—, or —S—; then each $Z^2$ is independently selected from: —$C(R^Z)_2$—. In some embodiments, when the $Z^2$ bound to $Z^1$ is —$N(R^Z)$—, —$N^+(—O^-)$, —O—, or —S—; then $Z^1$ is selected from: —$C(R^Z)_2$—. In some embodiments, when any $Z^2$ is —$N(R^Z)$—, —$N^+(—O^-)$, —O—, or —S—; then $Z^1$ is selected from: —$C(R^Z)_2$, —.

In some embodiments, for a compound or salt of Formula (Id), when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen, —$NO_2$, —$N_3$, —CN, and —$SR^{10b}$; $C_{1-6}$ alkyl optionally substituted with one or more substituents independently selected from halogen, —$OR^{10b}$, —$SR^{10b}$, —$N(R^{10b})_2$, =O, and —CN; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, =O, —$N_3$, —CN, and $C_{1-6}$ alkyl. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen, —$NO_2$, —$N_3$, —CN, and —$SR^{10b}$; and $C_{1-6}$ alkyl optionally substituted with one or more substituents independently selected from halogen, —$OR^{10b}$, —$SR^{10b}$, —$N(R^{10b})_2$, =O, and —CN. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen, —CN; and $C_{1-6}$ alkyl optionally substituted with one or more substituents independently selected from halogen, —$OR^{10b}$, and —CN. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen, —CN; and $C_{1-6}$ alkyl optionally substituted with one or more substituents independently selected from fluoro. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen, —CN; and $C_{1-6}$ alkyl. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen, —CN; and $C_1$ alkyl. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: halogen and —CN. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: fluoro and —CN. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: fluoro. In some embodiments, when $X^1$ is selected from $C(R^{1a})$, $X^2$ is selected from $C(R^{1b})$, $X^3$ is selected from $C(R^{1c})$, and $X^4$ is selected from $C(R^{1d})$; then $R^{9bC}$ is selected from: —CN. In some embodiments, when $X^1$ is selected from C(H), $X^2$ is selected from C(H), $X^3$ is selected from C(H), and $X^4$ is selected from C(H); then $R^{9bC}$ is selected from: halogen, —$NO_2$, —$N_3$, —CN, and —$SR^{10b}$; $C_{1-6}$ alkyl optionally substituted with one or more substituents independently selected from halogen, —$OR^{10b}$, —$SR^{10b}$, —$N(R^{10b})_2$, =O, and —CN; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, =O, —$N_3$, —CN, and $C_{1-6}$ alkyl. In some embodiments, when $X^1$ is selected from C(H), $X^2$ is selected from C(H), $X^3$ is selected from C(H), and $X^4$ is selected from C(H); then $R^{9bC}$ is selected from: halogen, —$NO_2$, —$N_3$, —CN, and —$SR^{10b}$; and $C_{1-6}$ alkyl optionally substituted with one or more substituents independently selected from halogen, —$OR^{10b}$, —$SR^{10b}$, —$N(R^{10b})_2$, =O, and —CN. In some embodiments, when $X^1$ is selected from C(H), $X^2$ is selected from C(H), $X^3$ is selected from C(H), and $X^4$ is selected from C(H); then $R^{9bC}$ is selected from: halogen, —CN; and $C_{1-6}$ alkyl optionally substituted with one or more substituents independently selected from halogen, —$OR^{10b}$, and —CN. In some embodiments, when $X^1$ is selected from C(H), $X^2$ is selected from C(H), $X^3$ is selected from C(H), and $X^4$ is selected from C(H); then $R^{9bC}$ is selected from: halogen, —CN; and $C_{1-6}$ alkyl optionally substituted with one or more substituents independently selected from fluoro. In some embodiments, when $X^1$ is selected from C(H), $X^2$ is selected from C(H), $X^3$ is selected from C(H), and $X^4$ is selected from C(H); then $R^{9bC}$ is selected from: halogen, —CN; and $C_{1-6}$ alkyl. In some embodiments, when $X^1$ is selected from C(H), $X^2$ is selected from C(H), $X^3$ is selected from C(H), and $X^4$ is selected from C(H); then $R^{9bC}$ is selected from: halogen, —CN; and $C_1$ alkyl. In some embodiments, when $X^1$ is selected from C(H), $X^2$ is selected from C(H), $X^3$ is selected from C(H), and $X^4$ is selected from C(H); then $R^{9bC}$ is selected from: halogen and —CN. In some embodiments, when $X^1$ is selected from C(H), $X^2$ is selected from C(H), $X^3$ is selected from C(H), and $X^4$ is selected from C(H); then $R^{9bC}$ is selected from: fluoro and —CN. In some embodiments, when $X^1$ is selected from C(H), $X^2$ is selected from C(H), $X^3$ is selected from C(H), and $X^4$ is selected from C(H); then $R^{9bC}$ is selected from: fluoro. In some embodiments, when $X^1$ is selected from C(H), $X^2$ is selected from C(H), $X^3$ is selected from C(H), and $X^4$ is selected from C(H); then $R^{9bC}$ is selected from: —CN.

In some embodiments, for a compound or salt of Formula (Id), when $R^7$ is —$CH_3$, and $R^8$ is —$CH_3$, and $X^4$ is N or —$N^+$(—$O^-$), then $R^{1c}$ is selected from hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from chloro, bromo, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; $C_1$ alkyl substituted with one —F or two —F; $C_{2-6}$ alkyl substituted with one or more —F; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$. In some embodiments, when $R^7$ is —$CH_3$, and $R^8$ is —$CH_3$, and $X^4$ is N or —$N^+$(—$O^-$), then $R^{1c}$ is selected from hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from chloro, bromo, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; $C_{2-6}$ alkyl substituted with one or more —F; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$. In some embodiments, when $R^7$ is —$CH_3$, and $R^8$ is —$CH_3$, and $X^4$ is N or —$N^+$(—$O^-$), then $R^{1c}$ is selected from hydrogen; halogen, —$NO_2$, —CN;

$C_{1-6}$ alkyl, optionally substituted with one or more substituents independently selected from chloro, bromo, —$OR^{10a}$, —$SR^{10a}$, —$N(R^{10a})_2$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, =O—CN, and $C_{1-6}$ alkyl. In some embodiments, when $R^7$ is —$CH_3$, and $R^8$ is —$CH_3$, and $X^4$ is N or —$N^+(—O^-)$, then $R^{1c}$ is selected from hydrogen; halogen, —$NO_2$, —CN, —$OR^{10a}$, —$SR^{10a}$, and —$N(R^{10a})_2$. In some embodiments, when $R^7$ is —$CH_3$, and $R^8$ is —$CH_3$, and $X^4$ is N or —$N^+(—O^-)$, then $R^{1c}$ is selected from hydrogen; halogen, —CN, —OH, —$O(CH_3)$, and —$CH_3$. In some embodiments, when $R^7$ is —$CH_3$, and $R^8$ is —$CH_3$, and $X^4$ is N or —$N^+(—O^-)$, then $R^{1c}$ is selected from hydrogen; fluoro and —CN. In some embodiments, when $R^7$ is —$CH_3$, and $R^8$ is —$CH_3$, and $X^4$ is N or —$N^+(—O^-)$, then $R^{1c}$ is selected from hydrogen; and fluoro. In some embodiments, when $R^7$ is —$CH_3$, and $R^8$ is —$CH_3$, and $X^4$ is N or —$N^+(—O^-)$, then $R^{1c}$ is selected from hydrogen, In some embodiments, when $R^7$ is —$CH_3$, and $R^8$ is —$CH_3$, and $X^4$ is N or —$N^+(—O^-)$, then $R^{1c}$ is selected from fluoro, In some embodiments, when $R^7$ is —$CH_3$, and $R^8$ is —$CH_3$, and $X^4$ is N, then $R^{1c}$ is selected from: hydrogen; halogen, —$NO_2$, —$N_3$, —CN, —$OR^{10a}$, and —$SR^{10a}$; $C_{1-6}$ alkyl, optionally substituted with one or more substituents independently selected from chloro, bromo, —$OR^{10a}$, —$SR^{10a}$, —$N(R^{10a})_2$, =O, —CN, $C_{3-10}$ carbocycle and 3- to 10-membered heterocycle, wherein the $C_{3-10}$ carbocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —CN, and $C_{1-6}$ alkyl. In some embodiments, when $R^7$ is —$CH_3$, and $R^8$ is —$CH_3$, and $X^4$ is N, then $R^{1c}$ is selected from: hydrogen; halogen, —$NO_2$, —$N_3$, —CN, —$OR^{10a}$, and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $R^7$ is —$CH_3$, and $R^8$ is —$CH_3$, and $X^4$ is N, then $R^{1c}$ is selected from: hydrogen; halogen, —CN, —$OR^{10a}$, and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $R^7$ is —$CH_3$, and $R^8$ is —$CH_3$, and $X^4$ is N, then $R^{1c}$ is selected from: hydrogen, halogen, —CN, and —$OR^{10a}$. In some embodiments, when $R^7$ is —$CH_3$, then $R^{1c}$ is selected from: hydrogen; halogen, —$NO_2$, —$N_3$, —CN, —$OR^{10a}$, and —$SR^{10a}$; $C_{1-6}$ alkyl, optionally substituted with one or more substituents independently selected from chloro, bromo, —$OR^{10a}$, —$SR^{10a}$, —$N(R^{10a})_2$, =O, —CN, $C_{3-10}$ carbocycle and 3- to 10-membered heterocycle, wherein the $C_{3-10}$ carbocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —CN, and $C_{1-6}$ alkyl. In some embodiments, when $R^7$ is —$CH_3$, then $R^{1c}$ is selected from: hydrogen; halogen, —$NO_2$, —$N_3$, —CN, —$OR^{10a}$, and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $R^7$ is —$CH_3$, then $R^{1c}$ is selected from: hydrogen; halogen, —CN, —$OR^{10a}$ and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $R^7$ is —$CH_3$, then $R^{1c}$ is selected from: hydrogen, halogen, —CN, and —$OR^{10a}$ In some embodiments, when $R^8$ is —$CH_3$, then $R^{1c}$ is selected from: hydrogen; halogen, —$NO_2$, —$N_3$, —CN, —$OR^{10a}$, and —$SR^{10a}$; $C_{1-6}$ alkyl, optionally substituted with one or more substituents independently selected from chloro, bromo, —$OR^{10a}$, —$SR^{10a}$, —$N(R^{10a})_2$, =O, —CN, $C_{3-10}$ carbocycle and 3- to 10-membered heterocycle, wherein the $C_{3-10}$ carbocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —CN, and $C_{1-6}$ alkyl. In some embodiments, when $R^8$ is —$CH_3$, then $R^{1c}$ is selected from: hydrogen; halogen, —$NO_2$, —$N_3$, —CN, —$OR^{10a}$, and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $R^8$ is —$CH_3$, then $R^{1c}$ is selected from: hydrogen; halogen, —CN, —$OR^{10a}$ and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $R^8$ is —$CH_3$, then $R^{1c}$ is selected from: hydrogen, halogen, —CN, and —$OR^{10a}$.

In some embodiments, for a compound or salt of Formula (Id), when $X^4$ is N, then $R^7$ is H, $C_{2-6}$ alkyl, $C_{3-10}$ carbocycle or 3- to 10-membered heterocycle. In some embodiments, when $X^4$ is N, then $R^7$ is H. In some embodiments, when $X^4$ is N, then $R^8$ is H, $C_{2-6}$ alkyl, $C_{3-10}$ carbocycle or 3- to 10-membered heterocycle. In some embodiments, when $X^4$ is N, then $R^8$ is H. In some embodiments, when $X^4$ is N or —$N^+(—O^-)$, then $R^{1c}$ is selected from: hydrogen; halogen, —$NO_2$, —$N_3$, —CN, —$OR^{10a}$, and —$SR^{10a}$; $C_{1-6}$ alkyl, optionally substituted with one or more substituents independently selected from chloro, bromo, —$OR^{10a}$, —$SR^{10a}$, —$N(R^{10a})_2$, =O, —CN, $C_{3-10}$ carbocycle and 3- to 10-membered heterocycle, wherein the $C_{3-10}$ carbocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —CN, and $C_{1-6}$ alkyl. In some embodiments, when $X^4$ is N, then $R^{1c}$ is selected from: hydrogen; halogen, —$NO_2$, —$N_3$, —CN, —$OR^{10a}$, and —$SR^{10a}$; $C_{1-6}$ alkyl, optionally substituted with one or more substituents independently selected from chloro, bromo, —$OR^{10a}$, —$SR^{10a}$, —$N(R^{10a})_2$, =O, —CN, $C_{3-10}$ carbocycle and 3- to 10-membered heterocycle, wherein the $C_{3-10}$ carbocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —CN, and $C_{1-6}$ alkyl. In some embodiments, when $X^4$ is N, then $R^{1c}$ is selected from: hydrogen; halogen, —$NO_2$, —$N_3$, —CN, —$OR^{10a}$, and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $X^4$ is N, then $R^{1c}$ is selected from: hydrogen; halogen, —CN, —$OR^{10a}$, and —$SR^{10a}$; $C_{1-6}$ alkyl; and $C_{3-10}$ carbocycle and 3- to 10-membered heterocycle, each of which is optionally substituted with one or more substituents independently selected from halogen and —CN. In some embodiments, when $X^4$ is N, then $R^{1c}$ is selected from: hydrogen, halogen, —CN, and —$OR^{10a}$. In some embodiments, when $X^4$ is N, then $R^{1c}$ is selected from: hydrogen, halogen, and —CN. In some embodiments, when $X^4$ is N, then $R^{1c}$ is selected from: hydrogen, fluoro, and —CN. In some embodiments, when $X^4$ is N, then $R^{1c}$ is selected from: hydrogen, and fluoro.

In some embodiments, for a compound or salt of Formula (Id), when one $R^{9bC}$ is —$CH_3$, then each additional $R^{9bC}$ is selected from halogen, —$NO_2$, —$N_3$, —CN, —OH, —O($C_{2-6}$ alkyl), —O($C_{1-6}$ haloalkyl), —$SR^{10b}$, —NH($C_{1-6}$ alkyl), —N($C_{1-6}$ alkyl)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_1$ alkyl substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —$N_3$, —CN, $C_{3-10}$ carbocycle and 3- to 10-membered heterocycle; and $C_{2-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —$N_3$, —CN, $C_{1-6}$ alkyl, $C_{2-6}$ alkenyl, and $C_{2-6}$ alkynyl. In some embodiments, when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro, chloro, iodo, —$NO_2$, —$N_3$, —CN, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —$N_3$, —CN, $C_{1-6}$ alkyl, $C_{2-6}$ alkenyl, and $C_{2-6}$ alkynyl. In some embodiments, when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro, chloro, —CN, —$OR^{10b}$, $C_{1-6}$ alkyl, optionally substituted with one or more substituents independently selected from halogen and —$OR^{10b}$; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —CN, and $C_{1-6}$ alkyl. In some embodiments, when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro, —CN, —OH, —O($CH_3$), —$CH_3$, and —$CF_3$. In some embodiments, when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro and —CN. In some embodiments, when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: fluoro. In some embodiments, when $X^1$ is C(H), and $X^2$ is C(H), and $X^3$ is C(H), and $X^4$ is C(H), and $Z^1$ is —$CH_2$—, and u is 2, and each $Z^2$ is —$CH_2$— or —O—, and $Y^2$ is C(H), and $Y^3$ is C(H), and $Y^4$ is C(H); then $R^{9bE}$ is selected from: —CN. In some embodiments, when $X^1$ is C(H), and $X^2$ is C(H), and $X^3$ is C(H), and $X^4$ is C(H), then $R^{9bE}$ is selected from: fluoro, —CN, —OH, —O($CH_3$), —$CH_3$, and —$CF_3$. In some embodiments, when $Z^1$ is —$CH_2$—, then $R^{9bE}$ is selected from: fluoro, —CN, —OH, —O($CH_3$), —$CH_3$, and —$CF_3$. In some embodiments, when each $Z^2$ is —$CH_2$— or —O—, and $Y^2$ is C(H), and $Y^3$ is C(H), and $Y^4$ is C(H); then $R^{9bE}$ is selected from: fluoro, —CN, —OH, —O($CH_3$), —$CH_3$, and —$CF_3$. In some embodiments, when each $Z^2$ is —$CH_2$— or —O—, and $Y^2$ is C(H), and $Y^3$ is C(H), and $Y^4$ is C(H); then $R^{9bE}$ is selected from: fluoro, —CN, —OH, —O($CH_3$), —$CH_3$, and —$CF_3$. In some embodiments, when $Y^2$ is C(H), and $Y^3$ is C(H), and $Y^4$ is C(H); then $R^{9bE}$ is selected from: fluoro, —CN, —OH, —O($CH_3$), —$CH_3$, and —$CF_3$.

In some embodiments, for a compound or salt of Formula (Id), when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from hydrogen; chloro, bromo, iodo, —$NO_2$, —$N_3$, —CN, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —$N_3$, —CN, $C_{1-6}$ alkyl, $C_{2-6}$ alkenyl, and $C_{2-6}$ alkynyl. In some embodiments, when $X^t$ is C(H), and $X^2$ is C(H), and $X^3$ is C(H), and $X^4$ is C(H), and $Z^t$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from hydrogen; chloro, —CN, —$OR^{10b}$, —$SR^{10b}$, —N($R^{10b}$)$_2$; $C_{1-6}$ alkyl, optionally substituted with one or more substituents independently selected from halogen; and $C_{3-10}$ carbocycle and 3- to 10-membered heterocycle. In some embodiments, when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from hydrogen; chloro, —CN, —$OR^{10b}$, —$SR^{10b}$, —$N(R^{10b})_2$; and $C_{1-6}$ alkyl. In some embodiments, when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from hydrogen; —CN, —OH, —$O(CH_3)$, and —$CH_3$. In some embodiments, when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from hydrogen and —CN. In some embodiments, when $X^1$ is C(H), and $X^2$ is C(H), and $X^3$ is C(H), and $X^4$ is C(H), and $Z^1$ is —$CH_2$—, and u is 1, and $Z^2$ is —$CH_2$—, and $Y^5$ is C(H), and $Y^3$ is C(H), and $Y^4$ is C(H); then $R^{9bB}$ is selected from hydrogen.

In some embodiments, the compound or salt of formula (Id) is selected from compounds: 9, 10, 44, 48, 43, 46, 57, 701, 702, and 703, or a salt of any one thereof. In some embodiments, the compound or salt of formula (Id) is selected from compound 55, or a salt thereof.

In some embodiments, for compound or salt of Formula (Id), $R^2$ is:

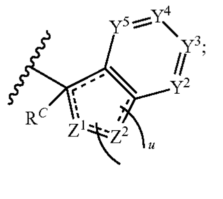

$R^C$ is absent; each ---- is independently selected from a single bond and a double bond; and when u is greater than 1; then each bond between each $Z^2$ is ----, wherein each ---- is independently selected from a single bond and a double bond. In some embodiments, $Z^1$ is $C(R^Z)$. In some embodiments, $Z^1$ is C(H). In some embodiments, each $Z^2$ is selected from $C(R^Z)$ and N. In some embodiments, each $Z^2$ is selected from $C(R^Z)$. In some embodiments, each $Z^2$ is selected from C(H). In some embodiments, u is 1 or 2. In some embodiments, u is 2. In some embodiments, u is 2. In some embodiments, the ring comprising $Z^1$ and each $Z^2$ is aromatic. In some embodiments, the ring comprising $Z^1$ and each $Z^2$ is heteroaromatic. In some embodiments, the compound or salt of formula (Id") is compound 5002,or a salt thereof, optionally substituted with one or more substituents, each of which is independently selected from —F, —$C_1$, —CN, —OH, and —$CH_3$. In some embodiments, the compound or salt of formula (Id) is compound 5002, or a salt thereof.

In some embodiments, the compound or salt of Formula (Id) is compound 9, 10, 44, 48, 43, 46, 55, 57, 701, 702, or 703, or a salt thereof. In some embodiments, the compound or salt of Formula (Id) is compound 9, 10, 44, 48, 43, 46, 55, 57, 701, or 702, or a salt thereof. In some embodiments, the compound or salt of Formula (Id) is selected from: compound 701, 9, 702, 48, 57, 10, 44, 46, and 55, or a salt thereof. In some embodiments, the compound or salt of Formula (Id) is selected from: compound 701, 9, 702, 48, and 57, or a salt thereof. In some embodiments, the compound or salt of Formula (Id) is selected from: compound 701, 9, 702, 48, and 57, or a salt thereof. In some embodiments, the compound or salt of Formula (Id) is selected from: compound 701, 9, 702, and 48, or a salt thereof. In some embodiments, the compound or salt of Formula (Id) is selected from: compound 701 and 9, or a salt thereof. In some embodiments, the compound or salt of Formula (Id) is selected from: compound 701 or a salt thereof. In some embodiments, the compound or salt of Formula (Id) is selected from: compound 701, 9, 48, 57, 702, 44, and 10 or a salt thereof. In some embodiments, the compound or salt of Formula (Id) is selected from: compound 701, 9, 48, 57, 702, and 44, or a salt thereof. In some embodiments, the compound or salt of Formula (Id) is selected from: compound 701, 9, and 48, or a salt thereof.

In some embodiments, the compound or salt of Formula (Id) is not: 3(2H)-Quinazolineacetamide, 1,4-dihydro-2,4-dioxo-N-(1,2,3,4-tetrahydro-1-naphthalenyl)-; N-(3,4-Dihydro-2H-1-benzopyran-4-yl)-1,4-dihydro-2,4-dioxo-3(2H)-quinazolineacetamide; N-(6-Amino-1,2,3,4-tetrahydro-1-naphthalenyl)-1,4-dihydro-2,4-dioxo-3(2H)-quinazolineacetamide; 3(2H)-Quinazolineacetamide, N-(6-amino-1,2,3,4-tetrahydro-1-naphthalenyl)-1,4-dihydro-2,4-dioxo-, hydrochloride (1:1); 1,4-Dihydro-2,4-dioxo-N-(1,2,3,4-tetrahydro-4,4-dimethyl-1-naphthalenyl)-3(2H)-quinazolineacetamide; 1,4-Dihydro-2,4-dioxo-N-9H-xanthen-9-yl-3(2H)-quinazolineacetamide; N-(4-Fluoro-2,3-dihydro-1H-inden-1-yl)-1,4-dihydro-2,4-dioxo-3(2H)-quinazolineacetamide; N-(6-Bromo-3,4-dihydro-2H-1-benzopyran-4-yl)-1,4-dihydro-2,4-dioxo-3(2H)-quinazolineacetamide; N-(2,3-Dihydro-5,6-dimethoxy-1H-inden-1-yl)-1,4-dihydro-2,4-dioxo-3(2H)-quinazolineacetamide; N-(2,3-Dihydro-5,6-dimethoxy-1H-inden-1-yl)-α-ethyl-1,4-dihydro-2,4-dioxo-3(2H)-quinazolineacetamide; (αS)—N-(2,3-Dihydro-5,6-dimethoxy-1H-inden-1-yl)-1,4-dihydro-α-[2-(methylthio)ethyl]-2,4-dioxo-3(2H)-quinazolineacetamide; 1,4-Dihydro-N-methyl-2,4-dioxo-N-(1,2,3,4-tetrahydro-1-naphthalenyl)-3(2H)-quinazolineacetamide; N1-(5-Chloro-2,4-dimethoxyphenyl)-2,4-dioxo-N3-(1,2,3,4-tetrahydro-1-naphthalenyl)-1,3(2H,4H)-quinazolinediacetamide; or 1,4-Dihydro-N,1-dimethyl-2,4-dioxo-N-(1,2,3,4-tetrahydro-1-naphthalenyl)-7-(trifluoromethyl)pyrido[2,3-d]pyrimidine-3(2H)-acetamide. In some embodiments, the compound or salt of Formula (Id) is not: 2921029-47-0, 1277962-78-3, 1840550-12-0, 1840550-13-1, 1288248-72-5, 1318358-42-7, 2249087-56-5, 1318507-92-4, 2108485-31-8, 2701290-29-9, 2700159-15-3, 1100076-80-9, 1052722-56-1, or 1089998-38-8, wherein said numbers are CAS registry numbers.

Therapeutic Applications—Muscle Myosin

Methods of administration of a compound or salt or pharmaceutical composition or N-oxide of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep), discussed herein may be used for the treatment of diseases and disorders resulting from the dysfunction of muscle myosin. Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep), discussed herein may be used for the treatment of diseases and disorders through the modulation of muscle myosin. In some embodiments, the muscle myosin is cardiac muscle myosin (e.g., of ventircular or atrial tissue). In some embodiments, the muscle myosin is skeletal muscle myosin.

Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the treatment of diseases and disorders through the modulation of myosin cross-bridge cycling.

Cardiac Muscle Myosin

Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the modulation of cardiac muscle myosin. Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the treatment of cardiac diseases and disorders. Examples of cardiac diseases and disorders include but are not limited to heart attack, heart failure, heart infection, endocarditis, myocarditis, pericarditis, arrhythmia, abnormal heart rhythms, aorta disease, Marfan syndrome, vascular disease, stroke, congenital heart disease, coronary artery disease, rhematic heart disease, peripheral vascular disease, heart valve disease, pericardial disease, heart muscle disease, cardiomyopathy, deep vein thrombosis, and embolism (e.g., pulmonary embolism). Examples of heart infections include but are not limited to endocarditis, myocarditis, and pericarditis.

Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the treatment of one or more myopathy (myopathies).

In some embodiments, the myopathy is a cardiac myopathy. In some embodiments, the present disclosure provides a method of treating a condition selected from hypertrophic cardiomyopathy (HCM). In some embodiments, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina. In some embodiments, the present disclosure provides a compound for use in treating one or more condition(s) selected from: hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina. In some embodiments, said heart failure with preserved ejection fraction (HFpEF) comprises one or more disorders selected from disorders of relaxation and disorders of chamber stiffness (diabetic HFpEF). In some embodiments, said heart failure with preserved ejection fraction (HFpEF) comprises HFpEF related to hypertension. In some embodiments, said heart failure with preserved ejection fraction (HFpEF) comprises HFpEF related to aortic valvular disease. In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefllers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In an aspect, the present disclosure provides a method of treating hypertrophic cardiomyopathy or a related condition comprising administering to a subject in need thereof a compound or salt disclosed herein (e.g., a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep)). In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein. In an aspect, the present disclosure provides a method of treating a condition selected from hypertrophic cardiomyopathy (HCM); disorders of relaxation; ischemic cardiomyopathy; cardiac transplant allograft vasculopathy; restrictive cardiomyopathy; left ventricular (LV)

hypertrophy; ischemia; and andangin, the method comprising administering a ventricular-selective agent.

In an aspect, the present disclosure provides methods of treating atrial cardiopathy, Heart failure with ejection fraction (e.g., Heart failure with preserved ejection fraction (HFpEF), Heart failure with reduced ejection fraction (HFrEF)), arrhythmia (e.g., Atrial fibrillation), stroke (e.g., Cardioembolic stroke, Cryptogenic stroke), valve disease (e.g., Mitral valve disease, or Tricuspid valve disease), comprises administering an atrial-selective agent. In an aspect, the present disclosure provides methods of treating atrial cardiopathy, Heart failure with preserved ejection fraction (HFpEF), Heart failure with reduced ejection fraction (HFrEF), Atrial fibrillation, Cardioembolic stroke, Cryptogenic stroke, Mitral valve disease, or Tricuspid valve disease. In some embodiments, the method comprises administering an atrial-selective agent. In an aspect, the present disclosure provides methods of treating atrial cardiopathy. In some embodiments, the present disclosure provides a method of treating HFpEF. In some embodiments, the present disclosure provides a method of treating HFrEF. In some embodiments, the present disclosure provides a method of treating Atrial fibrillation. In some embodiments, the present disclosure provides a method of treating Cardioembolic stroke. In some embodiments, the present disclosure provides a method of treating Cryptogenic stroke. In some embodiments, the present disclosure provides a method of treating Mitral valve disease. In some embodiments, the present disclosure provides a method of treating Tricuspid valve disease. In some embodiments, the present disclosure provides a method of treating one or more diseases selected from atrial cardiopathy, HFpEF, HFrEF, Atrial fibrillation, Cardioembolic stroke, Cryptogenic stroke, Mitral valve disease, and Tricuspid valve disease. In some embodiments, the method comprises administering a compound of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In some embodiments, the compound of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) is for use in treating one or more diseases selected from atrial cardiopathy, HFpEF, HFrEF, Atrial fibrillation, Cardioembolic stroke, Cryptogenic stroke, Mitral valve disease, and Tricuspid valve disease, comprises an atrial-selective agent. In some embodiments, the atrial-selective agent selectively inhibits atrial myosin relative to ventricular myosin or relative to skeletal myosin. In some embodiments, the atrial-selective agent selectively inhibits atrial myosin regulatory light chain relative to ventricular myosin regulatory light chain, or relative to skeletal myosin regulatory light chain, or relative to both atrial myosin regulatory light chain and skeletal myosin regulatory light chain.

In an aspect, disclosed herein are methods to treat a disease by the administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep).

In an aspect, disclosed herein are methods to treat cardiac disease by the administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep).

In an aspect, disclosed herein are methods to treat cardiovascular disease or a related condition by the administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In an aspect, disclosed herein are methods to treat cardiovascular disease or a related condition by the administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep).

In an aspect, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; angina; and myocarditis. In some embodiments, the condition is cardiac dysfunction related to acute or chronic myocarditis. In some embodiments, the myocarditis is parasitic, bacterial, viral, or non-infectious. In some embodiments, the myocarditis is auto-immune myocarditis. In some embodiments, the myocarditis is eosinophilic myocarditis. In some embodiments, the condition is a myopathy. In some embodiments, the condition is a cardiomyopathy. In some embodiments, the cardiomyopathy is a toxic cardiomyopathy. In some embodiments, the toxic cardiomyopathy is related to exposure to chemotherapeutic agents, ethanol, cocaine, other toxic substances, or any combination thereof. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic subgroups, inherited subgroups, congenital heart disease subgroups. In some embodiments, said inflammatory subgroups comprise one or more subgroups selected from Loefllers and EMF. In some embodiments, said inflammatory subgroups comprise one or more subgroups selected from amyloid, sarcoid, and radiation (e.g., XRT, radiation therapy, or radiation injury). In some embodiments, said storage subgroups comprise one or more subgroups selected from hemochromatosis, Fabry, and glycogen storage disease. In some embodiments, said inherited subgroups is related to conditions associated with Troponin I (beta myosin Heavy Chain), Troponin T (e.g. alpha cardiac actin), or desmin. In some embodiments, said congenital heart disease subgroups comprises one or more subgroups selected from pressure-overloaded right ventricle (RV), Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

In some embodiments, the present disclosure provides a method of treating dilated (DCM) cardiomyopathy. In some embodiments, the present disclosure provides a method of treating sudden cardiac death.

In an aspect, the present disclosure provides a method of treating a cardiac disease or disorder, the method comprising administering a compound or salt of any one of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) to a subject in need thereof. In some embodiments, administering the compound or salt of the present disclosure modulates the subject's heart rate (HR), end diastolic volume (EDV), or fractional shortening (FS). In some embodiments, the administering the compound or salt increases the subject's HR. In some embodiments, the administering the compound or salt increases the subject's FS. In some embodiments, the administering the compound or salt increases the subject's EDV. In some embodiments, the administering the compound or salt decreases the subject's HR. In some embodiments, the administering the compound or salt decreases the subject's FS. In some embodiments, the administering the compound or salt decreases the subject's EDV. In some embodiments the administering the compound or salt does not change (e.g., does not significantly change) the subject's HR. In some embodiments the administering the compound or salt does not change (e.g., does not significantly change) the subject's FS. In some embodiments the administering the compound or salt does not change (e.g., does not significantly change) the subject's EDV. In some embodiments, the administering the compound or salt modulates an index of left-ventricular fractional shortening (FS) and systolic wall-thickening index (SWT). In some embodiments, the administering the compound or salt modulates an index of left-ventricular fractional shortening (FS). In some embodiments, the administering the compound or salt modulates an index of systolic wall-thickening index (SWT). In some embodiments, administering the compound or salt of any one of the present disclosure modulates the subject's isovolumic contraction time (IVCT), or Pre-ejection period, or isovolumic relaxation time (IVRT), or ejection fraction (EF). In some embodiments, the administering the compound or salt increases the subject's IVCT. In some embodiments, the administering the compound or salt increases the subject's Pre-ejection period. In some embodiments, the administering the compound or salt increases the subject's IVRT. In some embodiments, the administering the compound or salt increases the subject's EF. In some embodiments, the administering the compound or salt decreases the subject's IVCT. In some embodiments, the administering the compound or salt decreases the subject's Pre-ejection period. In some embodiments, the administering the compound or salt decreases the subject's IVRT. In some embodiments, the administering the compound or salt decreases the subject's EF. In some embodiments, the administering the compound or salt does not change (e.g., does not significantly change) the subject's IVCT. In some embodiments, the administering the compound or salt does not change (e.g., does not significantly change) the subject's Pre-ejection period. In some embodiments, the administering the compound or salt does not change (e.g., does not significantly change) the subject's IVRT. In some embodiments, the administering the compound or salt does not change (e.g., does not significantly change) the subject's EF. In some embodiments, the administering the compound or salt modulates actomyosin cycling rates. In some embodiments, the administering the compound or salt modulates peak E-wave velocity (E). In some embodiments, the administering the compound or salt modulates peak A-wave velocity (A). In some embodiments, the administering the compound or salt modulates peak early diastolic mitral annular velocity (e'). In some embodiments, E-wave and A-wave may refer two distinct periods of filling of the ventricle (e.g., left ventricle) with blood from the atrium (e.g., left atrium), e.g., wherein the E-wave may occur early in diastole, and e.g., wherein the A-wave may occur late in diastole, e.g., when the atrium contracts. In some embodiments, the change in HR, FS, SWT, IVCT, IVRT, EF, or pre-ejection period is from about 1% from baseline to about 30% from baseline.

In some embodiments, the methods disclosed herein further comprise administering an additional active agent.

In an aspect, the present disclosure provides a pharmaceutical composition comprising the compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) and one or more excipient(s) (e.g., a pharmaceutically acceptable excipient(s)).

In an aspect, the present disclosure provides a method of modulating a light chain (e.g., a myosin light chain). Alternatively, or in addition, in some embodiments, the present disclosure provides a method of modulating a heavy chain (e.g., a myosin heavy chain). In some embodiments, a compound or salt of the present disclosure (e.g Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep)) modulates a light chain. In some embodiments, a compound or salt of the present disclosure modulates a regulatory light chain (RLC) (e.g., a myosin regulatory light chain). In some embodiments, a compound or salt of the present disclosure modulates an essential light chain (ELC) (e.g., a myosin essential light chain). In some embodiments, the regulatory light chain is a cardiac myosin regulatory light chain. In some embodiments, the modulating the regulatory light chain is inhibiting the regulatory light chain (e.g., inhibiting the function of the RLC). Alternatively, or in addition, in some embodiments, the modulating the rlc is activating the RLC (e.g., activating the function of the RLC). In some embodiments, the method changes the ability of a myosin lever arm to develop force. In some embodiments, the method modulates cross bridge cycling. In some embodiments, administering the compound or salt overcomes a disturbance in an interaction between myosin regulatory light chain and myosin heavy chain. In some embodiments, the disturbance is caused by a genetic mutation. In some embodiments, the method of modulating an RLC is for use in treating hypertrophic cardiomyopathy. In some embodiments, a compound or salt of the present disclosure directly binds myosin RLC. Alternatively, on in addition, in some embodiments, a compound or salt of the present disclosure indirectly modulates one or more other protein(s) (e.g., other sarcomeric protein(s), or e.g., protein(s) other than myosin RLC). In some embodiments, a compound or salt of the present disclosure indirectly modulates myosin or myosin binding protein C, or one or more thin-filament protein(s).

In some embodiments, the compound or salt is an inhibitor of myosin ATP-ase. In some embodiments, administering a compound of the present disclosure modulates ATP cycling rates of one or more sarcomeric protein(s) (e.g., actomyosin cycling). In some embodiments, administering a compound of the present disclosure activates ATP cycling rates of sarcomeric proteins. Alternatively, in some embodiments, administering a compound of the present disclosure inhibits ATP cycling rates of sarcomeric proteins. In some embodiments, the modulating ATP cycling rates of sarcomeric proteiens is through interactions (e.g., binding) with one or more sarcomere protein(s) (e.g., myosin, myosin regulatory light chain, myosin essential light chain, or myosin binding protein-c).

In some embodiments, administering a compound or salt of the present disclosure modulates actin floating on myosin. In some embodiments, administering a compound or salt of the present disclosure modulates actin floating on myosin in a different way than a direct myosin inhibitor modulates actin floating on myosin (e.g., as shown in a Motility assay).

In an aspect, administering a compound or salt of the disclosure (e.g., a compound or salt of any one Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) modulates one or more sarcomeric protein(s). In an aspect, administering a compound or salt of the disclosure modulates a myosin (e.g., myosin in cardiac muscle, myosin in skeletal muscle). In an aspect, administering a compound or salt of the disclosure (e.g., a compound or salt of any one Formula (I), Formula (II), or Formula (III)) modulates a myosin light chain (e.g., essential myosin light chain, regulatory myosin light chain). In some embodiments, administering a compound or salt of the disclosure modulates a regulatory light chain (e.g., myosin regulatory light chain). In some embodiments, the compound or salt of the disclosure inhibits a regulatory light chain. Alternatively, in some embodiments, the compound or salt of the disclosure activates a myosin regulatory light chain.

In an aspect, administering a compound of the present disclosure treats a patient (e.g., with HCM) through modulation of a myosin regulatory light chain (e.g., cardiac myosin regulatory light chain).

In some embodiments, the patient to which a compound of the present disclosure is administered exhibits a myosin heavy chain mutation (e.g., on chromosome 14 q11.2-3, e.g., MYH7). In some embodiments, the patient exhibits a β-myosin heavy chain mutation (e.g., on chromosome 14 q11.2-3, e.g., MYH7). In some embodiments, the patient exhibits an insertion/deletion polymorphism in the gene encoding for angiotensin converting enzyme (e.g., ACE). In some embodiments, the patient with the insertion/deletion polymorphism in the gene encoding for ACE exhibits more marked hypertrophy of the left ventricle. In some embodiments, the patient exhibits a troponin mutation (e.g., troponin T or troponin C). In some embodiments, the patient exhibits a myosin binding protein C (MYBPC) mutation. In some embodiments, the patient exhibits a myosin 7 mutation. In some embodiments, the patient exhibits multiple mutations selected from troponin, RLC, MYBPC, myosin 7, myosin heavy chain, and ACE. In some embodiments, the patient exhibits multiple mutations selected from troponin, RLC, MYBPC, and myosin 7.

In some embodiments, the patient to which a compound of the present disclosure is administered exhibits a myosin regulatory light chain mutation (e.g., E22K mutation). In some embodiments, the myosin regulatory light chain mutation disturbs the interaction of myosin regulatory light chain with myosin heavy chain. In some embodiments, the disturbance in the interaction between myosin regulatory light chain and myosin heavy chain leads to structural abnormalities in the myosin cross bridge (e.g., in the myosin cross bridge, e.g., in the lever arm of the myosin cross bridge). In some embodiments, the mutation in the myosin regulatory light chain leads to reduced contractility. In some embodiments, the mutation in the myosin regulatory light chain leads to decreased cardiac output.

In some embodiments, modulation of the myosin regulatory light chain overcomes a disturbance in an interaction between myosin regulatory light chain and myosin heavy chain (e.g., which leads to structural abnormalities in the myosin cross bridge, e.g., in the lever arm of the myosin cross bridge). In some embodiments, administering a compound of the present disclosure (e.g., to a patient with an RLC mutation) changes a myosin lever arm's ability to develop force. In some embodiments, the myosin lever arm's changed ability to develop force results in slowed contraction. In some embodiments, the myosin lever arm's changed ability to develop force results in accelerated relaxation. In some embodiments, the myosin lever arm's changed ability to develop force results in slowed contraction and accelerated relaxation. In some embodiments, this helps overcome mutations (e.g., that enhance the proportion of force-developing myosin heads, e.g., HCM mutations). In some embodiments, this action (e.g., slowed contraction or accelerated relaxation) is greater at low calcium (e.g., diastolic) compared to high calcium (e.g., systolic) (e.g., which may modulate its inhibitory action as the heart contracts and relaxes). In some embodiments, modulation of the myosin regulatory light chain leads to reduced contractility. In some embodiments, modulation of the myosin regulatory light chain leads to decreased cardiac output. In some embodiments, modulation of the myosin regulatory light chain leads to slowing of early contraction (e.g., resulting from slower walking of myosin heads along actin). In some embodiments, the slowing of early contraction is used to treat HCM (e.g., obstructive HCM, oHCM). In some embodiments, treatment through this mechanism is administered for genetic HCM or non-genetic HCM.

In some embodiments, one or more cardiac mutation(s) (e.g., a mutation in the myosin regulatory light chain) in a patient (e.g., a patient with HCM) modulate(s) a spatial gradient of myosin regulatory light chain phosphorylation (e.g., modulate relative to that in the heart of a patient without HCM). In some embodiments, a mutation in the myosin regulatory light chain modulates the spatial gradient of myosin regulatory light chain phosphorylation. In some embodiments, a mutation in the myosin regulatory light chain decreases cardiac torsion (e.g., so that blood is less efficiently wrung out of the heart). In some embodiments, a mutation in the myosin regulatory light chain decreases cardiac torsion by altering the mechanism by which the spatial gradient of myosin light chain phosphorylation across the heart inversely alters tension production. In some embodiments, a mutation in the myosin regulatory light chain decreases cardiac torsion by altering the mechanism by which the spatial gradient of myosin light chain phosphorylation across the heart inversely alters the stretch activation response. In some embodiments, a mutation in the myosin regulatory light chain decreases cardiac torsion by modulating a mechanism by which the spatial gradient of myosin light chain phosphorylation across the heart inversely alters tension production and the stretch activation response. In some embodiments, treatment through this mechanism is administered for genetic HCM or non-genetic HCM.

In some embodiments, modulation of the myosin regulatory light chain increases cardiac torsion in a patient (e.g., with HCM) relative to a patient without HCM. In some embodiments, modulation of myosin regulatory light chain increases torsion by modulating the spatial gradient of myosin light chain phosphorylation across the heart.

In some embodiments, the myosin regulatory light chain mutation decreases calcium-activated tension. In some embodiments, the myosin regulatory light chain mutation decreases calcium-activated stiffness. In some embodiments, the myosin regulatory light chain mutation reduces myofilament $Ca^{2+}$ sensitivity. In some embodiments, modulation of the myosin regulatory light chain increases calcium-activated tension. In some embodiments, modulation of the myosin regulatory light chain increases calcium-activated stiffness. In some embodiments, modulation of the myosin regulatory light chain increases myofilament $Ca^{2+}$ sensitivity. In some embodiments, upon administration of a compound or salt of the present disclosure, changes in calcium sensitivity are length dependent. In some embodiments, upon administration of a compound or salt of the present disclosure, changes in calcium sensitivity are length dependent (e.g., except with decreases in calcium sensitivity at long sarcomere lengths). In some embodiments, administering a compound of the present disclosure changes calcium sensitivity. In some embodiments, administering a compound of the present disclosure changes calcium sensitivity when the sarcomere is stretched. In some embodiments, treatment through this mechanism is administered for genetic HCM or non-genetic HCM.

In an aspect, a compound or salt of the present disclosure (e.g., a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep)) selectively inhibits function of ventricular myosin. In some embodiments, a compound of the present disclosure selectively inhibits function of atrial myosin. In some embodiments, a compound of the present disclosure selectively inhibits function of skeletal myosin. In some embodiments, a compound of the present disclosure selectively inhibits function of ventricular myosin relative to atrial myosin. In some embodiments, a compound of the present disclosure selectively inhibits function of ventricular myosin relative to skeletal myosin. In some embodiments, a compound of the present disclosure selectively inhibits function of ventricular myosin relative to atrial myosin and skeletal myosin. In some embodiments, a compound of the present disclosure selectively inhibits function of atrial myosin relative to ventricular myosin. In some embodiments, a compound of the present disclosure selectively inhibits function of atrial myosin relative to skeletal myosin. In some embodiments, a compound of the present disclosure selectively inhibits function of atrial myosin relative to ventricular myosin and skeletal myosin. In some embodiments, a compound of the present disclosure selectively inhibits function of skeletal myosin relative to atrial myosin. In some embodiments, a compound of the present disclosure selectively inhibits function of skeletal myosin relative to ventricular myosin. In some embodiments, a compound of the present disclosure selectively inhibits function of skeletal myosin relative to atrial myosin and ventricular myosin. In an aspect, a compound or salt of the present disclosure selectively activates function of ventricular myosin. In some embodiments, a compound of the present disclosure selectively activates function of atrial myosin. In some embodiments, a compound of the present disclosure selectively activates function of skeletal myosin. In some embodiments, a compound of the present disclosure selectively activates function of ventricular myosin relative to atrial myosin. In some embodiments, a compound of the present disclosure selectively activates function of ventricular myosin relative to skeletal myosin. In some embodiments, a compound of the present disclosure selectively activates function of ventricular myosin relative to atrial myosin and skeletal myosin. In some embodiments, a compound of the present disclosure selectively activates function of atrial myosin relative to ventricular myosin. In some embodiments, a compound of the present disclosure selectively activates function of atrial myosin relative to skeletal myosin. In some embodiments, a compound of the present disclosure selectively activates function of atrial myosin relative to ventricular myosin and skeletal myosin. In some embodiments, a compound of the present disclosure selectively activates function of skeletal myosin relative to atrial myosin. In some embodiments, a compound of the present disclosure selectively activates function of skeletal myosin relative to ventricular myosin. In some embodiments, a compound of the present disclosure selectively activates function of skeletal myosin relative to atrial myosin and ventricular myosin.

In some embodiments, administering a compound or salt of the present disclosure does not modulate myosin heavy chain. In some embodiments, the compound or salt of the present disclosure does not bind myosin heavy chain. In some embodiments, the compound or salt of the present disclosure does not inhibit myosin heavy chain. In some embodiments, the compound or salt of the present disclosure does not activate myosin heavy chain.

In some embodiments, the term selective inhibition refers to a 10-fold decrease in activity (e.g., in some embodiments, selective inhibition of ventricular myosin relative to atrial myosin refers to a state wherein the $EC_{25}$ value for ventricular myosin is 10-times lower than that of atrial myosin). In some embodiments, the term selective inhibition refers to a decrease in activity that is at least about 2-fold, at least about 3-fold, at least about 4-fold, at least about 5-fold, at least about 7-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold, at least about 125-fold, at least about 150-fold, at least about 175-fold, at least about 200-fold, at least about 300-fold, at least about 400-fold, at least about 500-fold, at least about 600-fold, at least about 700-fold, at least about 800-fold, at least about 900-fold, at least about 1000-fold, at least about 2000-fold, at least about 10,000-fold, or more. Alternatively, or in addition, in some embodiments, the term selective inhibition refers to a decrease in activity that is at most about 2-fold, at most about 3-fold, at most about 4-fold, at most about 5-fold, at most about 7-fold, at most about 10-fold, at most about 15-fold, at most about 20-fold, at most about 30-fold, at most about 40-fold, at most about 50-fold, at most about 60-fold, at most about 70-fold, at most about 80-fold, at most about 90-fold, at most about 100-fold, at most about 125-fold, at most about 150-fold, at most about 175-fold, at most about 200-fold, at most about 300-fold, at most about 400-fold, at most about 500-fold, at most about 600-fold, at most about 700-fold, at most about 800-fold, at most about 900-fold, at most about 1000-fold, at most about 2000-fold, at most about 10,000-fold, or less. In some embodiments, the term selective inhibition refers to a decrease in activity that is about 1-fold to about 5,000-fold. In some embodiments, the term selective inhibition refers to a decrease in activity that is at least about 1-fold. In some embodiments, the term selective inhibition refers to a decrease in activity that is at most about 5,000-fold. In some embodiments, the term selective inhibition refers to a decrease in activity that is about 1-fold to about 2-fold, about 1-fold to about 5-fold, about 1-fold to about 10-fold, about 1-fold to about 25-fold, about 1-fold to about 50-fold, about 1-fold to about 75-fold, about 1-fold to about 100-fold, about 1-fold to about 200-fold, about 1-fold to about 500-fold, about 1-fold to about 1,000-fold, about 1-fold to about 5,000-fold, about 2-fold to about 5-fold, about 2-fold to about 10-fold, about 2-fold to about 25-fold, about 2-fold to about 50-fold, about 2-fold to about 75-fold, about 2-fold to about 100-fold, about 2-fold to about 200-fold, about 2-fold to about 500-fold, about 2-fold to about 1,000-fold, about 2-fold to about 5,000-fold, about 5-fold to about 10-fold, about 5-fold to about 25-fold, about 5-fold to about 50-fold, about 5-fold to about 75-fold, about 5-fold to about 100-fold, about 5-fold to about 200-fold, about 5-fold to about 500-fold, about 5-fold to about 1,000-fold, about 5-fold to about 5,000-fold, about 10-fold to about 25-fold, about 10-fold to about 50-fold, about 10-fold to about 75-fold, about 10-fold to about 100-fold, about 10-fold to about 200-fold, about 10-fold to about 500-fold, about 10-fold to about 1,000-fold, about 10-fold to about 5,000-fold, about 25-fold to about 50-fold, about 25-fold to about 75-fold, about 25-fold to about 100-fold, about 25-fold to about 200-fold, about 25-fold to about 500-fold, about 25-fold to about 1,000-fold, about 25-fold to about 5,000-fold, about 50-fold to about 75-fold, about 50-fold to about 100-fold, about 50-fold to about 200-fold, about 50-fold to about 500-fold, about 50-fold to about 1,000-fold, about 50-fold to about 5,000-fold, about 75-fold to about 100-fold, about 75-fold to about 200-fold, about 75-fold to about 500-fold, about 75-fold to about 1,000-fold, about 75-fold to about 5,000-fold, about 100-fold to about 200-fold, about 100-fold to about 500-fold, about 100-fold to about 1,000-fold, about 100-fold to about 5,000-fold, about 200-fold to about 500-fold, about 200-fold to about 1,000-fold, about 200-fold to about 5,000-fold, about 500-fold to about 1,000-fold, about 500-fold to about 5,000-fold, or about 1,000-fold to about 5,000-fold, or about 2-fold to about 10,000 fold. In some embodiments, the term selective inhibition refers to a decrease in activity that is about 1-fold, about 2-fold, about 5-fold, about 10-fold, about 25-fold, about 50-fold, about 75-fold, about 100-fold, about 200-fold, about 500-fold, about 1,000-fold, about 5,000-fold, about 10,000-fold, or 100,000-fold.

In some embodiments, the term selective activation refers to a 10-fold increase in activity (e.g., in some embodiments, selective activation of ventricular myosin relative to atrial myosin refers to a state wherein the $EC_{25}$ value for ventricular myosin is 10-times higher than that of atrial myosin). In some embodiments, the term selective activation refers to an increase in activity that is at least about 2-fold, at least about 3-fold, at least about 4-fold, at least about 5-fold, at least about 7-fold, at least about 10-fold, at least about 15-fold, at least about 20-fold, at least about 30-fold, at least about 40-fold, at least about 50-fold, at least about 60-fold, at least about 70-fold, at least about 80-fold, at least about 90-fold, at least about 100-fold, at least about 125-fold, at least about 150-fold, at least about 175-fold, at least about 200-fold, at least about 300-fold, at least about 400-fold, at least about 500-fold, at least about 600-fold, at least about 700-fold, at least about 800-fold, at least about 900-fold, at least about 1000-fold, at least about 2000-fold, at least about 10,000-fold, or more. Alternatively, or in addition, in some embodiments, the term selective activation refers to an increase in activity that is at most about 2-fold, at most about 3-fold, at most about 4-fold, at most about 5-fold, at most about 7-fold, at most about 10-fold, at most about 15-fold, at most about 20-fold, at most about 30-fold, at most about 40-fold, at most about 50-fold, at most about 60-fold, at most about 70-fold, at most about 80-fold, at most about 90-fold, at most about 100-fold, at most about 125-fold, at most about 150-fold, at most about 175-fold, at most about 200-fold, at most about 300-fold, at most about 400-fold, at most about 500-fold, at most about 600-fold, at most about 700-fold, at most about 800-fold, at most about 900-fold, at most about 1000-fold, at most about 2000-fold, at most about 10,000-fold, or less. In some embodiments, the term selective activation refers to an increase in activity that is about 1-fold to about 5,000-fold. In some embodiments, the term selective activation refers to an increase in activity that is at least about 1-fold. In some embodiments, the term selective activation refers to an increase in activity that is at most about 5,000-fold. In some embodiments, the term selective activation refers to an increase in activity that is about 1-fold to about 2-fold, about 1-fold to about 5-fold, about 1-fold to about 10-fold, about 1-fold to about 25-fold, about 1-fold to about 50-fold, about 1-fold to about 75-fold, about 1-fold to about 100-fold, about 1-fold to about 200-fold, about 1-fold to about 500-fold, about 1-fold to about 1,000-fold, about 1-fold to about 5,000-fold, about 2-fold to about 5-fold, about 2-fold to about 10-fold, about 2-fold to about 25-fold, about 2-fold to about 50-fold, about 2-fold to about 75-fold, about 2-fold to about 100-fold, about 2-fold to about 200-fold, about 2-fold to about 500-fold, about 2-fold to about 1,000-fold, about 2-fold to about 5,000-fold, about 5-fold to about 10-fold, about 5-fold to about 25-fold, about 5-fold to about 50-fold, about 5-fold to about 75-fold, about 5-fold to about 100-fold, about 5-fold to about 200-fold, about 5-fold to about 500-fold, about 5-fold to about 1,000-fold, about 5-fold to about 5,000-fold, about 10-fold to about 25-fold, about 10-fold to about 50-fold, about 10-fold to about 75-fold, about 10-fold to about 100-fold, about 10-fold to about 200-fold, about 10-fold to about 500-fold, about 10-fold to about 1,000-fold, about 10-fold to about 5,000-fold, about 25-fold to about 50-fold, about 25-fold to about 75-fold, about 25-fold to about 100-fold, about 25-fold to about 200-fold, about 25-fold to about 500-fold, about 25-fold to about 1,000-fold, about 25-fold to about 5,000-fold, about 50-fold to about 75-fold, about 50-fold to about 100-fold, about 50-fold to about 200-fold, about 50-fold to about 500-fold, about 50-fold to about 1,000-fold, about 50-fold to about 5,000-fold, about 75-fold to about 100-fold, about 75-fold to about 200-fold, about 75-fold to about 500-fold, about 75-fold to about 1,000-fold, about 75-fold to about 5,000-fold, about 100-fold to about 200-fold, about 100-fold to about 500-fold, about 100-fold to about 1,000-fold, about 100-fold to about 5,000-fold, about 200-fold to about 500-fold, about 200-fold to about 1,000-fold, about 200-fold to about 5,000-fold, about 500-fold to about 1,000-fold, about 500-fold to about 5,000-fold, or about 1,000-fold to about 5,000-fold, or about 2-fold to about 10,000 fold. In some embodiments, the term selective activation refers to an increase in activity that is about 1-fold, about 2-fold, about 5-fold, about 10-fold, about 25-fold, about 50-fold, about 75-fold, about 100-fold, about 200-fold, about 500-fold, about 1,000-fold, or about 5,000-fold.

In an aspect, the present disclosure provides methods of treating atrial cardiopathy, Heart failure with ejection fraction (e.g., Heart failure with preserved ejection fraction (HFpEF), Heart failure with reduced ejection fraction (HFrEF)), arrhythmia (e.g., Atrial fibrillation), stroke (e.g., Cardioembolic stroke, Cryptogenic stroke), valve disease (e.g., Mitral valve disease, or Tricuspid valve disease), comprises administering an atrial-selective agent. In an aspect, the present disclosure provides methods of treating atrial cardiopathy, Heart failure with preserved ejection fraction (HFpEF), Heart failure with reduced ejection fraction (HFrEF), Atrial fibrillation, Cardioembolic stroke, Cryptogenic stroke, Mitral valve disease, or Tricuspid valve disease, comprises administering an atrial-selective agent. In an aspect, the present disclosure provides methods of treating atrial cardiopathy. In some embodiments, the present disclosure provides a method of treating HFpEF. In some embodiments, the present disclosure provides a method of treating HFrEF. In some embodiments, the present disclosure provides a method of treating Atrial fibrillation. In some embodiments, the present disclosure provides a method of treating Cardioembolic stroke. In some embodiments, the present disclosure provides a method of treating Cryptogenic stroke. In some embodiments, the present disclosure provides a method of treating Mitral valve disease. In some embodiments, the present disclosure provides a method of treating Tricuspid valve disease.

In some embodiments, the present disclosure provides a method of treating one or more diseases selected from atrial cardiopathy, HFpEF, HFrEF, Atrial fibrillation, Cardioembolic stroke, Cryptogenic stroke, Mitral valve disease, and Tricuspid valve disease. In some embodiments, the method comprises administering a compound of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In some embodiments, the compound of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) is for use in treating one or more diseases selected from atrial cardiopathy, HFpEF, HFrEF, Atrial fibrillation, Cardioembolic stroke, Cryptogenic stroke, Mitral valve disease, and Tricuspid valve disease, comprises an atrial-selective agent. In some embodiments, the atrial-selective agent selectively inhibits atrial myosin relative to ventricular myosin or relative to skeletal myosin. In some embodiments, the atrial-selective agent selectively inhibits atrial myosin regulatory light chain relative to ventricular myosin regulatory light chain, or relative to skeletal myosin regulatory light chain, or relative to both atrial myosin regulatory light chain and skeletal myosin regulatory light chain. In an aspect, the present disclosure provides a method of treating activity-induced muscle damage, a movement disorder, a neuromuscular condition, or a metabolic myopathy, the method comprising administering a compound or salt of the present disclosure to a subject in need thereof. In some embodiments, the compound or salt of the present disclosure inhibits skeletal muscle myosin. In some embodiments, said movement disorder comprises muscle spasticity. In some embodiments, said muscle spasticity may be selected from spasticity associated with multiple sclerosis, Parkinson's disease, Alzheimer's disease, or cerebral palsy, or injury, or a traumatic event such as stroke, traumatic brain injury, spinal cord injury, hypoxia, meningitis, encephalitis, phenylketonuria, or amyotrophic lateral sclerosis.

Methods of administration of a compound or salt of the present disclosure discussed herein may be used for the treatment of cardiac conditions. In an aspect, the present disclosure provides a method of treating a condition selected from hypertrophic cardiomyopathy (HCM); heart failure with preserved ejection fraction (HFpEF); disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; ischemia; and angina. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefllers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In an aspect, the present disclosure provides a method of treating hypertrophic cardiomyopathy or a related condition comprising administering to a subject in need thereof a compound or salt disclosed herein.

In an aspect, the present disclosure provides a method of treating obstructive hypertrophic cardiomyopathy comprising administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

In an aspect, the present disclosure provides a method of administering to a subject in need thereof a compound or salt disclosed herein. In an aspect, the present disclosure provides a method of treating non-obstructive hypertrophic cardiomyopathy comprising administering to a subject in need thereof a compound or salt of disclosed herein. In an aspect, the present disclosure provides a method of treating heart failure with preserved ejection fraction comprising administering to a subject in need thereof a compound or disclosed herein. In an aspect, the present disclosure provides a method of treating left ventricle stiffness comprising administering to a subject in need thereof a compound or salt disclosed herein.

Skeletal Muscle Myosin

In an aspect, methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the modulation of skeletal muscle myosin. In some embodiments, the modulation of skeletal muscle myosin is inhibition of skeletal muscle myosin. In an aspect, methods of administration of a compound or salt of the present disclosure may be used for the treatment of one or more neuromuscular condition(s) or movement disorder(s) or activity-induced muscle damage or one or more metabolic myopathy (myopathies). In an aspect, the present disclosure provides a method of treating a myopathy of skeletal muscle.

In some embodiments, the present disclosure provides a method of modulating certain aspects of cardiac myopathy (e.g., HR, FS, EDV, IVRT, EF, IVCT, Pre-ejection period, E, A, or e') in a patient who also has one or more condition(s) that include(s) a cardiac myopathy (e.g. BMD, or DMD, or other neuromuscular conditions).

In some embodiments, skeletal muscle is mainly composed of two types of fibers, slow-twitch muscle fiber (e.g., type I) and fast-twitch muscle fiber (e.g., type II). In each muscle, the two types of fibers may be configured in a mosaic-like arrangement, e.g., with differences in fiber type composition in different muscles and at different points in growth and development. Slow-twitch muscle fibers may have excellent aerobic energy production ability. Contraction rate of the slow-twitch muscle fiber may be low. but tolerance to fatigue may be high. Slow-twitch muscle fibers may have a higher concentration of mitochondria and myoglobin than do fast-twitch fibers and may be surrounded by more capillaries than are fast-twitch fibers. Slow-twitch fibers may contract at a slower rate due to lower myosin ATPase activity and produce less power compared to fast-twitch fibers, but they may be able to maintain contractile function over longer-terms, such as in stabilization, postural control, and endurance exercises.

Fast twitch muscle fibers in humans may be further divided into two main fiber types depending on the specific fast skeletal myosin they express (Type IIa, IIx/d). A third type of fast fiber (Type IIb) exists in other mammals but may be rarely identified in human muscle. Fast-twitch muscle fibers may have excellent anaerobic energy production ability and are able to generate high amounts of tension over a short period of time. Typically, fast-twitch muscle fibers may have lower concentrations of mitochondria, myoglobin, and capillaries compared to slow-twitch fibers, and thus can fatigue more quickly. Fast-twitch muscles may produce quicker force required for power and resistance activities.

The proportion of the type I and type II can vary in different individuals. For example, non-athletic individuals can have close to 50% of each muscle fiber types. Power athletes can have a higher ratio of fast-twitch fibers, e.g., 70-75% type II in sprinters. Endurance athletes can have a higher ratio of slow-twitch fibers, e.g., 70-80% in distance runners. The proportion of the type I and type II fibers can also vary depending on the age of an individual. The proportion of type II fibers, especially the type Ix, can decline as an individual ages, resulting in a loss in lean muscle mass. The proportion of type II fibers can also increase with fat mass.

The contractile action of skeletal muscle may lead to muscle damage in subjects with neuromuscular disease, e.g., DMD, and this damage may be more prevalent in fast fibers. It has been observed that acute force drop after lengthening injury may be greater in predominantly fast type II fiber muscles compared to predominantly slow type I fiber muscles in dystrophy mouse models. The degree of acute force drop and histological damage in dystrophy mouse models may be proportional to peak force development during lengthening injury. Excessive contraction-induced injuries, which may precede the inflammation and irreversible fibrosis that may characterize late-stage DMD pathology. Contraction-induced muscle damage in these patients may be reduced by limiting peak force generation in type II fibers and possibly increasing reliance on healthier type I fibers.

When healthy muscle is subjected to excessive, unaccustomed exercise, it develops soreness and sustained reductions in strength and range of motion. Proteins also leak from injured muscle fibers into circulation, including creatine kinase (CK), lactate dehydrogenase and myoglobin. These biomarkers are not unique to either fast or slow fibers and so do not provide detail regarding differences in fiber responses to injury. Troponin I (TNNI) is a component of the troponin complex that controls initiation of contraction of muscle by calcium. It is distinct in that there is a different isoform for each type of striated muscle: TNNI1 in slow skeletal muscle, TNNI2 in fast skeletal muscle and TNNI3 in cardiac muscle. Selective enzyme-linked immunosorbent assays (ELISAs) have been used to demonstrate that TNNI2 but not TNNI1 is elevated in circulation after injurious exercise, even under extreme conditions.

DMD and BMD are caused by an absence (DMD) or truncation (BMD) of the dystrophin protein. Dystrophin provides a structural link between the actin cytoskeleton and the basement membrane through the dystrophin-glycoprotein complex. When dystrophin is absent or truncated, contraction of muscle leads to heightened muscle stress and injury with normal use. While the sensitivity to injury is much higher in DMD muscle than in BMD or healthy muscle, fast fibers still appear to be more susceptible than slow fibers, with young DMD patients exhibiting histological evidence of disruption in fast fibers and early loss of type Ix fibers. These fibers may leak muscle contents, such as troponin, creatine kinase, or myoglobin.

Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for inhibiting or activating muscle myosin II (e.g., skeletal muscle myosin II). In some embodiments, the compounds and salts thereof may be used to treat activity-induced muscle damage. In some embodiments, the compounds may be used to treat neuromuscular conditions and movement disorders (which may comprise spasticity).

Methods of administration of a compound or salt of the present disclsosure discussed herein may be used for the treatment of activity-induced muscle damage, neuromuscular conditions, movement disorders, or metabolic myopathies. In some embodiments, activity-induced muscle damage, neuromuscular conditions, movement disorders, or metabolic myopathies are treated through administration of a skeletal inhibitor. Examples of neuromuscular conditions include but are not limited to Duchenne muscular dystrophy, Becker muscular dystrophy, myotonic dystrophy 1, myotonic dystrophy 2, facioscapulohumeral muscular dystrophy, oculopharyngeal muscular dystrophy, limb girdle muscular dystrophies, tendinitis and carpal tunnel syndrome. Examples of movement disorders include but are not limited to muscle spasticity disorders, spasticity associated with multiple sclerosis, Parkinson's disease, Alzheimer's disease, or cerebral palsy, or injury or a traumatic event such as stroke, traumatic brain injury, spinal cord injury, hypoxia, meningitis, encephalitis, phenylketonuria, or amyotrophic lateral sclerosis. Also included are other conditions that may respond to the inhibition or activation of skeletal myosin II, skeletal troponin C, skeletal troponin I, skeletal tropomyosin, skeletal troponin T, skeletal regulatory light chains, skeletal myosin binding protein C or skeletal actin. In some embodiments, neuromuscular conditions and movement disorders are selected from muscular dystrophies and myopathies. In some embodiments, muscular dystrophies are diseases that cause progressive weakness and loss of muscle mass where abnormal genes (mutations) interfere with the production of proteins needed to form healthy muscle. In some embodiments, muscular dystrophies are selected from Becker muscular dystrophy (BMD), Congenital muscular dystrophies (CMD), Duchenne muscular dystrophy (DMD), Emery-Dreifuss muscular dystrophy (EDMD), Facioscapulohumeral muscular dystrophy (FSHD), Limb-girdle muscular dystrophies (LGMD), Myotonic dystrophy (DM), and Oculopharyngeal muscular dystrophy (OPMD). In some embodiments, Congenital muscular dystrophies (CMD) is selected from Bethlem CMD, Fukuyama CMD, Muscle-eye-brain diseases (MEBs), Rigid spine syndromes, Ullrich CMD, and Walker-Warburg syndromes (WWS). In some embodiments, myopathies are diseases of muscle that are not caused by nerve disorders. Myopathies may cause the muscles to become weak or shrunken (atrophied). In some embodiments, myopathies are selected from congenital myopathies, distal myopathies, endocrine myopathies, inflammatory myopathies, metabolic myopathies, myofibrillar myopathies (MFM), scapuloperoneal myopathy, and cardiomyopathies. In some embodiments, congenital myopathies are selected from cap myopathies, centronuclear myopathies, congenital myopathies with fiber type disproportion, core myopathies, central core disease, multiminicore myopathies, myosin storage myopathies, myotubular myopathy, and nemaline myopathies. In some embodiments, distal myopathies are selected from, gne myopathy/Nonaka myopathy/hereditary inclusion-body myopathy (HIBM), laing distal myopathy, Markesbery-Griggs late-onset distal myopathy, Miyoshi myopathy, Udd myopathy/tibial muscular dystrophy, VCP myopathy/IBMPFD, vocal cord and pharyngeal distal myopathy, and Welander distal myopathy. In some embodiments, endocrine myopathies are selected from, hyperthyroid myopathy, and hypothyroid myopathy. In some embodiments, inflammatory myopathies are selected from, dermatomyositis, inclusion-body myositis, and polymyositis. In some embodiments, metabolic myopathies are selected from, von Gierke's disease, Anderson disease, Fanconi-Bickel syndrome, aldolase A deficiency, acid maltase deficiency (Pompe disease), camitine deficiency, camitine palmitoyltransferase deficiency, debrancher enzyme deficiency (Cori disease, Forbes disease), lactate dehydrogenase deficiency, myoadenylate deaminase deficiency, phosphofructokinase deficiency (Tarui disease), phosphoglycerate kinase deficiency, phosphoglycerate mutase deficiency (Her's disease), and phosphorylase deficiency (e.g. McArdle's disease). In some embodiments, metabolic myopathies are selected from McArdle's disease. In some embodiments, cardiomyopathies are selected from intrinsic cardiomyopathies and extrinsic cardiomyopathies. In some embodiments, intrinsic cardiomyopathies are selected from genetic myopathies and acquired myopathies. In some embodiments, genetic myopathies are selected from Hypertrophic cardiomyopathy, arrhythmogenic right ventricular cardiomyopathy (ARVC), LV non-compaction, ion channelopathies, dilated cardiomyopathy (DCM), and restrictive cardiomyopathy (RCM). In some embodiments, acquired myopathies are selected from stress cardiomyopathy, myocarditis, eosinophilic myocarditis, and ischemic cardiomyopathy. In some embodiments, extrinsic cardiomyopathies are selected from metabolic cardiomyopathies, endomyocardial cardiomyopathies, endocrine cardiomyopathies, and cardiofacial cardiomyopathies. In some embodiments, metabolic cardiomyopathies are selected from Fabry's disease and hemochromatosis. In some embodiments, endomyocardial cardiomyopathies are selected from endomyocardial fibrosis and Hypereosinophilic syndrome. In some embodiments, endocrine cardiomyopathies are selected from diabetes mellitus, hyperthyroidism, and acromegaly. In some embodiments, the Cardiofacial cardiomyopathy is Noonan syndrome.

In some embodiments, the disease (e.g., activity-induced muscle damage, neuromuscular condition, movement disorder, or metabolic myopathy) comprises muscle wasting. In some embodiments, the muscle wasting comprises Cachexia. In some embodiments, the Cachexia is associated with one or more cancer(s). In some embodiments, the one or more cancer(s) is selected from renal cell carcinoma. In some embodiments, the muscle wasting arises from inactivity. In some embodiments, the muscle wasting comprises acute quadriplegic myopathy. In some embodiments, the muscle wasting arises from a reaction against anesthetics. In some embodiments, the muscle wasting comprises rhabdomyolysis. In some embodiments, the muscle wasting comprises Compartment syndrome. In some embodiments, the disease comprises muscle pain. In some embodiments, the disease comprises back pain. In some embodiments, the disease comprises lower-back pain. In some embodiments, the disease comprises chronic back pain. In some embodiments, the disease comprises insomnia. In some embodiments, the disease is insomnia. In some embodiments, the compound or salt is administered in a low dose. In some embodiments, the disease is insomnia, and the compound or salt is administered in a low dose. In some embodiments, the subject in need thereof experiences enhanced strength and enhanced fatiguability. In some embodiments, the subject in need thereof does not experience muscle leakiness.

In some embodiments, the present disclosure provides methods of treating a cardiomyopathy in a patient with a neuromuscular condition (e.g., Duchenne Muscular Dystrophy, Becker Muscular Dystrophy, Limb-Girdle Muscular Dystrophy, e.g., susceptible LGMD), the methods comprising administering a compound or salt of the present disclosure.

In an aspect, methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the modulation of skeletal muscle myosin. In some embodiments, the modulation of skeletal muscle myosin is activation of skeletal muscle myosin. In some embodiments, the compound or salt of the present disclosure is an activator of myosin ATP-ase. Methods of administration of a compound or salt of the present disclosure may be used for the treatment of metabolic diseases and disorders. Examples of metabolic diseases and disorders include but are not limited to: obesity, morbid obesity, super morbid obesity, pre-diabetes, diabetes, (e.g., type 1 diabetes, type 2 diabetes), or metabolic syndrome (e.g., comprising one or more of the following: high blood pressure, high blood sugar, too much body fat around the waist, or irregular cholesterol levels). In some embodiments, the subject's blood pressure exceeds about 130/85 mmHg. In some embodiments, the subject's fasting blood sugar levels exceeds about 100 mg/dL. In some embodiments, the subject's triglyceride levels exceeds about 150 mg/dL. In some embodiments, the subject's HDL cholesterol levels is lower than about 50 mg/dL for men or about 40 mg/dL for women. In some embodiments, the subject's waist circumference exceeds about 40 in for men or 35 inches for women.

In an aspect, the present disclosure provides a method of treating a metabolic condition or a related condition, in a subject in need thereof, the method comprising administering a compound or salt of the present disclosure (e.g., a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In an aspect, the present disclosure provides a method of treating obesity or a related condition, in a subject in need thereof, the method comprising administering a compound or salt of the present disclosure. In some embodiments, the compound or salt of the present disclosure is an activator of myosin (e.g., skeletal myosin, ventricular myosin, or atrial myosin). In some embodiments, the compound or salt of the present disclosureis an activator of skeletal myosin.

In some embodiments, the present disclosure provides a method of inducing fast fiber ATPase activation in a patient in need thereof.

In an aspect, the present disclosure provides a method of inducing weight loss, in a subject in need thereof, the method comprising administering a compound or salt of the present disclosure (e.g., a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep)). In some embodiments, the present disclosure provides a method of inducing weight loss without necessarily increasing muscle mass by increasing basal metabolic rate, the method comprising administering a compound or salt of the present disclosure. Alternatively, in some embodiments, muscle mass is increased. In some embodiments, the present disclosure provides a method of inducing weight loss without necessarily increasing muscle mass by increasing basal metabolic rate, the method comprising administering a compound or salt of the present disclosure. In some embodiments, the present disclosure provides a method of preventing muscle loss in the background of one or more other weight loss strategie(s) (e.g., diet, exercise, or incretin therapeutics). In some embodiments, the compound of the present disclosure has a Rabbit Psoas Y125 value (e.g., a value corresponding to 125% activity relative to activity in the absence of exogenous compound) in Table 8. In some embodiments, the compound of the present disclosure does not have Rabbit Psoas Y75 value in Table 8 (e.g., because it does not inhibit skeletal muscle myosin). In some embodiments, the activation of skeletal muscle myosin increases baseline metabolic rate. In some embodiments, the activation of skeletal muscle myosin increases daily ATP consumption. In some embodiments, the activation of skeletal muscle myosin increases daily ATP consumption without necessarily increasing muscle mass. In some embodiments, the activation of skeletal muscle myosin increases daily ATP consumption, without necessarily increasing muscle mass, and decreases body fat. In some embodiments, the method comprises administering a compound or salt that is an activator of skeletal muscle myosin. In some embodiments, the method comprises administering a compound or salt that has a Rabbit Psoas Y125 value in Table 8. In some embodiments, the method comprises administering a compound or salt that does not have a Rabbit Psoas Y75 value in Table 8.

In some embodiments, the subject in need thereof is overweight, obese, morbidly obese, or super morbidly obese. In some embodiments, the subject in need thereof exhibits Class I, Class II, or Class III obesity. In some embodiments, obesity of the subject is linked to genetic factors.

In some embodiments, administering a compound or salt of the present disclosure does not change muscle mass. In some embodiments, administering a compound or salt of the present disclsoure increases resting fast muscle ATP turnover without changes in baseline tension. In some embodiments, administering a compound or salt of the present disclosure prevents muscle loss that occurs with obesity treatments (e.g., diet, exercise, SGLT2/GLP1/bariatric surgery, other surgeries)

In some embodiments, increases to baseline energy consumption in skeletal muscle leads to weight loss in a patient in need there of In some embodiments, increases to baseline energy consumption in skeletal muscle leads to positive health impacts other than weight loss (e.g., in addition to weight loss), such as, for example, glycemic control (e.g., in T2D) or alleviation of another condition. In some embodiments, the subject exhibits one or more condition(s) (or exhibits elevated risk of the one or more condition(s)), and administration of a compound or salt of the present disclosure alleviates or treats one or more of condition(s) (or alleviates risk of the one or more condition(s)), selected from: cardiovascular disease, pre-diabetes, diabetes (e.g., type 2 diabetes, type 1 diabetes), osteoarthritis, polycystic ovary syndrome, infertility, sleep apnea (e.g., obstructive sleep apnoea), breathing problems, asthma, a substance abuse disorder (e.g., alcoholism or addiction), peripheral vascular disease, venous thromboembolism, fatty liver (e.g., Nonalcoholic steatohepatitis (NASH), or nonalcoholic fatty liver disease (NAFLD)), high blood pressure, high LDL cholesterol, low HDL cholesterol, high levels of triglycerides, coronary heart disease, gallbladder disease, cancer, mental illness (e.g., depression, anxiety), addiction (e.g., alcoholism), chronic pain, long COVID, difficulty with physical functioning, stroke, and paralysis (e.g., full or partial paralysis). In some embodiments, the subject has experienced weight gain as a result of treatment for one or more diseases (e.g., through administration of certain psychiatric medications).

In some embodiments, the subject in need thereof has a BMI of at least about 15 $kg/m^2$, at least about 16 $kg/m^2$, at least about 17 $kg/m^2$, at least about 18 $kg/m^2$, at least about 19 $kg/m^2$, at least about 20 $kg/m^2$, at least about 21 $kg/m^2$, at least about 22 $kg/m^2$, at least about 23 $kg/m^2$, at least about 24 $kg/m^2$, at least about 25 $kg/m^2$, at least about 26 $kg/m^2$, at least about 27 $kg/m^2$, at least about 28 $kg/m^2$, at least about 29 $kg/m^2$, at least about 30 $kg/m^2$, at least about 31 $kg/m^2$, at least about 32 $kg/m^2$, at least about 33 $kg/m^2$, at least about 34 $kg/m^2$, at least about 35 $kg/m^2$, at least about 36 $kg/m^2$, at least about 37 $kg/m^2$, at least about 38 $kg/m^2$, at least about 39 $kg/m^2$, at least about 40 $kg/m^2$, at least about 41 $kg/m^2$, at least about 42 $kg/m^2$, at least about 43 $kg/m^2$, at least about 44 $kg/m^2$, at least about 45 $kg/m^2$, at least about 46 $kg/m^2$, at least about 47 $kg/m^2$, at least about 48 $kg/m^2$, at least about 49 $kg/m^2$, at least about 50 $kg/m^2$, at least about 51 $kg/m^2$, at least about 52 $kg/m^2$, at least about 53 $kg/m^2$, at least about 54 $kg/m^2$, at least about 55 $kg/m^2$, at least about 56 $kg/m^2$, at least about 57 $kg/m^2$, at least about 58 $kg/m^2$, at least about 59 $kg/m^2$, at least about 60 $kg/m^2$, at least about 65 $kg/m^2$, at least about 70 $kg/m^2$, at least about 75 $kg/m^2$, at least about 80 $kg/m^2$, or more. Alternatively, or in addition, in some embodiments, the subject has a BMI of at most about 15, at most about 16, at most about 17, at most about 18, at most about 19, at most about 20, at most about 21, at most about 22, at most about 23, at most about 24, at most about 25, at most about 26, at most about 27, at most about 28, at most about 29, at most about 30, at most about 31, at most about 32, at most about 33, at most about 34, at most about 35, at most about 36, at most about 37, at most about 38, at most about 39, at most about 40, at most about 41, at most about 42, at most about 43, at most about 44, at most about 45, at most about 46, at most about 47, at most about 48, at most about 49, at most about 50, at most about 51, at most about 52, at most about 53, at most about 54, at most about 55, at most about 56, at most about 57, at most about 58, at most about 59, at most about 60, at most about 65, at most about 70, at most about 75, at most about 80, or less. In some embodiments, the subject has a BMI of about 24 to about 55. In some embodiments, the subject has a BMI of at least about 24. In some embodiments, the subject has a BMI of at most about 55. In some embodiments, the subject has a BMI of about 24 to about 26, about 24 to about 28, about 24 to about 30, about 24 to about 32, about 24 to about 34, about 24 to about 36, about 24 to about 38, about 24 to about 40, about 24 to about 45, about 24 to about 50, about 24 to about 55, about 26 to about 28, about 26 to about 30, about 26 to about 32, about 26 to about 34, about 26 to about 36, about 26 to about 38, about 26 to about 40, about 26 to about 45, about 26 to about 50, about 26 to about 55, about 28 to about 30, about 28 to about 32, about 28 to about 34, about 28 to about 36, about 28 to about 38, about 28 to about 40, about 28 to about 45, about 28 to about 50, about 28 to about 55, about 30 to about 32, about 30 to about 34, about 30 to about 36, about 30 to about 38, about 30 to about 40, about 30 to about 45, about 30 to about 50, about 30 to about 55, about 32 to about 34, about 32 to about 36, about 32 to about 38, about 32 to about 40, about 32 to about 45, about 32 to about 50, about 32 to about 55, about 34 to about 36, about 34 to about 38, about 34 to about 40, about 34 to about 45, about 34 to about 50, about 34 to about 55, about 36 to about 38, about 36 to about 40, about 36 to about 45, about 36 to about 50, about 36 to about 55, about 38 to about 40, about 38 to about 45, about 38 to about 50, about 38 to about 55, about 40 to about 45, about 40 to about 50, about 40 to about 55, about 45 to about 50, about 45 to about 55, or about 50 to about 55. In some embodiments, the subject has a BMI of about 24, about 26, about 28, about 30, about 32, about 34, about 36, about 38, about 40, about 45, about 50, or about 55, wherein the units are $kg/m^2$. In some embodiments, the subject in need thereof has a BMI of about 18.5-24.9 $kg/m^2$.

In some embodiments, the subject in need thereof has a body fat percentage of at least about 10%, at least about 15%, at least about 20%, at least about 21%, at least about 22%, at least about 23%, at least about 24%, at least about 25%, at least about 26%, at least about 27%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, or more. Alternatively, or in addition, in some embodiments, the subject has a body fat percentage of at most about 10%, at most about 15%, at most about 20%, at most about 21%, at most about 22%, at most about 23%, at most about 24%, at most about 25%, at most about 26%, at most about 27%, at most about 29%, at most about 30%, at most about 31%, at most about 32%, at most about 33%, at most about 34%, at most about 35%, at most about 36%, at most about 37%, at most about 38%, at most about 39%, at most about 40%, at most about 41%, at most about 42%, at most about 43%, at most about 44%, at most about 45%, at most about 46%, at most about 47%, at most about 48%, at most about 49%, at most about 50%, at most about 51%, at most about 52%, at most about 53%, at most about 54%, at most about 55%, at most about 56%, at most about 57%, at most about 58%, at most about 59%, at most about 60%, at most about 61%, at most about 62%, at most about 63%, at most about 64%, at most about 65%, at most about 66%, at most about 67%, at most about 68%, at most about 69%, at most about 70%, at most about 71%, at most about 72%, at most about 73%, at most about 74%, at most about 75%, or less. In some embodiments, the subject has a body fat percentage of about 15% to about 70%. In some embodiments, the subject has a body fat percentage of at least about 15%. In some embodiments, the subject has a body fat percentage of at most about 70%. In some embodiments, the subject has a body fat percentage of about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 20% to about 25%, about 20% to about 30%, about 20% to about 35%, about 20% to about 40%, about 20% to about 45%, about 20% to about 50%, about 20% to about 55%, about 20% to about 60%, about 20% to about 65%, about 20% to about 70%, about 25% to about 30%, about 25% to about 35%, about 25% to about 40%, about 25% to about 45%, about 25% to about 50%, about 25% to about 55%, about 25% to about 60%, about 25% to about 65%, about 25% to about 70%, about 30% to about 35%, about 30% to about 40%, about 30% to about 45%, about 30% to about 50%, about 30% to about 55%, about 30% to about 60%, about 30% to about 65%, about 30% to about 70%, about 35% to about 40%, about 35% to about 45%, about 35% to about 50%, about 35% to about 55%, about 35% to about 60%, about 35% to about 65%, about 35% to about 70%, about 40% to about 45%, about 40% to about 50%, about 40% to about 55%, about 40% to about 60%, about 40% to about 65%, about 40% to about 70%, about 45% to about 50%, about 45% to about 55%, about 45% to about 60%, about 45% to about 65%, about 45% to about 70%, about 50% to about 55%, about 50% to about 60%, about 50% to about 65%, about 50% to about 70%, about 55% to about 60%, about 55% to about 65%, about 55% to about 70%, about 60% to about 65%, about 60% to about 70%, or about 65% to about 70%. In some embodiments, the subject has a body fat percentage of about 15%, about 20%, about 25%, about 30%, about 35%, about 40%, about 45%, about 50%, about 55%, about 60%, about 65%, or about 70%.

In some embodiments, compound 34, 504, 32, 527, 512, 31, 33, 70, or 404, or a salt of any thereof is an activator of skeletal, atrial, or ventricular myosin. In some embodiments, compound 34, 504, 32, 527, 512, 31, 33, 70, or 404, or a salt of any thereof, is an activator of skeletal myosin.

In some embodiments, compound 34, 504, 32, 527, 512, 31, 33, 70, or 404, or a salt of any thereof, modulates skeletal myosin RLC. In some embodiments, the modulation of RLC is allosteric. In some embodiments, the modulation of RLC is by direct binding.

Myosin hydrolyses ATP to drive conformational change and cyclic binding to muscle actin which regulates force of contraction. In resting (relaxed) muscle, myosin also exists in at least two additional energy states. These include a low energy state (super-relaxed or SRX) and a high energy state (disordered-relaxed or DRX). Both resting states of myosin are not engaged with actin but consume different levels of ATP. Research suggests that DRX myosin consumes approximately 5-10 times more ATP than SRX myosin.

Basal metabolic rate and skeletal muscle health can be benefited by either increasing muscle metabolic rate (e.g., increasing basal energy consumption in skeletal muscle by altering calcium or myosin ATPase) or increasing muscle turnover (e.g., increasing protein synthesis and/or degradation) by administering a compound or salt of the present disclosure. Such benefits can include an increase in protein synthesis and a decrease in fat.

In some embodiments, administering a compound or salt of the present disclosure increases basal energy states. In some embodiments, administering a compound or salt of the present disclosure modulates the population of skeletal myosin in the SRX, DRX, and actin-bound states. In some embodiments, administering a compound or salt of the present disclosure modulates the rate of ATP conversion to ADP of skeletal myosin in the SRX, DRX, and actin-bound states. In some embodiments, transition of myosin from SRX to DRX states does not change baseline tension but increases ATP consumption.

In some embodiments, compound 34, 504, 32, 527, 512, 31, 33, 70, or 404, or a salt of any thereof, is a modulator of skeletal myosin. In some embodiments, compound 34, 504, 32, 527, 512, 31, 33, 70, or 404, or a salt of any thereof, is an activator of skeletal myosin (e.g., skeletal myosin ATP-ase). In some embodiments, compound 34, 504, 32, 527, 512, 31, 33, 70, or 404, or a salt of any thereof, is an inhibitor of skeletal myosin. In some embodiments, compound 34, 504, 32, 527, 512, 31, 33, 70, or 404, or a salt of any thereof, is a modulator of skeletal myosin RLC. In some embodiments, compound 34, 504, 32, 527, 512, 31, 33, 70, or 404, or a salt of any thereof, is an activator of skeletal myosin RLC. In some embodiments, compound 34, 504, 32, 527, 512, 31, 33, 70, or 404, or a salt of any thereof, is an inhibitor of skeletal myosin RLC. In some embodiments, the modulation of RLC is allosteric. In some embodiments, the modulation is by direct binding. In some embodiments, compound 34, 504, 32, 527, 512, 31, 33, 70, or 404, or a salt of any thereof, is an activator of skeletal myosin ATP-ase.

In some embodiments, administering a compound or salt of the present disclosure modulates the population of skeletal myosin in the SRX and DRX states, thereby increasing ATP consumption without changing baseline tension. In some embodiments, administering a compound or salt of the present disclosure increases the population of muscle myosin (e.g., skeletal muscle myosin, e.g., fast muscle myosin) in the DRX state and decreases the population in the SRX state. In some embodiments, administering a compound or salt of the present disclosure increases the population of muscle myosin (e.g., skeletal muscle myosin, e.g., fast muscle myosin) in the DRX state by at least about 1%, at least about 2%, at least about 3%, at least about 5%, at least about 10%, at least about 12.5%, at least about 15%, at least about 17.5%, at least about 20%, at least about 25%, at least about 27.5%, at least about 30%, at least about 35%, at least about 40%, at least about 50%, or more. Alternatively, or in addition, in some embodiments, administering a compound or salt of the present disclosure decreases the population of muscle myosin (e.g., skeletal muscle myosin, e.g., fast muscle myosin) in the DRX state by at most about 1%, at most about 2%, at most about 3%, at most about 5%, at most about 10%, at most about 12.5%, at most about 15%, at most about 17.5%, at most about 20%, at most about 25%, at most about 27.5%, at most about 30%, at most about 35%, at most about 40%, at most about 50%, or less. In some embodiments, administering a compound or salt of the present disclosure increases the population of muscle myosin (e.g., skeletal muscle myosin, e.g., fast muscle myosin) in the DRX state (e.g., from the population in the SRX state) by about 1% to about 50%. In some embodiments, administering a compound or salt of the present disclosure increases the population of muscle myosin (e.g., skeletal muscle myosin, e.g., fast muscle myosin) in the DRX state (e.g., from the population in the SRX state) by at least about 1%. In some embodiments, administering a compound or salt of the present disclosure increases the population of muscle myosin (e.g., skeletal muscle myosin, e.g., fast muscle myosin) in the DRX state (e.g., from the population in the SRX state) by at most about 50%. In some embodiments, administering a compound or salt of the present disclosure increases the population of muscle myosin (e.g., skeletal muscle myosin, e.g., fast muscle myosin) in the DRX state (e.g., from the population in the SRX state) by about 1% to about 3%, about 1% to about 5%, about 1% to about 7.5%, about 1% to about 10%, about 1% to about 15%, about 1% to about 20%, about 1% to about 25%, about 1% to about 30%, about 1% to about 35%, about 1% to about 40%, about 1% to about 50%, about 3% to about 5%, about 3% to about 7.5%, about 3% to about 10%, about 3% to about 15%, about 3% to about 20%, about 3% to about 25%, about 3% to about 30%, about 3% to about 35%, about 3% to about 40%, about 3% to about 50%, about 5% to about 7.5%, about 5% to about 10%, about 5% to about 15%, about 5% to about 20%, about 5% to about 25%, about 5% to about 30%, about 5% to about 35%, about 5% to about 40%, about 5% to about 50%, about 7.5% to about 10%, about 7.5% to about 15%, about 7.5% to about 20%, about 7.5% to about 25%, about 7.5% to about 30%, about 7.5% to about 35%, about 7.5% to about 40%, about 7.5% to about 50%, about 10% to about 15%, about 10% to about 20%, about 10% to about 25%, about 10% to about 30%, about 10% to about 35%, about 10% to about 40%, about 10% to about 50%, about 15% to about 20%, about 15% to about 25%, about 15% to about 30%, about 15% to about 35%, about 15% to about 40%, about 15% to about 50%, about 20% to about 25%, about 20% to about 30%, about 20% to about 35%, about 20% to about 40%, about 20% to about 50%, about 25% to about 30%, about 25% to about 35%, about 25% to about 40%, about 25% to about 50%, about 30% to about 35%, about 30% to about 40%, about 30% to about 50%, about 35% to about 40%, about 35% to about 50%, or about 40% to about 50%. In some embodiments, administering a compound or salt of the present disclosure increases the population of muscle myosin (e.g., skeletal muscle myosin, e.g., fast muscle myosin) in the DRX state (e.g., from the population in the SRX state) by about 1%, about 3%, about 5%, about 7.5%, about 10%, about 15%, about 20%, about 25%, about 30%, about 35%, about 40%, or about 50%.

In some embodiments, increasing the population of muscle myosin (e.g., skeletal muscle myosin, e.g., fast muscle myosin) from an SRX to a DRX state would increase resting energy consumption (REC) (e.g., in some embodiments, increasing DRX by 30% would increase REC by approx. 154 kCal/day, e.g., assuming approximately 50% of total muscle can be fast skeletal fibers, 40% of muscle weight can be myosin, 1 ATP can bind to 1 myosin head, and that the ATPase activity of DRX myosin can be 0.03 ATP/see, 7.3 kcal mol-1 ATP consumed, and e.g., in some embodiments this would translate to 7.3 kg fat mass, wherein, e.g., 1 kg fat may equal 7700 kcal).

In some embodiments, administering a compound or salt of the present disclosure change(s) the rate of myosin (e.g., skeletal myosin) entering the DRX state, e.g., from the SRX state.

In some embodiments, phosphorylation of myosin RLC can increase with preconditioning contractions in both fast and slow fibers. In some embodiments, RLC phosphorylation can increase the population of myosin in the DRX state, e.g., disrupting the SRX helical organization. In some embodiments, such disrupting may only occur in fast fibers. In some embodiments, temperature regulation may be independent of phosphorylation, and, e.g., may inhibit phosphorylation effects on twitch potentiation of fast muscle in mammals and humans.

In some embodiments, administering a compound or salt of the present disclosure (e.g., compound 34, 504, 32, 527, 512, 31, 33, 70, or 404, or a salt of any thereof) increases contraction-induced stress (e.g., in normal skeletal muscle, e.g., muscle in a patient that does not have a neuromuscular condition, or e.g., in a patient that does not have a muscular dystrophy). In some embodiments, the contraction induced stress comprises membrane stress. In some embodiments, the contraction induced stress leads to skeletal muscle adaptation (e.g., similar to a response to exercise training). In some embodiments, membrane stress activates stem cells. In some embodiments, stress (e.g., contraction induced, membrane) leads to protein synthesis or degradation or controlled muscle injury. In some embodiments, contraction stress causes increases in muscle injury biomarkers (e.g., creatine kinase, e.g., fsTnl, myoglobin, or ssTNL). In some embodiments, contraction induced stress leads to higher baseline VO2max.

In some embodiments, MLCK phosphorylates RLC to transiently increase the proportion of DRX heads, e.g., with genetic variation in MLCK-coding genes possibly altering efficiency of phosphorylation.

In some embodiments, a compound or salt of the present disclosure is a selective (or partially selective) myosin activator. In some embodiments, a compound or salt of the present disclosure activates myosin ATPase in both native muscle and purified motor-domain preparations. In some embodiments, a compound or salt of the present disclosure increases calcium sensitivity and maximal force output, e.g., in isolated single permeabilized fast skeletal muscle fibers, e.g., from rabbit muscle (e.g., rabbit psoas). In some embodiments, administering a compound or salt of the present disclosure increases the fraction of the myosin filament in a DRX state in single fibers from rabbit skeletal muscle. In some embodiments, administering a compound or salt of the present disclosure increases the ATPase rate of all myosin in the DRX, SRX, or actin bound state (e.g., by at least about 1%, at least about 10%, at least about 20%, at least about 50%, at least about 75%, at least about 100%, at least about 150%, or more, or, alternatively or in addition, by at most about 1%, at most about 10%, at most about 20%, at most about 50%, at most about 75%, at most about 100%, at most about 150%, or less). In some embodiments, administering a compound or salt of the present disclosure increases submaximal force with enhanced injury force drop, e.g., relative to a control molecule. In some embodiments, administering a compound or salt of the present disclosure accelerates force drop in muscles undergoing eccentric exercise (e.g., in healthy mouse muscle with changing maximal force development), e.g., relative to a control molecule. In some embodiments, eccentric (e.g., lengthening) contractions stress healthy muscle. In some embodiments, the stress leads to accentuated force drop compared to fixed-length contractions (e.g., isometric).

In some embodiments, a compound or salt of the present disclosure is an activator that is skeletal selective and/or is a non-myosin activator. In some embodiments, administering a compound or salt of the present disclosure increases calcium sensitivity. In some embodiments, administering a compound or salt of the present disclosure increases the rate of force development. In some embodiments, administering a compound or salt of the present disclosure decreases relaxation velocity.

In some embodiments, administering a compound or salt of the present disclosure increases both the extent (e.g., the fraction) and the rate of DRX myosin (e.g., in APT/sec). In some embodiments, administering a compound or salt of the present disclosure increases the fraction of the myosin filament in a DRX state in single fibers, e.g., from rabbit skeletal muscle. In some embodiments, administering a compound or salt of the present disclosure increases the ATPase rate of all myosin in the DRX state. In some embodiments, administering a compound or salt of the present disclosure mildly sensitizes force without injury enhancement (e.g., in EDL muscle ex vivo). In some embodiments, the compound or salt increases force at low frequencies, e.g., in an ex vivo assay, (e.g., by at least about 1%, at least about5%, at least about 10%, at least about 25%, at least about 30%, at least about 50% or more). In some embodiments, the compound or salt increases relaxation time. In some embodiments, the compound or salt of the present disclosure increases 02 consumption. In some embodiments, the compound or salt of the present disclosure increases respiratory rate, body temperature, or activity. In some embodiments, the compound or salt of the present disclosure does not one or more of change respiratory rate, body temperature, and activity.

In some embodiments, the compound or salt of the present disclosure increases insulin resistance, insulin sensitivity, glucose uptake (e.g., from circulation), oxidation potential, or a combination thereof.

In some embodiments, a patient is administered a compound or salt of the present disclosure in combination with a GLP-1 agonist, and the patient exhibits diminished skeletal muscle loss relative to a patient to whom a compound or salt of the present disclosure was not administered.

In some embodiments, skeletal muscle has two major fiber types (e.g., Type 1—slow, Type IIa—fast fatigue-resistance, type II x/d—fast fatigable). In some embodiments, type 1 fibers are injury resistant, and exhibit high oxidative capacity and high turnover. In some embodiments, type II fibers are injury susceptible, and exhibit low oxidative capacity and low turnover. In some embodiments, slow fibers have high protein overlap with cardiac muscle. In some embodiments, obesity drives fast fibers and shifts energy consumption. In some embodiments, as body fat percentage decreases, the percentage of type 1 fibers increase. In some embodiments, the compound or salt of the present disclosure targets slow fibers. In some embodiments, slow fibers are more present in obese patients than in healthy patients.

Methods of administration of a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) discussed herein may be used for the treatment of obesity, sarcopenia, wasting syndrome, frailty, cachexia, muscle spasm, post-surgical and post-traumatic muscle weakness, neuromuscular disease, and other indications in a mammal.

In some embodiments, "obesity" means having a body mass index (BMI) greater than or equal to 30 $kg/m^2$.

In some embodiments, BMI refers to weight (kg) divided by height (m2).

In some embodiments, the term "obesity" may encompasse hyperplastic obesity, (e.g., an increase in the number of fat cells relative to a non-obese person). In some embodiments, the term "obesity" encompasses hypertrophic obesity (e.g., an increase in the size of the fat cells relative to a non-obese person).

In some embodiments, "overweight" may be defined as having a BMI from 25 to 30 $kg/m^2$. In some embodiments, severe (e.g., morbid) obesity is defined as a BMI greater than or equal to 40 $kg/m^2$.

In some embodiments, "sarcopenia" may mean a loss of skeletal muscle mass, quality, and strength. Sarcopenia may attributed to ageing or HIV infection or other causes. Sarcopenia may lead to frailty, for example, in the elderly.

In some embodiments, "wasting syndrome" may mean a condition characterized by involuntary weight loss and may be associated with chronic fever and diarrhea. In some embodiments, patients with wasting syndrome lose 10% of baseline body weight within one month.

In some embodiments, abnormal contraction of skeletal muscle may be a pathogenetic cause of several disorders, including obesity, sarcopenia, wasting syndrome, frailty, cachexia, muscle spasm, post-surgical and post-traumatic muscle weakness, and neuromuscular disease, which pose serious health problems as adult diseases. In some embodiments, the contraction and relaxation of skeletal muscle are mainly controlled by increases and decreases of intracellular calcium. In some embodiments, intracellular calcium may bind with calmodulin, e.g., to activate myosin light chain phosphorylation enzyme. In some embodiments, the activation of myosin light chain phosphorylation enzyme results in phosphorylation of the myosin light chain. In some embodiments, the phosphorylation of myosin light chain causes contraction of skeletal muscles.

In some embodiments, a compound or salt of the present disclosure modulates (e.g., reduces or increases) intracellular calcium. In some embodiments, a compound or salt of the present disclosure distends blood vessels. In some embodiments, when a compound or salt of the present disclosure decreases intracellular calcium, then blood vessels are distended.

Alternatively, or in addition, in some embodiments, skeletal muscle contraction is independent of intracellular calcium level. In some embodiments, pharmaceutical agents which only reduce intracellular calcium may be insufficient to treat diseases caused by abnormal skeletal muscle contraction.

Formula III and Related Compounds and Applications

In an aspect, disclosed herein is a compound or salt of Formula (IIIa). In an aspect, disclosed herein is a method of treating a cardiovascular disease or a related condition comprising administering to a subject in need thereof a compound of Formula (IIIa):

(IIIa)

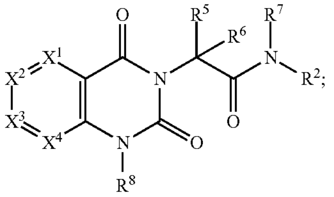

or a salt thereof, wherein $X^1$, $X^2$, $X^3$, and $X^4$ are each independently selected from C(R), N, and $N^+(—O^-)$; wherein no more than two of $X^1$, $X^2$, $X^3$, and $X^4$ are N or $N^+(—O^-)$; each $R^1$ is independently selected from: hydrogen; halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$; $R^2$ is selected from: $C_{1-6}$ alkyl, $C_{2-6}$ alkenyl, and $C_{2-6}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—C(O)OR^{10b}$, $—OC(O)R^{10b}$, $—N(R^{10b})C(O)N(R^{10b})_2$, $—OC(O)N(R^{10b})_2$, $—N(R^{10b})C(O)OR^{10b}$, $—S(O)R^{10b}$, $—S(O)_2R^{10b}$, $—NO_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; and $C_{3-10}$ carbocycle and 3- to 10-membered heterocycle, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9b}$; $R^5$ and $R^6$ are each independently selected from: hydrogen, halogen, $—OR^{10b}$, $—SR^{10b}$, $—N(R^{10b})_2$, $—NO_2$, and —CN; $C_{1-6}$ alkyl, $C_{2-6}$ alkenyl, and $C_{2-6}$ alkynyl, any of which is optionally substituted at each occurrence with one or more substituents independently selected from halogen, $—OR^{10c}$, $—SR^{10c}$, $—N(R^{10c})_2$, $—NO_2$, —CN, and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; and $C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9c}$; $R^7$ is selected from: hydrogen and $C_{1-6}$ alkyl optionally substituted with one or more substituents independently selected from halogen, $—OR^{10d}$, $—SR^{10d}$, $—N(R^{10d})_2$, $—NO_2$, and —CN; $R^8$ is selected from: hydrogen; and $C_1$ alkyl optionally substituted with one or more substituents independently selected from halogen, $—OR^{10e}$, $—SR^{10e}$, $—N(R^{10e})_2$, $—NO_2$, —CN, and 3- to 10-membered heterocycle, wherein each 3- to 10-membered heterocycle is optionally substituted with one or more substituents independently selected from halogen, $—OR^{10e}$, $—SR^{10e}$, $—N(R^{10e})_2$, $—NO_2$, and —CN; $C_{2-6}$ alkyl optionally substituted with one or more substituents independently selected from halogen, $—OR^{10e}$, $—SR^{10e}$, $—N(R^{10e})_2—NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, $—OR^{10e}$, $—SR^{10e}$, $—N(R^{10e})_2$, $—NO_2$, and —CN; each $R^{9a}$ is independently selected from: halogen, —OH, $—OC_{2-6}$ alkyl), $—O(C_{1-6}$ haloalkyl), $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, and —CN; each $R^{9b}$ is independently selected from: halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10b}$, $—SR^{10b}$, $—N(R^{10b})_2$, $—C(O)R^{10b}$, $—C(O)N(R^{10b})_2$, $—N(R^{10b})C(O)R^{10b}$, $—N(R^{10b})C(O)N(R^{10b})_2$, $—OC(O)N(R^{10b})_2$, $—N(R^{10b})C(O)OR^{10b}$, $—C(O)OR^{10b}$, $—OC(O)R^{10b}$, $—S(O)R^{10b}$, $—S(O)_2R^{10b}$, $—NO_2$, =O, =S, $=N(R^{10b})$, and —CN; each $R^{9c}$ is independently selected from: halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, $—S(O)R^{10c}$, $—S(O)_2R^{10c}$, $—NO_2$, =O, =S, $=N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, —S(O)$R^{10c}$, —S(O)$_2R^{10c}$, —$NO_2$, =O, =S, =N($R^{10c}$), and —CN; each $R^{10a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl; each $R^{10e}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein when $R^5$ or $R^6$ is isopropyl; then $R^2$ is selected from: $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; $C_{3-10}$ carbocycle, 3- to 4-membered heterocycle, and 6- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9b}$; and 5-membered heterocycle, optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{2-6}$ alkyl, $C_{2-6}$ alkenyl, and $C_{2-6}$ alkynyl, wherein $C_{2-6}$ alkyl, $C_{2-6}$ alkenyl, and $C_{2-6}$ alkynyl are each optionally substituted with one or more substituents independently selected from $R^{9b}$.

In an aspect, disclosed herein is a method of treating a cardiovascular disease or a related condition comprising administering to a subject in need thereof a compound or salt of of Formula (IIIa) that is represented by Formula (IIIa-ep):

(IIIa-ep)

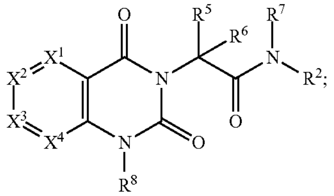

or a salt thereof, wherein $X^1$, $X^2$, $X^3$, and $X^4$ are each independently selected from C(R'), and N; wherein no more than two of $X^1$, $X^2$, $X^3$, and $X^4$ are N; each $R^1$ is independently selected from: hydrogen; halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{1-6}$ haloalkyl, and $C_{1-6}$ alkyl; $R^2$ is selected from: $C_{1-6}$ alkyl, optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{1-6}$ haloalkyl, and $C_{1-6}$ alkyl; and $C_{3-10}$ carbocycle and 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; $R^5$ and $R^6$ are each independently selected from: hydrogen, halogen, and —CN; $C_{1-6}$ alkyl, optionally substituted at each occurrence with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{3-10}$ carbocycle and 3- to 10-membered heterocycle, each of which is optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{1-6}$ haloalkyl, and $C_{1-6}$ alkyl; and $C_{3-10}$ carbocycle and 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; or $R^5$ together with $R^6$ form a 3- to 10-membered heterocycle or $C_{3-10}$ carbocycle, optionally substituted with one or more substituents independently selected from $C_{3-10}$ carbocycle and 3- to 10-membered heterocycle, each of which is optionally substituted with one or more substituents independently selected from: halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$; and $C_{1-6}$ alkyl, optionally substituted with one or more substituents independently selected from halogen, —$NO_2$, —CN, —OH, —O($C_{1-6}$ alkyl), —O($C_{1-6}$ haloalkyl), —SH, —S($C_{1-6}$ alkyl), —$NH_2$, —NH($C_{1-6}$ alkyl), and —N($C_{1-6}$ alkyl)$_2$, $C_{3-10}$ carbocycle and 3- to 10-membered heterocycle; $R^7$ is selected from: hydrogen; and $R^8$ is selected from: hydrogen.

In some embodiments, for a compound or salt of Formula (IIIa), $X^1$, $X^2$, $X^3$, and $X^4$ are each independently selected from C($R^1$) and N and $N^+$(—$O^-$). In some embodiments, $X^1$, $X^2$, $X^3$, and $X^4$ are each independently selected from C($R^1$) and N. In some embodiments, one of $X^1$, $X^2$, $X^3$, or $X^4$ is N. In some embodiments, $X^1$ is N. In some embodiments, $X^2$ is N. In some embodiments, $X^3$ is N. In some embodiments, $X^4$ is N. In some embodiments, two of $X^1$, $X^2$, $X^3$, or $X^4$ is N. In some embodiments, $X^1$ and $X^3$ are N; or $X^2$ and $X^4$ are N. In some embodiments, $X^1$, $X^2$, $X^3$, and $X^4$ are each independently selected from C(R'). In some embodiments, none of $X^1$, $X^2$, $X^3$, and $X^4$ need be N or $N^+$(—$O^-$). In some embodiments, no more than one of of $X^1$, $X^2$, $X^3$, and $X^4$ is N or $N^+$(—$O^-$). In some embodiments, no more than two of of $X^1$, $X^2$, $X^3$, and $X^4$ are N or $N^+$(—$O^-$). In some embodiments, no more than three of of $X^1$, $X^2$, $X^3$, and $X^4$ are N or $N^+$(—$O^-$).

In some embodiments, for a compound or salt of Formula (IIIa), each $R^1$ is independently selected from: hydrogen; halogen, —$NO_2$, —CN, —$OR^{10a}$, —$SR^{10a}$, —N($R^{10a}$)$_2$, —C(O)$R^{10a}$, and —C(O)N($R^{10a}$)$_2$; $C_{1-6}$ alkyl, optionally substituted with one or more substituents independently selected from halogen, —$OR^{10a}$, —$SR^{10a}$, —N($R^{10a}$)$_2$, —C(O)$R^{10a}$, —$NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —CN, $C_{1-6}$ alkyl optionally substituted with one or more $R^{9a}$. In some embodiments, each $R^1$ is independently selected from: hydrogen; halogen, —$NO_2$, —CN, —$OR^{10a}$, —$SR^{10a}$, —N($R^{10a}$)$_2$, —C(O)$R^{10a}$, and —C(O)N($R^{10a}$)$_2$; $C_{1-6}$ alkyl, optionally substituted with one or more substituents independently selected from halogen, —CN, —$OR^{10a}$, —$SR^{10a}$, and —N($R^{10a}$)$_2$; and $C_{3-10}$ carbocycle and 3- to 10-membered heterocycle, each of which is optionally substituted with one or more substituents independently selected from halogen, —$OR^{10a}$, and —CN. In some embodiments, each $R^1$ is independently selected from: hydrogen; halogen, —$NO_2$, —CN, —$OR^{10a}$, —$SR^{10a}$, —N($R^{10a}$)$_2$, —C(O)$R^{10a}$, and —C(O)N($R^{10a}$)$_2$; and $C_{1-6}$ alkyl, optionally substituted with one or more substituents independently selected from halogen, —CN, —$OR^{10a}$, —$SR^{10a}$ and —N($R^{10a}$)$_2$. In some embodiments, each $R^1$ is independently selected from: hydrogen; halogen, —$NO_2$, —CN, —$OR^{10a}$, —$SR^{10a}$, —N($R^{10a}$)$_2$, —C(O)$R^{10a}$, and —C(O)N($R^{10a}$)$_2$; and $C_{1-6}$ alkyl, optionally substituted with one or more substituents independently selected from fluoro and —CN. In some embodiments, each $R^1$ is independently selected from: hydrogen; halogen, —CN, —$OR^{10a}$, —$SR^{10a}$, —N($R^{10a}$)$_2$; and $C_{1-6}$ alkyl. In some embodiments, each $R^1$ is independently selected from: hydrogen; fluoro, chloro, —CN, —$OR^{10a}$, and $C_{1-6}$ alkyl. In some embodiments, each $R^1$ is independently selected from: hydrogen; fluoro, chloro, —CN, —OH, —O($CH_3$), and $C_{1-6}$ alkyl. In some embodiments, each $R^1$ is independently selected from: hydrogen; fluoro, chloro, and —CN. In some embodiments, each $R^1$ is independently selected from: hydrogen, fluoro, and —CN.

In some embodiments, for a compound or salt of Formula (IIIa), $R^2$ is selected from: $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9b}$. In some embodiments, $R^2$ is selected from $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. In some embodiments, $R^2$ is selected from $C_{1-6}$ alkyl, optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, =O, —CN, and $C_{1-6}$ alkyl, wherein each $C_{1-6}$ alkyl is optionally substituted with one or more $R^{9b}$. In some embodiments, $R^2$ is selected from $C_{1-6}$ alkyl, optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —OH, and —CN. In some embodiments, $R^2$ is selected from $C_{1-6}$ alkyl, optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_{1-6}$ alkyl, optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_{1-6}$ alkyl, optionally substituted with one or more substituents independently selected from halogen, —OH, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_{1-6}$ alkyl optionally substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_{1-6}$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_{1-3}$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_2$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more $R^{9b}$. In some embodiments, $R^2$ is selected from $C_2$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more substituents independently selected from chloro, fluoro, —CN, —$CH_3$, and —OH. In some embodiments, $R^2$ is a substituent represented by the following:

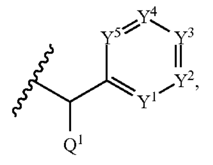

wherein, $Y^1$, $Y^2$, $Y^3$, $Y^4$, and $Y^5$ are each independently selected from N, C(H), C(F), C(CN), C($CH_3$), C(Cl), and C(OH); and $Q^1$ is a $C_{1-3}$ alkyl optionally substituted with one or more substituents selected from —OH and —F. In some embodiments, $R^2$ is a substituent represented by the following:

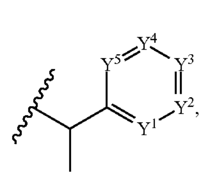

wherein $Y^1$, $Y^2$, $Y^3$, $Y^4$, and $Y^5$ are each independently selected from N, C(H), C(F), C(CN), C($CH_3$), C(Cl), and C(OH). In some embodiments $R^2$ is selected from

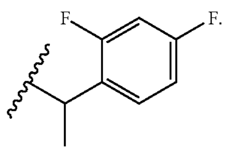 [SMILES: *C(C)c1ccc(F)cc1F]

In some embodiments, $R^2$ is selected from

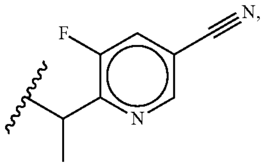
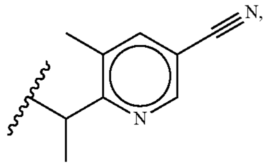
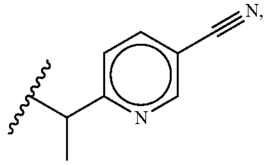
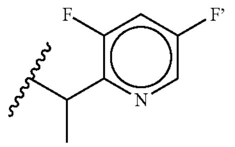
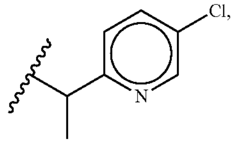
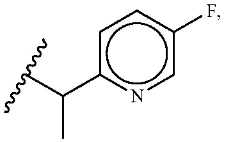
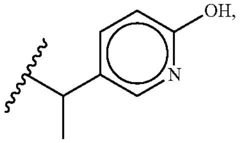
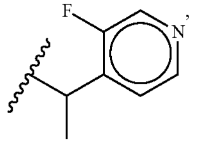
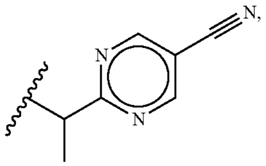
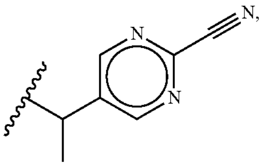
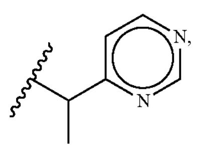
and
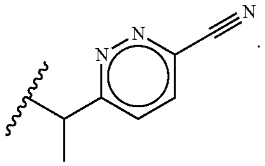

In some embodiments, for a compound or salt of Formula (IIIa), $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. In some embodiments, $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. In some embodiments, $R^5$ and $R^6$ are each independently selected from: hydrogen and $C_{1-4}$ alkyl. In some embodiments, $R^5$ and $R^6$ are each independently selected from: hydrogen, methyl, benzyl, and isobutyl. In some embodiments, $R^5$ and $R^6$ are each hydrogen. In some embodiments, $R^5$ is selected from: halogen. In some embodiments, $R^5$ is selected from: fluoro. In some embodiments, $R^6$ is selected from: halogen. In some embodiments, $R^6$ is selected from: fluoro. In some embodiments, $R^5$ together with $R^6$ form a $C_{3-10}$ carbocycle or 3- to 10-membered heterocycle optionally substituted with one or more $R^{9c}$. In some embodiments, $R^5$ together with $R^6$ form a cyclopropyl optionally substituted with one or more $R^{9c}$. In some embodiments, $R^5$ together with $R^6$ form a cyclopropyl optionally substituted with one or more F. In some embodiments, $R^5$ together with $R^6$ form a cyclopropyl.

In some embodiments, for a compound or salt of Formula (IIIa), $R^7$ is selected from hydrogen and $C_{1-6}$ alkyl optionally substituted with one or more substituents independently selected from halogen. In some embodiments, $R^7$ is selected from hydrogen.

In some embodiments, for a compound or salt of Formula (IIIa), $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle. In some embodiments, $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. In some embodiments, $R^8$ is selected from hydrogen. In some embodiments, each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN.

In some embodiments, for a compound or salt of Formula (IIIa), each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: halogen, —OH, —O($C_{1-6}$ haloalkyl), —O($C_{2-6}$ alkyl) —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: halogen, —OH, —O($C_{1-6}$ haloalkyl), —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: halogen, —OH, —O($C_{2-6}$ haloalkyl), —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. In some embodiments, each $R^{9a}$ is independently selected from: halogen, —OH, —$N(R^{10a})_2$, =O, and —CN; and $C_{1-3}$ alkyl optionally substituted with one or more substituents independently selected from halogen. In some embodiments, each $R^{9a}$ is independently selected from: halogen, —OH, —CN, and —$CH_3$. In some embodiments, each $R^{9a}$ is independently selected from: halogen, —CN, and —$CH_3$. In some embodiments, each $R^{9a}$ is independently selected from: fluoro, chloro, —CN, and —$CH_3$. In some embodiments, each $R^{9a}$ is independently selected from: fluoro, —CN, and —$CH_3$. In some embodiments, each $R^{9a}$ is independently selected from: fluoro and —CN. In some embodiments, for a compound or salt of Formula (IIIa), each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN. In some embodiments, each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. In some embodiments, each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. In some embodiments, each $R^{9b}$ is independently selected from halogen and —CN. In some embodiments, each $R^{9b}$ is independently selected from fluoro and —CN. In some embodiments, for a compound or salt of Formula (IIIa), each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$NO_2$, =O, and —CN. In some embodiments, for a compound or salt of Formula (IIIa), each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from halogen, —$OR^{10c}$, —$SR^{10c}$, —$N(R^{10c})_2$, —$C(O)R^{10c}$, —$NO_2$, =O, and —CN.

In some embodiments, for a compound or salt of Formula (IIIa), each $R^{10a}$ is independently selected from hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{3-10}$ carbocycle, 3- to 10-membered heterocycle, and $C_{1-6}$ haloalkyl. In some embodiments, each $R^{10a}$ is independently selected from hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, and —$NH(C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, —$NH(C_{1-6}$ alkyl), $C_{1-6}$ alkyl, and $C_{1-6}$ haloalkyl. In some embodiments, each $R^{10a}$ is independently selected from hydrogen; and $C_{1-6}$ alkyl optionally substituted with one or more substituents independently selected from halogen, —CN, —OH, —SH, —$NO_2$, —$NH_2$, and =O; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, —$NH(C_{1-6}$ alkyl), $C_{1-6}$ alkyl, and $C_{1-6}$ haloalkyl. In some embodiments, each $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. In some embodiments, for a compound or salt of Formula (IIIa), each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, and —$NH(C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{1-6}$ haloalkyl. In some embodiments, each $R^{10b}$ is independently selected from: hydrogen; and $C_{1-6}$ alkyl. In some embodiments, each $R^{10b}$ is hydrogen. In some embodiments, each $R^{10c}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. In some embodiments, for a compound or salt of Formula (IIIa), each $R^{10c}$ is independently selected from: hydrogen; and $C_{1-6}$ alkyl. In some embodiments, each $R^{10c}$ is hydrogen. In some embodiments, each $R^{10d}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. In some embodiments, for a compound or salt of Formula (IIIa), each $R^{10a}$ is independently selected from: hydrogen; and $C_{1-6}$ alkyl. In some embodiments, each $R^{10a}$ is hydrogen. In some embodiments, each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. In some embodiments, for a compound or salt of Formula (IIIa), each $R^{10e}$ is independently selected from: hydrogen; and $C_{1-6}$ alkyl. In some embodiments, each $R^{10e}$ is hydrogen.

In some embodiments, for a compound or salt of Formula (IIIa), when $R^5$ or $R^6$ is isopropyl; then $R^2$ is selected from: $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; $C_{3-10}$ carbocycle, 3- to 4-membered heterocycle, and 6- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9b}$; and 5-membered heterocycle, optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{2-6}$ alkyl, $C_{2-6}$ alkenyl, and $C_{2-6}$ alkynyl, wherein $C_{2-6}$ alkyl, $C_{2-6}$ alkenyl, and $C_{2-6}$ alkynyl are each optionally substituted with one or more substituents independently selected from $R^{9b}$. In some embodiments, when $R^5$ or $R^6$ is isopropyl; then $R^2$ is selected from: $C_{1-6}$ alkyl, optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; $C_{3-10}$ carbocycle, 3- to 4-membered heterocycle, and 6- to 10-membered heterocycle, each of which is optionally substituted with one or more substituents independently selected from halogen, —O$R^{10b}$, —S$R^{10b}$, —N($R^{10b}$)$_2$, =O, —CN, and $C_1$-6; and 5-membered heterocycle, optionally substituted with one or more substituents independently selected from halogen, —O$R^{10b}$, —S$R^{10b}$, —N($R^{10b}$)$_2$, =O, and —CN. In some embodiments, when $R^5$ or $R^6$ is isopropyl; then $R^2$ is selected from: $C_{1-6}$ alkyl, optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; and $C_{3-10}$ carbocycle, 3- to 4-membered heterocycle, and 6- to 10-membered heterocycle, each of which is optionally substituted with one or more substituents independently selected from halogen, —O$R^{10b}$, —S$R^{10b}$, —N($R^{10b}$)$_2$, =O, and —CN. In some embodiments, when $R^5$ or $R^6$ is isopropyl; then $R^2$ is selected from: $C_{1-6}$ alkyl, optionally substituted with one or more substituents independently selected from halogen, —O$R^{10b}$, —S$R^{10b}$, —N($R^{10b}$)$_2$, =O, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$. In some embodiments, when $R^5$ or $R^6$ is isopropyl; then $R^2$ is selected from: $C_{1-6}$ alkyl, optionally substituted with one or more substituents independently selected from —F, —OH, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$. In some embodiments, when $R^5$ or $R^6$ is isopropyl; then $R^2$ is selected from: $C_{1-6}$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$. In some embodiments, when $R^5$ or $R^6$ is isopropyl; then $R^2$ is selected from: $C_{1-6}$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more substituents independently selected from —CN and —F.

In some embodiments, for a compound or salt of Formula (IIIa), cardiovascular disease or a related condition is selected from: hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina. In some embodiments, said heart failure with preserved ejection fraction (HFpEF) comprises one or more disorders selected from disorders of relaxation and disorders of chamber stiffness (diabetic HFpEF). In some embodiments, said left ventricular (LV) hypertrophy is malignant left ventricular (LV) hypertrophy. In some embodiments, said restrictive cardiomyopathy comprises one or more subgroups selected from inflammatory subgroups, infiltrative subgroups, storage subgroups, idiopathic/inherited subgroups, congenital heart disease subgroups. In some embodiments, said inflammatory subgroups comprise one or more subgroups selected from Loefilers and EMF. In some embodiments, said inflammatory subgroups comprise one or more subgroups selected from amyloid, sarcoid, and XRT. In some embodiments, said storage subgroups comprise one or more subgroups selected from hemochromatosis, Fabry, and glycogen storage disease. In some embodiments, said idiopathic/inherited subgroups comprise one or more subgroups selected from Trop I (beta myosin HC), Trop T (alpha cardiac actin), and desmin related subgroups. In some embodiments, said congenital heart disease subgroups comprise one or more subgroups selected from pressure-overloaded RV, Tetralogy of Fallot, and pulmonic stenosis. In some embodiments, cardiovascular disease or a related condition is hypertrophic cardiomyopathy. In some embodiments, cardiovascular disease or a related condition is obstructive hypertrophic cardiomyopathy. In some embodiments, cardiovascular disease or a related condition is non-obstructive hypertrophic cardiomyopathy. In some embodiments, cardiovascular disease or a related condition is heart failure with preserved ejection fraction. In some embodiments, cardiovascular disease or a related condition is left ventricle stiffness.

In some embodiments, for a compound or salt of Formula (IIIa), when $R^2$ is phenyl, benzyl, cyclohexyl, $C_{1-6}$ alkyl substituted with =O, methyl, or —$CH_2$(4-pyridyl); then at least one of $X^1$, $X^2$, $X^3$, and $X^4$ is N. In some embodiments, when $R^2$ is phenyl, benzyl, cyclohexyl, $C_{1-6}$ alkyl substituted with =O, methyl, or —$CH_2$(4-pyridyl); then $X^1$ is N. In some embodiments, when $R^2$ is phenyl, benzyl, cyclohexyl, $C_{1-6}$ alkyl substituted with =O, methyl, or —$CH_2$(4-pyridyl); then $X^2$ is N. In some embodiments, when $R^2$ is phenyl, benzyl, cyclohexyl, $C_{1-6}$ alkyl substituted with =O, methyl, or —$CH_2$(4-pyridyl); then $X^3$ is N. In some embodiments, when $R^2$ is phenyl, benzyl, cyclohexyl, $C_{1-6}$ alkyl substituted with =O, methyl, or —$CH_2$(4-pyridyl); then $X^4$ is N. In some embodiments, when $R^2$ is phenyl, benzyl, cyclohexyl, $C_{1-6}$ alkyl substituted with =O, methyl, or —$CH_2$(4-pyridyl); then each $R^1$ is independently selected from: halogen, —$NO_2$, —CN, —O$R^{10a}$, —S$R^{10a}$, —N($R^{10a}$)$_2$; $C_{1-6}$ alkyl optionally substituted with one or more substituents independently selected from halogen, —$OR^{10a}$, —$SR^{10a}$, —$N(R^{10a})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —CN, and $C_{1-6}$ alkyl optionally substituted with one or more $R^{9a}$. In some embodiments, when $R^2$ is phenyl, benzyl, cyclohexyl, $C_{1-6}$ alkyl substituted with =O, methyl, or —$CH_2$(4-pyridyl); then each $R^1$ is independently selected from: halogen, —CN, —$OR^{10a}$; $C_{1-6}$ alkyl optionally substituted with one or more substituents independently selected from halogen, —$OR^{10a}$, and —CN; and $C_{3-10}$ carbocycle and 3- to 10-membered heterocycle, each of which is optionally substituted with one or more substituents independently selected from halogen and —CN. In some embodiments, when $R^2$ is phenyl, benzyl, cyclohexyl, $C_{1-6}$ alkyl substituted with =O, methyl, or —$CH_2$(4-pyridyl); then each $R^1$ is independently selected from: halogen, —CN, —$OR^{10a}$, and $C_{1-6}$ alkyl optionally substituted with one or more substituents independently selected from halogen and —CN. In some embodiments, when $R^2$ is phenyl, benzyl, cyclohexyl, $C_{1-6}$ alkyl substituted with =O, methyl, or —$CH_2$(4-pyridyl); then each $R^1$ is independently selected from: halogen, —CN, —OH, and $C_{1-6}$ alkyl. In some embodiments, when $R^2$ is phenyl, benzyl, cyclohexyl, $C_{1-6}$ alkyl substituted with =O, methyl, or —$CH_2$(4-pyridyl); then each $R^1$ is independently selected from: fluoro and —CN. In some embodiments, when $R^2$ is phenyl, benzyl, cyclohexyl, $C_{1-6}$ alkyl substituted with =O, methyl, or —$CH_2$(4-pyridyl); then at least one of $X^1$, $X^2$, $X^3$, and $X^4$ is N; or each $R^1$ is independently selected from: halogen, —CN, —$OR^{10a}$, and $C_{1-6}$ alkyl optionally substituted with one or more substituents independently selected from halogen and —CN.

In some embodiments, for a compound or salt of Formula (IIIa), when $X^2$ is C(R'), and the $R^1$ of $X^2$ is a $C_1$ alkyl that is substituted with one =O and one heterocycle; then $R^2$ is selected from: $C_{1-2}$ alkyl, substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; $C_{3-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9b}$. In some embodiments, when $X^2$ is $C(R^1)$, and the $R^1$ of $X^2$ is a $C_1$ alkyl that is substituted with one =O and one heterocycle; then $R^2$ is selected from: $C_{1-2}$ alkyl, substituted with one or more substituents independently selected from halogen, —$OR^{10b}$, —$SR^{10b}$, —$N(R^{10b})_2$, =O, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, =O, —CN, and $C_{1-6}$ alkyl, wherein each $C_{1-6}$ alkyl is optionally substituted with one or more substituents independently selected from $R^{9b}$. In some embodiments, when $X^2$ is $C(R^1)$, and the $R^1$ of $X^2$ is a $C_1$ alkyl that is substituted with one =O and one heterocycle; then $R^2$ is selected from: $C_{1-2}$ alkyl, substituted with one or more substituents independently selected from halogen, —OH, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$; and $C_{3-10}$ carbocycle and 3- to 10-membered heterocycle, each of which is optionally substituted with one or more substituents independently selected from halogen, —$OR^{10b}$, =O, —CN, and $C_{1-6}$ alkyl. In some embodiments, when $X^2$ is $C(R^1)$, and the $R^1$ of $X^2$ is a $C_1$ alkyl that is substituted with one =O and one heterocycle; then $R^2$ is selected from: $C_{1-2}$ alkyl, substituted with one or more substituents independently selected from —F, —OH, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9b}$.

In some embodiments, the compound or salt of formula (IIIa) is not: 1-[1,4-Dihydro-6-[(1-methoxy-2-methyl-3-indolizinyl)carbonyl]-2,4-dioxo-3(2H)-quinazolinyl]-N,N-diethylcyclopropanecarboxamide; 1,4-Dihydro-6-[(1-methoxy-2-methyl-3-indolizinyl)carbonyl]-N,N,1-trimethyl-2,4-dioxo-3(2H)-quinazolineacetamide; N,N-Diethyl-1,4-dihydro-6-[(1-methoxy-2-phenyl-3-indolizinyl)carbonyl]-α-methyl-2,4-dioxo-3(2H)-quinazolineacetamide; N-Ethyl-1,4-dihydro-6-[(1-methoxy-2-phenyl-3-indolizinyl)carbonyl]-α-methyl-2,4-dioxo-3(2H)-quinazolineacetamide; (αR)-1,4-Dihydro-6-[(1-methoxy-2-phenyl-3-indolizinyl)carbonyl]-N,N,α-trimethyl-2,4-dioxo-3(2H)-quTinazolineacetamide; 1,4-Dihydro-6-[(1-methoxy-2-phenyl-3-indolizinyl)carbonyl]-N,N,α-trimethyl-2,4-dioxo-3(2H)-quinazolineacetamide; N,N-Diethyl-1,4-dihydro-6-[(1-methoxy-2-phenyl-3-indolizinyl)carbonyl]-2,4-dioxo-3(2H)-quinazolineacetamide; 1,4-Dihydro-6-[(1-methoxy-2-methyl-3-indolizinyl)carbonyl]-N,N,α-trimethyl-2,4-dioxo-3(2H)-quinazolineacetamide; 1,4-Dihydro-6-[(1-methoxy-2-phenyl-3-indolizinyl)carbonyl]-N,N-dimethyl-2,4-dioxo-3(2H)-quinazolineacetamide; 1,4-Dihydro-6-[(1-methoxy-2-phenyl-3-indolizinyl)carbonyl]-N-methyl-2,4-dioxo-3(2H)-quinazolineacetamide; 1,4-Dihydro-6-[(1-methoxy-2-methyl-3-indolizinyl)carbonyl]-N,N-dimethyl-2,4-dioxo-3(2H)-quinazolineacetamide; Ethyl 2-[[(2S)-2-(1,4-dihydro-2,4-dioxo-3(2H)-quinazolinyl)-3-methyl-1-oxobutyl]amino]-4-methyl-5-thiazolecarboxylate; (1-Iminoethyl)azanyl 2-[[(2S)-2-(1,4-dihydro-2,4-dioxo-3(2H)-quinazolinyl)-3-methyl-1-oxobutyl]amino]-4-methyl-5-thiazolecarboxylate; 2-[[(2S)-2-(1,4-Dihydro-2,4-dioxo-3(2H)-quinazolinyl)-3-methyl-1-oxobutyl]amino]-4-methyl- 5-thiazolecarboxylic acid 2-acetylhydrazide; (αS)—N-(5-Cyano-4-methyl-2-thiazolyl)-1,4-dihydro-α-(1-methylethyl)-2,4-dioxo-3(2H)-quinazolineacetamide; 2-[[(2S)-2-(1,4-Dihydro-2,4-dioxo-3(2H)-quinazolinyl)-3-methyl-1-oxobutyl]amino]-4-methyl-5-thiazolecarboxylic acid; (αS)-1,4-Dihydro-α-(1-methylethyl)-N-[4-methyl-S-(5-methyl-1,2,4-oxadiazol-3-yl)-2-thiazolyl]-2,4-dioxo-3(2H)-quinazolineacetamide; (αS)-1,4-Dihydro-α-(1-methylethyl)-N-[4-methyl-5-(3-methyl-1,2,4-oxadiazol-S-yl)-2-thiazolyl]-2,4-dioxo-3(2H)-quinazolineacetamide; (αS)-1,4-Dihydro-α-(1-methylethyl)-N-[4-methyl-S-(5-methyl-1,3,4-oxadiazol-2-yl)-2-thiazolyl]-2,4-dioxo-3(2H)-quinazolineacetamide; Ethyl 2-[[(2S)-2-(1,4-dihydro-2,4-dioxo-3(2H)-quinazolinyl)-3-methyl-1-oxobutyl]amino]-4-(trifluoromethyl)-5-thiazolecarboxylate; N-(Aminoiminomethyl)-6-bromo-1,4-dihydro-1-methyl-2,4-dioxo-3(2H)-quinazolineacetamide; N-(Aminoiminomethyl)-1,4-dihydro-2,4-dioxo-1-(phenylmethyl)-3(2H)-quinazolineacetamide; N-(Aminoiminomethyl)-1,4-dihydro-α,1-dimethyl-2,4-dioxo-3(2H)-quinazolineacetamide; N-(Aminoiminomethyl)-1,4-dihydro-1-methyl-2,4-dioxo-3(2H)-quinazolineacetamide; 1,4-Dihydro-2,4-dioxo-N-(4-pyridinylmethyl)-3(2H)-quinazolineacetamide; 3-[3-[[1,2,3,4-Tetrahydro-3-[(1R)-1-methyl-2-(methylamino)-2-oxoethyl]-2,4-dioxo-6-quinazolinyl]carbonyl]imidazo[1,5-a]pyridin-1-yl]benzoic acid; or D-Prolinamide, N-[(2S)-2-(1,4-dihydro-2,4-dioxo-3(2H)-quinazolinyl)-4-methyl-1-oxopentyl]-L-α-aspartyl-L-phenylalanyl- (9CI).

In some embodiments, the compound or salt of formula (IIIa) is not: 1354709-19-5, 1354709-18-4, 1354709-17-3, 1354709-16-2, 1354709-15-1, 1354709-14-0, 1354709-07-1, 1354709-04-8, 1354708-91-0, 1354708-90-9, 1354708-85-2, 672926-32-8, 1369787-02-9, 1369786-20-8, 672926-40-8, 672926-39-5, 672926-35-1, 672926-34-0, 672926-33-9, 672926-31-7, 2762342-08-3, 2762342-07-2, 2762342-06-1, 2762342-05-0, 919743-37-6, 1354902-70-7, or 209601-20-7, wherein said numbers are CAS registry numbers.

In some embodiments, the compound or salt of Formula (Ia), (Ib), (IIa), (IIb), (Ic), (Id), and (IIIa) may not include one or more of compound(s) selected from: 97, 105, 98, 99, 100, 213, 214, 215, 95, 96, 301, 303, 142, 405, 406, 408, 42, 508, 509, 510, 513, 514, 515, 516, 517, 518, 519, 520, 522, 523, 525, 526, 527, 528, 529, 530, 531, 532, 533, 534, 535, 601, 602, 603, 604, 605, 606, 43, 703, 5001, 5002, 5003, 5004, 5005, 5006, 5007, 5008, 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169, 34, 29, 501, 141, 3003, 204, 101, 102, 2, 11, 5, 3, 15, 19, 27, 28, 47, 106, 201, 202, 205, 207, 209, 211, 212, 59, 65, 302, 33, 69, 143, 401, 402, 403, 404, 407, 31, 32, 49, 50, 70, 71, 87, 166, 502, 504, 505, 506, 507, 511, 512, 521, 524, 10, 44, 46, 55, 3001, 3014, and 5009, and salt(s) of any one thereof.

In some embodiments, the compound or salt of Formula (IIIa) is selected from: compounds 97, 105, 98, 99, 100, 213, 214, 215, 95, 96, 301, 303, 142, 405, 406, 408, 42, 508, 509, 510, 513, 514, 515, 516, 517, 518, 519, 520, 522, 523, 525, 526, 527, 528, 529, 530, 531, 532, 533, 534, 535, 601, 602, 603, 604, 605, 606, 43, 703, 5001, 5002, 5003, 5004, 5005, 5006, 5007, 5008, 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169, 34, 29, 501, 141, 3003, 204, 101, 102, 2, 11, 5, 3, 15, 19, 27, 28, 47, 106, 201, 202, 205, 207, 209, 211, 212, 59, 65, 302, 33, 69, 143, 401, 402, 403, 404, 407, 31, 32, 49, 50, 70, 71, 87, 166, 502, 504, 505, 506, 507, 511, 512, 521, 524, 10, 44, 46, 55, 3001, 3014, and 5009, or a salt thereof. In some embodiments, the compound or salt of Formula (IIIa) is selected from: compounds 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, 213, 214, 215, 3001, 3002, 3003, 3004, 3005, 3006, 3007, 3008, 3009, 3010, 3011, 3013, 3014, 3015, 142, 405, 406, 408, 155, 72, 136, 39, 104, 154, 36, 35, 38, 40, 51, 37, 41, 34, 33, 143, 402, 403, 404, 407, 31, 32, 42, 50, 87, 101, 102, 501, 502, 504, 506, 507, 508, 509, 510, 511, 512, 513, 514, 517, 518, 519, 520, 521, 522, 523, 524, 525, 526, 527, 528, 529, 530, 533, and 534, or a salt thereof. In some embodiments, the compound or salt of Formula (IIIa) is selected from: compounds, 97, 105, 98, 99, 100, 213, 214, 215, 95, 96, 142, 405, 406, 408, 42, 508, 509, 510, 513, 514, 517, 518, 519, 520, 522, 523, 525, 526, 527, 528, 529, 530, 533, 534, 601, 602, 603, 604, 606, 43, 703, 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, 48, 17, 3015, 3005, 51, 16, 203, 37, 1, 14, 57, 41, 34, 29, 501, 141, 3003, 204, 101, 102, 2, 11, 5, 3, 15, 19, 27, 28, 47, 106, 201, 202, 205, 207, 209, 211, 212, 59, 33, 143, 402, 403, 404, 407, 31, 32, 50, 87, 502, 504, 506, 507, 511, 512, 521, 524, 10, 44, 46, 55, 3001, and 3014, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006,6, 3007, 104, 206, 3013, 154, 36, 7, 35, 3010, 30, 12, 38, 4, 18, 40, 20, 3011, 702, 48, 17, 3015, 3005, 51, 16, 203, 37, 1, 14, 57, 41, 34, 29, 501, 141, 3003, 204, 101, 102, 2, 11, 5, 3, 15, 19, 27, 28, 47, 106, 201, 202, 205, 207, 209, 211, 212, 59, 33, 143, 402, 403, 404, 407, 31, 32, 50, 87, 502, 504, 506, 507, 511, 512, 521, 524, 10, 44, 46, 55, 3001, and 3014, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, 48, 17, 3015, 3005, 51, 16, 203, 37, 1, 14, 57, 41, 34, 29, 501, 141, 3003, 204, 101, and 102, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, and 48, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, and 104, or a salt thereof. In some embodiments, the compound or salt of Formula (IIIa) is selected from: compounds 701 and 3008 or a salt thereof. In some embodiments, the compound or salt of Formula (IIIa) is selected from: compounds 97, 105, 98, 99, 100, 213, 214, 215, 95, 96, 301, 303, 142, 405, 406, 408, 42, 508, 509, 510, 513, 514, 515, 516, 517, 518, 519, 520, 522, 523, 525, 526, 527, 528, 529, 530, 531, 532, 533, 534, 535, 601, 602, 603, 604, 605, 606, 43, 703, 5001, 5002, 5003, 5004, 5005, 5006, 5007, 5008, 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169, 34, 29, 501, 141, 3003, 204, 101, 102, 2, 11, 5, 3, 15, 19, 27, 28, 47, 106, 201, 202, 205, 207, 209, 211, 212, 59, 65, 302, 33, 69, 143, 401, 402, 403, 404, 407, 31, 32, 49, 50, 70, 71, 87, 166, 502, 504, 505, 506, 507, 511, 512, 521, 524, 10, 44, 46, 55, 3001, 3014, and 5009, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169, 34, 29, 501, 141, 3003, 204, 101, 102, 2, 11, 5, 3, 15, 19, 27, 28, 47, 106, 201, 202, 205, 207, 209, 211, 212, 59, 65, 302, 33, 69, 143, 401, 402, 403, 404, 407, 31, 32, 49, 50, 70, 71, 87, 166, 502, 504, 505, 506, 507, 511, 512, 521, 524, 10, 44, 46, 55, 3001, 3014, and 5009, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169, 34, 29, 501, 141, 3003, 204, 101, and 102, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, and 48, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, and 104, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, 1, 101, 57, 3, 102, 12, 3011, 3003, 41, 47, 29, 21, 3015, 3010, 143, 20, 511, 203, 169, 3005, 141, 702, 65, 15, 3001, 87, 205, 14, 11, 202, 19, 2, 44, 201, 502, 34, 28, 32, 524, 504, 30, 501, 204, 27, 106, 207, 209, 211, 212, 302, 402, 166, 521, 10, 5009, and 3014, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, 1, 101, 57, 3, 102, 12, 3011, 3003, 41, 47, 29, 21, 3015, 3010, 143, 20, 511, 203, 169, 3005, 141, 702, 65, 15, 3001, 87, 205, 14, 11, 202, 19, 2, 44, 201, 502, 34, 28, 32, 524, and 504, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, 1, 101, 57, 3, 102, 12, 3011, 3003, 41, 47, 29, 21, 3015, 3010, 143, 20, 511, 203, 169, 3005, 141, 702, 65, 15, 3001, 87, 205, 14, 11, and 202, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, and 1, or a salt thereof. In some embodiments, the compound or salt of Formula (IIIa) is selected from: compounds 13, 104, 39, 3008, 155, 701, 9, 36, 22, 35, 208, 8, and 3009, or a salt thereof. In some embodiments, the compound or salt of Formula (IIIa) is selected from: compounds 13 and 104.

In some embodiments, the compound or salt of Formula (IIIa) is selected from: compounds 97, 105, 98, 99, 100, 213, 214, 215, 95, 96, 301, 303, 142, 405, 406, 408, 42, 508, 509, 510, 513, 514, 515, 516, 517, 518, 519, 520, 522, 523, 525, 526 528, 529, 530, 531, 532, 533, 534, 535, 601, 602, 603, 604, 605, 606, 43, 703, 5001, 5002, 5003, 5004, 5005, 5006, 5007, 5008, 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169 29, 501, 141, 3003, 204, 101, 102, 2, 11, 5, 3, 15, 19, 27, 28, 47, 106, 201, 202, 205, 207, 209, 211, 212, 59, 65, 302 69, 143, 401, 402, 403 407, 49, 5071, 87, 166, 502 505, 506, 507, 511 521, 524, 10, 44, 46, 55, 3001, 3014, and 5009, or a salt thereof. In some embodiments, the compound or salt of Formula (IIIa) is selected from: compounds 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, 213, 214, 215, 3001, 3002, 3003, 3004, 3005, 3006, 3007, 3008, 3009, 3010, 3011, 3013, 3014, 3015, 142, 405, 406, 408, 155, 72, 136, 39, 104, 154, 36, 35, 38, 40, 51, 37, 41, 143, 402, 403 407, 42, 50, 87, 101, 102, 501, 502 506, 507, 508, 509, 510, 511 513, 514, 517, 518, 519, 520, 521, 522, 523, 524, 525, 526 528, 529, 530, 533, and 534, or a salt thereof. In some embodiments, the compound or salt of Formula (IIIa) is selected from: compounds, 97, 105, 98, 99, 100, 213, 214, 215, 95, 96, 142, 405, 406, 408, 42, 508, 509, 510, 513, 514, 517, 518, 519, 520, 522, 523, 525, 526 528, 529, 530, 533, 534, 601, 602, 603, 604, 606, 43, 703, 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, 48, 17, 3015, 3005, 51, 16, 203, 37, 1, 14, 57, 41 29, 501, 141, 3003, 204, 101, 102, 2, 11, 5, 3, 15, 19, 27, 28, 47, 106, 201, 202, 205, 207, 209, 211, 212, 59 143, 402, 403 407, 50, 87, 502 506, 507, 511 521, 524, 10, 44, 46, 55, 3001, and 3014, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, 48, 17, 3015, 3005, 51, 16, 203, 37, 1, 14, 57, 4129, 501, 141, 3003, 204, 101, 102, 2, 11, 5, 3, 15, 19, 27, 28, 47, 106, 201, 202, 205, 207, 209, 211, 212, 59 143, 402, 403 407, 50, 87, 502 506, 507, 511 521, 524, 10, 44, 46, 55, 3001, and 3014, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, 48, 17, 3015, 3005, 51, 16, 203, 37, 1, 14, 57, 41 29, 501, 141, 3003, 204, 101, and 102, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, 104, 206, 3013, 154, 36, 7, 35, 3010, 30, 12, 38, 4, 18, 40, 20, 3011, 702, and 48, or a salt thereof. In some embodiments, the compound or salt of Formula (IIIa) is selected from: compounds 701, 3008, 13, 155, 22, 3002, 3009, 208, 136, 39, 8, 3004, 9, 210, 21, 3006, 6, 3007, and 104, or a salt thereof. In some embodiments, the compound or salt of Formula (IIIa) is selected from: compounds 701 and 3008 or a salt thereof. In some embodiments, the compound or salt of Formula (IIIa) is selected from: compounds 97, 105, 98, 99, 100, 213, 214, 215, 95, 96, 301, 303, 142, 405, 406, 408, 42, 508, 509, 510, 513, 514, 515, 516, 517, 518, 519, 520, 522, 523, 525, 526 528, 529, 530, 531, 532, 533, 534, 535, 601, 602, 603, 604, 605, 606, 43, 703, 5001, 5002, 5003, 5004, 5005, 5006, 5007, 5008, 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169 29, 501, 141, 3003, 204, 101, 102, 2, 11, 5, 3, 15, 19, 27, 28, 47, 106, 201, 202, 205, 207, 209, 211, 212, 59, 65, 302 69, 143, 401, 402, 403 407, 49, 5071, 87, 166, 502 505, 506, 507, 511 521, 524, 10, 44, 46, 55, 3001, 3014, and 5009, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169 29, 501, 141, 3003, 204, 101, 102, 2, 11, 5, 3, 15, 19, 27, 28, 47, 106, 201, 202, 205, 207, 209, 211, 212, 59, 65, 302 69, 143, 401, 402, 403 407, 49, 50 71, 87, 166, 502 505, 506, 507, 511 521, 524, 10, 44, 46, 55, 3001, 3014, and 5009, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, 48, 17, 3015, 3005, 51, 16, 203, 37, 1, 14, 57, 41, 169 29, 501, 141, 3003, 204, 101, and 102, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, 104, 206, 3013, 154, 36, 7, 503, 35, 3010, 30, 12, 38, 4, 18, 40, 167, 20, 3011, 702, and 48, or a salt thereof. In some embodiments, the compound or salt of Formula (IIIa) is selected from: compounds 701, 3008, 13, 155, 22, 3002, 3009, 72, 208, 136, 39, 8, 3004, 9, 210, 21, 3006, 6, 73, 3007, and 104, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, 1, 101, 57, 3, 102, 12, 3011, 3003, 41, 47, 29, 21, 3015, 3010, 143, 20, 511, 203, 169, 3005, 141, 702, 65, 15, 3001, 87, 205, 14, 11, 202, 19, 2, 44, 201, 50228, 52430, 501, 204, 27, 106, 207, 209, 211, 212, 302, 402, 166, 521, 10, 5009, and 3014, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, 1, 101, 57, 3, 102, 12, 3011, 3003, 41, 47, 29, 21, 3015, 3010, 143, 20, 511, 203, 169, 3005, 141, 702, 65, 15, 3001, 87, 205, 14, 11, 202, 19, 2, 44, 201, 502 28, and 524, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, 1, 101, 57, 3, 102, 12, 3011, 3003, 41, 47, 29, 21, 3015, 3010, 143, 20, 511, 203, 169, 3005, 141, 702, 65, 15, 3001, 87, 205, 14, 11, and 202, or a salt thereof. In some embodiments, the compound or salt of Formula (IIIa) is selected from: compounds 13, 104, 39, 3008, 155, 701, 9, 36, 22, 35, 208, 8, 3009, 503, 40, 3002, 6, 73, 72, 210, 154, 4, 3004, 38, 3013, 5, 51, 3006, 206, 3007, 407, 7, 18, 48, 17, 16, 37, and 1, or a salt thereof. In some embodiments, the compound or salt of Formula (IIIa) is selected from: compounds 13, 104, 39, 3008, 155, 701, 9, 36, 22, 35, 208, 8, and 3009, or a salt thereof. In some embodiments, the compound or salt of Formula (IIIa) is selected from: compounds 13 and 104.

In some embodiments, the compound or salt of Formula (IIIa) is selected from compounds: 34, 504, 32, 527, 512, 31, 33, 70, and 404, or a salt thereof. In some embodiments, Formula III-Q comprises 34, 504, 32, 527, 512, 31, 33, 70, and 404 and salts thereof. In some embodiments, the compound or salt of Formula (IIIa) is selected from compounds: 34, 504, 32, 527, 512, 31, 33, and 70, or a salt thereof. In some embodiments, the compound or salt of Formula (IIIa) is selected from compound: 34, 504, and 32, or a salt thereof. In some embodiments, the compound or salt of Formula (IIIa) is selected from compound: 34.

In some embodiments, the compound or salt of Formula (IIIa) is a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In some embodiments, the compound or salt of Formula (IIIa) is a compound or salt of Formula (I). In some embodiments, the compound or salt of Formula (IIIa) is a compound or salt of Formula (Ia). In some embodiments, the compound or salt of Formula (IIIa) is a compound or salt of Formula (Ib). In some embodiments, the compound or salt of Formula (IIIa) is a compound or salt of Formula (Ic). In some embodiments, the compound or salt of Formula (IIIa) is a compound or salt of Formula (Id). In some embodiments, the compound or salt of Formula (IIIa) is a compound or salt of Formula (Ia-ep). In some embodiments, the compound or salt of Formula (IIIa) is a compound or salt of Formula (Ib-ep). In some embodiments, the compound or salt of Formula (IIIa) is a compound or salt of Formula (Ic-ep). In some embodiments, the compound or salt of Formula (IIIa) is a compound or salt of Formula (Id-ep). In some embodiments, the compound or salt of Formula (IIIa) is a compound or salt of Formula (Ia-e). In some embodiments, the compound or salt of Formula (IIIa) is a compound or salt of Formula (Ib-e). In some embodiments, the compound or salt of Formula (IIIa) is a compound or salt of Formula (Ic-e). In some embodiments, the compound or salt of Formula (IIIa) is a compound or salt of Formula (Id-e). In some embodiments, the compound or salt of Formula (IIIa) is a compound or salt of Formula (II). In some embodiments, the compound or salt of Formula (IIIa) is a compound or salt of Formula (IIa). In some embodiments, the compound or salt of Formula (IIIa) is a compound or salt of Formula (IIb). In some embodiments, the compound or salt of Formula (IIIa) is a compound or salt of Formula (IIa-e). In some embodiments, the compound or salt of Formula (IIIa) is a compound or salt of Formula (IIb-e). In some embodiments, the compound or salt of Formula (IIIa) is a compound or salt of Formula (IIa-ep). In some embodiments, the compound or salt of Formula (IIIa) is a compound or salt of Formula (IIb-ep). In some embodiments, the compound or salt of Formula (IIIa) is a compound or salt of Formula (III). In some embodiments, the compound or salt of Formula (IIIa) is a compound or salt of Formula (IIIa-e).In some embodiments, the compound or salt of Formula (IIIa) is a compound or salt of Formula (IIIa-ep).

In some embodiments, the compound or salt of Formula (I) is a compound or salt of Formula (Ia). In some embodiments, the compound or salt of Formula (I) is a compound or salt of Formula (Ib). In some embodiments, the compound or salt of Formula (I) is a compound or salt of Formula (Ic). In some embodiments, the compound or salt of Formula (I) is a compound or salt of Formula (Id). In some embodiments, the compound or salt of Formula (I) is a compound or salt of Formula (Ia-e). In some embodiments, the compound or salt of Formula (I) is a compound or salt of Formula (Ib-e). In some embodiments, the compound or salt of Formula (I) is a compound or salt of Formula (Ic-e). In some embodiments, the compound or salt of Formula (I) is a compound or salt of Formula (Id-e).In some embodiments, the compound or salt of Formula (I) is a compound or salt of Formula (Ia-ep). In some embodiments, the compound or salt of Formula (I) is a compound or salt of Formula (Ib-ep). In some embodiments, the compound or salt of Formula (I) is a compound or salt of Formula (Ic-ep). In some embodiments, the compound or salt of Formula (I) is a compound or salt of Formula (Id-ep).

In some embodiments, the compound or salt of Formula (II) is a compound or salt of Formula (IIa). In some embodiments, the compound or salt of Formula (II) is a compound or salt of Formula (IIb). In some embodiments, the compound or salt of Formula (II) is a compound or salt of Formula (IIa-e). In some embodiments, the compound or salt of Formula (II) is a compound or salt of Formula (IIb-e).In some embodiments, the compound or salt of Formula (II) is a compound or salt of Formula (IIa-ep). In some embodiments, the compound or salt of Formula (II) is a compound or salt of Formula (IIb-ep).

Pharmaceutical Compositions

In aspect, the disclosed herein is a pharmaceutical composition comprising any compound or salt thereof disclosed herein and a pharmaceutically acceptable excipient. In aspect, disclosed herein is a pharmaceutical composition comprising a compound or salt of any one of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In aspect, the disclosed herein is a pharmaceutical composition comprising a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep). In aspect, the disclosed herein is a pharmaceutical composition comprising a compound or salt of any one of formula (I). In aspect, the disclosed herein is a pharmaceutical composition comprising a compound or salt of any one of formula (Ia). In aspect, the disclosed herein is a pharmaceutical composition comprising a compound or salt of any one of formula (Ia-ep). In aspect, the disclosed herein is a pharmaceutical composition comprising a compound or salt of any one of formula (Ib). In aspect, the disclosed herein is a pharmaceutical composition comprising a compound or salt of any one of formula (Ib-ep). In aspect, the disclosed herein is a pharmaceutical composition comprising a compound or salt of any one of formula (Ic). In aspect, the disclosed herein is a pharmaceutical composition comprising a compound or salt of any one of formula (Ic-ep). In aspect, the disclosed herein is a pharmaceutical composition comprising a compound or salt of any one of formula (II). In aspect, the disclosed herein is a pharmaceutical composition comprising a compound or salt of any one of formula (IIa). In aspect, the disclosed herein is a pharmaceutical composition comprising a compound or salt of any one of formula (IIa-ep). In aspect, the disclosed herein is a pharmaceutical composition comprising a compound or salt of any one of formula (IIb). In aspect, the disclosed herein is a pharmaceutical composition comprising a compound or salt of any one of formula (IIb-ep). In aspect, the disclosed herein is a pharmaceutical composition comprising a compound or salt of any one of formula (III). In aspect, the disclosed herein is a pharmaceutical composition comprising a compound or salt of any one of formula (IIIa). In aspect, the disclosed herein is a pharmaceutical composition comprising a compound or salt of any one of formula (IIIa-ep).

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually hours, days, weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

The chemical entities described herein (e.g., a compound or salt of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep))) can be co-administered with, and the pharmaceutical compositions can include, the additional active agent (e.g., pharmaceutical agents, adjuvants, and the like).

In certain embodiments, a compound or salt of the disclosure may be administered in combination with a corticosteroid. In certain embodiments, a compound or salt of the disclosure is administered in combination with deflazacort. In certain embodiments, a compound or salt of the disclosure is administered in combination with prednisone. In certain embodiments, a compound or salt of the disclosure is administered in combination with a morpholino antisense oligomer. In certain embodiments, a compound or salt of the disclosure is administered in combination with and exon skipping therapy. In certain embodiments, the additional therapeutic agent is eteplirsen or ataluren. In certain embodiments, a compound or salt of the disclosure is administered in combination with givinostat.

In certain embodiments, a compound or salt of the disclosure is used in combination with a gene therapy. In certain embodiments, the compound or salt of the disclosure is used in combination with adeno-associated virus (AAV) containing genes encoding replacement proteins, e.g., dystrophin, or truncated version thereof, e.g., microdystrophin. In certain embodiments, a compound or salt of the disclosure is administered in combination with vamorolone.

In certain embodiments, a compound or salt of the disclosure is administered in combination with one or more incretin therapeutic(s).

In certain embodiments, a compound or salt of the disclosure (such as compound 34, 504, 32, 527, 512, 31, 33, 70, or 404, or a salt of any thereof), or a compound or salt with a Y125 value in Table 8, may be administered in combination with one or more agents selected from a GLP-1 (e.g., Glucagon-like peptide-1) modulator (e.g., a GLP-1 agonist). In some embodiments, a compound or salt of the present disclosure may be administered in combination with a GLP-1 agonist. In some embodiments, a compound or salt of the present disclosure may be administered in combination with an SGLT2 inhibitor. In some embodiments, a compound or salt of the present disclosure may be administered in combination with a GIP agonist. In some embodiments, a compound or salt of the present disclosure may be administered in combination with a lipase inhibitor (e.g., orlistat). In certain embodiments, a compound or salt of the disclosure may be administered in combination with one or more agents selected from a GIP (e.g., glucose-dependent insulinotropic polypeptide) modulator (e.g., a GIP agonist). In certain embodiments, a compound or salt of the disclosure may be administered in combination with one or more antidiabetic medication(s). In certain embodiments, a compound or salt of the disclosure may be administered in combination with one or more agents selected from Dulaglutide, Exenatide, Semaglutide, Liraglutide, Lixisenatide, and Tirzepatide. In certain embodiments, a compound or salt of the disclosure may be administered in combination with one or more SGLT2 inhibitors (e.g., Dapagliflozin, Canagliflozin, Empagliflozin, or Remogliflozin). In certain embodiments, a compound or salt of the disclosure may be administered in combination with one or more insulin sensitizers, such as a buiguanide (e.g., such as metformin, phenformin, or buformin), a thiazolidinedione (e.g., Rosiglitazone, Pioglitazone, or Troglitazone), or a Lyn kinase activator, such as tolimidone. In certain embodiments, a compound or salt of the disclosure may be administered in combination with one or more Secretagogues (e.g., one or more stimulators of beta cells), such as a "sulfonylureas" type secretagogue (e.g., a First-generation agent, such as tolbutamide, acetohexamide, tolazamide, chlorpropamide; or a Second-generation agent, such as glipizide, glyburide or glibenclamide, glimepiride, gliclazide, glyclopyramide, or gliquidone); or a "Meglitinides-type" secretagogue (e.g., repaglinide, nateglinide). In certain embodiments, a compound or salt of the disclosure may be administered in combination with one or more Alpha-glucosidase inhibitors (e.g., decreasing the rate at which glucose is absorbed from the gastrointestinal tract), such as miglitol, acarbose, or voglibose.

In certain embodiments, a compound or salt of the disclosure may be administered in combination with a modulator of one or more targets selected from: skeletal myosin, skeletal actin, skeletal tropomyosin, skeletal troponin C, skeletal troponin I, skeletal troponin T, and skeletal muscle, including fragments and isoforms thereof, and the skeletal sarcomere. In certain embodiments, a compound or salt of the disclosure may be administered in combination with one or more therapeutic agent(s) useful in the treatment of the aforementioned disorders including: anti-obesity agents, anti-sarcopenia agents, anti-wasting syndrome agents, anti-frailty agents, anti-cachexia agents, anti-muscle spasm agents, agents against post-surgical and post-traumatic muscle weakness, and anti-neuromuscular disease agents.

EXAMPLES

The invention now being generally described, it will be more readily understood by reference to the following examples which are included merely for purposes of illustration of certain aspects and embodiments of the present invention and are not intended to limit the invention in any way.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

The compounds of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) (e.g., compounds of Tables 1-4), can be made using conventional organic syntheses and commercially available starting materials. By way of example and not limitation, compounds of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) (e.g., compounds of Tables 1-4), can be prepared as outlined in Scheme 1, shown below, as well as in the examples set forth herein. It should be noted that one skilled in the art would know how to modify the procedures set forth in the illustrative schemes and examples to arrive at the desired products.

The compounds of the present disclosure can be made using conventional organic syntheses and commercially available starting materials. By way of example and not limitation, Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) can be prepared as outlined in Scheme 1, shown below, as well as in the examples set forth herein. It should be noted that one skilled in the art would know how to modify the procedures set forth in the illustrative schemes and examples to arrive at the desired products.

Scheme 1

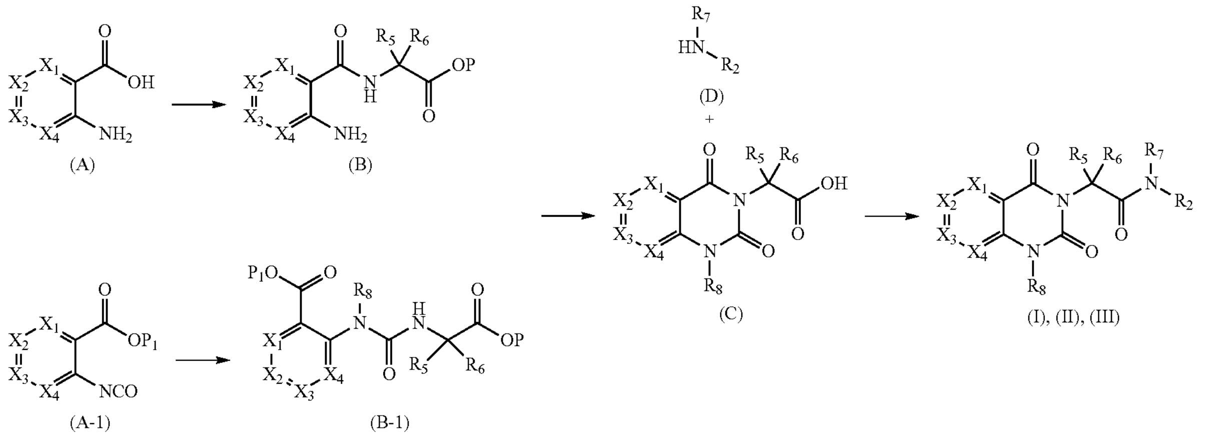

As shown in Scheme 1, compounds of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (Ia), Formula (IIa-e), Formula (IIa-ep), Formula (IIb), Formula (IIb-e), Formula (IIb-ep), Formula (III), Formula (IIa), Formula (IIIa-e), or Formula (IIIa-ep) or of Table 1, Table 2, Table 3, Table 4, Table 5, or Table 6, or Table 7, wherein $R^2$, $R^3$, $R^4$, $R^5$, $R^6$ and $R^7$ are as defined herein, can be prepared starting from appropriately derivatized amines (D) and substituted heteroaryl dioxodihydroquinazolinacetic acid (C), wherein $X^1$, $X^2$, $X^3$, and $X^4$ is either C or N. Aminobenzoic acids (A), isocyanatobenzoates (A-1) and amines (D) are commercially available or may be prepared according to known methods (see, e.g., D. Liu et al, *Bioorganic & Medicinal Chemistry*, 2013, 21 (11), 2960-2967). Aminoglycinate (B) wherein P is Me, can be obtained by treatment of appropriately substituted amino benzoic acid (A) with a substituted amino acid, in the presence of a base, such as DIEA and DMAP in a solvent, such as DMF, and a coupling reagent, such as hexafluorophosphate azabenzotriazole tetramethyl uronium, hydroxybenzotriazole, or 1-ethyl-3-(3-dimethylaminopropyl)carbodiimide hydrochloride at temperatures ranging from 0° C. to 25° C. Ureidobenzoate (B-1) wherein P and $P_1$ are Me, can be obtained by treatment of appropriately substituted isocyantobenzoates (A-1) with a substituted amino acid, in the presence of a base, such as triethyl amine, in a solvent, such as THF, at temperatures ranging from 0° C. to 25° C. Dioxodihydroquinazolinacetic acid (C) may be obtained by treatment of aminoglycinate (B) wherein P is Me, with CDI in the presence of a base, such as DBU, in a solvent, such as DCM or THF, at temperatures ranging from 0° C. to 50° C. Alternatively, dioxodihydroquinazolinacetic acid (C) may be obtained by treatment of ureidobenzoate (B-1) wherein P is Me, with DMAP in the presence of a base, such as triethylamine, in a solvent, such as MeOH, at temperatures ranging from 0° C. to 50° C. Instances wherein (C) exists as an ester, P=Me, acids (C) can be obtained using known methods of hydrolysis, using a base such as LiOH, or NaOH in a solvent, such as MeOH or EtOH and water, at temperatures ranging from 0° C. to 25° C. Coupling of derivatized amine (D) and dioxodihydroquinazolinacetic acid (C) in a solvent, such as DMF or THF in the presence of a base, such as DIPEA or DMAP, and a coupling reagent, such as hydroxybenzotriazole and 1-ethyl-3-(3-dimethylaminopropyl)carbodiimide hydrochloride or hexafluorophosphate azabenzotriazole aetramethyl uronium, at temperatures ranging from about 0° C. to about 25° C. provide compounds of compounds of Formula (I), Formula (Ia), Formula (Ia-e), Formula (Ia-ep), Formula (Ib), Formula (Ib-e), Formula (Ib-ep), Formula (Ic), Formula (Ic-e), Formula (Ic-ep), Formula (Id), Formula (Id-e), Formula (Id-ep), Formula (II), Formula (IIa), Formula (IIa-e), Formula (IIa-ep), Formula (IIb), Formula (IIb-e), Formula (IIb-ep), Formula (III), Formula (IIIa), Formula (IIIa-e), or Formula (IIIa-ep) or of Tables 1, Table 2, Table 3, Table 4, Table 5, or Table 6, or Table 7.

Example 1: (R*)—N-[(1S)-1-(2,4-difluorophenyl) ethyl]-2-(5-hydroxy-2,4-dioxo-1H-quinazolin-3-yl) propanamide (compound 35) and (R*)—N-[(1S)-1-(2,4-difluorophenyl)ethyl]-2-(5-hydroxy-2,4-dioxo-1H-quinazolin-3-yl)propanamide

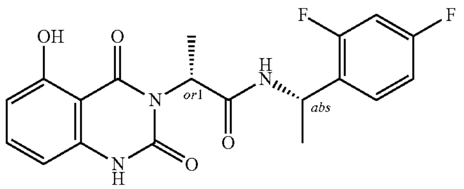

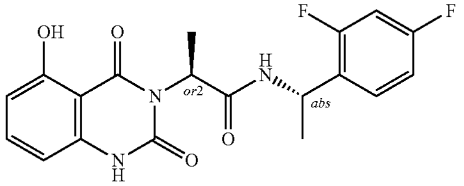

tert-butyl 2-[(2-amino-6-methoxyphenyl)formamido]propanoate. A solution of 2-amino-6-methoxybenzoic acid (3 g, 17.9 mmol, 1 equiv) and tert-butyl 2-aminopropanoate (2.61 g, 17.9 mmol, 1 equiv), EDCI (4.47 g, 23.3 mmol, 1.3 equiv), HOBT (3.15 g, 23.3 mmol, 1.3 equiv), DIEA (4.64 g, 35.9 mmol, 2 equiv) in DMF (30 mL) was stirred for 2 h at room temperature under air atmosphere The resulting mixture was diluted with water, extracted with EtOAc, the combined organic layers were concentrated under reduced pressure, and purified by silica gel column chromatography to afford tert-butyl 2-[(2-amino-6-methoxyphenyl)formamido]propanoate (4.2 g, 79.51%). LCMS (ES, m/z): 295 $[M+H]^+$ tert-butyl 2-(5-methoxy-2,4-dioxo-1H-quinazolin-3-yl) propanoate. A solution of tert-butyl 2-[(2-amino-6-methoxyphenyl)formamido]propanoate (4.2 g, 14.3 mmol, 1 equiv) and CDI (4.63 g, 28.5 mmol, 2 equiv), DBU (4.34 g, 28.5 mmol, 2 equiv) in DCM (40 mL) was stirred for 2 h at room temperature under air atmosphere. The resulting mixture was concentrated under vacuum and purified by silica gel column chromatography to afford tert-butyl 2-(5-methoxy-2,4-dioxo-TH-quinazolin-3-yl)propanoate (3.2 g, 70.01%). LCMS (ES, m/z): 321 $[M+H]^+$ N-[(1S)-1-(2,4-difluorophenyl)ethyl]-2-(5-fluoro-2-oxo-1H-1,6-naphthyridin-3-yl)propenamide To a stirred solution of tert-butyl 2-(5-methoxy-2,4-dioxo-TH-quinazolin-3-yl) propanoate (1 g, 3.1 mmol, 1 equiv) in DCM (1 mL) was added TFA (0.2 mL) dropwise at 0° C. under air atmosphere. The resulting mixture was stirred for 2 h at room temperature under air atmosphere. The resulting mixture was concentrated under reduced pressure and the crude product was used in the next step directly without further purification. LCMS (ES, m/z): 265 $[M+H]^+$ N-[(1S)-1-(2,4-difluorophenyl)ethyl]-2-(5-fluoro-2-oxo-1H-1,6-naphthyridin-3-yl)propenamide. A solution of 2-(5-methoxy-2,4-dioxo-1H-quinazolin-3-yl)propanoic acid (420 mg, 1.59 mmol, 1 equiv) and (1S)-1-(2,4-difluorophenyl) ethanamine (249.8 mg, 1.59 mmol, 1 equiv), EDCI (396.1 mg, 2.1 mmol, 1.3 equiv), HOBT (279.2 mg, 2.1 mmol, 1.3 equiv), DIEA (410.8 mg, 3.18 mmol, 2 equiv) in DMF (5 mL) was stirred for overnight at room temperature under air atmosphere. The resulting mixture was diluted with water, extracted with EtOAc and the combined organic layers were concentrated under reduced pressure. The residue was purified by silica gel column chromatography to afford N-[(1S)-1-(2,4-difluorophenyl)ethyl]-2-(5-methoxy-2,4-dioxo-TH-quinazolin-3-yl)propanamide (350 mg, 54.59%) as a white solid. LCMS (ES, m/z): 404 $[M+H]^+$ N-[(1S)-1-(2,4-difluorophenyl)ethyl]-2-(5-hydroxy-2,4-dioxo-1H-quinazolin-3-yl)propenamide. To a stirred solution of N-[(1S)-1-(2,4-difluorophenyl)ethyl]-2-(5-methoxy-2,4-dioxo-H-quinazolin-3-yl)propanamide (220 mg, 0.55 mmol, 1 equiv) in DCM (5 mL) was added $BBr_3$ (409.9 mg, 1.63 mmol, 3 equiv) dropwise at 0° C. under air atmosphere. The resulting mixture was stirred for 2 h at room temperature under air atmosphere. The resulting mixture was concentrated under vacuum. The residue was purified by reversed-phase flash chromatography with the following conditions: column, C18; mobile phase, MeCN in Water (0.1% FA), 10% to 50% gradient in 30 min; detector, UV 254 nm to afford N-[(1S)-1-(2,4-difluorophenyl)ethyl]-2-(5-hydroxy-2,4-dioxo-TH-quinazolin-3-yl)propanamide (160 mg, 75.35%) as a white solid. LCMS (ES, m/z): 390 $[M+H]^+$ (2R*)—N-[(1S)-1-(2,4-difluorophenyl)ethyl]-2-(5-hydroxy-2,4-dioxo-1H-quinazolin-3-yl)propenamide. The N-[(1S)-1-(2,4-difluorophenyl)ethyl]-2-(5-hydroxy-2,4-dioxo-1H-quinazolin-3-yl)propanamide (160 mg) was purified by Chiral-HPLC with the following conditions: Column: CHIRALPAK IF, 2*25 cm, 5 μm; Mobile Phase A: Hex(10 mM $NH_3$-MeOH), Mobile Phase B: EtOH—HPLC; Flow rate: 20 mL/min; Gradient: 30% B to 30% B in 15 min; Wave Length: 230/254 nm; $RT_1$(min): 4.87; $RT_2$(min): 8.52; Sample Solvent: DCM:ACN=1:1; Injection Volume: 0.65 mL; to afford (2R*)—N-[(1S)-1-(2,4-difluorophenyl)ethyl]-2-(5-hydroxy-2,4-dioxo-1H-quinazolin-3-yl)propanamide (54.9 mg, 34.31%). LCMS (ES, m/z): 389.8 $[M+H]^+$ $^1H$ NMR (400 MHz, DMSO-$d_6$) δ11.59 (s, 1H), 11.50 (s, 1H), 8.24 (d, J=7.6 Hz, 1H), 7.53-7.49 (m, 1H), 7.42-7.36 (m, 1H), 7.19-7.13 (m, 1H), 7.08-7.03 (m, 1H), 6.60 (dd, J=10.6, 8.0 Hz, 2H), 5.27-5.22 (m, 1H), 5.19-5.11 (m, 1H), 1.45 (d, J=6.8 Hz, 3H), 1.27 (d, J=6.8 Hz, 3H).

(2R*)—N-[(1S)-1-(2,4-difluorophenyl)ethyl]-2-(5-hydroxy-2,4-dioxo-1H-quinazolin-3-yl)propenamide. The N-[(1S)-1-(2,4-difluorophenyl)ethyl]-2-(5-hydroxy-2,4-dioxo-1H-quinazolin-3-yl)propanamide (160 mg) was purified by Chiral-HPLC with the following conditions: Column: CHIRALPAK IF, 2*25 cm, 5 μm; Mobile Phase A: Hex(10 mM $NH_3$-MeOH), Mobile Phase B: EtOH—HPLC; Flow rate: 20 mL/min; Gradient: 30% B to 30% B in 15 min; Wave Length: 230/254 nm; RT1(min): 4.87; RT2(min): 8.52; Sample Solvent: DCM:ACN=1:1; Injection Volume: 0.65 mL; Number Of Runs: 4 to afford (2R*)—N-[(1S)-1-(2,4-difluorophenyl)ethyl]-2-(5-hydroxy-2,4-dioxo-1H-quinazolin-3-yl)propanamide (58.8 mg, 36.75%). LCMS (ES, m/z): 389.8 [M+H]+$^1H$ NMR (400 MHz, DMSO-d6) δ11.64 (s, 1H), 11.43 (s, 1H), 8.33 (d, J=7.6 Hz, 1H), 7.55-7.50 (m, 1H), 7.35-7.29 (m, 1H), 7.16-7.10 (m, 1H), 6.94-6.89 (m, 1H), 6.65-6.60 (m, 2H), 5.33-5.27 (m, 1H), 5.16-5.09 (m, 1H), 1.42 (d, J=6.8 Hz, 3H), 1.30 (d, J=6.8 Hz, 3H).

Example 2: (2S)—N-[(1S)-1-(2,4-Difluorophenyl) ethyl]-2-(2,4-dioxo-1H-quinazolin-3-yl)propenamide (compound 102)

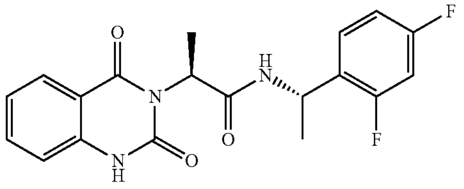 [SMILES: C[C@H](NC(=O)[C@H](C)n1c(=O)[nH]c2ccccc2c1=O)c1ccc(F)cc1F]

Methyl 2-isocyanatobenzoate. A mixture of methyl anthranilate (400 mg, 3 mmol, 1 equiv), TEA (937.19 mg, 9.26 mmol, 3.5 equiv) and triphosgene (314.07 mg, 1.06 mmol, 0.4 equiv) in THF (1 mL) was stirred for 2 h at room temperature. The resulting mixture was used in the next step directly without further purification. LCMS (ES, m/z): 178 $[M+H]^+$.

Methyl 2-({[(2S)-1-methoxy-1-oxopropan-2-yl] carbamoyl}amino)benzoate. A solution of methyl 2-isocyanatobenzoate (400 mg, 2 mmol, 1 equiv) and D-alanyl ester (349.25 mg, 3.4 mmol, 1.5 equiv) in THF (1 mL) was stirred for 2 h at room temperature. The resulting mixture was diluted with water and extracted with EtOAc. The combined organic layers were washed with water and dried over anhydrous $Na_2SO_4$. The filtrate was concentrated under reduced pressure and purified by Prep-TLC to afford methyl 2-({[(2S)-1-methoxy-1-oxopropan-2-yl]carbamoyl}amino) benzoate (400 mg, 59.41%). LCMS (ES, m/z): 281 $[M+H]^+$.

Methyl (2S)-2-(2,4-dioxo-1H-quinazolin-3-yl)propanoate. A mixture of methyl 2-({[(2S)-1-methoxy-1-oxopropan-2-yl]carbamoyl}amino)benzoate (400 mg, 1 mmol, 1 equiv), TEA (216.63 mg, 2.14 mmol, 1.5 equiv) and DMAP (17.44 mg, 0.14 mmol, 0.1 equiv) in MeOH (1 mL) was stirred for 2 h at 50° C. The resulting mixture was concentrated under reduced pressure and purified by Prep-TLC to afford methyl (2S)-2-(2,4-dioxo-1H-quinazolin-3-yl)propanoate (300 mg, 84.68%). LCMS (ES, m/z): 249 $[M+H]^+$.

Tert-butyl 2-(5-chloro-6-fluoro-2,2-dioxo-1,4-dihydro-2lambda6,1,3-benzothiadiazin-3-yl)acetate. A mixture of methyl (2S)-2-(2,4-dioxo-1H-quinazolin-3-yl)propanoate (300 mg, 1 mmol, 1 equiv) and LiOH (43.42 mg, 1.81 mmol, 1.5 equiv) in MeOH (1 mL) was stirred for 2 h at room temperature. The resulting mixture was concentrated under reduced pressure and purified by trituration with MeCN (5 mL). This resulted in (2S)-2-(2,4-dioxo-1H-quinazolin-3-yl) propanoic acid (200 mg, 70.66%). LCMS (ES, m/z): 235 $[M+H]^+$.

(2S)—N-[(1S)-1-(2,4-Difluorophenyl)ethyl]-2-(2,4-dioxo-1H-quinazolin-3-yl)propanamide.

Into a 10-mL round-bottom flask, (2S)-2-(2,4-dioxo-1H-quinazolin-3-yl)propanoic acid (100.00 mg, 0.43 mmol, 1.00 equiv), (1S)-1-(2,4-difluorophenyl)ethanamine (67.10 mg, 0.43 mmol, 1.00 equiv), HATU (243.52 mg, 0.64 mmol, 1.50 equiv), DMF (2.00 mL) and DIEA (82.77 mg, 0.64 mmol, 1.50 equiv) were placed and stirred for 2 h at room temperature. The reaction was then quenched by the addition of 3 mL of water. The resulting solution was extracted with ethyl acetate dried over anhydrous sodium sulfate and concentrated under vacuum. The residue was purified by reversed-phase flash chromatography with the following conditions: column, $C_{18}$; mobile phase, MeCN in water (0.1% FA), 10% to 50% gradient in 40 min; detector, UV 254 nm. This resulted in 60 mg (37.64%) of (2S)—N-[(1S)-1-(2,4-difluorophenyl)ethyl]-2-(2,4-dioxo-1H-quinazolin-3-yl)propanamide. LCMS (ES, m/z): 374.25 $[M+H]^+$. $^1H$ NMR (300 MHz, DMSO-d6) δ 11.48 (d, J=17.4 Hz, $^1H$), 8.27-8.16 (m, $^1H$), 7.96-7.93 (m, $^1H$), 7.72-7.64 (m, $^1H$), 7.41-7.31 (m, $^1H$), 7.26-7.17 (m, $^2H$), 7.21-7.08 (m, $^1H$), 7.13-6.89 (m, $^1H$), 5.35-5.27 (m, $^1H$), 5.18-5.10 (m, $^1H$), 1.46-1.42 (m, $^3H$), 1.30-1.25 (m, $^3H$).

Example 3: (2R)—N-[(1S)-1-(2,4-Difluorophenyl) ethyl]-2-(2,4-dioxo-1H-quinazolin-3-yl)propanamide (compound 101)

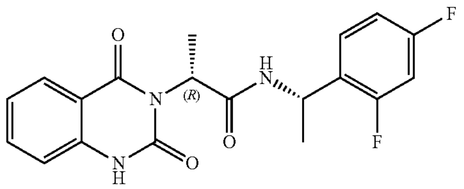

Methyl 2-isocyanatobenzoate. A mixture of methyl anthranilate (500 mg, 3.3 mmol, 1 equiv), triphosgene (392.59 mg, 1.32 mmol, 0.4 equiv) and TEA (1171.49 mg, 11.58 mmol, 3.5 equiv) in THF (5 mL) was stirred for 2 h at room temperature under air atmosphere. The resulting mixture was diluted with water (10 mL). The aqueous layer was extracted with EA. and concentrated under reduced pressure. The residue was purified by silica gel column chromatography to afford methyl 2-isocyanatobenzoate (500 mg, 85.33%) as a white solid. LCMS (ES, m/z): 178 $[M+H]^+$.

Methyl 2-({[(2R)-1-methoxy-1-oxopropan-2-yl] carbamoyl}amino)benzoate. A mixture of methyl 2-isocyanatobenzoate (500 mg, 3 mmol, 1 equiv), methyl (2R)-2-aminopropanoate (436.56 mg, 4.23 mmol, 1.5 equiv) and TEA (428.40 mg, 4.23 mmol, 1.5 equiv) in THF (5 mL) was stirred for 2 h at room temperature under air atmosphere. The resulting mixture was diluted with water (10 mL). The aqueous layer was extracted with EA and concentrated under reduced pressure and purified by silica gel column chromatography to afford methyl 2-({[(2R)-1-methoxy-1-oxopropan-2-yl]carbamoyl}amino)benzoate (500 mg, 63.21%). LCMS (ES, m/z): 281 $[M+H]^+$.

Methyl (2R)-2-(2,4-dioxo-1H-quinazolin-3-yl)propanoate. A mixture of methyl 2-({[(2R)-1-methoxy-1-oxopropan-2-yl]carbamoyl}amino)benzoate (500 mg, 2 mmol, 1 equiv), TEA (270.78 mg, 2.68 mmol, 1.5 equiv) and DMAP (21.79 mg, 0.18 mmol, 0.1 equiv) in MeOH (5 mL) was stirred for 2 h at 50° C. under air atmosphere. The resulting mixture was concentrated under reduced pressure. The resulting mixture was diluted with water. The aqueous layer was extracted with EA. The resulting mixture was concentrated under reduced pressure and purified by silica gel column chromatography to afford methyl (2R)-2-(2,4-dioxo-1H-quinazolin-3-yl)propanoate (400 mg, 90.33%) as a white solid. LCMS (ES, m/z): 249 $[M+H]^+$.

(2R)-2-(2,4-Dioxo-1H-quinazolin-3-yl)propanoic acid. A mixture of methyl (2R)-2-(2,4-dioxo-1H-quinazolin-3-yl) propanoate (400 mg, 1.611 mmol, 1 equiv) and LiOH (57.89 mg, 2.42 mmol, 1.5 equiv) in MeOH (4 mL) and $H_2O$ (4 mL) was stirred for 4 h at room temperature under air atmosphere. The resulting mixture was concentrated under reduced pressure. The mixture was acidified to pH 5 with HCl (1 M in $H_2O$). The precipitated solids were collected by filtration and washed with water resulting in (2R)-2-(2,4-dioxo-TH-quinazolin-3-yl)propanoic acid (300 mg, 79.49%). LCMS (ES, m/z): 235 $[M+H]^+$.

(2R)—N-[(1S)-1-(2,4-Difluorophenyl)ethyl]-2-(2,4-dioxo-1H-quinazolin-3-yl)propanamide.

A mixture of (2R)-2-(2,4-dioxo-1H-quinazolin-3-yl)propanoic acid (100 mg, 0.427 mmol, 1 equiv), (1S)-1-(2,4-difluorophenyl)ethanamine (80.52 mg, 0.52 mmol, 1.2 equiv), HATU (194.82 mg, 0.52 mmol, 1.2 equiv) and DIEA (165.55 mg, 1.28 mmol, 3 equiv) in DMF (2 mL) was stirred for 2 h at room temperature under air atmosphere. The residue was purified by reversed-phase flash chromatography with the following conditions: column, C18; mobile phase, MeCN in Water (0.1% FA), 10% to 50% gradient in 50 min; detector, UV 254 nm. This resulted in (2R)—N-[(1S)-1-(2,4-difluorophenyl)ethyl]-2-(2,4-dioxo-1H-quinazolin-3-yl)propanamide (40 mg, 25.09%). LCMS (ES, m/z): 374.20 $[M+H]^+$. $^1H$ NMR (300 MHz, DMSO-$d_6$) δ 11.48 (s, $^1H$), 8.27-8.16 (m, $^1H$), 7.95-7.93 (m, $^1H$), 7.72-7.64 (m, $^1H$), 7.52-7.32 (m, $^1H$), 7.23-7.17 (m, $^3H$), 6.99-6.91 (m, $^1H$), 5.35-5.32 (m, $^1H$), 5.18-5.11 (m, $^1H$), 1.45-1.41 (m, $^3H$), 1.30-1.25 (m, $^3H$).

Example 4: 2-(6-Chloro-2,4-dioxo-1H-quinazolin-3-yl)-N-[(1S)-1-(2,4-difluorophenyl)ethyl]acetamide (compound 104)

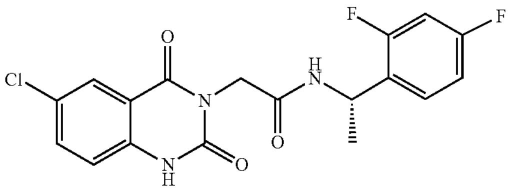 [SMILES: C[C@H](NC(=O)Cn1c(=O)[nH]c2ccc(Cl)cc2c1=O)c1ccc(F)cc1F]

Methyl 5-chloro-2-isocyanatobenzoate. A mixture of methyl 2-amino-S-chlorobenzoate (400 mg, 2 mmol, 1 equiv) and triphosgene (255.79 mg, 0.86 mmol, 0.4 equiv) in THF was stirred for 2 h at room temperature under air atmosphere. The resulting mixture was concentrated under reduced pressure and purified by silica gel column chromatography to afford methyl 5-chloro-2-isocyanatobenzoate (400 mg, 87.72%). LCMS (ES, m/z): 212 $[M+H]^+$.

Methyl 5-chloro-2-{[(2-methoxy-2-oxoethyl)carbamoyl]amino}benzoate. To a stirred mixture of methyl 5-chloro-2-isocyanatobenzoate (340 mg, 2 mmol, 1 equiv) and methyl 2-aminoacetate (214.74 mg, 2.41 mmol, 1.5 equiv) in THF was added TEA (325.19 mg, 3.21 mmol, 2 equiv) at room temperature under air atmosphere. The resulting mixture was stirred for 2 h at 50° C. under air atmosphere. The resulting mixture was concentrated under reduced pressure and purified by silica gel column chromatography to afford methyl 5-chloro-2-{[(2-methoxy-2-oxoethyl)carbamoyl]amino}benzoate (300 mg, 62.09%). LCMS (ES, m/z): 301 $[M+H]^+$.

Methyl 2-(6-chloro-2,4-dioxo-1H-quinazolin-3-yl)acetate. TEA (151.44 mg, 1.50 mmol, 1.5 equiv) was added to a stirred mixture of methyl 5-chloro-2-{[(2-methoxy-2-oxoethyl)carbamoyl]amino}benzoate (300 mg, 1 mmol, 1 equiv) and DMAP (12.19 mg, 0.10 mmol, 0.1 equiv) in THF at room temperature under air atmosphere. The resulting mixture was stirred for 2 h. concentrated under reduced pressure and purified by silica gel column chromatography to afford methyl 2-(6-chloro-2,4-dioxo-1H-quinazolin-3-yl)acetate (260 mg, 97.01%). LCMS (ES, m/z): 269$[M+H]^+$.

N-[(1S)-1-(5-Cyanopyridin-2-yl)ethyl]-2-{8-methyl-1,1,3-trioxo-4H-1lambda6-pyrido[4,3-e][1,2,4]thiadiazin-2-yl}acetamide. $H_2O$ (5 mL, 277.55 mmol, 286.78 equiv) was added to a stirred mixture of methyl 2-(6-chloro-2,4-dioxo-TH-quinazolin-3-yl)acetate (260 mg, 1 mmol, 1 equiv) and LiOH (92.72 mg, 3.87 mmol, 4 equiv) in MeOH at room temperature under air atmosphere. The resulting mixture was stirred for 4 h at 50° C. under air atmosphere. The mixture was neutralized to pH 7 with 3N HCl. The precipitated solids were collected by filtration and washed with $H_2O$. This resulted in (6-chloro-2,4-dioxo-TH-quinazolin-3-yl)acetic acid (180 mg, 73.04%). LCMS (ES, m/z): 255 $[M+H]^+$.

2-(6-Chloro-2,4-dioxo-1H-quinazolin-3-yl)-N-[(1S)-1-(2,4-difluorophenyl)ethyl]acetamide. HATU (447.99 mg, 1.18 mmol, 1.2 equiv), DIEA (380.74 mg, 2.95 mmol, 3 equiv) was added to a stirred mixture of (6-chloro-2,4-dioxo-TH-quinazolin-3-yl)acetic acid (250 mg, 1 mmol, 1 equiv) and (1S)-1-(2,4-difluorophenyl)ethanamine (185.17 mg, 1.178 mmol, 1.2 equiv) in DMF (4 mL) at room temperature under air atmosphere. The resulting mixture was stirred for 2 h and concentrated under reduced pressure then purified by reversed-phase flash chromatography with the following conditions: (column, $C_{18}$ silica gel; mobile phase, MeCN in Water (0.1% FA), 0% to 100% gradient in 50 min; detector, UV 254 nm). This resulted in 2-(6-chloro-2,4-dioxo-TH-quinazolin-3-yl)-N-[(1S)-1-(2,4-difluorophenyl)ethyl]acetamide (80 mg, 20.69%). LCMS (ES, m/z): 394.05 $[M+H]^+$. $^1H$ NMR (300 MHz, DMSO-d6) δ 11.66 (s, $^1H$), 8.69 (d, J=7.5 Hz, $^1H$), 7.87 (d, J=2.4 Hz, $^1H$), 7.74 (dd, J=8.7, 2.4 Hz, $^1H$), 7.50-7.36 (m, $^1H$), 7.28-7.14 (m, $^2H$), 7.14-7.03 (m, $^1H$), 5.08 (m, $^1H$), 4.52 (s, $^2H$), 1.36 (d, J=7.0 Hz, $^3H$).

Example 5: N-[(1S)-1-(2,4-difluorophenyl)ethyl]-2-(2,4-dioxo-1H-quinazolin-3-yl)-3-hydroxypropanamide (compound 511)

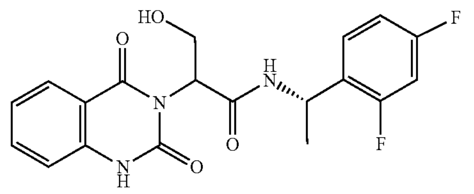 [SMILES: C[C@H](NC(=O)C(CO)n1c(=O)[nH]c2ccccc2c1=O)c1ccc(F)cc1F]

Methyl 2-isocyanatobenzoate. A mixture of methyl anthranilate (5 g, 33 mmol, 1 equiv), TEA (16.09 mL, 115.77 mmol, 3.5 equiv) and triphosgene (3.93 g, 13.23 mmol, 0.4 equiv) in THF (50 mL) was stirred for 2 h at room temperature. The resulting mixture was concentrated under reduced pressure. The methyl 2-isocyanatobenzoate (4 g, 68.26%) was used in the next step directly without further purification. LC-MS: (ESI, m z): $[M+H]^+$=178.

Methyl 2-[[(3-hydroxy-1-methoxy-1-oxopropan-2-yl)carbamoyl]amino]benzoate. Into a 40-mL round-bottom flask, methyl 2-isocyanatobenzoate (500.00 mg, 2.82 mmol, 1.00 equiv), THF (5.00 mL), methyl 2-amino-3-hydroxypropanoate hydrochloride (768.42 mg, 4.94 mmol, 1.75 equiv), and TEA (431.24 mg, 4.26 mmol, 1.51 equiv) were placed and stirred for 2 h at room temperature. The resulting mixture was concentrated under reduced pressure and purified using silica gel column chromatography to afford methyl 2-[[(3-hydroxy-1-methoxy-1-oxopropan-2-yl)carbamoyl]amino]benzoate (300 mg, 35.88%). LC-MS: (ESI, m z): $[M+H]^+$=297.

Methyl 2-(2,4-dioxo-1H-quinazolin-3-yl)-3-hydroxypropanoate. Into a 40-mL round-bottom flask, methyl 2-[[(3-hydroxy-1-methoxy-1-oxopropan-2-yl)carbamoyl]amino]benzoate (500.00 mg, 1.69 mmol, 1.00 equiv), methanol (5.00 mL), TEA (341.54 mg, 3.37 mmol, 2.00 equiv), and DMAP (20.62 mg, 0.17 mmol, 0.10 equiv) were placed and stirred for 2 h at 50° C. The resulting mixture was concentrated under reduced pressure and purified using silica gel column chromatography to afford methyl 2-(2,4-dioxo-1H-quinazolin-3-yl)-3-hydroxypropanoate (220 mg, 49.34%). LC-MS: (ESI, m z): $[M+H]^+$=265.

2-(2,4-Dioxo-1H-quinazolin-3-yl)-3-hydroxypropanoic acid. Into a 10-mL round-bottom flask, methyl 2-(2,4-dioxo-1H-quinazolin-3-yl)-3-hydroxypropanoate (200.00 mg, 0.76 mmol, 1.00 equiv), $LiOH \cdot H_2O$ (63.52 mg, 1.51 mmol, 2.00 equiv), MeOH (1.50 mL), NaOH (30.27 mg, 0.76 mmol, 1.00 equiv), and $H_2O$ (0.50 mL) were placed. The resulting solution was stirred for 2 h at room temperature. The resulting mixture was concentrated under reduced pressure and purified by silica gel column chromatography to afford 2-(2,4-dioxo-1H-quinazolin-3-yl)-3-hydroxypropanoic acid (110 mg, 58.08%). LC-MS: (ESI, m z): $[M+H]^+$=251.

N-[(1S)-1-(2,4-difluorophenyl)ethyl]-2-(2,4-dioxo-1H-quinazolin-3-yl)-3-hydroxypropanamide. Into a 10-mL round-bottom flask, 2-(2,4-dioxo-1H-quinazolin-3-yl)-3-hydroxypropanoic acid (100.00 mg, 0.40 mmol, 1.00 equiv), DMF (1.00 mL), (1S)-1-(2,4-difluorophenyl)ethanamine (70.00 mg, 0.45 mmol, 1.11 equiv), HATU (168.00 mg, 0.44 mmol, 1.11 equiv), DIEA (103.00 mg, 0.80 mmol, 1.99 equiv) were placed and stirred for 1 h at room temperature. The residue was purified using silica gel column chromatography to afford N-[(1S)-1-(2,4-difluorophenyl)ethyl]-2-

(2,4-dioxo-1H-quinazolin-3-yl)-3-hydroxypropanamide (20 mg, 12.85%). LC-MS: (ESI, m z): $[M+H]^+$=390.20. $^{1}$H NMR (300 MHz, DMSO-$d_6$) δ11.44 (d, J=20.4 Hz, $^{1}$H), 8.32-8.20 (m, $^{1}$H), 7.95 (t, J=4.8 Hz, $^{1}$H), 7.71-7.65 (m, $^{1}$H), 7.43-7.35 (m, $^{1}$H), 7.25-7.18 (m, $^{3}$H), 7.07 (d, J=5.1 Hz, $^{1}$H), 5.42-5.35 (m, $^{1}$H), 5.14 (q, J=14.7, 7.5 Hz, $^{1}$H), 4.18-4.03 (m, $^{1}$H), 3.96-3.86 (m, $^{1}$H), 1.29 (t, J=7.8 Hz, $^{3}$H).

Example 6: N-[(1S)-5,7-Difluoro-2,3-dihydro-1H-inden-1-yl]-2-{2,4-dioxo-1H-pyrido[4,3-d]pyrimidin-3-yl}acetamide (compound 44)

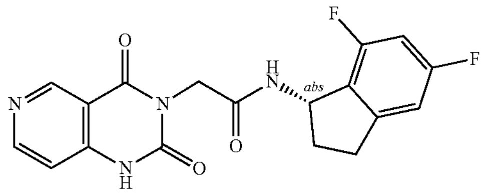 [SMILES: O=C(Cn1c(=O)[nH]c2ccncc2c1=O)N[C@H]1CCc2cc(F)cc(F)c21]

Methyl 2-[(4-aminopyridin-3-yl) formamido] acetate. HATU (6.06 g, 15.93 mmol, 1.1 equiv) and DIEA (5.61 g, 43.44 mmol, 3 equiv) were added to a stirred solution of 4-aminopyridine-3-carboxylic acid (2 g, 14 mmol, 1 equiv) and methyl 2-aminoacetate (1.42 g, 15.93 mmol, 1.1 equiv) in DMF (30 mL) were added at room temperature under air atmosphere. The residue was purified by reversed-phase flash chromatography with the following conditions: column, $C_{18}$ silica gel; mobile phase, MeCN in water (10 mmol/L $NH_4HCO_3$), 10% to 50% gradient in 10 min; detector, UV 254 nm. This resulted in methyl 2-[(4-amino-pyridin-3-yl) formamido] (660 mg, 10.89%). LCMS (ES, m/z): 210 $[Ms+H]^+$.

Methyl 2-{2,4-dioxo-1H-pyrido[4,3-d]pyrimidin-3-yl} acetate. DBU (1164.34 mg, 7.65 mmol, 2.5 equiv) was added to a stirred solution of methyl 2-[(4-aminopyridin-3-yl) formamido] acetate (640 mg, 3 mmol, 1 equiv) and CDI (1240.14 mg, 7.65 mmol, 2.5 equiv) in DCM (5 mL) at room temperature under air atmosphere and stirred for 3 h. The resulting mixture was concentrated under reduced pressure and purified by silica gel column chromatography to afford methyl 2-{2,4-dioxo-1H-pyrido[4,3-d]pyrimidin-3-yl} acetate (490 mg, 68.10%). LCMS (ES, m/z): 236 $[Ms+H]^+$.

{2,4-Dioxo-1H-pyrido[4,3-d]pyrimidin-3-yl} acetic acid. $H_2O$ (3 mL) was added to a stirred solution of methyl 2-{2,4-dioxo-1H-pyrido[4,3-d]pyrimidin-3-yl} acetate (480 mg, 2 mmol, 1 equiv) and LiOH (58.65 mg, 2.45 mmol, 1.2 equiv) in MeOH (3 mL) at room temperature under air atmosphere and stirred for 3 h. The resulting mixture was concentrated under reduced pressure resulting in {2,4-dioxo-1H-pyrido[4,3-d]pyrimidin-3-yl} acetic acid (420 mg, 93.05%). LCMS (ES, m/z): 222 $[Ms+H]^+$.

N-[(1S)-5,7-Difluoro-2,3-dihydro-1H-inden-1-yl]-2-{2,4-dioxo-1H-pyrido[4,3-d]pyrimidin-3-yl}acetamide. EDCI (136.87 mg, 0.88 mmol, 1.5 equiv) and HOBT (119.14 mg, 0.88 mmol, 1.5 equiv) were added to a stirred solution of {2,4-dioxo-1H-pyrido[4,3-d]pyrimidin-3-yl} acetic acid (130 mg, 0.59 mmol, 1 equiv) and (1S)-5,7-difluoro-2,3-dihydro-1H-inden-1-amine (109.38 mg, 0.65 mmol, 1.1 equiv) in DMF (2 mL) at room temperature under air atmosphere. The resulting mixture was stirred for 2 h at 60° C. under air atmosphere. The residue was purified by reversed-phase flash chromatography with the following conditions: column, C18 silica gel; mobile phase, MeCN in water (10 mmol/L $NH_4HCO_3$), 10% to 50% gradient in 10 min; detector, UV 254 nm. This resulted in N-[(1S)-5,7-difluoro-2,3-dihydro-1H-inden-1-yl]-2-{2,4-dioxo-1H-pyrido[4,3-d]pyrimidin-3-yl}acetamide (6 mg, 2.74%). LCMS (ES, m/z): 373.2 [Ms+H]+. $^{1}$H NMR (300 MHz, DMSO-$d_6$) δ11.86 (s, $^{1}$H), 8.958 (s, $^{1}$H), 8.63 (d, J=5.7 Hz, $^{1}$H), 8.54 (d, J=8.4 Hz, $^{1}$H), 7.12 (d, J=5.7 Hz, $^{1}$H), 7.04-6.99 (m, $^{2}$H), 5.42-5.40 (m, $^{1}$H), 4.45 (s, $^{2}$H), 3.02-3.00 (m, $^{1}$H), 2.86-2.83 (m, $^{1}$H), 2.43-2.37 (m, $^{1}$H), 1.56-1.84 (m, $^{1}$H).

Example 7: (2R*)—N-[(1S)-1-(2,4-Difluorophenyl) ethyl]-2-(6-fluoro-2,4-dioxo-1H-quinazolin-3-yl) propanamide- and (2R*)—N-[(1S)-1-(2,4-Difluoro-phenyl)ethyl]-2-(6-fluoro-2,4-dioxo-1H-quinazolin-3-yl)propanamide (compound 40 and compound 41)

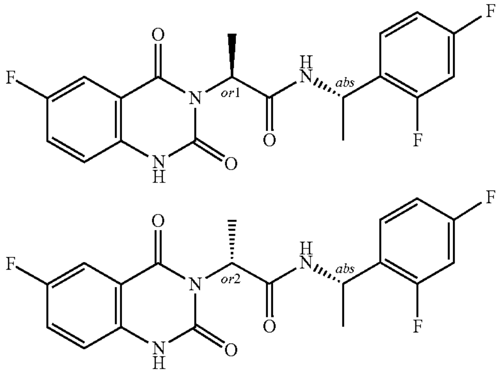

Methyl 2-[(2-amino-5-fluorophenyl)formamido]propanoate. A solution of 2-amino-5-fluorobenzoic acid (1 g, 6 mmol, 1 equiv) and methyl 2-aminopropanoate hydrochloride (0.90 g, 6.45 mmol, 1 equiv), EDCI (1.48 g, 7.74 mmol, 1.2 equiv), HOBt (1.05 g, 7.74 mmol, 1.2 equiv), DIEA (1.67 g, 12.89 mmol, 2 equiv) in DMF (10 mL) was stirred for 2 h at room temperature under air atmosphere. The resulting mixture was diluted with water (100 mL). The resulting mixture was extracted with EtOAc and the combined organic layers were concentrated under reduced pressure and purified by silica gel column chromatography to afford methyl 2-[(2-amino-5-fluorophenyl)formamido]propanoate (650 mg, 41.97%). LCMS (ES, m/z): 241 $[M+H]^+$ Methyl 2-(6-fluoro-2,4-dioxo-1H-quinazolin-3-yl)propanoate. DBU (760.46 mg, 5.00 mmol, 2 equiv) was added dropwise to a stirred solution of methyl 2-[(2-amino-5-fluorophenyl)formamido]propanoate (600 mg, 2 mmol, 1 equiv) and CDI (809.97 mg, 5.00 mmol, 2 equiv) in THF (6 mL) at 0° C. under air atmosphere. The resulting mixture was stirred for 2 h at room temperature under air atmosphere and concentrated under vacuum. The residue was purified by silica gel column chromatography to afford methyl 2-(6-fluoro-2,4-dioxo-1H-quinazolin-3-yl)propanoate (500 mg, 75.20%). LCMS (ES, m/z): 267 $[M+H]^+$ 2-(6-Fluoro-2,4-dioxo-1H-quinazolin-3-yl)propanoic acid. A solution of methyl 2-(6-fluoro-2,4-dioxo-1H-quinazolin-3-yl)propanoate (500 mg, 2 mmol, 1 equiv) and LiOH (134.94 mg, 5.63 mmol, 3 equiv) in MeOH (4.5 mL) and $H_2O$ (1.5 mL) was stirred for overnight at 45° C. under air atmosphere. The mixture was neutralized to pH 7 with HCl (aq.) and the precipitated solids were collected by filtration and washed with acetonitrile to afford 2-(6-fluoro-2,4-dioxo-1H-quinazolin-3-yl)propanoic acid (380 mg, 80.23%). LCMS (ES, m/z): 253 $[M+H]^+$ N-[(1S)-1-(2,4-Difluorophenyl)ethyl]-2-(6-fluoro-2,4-dioxo-1H-quinazolin-3-yl)propanamide. A solution of 2-(6-fluoro-2,4-dioxo-1H-quinazolin-3-yl)propanoic acid (250 mg, 1 mmol, 1 equiv) and HATU (452.30 mg, 1.19 mmol, 1.2 equiv), DIEA (256.24 mg, 1.98 mmol, 2 equiv) in DMF (3 mL) was stirred for 20 min at room temperature under air atmosphere. (1S)-1-(2,4-difluorophenyl)ethanamine (155.79 mg, 0.991 mmol, 1 equiv) was added to the mixture at room temperature. The resulting mixture was stirred for additional 2 h at room temperature. And the resulting mixture was concentrated under vacuum. The residue was purified by silica gel column chromatography to afford N-[(1S)-1-(2,4-difluorophenyl)ethyl]-2-(6-fluoro-2,4-dioxo-1H-quinazolin-3-yl)propanamide (200 mg, 51.56%). LCMS (ES, m/z): 392 $[M+H]^+$ (2R*)—N-[(1S)-1-(2,4-Difluorophenyl)ethyl]-2-(6-fluoro-2,4-dioxo-1H-quinazolin-3-yl)propanamide. The product (200 mg) was purified by Chiral-HPLC to afford (2R*)—N-[(1S)-1-(2,4-difluorophenyl)ethyl]-2-(6-fluoro-2,4-dioxo-1H-quinazolin-3-yl)propanamide (71.4 mg, 35.70%). LCMS (ES, m/z): 390.10 $[M-H]^{-1}$H NMR (400 MHz, DMSO-$d_6$) δ11.53 (s, $^1$H), 8.15 (d, J=7.6 Hz, $^1$H), 7.65-7.56 (m, $^2$H), 7.44-7.36 (m, $^1$H), 7.24-7.03 (m, $^3$H), 5.26 (dd, J=13.6, 6.4 Hz, $^1$H), 5.16-5.12 (m, $^1$H), 1.44 (d, J=6.8 Hz, $^3$H), 1.26 (d, J=7.2 Hz, $^3$H).

(2R*)—N-[(1S)-1-(2,4-Difluorophenyl)ethyl]-2-(6-fluoro-2,4-dioxo-1H-quinazolin-3-yl)propanamide. The product (200 mg) was purified by Chiral-HPLC to afford (2R*)—N-[(1S)-1-(2,4-difluorophenyl)ethyl]-2-(6-fluoro-2,4-dioxo-1H-quinazolin-3-yl)propanamide (65.6 mg, 32.80%). LCMS (ES, m/z): 390.10 $[M-H]^{-1}$H NMR (300 MHz, DMSO-$d_6$) δ11.57 (s, $^1$H), 8.24 (d, J=7.5 Hz, $^1$H), 7.67-7.57 (m, $^2$H), 7.39-7.31 (m, $^1$H), 7.27-7.22 (m, $^1$H), 7.18-7.10 (m, $^1$H), 6.99-6.93 (m, $^1$H), 5.36-5.29 (m, $^1$H), 5.15-5.10 (m, $^1$H), 1.43 (d, J=6.9 Hz, $^3$H), 1.30 (d, J=6.9 Hz, $^3$H). $^1$H NMR (400 MHz, DMSO-$d_6$) δ11.48 (s, $^1$H), 11.35 (s, $^1$H), 8.32 (d, J=7.6 Hz, $^1$H), 7.51-7.34 (m, $^2$H), 7.23-7.14 (m, $^1$H), 7.18-7.12 (m, $^2$H), 7.12-7.03 (m, $^4$H), 6.53 (d, J=8.2 Hz, $^2$H), 5.53 (dd, J=10.3, 5.3 Hz, $^1$H), 5.21 (p, J=7.1 Hz, $^1$H), 3.54 (dd, J=13.8, 5.3 Hz, $^1$H), 3.26 (dd, J=13.9, 10.4 Hz, $^1$H), 1.30 (d, J=7.1 Hz, $^3$H).

Example 8: (2R*)-3-Cyclopropyl-N-[(1S)-1-(2,4-difluorophenyl) ethyl]-2-(2,4-dioxo-1H-quinazolin-3-yl) propanamide (compound 502)

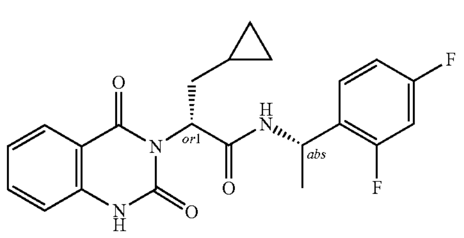 [SMILES: C[C@H](NC(=O)[C@@H](CC1CC1)n1c(=O)[nH]c2ccccc2c1=O)c1ccc(F)cc1F]

Methyl 3-cyclopropyl-2-[(2-nitrophenyl) formamido] propanoate. 2-Nitrobenzoic acid (3 g, 18 mmol, 1 equiv), DIEA (6.96 g, 53.85 mmol, 3 equiv), HATU (8.19 g, 21.54 mmol, 1.2 equiv), methyl 2-amino-3-cyclopropylpropanoate (2.57 g, 17.95 mmol, 1 equiv) and DMF (30 mL) were added into a 100 mL 3-necked round-bottom flask at room temperature and stirred for 4 h. The reaction was added water (20 mL) at room temperature. The resulting mixture was extracted with EtOAc. The combined organic layers were washed with brine, dried over anhydrous $Na_2SO_4$. The filtrate was concentrated under reduced pressure and purified by silica gel column chromatography to afford methyl 3-cyclopropyl-2-[(2-nitrophenyl) formamido] propanoate (3.1 g, 59.08%). LCMS (ES, m/z): $[M+H]^+$=293.

Methyl 2-[(2-aminophenyl) formamido]-3-cyclopropyl-propanoate. Methyl 3-cyclopropyl-2-[(2-nitrophenyl)formamido] propanoate (3.2 g, 10.9 mmol, 1 equiv), Pd/C (320 mg, 3 mmol, 0.27 equiv) and MeOH (30 mL) were stirred at room temperature. The resulting mixture was stirred for 3 h at room temperature under hydrogen atmosphere. The resulting mixture was filtered, the filter cake was washed with MeOH. The filtrate was concentrated under reduced pressure. This resulted in methyl 2-[(2-aminophenyl)formamido]-3-cyclopropylpropanoate (2.6 g, 90.54%). LCMS (ES, m/z): $[M+H]^+$=263.

Methyl 3-cyclopropyl-2-(2,4-dioxo-1H-quinazolin-3-yl) propanoate. Methyl 2-[(2-aminophenyl)formamido]-3-cyclopropylpropanoate (2.6 g, 9.9 mmol, 1 equiv), CDI (4.02 g, 24.78 mmol, 2.5 equiv), DBU (3.77 g, 24.78 mmol, 2.5 equiv) and THF (20 mL) were stirred at 0° C. The resulting mixture was stirred for 4 h at room temperature. The reaction was added water (20 mL) at 0° C. The resulting mixture was extracted with EtOAc. The combined organic layers were washed with brine, dried over anhydrous $Na_2SO_4$. The filtrate was concentrated under reduced pressure and purified by silica gel column chromatography to afford methyl 3-cyclopropyl-2-(2,4-dioxo-1H-quinazolin-3-yl)propanoate (2.1 g, 73.49%). LCMS (ES, m/z): $[M+H]^+$=289.

3-Cyclopropyl-2-(2,4-dioxo-1H-quinazolin-3-yl) propanoic acid. Methyl 3-cyclopropyl-2-(2,4-dioxo-1H-quinazolin-3-yl)propanoate (2.1 g, 7.284 mmol, 1 equiv), KOH (3.89 mg, 0.070 mmol, 2 equiv) and MeOH:$H_2O$ (v:v=5:1, 6 mL) were added into a 10 mL sealed tube were added at room temperature. The resulting mixture was stirred for 2 h at 50° C. The mixture was acidified to pH 5 with HCl (aq.). The aqueous layer was extracted with EtOEt. This resulted in 3-cyclopropyl-2-(2,4-dioxo-1H-quinazolin-3-yl)propanoic acid (1.8 g, 90.10%). LCMS (ES, m/z): $[M+H]^+$=275.

3-Cyclopropyl-N-[(1S)-1-(2,4-difluorophenyl) ethyl]-2-(2,4-dioxo-1H-quinazolin-3-yl) propanamide. 3-Cyclopropyl-2-(2,4-dioxo-1H-quinazolin-3-yl)propanoic acid (200 mg, 0.7 mmol, 1 equiv), DMAP (17.82 mg, 0.15 mmol, 0.2 equiv), (1S)-1-(2,4-difluorophenyl)ethanamine (114.60 mg, 0.73 mmol, 1 equiv)) and DCM (5 mL) were added into a 40 mL sealed tube were added at room temperature. The resulting mixture was stirred for 4 h at room temperature. The resulting mixture was concentrated under reduced pressure and purified by reverse flash chromatography with the following conditions: column, $C_{18}$ silica gel; mobile phase, MeCN in Water (10 mmol/L $NH_4HCO_3$), 10% to 50% gradient in 30 min; detector, UV 254 nm. This resulted in 3-cyclopropyl-N-[(1S)-1-(2,4-difluorophenyl)ethyl]-2-(2,4-dioxo-1H-quinazolin-3-yl)propanamide (250 mg, 82.93%). LCMS (ES, m/z): $[M+H]^+$=414.

(2R*)-3-Cyclopropyl-N-[(1S)-1-(2,4-difluorophenyl) ethyl]-2-(2,4-dioxo-1H-quinazolin-3-yl) propanamide. The crude product (250 mg) was purified by Chiral-Prep-HPLC to afford (2R*)-3-cyclopropyl-N-[(1S)-1-(2,4-difluorophenyl)ethyl]-2-(2,4-dioxo-1H-quinazolin-3-yl)propanamide (106.7 mg, 42.68%). LCMS (ES, m/z): $[M+H]^+$=414.10. $^1$H NMR (300 MHz, DMSO-$d_6$) δ11.49 (s, $^1$H), 8.23 (d, J=7.5 Hz, $^1$H), 7.96 (d, J=7.5 Hz, $^1$H), 7.71-7.65 (m, $^1$H), 7.36-7.34

(m, $^{1}$H), 7.26-7.20 (m, $^{2}$H), 7.16-7.09 (m, $^{1}$H), 6.96-6.92 (m, $^{1}$H), 5.45-5.40 (m, $^{1}$H), 5.13 (p, J=7.2 Hz, $^{1}$H), 2.18-2.13 (m, $^{1}$H), 1.75-1.71 (m, $^{1}$H), 1.29 (d, J=7.2 Hz, $^{3}$H), 0.52 (d, J=7.2 Hz, $^{1}$H), 0.28-0.18 (m, $^{2}$H), −0.06 (s, $^{1}$H), −0.00--0.04 (m, $^{1}$H), −0.16--0.18 (m, $^{1}$H).

(2R*)-3-Cyclopropyl-N-[(1S)-1-(2,4-difluorophenyl) ethyl]-2-(2,4-dioxo-1H-quinazolin-3-yl) propanamide. The crude product (250 mg) was purified by Chiral-Prep-HPLC to afford (2R*)-3-cyclopropyl-N-[(1S)-1-(2,4-difluorophenyl)ethyl]-2-(2,4-dioxo-1H-quinazolin-3-yl)propanamide (118.5 mg, 47.40%). LCMS (ES, m/z): $[M+H]^+$=414.10. $^{1}$H NMR (400 MHz, DMSO-d6) δ11.44 (s, $^{1}$H), 8.16 (d, J=7.6 Hz, $^{1}$H), 7.95 (d, J=8.0 Hz, $^{1}$H), 7.68 (s, $^{1}$H), 7.39 (t, J=8.0 Hz, $^{1}$H), 7.21-7.13 (m, $^{3}$H), 7.07 (d, J=8.8 Hz, $^{1}$H), 5.38 (d, J=5.6 Hz, $^{1}$H), 5.16 (t, J=7.6 Hz, $^{1}$H), 2.17 (t, J=10.0 Hz, $^{1}$H), 1.81-1.74 (m, $^{1}$H), 1.26 (d, J=7.2 Hz, $^{3}$H), 0.54 (s, $^{1}$H), 0.23 (d, J=8.8 Hz, $^{2}$H), 0.00 (s, $^{1}$H), −0.17 (s, $^{1}$H).

Example 9: N-[(1S)-1-(5-Cyano-3-fluoropyridin-2-yl)ethyl]-2-(5,6-difluoro-2,4-dioxo-1H-quinazolin-3-yl)acetamide (compound 22)

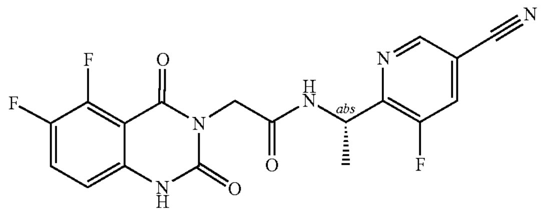 [SMILES: C[C@H](NC(=O)Cn1c(=O)[nH]c2ccc(F)c(F)c2c1=O)c1ncc(C#N)cc1F]

2-[(6-Amino-2,3-difluorophenyl)formamido]acetate A solution of 6-amino-2,3-difluorobenzoic acid (1 g, 6 mmol, 1 equiv), methyl 2-aminoacetate (1.03 g, 11.55 mmol, 2 equiv), HATU (3.29 g, 8.66 mmol, 1.5 equiv) and DIEA (2.24 g, 17.33 mmol, 3 equiv) in DMF (3 mL) was stirred for 3 h at room temperature under air atmosphere. The residue was purified by reversed-phase flash chromatography with the following conditions: (column, $C_{18}$ silica gel; mobile phase, MeCN in Water (0.1% $NH_3 \cdot H_2O$), 0% to 100% gradient in 50 min; detector, UV 254 nm). to afford methyl 2-[(6-amino-2,3-difluorophenyl)formamido]acetate (1.2 g, 85.07%). LCMS (ES, m/z): 245 $[M+H]^+$.

Methyl 2-(5,6-difluoro-2,4-dioxo-1H-quinazolin-3-yl)acetate. A solution of methyl 2-[(6-amino-2,3-difluorophenyl) formamido]acetate (1.1 g, 4.5 mmol, 1 equiv), CDI (1.46 g, 9.01 mmol, 2 equiv) and DBU (1.37 g, 9.01 mmol, 2 equiv) in DCM (20 mL) was stirred for 3 h at room temperature under air atmosphere. The resulting mixture was concentrated under reduced pressure and purified by silica gel column chromatography to afford methyl 2-(5,6-difluoro-2,4-dioxo-1H-quinazolin-3-yl)acetate (900 mg, 78.00%). LCMS (ES, m/z): 271 $[M+H]^+$.

(5,6-Difluoro-2,4-dioxo-1H-quinazolin-3-yl)acetic acid. A solution of methyl 2-(5,6-difluoro-2,4-dioxo-1H-quinazolin-3-yl)acetate (1 g, 3 mmol, 1 equiv), NaOH (0.30 g, 7.40 mmol, 2 equiv) and EtOH (6 mL) in water (6 mL) was stirred for 3 h at room temperature under air atmosphere. The resulting mixture was concentrated under reduced pressure and water (4 mL) was added. The mixture was acidified to pH 4 with HCl (1 M) and the precipitated solids were collected by filtration and washed with MeCN resulting in (5,6-difluoro-2,4-dioxo-1H-quinazolin-3-yl)acetic acid (800 mg, 84.38%). LCMS (ES, m/z): 257 $[M+H]^+$.

N-[(1S)-1-(5-Cyano-3-fluoropyridin-2-yl)ethyl]-2-(5,6-difluoro-2,4-dioxo-1H-quinazolin-3-yl)acetamide. A solution of (5,6-difluoro-2,4-dioxo-1H-quinazolin-3-yl)acetic acid (100 mg, 0.4 mmol, 1 equiv), 6-[(1S)-1-aminoethyl]-5-fluoropyridine-3-carbonitrile (77.37 mg, 0.47 mmol, 1.2 equiv), EDCI (89.80 mg, 0.47 mmol, 1.2 equiv) and DMAP (19.08 mg, 0.16 mmol, 0.4 equiv) in DMF (2 mL) was stirred for 2 h at room temperature under air atmosphere. The residue was purified by reversed-phase flash chromatography with the following conditions: (column, C18 silica gel; mobile phase, MeCN in Water (10 mmol/L $NH_4HCO_3$), 0% to 100% gradient in 50 min; detector, UV 254 nm). This resulted in N-[(1S)-1-(5-cyano-3-fluoropyridin-2-yl)ethyl]-2-(5,6-difluoro-2,4-dioxo-1H-quinazolin-3-yl)acetamide (121.4 mg, 76.03%). LCMS (ES, m/z): 404.10 $[M+H]^+$. $^{1}$H NMR (300 MHz, DMSO-d6) δ11.64 (s, $^{1}$H), 8.90-8.84 (m, $^{1}$H), 8.83-8.81 (m, $^{1}$H), 8.41-8.37 (m, $^{1}$H), 7.83-7.73 (m, $^{1}$H), 7.02-6.97 (m, $^{1}$H), 5.30-5.21 (m, $^{1}$H), 4.47 (s, $^{2}$H), 1.40 (d, J=7.2 Hz, $^{3}$H).

Example 10: N-[(1S)-1-(5-Cyano-3-fluoropyridin-2-yl)ethyl]-2-{5-methyl-2,4-dioxo-1H-pyrido[4,3-d] pyrimidin-3-yl}acetamide (compound 20)

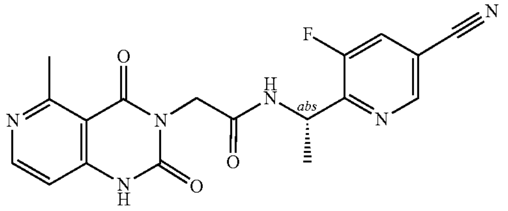 [SMILES: Cc1nccc2[nH]c(=O)n(CC(=O)N[C@@H](C)c3ncc(C#N)cc3F)c(=O)c12]

Methyl 4-[(tert-butoxycarbonyl)amino]-2-chloropyridine-3-carboxylate. LiHMDS (23.04 mL, 23.04 mmol, 2 equiv) was added to a solution of methyl 4-amino-2-chloropyridine-3-carboxylate (2.15 g, 11.52 mmol, 1 equiv) in tetrahydrofuran (35 mL) at 0° C. under Ar atmosphere. The mixture was stirred for 30 min at 0° C. under Ar atmosphere. A solution of $(Boc)_2O$ (2.64 g, 12.10 mmol, 1.05 equiv) in THF (5 mL) was then added and the mixture was heated to room temperature and stirred for 3 h. The reaction mixture was quenched by $NH_4Cl$ (saturated). The resulting mixture was extracted with EA. The combined organic layers were dried over anhydrous $Na_2SO_4$. The filtrate was concentrated under reduced pressure and purified by silica gel column chromatography to afford methyl 4-[(tert-butoxycarbonyl) amino]-2-chloropyridine-3-carboxylate (2.58 g, 74.19%). LCMS (ES, m/z): 287 $[M+H]^+$.

Methyl 4-[(tert-butoxycarbonyl)amino]-2-methylpyridine-3-carboxylate. $K_2CO_3$ (2.70 g, 19.532 mmol, 2.5 equiv) and $Pd(dppf)Cl_2$ (0.57 g, 0.781 mmol, 0.1 equiv) were added to a solution of methyl 4-[(tert-butoxycarbonyl) amino]-2-chloropyridine-3-carboxylate (2.24 g, 7.81 mmol, 1 equiv) and trimethyl-1,3,5,2,4,6-trioxatriborinane (5.46 mL, 39.07 mmol, 5 equiv) in dioxane (35 mL). After stirring for 3 h at 100° C. under an argon atmosphere. Then the resulting mixture was concentrated under reduced pressure and purified by silica gel column chromatography to afford methyl 4-[(tert-butoxycarbonyl)amino]-2-methylpyridine-3-carboxylate (2.02 g, 97.09%). LCMS (ES, m/z): 267 $[M+H]^+$.

4-[(Tert-butoxycarbonyl)amino]-2-methylpyridine-3-carboxylic acid. LiOH (0.54 g, 22.530 mmol, 3 equiv) was added to a solution of methyl 4-[(tert-butoxycarbonyl) amino]-2-methylpyridine-3-carboxylate (2.0 g, 7.5 mmol, 1 equiv) in MeOH (18 mL) and $H_2O$ (9 mL) and stirred for 16 h at room temperature. Then the resulting mixture was concentrated under reduced pressure. The resulting mixture was diluted with water and the mixture was acidified to pH 5 with HCl (2 M). The resulting mixture was filtered, the filter cake was washed with water. The solid was dried under reduced pressure to afford 4-[(tert-butoxycarbonyl)amino]-2-methylpyridine-3-carboxylic acid (1.56 g, 82.34%). LCMS (ES, m/z): 253 $[M+H]^+$.

Methyl 2-({4-[(tert-butoxycarbonyl)amino]-2-methylpyridin-3-yl}formamido)acetate. HATU (2.71 g, 7.1 mmol, 1.2 equiv) and DIEA (3.07 g, 23.78 mmol, 4 equiv) were added to a solution of 4-[(tert-butoxycarbonyl)amino]-2-methylpyridine-3-carboxylic acid (1.5 g, 5.946 mmol, 1 equiv) in DMF (30 mL), then methyl 2-aminoacetate (0.64 g, 7.14 mmol, 1.2 equiv) was added. The mixture was stirred for 4 h at room temperature under air atmosphere. The resulting mixture was diluted with water and extracted with EA. The combined organic layers were washed with water, dried over anhydrous $Na_2SO_4$ and filtered. The filtrate was concentrated under reduced pressure and purified by silica gel column chromatography to afford methyl 2-({4-[(tert-butoxycarbonyl)amino]-2-methylpyridin-3-yl}formamido) acetate (1.23 g, 63.97%). LCMS (ES, m/z): 324 $[M+H]^+$.

Methyl 2-[(4-amino-2-methylpyridin-3-yl)formamido] acetate. Trifluoroacetaldehyde (5 mL) was added to a solution of methyl 2-({4-[(tert-butoxycarbonyl)amino]-2-methylpyridin-3-yl}formamido)acetate (1.2 g, 3.7 mmol, 1 equiv) in DCM (15 mL, 236 mmol, 63.58 equiv) and stirred for 4 h at room temperature. Then the resulting mixture was concentrated under reduced pressure to afford methyl 2-[(4-amino-2-methylpyridin-3-yl)formamido]acetate (800 mg, 96.57%). The crude product was used in the next step directly without further purification. LCMS (ES, m/z): 224 $[M+H]^+$ Methyl 2-{5-methyl-2,4-dioxo-1H-pyrido[4,3-d]pyrimidin-3-yl}acetate. CDI (1743.32 mg, 10.75 mmol, 3 equiv) and DBU (1636.77 mg, 10.75 mmol, 3 equiv) were added to a solution of methyl 2-[(4-amino-2-methylpyridin-3-yl)formamido]acetate (800 mg, 3.6 mmol, 1 equiv) in DCM (10 mL). After stirring for 3 h at room temperature under air atmosphere. Then the resulting mixture was concentrated under reduced pressure and purified by silica gel column chromatography to afford methyl 2-{5-methyl-2,4-dioxo-1H-pyrido[4,3-d]pyrimidin-3-yl}acetate (700 mg, 78.37%). LCMS (ES, m/z): 250 $[M+H]^+$ {5-Methyl-2,4-dioxo-1H-pyrido[4,3-d]pyrimidin-3-yl}acetic acid. LiOH (209.01 mg, 8.73 mmol, 3 equiv) was added to a solution of methyl 2-{5-methyl-2,4-dioxo-TH-pyrido[4,3-d]pyrimidin-3-yl}acetate (725 mg, 3 mmol, 1 equiv) in MeOH (5 mL) and $H_2O$ (5 mL) and stirred for 6 h at 50° C. under an air atmosphere. The resulting mixture was concentrated under reduced pressure, then diluted with $H_2O$. The mixture was acidified to pH 5 with HCl (1 M) and the precipitated solids were collected by filtration and washed with water. The resulting solid was dried under vacuum to afford {5-methyl-2,4-dioxo-TH-pyrido[4,3-d]pyrimidin-3-yl}acetic acid (490 mg, 71.62%). LCMS (ES, m/z): 236 $[M+H]^+$ N-[(1S)-1-(5-Cyano-3-fluoropyridin-2-yl)ethyl]-2-{5-methyl-2,4-dioxo-1H-pyrido[4,3-d]pyrimidin-3-yl}acetamide. EDCI (78.25 mg, 0.41 mmol, 1.2 equiv) and DMAP (16.62 mg, 0.14 mmol, 0.4 equiv) were added to a solution of {5-methyl-2,4-dioxo-TH-pyrido[4,3-d]pyrimidin-3-yl}acetic acid (80 mg, 0.3 mmol, 1 equiv) in DMF (2 mL), then 6-[(1S)-1-aminoethyl]-5-fluoropyridine-3-carbonitrile (67.42 mg, 0.41 mmol, 1.2 equiv) was added. After stirring for 4 h at room temperature under an air atmosphere, the residue was purified by reversed-phase flash chromatography with the following conditions: (column, $C_{18}$ silica gel; mobile phase, 0.1% FA in ACN, 0% to 100% gradient in 60 min; detector, UV 254 nm.) to afford N-[(1S)-1-(5-cyano-3-fluoropyridin-2-yl)ethyl]-2-{5-methyl-2,4-dioxo-TH-pyrido[4,3-d]pyrimidin-3-yl}acetamide (118.2 mg, 89.34%). LCMS (ES, m/z): 383.10 $[M+H]^+$ $^1H$ NMR (300 MHz, DMSO-$d_6$) δ11.64 (s, $^1H$), 8.90 (s, $^1H$), 8.83 (d, J=7.2 Hz, $^1H$), 8.41-8.37 (m, $^1H$), 7.83-7.73 (m, $^1H$), 7.02-6.97 (m, $^1H$), 5.30-5.21 (m, $^1H$), 4.47 (s, $^2H$), 1.40 (d, J=7.2 Hz, $^3H$)

Example 11: 2-(6-Cyano-2,4-dioxo-1H-quinazolin-3-yl)-N-[(1S)-1-(5-cyano-3-fluoropyridin-2-yl)ethyl] acetamide (compound 16)

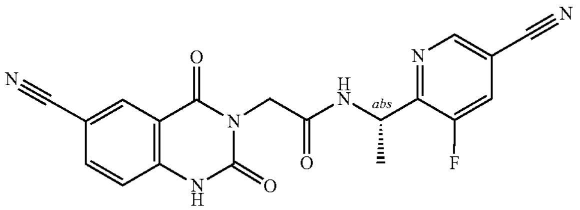 [SMILES: C[C@H](NC(=O)Cn1c(=O)[nH]c2ccc(C#N)cc2c1=O)c1ncc(C#N)cc1F]

Methyl 2-[(2-amino-5-bromophenyl)formamido]acetate. A solution of 5-bromoanthranilic acid (4 g, 19 mmol, 1 equiv), methyl 2-aminoacetate hydrochloride (2.79 g, 22.22 mmol, 1.2 equiv), HATU (8.45 g, 22.22 mmol, 1.2 equiv) and DIEA (5.98 g, 46.29 mmol, 2.5 equiv) in DMF (50 mL) was stirred for 6 h at room temperature under nitrogen atmosphere. The resulting mixture was diluted with water and extracted with EtOAc. The combined organic layers were washed with brine and dried over anhydrous $Na_2SO_4$. The filtrate was concentrated under reduced pressure and purified by silica gel column chromatography to afford methyl 2-[(2-amino-5-bromophenyl)formamido]acetate (4.3 g, 80.89%). LCMS (ES, m/z): 287 $[M+H]^+$.

Methyl 2-(6-bromo-2,4-dioxo-1H-quinazolin-3-yl)acetate. A solution of methyl 2-[(2-amino-5-bromophenyl) formamido]acetate (4.3 g, 15.0 mmol, 1 equiv), CDI (4.86 g, 29.95 mmol, 2 equiv) and DBU (4.56 g, 29.95 mmol, 2 equiv) in DCM (80 mL) was stirred for 3 h at room temperature under nitrogen atmosphere. The resulting mixture was diluted with water and extracted with $CH_2Cl_2$. The combined organic layers were dried over anhydrous $Na_2SO_4$. The filtrate was concentrated under reduced pressure and purified by silica gel column chromatography to afford methyl 2-(6-bromo-2,4-dioxo-1H-quinazolin-3-yl)acetate (2.8 g, 59.71%). LCMS (ES, m/z): 313 $[M+H]^+$ Methyl 2-(6-cyano-2,4-dioxo-1H-quinazolin-3-yl)acetate. A solution of methyl 2-(6-bromo-2,4-dioxo-1H-quinazolin-3-yl)acetate (1.5 g, 4.79 mmol, 1 equiv), Pd(dppf)$Cl_2$ (0.70 g, 0.96 mmol, 0.2 equiv), $Zn(CN)_2$ (1.13 g, 9.58 mmol, 2 equiv) and Zn (0.31 g, 4.79 mmol, 1 equiv) in DMF (30 mL) was stirred for 2 h at 120° C. under argon atmosphere. The resulting mixture was diluted with water and extracted with EtOAc. The combined organic layers were washed with brine, dried over anhydrous $Na_2SO_4$. The filtrate was concentrated under reduced pressure and purified by silica gel column chromatography to afford methyl 2-(6-cyano-2,4-dioxo-1H-quinazolin-3-yl)acetate (1.1 g, 88.58%). LCMS (ES, m/z): 260 $[M+H]^+$ (6-Cyano-2,4-dioxo-1H-quinazolin-3-yl)acetic acid. A solution of methyl 2-(6-cyano-2,4-dioxo-1H-quinazolin-3-yl)acetate (1.1 g, 4.2 mmol, 1 equiv) and LiOH (509.18 mg, 12.73 mmol, 3 equiv) in MeOH (10 mL) and $H_2O$ (10 mL) was stirred for 3 h at room temperature under nitrogen atmosphere. The resulting mixture was concentrated under vacuum and the residue was acidified to pH 5 with 2N HCl (aq.). The precipitated solids were collected by filtration and washed with water to afford (6-cyano-2,4-dioxo-1H-quinazolin-3-yl)acetic acid (880 mg, 84.58%). LCMS (ES, m/z): 260 $[M+H]^+$ 2-(6-Cyano-2,4-dioxo-1H-quinazolin-3-yl)-N-[(1S)-1-(5-cyano-3-fluoropyridin-2-yl)ethyl]acetamide. A solution of (6-cyano-2,4-dioxo-1H-quinazolin-3-yl)acetic acid (130 mg, 0.5 mmol, 1 equiv), 6-[(1S)-1-aminoethyl]-5-fluoropyridine-3-carbonitrile (105.09 mg, 0.64 mmol, 1.2 equiv), EDCI (121.97 mg, 0.64 mmol, 1.2 equiv) and DMAP (32.39 mg, 0.27 mmol, 0.5 equiv) in DMF (2 mL) was stirred for 2 h at room temperature. The crude product was purified by Prep-HPLC to afford 2-(6-cyano-2,4-dioxo-1H-quinazolin-3-yl)-N-[(1S)-1-(5-cyano-3-fluoropyridin-2-yl)ethyl]acetamide (50.5 mg, 23.89%). LCMS (ES, m/z): 393.05 [M+H]+. $^1H$ NMR (300 MHz, DMSO-$d_6$) δ11.92 (br, $^1H$), 8.92-8.90 (m, $^1H$), 8.85 (d, J=7.2 Hz, $^1H$), 8.39 (dd, J=9.9, 1.8 Hz, $^1H$), 8.30 (d, J=1.8 Hz, $^1H$), 8.06 (dd, J=8.7, 2.1 Hz, $^1H$), 7.31 (d, J=8.4 Hz, $^1H$), 5.25-5.23 (m, $^1H$). 4.51 (d, J=1.4 Hz, $^2H$), 1.40 (d, J=6.9 Hz, $^3H$).

In some embodiments, compounds of the disclosure are below in Table 1, Table 2, Table 3, Table 4, Table 5, and Table 6, and Table 7.

In an aspect, the present disclosure provides the compounds of Table 1 and salts thereof. In some embodiments, the compound or salt of Formula (Ia) is selected from a compound of Table 1, or a salt thereof.

TABLE 1

| Compound No. | Structure | Name | Mass Spec |
|---|---|---|---|
| 1 | 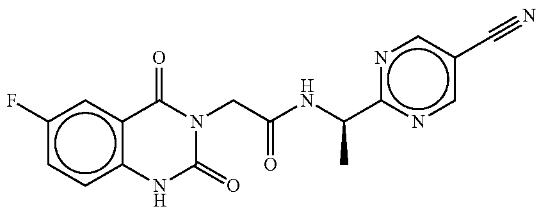 | (R)-N-(1-(5-cyanopyrimidin-2-yl)ethyl)-2-(6-fluoro-2,4-dioxo-1,4-dihydroquinazolin-3(2H)-yl)acetamide | 369.05 |
| 2 | 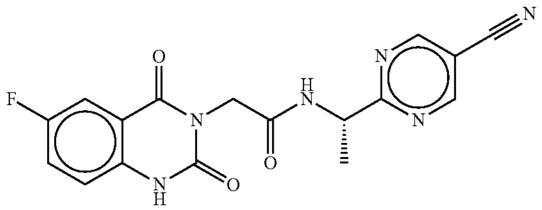 | (S)-N-(1-(5-cyanopyrimidin-2-yl)ethyl)-2-(6-fluoro-2,4-dioxo-1,4-dihydroquinazolin-3(2H)-yl)acetamide | 369 |
| 11 | 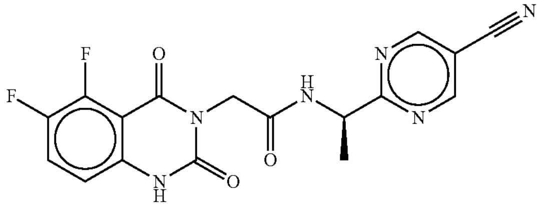 | (R)-N-(1-(5-cyanopyrimidin-2-yl)ethyl)-2-(5,6-difluoro-2,4-dioxo-1,4-dihydroquinazolin-3(2H)-yl)acetamide | 385.15 |
| 12 | 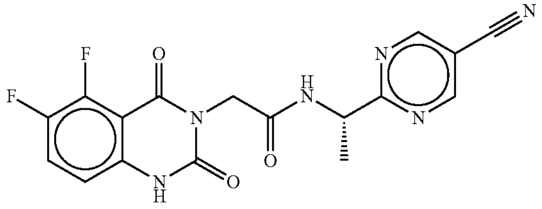 | (S)-N-(1-(5-cyanopyrimidin-2-yl)ethyl)-2-(5,6-difluoro-2,4-dioxo-1,4-dihydroquinazolin-3(2H)-yl)acetamide | 385.2 |
| 5 | 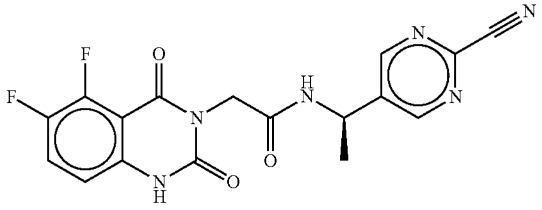 | (R)-N-(1-(2-cyanopyrimidin-5-yl)ethyl)-2-(5,6-difluoro-2,4-dioxo-1,4-dihydroquinazolin-3(2H)-yl)acetamide | 385 |

TABLE 1-continued

| Compound No. | Structure | Name | Mass Spec |
|---|---|---|---|
| 6 | 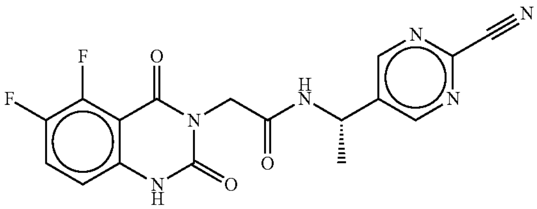 | (S)-N-(1-(2-cyanopyrimidin-5-yl)ethyl)-2-(5,6-difluoro-2,4-dioxo-1,4-dihydroquinazolin-3(2H)-yl)acetamide | 384.95 |
| 97 | 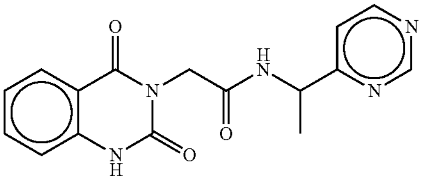 | 2-(2,4-dioxo-1,4-dihydroquinazolin-3(2H)-yl)-N-(1-(pyrimidin-4-yl)ethyl)acetamide | 325.0 |
| 3 | 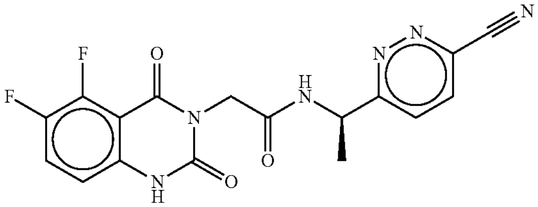 | (R)-N-(1-(6-cyanopyridazin-3-yl)ethyl)-2-(5,6-difluoro-2,4-dioxo-1,4-dihydroquinazolin-3(2H)-yl)acetamide | 387.05 |
| 4 | 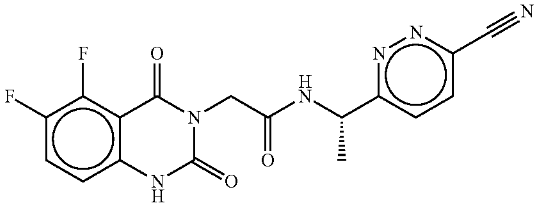 | (S)-N-(1-(6-cyanopyridazin-3-yl)ethyl)-2-(5,6-difluoro-2,4-dioxo-1,4-dihydroquinazolin-3(2H)-yl)acetamide | 387.05 |
| 7 | 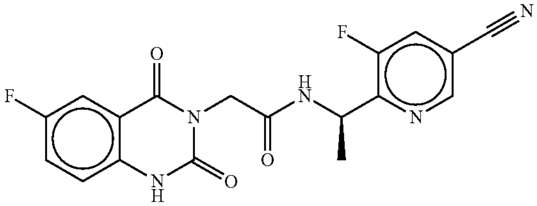 | (R)-N-(1-(5-cyano-3-fluoropyridin-2-yl)ethyl)-2-(6-fluoro-2,4-dioxo-1,4-dihydroquinazolin-3(2H)-yl)acetamide | 385.95 |
| 8 | 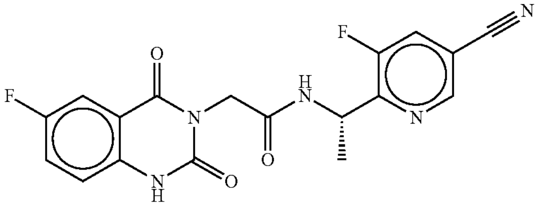 | (S)-N-(1-(5-cyano-3-fluoropyridin-2-yl)ethyl)-2-(6-fluoro-2,4-dioxo-1,4-dihydroquinazolin-3(2H)-yl)acetamide | 385.95 |
| 13 | 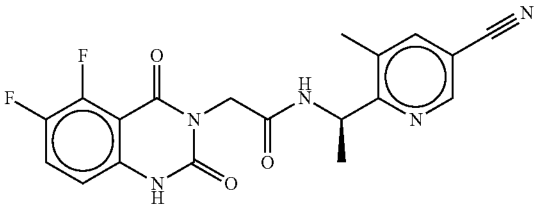 | (R)-N-(1-(5-cyano-3-methylpyridin-2-yl)ethyl)-2-(5,6-difluoro-2,4-dioxo-1,4-dihydroquinazolin-3(2H)-yl)acetamide | 400.2 |

TABLE 1-continued

| Compound No. | Structure | Name | Mass Spec |
| --- | --- | --- | --- |
| 14 | 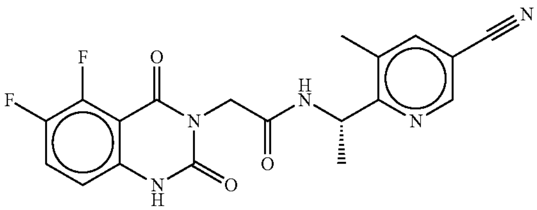 | (S)-N-(1-(5-cyano-3-methylpyridin-2-yl)ethyl)-2-(5,6-difluoro-2,4-dioxo-1,4-dihydroquinazolin-3(2H)-yl)acetamide | 400.20 |
| 15 | 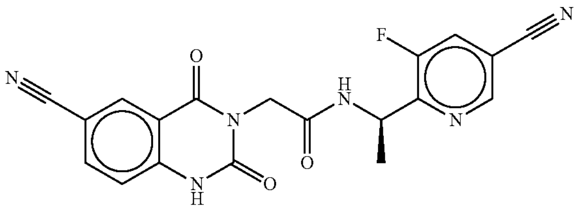 | (R)-2-(6-cyano-2,4-dioxo-1,4-dihydroquinazolin-3(2H)-yl)-N-(1-(5-cyano-3-fluoropyridin-2-yl)ethyl)acetamide | 393.05 |
| 16 | 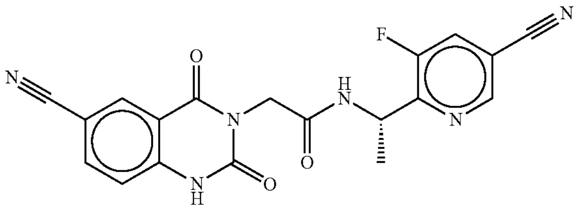 | (S)-2-(6-cyano-2,4-dioxo-1,4-dihydroquinazolin-3(2H)-yl)-N-(1-(5-cyano-3-fluoropyridin-2-yl)ethyl)acetamide | 393.05 |
| 17 | 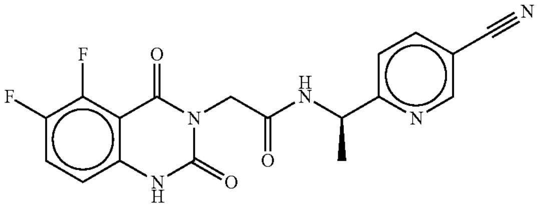 | (R)-N-(1-(5-cyanopyridin-2-yl)ethyl)-2-(5,6-difluoro-2,4-dioxo-1,4-dihydroquinazolin-3(2H)-yl)acetamide | 386.0 |
| 18 | 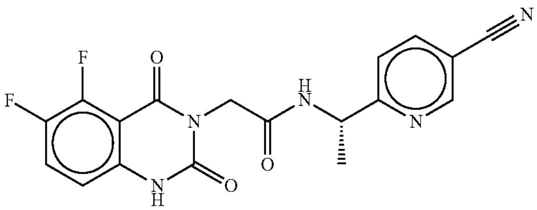 | (S)-N-(1-(5-cyanopyridin-2-yl)ethyl)-2-(5,6-difluoro-2,4-dioxo-1,4-dihydroquinazolin-3(2H)-yl)acetamide | 386.0 |
| 19 | 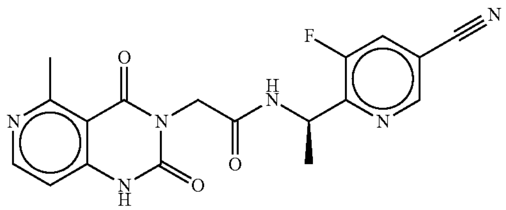 | (R)-N-(1-(5-cyano-3-fluoropyridin-2-yl)ethyl)-2-(5-methyl-2,4-dioxo-1,4-dihydropyrido[4,3-d]pyrimidin-3(2H)-yl)acetamide | 383.1 |

TABLE 1-continued

| Compound No. | Structure | Name | Mass Spec |
|---|---|---|---|
| 20 | 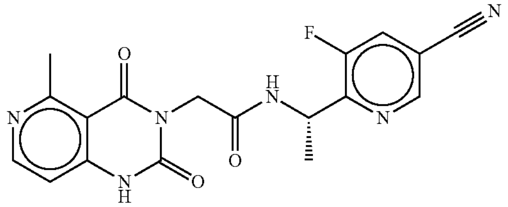 | (S)-N-(1-(5-cyano-3-fluoropyridin-2-yl)ethyl)-2-(5-methyl-2,4-dioxo-1,4-dihydropyrido[4,3-d]pyrimidin-3(2H)-yl)acetamide | 383.1 |
| 21 | 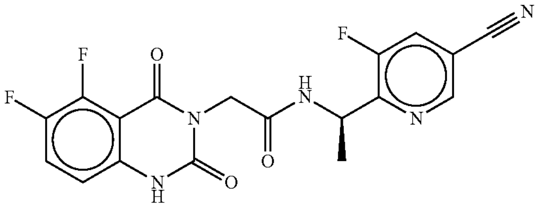 | (R)-N-(1-(5-cyano-3-fluoropyridin-2-yl)ethyl)-2-(5,6-difluoro-2,4-dioxo-1,4-dihydroquinazolin-3(2H)-yl)acetamide | 404.15 |
| 22 | 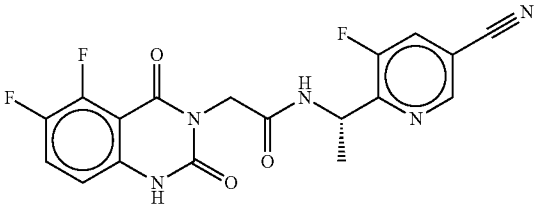 | (S)-N-(1-(5-cyano-3-fluoropyridin-2-yl)ethyl)-2-(5,6-difluoro-2,4-dioxo-1,4-dihydroquinazolin-3(2H)-yl)acetamide | 404.1 |
| 27 | 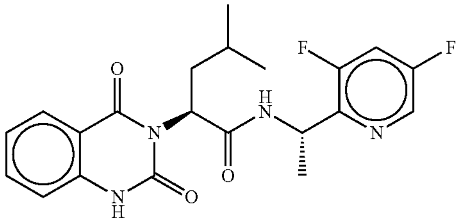 | (S)-N-((S)-1-(3,5-difluoropyridin-2-yl)ethyl)-2-(2,4-dioxo-1,4-dihydroquinazolin-3(2H)-yl)-4-methylpentanamide | 417.1 |
| 28 | 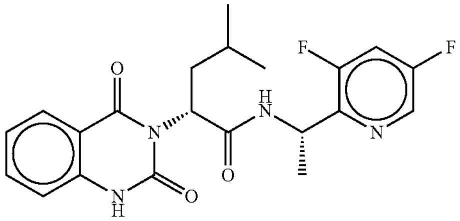 | (R)-N-((S)-1-(3,5-difluoropyridin-2-yl)ethyl)-2-(2,4-dioxo-1,4-dihydroquinazolin-3(2H)-yl)-4-methylpentanamide | 417.10 |
| 29 | 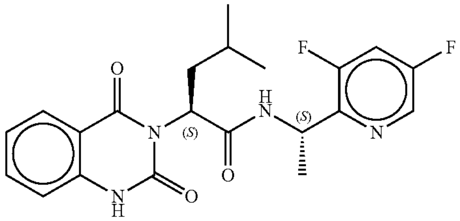 | (S)-N-((S)-1-(5-cyano-3-fluoropyridin-2-yl)ethyl)-2-(2,4-dioxo-1,4-dihydroquinazolin-3(2H)-yl)-4-methylpentanamide | 422.05 |

TABLE 1-continued

| Compound No. | Structure | Name | Mass Spec |
|---|---|---|---|
| 30 | 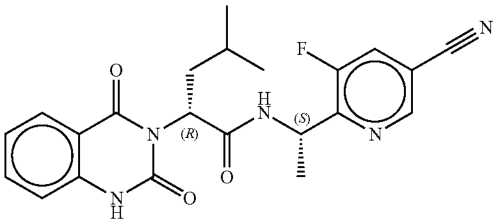 | (R)-N-((S)-1-(5-cyano-3-fluoropyridin-2-yl)ethyl)-2-(2,4-dioxo-1,4-dihydroquinazolin-3(2H)-yl)-4-methylpentanamide | 422.1 |
| 47 | 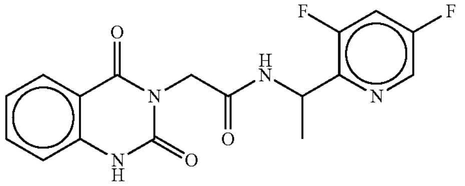 | N-(1-(3,5-difluoropyridin-2-yl)ethyl)-2-(2,4-dioxo-1,4-dihydroquinazolin-3(2H)-yl)acetamide | 361.0 |
| 105 | 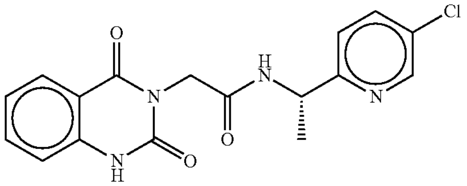 | (S)-N-(1-(5-chloropyridin-2-yl)ethyl)-2-(2,4-dioxo-1,4-dihydroquinazolin-3(2H)-yl)acetamide | 360.0 |
| 106 | 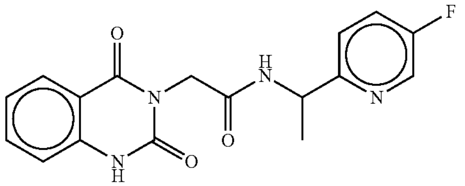 | 2-(2,4-dioxo-1,4-dihydroquinazolin-3(2H)-yl)-N-(1-(5-fluoropyridin-2-yl)ethyl)acetamide | 343.0 |
| 98 | 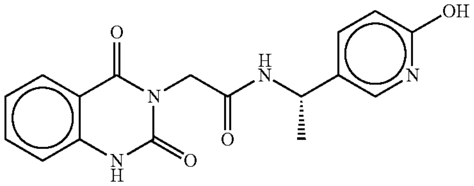 | (S)-2-(2,4-dioxo-1,4-dihydroquinazolin-3(2H)-yl)-N-(1-(6-hydroxypyridin-3-yl)ethyl)acetamide | 341.0 |
| 99 | 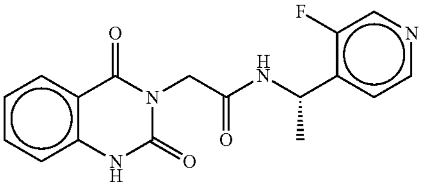 | (S)-2-(2,4-dioxo-1,4-dihydroquinazolin-3(2H)-yl)-N-(1-(3-fluoropyridin-4-yl)ethyl)acetamide | 343.05 |
| 100 | 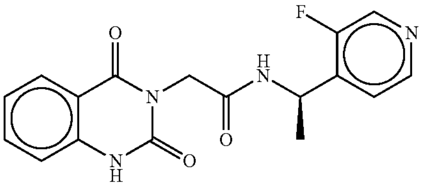 | (R)-2-(2,4-dioxo-1,4-dihydroquinazolin-3(2H)-yl)-N-(1-(3-fluoropyridin-4-yl)ethyl)acetamide | 343.05 |

TABLE 1-continued

| Compound No. | Structure | Name | Mass Spec |
|---|---|---|---|
| 201 | 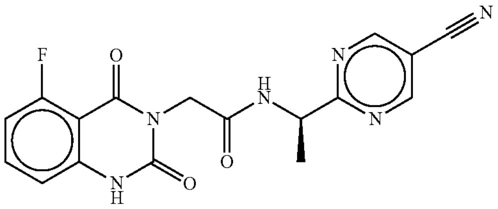 | (R)-N-(1-(5-cyanopyrimidin-2-yl)ethyl)-2-(5-fluoro-2,4-dioxo-1,4-dihydroquinazolin-3(2H)-yl)acetamide | 367.0 |
| 202 | 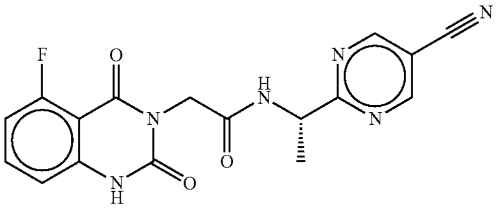 | (S)-N-(1-(5-cyanopyrimidin-2-yl)ethyl)-2-(5-fluoro-2,4-dioxo-1,4-dihydroquinazolin-3(2H)-yl)acetamide | 369.1 |
| 203 | 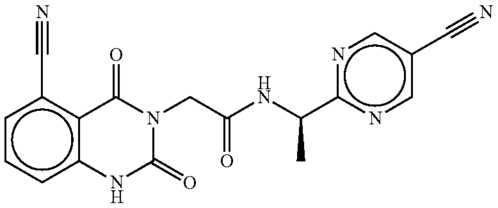 | (R)-2-(5-cyano-2,4-dioxo-1,4-dihydroquinazolin-3(2H)-yl)-N-(1-(5-cyanopyrimidin-2-yl)ethyl)acetamide | 369.1 |
| 204 | 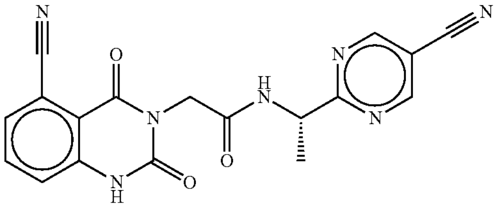 | (S)-2-(5-cyano-2,4-dioxo-1,4-dihydroquinazolin-3(2H)-yl)-N-(1-(5-cyanopyrimidin-2-yl)ethyl)acetamide | 376.15 |
| 205 | 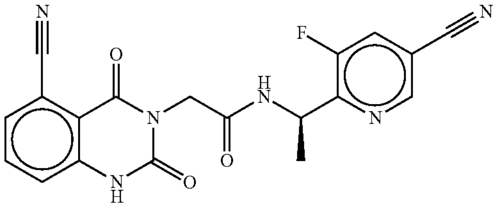 | (R)-2-(5-cyano-2,4-dioxo-1,4-dihydroquinazolin-3(2H)-yl)-N-(1-(5-cyano-3-fluoropyridin-2-yl)ethyl)acetamide | 376.15 |
| 206 | 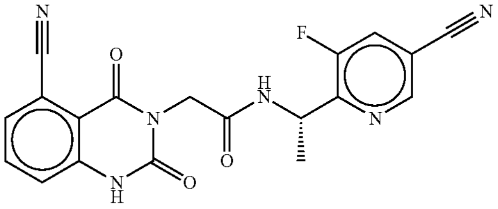 | (S)-2-(5-cyano-2,4-dioxo-1,4-dihydroquinazolin-3(2H)-yl)-N-(1-(5-cyano-3-fluoropyridin-2-yl)ethyl)acetamide | 391.0 |
| 207 | 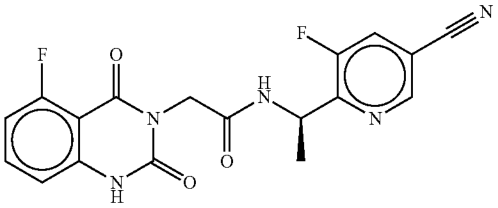 | (R)-N-(1-(5-cyano-3-fluoropyridin-2-yl)ethyl)-2-(5-fluoro-2,4-dioxo-1,4-dihydroquinazolin-3(2H)-yl)acetamide | 386.1 |

TABLE 1-continued

| Compound No. | Structure | Name | Mass Spec |
|---|---|---|---|
| 208 | 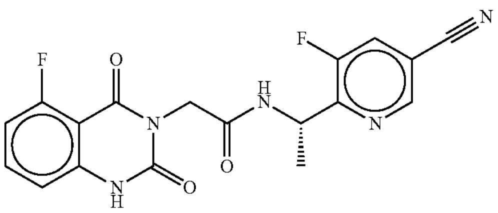 | (S)-N-(1-(5-cyano-3-fluoropyridin-2-yl)ethyl)-2-(5-fluoro-2,4-dioxo-1,4-dihydroquinazolin-3(2H)-yl)acetamide | 386.15 |
| 209 | 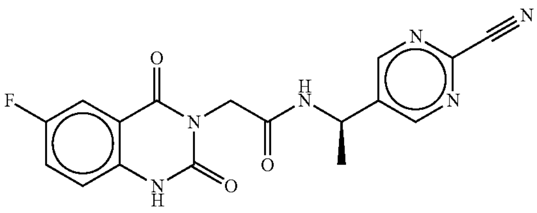 | (R)-N-(1-(2-cyanopyrimidin-5-yl)ethyl)-2-(6-fluoro-2,4-dioxo-1,4-dihydroquinazolin-3(2H)-yl)acetamide | 369.0 |
| 210 | 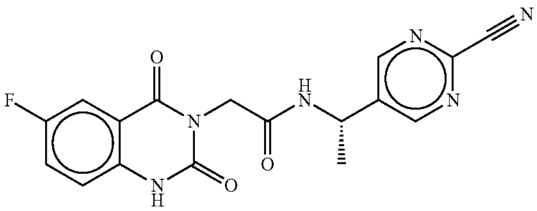 | (S)-N-(1-(2-cyanopyrimidin-5-yl)ethyl)-2-(6-fluoro-2,4-dioxo-1,4-dihydroquinazolin-3(2H)-yl)acetamide | 369.0 |
| 211 | 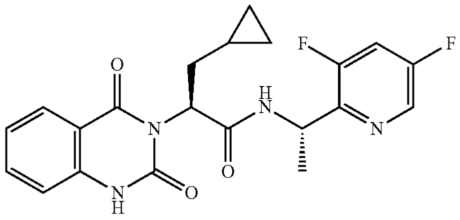 [SMILES: C[C@H](NC(=O)[C@H](CC1CC1)n1c(=O)[nH]c2ccccc2c1=O)c1ncc(F)cc1F] | (S)-3-cyclopropyl-N-((S)-1-(3,5-difluoropyridin-2-yl)ethyl)-2-(2,4-dioxo-1,4-dihydroquinazolin-3(2H)-yl)propanamide | 415.05 |
| 212 | 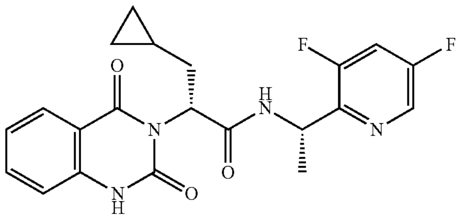 [SMILES: C[C@H](NC(=O)[C@@H](CC1CC1)n1c(=O)[nH]c2ccccc2c1=O)c1ncc(F)cc1F] | (R)-3-cyclopropyl-N-((S)-1-(3,5-difluoropyridin-2-yl)ethyl)-2-(2,4-dioxo-1,4-dihydroquinazolin-3(2H)-yl)propanamide | 415.0 |
| 214 | 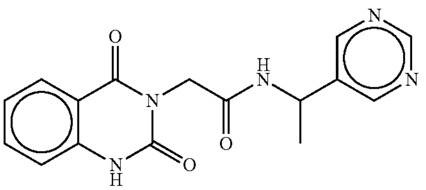 | 2-(2,4-dioxo-1,4-dihydroquinazolin-3(2H)-yl)-N-(1-(pyrimidin-5-yl)ethyl)acetamide | 326.1 |

TABLE 1-continued

| Compound No. | Structure | Name | Mass Spec |
| --- | --- | --- | --- |
| 3001 | 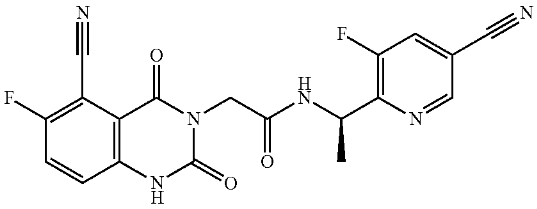 [SMILES: C[C@@H](NC(=O)Cn1c(=O)[nH]c2ccc(F)c(C#N)c2c1=O)c1ncc(C#N)cc1F] | (R)-N-(1-(5-cyano-3-fluoropyridin-2-yl)ethyl)-2-(5-cyano-6-fluoro-2,4-dioxo-1,4-dihydroquinazolin-3(2H)-yl)acetamide | 411.05 |
| 3002 | 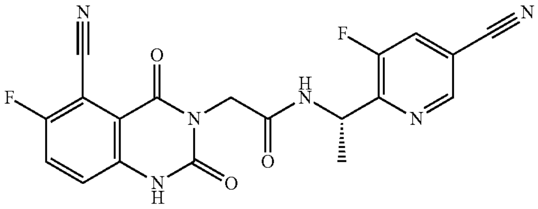 [SMILES: C[C@H](NC(=O)Cn1c(=O)[nH]c2ccc(F)c(C#N)c2c1=O)c1ncc(C#N)cc1F] | (S)-N-(1-(5-cyano-3-fluoropyridin-2-yl)ethyl)-2-(5-cyano-6-fluoro-2,4-dioxo-1,4-dihydroquinazolin-3(2H)-yl)acetamide | 411.05 |
| 3003 | 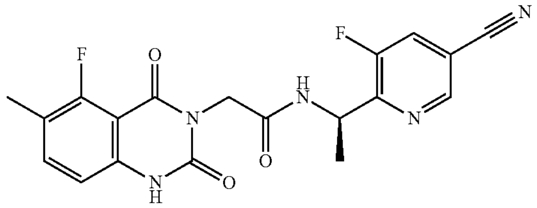 [SMILES: Cc1ccc2[nH]c(=O)n(CC(=O)N[C@H](C)c3ncc(C#N)cc3F)c(=O)c2c1F] | (R)-N-(1-(5-cyano-3-fluoropyridin-2-yl)ethyl)-2-(5-fluoro-6-methyl-2,4-dioxo-1,4-dihydroquinazolin-3(2H)-yl)acetamide | 400.1 |
| 3004 | 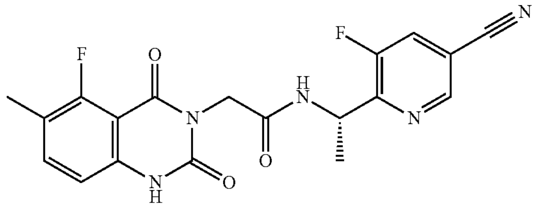 [SMILES: Cc1ccc2[nH]c(=O)n(CC(=O)N[C@@H](C)c3ncc(C#N)cc3F)c(=O)c2c1F] | (S)-N-(1-(5-cyano-3-fluoropyridin-2-yl)ethyl)-2-(5-fluoro-6-methyl-2,4-dioxo-1,4-dihydroquinazolin-3(2H)-yl)acetamide | 400.1 |
| 3005 | 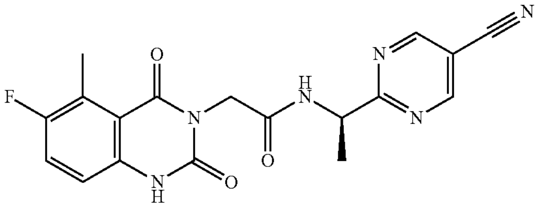 [SMILES: Cc1c(F)ccc2[nH]c(=O)n(CC(=O)N[C@H](C)c3ncc(C#N)cn3)c(=O)c12] | (R)-N-(1-(5-cyanopyrimidin-2-yl)ethyl)-2-(6-fluoro-5-methyl-2,4-dioxo-1,4-dihydroquinazolin-3(2H)-yl)acetamide | 383.15 |
| 3006 | 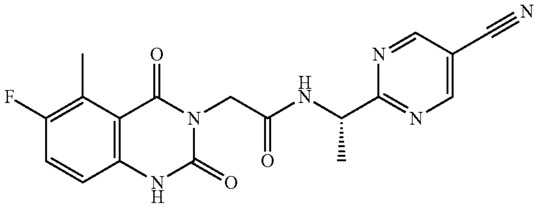 [SMILES: Cc1c(F)ccc2[nH]c(=O)n(CC(=O)N[C@@H](C)c3ncc(C#N)cn3)c(=O)c12] | (S)-N-(1-(5-cyanopyrimidin-2-yl)ethyl)-2-(6-fluoro-5-methyl-2,4-dioxo-1,4-dihydroquinazolin-3(2H)-yl)acetamide | 381.1 |
| 3007 | 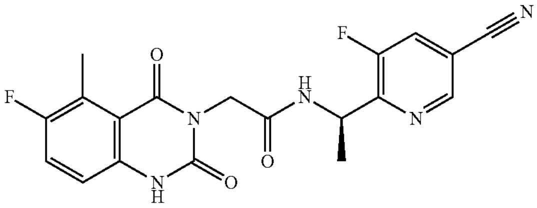 [SMILES: Cc1c(F)ccc2[nH]c(=O)n(CC(=O)N[C@H](C)c3ncc(C#N)cc3F)c(=O)c12] | (R)-N-(1-(5-cyano-3-fluoropyridin-2-yl)ethyl)-2-(6-fluoro-5-methyl-2,4-dioxo-1,4-dihydroquinazolin-3(2H)-yl)acetamide | 398.0 |

TABLE 1-continued

| Compound No. | Structure | Name | Mass Spec |
|---|---|---|---|
| 3008 | 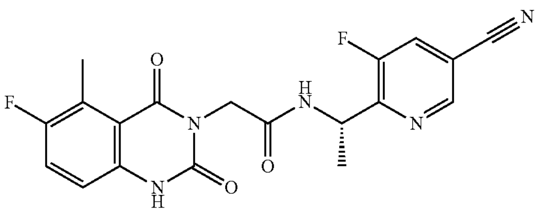 [SMILES: Cc1c(F)ccc2[nH]c(=O)n(CC(=O)N[C@@H](C)c3ncc(C#N)cc3F)c(=O)c12] | (S)-N-(1-(5-cyano-3-fluoropyridin-2-yl)ethyl)-2-(6-fluoro-5-methyl-2,4-dioxo-1,4-dihydroquinazolin-3(2H)-yl)acetamide | 397.95 |
| 3009 | 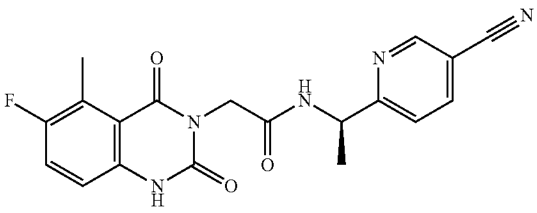 [SMILES: Cc1c(F)ccc2[nH]c(=O)n(CC(=O)N[C@H](C)c3ccc(C#N)cn3)c(=O)c12] | (R)-N-(1-(5-cyanopyridin-2-yl)ethyl)-2-(6-fluoro-5-methyl-2,4-dioxo-1,4-dihydroquinazolin-3(2H)-yl)acetamide | 382.1 |
| 3010 | 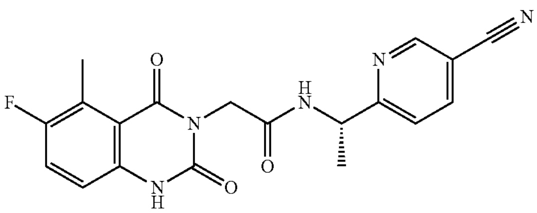 [SMILES: Cc1c(F)ccc2[nH]c(=O)n(CC(=O)N[C@@H](C)c3ccc(C#N)cn3)c(=O)c12] | (S)-N-(1-(5-cyanopyridin-2-yl)ethyl)-2-(6-fluoro-5-methyl-2,4-dioxo-1,4-dihydroquinazolin-3(2H)-yl)acetamide | 382.1 |
| 3011 | 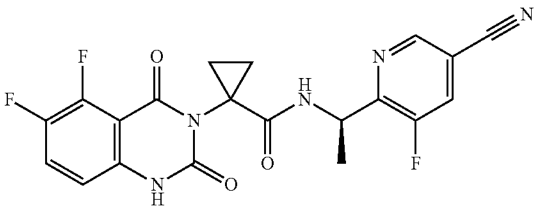 [SMILES: C[C@@H](NC(=O)C1(n2c(=O)[nH]c3ccc(F)c(F)c3c2=O)CC1)c1ncc(C#N)cc1F] | (R)-N-(1-(5-cyano-3-fluoropyridin-2-yl)ethyl)-1-(5,6-difluoro-2,4-dioxo-1,4-dihydroquinazolin-3(2H)-yl)cyclopropane-1-carboxamide | 430.0 |
| 3013 | 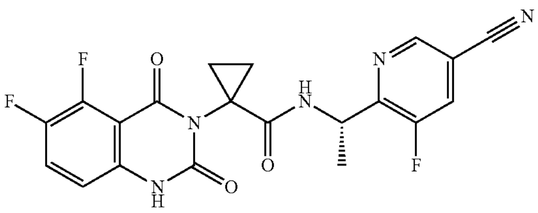 [SMILES: C[C@H](NC(=O)C1(n2c(=O)[nH]c3ccc(F)c(F)c3c2=O)CC1)c1ncc(C#N)cc1F] | (S)-N-(1-(5-cyano-3-fluoropyridin-2-yl)ethyl)-1-(5,6-difluoro-2,4-dioxo-1,4-dihydroquinazolin-3(2H)-yl)cyclopropane-1-carboxamide | 430. |
| 3014 | 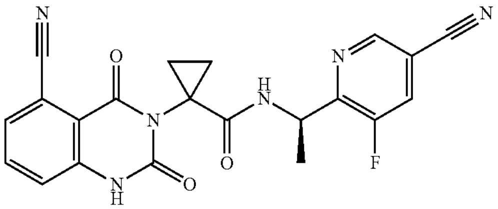 [SMILES: C[C@@H](NC(=O)C1(n2c(=O)[nH]c3cccc(C#N)c3c2=O)CC1)c1ncc(C#N)cc1F] | (R)-1-(5-cyano-2,4-dioxo-1,4-dihydroquinazolin-3(2H)-yl)-N-(1-(5-cyano-3-fluoropyridin-2-yl)ethyl)cyclopropane-1-carboxamide | 419.1 |

TABLE 1-continued

| Compound No. | Structure | Name | Mass Spec |
|---|---|---|---|
| 3015 | 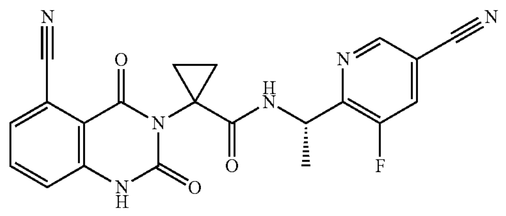 [SMILES: C[C@H](NC(=O)C1(n2c(=O)[nH]c3cccc(C#N)c3c2=O)CC1)c1ncc(C#N)cc1F] | (S)-1-(5-cyano-2,4-dioxo-1,4-dihydroquinazolin-3(2H)-yl)-N-(1-(5-cyano-3-fluoropyridin-2-yl)ethyl)cyclopropane-1-carboxamide | 419.1 |

In an aspect, the present disclosure provides the compounds of Table 2 and salts thereof. In some embodiments, the compound or salt of Formula (Ib) is selected from a compounds of Table 2, or a salt thereof.

In an aspect, the present disclosure provides the compounds of Table 3 and salts thereof. In some embodiments, the compound or salt of Formula (IIa) is selected from a compound of Table 3, or a salt thereof.

TABLE 2

| Compound No. | Structure | Name | Mass Spec |
|---|---|---|---|
| 59 | 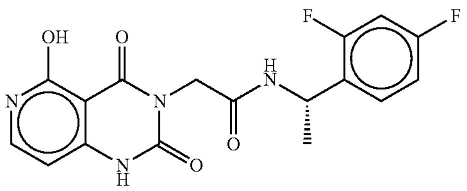 | (S)-N-(1-(2,4-difluorophenyl)ethyl)-2-(5-hydroxy-2,4-dioxo-1,4-dihydropyrido[4,3-d]pyrimidin-3(2H)-yl)acetamide | 377.10 |
| 65 | 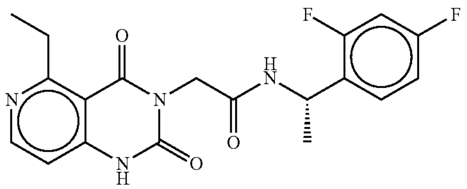 | (S)-N-(1-(2,4-difluorophenyl)ethyl)-2-(5-methoxy-2,4-dioxo-1,4-dihydropyrido[4,3-d]pyrimidin-3(2H)-yl)acetamide | 391.05 |
| 95 | 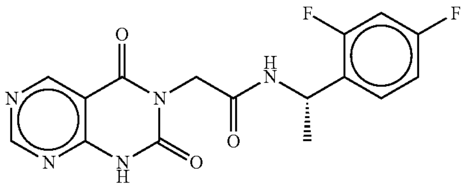 | (S)-N-(1-(2,4-difluorophenyl)ethyl)-2-(2,4-dioxo-1,4-dihydropyrimido[4,5-d]pyrimidin-3(2H)-yl)acetamide | 362.0 |
| 96 | 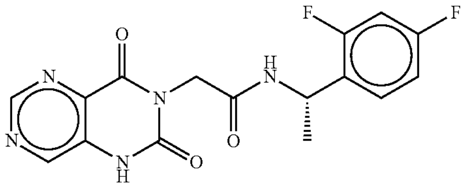 | (S)-N-(1-(2,4-difluorophenyl)ethyl)-2-(2,4-dioxo-1,4-dihydropyrimido[5,4-d]pyrimidin-3(2H)-yl)acetamide | 362.0 |
| 141 | 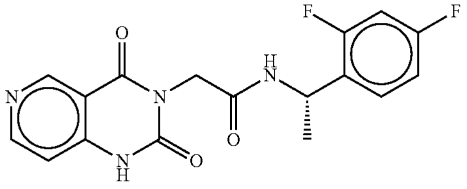 | (S)-N-(1-(2,4-difluorophenyl)ethyl)-2-(2,4-dioxo-1,4-dihydropyrido[4,3-d]pyrimidin-3(2H)-yl)acetamide | 362.05 |

TABLE 3

| Compound No. | Structure | Name | NMR | Mass Spec |
|---|---|---|---|---|
| 33 | 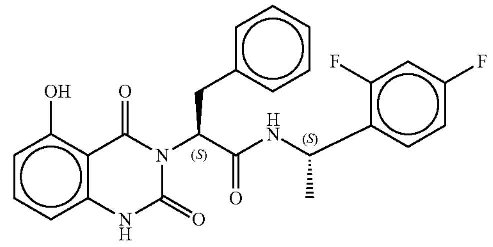 | (S)-N-((S)-1-(2,4-difluorophenyl)ethyl)-2-(5-hydroxy-2,4-dioxo-1,4-dihydroquinazolin-3(2H)-yl)-3-phenylpropanamide | | 466.0 |
| 34 | 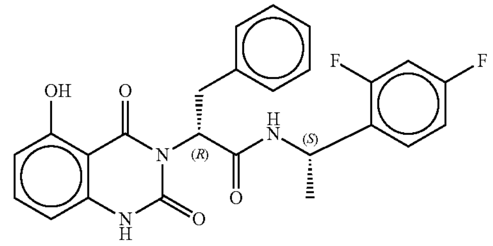 | (R)-N-((S)-1-(2,4-difluorophenyl)ethyl)-2-(5-hydroxy-2,4-dioxo-1,4-dihydroquinazolin-3(2H)-yl)-3-phenylpropanamide | | 466.0 |
| 35 | 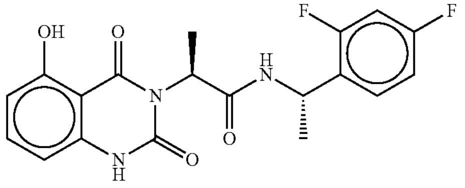 | (S)-N-((S)-1-(2,4-difluorophenyl)ethyl)-2-(5-hydroxy-2,4-dioxo-1,4-dihydroquinazolin-3(2H)-yl)propanamide | $^1$H NMR (400 MHz, DMSO-d6) δ 11.64 (s, 1H), 11.43 (s, 1H), 8.33 (d, J = 7.6 Hz, 1H), 7.55-7.50 (m, 1H), 7.35-7.29 (m, 1H), 7.16-7.10 (m, 1H), 6.94-6.89 (m, 1H), 6.65-6.60 (m, 2H), 5.33-5.27 (m, 1H), 5.16-5.09 (m, 1H) 1.42 (d, J = 6.8 Hz, 3H), 1.30 (d, J = 6.8 Hz, 3H). | 389.80 |
| 36 | 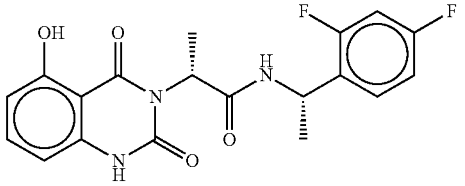 | (R)-N-((S)-1-(2,4-difluorophenyl)ethyl)-2-(5-hydroxy-2,4-dioxo-1,4-dihydroquinazolin-3(2H)-yl)propanamide | $^1$H NMR (400 MHz, DMSO-d6) δ 11.59 (s, 1H), 11.50 (s, 1H), 8.24 (d, J = 7.6 Hz, 1H), 7.53-7.49 (m, 1H), 7.42-7.36 (m, 1H), 7.19-7.13 (m, 1H), 7.08-7.03 (m, 1H), 6.60 (dd, J = 10.6, 8.0 Hz, 2H), 5.27-5.22 (m, 1H), 5.19-5.11 (m, 1H), 1.45 (d, J = 6.8 Hz, 3H), 1.27 (d, J = 6.8 Hz, 3H). | 389.80 |
| 37 | 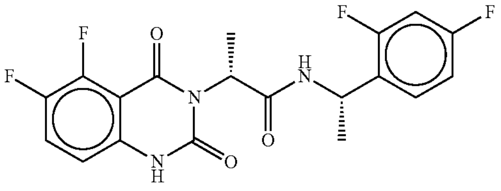 | (R)-2-(5,6-difluoro-2,4-dioxo-1,4-dihydroquinazolin-3(2H)-yl)-N-((S)-1-(2,4-difluorophenyl)ethyl)propanamide | | 410.05 |
| 38 | 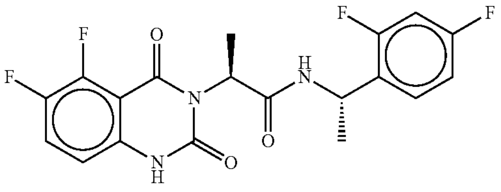 | (S)-2-(5,6-difluoro-2,4-dioxo-1,4-dihydroquinazolin-3(2H)-yl)-N-((S)-1-(2,4-difluorophenyl)ethyl)propanamide | | 410.05 |
| 39 | 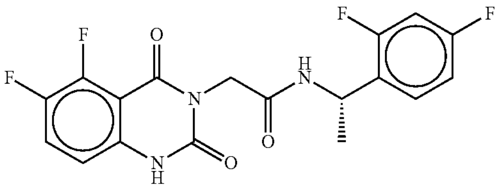 | (S)-2-(5,6-difluoro-2,4-dioxo-1,4-dihydroquinazolin-3(2H)-yl)-N-(1-(2,4-difluorophenyl)ethyl)acetamide | | 396.05 |

TABLE 3-continued

| Compound No. | Structure | Name | NMR | Mass Spec |
|---|---|---|---|---|
| 40 | 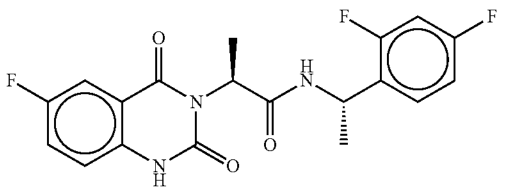 | (S)-N-((S)-1-(2,4-difluorophenyl)ethyl)-2-(6-fluoro-2,4-dioxo-1,4-dihydroquinazolin-3(2H)-yl)propanamide | | 392.05 |
| 41 | 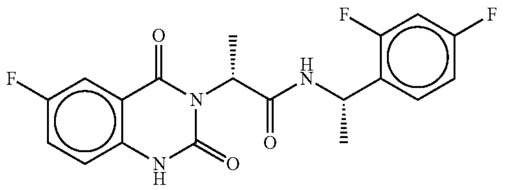 | (R)-N-((S)-1-(2,4-difluorophenyl)ethyl)-2-(6-fluoro-2,4-dioxo-1,4-dihydroquinazolin-3(2H)-yl)propanamide | | 392.05 |
| 51 | 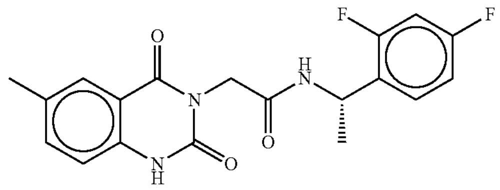 | (S)-N-(1-(2,4-difluorophenyl)ethyl)-2-(6-methyl-2,4-dioxo-1,4-dihydroquinazolin-3(2H)-yl)acetamide | | 374.05 |
| 69 | 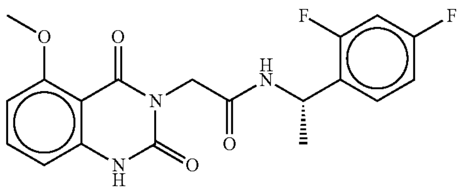 | (S)-N-(1-(2,4-difluorophenyl)ethyl)-2-(5-methoxy-2,4-dioxo-1,4-dihydroquinazolin-3(2H)-yl)acetamide | | 390.00 |
| 72 | 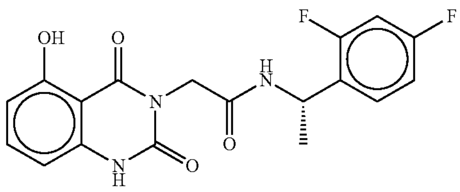 | (S)-N-(1-(2,4-difluorophenyl)ethyl)-2-(5-hydroxy-2,4-dioxo-1,4-dihydroquinazolin-3(2H)-yl)acetamide | | 376.10 |
| 73 | 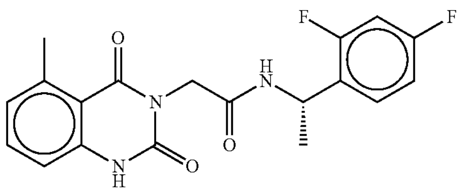 | (S)-N-(1-(2,4-difluorophenyl)ethyl)-2-(5-methyl-2,4-dioxo-1,4-dihydroquinazolin-3(2H)-yl)acetamide | | 374.05 |
| 104 | 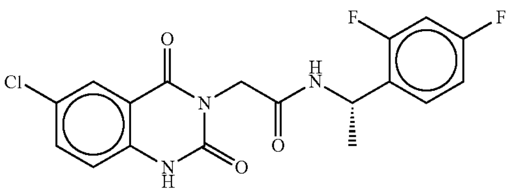 | (S)-2-(6-chloro-2,4-dioxo-1,4-dihydroquinazolin-3(2H)-yl)-N-(1-(2,4-difluorophenyl)ethyl) acetamide | | 395.0 |

TABLE 3-continued

| Compound No. | Structure | Name | NMR | Mass Spec |
|---|---|---|---|---|
| 402 | 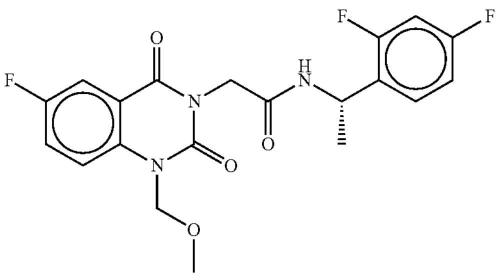 | (S)-N-(1-(2,4-difluorophenyl)ethyl)-2-(6-fluoro-1-(methoxymethyl)-2,4-dioxo-1,4-dihydroquinazolin-3(2H)-yl)acetamide | | 422.0 |
| 403 | 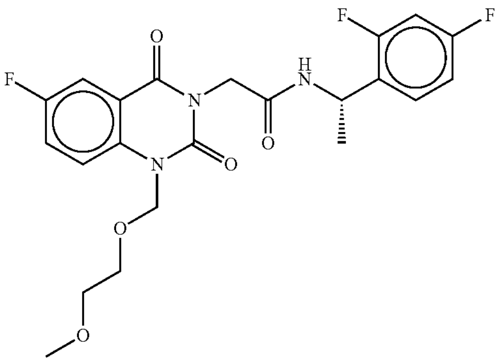 | (S)-N-(1-(2,4-difluorophenyl)ethyl)-2-(6-fluoro-1-((2-methoxyethoxy)methyl)-2,4-dioxo-1,4-dihydroquinazolin-3(2H)-yl)acetamide | | 392.0 |
| 404 | 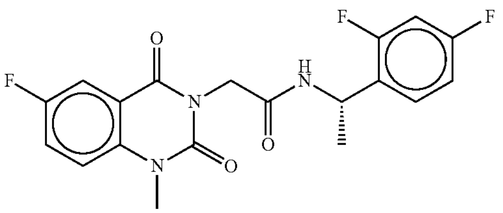 | (S)-N-(1-(2,4-difluorophenyl)ethyl)-2-(6-fluoro-1-methyl-2,4-dioxo-1,4-dihydroquinazolin-3(2H)-yl)acetamide | | 392.0 |

In an aspect, the present disclosure provides the compounds of Table 4 and salts thereof. In some embodiments, the compound or salt of Formula (IIb) is selected from a compound of Table 4, or a salt thereof.

TABLE 4

| Compound No. | Structure | Name | Mass Spec |
|---|---|---|---|
| 31 | 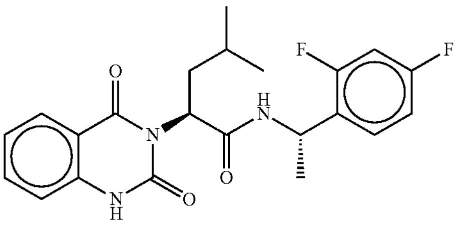 | (S)-N-((S)-1-(2,4-difluorophenyl)ethyl)-2-(2,4-dioxo-1,4-dihydroquinazolin-3(2H)-yl)-4-methylpentanamide | 416.2 |
| 32 | 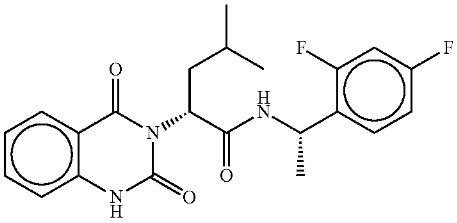 | (R)-N-((S)-1-(2,4-difluorophenyl)ethyl)-2-(2,4-dioxo-1,4-dihydroquinazolin-3(2H)-yl)-4-methylpentanamide | 416.20 |

TABLE 4-continued

| Compound No. | Structure | Name | Mass Spec |
|---|---|---|---|
| 42 | 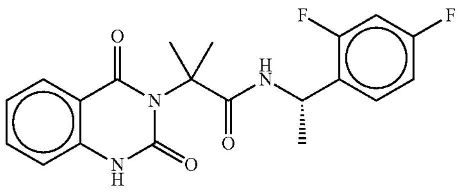 | (S)-N-(1-(2,4-difluorophenyl)ethyl)-2-(2,4-dioxo-1,4-dihydroquinazolin-3(2H)-yl)-2-methylpropanamide | 388.0 |
| 49 | 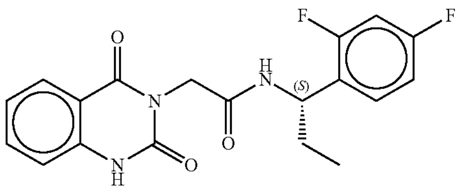 | (S)-N-(1-(2,4-difluorophenyl)propyl)-2-(2,4-dioxo-1,4-dihydroquinazolin-3(2H)-yl)acetamide | 374.0 |
| 50 | 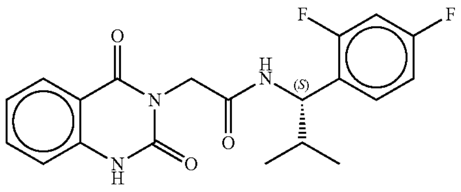 | (S)-N-(1-(2,4-difluorophenyl)-2-methylpropyl)-2-(2,4-dioxo-1,4-dihydroquinazolin-3(2H)-yl)acetamide | 388.0 |
| 70 | 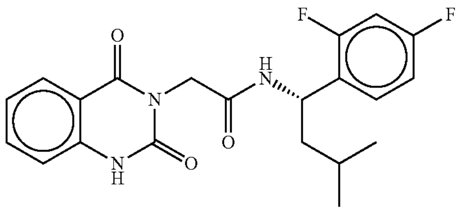 | (S)-N-(1-(2,4-difluorophenyl)-3-methylbutyl)-2-(2,4-dioxo-1,4-dihydroquinazolin-3(2H)-yl)acetamide | 402.00 |
| 71 | 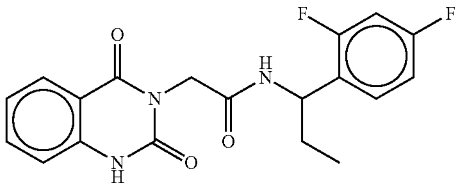 | N-(1-(2,4-difluorophenyl)propyl)-2-(2,4-dioxo-1,4-dihydroquinazolin-3(2H)-yl)acetamide | 374.1 |
| 87 | 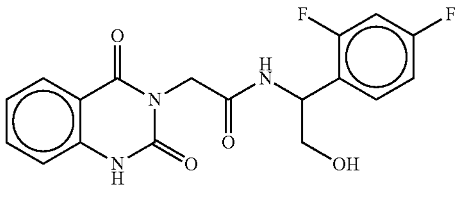 | N-(1-(2,4-difluorophenyl)-2-hydroxyethyl)-2-(2,4-dioxo-1,4-dihydroquinazolin-3(2H)-yl)acetamide | 376.1 |
| 101 | 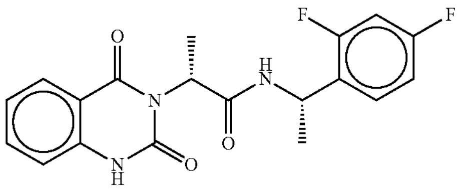 | (R)-N-((S)-1-(2,4-difluorophenyl)ethyl)-2-(2,4-dioxo-1,4-dihydroquinazolin-3(2H)-yl)propanamide | 374.1 |

TABLE 4-continued

| Compound No. | Structure | Name | Mass Spec |
|---|---|---|---|
| 102 | 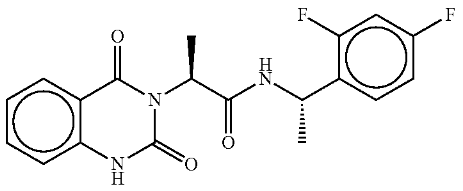 | (S)-N-((S)-1-(2,4-difluorophenyl)ethyl)-2-(2,4-dioxo-1,4-dihydroquinazolin-3(2H)-yl)propanamide | 374.1 |
| 501 | 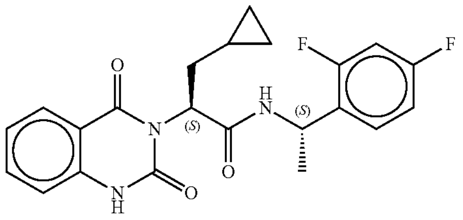 | (S)-3-cyclopropyl-N-((S)-1-(2,4-difluorophenyl)ethyl)-2-(2,4-dioxo-1,4-dihydroquinazolin-3(2H)-yl)propanamide | 414.10 |
| 502 | 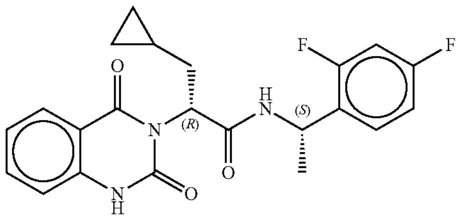 | (R)-3-cyclopropyl-N-((S)-1-(2,4-difluorophenyl)ethyl)-2-(2,4-dioxo-1,4-dihydroquinazolin-3(2H)-yl)propanamide | 414.1 |
| 504 | 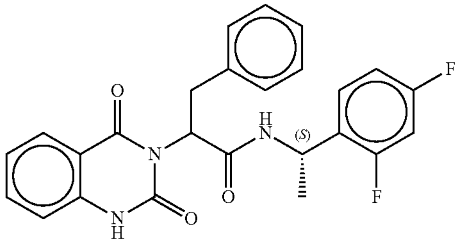 | N-((S)-1-(2,4-difluorophenyl)ethyl)-2-(2,4-dioxo-1,4-dihydroquinazolin-3(2H)-yl)-3-phenylpropanamide | 450.20 |
| 506 | 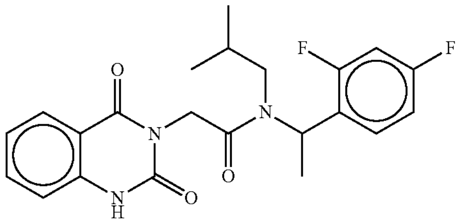 | N-(1-(2,4-difluorophenyl)ethyl)-2-(2,4-dioxo-1,4-dihydroquinazolin-3(2H)-yl)-N-isobutylacetamide | 416.1 |
| 507 | 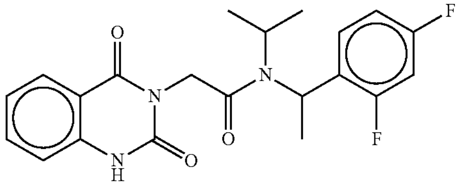 | N-(1-(2,4-difluorophenyl)ethyl)-2-(2,4-dioxo-1,4-dihydroquinazolin-3(2H)-yl)-N-isopropylacetamide | 401.4 |

TABLE 4-continued

| Compound No. | Structure | Name | Mass Spec |
|---|---|---|---|
| 508 | 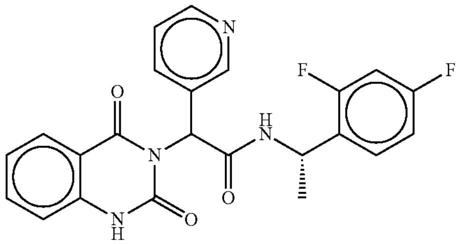 | N-((S)-1-(2,4-difluorophenyl)ethyl)-2-(2,4-dioxo-1,4-dihydroquinazolin-3(2H)-yl)-2-(pyridin-3-yl)acetamide | 437.25 |
| 509 | 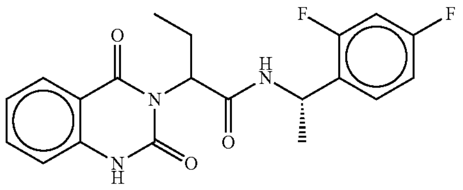 | N-((S)-1-(2,4-difluorophenyl)ethyl)-2-(2,4-dioxo-1,4-dihydroquinazolin-3(2H)-yl)butanamide | 388.10 |
| 510 | 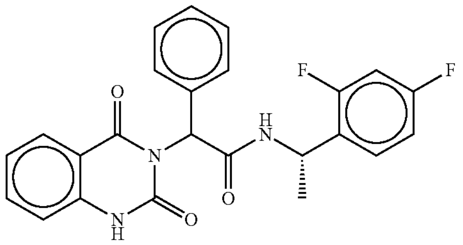 | N-((S)-1-(2,4-difluorophenyl)ethyl)-2-(2,4-dioxo-1,4-dihydroquinazolin-3(2H)-yl)-2-phenylacetamide | 436.20 |
| 511 | 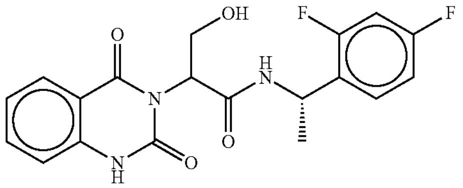 | N-((S)-1-(2,4-difluorophenyl)ethyl)-2-(2,4-dioxo-1,4-dihydroquinazolin-3(2H)-yl)-3-hydroxypropanamide | 390.2 |
| 512 | 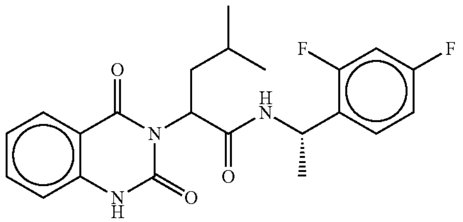 | N-((S)-1-(2,4-difluorophenyl)ethyl)-2-(2,4-dioxo-1,4-dihydroquinazolin-3(2H)-yl)-4-methylpentanamide | 416.55 |
| 513 | 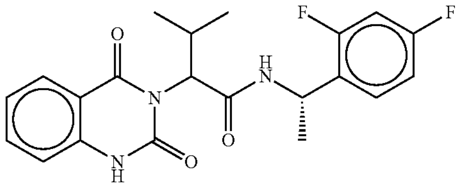 | N-((S)-1-(2,4-difluorophenyl)ethyl)-2-(2,4-dioxo-1,4-dihydroquinazolin-3(2H)-yl)-3-methylbutanamide | 402.15 |

In an aspect, the present disclosure provides the compounds of Table 5 and salts thereof. In some embodiments, the compound or salt of Formula (Ic) is selected from a compound of Table 5, or a salt thereof. In some embodiments, the compound or salt of Formula (Ic) is not compound 601, 602, 603, 604, 605, 606, or a salt of any thereof.

TABLE 5

| Compound No. | Structure | Name |
|---|---|---|
| 601 | 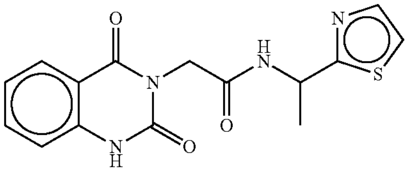 | 2-(2,4-dioxo-1,4-dihydroquinazolin-3(2H)-yl)-N-(1-(thiazol-2-yl)ethyl)acetamide |
| 602 | 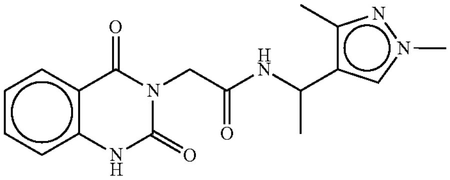 | N-(1-(1,3-dimethyl-1H-pyrazol-4-yl)ethyl)-2-(2,4-dioxo-1,4-dihydroquinazolin-3(2H)-yl)acetamide |
| 603 | 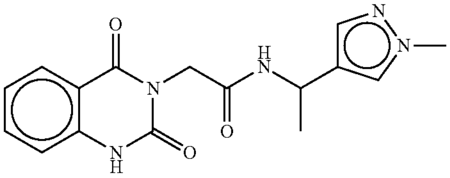 | 2-(2,4-dioxo-1,4-dihydroquinazolin-3(2H)-yl)-N-(1-(1-methyl-1H-pyrazol-4-yl)ethyl)acetamide |
| 604 | 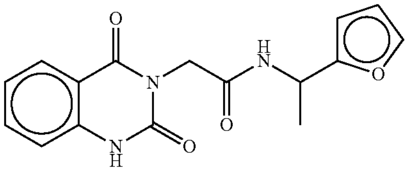 | 2-(2,4-dioxo-1,4-dihydroquinazolin-3(2H)-yl)-N-(1-(furan-2-yl)ethyl)acetamide |
| 605 | 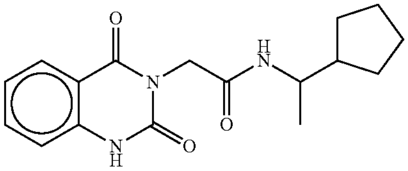 | N-(1-cyclopentylethyl)-2-(2,4-dioxo-1,4-dihydroquinazolin-3(2H)-yl)acetamide |
| 606 | 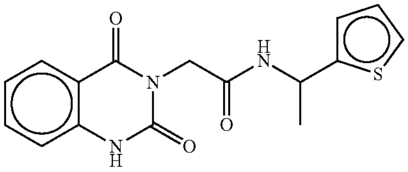 | 2-(2,4-dioxo-1,4-dihydroquinazolin-3(2H)-yl)-N-(1-(thiophen-2-yl)ethyl)acetamide |

In an aspect, the present disclosure provides the compounds of Table 6 and salts thereof. In some embodiments, the compound or salt of Formula (Id) is selected from a compound of Table 6, or a salt thereof.

TABLE 6

| Compound No. | Structure | Name | Mass Spec |
|---|---|---|---|
| 9 | 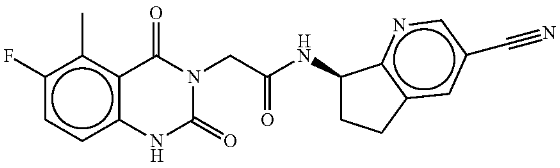 | (R)-N-(3-cyano-6,7-dihydro-5H-cyclopenta[b]pyridin-7-yl)-2-(6-fluoro-5-methyl-2,4-dioxo-1,4-dihydroquinazolin-3(2H)-yl)acetamide | 394.2 |

TABLE 6-continued

| Compound No. | Structure | Name | Mass Spec |
|---|---|---|---|
| 10 | 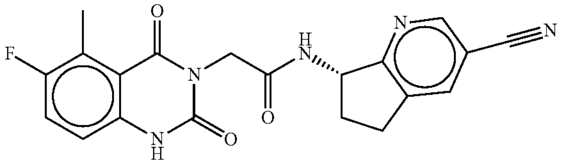 | (S)-N-(3-cyano-6,7-dihydro-5H-cyclopenta[b]pyridin-7-yl)-2-(6-fluoro-5-methyl-2,4-dioxo-1,4-dihydroquinazolin-3(2H)-yl)acetamide | 394.25 |
| 44 | 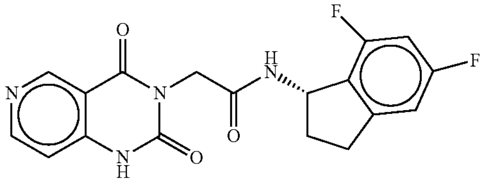 | (S)-N-(5,7-difluoro-2,3-dihydro-1H-inden-1-yl)-2-(2,4-dioxo-1,4-dihydropyrido[4,3-d]pyrimidin-3(2H)-yl)acetamide | 37.1 |
| 48 | 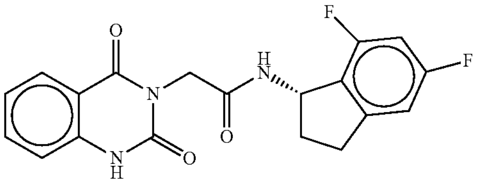 | (S)-N-(5,7-difluoro-2,3-dihydro-1H-inden-1-yl)-2-(2,4-dioxo-1,4-dihydroquinazolin-3(2H)-yl)acetamide | 372.05 |
| 43 | 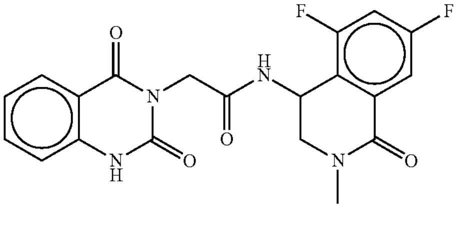 | N-(5,7-difluoro-2-methyl-1-oxo-1,2,3,4-tetrahydroisoquinolin-4-yl)-2-(2,4-dioxo-1,4-dihydroquinazolin-3(2H)-yl)acetamide | 415.05 |
| 46 | 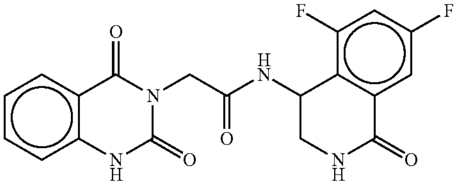 | N-(5,7-difluoro-1-oxo-1,2,3,4-tetrahydroisoquinolin-4-yl)-2-(2,4-dioxo-1,4-dihydroquinazolin-3(2H)-yl)acetamide | 401.0 |
| 55 | 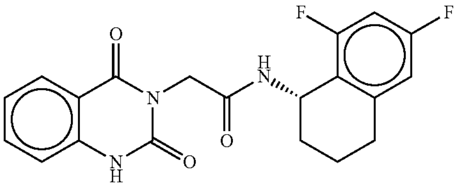 | (S)-N-(6,8-difluoro-1,2,3,4-tetrahydronaphthalen-1-yl)-2-(2,4-dioxo-1,4-dihydroquinazolin-3(2H)-yl)acetamide | 386.05 |

TABLE 6-continued

| Compound No. | Structure | Name | Mass Spec |
|---|---|---|---|
| 57 | 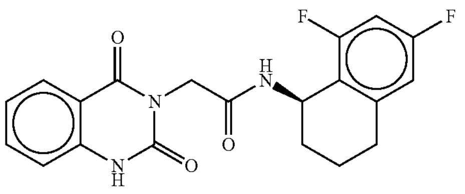 | (R)-N-(6,8-difluoro-1,2,3,4-tetrahydronaphthalen-1-yl)-2-(2,4-dioxo-1,4-dihydroquinazolin-3(2H)-yl)acetamide | 386.05 |
| 701 | 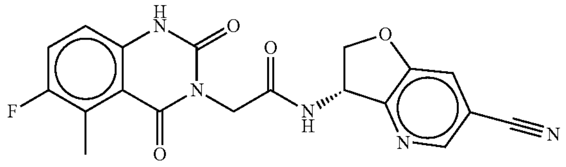 | (S)-N-(6-cyano-2,3-dihydrofuro[3,2-b]pyridin-3-yl)-2-(6-fluoro-5-methyl-2,4-dioxo-1,4-dihydroquinazolin-3(2H)-yl)acetamide | 396.1 |
| 702 | 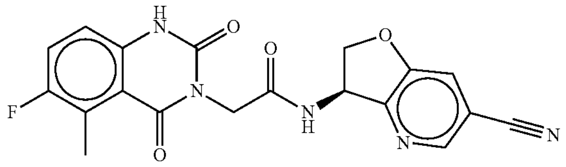 | (R)-N-(6-cyano-2,3-dihydrofuro[3,2-b]pyridin-3-yl)-2-(6-fluoro-5-methyl-2,4-dioxo-1,4-dihydroquinazolin-3(2H)-yl)acetamide | 396.05 |

TABLE 7

In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof.

| Compound No. | Structure | Name | Mass Spec |
|---|---|---|---|
| 5001 | 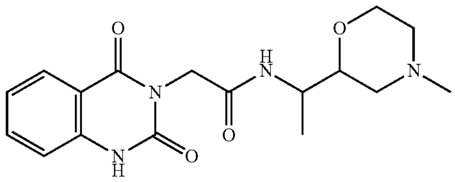 [SMILES: CC(NC(=O)Cn1c(=O)[nH]c2ccccc2c1=O)C1CN(C)CCO1] | 2-(2,4-dioxo-1,4-dihydroquinazolin-3(2H)-yl)-N-(1-(4-methylmorpholin-2-yl)ethyl)acetamide | |
| 5002 | 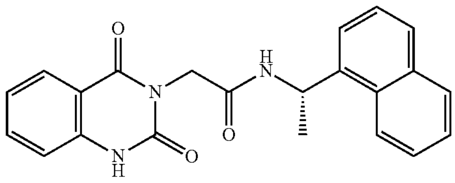 [SMILES: C[C@H](NC(=O)Cn1c(=O)[nH]c2ccccc2c1=O)c1cccc2ccccc12] | (S)-2-(2,4-dioxo-1,4-dihydroquinazolin-3(2H)-yl)-N-(1-(naphthalen-1-yl)ethyl)acetamide | |
| 5003 | 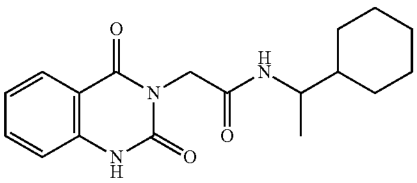 [SMILES: CC(NC(=O)Cn1c(=O)[nH]c2ccccc2c1=O)C1CCCCC1] | N-(1-cyclohexylethyl)-2-(2,4-dioxo-1,4-dihydroquinazolin-3(2H)-yl)acetamide | |

TABLE 7-continued

In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof.

| Compound No. | Structure | Name | Mass Spec |
|---|---|---|---|
| 5004 | 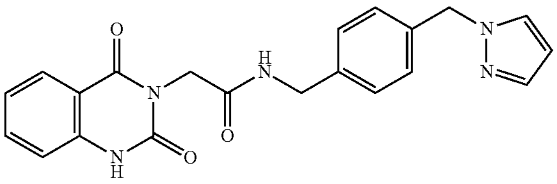 [SMILES: O=C(Cn1c(=O)[nH]c2ccccc2c1=O)NCc1ccc(Cn2cccn2)cc1] | N-(4-((1H-pyrazol-1-yl)methyl)benzyl)-2-(2,4-dioxo-1,4-dihydroquinazolin-3(2H)-yl)acetamide | |
| 5005 | 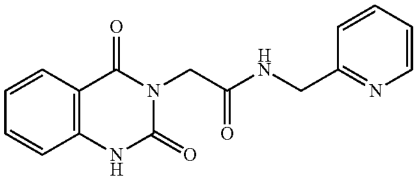 [SMILES: O=C(Cn1c(=O)[nH]c2ccccc2c1=O)NCc1ccccn1] | 2-(2,4-dioxo-1,4-dihydroquinazolin-3(2H)-yl)-N-(pyridin-2-ylmethyl)acetamide | |
| 5006 | 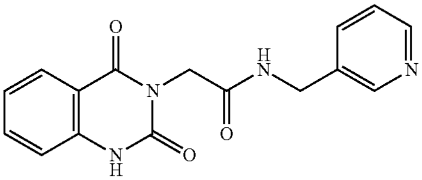 [SMILES: O=C(Cn1c(=O)[nH]c2ccccc2c1=O)NCc1cccnc1] | 2-(2,4-dioxo-1,4-dihydroquinazolin-3(2H)-yl)-N-(pyridin-3-ylmethyl)acetamide | |
| 5007 | 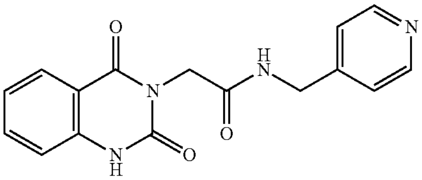 [SMILES: O=C(Cn1c(=O)[nH]c2ccccc2c1=O)NCc1ccncc1] | 2-(2,4-dioxo-1,4-dihydroquinazolin-3(2H)-yl)-N-(pyridin-4-ylmethyl)acetamide | |
| 5008 | 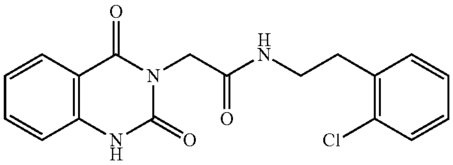 [SMILES: O=C(Cn1c(=O)[nH]c2ccccc2c1=O)NCCc1ccccc1Cl] | N-(2-chlorophenethyl)-2-(2,4-dioxo-1,4-dihydroquinazolin-3(2H)-yl)acetamide | |
| 5009 | 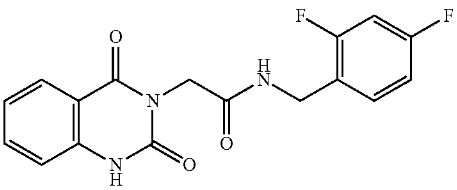 [SMILES: O=C(Cn1c(=O)[nH]c2ccccc2c1=O)NCc1ccc(F)cc1F] | N-(2,4-difluorobenzyl)-2-(2,4-dioxo-1,4-dihydroquinazolin-3(2H)-yl)acetamide | |
| 213 | 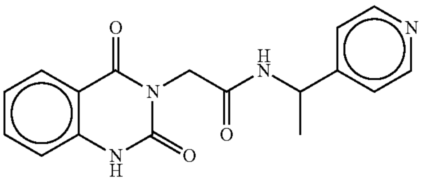 | 2-(2,4-dioxo-1,4-dihydroquinazolin-3(2H)-yl)-N-(1-(pyridin-4-yl)ethyl)acetamide | |

TABLE 7-continued

In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof.

| Compound No. | Structure | Name | Mass Spec |
| --- | --- | --- | --- |
| 215 | 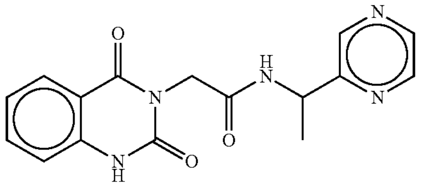 | 2-(2,4-dioxo-1,4-dihydroquinazolin-3(2H)-yl)-N-(1-(pyrazin-2-yl)ethyl)acetamide | |
| 301 | 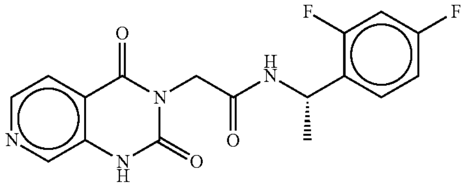 | (S)-N-(1-(2,4-difluorophenyl)ethyl)-2-(2,4-dioxo-1,4-dihydropyrido[3,4-d]pyrimidin-3(2H)-yl)acetamide | |
| 302 | 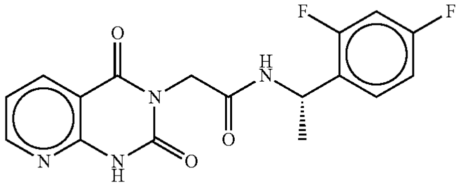 | (S)-N-(1-(2,4-difluorophenyl)ethyl)-2-(2,4-dioxo-1,4-dihydropyrido[2,3-d]pyrimidin-3(2H)-yl)acetamide | |
| 303 | 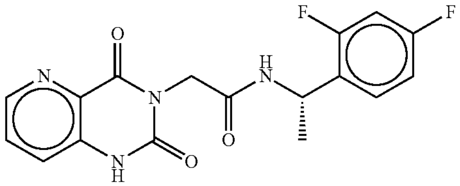 | (S)-N-(1-(2,4-difluorophenyl)ethyl)-2-(2,4-dioxo-1,4-dihydropyrido[3,2-d]pyrimidin-3(2H)-yl)acetamide | |
| 136 | 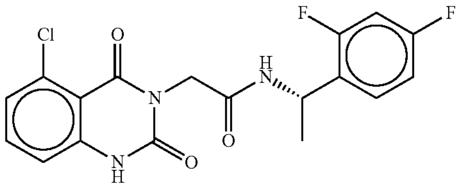 | (S)-2-(5-chloro-2,4-dioxo-1,4-dihydroquinazolin-3(2H)-yl)-N-(1-(2,4-difluorophenyl)ethyl) acetamide | |
| 142 | 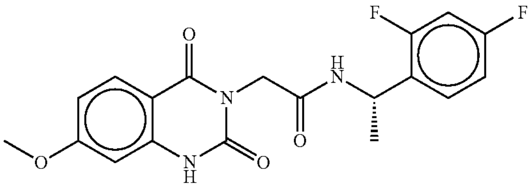 | (S)-N-(1-(2,4-difluorophenyl)ethyl)-2-(7-methoxy-2,4-dioxo-1,4-dihydroquinazolin-3(2H)-yl)acetamide | |
| 143 | 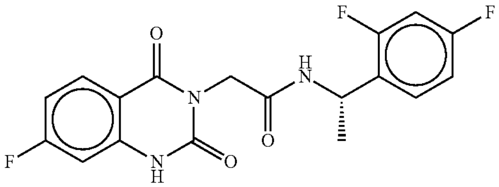 | (S)-N-(1-(2,4-difluorophenyl)ethyl)-2-(7-fluoro-2,4-dioxo-1,4-dihydroquinazolin-3(2H)-yl)acetamide | |

TABLE 7-continued

In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof.

| Compound No. | Structure | Name | Mass Spec |
|---|---|---|---|
| 154 | 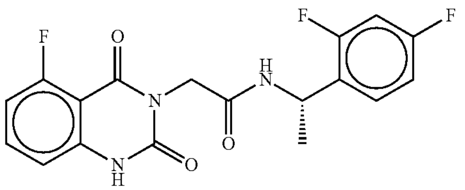 | (S)-N-(1-(2,4-difluorophenyl)ethyl)-2-(5-fluoro-2,4-dioxo-1,4-dihydroquinazolin-3(2H)-yl)acetamide | |
| 155 | 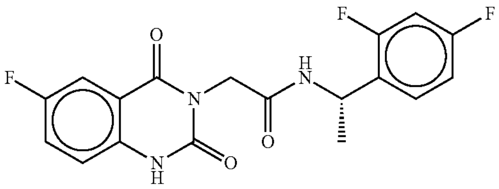 | (S)-N-(1-(2,4-difluorophenyl)ethyl)-2-(6-fluoro-2,4-dioxo-1,4-dihydroquinazolin-3(2H)-yl)acetamide | |
| 401 | 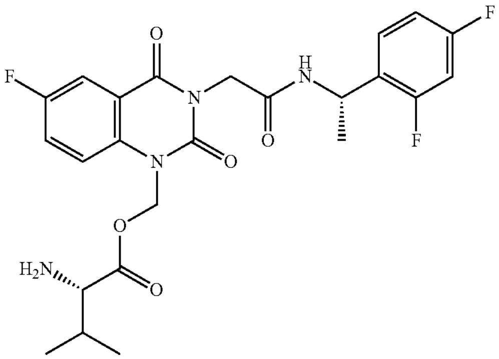 [SMILES: CC(C)[C@H](N)C(=O)OCn1c(=O)n(CC(=O)N[C@@H](C)c2ccc(F)cc2F)c(=O)c2cc(F)ccc21] | (3-(2-(((S)-1-(2,4-difluorophenyl)ethyl)amino)-2-oxoethyl)-6-fluoro-2,4-dioxo-3,4-dihydroquinazolin-1(2H)-yl)methyl L-valinate | 507.1 |
| 405 | 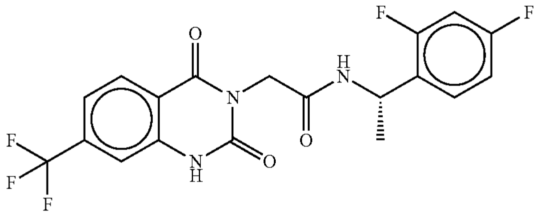 | (S)-N-(1-(2,4-difluorophenyl)ethyl)-2-(2,4-dioxo-7-(trifluoromethyl)-1,4-dihydroquinazolin-3(2H)-yl)acetamide | |
| 406 | 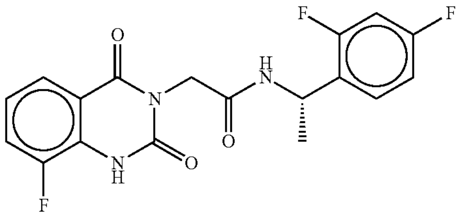 | (S)-N-(1-(2,4-difluorophenyl)ethyl)-2-(8-fluoro-2,4-dioxo-1,4-dihydroquinazolin-3(2H)-yl)acetamide | |
| 407 | 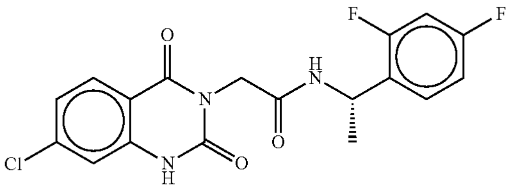 | (S)-2-(7-chloro-2,4-dioxo-1,4-dihydroquinazolin-3(2H)-yl)-N-(1-(2,4-difluorophenyl)ethyl)acetamide | |

TABLE 7-continued

| In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof. | | | |
|---|---|---|---|
| Compound No. | Structure | Name | Mass Spec |
| 408 | 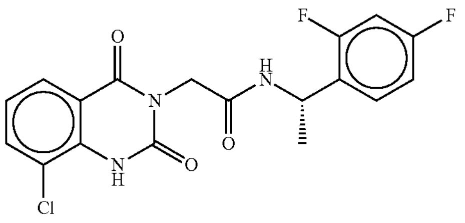 | (S)-2-(8-chloro-2,4-dioxo-1,4-dihydroquinazolin-3(2H)-yl)-N-(1-(2,4-difluorophenyl)ethyl) acetamide | |
| 166 | 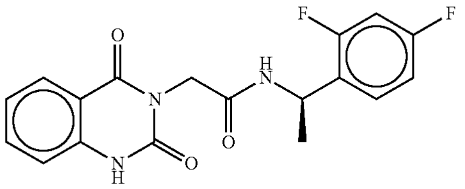 | (R)-N-(1-(2,4-difluorophenyl)ethyl)-2-(2,4-dioxo-1,4-dihydroquinazolin-3(2H)-yl)acetamide | |
| 167 | 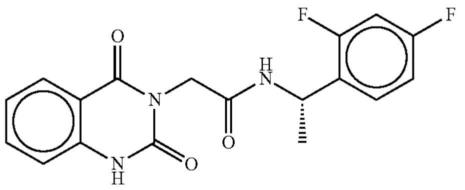 | (S)-N-(1-(2,4-difluorophenyl)ethyl)-2-(2,4-dioxo-1,4-dihydroquinazolin-3(2H)-yl)acetamide | |
| 169 | 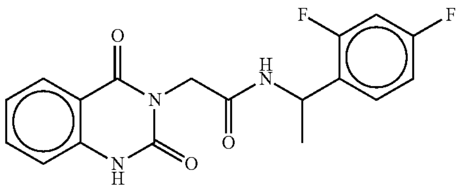 | N-(1-(2,4-difluorophenyl)ethyl)-2-(2,4-dioxo-1,4-dihydroquinazolin-3(2H)-yl)acetamide | |
| 503 | 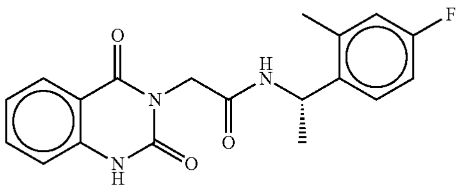 | (S)-2-(2,4-dioxo-1,4-dihydroquinazolin-3(2H)-yl)-N-(1-(4-fluoro-2-methylphenyl)ethyl) acetamide | 356.10 |
| 505 | 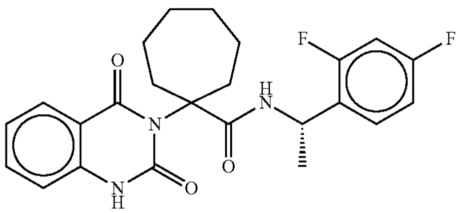 | (S)-N-(1-(2,4-difluorophenyl)ethyl)-1-(2,4-dioxo-1,4-dihydroquinazolin-3(2H)-yl)cycloheptane-1-carboxamide | 440.20 |
| 514 | 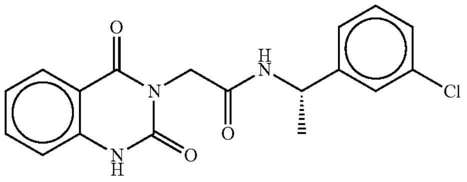 | (S)-N-(1-(3-chlorophenyl)ethyl)-2-(2,4-dioxo-1,4-dihydroquinazolin-3(2H)-yl)acetamide | 359.0 |

TABLE 7-continued

| In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof. | | | |
|---|---|---|---|
| Compound No. | Structure | Name | Mass Spec |
| 515 | 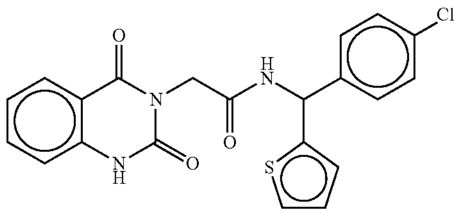 | N-((4-chlorophenyl)(thiophen-2-yl)methyl)-2-(2,4-dioxo-1,4-dihydroquinazolin-3(2H)-yl)acetamide | |
| 516 | 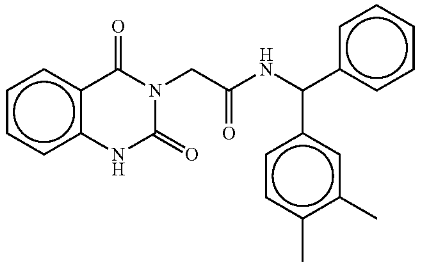 | N-((3,4-dimethylphenyl)(phenyl)methyl)-2-(2,4-dioxo-1,4-dihydroquinazolin-3(2H)-yl)acetamide | |
| 517 | 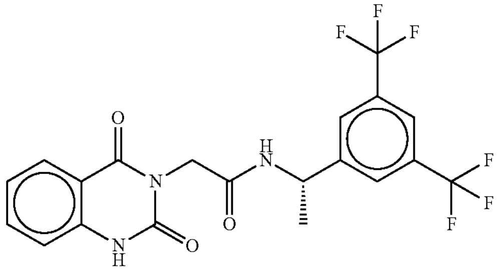 | (S)-N-(1-(3,5-bis(trifluoromethyl)phenyl)ethyl)-2-(2,4-dioxo-1,4-dihydroquinazolin-3(2H)-yl)acetamide | |
| 518 | 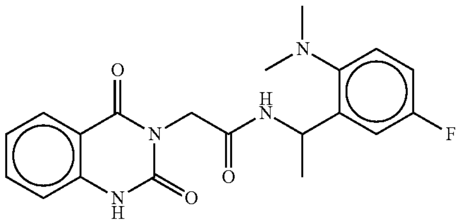 | N-(1-(2-(dimethylamino)-5-fluorophenyl)ethyl)-2-(2,4-dioxo-1,4-dihydroquinazolin-3(2H)-yl)acetamide | |
| 519 | 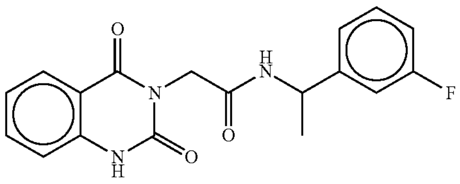 | 2-(2,4-dioxo-1,4-dihydroquinazolin-3(2H)-yl)-N-(1-(3-fluorophenyl)ethyl)acetamide | |
| 520 | 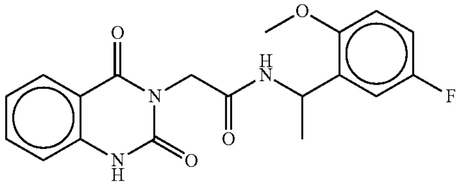 | 2-(2,4-dioxo-1,4-dihydroquinazolin-3(2H)-yl)-N-(1-(5-fluoro-2-methoxyphenyl)ethyl)acetamide | |

TABLE 7-continued

In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof.

| Compound No. | Structure | Name | Mass Spec |
|---|---|---|---|
| 521 | 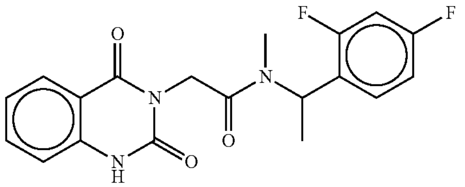 | N-(1-(2,4-difluorophenyl)ethyl)-2-(2,4-dioxo-1,4-dihydroquinazolin-3(2H)-yl)-N-methylacetamide | |
| 522 | 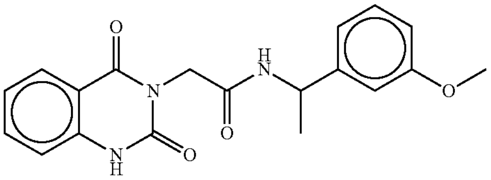 | 2-(2,4-dioxo-1,4-dihydroquinazolin-3(2H)-yl)-N-(1-(3-methoxyphenyl)ethyl) acetamide | |
| 523 | 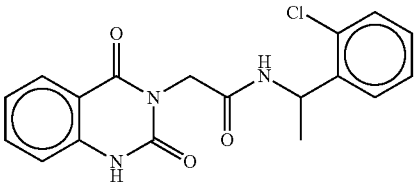 | N-(1-(2-chlorophenyl)ethyl)-2-(2,4-dioxo-1,4-dihydroquinazolin-3(2H)-yl)acetamide | |
| 524 | 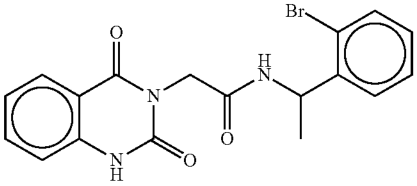 | N-(1-(2-bromophenyl)ethyl)-2-(2,4-dioxo-1,4-dihydroquinazolin-3(2H)-yl)acetamide | |
| 525 | 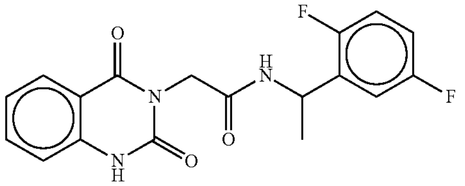 | N-(1-(2,5-difluorophenyl)ethyl)-2-(2,4-dioxo-1,4-dihydroquinazolin-3(2H)-yl)acetamide | |
| 526 | 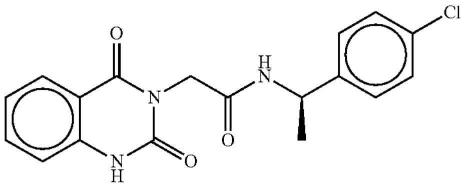 | (R)-N-(1-(4-chlorophenyl)ethyl)-2-(2,4-dioxo-1,4-dihydroquinazolin-3(2H)-yl)acetamide | |
| 527 | 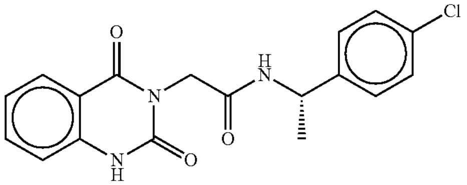 | (S)-N-(1-(2,4-difluorophenyl)ethyl)-2-(1-methyl-2,4-dioxo-1,4-dihydroquinazolin-3(2H)-yl)acetamide | |

TABLE 7-continued

In an aspect, the present disclosure provides the compounds of Table 7 and salts thereof. In some embodiments, the compound or salt of Formula (IIIa) is selected from a compound of Table 7, or a salt thereof. In some embodiments, the compound or salt of Formula (IIIa) is selected from a compound of Table 1, Table 2, Table 3, Table 4, Table 5, and Table 6, or a salt thereof.

| Compound No. | Structure | Name | Mass Spec |
|---|---|---|---|
| 528 | 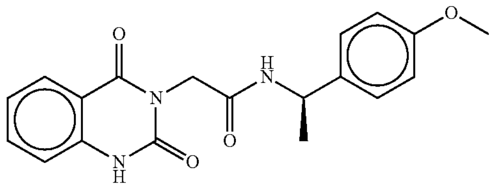 | (R)-2-(2,4-dioxo-1,4-dihydroquinazolin-3(2H)-yl)-N-(1-(4-methoxyphenyl)ethyl) acetamide | |
| 529 | 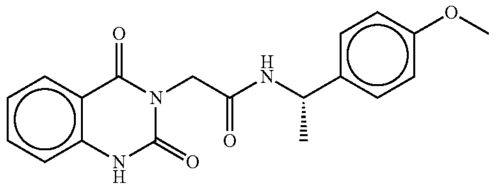 | (S)-2-(2,4-dioxo-1,4-dihydroquinazolin-3(2H)-yl)-N-(1-(4-methoxyphenyl)ethyl) acetamide | |
| 530 | 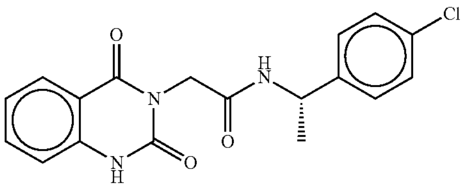 | (S)-N-(1-(4-chlorophenyl)ethyl)-2-(2,4-dioxo-1,4-dihydroquinazolin-3(2H)-yl)acetamide | |
| 533 | 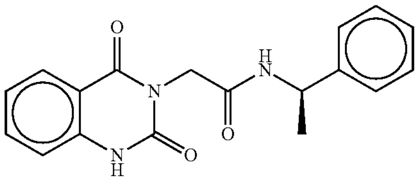 | (R)-2-(2,4-dioxo-1,4-dihydroquinazolin-3(2H)-yl)-N-(1-phenylethyl)acetamide | |
| 534 | 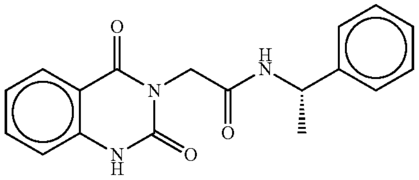 | (S)-2-(2,4-dioxo-1,4-dihydroquinazolin-3(2H)-yl)-N-(1-phenylethyl)acetamide | |
| 703 | 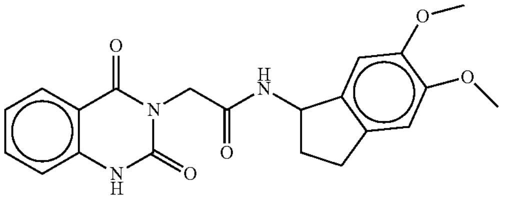 | N-(5,6-dimethoxy-2,3-dihydro-1H-inden-1-yl)-2-(2,4-dioxo-1,4-dihydroquinazolin-3(2H)-yl)acetamide | |

Example 12: Myofibril ATPase Assay

Myofibril ATPase assays are known in the art to be useful in evaluating small molecules for the treatment of HCM and other cardiac indications. Myosin ATPase activity is assessed by using a coupled reaction system, in which ADP generated by the myosin ATPase function is coupled to the disappearance of NADH through the pyruvate kinase/lactate dehydrogenase (PK-LDH) system. ATPase activity produces ADP, which is used as a substrate for PK to produce pyruvate and regenerate ATP. The pyruvate is then used as a substrate by LDH to oxidize NADH to NAD+. The rate of the reaction is monitored through the time-dependent disappearance of NADH using absorbance at 340 nm, which, when the couple system is in stoichiometric excess, is directly correlated to the ATPase activity of the myosin.

Inhibition of ATPase activity by the assayed compounds is indicated by a reduced rate of NADH loss, relative to vehicle-treated controls, over the experimental time window. Porcine Ventricle are the primary sources of myofibril material.

Materials: The following stock solutions and reagents were used in the Myofibril ATPase Assay: Stock Solutions; PIPES, 200 mM and 120 mM in H2O, pH 7.0; MgCl2 in H2O, 200 mM; PM12 Buffer, 10×: 120 mM PIPES (from 200 mM stock), 20 mM MgCl2 (from 200 mM stock); PBS Buffer, 1X: 135 mM NaCl, 27 mM KCl, 10 mM Na(PO4)2, 1.8 mM K2(PO4), pH 7.4; EGTA in H2O, 250 mM; $CaCl_2$) in H2O, 500 mM; DTT in H2O, 1 M; BSA in H2O, 10 mg/mL; ATP in 1×PBS, 50 mM; NADH in 1X PM12 and 1 mM DTT, 26 mM; PEP in 1X PM12, 78 mM, pH 7.0.

Stock Solutions of pCa buffer. Combine PIPES, $CaCl_2$, and EGTA solutions with water. Adjust pH to 7.0 and bring final volume to 100 mL.

Preparation of Stocks Solutions for 100 mL of pCa buffer

| pCA | 120 mM PIPES (mL) | Approx. Water (mL) | $CaCl_2$ (mL) | EGTA (mL) |
|---|---|---|---|---|
| 4.0 | 10 | 59.797 | 10.203 | 20 |
| 4.5 | 10 | 59.959 | 10.041 | 20 |
| 5.0 | 10 | 60.060 | 9.940 | 20 |
| 5.5 | 10 | 60.244 | 9.756 | 20 |
| 5.75 | 10 | 60.434 | 9.566 | 20 |
| 6.0 | 10 | 60.750 | 9.250 | 20 |
| 6.25 | 10 | 61.262 | 8.738 | 20 |
| 6.5 | 10 | 62.045 | 7.955 | 20 |
| 6.75 | 10 | 63.138 | 6.862 | 20 |
| 7.0 | 10 | 64.484 | 5.516 | 20 |
| 8.0 | 10 | 68.905 | 1.095 | 20 |
| 10.0 | 10 | 69.988 | 0.012 | 20 |

Buffer A & Buffer B. Prepare buffers A and B according to the table below.

| Total Well Volume (µL) | 50 | Component | Stock Concentrations Value Unit | Final Concentrations in Specific Buffer | Reaction Concentrations | Volume per well (µL) | Number of Wells Total Volume (µL) | 400 | 1200 |
|---|---|---|---|---|---|---|---|---|---|
| Buffer A (µL) | 25 | PM12 Buffer | 10 x | 1.00 x | 1.00 x | 2.50 | 1000.00 | 1300.00 | PM12 Buffer (1 x) |
| | | KCl | 2000 mM | 0.00 mM | 0.00 mM | 0.00 | 0.00 | 0.00 | KCl (0 m M) |
| | | pCa Solution | 10 x | 0.00 x | 0.00 x | 0.00 | 0.00 | 0.00 | pCa Solution (0.x) |
| | | Compound | 100% | 0.00% | 0.00% | 0.00 | 0.00 | 0.00 | Compound (0%) |
| | | BSA | 10 mg/mL | 0.10 mg/mL | 0.10 mg/mL | 0.25 | 100.00 | 130.00 | BSA (0.1 mg/mL) |
| | | DTT | 1000 mM | 1.00 mM | 1.00 mM | 0.03 | 10.00 | 13.00 | DTT (1 mM) |
| | | PK/LDH | 200 x | 2.00 x | 1.00 x | 0.25 | 100.00 | 130.00 | PK/LDH (1x) |
| | | Ventricle Prep 18 | 8.2 mg/mL | 1.00 mg/mL | 0.50 mg/mL | 3.05 | 1219.51 | 1585.37 | Ventricle Prep 18 (0.5 mg/mL) |
| | | Antifoam | 1.00% | 0.01% | 0.01% | 0.25 | 100.00 | 130.00 | Antifoam (0.01%) |
| | | Water | | | | 18.68 | 7470.49 | 9711.63 | Water |
| | | | | | | 25.00 | 10000.00 | 13000.00 | Total |
| Buffer B (µL) | 25 | PM12 Buffer | 10 x | 1.00 x | 1.00 x | 2.50 | 1000.00 | 1300.00 | PM12 Buffer (1 x) |
| | | KCl | 1000 mM | 0.00 mM | 30.00 mM | 0.00 | 0.00 | 0.00 | KCl (30 mM) |
| | | Compound | 100% | 0.00% | 0.00% | 0.00 | 0.00 | 0.00 | Compound (0%) |
| | | pCa Solution | 10 x | 2.00 x | 1.00 x | 5.00 | 2000.00 | 2600.00 | pCa Solution (1 x) |
| | | BSA | 10 mg/mL | 0.10 mg/mL | 0.10 mg/mL | 0.25 | 100.00 | 130.00 | BSA (0.1 mg/mL) |
| | | DTT | 1000 mM | 1.00 mM | 1.00 mM | 0.03 | 10.00 | 13.00 | DTT (1 mM) |
| | | ATP | 50 mM | 0.50 mM | 0.25 mM | 0.25 | 100.00 | 130.00 | ATP (0.25 mM) |
| | | NADH | 26 mM | 1.00 mM | 0.50 mM | 0.96 | 384.62 | 500.00 | NADH (0.5 mM) |
| | | PEP | 78 mM | 3.00 mM | 1.50 mM | 0.96 | 384.62 | 500.00 | PEP (1.5 mM) |
| | | Antifoam | 1.00% | 0.01% | 0.01% | 0.25 | 100.00 | 130.00 | Antifoam (0.01%) |
| | | Water | | | | 14.80 | 5920.77 | 7697.00 | Water |
| | | | | | | 25.00 | 10000.00 | 13000.00 | |

Myofibril ATPase Assay Procedure: BSA, ATP, NADH, PEP, and DTT solutions were thawed at room temperature, then transferred to ice. Pellet-frozen myofibrils were transferred with approximately twice the required volume into a sufficiently large tube and capped. Myofibrils were thawed by rolling in a water bath for approximately 15 min at room temperature and cooled on ice. Buffers A and B were prepared by adjusting volumes as necessary for required number of wells and stored on ice. 0.5 µL of the compounds to be assayed were added into wells. 25 µL of Buffer A was dispensed into the wells, followed by 25 µL of Buffer B. The wells were measured for absorbance at 340 nm, using a kinetic protocol in which the wells are read every 1.5-2 min for 75 min. Assay data analysis was performed using a python script that filtered the raw data to retain those points falling between a starting and ending time and between a maximum and minimum absorbance, then used the filtered time-domain 340 nm absorbance data in each well to calculate a slope via linear regression analysis in units of mAU/min. Compound slopes were normalized between 100% and 0% activity, where 100% represented the slope of wells containing only compound vehicle, and fit to a 4-parameter logistic model. In addition to the fit parameters, the $EC_{25\%}$ values were calculated, relative to the 100% normalized value. Additionally, the Y125 values were calculated for compounds that increased myosin ATP-ase activity. Fit parameters, calculated effective concentrations, filtered raw data, and calculated slopes were exported, in addition to compound-specific graphs of normalized ATPase activity versus concentration in µM. Each value reported in Table 8 is either a Y75 value or a Y125 value. Values without pound sign, #, are Y75 values, which reflect the concentration required to reduce myosin ATP-ase activity by 25% (e.g., Y-axis activity value is 75% of initial value), relative to myosin ATP-ase activity in the absence of exogenous compound. Values with a pound sign, #, next to the value, are Y125 values, which reflect the concentration required to increase myosin ATP-ase activity by 25% (e.g., Y-axis activity value is 125% of initial value), relative to myosin ATP-ase activity in the absence of exogenous compound. The results are shown in Table 8.

Skeletal Myofibril Isolation:

Myofibrils from various animals and tissue types were acquired from a variety of sources: rabbit psoas muscle was purchased from Pel-Freez Biologicals (Rogers, AR) and porcine cardiac muscle was purchased from Exemplar Genetics. All myofibrils were prepared using a method based upon those described in Herrmann et al. (1993) and summarized here. Minced tissue was homogenized for 50 sec with a Polytron homogenizer into 10 volumes (relative to weight in grams) of Isolation Buffer A (50 mM Tris, pH 8.0, 0.1 M potassium acetate, 5 mM KCl, 2 mM DTT, 5 mM EDTA, 0.5% v/v Triton X-100) supplemented with 0.1 mM PMSF, 10 μM leupeptin, 5 μM pepstatin, and 0.5 mM sodium azide. The myofibrils were recovered by centrifugation (Beckman Allegra 6R, 1200 g, 10 min) and resuspended in 10 volumes Isolation Buffer B (Buffer A above without protease inhibitors or sodium azide). The myofibrils were further homogenized as before and recovered by centrifugation. Cellular membranes and debris were removed by 2 washes in Isolation Buffer B, centrifuging each as before. The myofibrils were then suspended in Isolation Buffer C (Tris, potassium acetate, KCl, and DTT as above, supplemented with 2 mM magnesium acetate) and homogenized as described above. The myofibrils were collected by centrifugation and washed 3 times with Isolation Buffer C before being passed through a 100 μM nylon mesh sheet (Spectrum Laboratories) to remove the larger particles. The sieved myofibrils were centrifuged at 1200 g for 15 min and resuspended in 2 to 3 volumes of PM12-60 buffer (12 mM PIPES, pH 6.8, 2 mM $MgCl_2$, 60 mM KCl, 1 mM DTT). D-sucrose was added to 10% and the myofibril suspension was drop-frozen into liquid nitrogen at stored at −80° C.

Cardiac Myofibril Isolation:

Myofibrils from porcine cardiac muscle was isolated from the left ventricle of Yucatan minipigs. Myofibrils were prepared using a method based upon those described in Herrmann et al. (1993) and summarized here. Minced tissue was homogenized for 50 sec with a Polytron homogenizer into 10 volumes (relative to weight in grams) of Isolation Buffer A (75 mM KCl, 10 mM Imidazole, 2 mM $MgCl_2$, 2 mM EGTA, 1 mM $NaN_3$, 1% v/v Triton X-100) supplemented with 4 mM Phosphocreatine, 1 mM ATP, 50 mM BDM, 1 mM DTT, 1 mM Benzamide HCl, 0.1 mM PMSF, 10 μM leupeptin, 5 μM pepstatin, and 10 mM EDTA. The myofibrils were recovered by centrifugation (Beckman Allegra 6R, 1200 g, 15 min) and resuspended in 10 volumes Isolation Buffer B (Buffer A above without supplemental reagents). The myofibrils were further homogenized described above and recovered by centrifugation for 7 mins. Cellular membranes and debris were removed by 3 washes in Isolation Buffer B, centrifuging each as before. The myofibrils were then suspended in Isolation Buffer C (Buffer A above without supplemental reagents and Triton) and homogenized as described above. The myofibrils were collected by centrifugation and washed 3 times with Isolation Buffer C before being passed through a 100 μM nylon mesh sheet (Spectrum Laboratories) to remove the larger particles. The sieved myofibrils were centrifuged at 1200 g for 15 min and resuspended in 2 to 3 volumes of PM12-60 buffer (12 mM PIPES, pH 6.8, 2 mM $MgCl_2$, 60 mM KCl, 1 mM DTT). D-sucrose was added to 1000 and the myofibril suspension was drop-frozen into liquid nitrogen at stored at −80° C. Certain compounds of the disclosure have ventricle and atrial $EC_{25}$ values as in Table 8. Skeletal EC25 refers to, e.g., Rabbit Psoas $EC_{25}$ (μM) (Rabbit Psoas Prep pCa 25 GEOM_MEAN). Atrial EC25 refers to, e.g., Porcine Atrial $EC_{25}$ (μM) (Porcine Atria Prep pCa 25 GEOM_MEAN), Ventricular EC25 refers to, e.g., Porcine Ventricular $EC_{25}$ (μM) (Porcine Ventricle Prep pCa 25 GEOM_MEAN). Certain compounds of the disclosure have skeletal, atrial, and ventricle $EC_{25}$ values as in Table 8.

TABLE 8

| Compound No. | Rabbit Psoas $EC_{25}$ (μM) | Porcine Atria $EC_{25}$ (μM) | Porcine Ventricle $EC_{25}$ (μM) |
|---|---|---|---|
| 1* | 0.59 | 0.699 | 20.04 |
| 2* | 86.83 | 24.53 | 100 |
| 11* | 50.791 | 6.642 | 100 |
| 12* | 1.571 | 1.271 | 3.176 |
| 5* | 100 | 0.235 | 100 |
| 6* | 0.113 | 0.111 | 0.692 |
| 97* | 100 | 100 | 100 |
| 3* | 2.538 | 1.074 | 100 |
| 4* | 0.204 | 0.178 | 4.869 |
| 7* | 5.692 | 0.3543 | 1.467 |
| 8* | 0.108 | 0.094 | 0.448 |
| 13* | 0.043 | 0.048 | 0.119 |
| 14* | 21.27 | 5.931 | 23.76 |
| 15* | 100 | 4.31 | 100 |
| 16* | 5.743 | 0.57 | 14.04 |
| 17* | 9.016 | 0.427 | 10.16 |
| 18* | 0.512 | 0.378 | 5.522 |
| 19* | 21.6 | 15.77 | 100 |
| 20v | 0.799 | 2.095 | 7.141 |
| 21* | 1.66 | 1.799 | 0.615 |
| 22* | 0.036 | 0.083 | 0.205 |
| 27** | 100 | 100 | 100 |
| 28** | 39.563 | 59.55 | 100 |
| 29** | 62.503 | 1.54 | 47.12 |
| 30** | 23.886 | 100 | 2.002 |
| 47* | 1.97 | 1.442 | 100 |
| 105* | 16.519 | 11.59 | 94.03 |
| 106* | 72.241 | 100 | 100 |
| 98* | 100 | 100 | 100 |
| 99* | 100 | 100 | 100 |
| 100* | 12.272 | 31.84 | 100 |
| 201* | 52.35 | 42.2 | 100 |
| 202* | 7.437 | 8.617 | 100 |
| 203* | 3.687 | 2.399 | 16.31 |
| 204* | 100 | 100 | 70.61 |
| 205* | 9.128 | 5.445 | 100 |
| 206* | 0.214 | 0.2933 | 1.018 |
| 207* | 4.593 | 100 | 100 |
| 208* | 0.065 | 0.085 | 0.254 |
| 209* | 39.51 | 100 | 100 |
| 210* | 0.174 | 0.118 | 0.559 |
| 211* | 100 | 100 | 100 |
| 212* | 100 | 100 | 100 |
| 214* | 100 | 100 | 100 |
| 59 | 100 | 100 | 100 |
| 65 | 8.499 | 3.241 | 100 |
| 95 | 100 | 100 | 100 |
| 96 | 100 | 100 | 100 |
| 141 | 1.48 | 3.009 | 61.78 |
| 33 | 51.2# | 100 | 100100 |
| 34 | 0.85# | 48.85 | 45.37 |
| 35 | 0.086 | 0.0835 | 1.64 |
| 36 | 0.104 | 0.0803 | 1.35 |
| 37 | 0.412 | 0.658 | 17.77 |
| 38 | 0.422 | 0.185 | 3.995 |
| 39 | 0.055 | 0.0536 | 0.3333 |
| 40 | 0.476 | 0.1074 | 6.567 |
| 41 | 0.828 | 1.375 | 28.36 |
| 51 | 0.984 | 0.2427 | 13.83 |
| 69 | 1.147 | 21.1 | 100 |
| 72 | 0.019 | 0.1151 | 0.2524 |
| 73 | 0.0495 | 0.1149 | 0.707 |
| 104 | 0.086 | 0.0488 | 0.9868 |
| 402 | 100 | 100 | 100 |
| 403 | 100 | 100 | 100 |
| 404 | 100# | 12.2 | 100 |
| 31* | 24.3# | 56.82 | 59.48 |
| 32* | 7.64# | 68.73 | 100 |
| 42 | 100 | 100 | 100 |
| 49* | 100 | 100 | 100 |

TABLE 8-continued

| Compound No. | Rabbit Psoas $EC_{25}$ (μM) | Porcine Atria $EC_{25}$ (μM) | Porcine Ventricle $EC_{25}$ (μM) |
|---|---|---|---|
| 50* | 100 | 100 | 100 |
| 70* | 90.27# | 100 | 100 |
| 71* | 3.86 | 12.67 | 53.2 |
| 87* | 0.817 | 5.405 | 100 |
| 101* | 1.521 | 1.036 | 87.37 |
| 102* | 0.761 | 1.175 | 99.13 |
| 501* | 84.531 | 100 | 50.21 |
| 502* | 13.814 | 43.27 | 100 |
| 504* | 3.28# | 20.67 | 43.467 |
| 506 | 65.656 | 33.59 | 29.03 |
| 507 | 63.841 | 100 | 100 |
| 508* | 100 | 100 | 100 |
| 509* | 100 | 100 | 100 |
| 510* | 100 | 100 | 100 |
| 511* | 35.849 | 2.118 | 100 |
| 512* | 23.575# | 30.14# | 100 |
| 513* | 100 | 100 | 100 |
| 601 | 100 | 100 | 100 |
| 602 | 100 | 100 | 100 |
| 603 | 100 | 100 | 100 |
| 604 | 100 | 100 | 100 |
| 605 | 100 | 100 | 100 |
| 606 | 100 | 100 | 100 |
| 9* | 0.631 | 0.078 | 0.547 |
| 10* | 100 | 100 | 100 |
| 44* | 1.145 | 36.5 | 100 |
| 48* | 0.156 | 0.4184 | 7.872 |
| 43 | 58.79 | 100 | 100 |
| 46 | 100 | 100 | 100 |
| 55* | 100 | 100 | 100 |
| 57* | 0.937 | 1.067 | 25.71 |
| 701* | 0.023 | 0.07 | 0.075 |
| 702* | 4.019 | 3.03 | 7.299 |
| 3001* | | 5.34 | 100.00 |
| 3002* | | 0.11 | 0.24 |
| 3003* | | 1.32 | 63.05 |
| 3004* | | 0.18 | 0.51 |
| 3005* | 2.34 | 2.78 | 11.35 |
| 3006* | | 0.29 | 0.62 |
| 3007* | 0.36 | 0.34 | 0.81 |
| 3008* | 0.01 | 0.06 | 0.09 |
| 3009* | 0.06 | 0.10 | 0.25 |
| 3010* | 1.59 | 1.97 | 1.90 |
| 3011* | 4.77 | 0.42 | 13.07 |
| 3013* | 0.40 | 0.19 | 1.04 |
| 3014* | 100.00 | 100.00 | 100.00 |
| 3015* | 0.89 | 1.89 | 10.96 |
| 5001 | 100 | | |
| 5002* | 100 | | |
| 5003 | 100 | | |
| 5004 | 100 | | |
| 5005 | 100 | | |
| 5006 | 100 | | |
| 5007 | 100 | | |
| 5008 | 100 | | |
| 5009 | 100 | 100 | 100 |
| 213 | 100 | 100 | 100 |
| 215 | 100 | 23.9 | 45.3 |
| 301 | 5.422 | 79 | 100 |
| 302 | 100 | 100 | 100 |
| 303 | 23 | 100 | 100 |
| 136 | 0.591 | | 0.256 |
| 142 | 100 | 100 | 100 |
| 143 | 9.2 | 2.081 | 100 |
| 154 | 0.11 | 0.1312 | 1.15 |
| 155 | 0.073 | 0.0623 | 0.1805 |
| 401 | 6.978 | 46.5 | 100 |
| 405 | 100 | 100 | 100 |
| 406 | 12.297 | 63.31 | 100 |
| 407 | 7.16 | 0.3539 | 100 |
| 408 | 100 | 100 | 100 |
| 166 | 100 | 100 | 100 |
| 167 | 0.52 | | 7.022 |
| 169 | 0.494 | 2.407 | 31.6 |
| 503* | 0.36 | 0.1046 | 1.526 |
| 505 | 100 | 100 | 100 |
| 514* | 100 | 100 | |
| 515 | 100 | 100 | 100 |
| 516 | 100 | 100 | 100 |
| 517* | 100 | 100 | 100 |
| 518 | 100 | 100 | 100 |
| 519 | 100 | 79.37 | 100 |
| 520 | 100 | 100 | 100 |
| 521 | 1.26 | 100 | 100 |
| 522 | 100 | 100 | 100 |
| 523 | 16.05 | 7.86 | 100 |
| 524 | 11.968 | 73.54 | 100 |
| 525 | 5.727 | 23.51 | 100 |
| 526* | 100 | 100 | 100 |
| 527* | 18.18# | 100 | 100 |
| 528* | 100 | 100 | 100 |
| 529* | 100 | 100 | 100 |
| 530* | 3.24 | 0.445 | 4.63 |
| 531 | | 0.462 | 1.844 |
| 533* | 100 | 100 | 100 |
| 534* | 100 | 100 | 100 |
| 703 | 100 | 100 | 100 |

*denotes that absolute stereochemistry is not yet known. Associated $IC_{25}$ values are to a single enantiomer with unknown absolute configuration.
**denotes that absolute stereochemistry is not yet known. Associated $IC_{25}$ values are to a single diastereomer with unknown absolute configuration.
***denotes a mixture of diastereomers.
****denotes racemic mixtures
#denotes that the number is a Y125 value, not a Y75 value.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Numbered Embodiments

Some numbered examples of embodiments follow. (1): A compound represented by Formula (I):

(I)

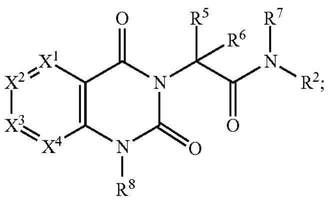

or a salt thereof, wherein: $X^1$, $X^2$, $X^3$, and $X^4$ are each independently selected from $C(R^1)$, N, and $N^+(—O^-)$, wherein at least one of $X^1$, $X^2$, $X^3$, or $X^4$ is N; and no more than two of X, $X^2$, $X^3$, and $X^4$ are N; each $R^1$ is independently selected from: hydrogen; halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —N($R^{10a}$)C(O)N($R^{10a}$)$_2$, —OC(O)N($R^{10a}$)$_2$, —N($R^{10a}$)C(O)O$R^{10a}$, —S(O)$R^{10a}$, —S(O)$_2R^{10a}$, —$NO_2$, =O, =S, =N($R^{10a}$), —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; $R^5$ and $R^6$ are each independently selected from: hydrogen, halogen, —O$R^{10c}$, —S$R^{10c}$, —N($R^{10c}$)$_2$, —$NO_2$, and —CN; $C_{1-6}$ alkyl, optionally substituted with one or more substituents independently selected from halogen, —O$R^{10c}$, —S$R^{10c}$, —N($R^{10c}$)$_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —O$R^{10c}$, —S$R^{10c}$, —N($R^{10c}$)$_2$, —$NO_2$, and —CN; and $C_{3-10}$ carbocycle and 3- to 10-membered heterocycle, each of which is optionally substituted with one or more substituents independently selected from halogen, —O$R^{10c}$, —S$R^{10c}$, —N($R^{10c}$)$_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{90}$; $R^7$ is selected from: hydrogen and $C_{1-6}$ alkyl optionally substituted with one or more substituents independently selected from halogen, —O$R^{10d}$, —S$R^{10d}$, —N($R^{10d}$)$_2$, —$NO_2$, and —CN; $R^8$ is selected from: hydrogen; and $C_{1-6}$ alkyl optionally substituted with one or more substituents independently selected from halogen, —O$R^{10e}$, —S$R^{10e}$, —N($R^{10e}$)$_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —O$R^{10e}$, —S$R^{10e}$, —N($R^{10e}$)$_2$, —$NO_2$, and —CN; each $R^{9a}$ is independently selected from: halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), and —CN; and $C_{1-3}$ alkyl, $C_{2-3}$ alkenyl, and $C_{2-3}$ alkynyl, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), and —CN; each $R^{9b}$ is independently selected from: halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN; and $C_{1-3}$ alkyl, $C_{2-3}$ alkenyl, and $C_{2-3}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN; each $R^{9c}$ is independently selected from: halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$°—N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$), and —CN; and $C_{1-3}$ alkyl, $C_{2-3}$ alkenyl, and $C_{2-3}$ alkynyl, each of which is optionally substituted with one or more substituents independently selected from halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —$NO_2$, =O, =S, =N($R^{10c}$), and —CN; and each $R^{10a}$, $R^{10b}$, $R^{10c}$, $R^{10d}$, and $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein if $X^3$ and $X^1$ are both N, then $R^8$ is selected from hydrogen and $C_{1-4}$ alkyl optionally substituted with one or more substituents independently selected from halogen, —O$R^{10}$, —S$R^{10}$, —N($R^{10}$)$_2$, —$NO_2$, and —CN. (2): The compound or salt of embodiment 1, wherein $X^1$, $X^2$, $X^3$, and $X^4$ are each independently selected from C($R^1$) and N. (3): The compound or salt of embodiment 1 or 2, wherein one of $X^1$, $X^2$, $X^3$, or $X^4$ is N. (4): The compound or salt of embodiment 3, wherein $X^1$ is N. (5): The compound or salt of embodiment 3, wherein $X^2$ is N. (6): The compound or salt of embodiment 3, wherein $X^3$ is N. (7): The compound or salt of embodiment 3, wherein $X^4$ is CH. (8): The compound or salt of embodiments 1 or 2, wherein two of $X^1$, $X^2$, $X^3$, and $X^4$ are N. (9): The compound or salt of embodiment 8, wherein $X^1$ and $X^3$ are N. (10): The compound or salt of embodiment 8, wherein $X^2$ and $X^4$ are N. (11): The compound or salt of any one of embodiments 1 to 10, wherein each $R^1$ is independently selected from: hydrogen; halogen, —$NO_2$, —CN, —O$R^{10a}$, —S$R^{10a}$, —N($R^{10a}$)$_2$, —C(O)$R^{10a}$, and —C(O)N($R^{10a}$)$_2$; $C_{1-6}$ alkyl, optionally substituted with one or more substituents independently selected from halogen, —$OR^{10a}$, —$SR^{10a}$, —N($R^{10a}$)$_2$, —C(O)$R^{10a}$, —$NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —CN, $C_{1-6}$ alkyl optionally substituted with one or more $R^{9a}$. (12): The compound or salt of any one of embodiments 1 to 11, wherein each $R^1$ is independently selected from: hydrogen; halogen, —$NO_2$, —CN, —$OR^{10a}$, —$SR^{10a}$, —N($R^{10a}$)$_2$, —C(O)$R^{10a}$ and —C(O)N($R^{10a}$)$_2$; $C_{1-6}$ alkyl, optionally substituted with one or more substituents independently selected from halogen, —$OR^{10a}$, —$SR^{10a}$, and —N($R^{10a}$)$_2$; and $C_{3-10}$ carbocycle and 3- to 10-membered heterocycle, each of which is optionally substituted with one or more substituents independently selected from halogen, —$OR^{10a}$, —$SR^{10a}$, and —N($R^{10a}$)$_2$. (13): The compound or salt of any one of embodiments 1 to 12, wherein each $R^1$ is independently selected from: hydrogen; halogen, CN, —$OR^{10a}$, and —C(O)N($R^{10a}$)$_2$; $C_{1-6}$ alkyl, optionally substituted with one or more substituents independently selected from halogen, and $C_{3-10}$ carbocycle optionally substituted with one or more substituents independently selected from halogen. (14): The compound or salt of any one of embodiments 1 to 13, wherein $R^1$ is hydrogen. (15): The compound or salt of any one of embodiments 1 to 10, wherein each $R^1$ is independently selected from hydrogen, halogen, —$NO_2$, —CN, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2R^{10a}$; (16): The compound or salt of any one of 1 to 10 or embodiment 15, wherein each $R^1$ is independently selected from hydrogen, $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —N($R^{10a}$)C(O)N($R^{10a}$)$_2$, —OC(O)N($R^{10a}$)$_2$, —N($R^{10a}$)C(O)O$R^{10a}$, —S(O)$R^{10a}$, —S(O)$_2R^{10a}$, —$NO_2$, =O, =S, =N($R^{10a}$), —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (17): The compound or salt of any one of embodiments 1 to 10 or embodiments 15 to 16, wherein each $R^1$ is independently selected from hydrogen, $C_{3-10}$ carbocycle and 3- to 10-membered heterocycle, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. (18): The compound or salt of any one of embodiments 1 to 10 or embodiments 15 to 17, wherein each $R^1$ is independently selected from: hydrogen; halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, and —NH($C_{1-6}$ alkyl); $C_{1-6}$ alkyl, $C_{2-6}$ alkenyl, and $C_{2-6}$ alkynyl, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{2-6}$ alkynyl. (19): The compound or salt of any one of embodiments 1 to 10 or embodiments 15 to 18, wherein each $R^1$ is independently selected from $C_{1-3}$ alkyl optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, —NH ($C_{1-6}$ alkyl), $C_{3-10}$ carbocycle and 3- to 10-membered heterocycle. (20): The compound or salt of any one of embodiments 1 to 10 or embodiments 15 to 19, wherein each $R^1$ is independently selected from $C_{3-5}$ carbocycle is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{2-6}$ alkynyl. (21): The compound or salt of any one of embodiments 1 to 10 or embodiments 15 to 20, wherein each $R^1$ is independently selected from hydrogen, —CN, —OH, —OMe, —OEt, —OiPr, —F, —Cl, —Br, —Me, —Et, —$CF_3$, —$CHF_2$, —$CH_2F$, $OCF_3$, —$OCHF_2$, —$OCH_2F$, —C(O)$NH_2$,

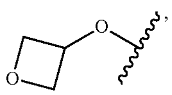, 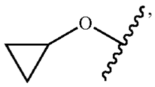, 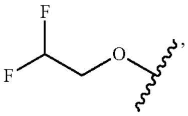,

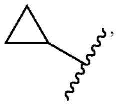, and 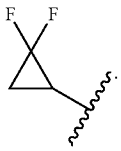.

(22): The compound or salt of any one of embodiments 1 to 21, wherein $R^2$ is selected from $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^b$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (23): The compound or salt of any one of embodiments 1 to 22, wherein $R^2$ is selected from $C_{1-6}$ alkyl, optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (24): The compound or salt of any one of embodiments 1 to 23, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (25): The compound or salt of any one of embodiments 1 to 24, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (26): The compound or salt of any one of embodiments 1 to 25, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (27): The compound or salt of any one of embodiments 1 to 21, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, O, S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (28): The compound or salt of any one of embodiments 1 to 21, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl, wherein the $C_{1-6}$ alkyl is optionally substituted with one or more $R^{9b}$. (29): The compound or salt of any one of embodiments 1 to 21 or embodiment 28, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (30): The compound or salt of any one of embodiments 1 to 21 or any one of embodiments 28 to 29, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (31): The compound or salt of any one of embodiments 1 to 21 or any one of embodiments 28 to 30, wherein $R^2$ is selected from $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (32): The compound or salt of any one of embodiments 1 to 21 or any one of embodiments 28 to 31, wherein $R^2$ is selected from $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, and —CN. (33): The compound or salt of any one of embodiments 1 to 21 or any one of embodiments 28 to 32, wherein $R^2$ is selected from $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (34): The compound or salt of any one of embodiments 1 to 21 or any one of embodiments 28 to 33, wherein $R^2$ is selected from $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$; and $C_{3-10}$ carbocycle and 3- to 10-membered heterocycle, each of which is optionally substituted with one or more substituents independently selected from F, and —CN. (35): The compound or salt of any one of embodiments 1 to 21 or any one of embodiments 28 to 34, wherein $R^2$ is selected from $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (36): The compound or salt of any one of embodiments 1 to 21 or any one of embodiments 28 to 35, wherein $R^2$ is selected from $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (37): The compound or salt of any one of embodiments 1 to 21 or embodiments 28 to 36, wherein $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$. (38): The compound or salt of any one of embodiments 1 to 34, wherein $R^2$ is a substituent represented by the following:

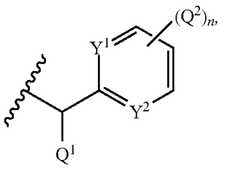

wherein, $Q^1$ is a $C_{1-3}$ alkyl optionally substituted with one or more substituents selected from OH and halo; $Y^1$ and $Y^2$ are each independently selected from N and $C(Q^3)$; and each $Q^2$ is independently selected from halo and CN; each $Q^3$ is independently selected from hydrogen, halo and CN; and n is 0, 1, or 2. (39): The compound or salt of embodiments 1 to 34 or embodiment 38, wherein $Q^1$ is a $C_1$ alkyl optionally substituted with one or more substituents selected from OH and fluoro; each $Q^2$ is independently selected from fluoro and CN; and each $Q^3$ is independently selected from hydrogen, fluoro and CN. (40): The compound or salt of any one of embodiments 1 to 36, wherein $R^2$ is selected from

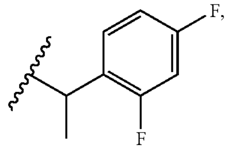 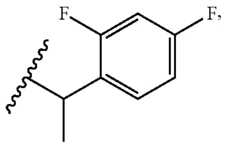

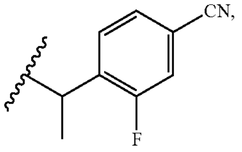 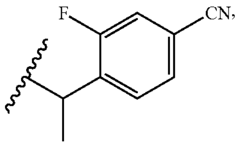

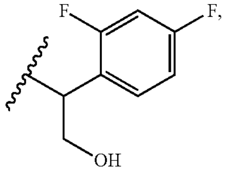 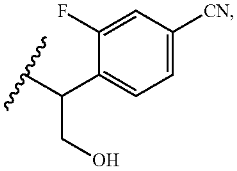

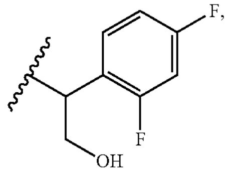 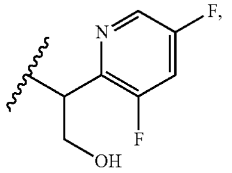

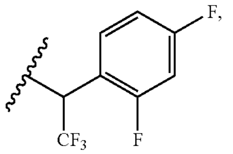 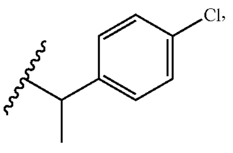

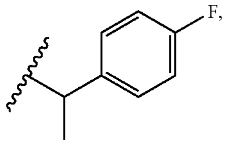 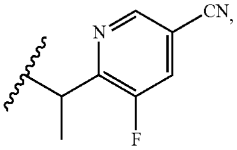

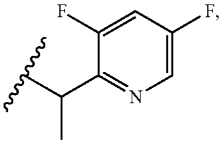 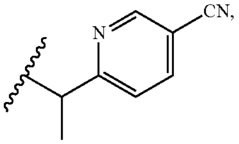

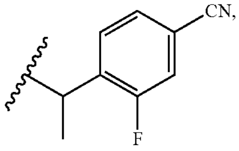 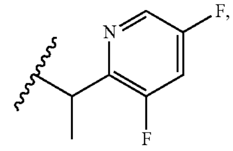

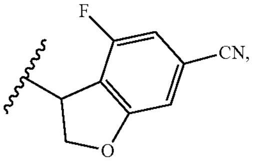 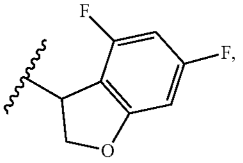 and

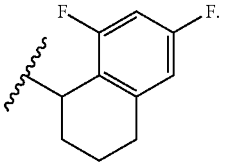

(41): The compound or salt of any one of embodiments 1 to 36, wherein $R^2$ is selected from

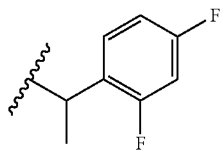

and

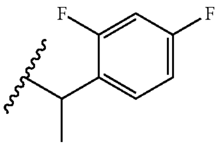

(42): The compound or salt of any one of embodiments 1 to 36, wherein $R^2$ is selected from

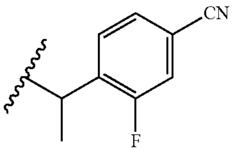

and

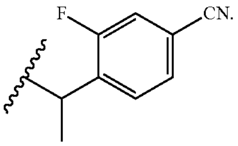

(43): The compound or salt of any one of embodiments 1 to 36, wherein $R^2$ is selected from

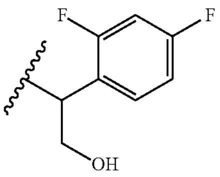

and

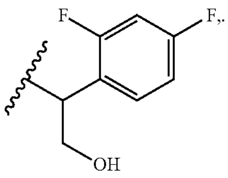

(44): The compound or salt of any one of embodiments 1 to 36, wherein $R^2$ is selected from

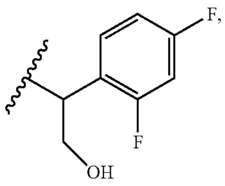

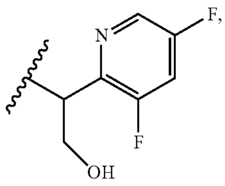

and

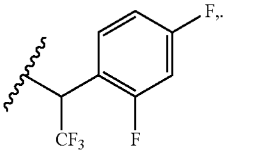

(45): The compound or salt of any one of embodiments 1 to 36, wherein $R^2$ is selected from,

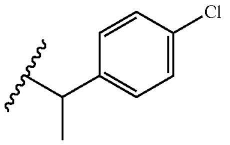

and

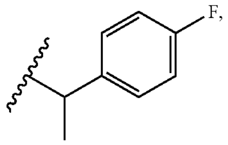

(46): The compound or salt of any one of embodiments 1 to 36, wherein $R^2$ is selected from

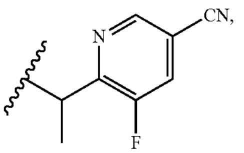

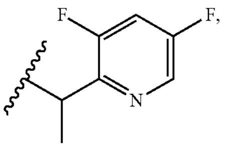

and

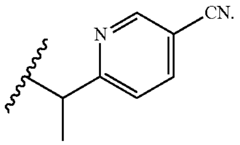

(47): The compound or salt of any one of embodiments 1 to 36, wherein $R^2$ is selected from

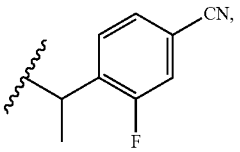

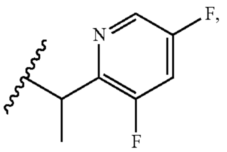

and

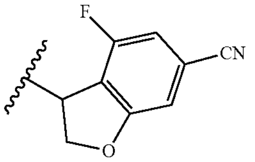

(48): The compound or salt of any one of embodiments 1 to 36, wherein $R^2$ is selected from

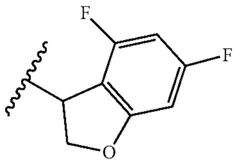

and

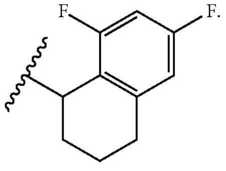

(49): The compound or salt of any one of embodiments 1 to 36, wherein $R^2$ is selected from

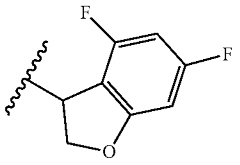

and

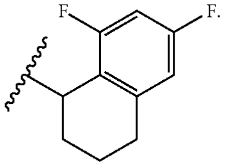

(50): The compound or salt of any one of embodiments 1 to 49, wherein $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (51): The compound or salt of any one of embodiments 1 to 50, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (52): The compound or salt of any one of embodiments 1 to 51, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. (53): The compound or salt of any one of embodiments 1 to 52, wherein $R^5$ and $R^6$ are each independently selected from: hydrogen and $C_{1-3}$ alkyl. (54): The compound or salt of any one of embodiments 1 to 53, wherein $R^5$ and $R^6$ are each independently selected from: hydrogen and methyl. (55): The compound or salt of any one of embodiments 1 to 54, wherein $R^7$ is selected from hydrogen and $C_{1-6}$ alkyl optionally substituted with one or more substituents independently selected from halogen. (56): The compound or salt of any one of embodiments 1 to 55, wherein $R^7$ is selected from hydrogen. (57): The compound or salt of any one of embodiments 1 to 56, wherein $R^8$ is selected from: hydrogen; and $C_{1-6}$ alkyl optionally substituted with one or more substituents independently selected from halogen, —$OR^{10c}$, —$SR^{10c}$, —$N(R^{10e})_2$, —$NO_2$, —CN, $C_{3-10}$ carbocycle, and 3- to 10-membered heterocycle. (58): The compound or salt of any one of embodiments 1 to 57, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. (59): The compound or salt of any one of embodiments 1 to 58, wherein $R^8$ is selected from hydrogen. (60): The compound or salt of any one of embodiments 1 to 59, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN. (61): The compound or salt of any one of embodiments 1 to 60, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. (62): The compound or salt of any one of embodiments 1 to 61, wherein each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN. (63): The compound or salt of any one of embodiments 1 to 62, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (64): The compound or salt of any one of embodiments 1 to 63, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (65): The compound or salt of any one of embodiments 1 to 64, wherein each $R^{9b}$ is independently selected from halogen and —CN. (66): The compound or salt of any one of embodiments 1 to 65, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$NO_2$, =O, and —CN. (67): The compound or salt of any one of embodiments 1 to 66, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from halogen, —$OR^{10c}$, —$SR^{10c}$, —$N(R^{10c})_2$, —$C(O)R^{10c}$, —$NO_2$, =O, and —CN. (68): The compound or salt of any one of embodiments 1 to 67, wherein each $R^{10a}$ is independently selected from hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{3-10}$ carbocycle, 3- to 10-membered heterocycle, and $C_{1-6}$ haloalkyl. (69): The compound or salt of any one of embodiments 1 to 68, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, and —$NH(C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, —$NH(C_{1-6}$ alkyl), $C_{1-6}$ alkyl, and $C_{1-6}$ haloalkyl. (70): The compound or salt of any one of embodiments 1 to 69, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, and =O; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —$N(C_{1-6}$ alkyl$)_2$, —$NH(C_{1-6}$ alkyl), $C_{1-6}$ alkyl, and $C_{1-6}$ haloalkyl. (71): The compound or salt of any one of embodiments 1 to 70, wherein each $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. (72): The compound or salt of any one of embodiments 1 to 71, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, and —$NH(C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{1-6}$ haloalkyl. (73): The compound or salt of any one of embodiments 1 to 72, wherein each $R^{10b}$ is independently selected from: hydrogen; and $C_{1-6}$ alkyl. (74): The compound or salt of any one of embodiments 1 to 73, wherein each $R^{10b}$ is hydrogen. (75): The compound or salt of any one of embodiments 1 to 74, wherein each $R^{10}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (76): The compound or salt of any one of embodiments 1 to 75, wherein each $R^{10}$ is independently selected from: hydrogen; and $C_{1-6}$ alkyl. (77): The compound or salt of any one of embodiments 1 to 76, wherein each $R^{10}$ is hydrogen. (78): The compound or salt of any one of embodiments 1 to 77, wherein each $R^{10a}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (79): The compound or salt of any one of embodiments 1 to 78, wherein each $R^{10a}$ is independently selected from: hydrogen; and $C_{1-6}$ alkyl. (80): The compound or salt of any one of embodiments 1 to 79, wherein each $R^{10d}$, is hydrogen. (81): The compound or salt of any one of embodiments 1 to 80, wherein each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (82): The compound or salt of any one of embodiments 1 to 81, wherein each $R^{10e}$ is independently selected from: hydrogen; and $C_{1-6}$ alkyl. (83): The compound or salt of any one of embodiments 1 to 82, wherein each $R^{10e}$ is hydrogen. (84): The compound or salt of any one of embodiments 1 to 83, wherein if $X^3$ and $X^1$ are both N, then $R^8$ is selected from hydrogen and $C_{1-4}$ alkyl optionally substituted with one or more substituents independently selected from halogen, —$OR^{10}$, and —CN. (85): The compound or salt of any one of embodiments 1 to 84, wherein if $X^3$ and $X^1$ are both N, then $R^8$ is selected from hydrogen and $C_{1-4}$ alkyl optionally substituted with one or more substituents independently selected from fluoro, —OH, and —CN. (86): The compound or salt of any one of embodiments 1 to 85, wherein if $X^3$ and $X^1$ are both N, then $R^8$ is selected from hydrogen and $C_{1-4}$ alkyl. (87): The compound or salt of any one of embodiments 1 to 86, wherein if $X^3$ and $X^1$ are both N, then $R^8$ is selected from hydrogen and $C_1$ alkyl. (88): The compound or salt of any one of embodiments 1 to 87, wherein if $X^3$ and $X^1$ are both N, then $R^8$ is selected from hydrogen. (89): The compound or salt of any one of embodiments 1 to 88, wherein the compound or salt is selected (90): The compound or salt of any one of embodiments 1 to 88, wherein the compound or salt is selected (91): The compound or salt of any one of embodiments 1 to 88, wherein the compound or salt is selected (92): A compound represented by Formula (II):

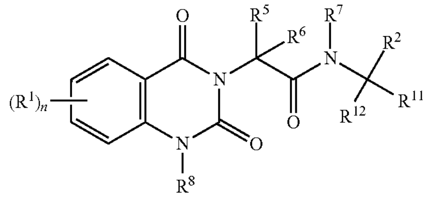

(II); or a salt thereof, wherein: n is 0, 1, 2, 3, or 4; each $R^1$ is independently selected from: halogen, —$NO_2$, —CN, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —N($R^{10a}$)C(O)N($R^{10a}$)$_2$, —OC(O)N($R^{10a}$)$_2$, —N($R^{10a}$)C(O)O$R^{10a}$, —S(O)$R^{10a}$, —S(O)$_2R^{10a}$, —$NO_2$, =O, =S, =N($R^{10a}$), —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: halogen, —$NO_2$, —CN, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —$NO_2$, =O, =S, =N($R^{10b}$), —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b}$; $R^5$ and $R^6$ are each independently selected from: hydrogen, halogen, —$OR^{10d}$, —$SR^{10d}$, —N($R^{10d}$)$_2$, —$NO_2$, and —CN; and $C_{1-6}$ alkyl optionally substituted with one or more substituents independently selected from halogen, —$OR^{10d}$, —$SR^{10d}$, —$N(R^{10d})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$; $R^7$ is selected from: hydrogen and $C_{1-6}$ alkyl optionally substituted with one or more substituents independently selected from halogen, —$OR^{10e}$, —$SR^{10e}$, —$N(R^{10e})_2$, —$NO_2$, and —CN; $R^8$ is selected from: hydrogen and $C_{1-6}$ alkyl optionally substituted with one or more substituents independently selected from halogen, —$OR^{10f}$, —$SR^{10f}$, —$N(R^{10f})_2$, —$NO_2$, and —CN; $R^{11}$ is selected from: halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, and —$S(O)_2R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =S, =$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$; $R^{12}$ is selected from hydrogen; $C_{1-6}$ alkyl optionally substituted with one or more substituents independently selected from the group consisting of halogen, CN, OH, $OR^{10h}$, —$N(R^{10h})_2$, $NO_2$, $C(O)R^{10h}$, —$SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, —$N(R^{10h})_2$, $NO_2$, —$C(O)R^{10h}$, —$SR^{10h}$, and $S(O)R^{10h}$; or $R^{12}$, $R^{11}$, and $R^2$ come together to form a $C_5$-$C_{10}$ bridged ring system; each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; each $R^{9b'}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; each $R^{9c}$ is independently selected from: halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —OC(O)N(Roc)$_2$°—$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; each $R^{9d}$ is independently selected from: halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, and —CN; each $R^{9g}$ is independently selected from: halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10}$ g$)_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, and —CN; each $R^{10a}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; each R$^{10c}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; each R$^{10a}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$haloalkyl; each R$^{10e}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; each R$^{10f}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; each R$^{10g}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; and each R$^{10h}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH (C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl. (93): The compound or salt of embodiment 92, wherein n is 0, 1, or 2. (94): The compound or salt of any one of embodiments 92 to 93, wherein n is 0. (95): The compound or salt of any one of embodiments 92 to 94, wherein n is 1 or 2. (96): The compound or salt of any one of embodiments 92 to 95, wherein n is 1. (97): The compound or salt of any one of embodiments 92 to 96, wherein n is 2. (98): The compound or salt of any one of embodiments 92 to 97, wherein each R$^1$ is independently selected from: halogen, —NO$_2$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, and —OC(O)R$^{10a}$; C$_{1-6}$ alkyl, C$_{2-6}$ alkenyl, and C$_{2-6}$ alkynyl, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —NO$_2$, =O, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$; and C$_{3-10}$ carbocycle and 3- to 10-membered heterocycle, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —NO$_2$, =O, —CN, C$_{1-6}$ alkyl, and C$_{2-6}$ alkenyl, wherein C$_{1-6}$ alkyl, and C$_{2-6}$ alkenyl, are each optionally substituted with one or more R$^{9a}$. (99): The compound or salt of any one of embodiments 92 to 98, wherein each R$^1$ is independently selected from: halogen, —NO$_2$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, and —OC(O)R$^{10a}$; C$_{1-6}$ alkyl and C$_{2-6}$ alkenyl each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —NO$_2$, =O, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$; and C$_{3-10}$ carbocycle and 3- to 10-membered heterocycle, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —NO$_2$, =O, —CN, C$_{1-6}$ alkyl, and C$_{2-6}$ alkenyl, wherein C$_{1-6}$ alkyl, and C$_{2-6}$ alkenyl, are each optionally substituted with one or more R$^{9a}$. (100): The compound or salt of any one of embodiments 92 to 99, wherein each R$^1$ is independently selected from: halogen, —NO$_2$, —CN, —OR$^{10a}$, —SR$^{10a}$, —N(R$^{10a}$)$_2$, and —C(O)R$^{10a}$; C$_{1-6}$ alkyl and C$_{2-6}$ alkenyl each of which is optionally substituted with one or more substituents independently selected from halogen, —OR$^{10a}$, —SR$^{10a}$, —N(R$^{10a}$)$_2$, —C(O)R$^{10a}$, —NO$_2$, =O, —CN, C$_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$NO_2$, =O, —CN, $C_{1-6}$ alkyl, and $C_{2-6}$ alkenyl, wherein $C_{1-6}$ alkyl, and $C_{2-6}$ alkenyl, are each optionally substituted with one or more $R^{9a}$. (101): The compound or salt of any one of embodiments 92 to 100, wherein each $R^1$ is independently selected from: halogen, —$NO_2$, —CN, —$OR^{10a}$, —$SR^{10a}$, —$N(R^{10a})_2$, and —$C(O)R^{10a}$; $C_{1-6}$ alkyl and $C_{2-6}$ alkenyl each of which is optionally substituted with one or more substituents independently selected from halogen, —$OR^{10a}$, —$SR^{10a}$, —$N(R^{10a})_2$, —$C(O)R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle. (102): The compound or salt of any one of embodiments 92 to 101, wherein each $R^1$ is independently selected from: halogen, —$NO_2$, —CN, —$OR^{10a}$, —$SR^{10a}$, —$N(R^{10a})_2$, and —$C(O)R^{10a}$; and $C_{1-6}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (103): The compound or salt of any one of embodiments 92 to 102, wherein each $R^1$ is independently selected from: halogen, —$NO_2$, —CN, —$OR^{10a}$, —$SR^{10a}$, —$N(R^{10a})_2$, and —$C(O)R^{10a}$; and $C_{1-6}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (104): The compound or salt of any one of embodiments 92 to 103, wherein each $R^1$ is independently selected from: halogen, —$NO_2$, —CN, —$OR^{10a}$, —$SR^{10a}$, —$N(R^{10a})_2$, and —$C(O)R^{10a}$; and $C_{1-6}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. (105): The compound or salt of any one of embodiments 92 to 104, wherein each $R^1$ is independently selected from: halogen, —$NO_2$, —CN, —$OR^{10a}$, —$SR^{10a}$, —$N(R^{10a})_2$, and —$C(O)R^{10a}$; and $C_{1-6}$ alkyl. (106): The compound or salt of any one of embodiments 92 to 105, wherein each $R^1$ is independently selected from: halogen, —$NO_2$, —CN, —$OR^{10a}$, —$SR^{10a}$, and —$N(R^{10a})_2$. (107): The compound or salt of any one of embodiments 92 to 106, wherein each $R^1$ is independently selected from: halogen and —CN. (108): The compound or salt of any one of embodiments 92 to 107, wherein each $R^1$ is independently selected from: fluoro, bromo, and —CN. (109): The compound or salt of any one of embodiments 92 to 108, wherein $R^2$ is selected from: halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, and —$OC(O)R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (110): The compound or salt of any one of embodiments 92 to 109, wherein $R^2$ is selected from: halogen, —$NO_2$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, and —$OC(O)R^{10b}$; $C_{1-6}$ alkyl and $C_{2-6}$ alkenyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (111): The compound or salt of any one of embodiments 92 to 110, wherein $R^2$ is selected from: halogen, —$NO_2$, —CN, —$OR^{10b}$, —$SR^{10b}$, and —$N(R^{10b})_2$; $C_{1-6}$ alkyl and $C_{2-6}$ alkenyl, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (112): The compound or salt of any one of embodiments 92 to 111, wherein $R^2$ is selected from: halogen, —$NO_2$, —CN, —$OR^{10b}$, —$SR^{10b}$, and —$N(R^{10b})_2$; $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (113): The compound or salt of any one of embodiments 92 to 112, wherein $R^2$ is selected from: halogen, —$NO_2$, —CN, —$OR^{10b}$, —$SR^{10b}$, and —$N(R^{10b})_2$; $C_{1-6}$ alkyl, optionally substituted with one or more —$OR^{10b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (114): The compound or salt of any one of embodiments 92 to 113, wherein $R^2$ is selected from: halogen, —$NO_2$, —CN, —$OR^{10b}$, —$SR^{10b}$, and —$N(R^{10b})_2$; $C_{1-6}$ alkyl; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (115): The compound or salt of any one of embodiments 92 to 114, wherein $R^2$ is selected from: $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (116): The compound or salt of any one of embodiments 92 to 115, wherein $R^2$ is selected from: $C_{3-10}$ carbocycle and 3- to 10-membered heterocycle, each of which is optionally substituted with one or more substituents independently selected from halogen, —$OR^{10b}$, —CN, $C_{1-6}$ alkyl, and $C_{2-6}$ alkenyl, wherein $C_{1-6}$ alkyl and $C_{2-6}$ alkenyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (117): The compound or salt of any one of embodiments 92 to 116, wherein $R^2$ is selected from: $C_{3-10}$ carbocycle and 3- to 10-membered heterocycle, each of which is optionally substituted with one or more substituents independently selected from halogen, —$OR^{10b}$, —CN, and $C_{1-6}$ alkyl, wherein $C_{1-6}$ alkyl is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (118): The compound or salt of any one of embodiments 92 to 117, wherein $R^2$ is selected from: $C_{3-10}$ carbocycle and 3- to 10-membered heterocycle, each of which is optionally substituted with one or more substituents independently selected from fluoro, bromo, —$OR^{10b}$, —CN, and $C_{1-6}$ alkyl, wherein $C_{1-6}$ alkyl is optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (119): The compound or salt of any one of embodiments 92 to 118, wherein $R^2$ is selected from: $C_{3-10}$ carbocycle and 3- to 10-membered heterocycle, each of which is optionally substituted with one or more substituents independently selected from fluoro, bromo, —OMe, —CN, and $C_{1-6}$ alkyl, wherein $C_{1-6}$ alkyl is optionally substituted with one or more $R^{9b}$. (120): The compound or salt of any one of embodiments 92 to 119, wherein $R^2$ is selected from: $C_{3-10}$ carbocycle and 3- to 10-membered heterocycle, each of which is optionally substituted with one or more substituents independently selected from fluoro, bromo, —OMe, —CN, and $C_{1-6}$ alkyl, wherein $C_{1-6}$ alkyl is optionally substituted with one or more fluoro. (121): The compound or salt of any one of embodiments 92 to 120, wherein $R^2$ is selected from: $C_{3-10}$ carbocycle and 3- to 10-membered heterocycle, each of which is optionally substituted with one or more substituents independently selected from fluoro, bromo, —OMe, —CN, and $C_1$ alkyl, wherein $C_1$ alkyl is optionally substituted with one or more fluoro. (122): The compound or salt of any one of embodiments 92 to 121, wherein $R^2$ is selected from phenyl, pyridyl, and pyrimidyl, wherein each phenyl, pyridyl, and pyrimidyl is optionally substituted with one or more substituents independently selected from fluoro, bromo, —OMe, —CN, and $C_1$ alkyl, wherein each $C_1$ alkyl is optionally substituted with one or more fluoro. (123): The compound or salt of any one of embodiments 92 to 122, wherein $R^2$ is selected from phenyl, 2-pyridyl, 2-pyrimidyl, and 6-pyrimidyl, wherein each phenyl, 2-pyridyl, 2-pyrimidyl, and 6-pyrimidyl is optionally substituted with one or more substituents independently selected from fluoro, bromo, —OMe, —CN, and $C_1$ alkyl, wherein each $C_1$ alkyl is optionally substituted with one or more fluoro. (124): The compound or salt of any one of embodiments 92 to 123, wherein $R^2$ is selected from

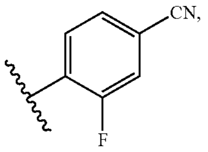
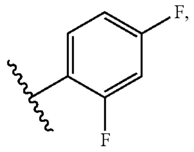
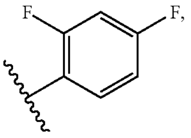
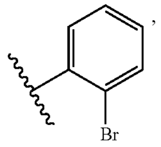
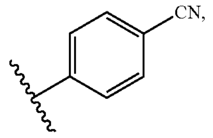
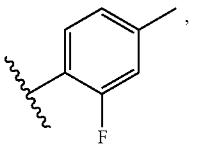
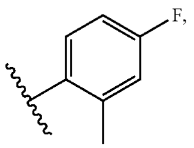
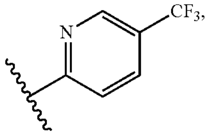
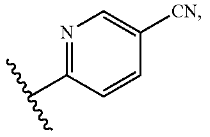
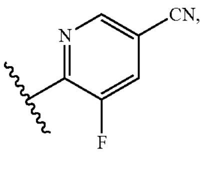
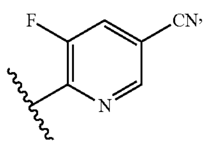

-continued

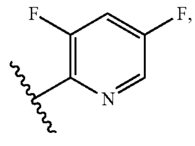 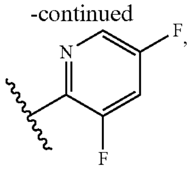 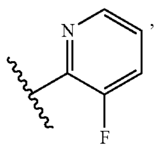

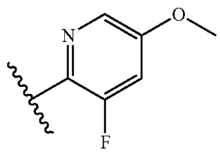, 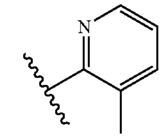, 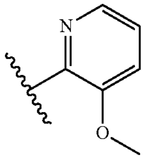,

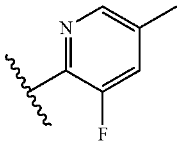, 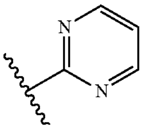, and 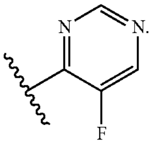

(125): The compound or salt of any one of embodiments 92 to 118, wherein $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$. (126): The compound or salt of any one of embodiments 92 to 118 or any one of embodiments 125, wherein $R^2$ together with $R^{11}$ form a 3- to 10-membered heterocycle or $C_{3-10}$ carbocycle, and wherein the 3- to 10-membered heterocycle or $C_{3-10}$ carbocycle is optionally substituted with one or more fluoro or CN. (127): The compound or salt of any one of embodiments 92 to 118 or any one of embodiments 125 to 126, wherein $R^2$ together with $R^{11}$ form a $C_{3-10}$ carbocycle or 3- to 10-membered heterocycle selected from dihydrobenzofuran and indene, each of which is optionally substituted with one or more substituents independently selected from fluoro and CN. (128): The compound or salt of any one of embodiments 92 to 118 or any one of embodiments 125 to 127, wherein $R^{12}$ is H and $R^2$ together with $R^{11}$ is selected from

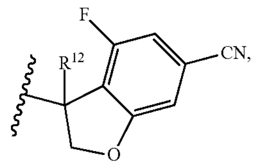 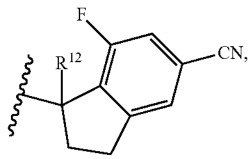 and

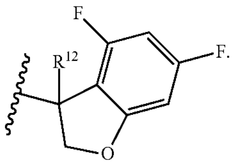

(129): The compound or salt of any one of embodiments 92 to 118, wherein $R^2$ is selected from

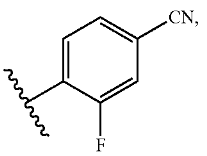 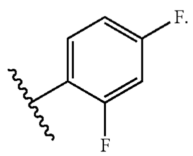

(130): The compound or salt of any one of embodiments 92 to 118, wherein $R^2$ is selected from

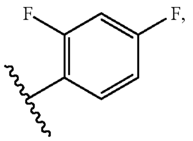 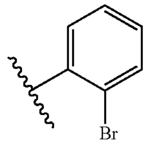

(131): The compound or salt of any one of embodiments 92 to 118, wherein $R^2$ is selected from

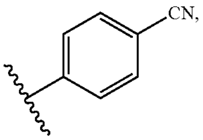 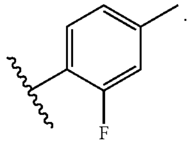

(132): The compound or salt of any one of embodiments 92 to 118, wherein $R^2$ is selected from

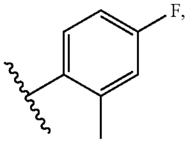 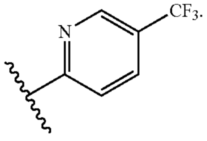

(133): The compound or salt of any one of embodiments 92 to 118, wherein $R^2$ is selected from,

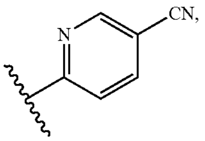 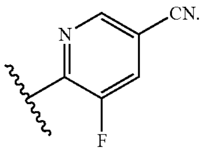

(134): The compound or salt of any one of embodiments 92 to 118, wherein $R^2$ is selected from

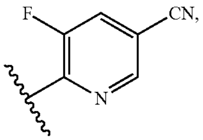 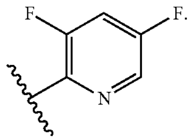

(135): The compound or salt of any one of embodiments 92 to 118, wherein $R^2$ is selected from

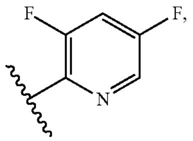 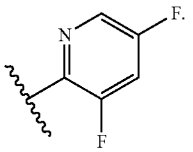

(136): The compound or salt of any one of embodiments 92 to 135, wherein $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. (137): The compound or salt of any one of embodiments 92 to 136, wherein $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl; or $R^5$ together with $R^6$ form a 3- to 10-membered heterocycle or $C_{3-10}$ carbocycle. (138): The compound or salt of any one of embodiments 92 to 137, wherein $R^5$ and $R^6$ are each independently selected from: hydrogen, halogen, —$OR^{10d}$, —$SR^{10d}$, —$N(R^{10d})_2$, —$NO_2$, and —CN; and $C_{1-6}$ alkyl. (139): The compound or salt of any one of embodiments 92 to 138, wherein $R^5$ and $R^6$ are each independently selected from: hydrogen, halogen, —$OR^{10d}$, —$SR^{10d}$, —$N(R^{10d})_2$, —$NO_2$, and —CN. (140): The compound or salt of any one of embodiments 92 to 139, wherein $R^5$ and $R^6$ are hydrogen. (141): The compound or salt of any one of embodiments 92 to 137, wherein $R^5$ and $R^6$ are each independently selected from: hydrogen; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. (142): The compound or salt of any one of embodiments 92 to 137 or embodiment 141, wherein $R^5$ and $R^6$ are each independently selected from: hydrogen; or $R^5$ together with $R^6$ form a 3- to 10-membered heterocycle or $C_{3-10}$ carbocycle. (143): The compound or salt of any one of embodiments 92 to 142, wherein $R^7$ is selected from: hydrogen, and $C_{1-3}$ alkyl. (144): The compound or salt of any one of embodiments 92 to 143, wherein $R^7$ is selected from: hydrogen. (145): The compound or salt of any one of embodiments 92 to 144, wherein $R^8$ is selected from: hydrogen and $C_{1-3}$ alkyl. (146): The compound or salt of any one of embodiments 92 to 145, wherein $R^8$ is selected from: hydrogen. (147): The compound or salt of any one of embodiments 92 to 146, wherein $R^{11}$ is selected from: halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, and —$OC(O)R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{98}$. (148): The compound or salt of any one of embodiments 92 to 147, wherein $R^{11}$ is selected from: halogen, —$NO_2$, —CN, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, and —$OC(O)R^{10g}$; and $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (149): The compound or salt of any one of embodiments 92 to 148, wherein $R^{11}$ is selected from: halogen, —$NO_2$, —CN, —$OR^{10g}$, —$SR^{10g}$, and —$N(R^{10g})_2$; and $C_{1-6}$ alkyl optionally substituted with one or more substituents independently selected from halogen, —$OR^{10g}$, —$SR^{10g}$, —$N(R^{10g})_2$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{98}$. (150): The compound or salt of any one of embodiments 92 to 149, wherein $R^{11}$ is selected from: halogen, —$NO_2$, —CN, —$OR^{10g}$, —$SR^{10g}$, and —$N(R^{10g})_2$; and $C_{1-6}$ alkyl optionally substituted with one or more substituents independently selected from halogen, —$OR^{10g}$, —$SR^{10g}$, —$N(R^{10g})_2$, —$NO_2$, =O, and —CN. (151): The compound or salt of any one of embodiments 92 to 146, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =O, =S, =$N(R^{10g})$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$. (152): The compound or salt of any one of embodiments 92 to 146 or embodiment 151, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (153): The compound or salt of any one of embodiments 92 to 146 or any one of embodiments 151 to 152, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, =O, —CN, and $C_{3-10}$ carbocycle and 3- to 10-membered heterocycle, wherein the $C_{3-10}$ carbocycle and 3- to 10-membered heterocycle are each optionally substituted with one or more $R^{9g}$. (154): The compound or salt of any one of embodiments 92 to 146 or any one of embodiments 151 to 153, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, =O, —CN, and $C_{3-10}$ carbocycle and 3- to 10-membered heterocycle. (155): The compound or salt of any one of embodiments 92 to 146 or any one of embodiments 151 to 154, wherein $R^{11}$ is selected from: $C_{1-6}$ alkyl optionally substituted with one or more substituents independently selected from halogen, —$OR^{10g}$, —$SR^{10g}$, —$N(R^{10g})_2$, —$C(O)R^{10g}$, —$NO_2$, =O, and —CN. (156): The compound or salt of any one of embodiments 92 to 146 or any one of embodiments 151 to 155, wherein $R^{11}$ is selected from: $C_{1-3}$ alkyl optionally substituted with one or more substituents independently selected from halogen and —$OR^{10g}$. (157): The compound or salt of any one of embodiments 92 to 146 or any one of embodiments 151 to 156, wherein $R^{11}$ is selected from: $C_{1-3}$ alkyl optionally substituted with one or more —$OR^{10g}$. (158): The compound or salt of any one of embodiments 92 to 146 or any one of embodiments 151 to 157, wherein $R^{11}$ is selected from: $C_{1-3}$ alkyl optionally substituted with one or more —OH. (159): The compound or salt of any one of embodiments 92 to 158, wherein $R^{12}$ is selected from hydrogen; $C_{1-6}$ alkyl optionally substituted with one or more substituents independently selected from the group consisting of halogen, CN, OH, $OR^{10h}$, —$N(R^{10h})_2$, $NO_2$, —$C(O)R^{10h}$, —$SR^{10h}$, and $S(O)R^{10h}$; and $C_{3-6}$ carbocycle and 3- to 10-membered heterocycle each optionally substituted with one or more substituents independently selected from the group consisting of halogen, CN, OH, $OR^{10h}$, —$N(R^{10h})_2$, $NO_2$, —$C(O)R^{10h}$, —$SR^{10h}$, and $S(O)R^{10h}$. (160): The compound or salt of any one of embodiments 92 to 159, wherein $R^{12}$ is selected from hydrogen; and $C_{1-6}$ alkyl optionally substituted with one or more substituents independently selected from the group consisting of halogen, CN, OH, $OR^{10h}$, —$N(R^{10h})_2$, $NO_2$, —$C(O)R^{10h}$, and $SR^{10h}$. (161): The compound or salt of any one of embodiments 92 to 160, wherein $R^{12}$ is selected from hydrogen; and $C_{1-6}$ alkyl. (162): The compound or salt of any one of embodiments 92 to 161, wherein $R^{12}$ is hydrogen. (163): The compound or salt of any one of embodiments 92 to 158, wherein $R^{12}$, $R^{11}$, and $R^2$ come together to form a $C_5$-$C_{10}$ bridged ring system. (164): The compound or salt of any one of embodiments 92 to 158 or embodiment 163, wherein $R^{12}$, $R^{11}$, and $R^2$ come together to form a $C_5$-$C_{10}$ bridged ring system selected from [1.1.1]bicyclopentane. (165): The compound or salt of any one of embodiments 92 to 164, wherein each $R^{9a}$ is independently selected from: halogen, —$OR^{10a}$, —$SR^{10a}$, —$N(R^{10a})_2$, —$C(O)R^{10a}$, —$NO_2$, =O, —CN; and $C_{1-3}$ alkyl, optionally substituted with one or more substituents independently selected from halogen, —$OR^{10a}$, —$SR^{10a}$, —$N(R^{10a})_2$, —$C(O)R^{10a}$, —$NO_2$, =O, and —CN. (166): The compound or salt of any one of embodiments 92 to 165, wherein each $R^{9a}$ is independently selected from: halogen, —$NO_2$, =O, —CN; and $C_{1-3}$ alkyl, optionally substituted with one or more substituents independently selected from halogen, —$NO_2$, =O, and —CN. (167): The compound or salt of any one of embodiments 92 to 166, wherein each $R^{9b}$ is independently selected from: halogen, —$OR^{10b}$, —$SR^{10b}$, —$N(R^{10b})_2$, —$C(O)R^{10b}$, —$NO_2$, =O, —CN; and $C_{1-3}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, and —CN. (168): The compound or salt of any one of embodiments 92 to 167, wherein each $R^{9b}$ is independently selected from: halogen, —$NO_2$, =O, —CN; and $C_{1-3}$ alkyl, optionally substituted with one or more substituents independently selected from halogen, —$NO_2$, =O, and —CN. (169): The compound or salt of any one of embodiments 92 to 168, wherein each $R^{9b}$ is independently selected from: halogen. (170): The compound or salt of any one of embodiments 92 to 169, wherein each $R^{9b}$ is independently selected from: fluoro. (171): The compound or salt of any one of embodiments 92 to 170, wherein each $R^{9b'}$ is independently selected from: halogen, —$OR^{10b}$, —$SR^{10b}$, —$N(R^{10b})_2$, —$C(O)R^{10b}$, —$NO_2$, =O, —CN; and $C_{1-3}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, and —CN. (172): The compound or salt of any one of embodiments 92 to 171, wherein each $R^{9b'}$ is independently selected from: halogen, —$NO_2$, =O, —CN; and $C_{1-3}$ alkyl, optionally substituted with one or more substituents independently selected from halogen, —$NO_2$, =O, and —CN. (173): The compound or salt of any one of embodiments 92 to 172, wherein each $R^{9b'}$ is independently selected from: halogen and CN. (174): The compound or salt of any one of embodiments 92 to 173, wherein each $R^{9b'}$ is independently selected from: fluoro and CN. (175): The compound or salt of any one of embodiments 92 to 174, wherein each $R^{9c}$ is independently selected from: halogen, —$OR^{10c}$, —$SR^{10c}$, —$N(R^{10c})_2$, —$C(O)R^{10c}$, —$NO_2$, =O, —CN; and $C_{1-3}$ alkyl, optionally substituted with one or more substituents independently selected from halogen, —$OR^{10c}$, —$SR^{10c}$, —$N(R^{10c})_2$, —$C(O)R^{10c}$, —$NO_2$, =O, and —CN. (176): The compound or salt of any one of embodiments 92 to 175, wherein each $R^{9c}$ is independently selected from: halogen, —$NO_2$, =O, —CN; and $C_{1-3}$ alkyl, optionally substituted with one or more substituents independently selected from halogen, —$NO_2$, =O, and —CN. (177): The compound or salt of any one of embodiments 92 to 176, wherein each $R^{9d}$ is independently selected from: halogen, —$OR^{10d}$, —$SR^{10d}$, —$N(R^{10d})_2$, —$C(O)R^{10d}$, —$NO_2$, =O, —CN; and $C_{1-3}$ alkyl, optionally substituted with one or more substituents independently selected from halogen, —$OR^{10d}$, —$SR^{10d}$, —$N(R^{10d})_2$, —$C(O)R^{10d}$, —$NO_2$, =O, and —CN. (178): The compound or salt of any one of embodiments 92 to 177, wherein each $R^{9d}$ is independently selected from: halogen, —$NO_2$, =O, —CN; and $C_{1-3}$ alkyl, optionally substituted with one or more substituents independently selected from halogen, —$NO_2$, =O, and —CN. (179): The compound or salt of any one of embodiments 92 to 178, wherein each $R^{9g}$ is independently selected from: halogen, —$OR^{10g}$, —$SR^{10g}$, —$N(R^{10g})_2$, —$C(O)R^{10g}$, —$NO_2$, =O, —CN; and $C_{1-3}$ alkyl, optionally substituted with one or more substituents independently selected from halogen, —$OR^{10g}$, —$SR^{10g}$, —$N(R^{10g})_2$, —$C(O)R^{10g}$, —$NO_2$, =O, and —CN. (180): The compound or salt of any one of embodiments 92 to 179, wherein each $R^{9g}$ is independently selected from: halogen, —$NO_2$, =O, —CN; and $C_{1-3}$ alkyl, optionally substituted with one or more substituents independently selected from halogen, —$NO_2$, =O, and —CN. (181): The compound or salt of any one of embodiments 92 to 180, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle. (182): The compound or salt of any one of embodiments 92 to 181, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl); and $C_{3-10}$ carbocycle, and 3- to 10-membered heterocycle. (183): The compound or salt of any one of embodiments 92 to 182, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl). (184): The compound or salt of any one of embodiments 92 to 183, wherein each $R^{10a}$ is independently selected from: hydrogen; and $C_{1-6}$ alkyl. (185): The compound or salt of any one of embodiments 92 to 184, wherein each $R^{10a}$ is independently selected from: hydrogen. (186): The compound or salt of any one of embodiments 92 to 185, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl), $C_{3-10}$ carbocycle, 3- to 10-membered heterocycle; and $C_{3-10}$ carbocycle, and 3- to 10-membered heterocycle. (187): The compound or salt of any one of embodiments 92 to 186, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH($C_{1-6}$ alkyl); and $C_{3-10}$ carbocycle, and 3- to 10-membered heterocycle. (188): The compound or salt of any one of embodiments 92 to 187, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl). (189): The compound or salt of any one of embodiments 92 to 188, wherein each $R^{10b}$ is independently selected from: hydrogen; and $C_{1-6}$ alkyl. (190): The compound or salt of any one of embodiments 92 to 189, wherein each $R^{10b}$ is independently selected from: $C_{1-3}$ alkyl. (191): The compound or salt of any one of embodiments 92 to 190, wherein each $R^{10b}$ is methyl. (192): The compound or salt of any one of embodiments 92 to 191, wherein each $R^{10c}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH ($C_{1-6}$ alkyl), $C_{3-10}$ carbocycle, 3- to 10-membered heterocycle; and $C_{3-10}$ carbocycle, and 3- to 10-membered heterocycle. (193): The compound or salt of any one of embodiments 92 to 192, wherein each $R^{10}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH ($C_{1-6}$ alkyl); and $C_{3-10}$ carbocycle, and 3- to 10-membered heterocycle. (194): The compound or salt of any one of embodiments 92 to 193, wherein each $R^{10c}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —NH ($C_{1-6}$ alkyl). (195): The compound or salt of any one of embodiments 92 to 194, wherein each $R^{10c}$ is independently selected from: hydrogen; and $C_{1-6}$ alkyl. (196): The compound or salt of any one of embodiments 92 to 195, wherein each $R^{10c}$ is hydrogen. (197): The compound or salt of any one of embodiments 92 to 196, wherein each $R^{10a}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle. (198): The compound or salt of any one of embodiments 92 to 197, wherein each $R^{10d}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. (199): The compound or salt of any one of embodiments 92 to 198, wherein each $R^{10d}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl). (200): The compound or salt of any one of embodiments 92 to 199, wherein each $R^{10d}$ is independently selected from: hydrogen; and $C_{1-6}$ alkyl. (201): The compound or salt of any one of embodiments 92 to 200, wherein each $R^{10d}$ is hydrogen. (202): The compound or salt of any one of embodiments 92 to 201, wherein each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle. (203): The compound or salt of any one of embodiments 92 to 202, wherein each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. (204): The compound or salt of any one of embodiments 92 to 203, wherein each $R^{10e}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl). (205): The compound or salt of any one of embodiments 92 to 204, wherein each $R^{10e}$ is independently selected from: hydrogen; and $C_{1-6}$ alkyl. (206): The compound or salt of any one of embodiments 92 to 205, wherein each $R^{10e}$ is hydrogen. (207): The compound or salt of any one of embodiments 92 to 206, wherein each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle. (208): The compound or salt of any one of embodiments 92 to 207, wherein each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. (209): The compound or salt of any one of embodiments 92 to 208, wherein each $R^{10f}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl). (210): The compound or salt of any one of embodiments 92 to 209, wherein each $R^{10f}$ is independently selected from: hydrogen; and $C_{1-6}$ alkyl. (211): The compound or salt of any one of embodiments 92 to 210, wherein each $R^{10f}$ is hydrogen. (212): The compound or salt of any one of embodiments 92 to 211, wherein each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle. (213): The compound or salt of any one of embodiments 92 to 212, wherein each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1-6}$ alkyl); and $C_{3-10}$ carbocycle, and 3- to 10-membered heterocycle. (214): The compound or salt of any one of embodiments 92 to 213, wherein each $R^{10g}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —$N(C_{1-6}$ alkyl$)_2$, —$NH(C_{1}$. 6 alkyl). (215): The compound or salt of any one of embodiments 92 to 214, wherein each $R^{10g}$ is independently selected from: hydrogen; and $C_{1-6}$ alkyl. (216): The compound or salt of any one of embodiments 92 to 215, wherein each $R^{10}$ is hydrogen. (217): The compound or salt of any one of embodiments 92 to 216, wherein each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle. (218): The compound or salt of any one of embodiments 92 to 217, wherein each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (219): The compound or salt of any one of embodiments 92 to 218, wherein each $R^{10h}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl). (220): The compound or salt of any one of embodiments 92 to 219, wherein each $R^{10h}$ is independently selected from: hydrogen; and $C_{1-6}$ alkyl. (221): The compound or salt of any one of embodiments 92 to 220, wherein each $R^{10h}$ is hydrogen. (222): The compound or salt of any one of embodiments 92 to 221, wherein the compound or salt is selected from (223): The compound or salt of any one of embodiments 92 to 221, wherein the compound or salt is selected (224): The compound or salt of any one of embodiments 92 to 221, wherein the compound or salt is selected (225): A compound represented by Formula (II-e):

(II-e)

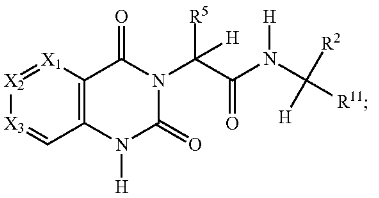

or a salt thereof, wherein: $X_1$ is N or $CR_1$; $X_2$ is N or $CR_1$; and $X_3$ is N or $CR_1$; wherein not all $X_1$, $X_2$, and $X_3$ can be CH at once; each $R^1$ is independently selected from: hydrogen, halogen, —$NO_2$, —CN, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —N($R^{10a}$)C(O)N($R^{10a}$)$_2$, —OC(O)N($R^{10a}$)$_2$, —N($R^{10a}$)C(O)O$R^{10a}$, —S(O)$R^{10a}$, —S(O)$_2R^{10a}$, —$NO_2$, =O, =S, =N($R^{10a}$), —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, =O, =S, =N($R^{10a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: $C_{3-10}$ carbocycle and 3- to 10-membered heterocycle, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; or $R^2$ together with $R^{11}$ form a 3- to 10-membered heterocycle or $C_{3-10}$ carbocycle, wherein the 3- to 10-membered heterocycle or $C_{3-10}$ carbocycle is optionally substituted with one or more $R^{9b'}$; $R^5$ is selected from hydrogen and $C_{1-6}$ alkyl; $R^7$ is selected from: hydrogen and $C_{1-6}$ alkyl optionally substituted with one or more substituents independently selected from halogen, —$OR^{10e}$, —$SR^{10e}$, —N($R^{10e}$)$_2$, —$NO_2$, and —CN; $R^8$ is selected from: hydrogen and $C_{1-6}$ alkyl optionally substituted with one or more substituents independently selected from halogen, —$OR^{10f}$, —$SR^{10f}$, —N($R^{10f}$)$_2$, —$NO_2$, and —CN; $R^{11}$ is selected from: halogen, —$NO_2$, —CN, —$OR^{10g}$, —$SR^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, and —S(O)$_2R^{10g}$; and $C_{1-6}$ alkyl, $C_{2-6}$ alkenyl, and $C_{2-6}$ alkynyl, each of which is optionally substituted with one or more substituents independently selected from halogen, —$OR^{10g}$, —$SR^{10g}$, —N($R^{10g}$)$_2$, —C(O)$R^{10g}$, —C(O)N($R^{10g}$)$_2$, —N($R^{10g}$)C(O)$R^{10g}$, —C(O)O$R^{10g}$, —OC(O)$R^{10g}$, —N($R^{10g}$)C(O)N($R^{10g}$)$_2$, —OC(O)N($R^{10g}$)$_2$, —N($R^{10g}$)C(O)O$R^{10g}$, —S(O)$R^{10g}$, —S(O)$_2R^{10g}$, —$NO_2$, =S, =N($R^{10g}$), —CN, $C_{3-10}$ carbocycle and 3- to 10-membered heterocycle, wherein the $C_{3-10}$ carbocycle and 3- to 10-membered heterocycle are each optionally substituted with one or more $R^{9g}$; each $R^{9b}$ is independently selected from: halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN; each $R^{9b'}$ is independently selected from: halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —$NO_2$, =O, =S, =N($R^{10b}$), and —CN; each $R^{9g}$ is independently selected from: halogen, —$OR^{10g}$, —$SR^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —$NO_2$, =O, =S, =N($R^{10g}$), and —CN; and $C_{1-3}$ alkyl, $C_{2-3}$ alkenyl, and $C_{2-3}$ alkynyl, each of which is optionally substituted with one or more substituents independently selected from halogen, —O$R^{10g}$, —S$R^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —$NO_2$, =O, =S, =N($R^{10g}$), and —CN; each $R^{10a}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10e}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10f}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl; each $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (226): A method of treating cardiovascular disease or a related condition comprising administering to a subject in need thereof a compound or salt of any one of embodiments 1 to 210. (227): A method of treating diastolic dysfunction or a related condition comprising administering to a subject in need thereof a compound or salt of any one of embodiments 1 to 210. (228): A method of treating a condition selected from hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina; the method comprising administering to a subject in need thereof a compound or salt of any one of embodiments 1 to 210. (229): The method of embodiment 227, wherein said heart failure with preserved ejection fraction (HFpEF) comprises one or more disorders selected from disorders of relaxation and disorders of chamber stiffness (diabetic HFpEF). (230): The method of embodiment 227, wherein said left ventricular (LV) hypertrophy is malignant left ventricular (LV) hypertrophy. (231): The method of embodiment 227, wherein said restrictive cardiomyopathy comprises one or more subgroups selected from inflammatory subgroups, infiltrative subgroups, storage subgroups, idiopathic/inherited subgroups, congenital heart disease subgroups. (232): The method of embodiment 229, wherein said inflammatory subgroups comprise one or more subgroups selected from Loefllers and EMF. (233): The method of embodiment 229, wherein said inflammatory subgroups comprise one or more subgroups selected from amyloid, sarcoid, and XRT. (234): The method of embodiment 229, wherein said storage subgroups comprise one or more subgroups selected from hemochromatosis, Fabry, and glycogen storage disease. (235): The method of embodiment 229, wherein said idiopathic/inherited subgroups comprise one or more subgroups selected from Trop I (beta myosin HC), Trop T (alpha cardiac actin), and desmin related subgroups. (236): The method of embodiment 229, wherein said congenital heart disease subgroups comprise one or more subgroups selected from pressure-overloaded RV, Tetralogy of Fallot, and pulmonic stenosis. (237): A method of treating hypertrophic cardiomyopathy or a related condition comprising administering to a subject in need thereof a compound or salt of any one of embodiments 1 to 210. (238): A method of treating obstructive hypertrophic cardiomyopathy comprising administering to a subject in need thereof a compound or salt of any one of embodiments 1 to 210. (239): A method of treating non-obstructive hypertrophic cardiomyopathy comprising administering to a subject in need thereof a compound or salt of any one of embodiments 1 to 210. (240): A method of treating heart failure with preserved ejection fraction comprising administering to a subject in need thereof a compound or salt of any one of embodiments 1 to 210. (241): A method of treating left ventricle stiffness comprising administering to a subject in need thereof a compound or salt of any one of embodiments 1 to 210.

(242): A method of treating a cardiovascular disease or a related condition comprising administering to a subject in need thereof a compound or salt of Formula (III):

(III)

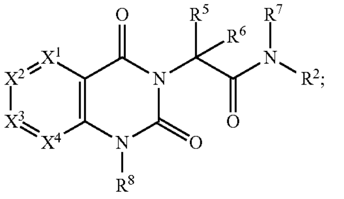

or a salt thereof, wherein $X^1$, $X^2$, $X^3$, and $X^4$ are each independently selected from C(R'), N, and $N^+$(—$O^-$); each $R^1$ is independently selected from: hydrogen; halogen, —$NO_2$, —CN, —$OR^{10a}$, —$SR^{10a}$, —$N(R^{10a})_2$, —C(O)$R^{10a}$, —C(O)$N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, ═O, ═S, ═$N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, ═O, ═S, ═$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, ═O, ═S, ═$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, ═O, ═S, ═$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, $C_{2-6}$ alkenyl, and $C_{2-6}$ alkynyl, any of which is optionally substituted at each occurrence with one or more substituents independently selected from halogen, —$OR^{10c}$, —$SR^{10c}$, —$N(R^{10c})_2$, —$NO_2$, —CN, and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^7$ is selected from: hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN; $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$, —$NO_2$, and —CN; each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, ═O, ═S, ═$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, ═O, ═S, ═$N(R^{10a})$, and —CN; each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, ═O, ═S, ═$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, ═O, ═S, ═$N(R^{10b})$, and —CN; each $R^{9c}$ is independently selected from: halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, ═O, ═S, ═$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, ═O, ═S, ═$N(R^{10c})$, and —CN; each $R^{10a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10e}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$haloalkyl; each $R^{10e}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, $—NO_2$, $—NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (243): The method of embodiment 241, wherein $X^1$, $X^2$, $X^3$, and $X^4$ are each independently selected from C($R^1$) and N. (244): The method of embodiment 241 or 242, wherein one of $X^1$, $X^2$, $X^3$, or $X^4$ is N. (245): The method of embodiment 243, wherein $X^1$ is N. (246): The method of embodiment 243, wherein $X^2$ is N. (247): The method of embodiment 243, wherein $X^3$ is N. (248): The method of embodiment 243, wherein $X^4$ is N. (249): The method of embodiments 241 or 242, wherein two of $X^1$, $X^2$, $X^3$, or $X^4$ is N. (250): The method of embodiment 248, wherein $X^1$ and $X^3$ are N; or $X^2$ and $X^4$ are N. (251): The method of embodiment 248, wherein $X^1$, $X^2$, $X^3$, and $X^4$ are each independently selected from C(R'). (252): The method of any one of embodiments 241 to 250, wherein each $R^1$ is independently selected from: hydrogen; halogen, $—NO_2$, —CN, $—OR^{10a}$, $—SR^{10a}$, $—N(R^{10a})_2$, $—C(O)R^{10a}$, and $—C(O)N(R^{10a})_2$; $C_{1-6}$ alkyl, optionally substituted with one or more substituents independently selected from halogen, $—OR^{10a}$, $—SR^{10a}$, $—N(R^{10a})_2$, $—C(O)R^{10a}$, $—NO_2$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, —CN, $C_{1-6}$ alkyl optionally substituted with one or more $R^{9a}$. (253): The method of any one of embodiments 241 to 251, wherein each $R^1$ is independently selected from: hydrogen; halogen, $—NO_2$, —CN, $—OR^{10a}$, $—SR^{10a}$, $—N(R^{10a})_2$, $—C(O)R^{10a}$, and $—C(O)N(R^{10a})_2$; $C_{1-6}$ alkyl, optionally substituted with one or more substituents independently selected from halogen, $—OR^{10a}$, $—SR^{10a}$, and $—N(R^{10a})_2$; and $C_{3-10}$ carbocycle and 3- to 10-membered heterocycle, each of which is optionally substituted with one or more substituents independently selected from halogen, $—OR^{10a}$, $—SR^{10a}$, and $—N(R^{10a})_2$. (254): The method of any one of embodiments 241 to 252, wherein each $R^1$ is independently selected from: hydrogen; halogen, CN, $—OR^{10a}$, and $—C(O)N(R^{10a})_2$; $C_{1-6}$ alkyl, optionally substituted with one or more substituents independently selected from halogen, and $C_{3-10}$ carbocycle optionally substituted with one or more substituents independently selected from halogen. (255): The method of any one of embodiments 241 to 253, wherein $R^1$ is hydrogen. (256): The method of any one of embodiments 241 to 250, wherein each $R^1$ is independently selected from hydrogen, halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; (257): The method of any one of embodiments 241 to 250 or embodiment 255, wherein each $R^1$ is independently selected from hydrogen, $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$. (258): The method of any one of embodiments 241 to 250 or embodiments 255 to 256, wherein each $R^1$ is independently selected from hydrogen, $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. (259): The method of any one of embodiments 241 to 250 or embodiments 255 to 257, wherein each $R^1$ is independently selected from: hydrogen; halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, and —$NH(C_{1-6}$ alkyl); $C_{1-6}$ alkyl, $C_{2-6}$ alkenyl, and $C_{2-6}$ alkynyl, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. (260): The method of any one of embodiments 241 to 250 or embodiments 255 to 258, wherein each $R^1$ is independently selected from $C_{1-3}$ alkyl optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle and 3- to 10-membered heterocycle. (261): The method of any one of embodiments 241 to 250 or embodiments 255 to 259, wherein each $R^1$ is independently selected from $C_{3-5}$ carbocycle is optionally substituted with one or more substituents independently selected from halogen, —$NO_2$, —CN, —CN, —OH, —SH, —$NO_2$, —$NH_2$, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, and $C_{2-6}$ alkynyl. (262): The method of any one of embodiments 241 to 250 or embodiments 255 to 260, wherein each $R^1$ is independently selected from hydrogen, —CN, —OH, —OMe, —OEt, —OiPr, —F, —Cl, —Br, —Me, —Et, —$CF_3$, —$CHF_2$, —$CH_2F$, $OCF_3$, —$OCHF_2$, —$OCH_2F$, —$C(O)NH_2$,

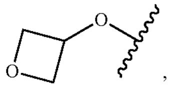 , 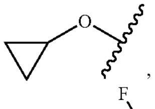 , 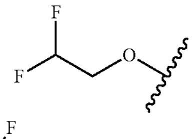 ,

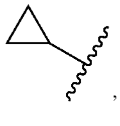 , and 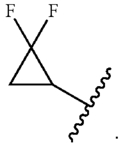 .

(263): The method of any one of embodiments 241 to 261, wherein $R^2$ is selected from $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (264): The method of any one of embodiments 241 to 262, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (265): The method of any one of embodiments 241 to 263, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (266): The method of any one of embodiments 241 to 264, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (267): The method of any one of embodiments 241 to 265, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (268): The method of any one of embodiments 241 to 261, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$. (269): The method of any one of embodiments 241 to 261, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl, wherein the $C_{1-6}$ alkyl is optionally substituted with one or more $R^{9b}$. (270): The method of any one of embodiments 241 to 261 or embodiment 268, wherein $R^2$ is selected from $C_{1-6}$ alkyl, optionally substituted with one or more substituents independently selected from halogen, —$OR^{10b}$, —$SR^{10b}$, —$N(R^{10b})_2$, —$C(O)R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (271): The method of any one of embodiments 241 to 261 or any one of embodiments 268 to 269, wherein $R^2$ is selected from $C_{1-6}$ alkyl, optionally substituted with one or more substituents independently selected from halogen, —$OR^{10b}$, —$SR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (272): The method of any one of embodiments 241 to 261 or any one of embodiments 268 to 270, wherein $R^2$ is selected from $C_{1-6}$ alkyl, optionally substituted with one or more substituents independently selected from halogen, —$OR^{10b}$, —$N(R^{10b})_2$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$NO_2$, =O, —CN, and $C_{1-6}$ alkyl. (273): The method of any one of embodiments 241 to 261 or any one of embodiments 268 to 271, wherein $R^2$ is selected from $C_{1-6}$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, and —CN. (274): The method of any one of embodiments 241 to 261 or any one of embodiments 268 to 272, wherein $R^2$ is selected from $C_{1-6}$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (275): The method of any one of embodiments 241 to 261 or any one of embodiments 268 to 273, wherein $R^2$ is selected from $C_{1-6}$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, 2-pyridyl, and 3-pyridyl, and each phenyl, 2-pyridyl, and 3-pyridyl is optionally substituted with one or more $R^{9b}$; and $C_{3-10}$ carbocycle and 3- to 10-membered heterocycle, each of which is optionally substituted with one or more substituents independently selected from F, and —CN. (276): The method of any one of embodiments 241 to 261 or any one of embodiments 268 to 274, wherein $R^2$ is selected from $C_2$ alkyl, optionally substituted with one or more substituents independently selected from halogen, —$OR^{10b}$, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (277): The method of any one of embodiments 241 to 261 or any one of embodiments 268 to 275, wherein $R^2$ is selected from $C_2$ alkyl, optionally substituted with one or more substituents independently selected from F, OH, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from F, and —CN. (278): The method of any one of embodiments 241 to 261 or embodiment 268 to 276, wherein $R^2$ is $C_2$ alkyl, optionally substituted with one or more substituents independently selected from F, OH, $C_{3-10}$ carbocycle and 3- to 10-membered heterocycle, wherein each $C_{3-10}$ carbocycle and 3- to 10-membered heterocycle is independently selected from phenyl, pyridyl, and pyrimidyl, and each phenyl, pyridyl, and pyrimidyl is optionally substituted with one or more $R^{9b}$. (279): The method of any one of embodiments 241 to 274, wherein $R^2$ is a substituent represented by the following:

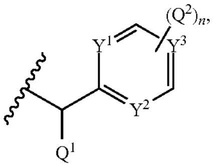

wherein, $Q^1$ is a $C_{1-3}$ alkyl optionally substituted with one or more substituents selected from OH and halo; $Y^1$, $Y^2$, and $Y_3$ are selected from N and $C(Q^3)$; and each $Q^2$ is independently selected from halo, CN, $C_{1-6}$ alkoxy, and $C_{1-6}$ alkyl optionally substituted with one or more substituents selected from halogen; each $Q^3$ is independently selected from hydrogen, halo, CN, $C_{1-6}$ alkoxy, and $C_{1-6}$ alkyl optionally substituted with one or more substituents selected from halogen; and n is 0 or 1. (280): The method of embodiments 241 to 274 or embodiment 278, wherein $Q^1$ is a $C_1$ alkyl optionally substituted with one or more substituents selected from OH and fluoro; n is 0; and each $Q^3$ is independently selected from hydrogen, fluoro, chloro, bromo, CN, methoxy, methyl, and trifluoromethyl. (281): The method of any one of embodiments 241 to 276, wherein $R^2$ is selected from

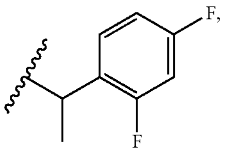 [SMILES: *C(C)c1ccc(F)cc1F] 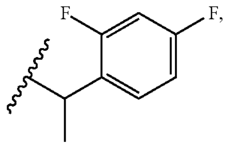

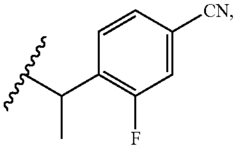 [SMILES: *C(C)c1ccc(C#N)cc1F] 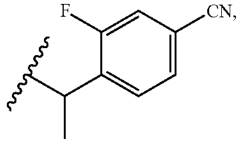

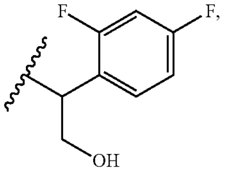 [SMILES: *C(CO)c1ccc(F)cc1F] 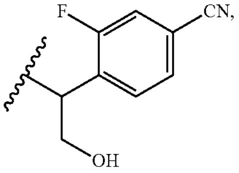

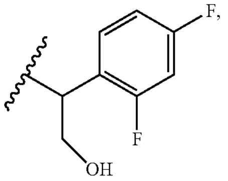 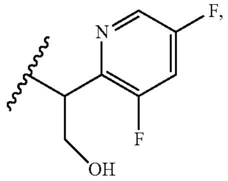 [SMILES: *C(CO)c1ncc(F)cc1F]

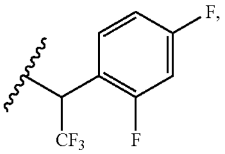 [SMILES: *C(c1ccc(F)cc1F)C(F)(F)F] 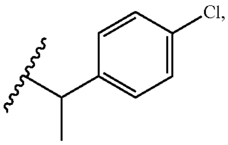

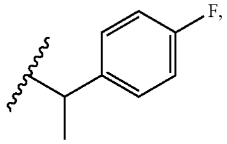 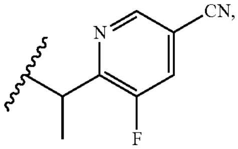

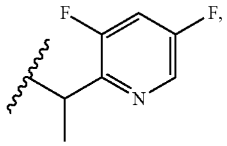 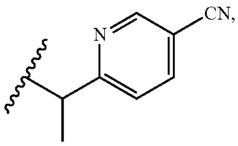

-continued

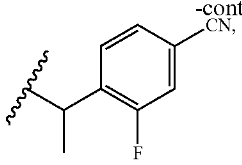 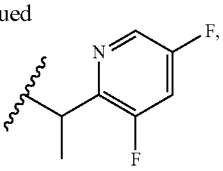

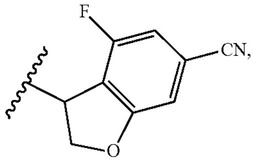 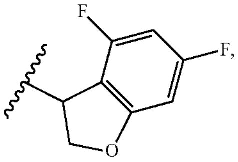

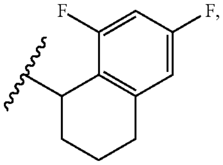 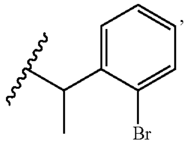

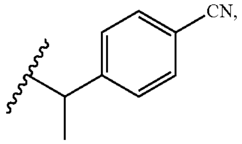 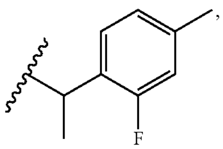

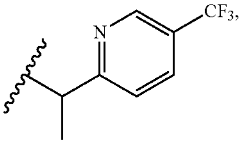 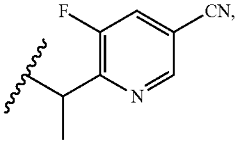

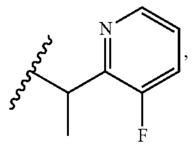 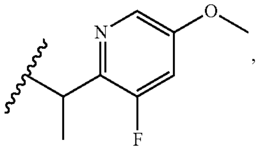

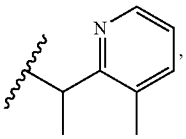 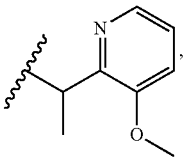

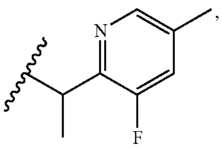 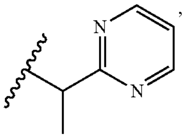

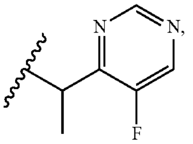 and 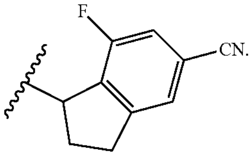

(282): The method of any one of embodiments 241 to 276, wherein $R^2$ is selected from

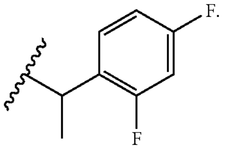

(283): The (284): The method of any one of embodiments 241 to 276, wherein $R^2$ is selected from

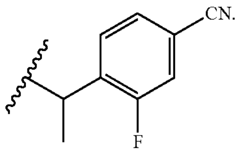

(285):

The method of any one of embodiments 241 to 276, wherein $R^2$ is selected from

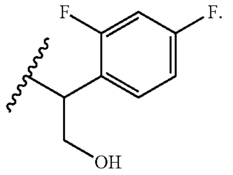

(286): The. (287): The method of any one of embodiments 241 to 276, wherein $R^2$ is selected from

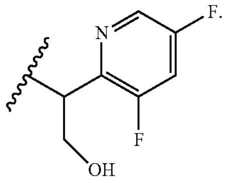

(288): The method of any one of embodiments 241 to 276, wherein $R^2$ is selected from

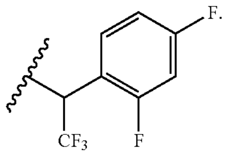

(289): The method of any one of embodiments 241 to 276, wherein $R^2$ is selected from

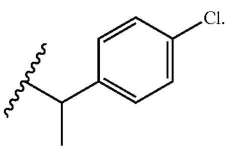 [SMILES: *C(C)c1ccc(Cl)cc1]

(290): The method of any one of embodiments 241 to 289, wherein $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, optionally substituted with one or more substituents independently selected from halogen, —$OR^{10c}$, —$SR^{10c}$, —$N(R^{10c})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (291): The method of any one of embodiments 241 to 290, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$. (292): The method of any one of embodiments 241 to 291, wherein $R^5$ and $R^6$ are each independently selected from: hydrogen, halogen, —$OR^{10c}$, —$SR^{10c}$, —$N(R^{10c})_2$, —$NO_2$, and —CN; and $C_{1-6}$ alkyl. (293): The method of any one of embodiments 241 to 292, wherein $R^5$ and $R^6$ are each independently selected from: hydrogen and $C_{1-3}$ alkyl. (294): The method of any one of embodiments 241 to 293, wherein $R^5$ and $R^6$ are each hydrogen. (295): The method of any one of embodiments 241 to 294, wherein $R^7$ is selected from hydrogen and $C_{1-6}$ alkyl optionally substituted with one or more substituents independently selected from halogen. (296): The method of any one of embodiments 241 to 295, wherein $R^7$ is selected from hydrogen. (297): The method of any one of embodiments 241 to 296, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle. (298): The method of any one of embodiments 241 to 297, wherein $R^8$ is selected from: hydrogen; and $C_{1-6}$ alkyl optionally substituted with one or more substituents independently selected from halogen, —$OR^{10e}$, —$SR^{10e}$, —$N(R^{10e})_2$, —$NO_2$, and —CN. (299): The method of any one of embodiments 241 to 298, wherein $R^8$ is selected from hydrogen. (300): The method of any one of embodiments 241 to 299, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$NO_2$, =O, and —CN. (301): The method of any one of embodiments 241 to 300, wherein each $R^{9a}$ is independently selected from: halogen, —$OR^{10a}$, —$SR^{10a}$, —$N(R^{10a})_2$, —$C(O)R^{10a}$, —$NO_2$, =O, and —CN; and $C_{1-3}$ alkyl optionally substituted with one or more substituents independently selected from halogen, —$OR^{10a}$, —$SR^{10a}$, —$N(R^{10a})_2$, —$C(O)R^{10a}$, —$NO_2$, =O, and —CN. (302): The method of any one of embodiments 241 to 301, wherein each $R^{9b}$ is independently selected from: halogen, —$OR^{10b}$, —$SR^{10b}$—, $N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$NO_2$, =O, and —CN. (303): The method of any one of embodiments 241 to 302, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (304): The method of any one of embodiments 241 to 303, wherein each $R^{9b}$ is independently selected from: halogen, —$OR^{10b}$, —$SR^{10b}$, —$N(R^{10b})_2$, —$NO_2$, =O, and —CN; and $C_{1-3}$ alkyl, optionally substituted with one or more substituents independently selected from halogen, —$OR^{10b}$, —$SR^{10b}$, —$N(R^{10b})_2$, —$NO_2$, =O, and —CN. (305): The method of any one of embodiments 241 to 304, wherein each $R^{9b}$ is independently selected from halogen and —CN. (306): The method of any one of embodiments 241 to 305, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, $C_{2-3}$ alkenyl, and $C_{2-3}$ alkynyl, each of which is optionally substituted with one or more substituents independently selected from halogen, —$OR^{10e}$, —$SR^{10c}$, —$N(R^{10c})_2$, —$C(O)R^{10c}$, —$NO_2$, =O, and —CN. (307): The method of any one of embodiments 241 to 306, wherein each $R^{9c}$ is independently selected from halogen, —$OR^{10c}$, —$SR^{10c}$, —$N(R^{10c})_2$, —$C(O)R^{10c}$, —$NO_2$, =O, and —CN; and $C_{1-3}$ alkyl, optionally substituted with one or more substituents independently selected from halogen, —$OR^{10c}$, —$SR^{10c}$, —$N(R^{10c})_2$, —$C(O)R^{10c}$, —$NO_2$, =O, and —CN. (308): The method of any one of embodiments 241 to 307, wherein each $R^{10a}$ is independently selected from hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{3-10}$ carbocycle, 3- to 10-membered heterocycle, and $C_{1-6}$ haloalkyl. (309): The method of any one of embodiments 241 to 308, wherein each $R^{10a}$ is independently selected from hydrogen; and $C_{1-}$ 6 alkyl, optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, —NH ($C_{1-6}$ alkyl), $C_{1-6}$ alkyl, and $C_{1-6}$ haloalkyl. (310): The method of any one of embodiments 241 to 309, wherein each $R^{10a}$ is independently selected from hydrogen; and $C_{1-6}$ alkyl, optionally substituted with one or more substituents independently selected from halogen, —CN, —OH, —SH, —$NO_2$, —$NH_2$, and =O; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —N($C_{1-6}$ alkyl)$_2$, —NH ($C_{1-6}$ alkyl), $C_{1-6}$ alkyl, and $C_{1-6}$ haloalkyl. (311): The method of any one of embodiments 241 to 310, wherein each $R^{10a}$ is independently selected from hydrogen; and $C_{1-6}$ alkyl optionally substituted with one or more substituents independently selected from halogen; and $C_{3-10}$ carbocycle, and 3- to 10-membered heterocycle. (312): The method of any one of embodiments 241 to 311, wherein each $R^{10b}$ is independently selected from: hydrogen; and $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, and —NH($C_{1-6}$ alkyl); and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, and $C_{1-6}$ haloalkyl. (313): The method of any one of embodiments 241 to 312, wherein each $R^{10b}$ is independently selected from: hydrogen; and $C_{1-6}$ alkyl. (314): The method of any one of embodiments 241 to 313, wherein each $R^{10b}$ is hydrogen. (315): The method of any one of embodiments 241 to 314, wherein each $R^{10c}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (316): The method of any one of embodiments 241 to 315, wherein each $R^{10c}$ is independently selected from: hydrogen; and $C_{1-6}$ alkyl. (317): The method of any one of embodiments 241 to 316, wherein each $R^{10c}$ is hydrogen. (318): The method of any one of embodiments 241 to 317, wherein each $R^{10a}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (319): The method of any one of embodiments 241 to 318, wherein each $R^{10d}$ is independently selected from: hydrogen; and $C_{1-6}$ alkyl. (320): The method of any one of embodiments 241 to 319, wherein each $R^{10d}$ is hydrogen. (321): The method of any one of embodiments 241 to 320, wherein each $R^{10e}$ is independently selected from: hydrogen; $C_{1-6}$ alkyl, optionally substituted with one or more substituents independently selected from halogen, —CN, —OH, —SH, —$NO_2$, —$NH_2$, =O, —O—$C_{1-6}$ alkyl, —S—$C_{1-6}$ alkyl, —N($C_{1-6}$ alkyl)$_2$, —NH($C_{1-6}$ alkyl); and $C_{3-10}$ carbocycle, and 3- to 10-membered heterocycle. (322): The method of any one of embodiments 241 to 321, wherein each $R^{10e}$ is independently selected from: hydrogen; and $C_{1-6}$ alkyl. (323): The method of any one of embodiments 241 to 322, wherein each $R^{10e}$ is hydrogen. (324): The method of any one of embodiments 241 to 323, wherein if $X^3$ and $X^1$ are both N, then $R^8$ is selected from hydrogen and $C_{1-4}$ alkyl optionally substituted with one or more substituents independently selected from halogen, —$OR^{10}$, —$SR^{10}$, —$N(R^{10})_2$, —$NO_2$, and —CN. (325): The method of any one of embodiments 241 to 324, wherein if $X^3$ and $X^1$ are both N, then $R^8$ is selected from hydrogen and $C_{1-4}$ alkyl optionally substituted with one or more substituents independently selected from halogen, —$OR^{10}$, and —CN. (326): The method of any one of embodiments 241 to 325, wherein if $X^3$ and $X^1$ are both N, then $R^8$ is selected from hydrogen and $C_{1-4}$ alkyl optionally substituted with one or more substituents independently selected from fluoro, —OH, and —CN. (327): The method of any one of embodiments 241 to 326, wherein if $X^3$ and $X^1$ are both N, then $R^8$ is selected from hydrogen and $C_{1-4}$ alkyl. (328): The method of any one of embodiments 241 to 327, wherein if $X^3$ and $X^1$ are both N, then $R^8$ is selected from hydrogen and $C_1$ alkyl. (329): The method of any one of embodiments 241 to 328, wherein if $X^3$ and $X^1$ are both N, then $R^8$ is selected from hydrogen. (330): The method of any one of embodiments 241 to 329, wherein the compound or salt is selected from (331): The method of any one of embodiments 241 to 330, wherein cardiovascular disease or a related condition is selected from: hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina. (332): The method of embodiment 331, wherein said heart failure with preserved ejection fraction (HFpEF) comprises one or more disorders selected from disorders of relaxation and disorders of chamber stiffness (diabetic HFpEF). (333): The method of embodiment 332, wherein said left ventricular (LV) hypertrophy is malignant left ventricular (LV) hypertrophy. (334): The method of embodiment 332, wherein said restrictive cardiomyopathy comprises one or more subgroups selected from inflammatory subgroups, infiltrative subgroups, storage subgroups, idiopathic/inherited subgroups, congenital heart disease subgroups. (335): The method of embodiment 334, wherein said inflammatory subgroups comprise one or more subgroups selected from Loefilers and EMF. (336): The method of embodiment 334, wherein said inflammatory subgroups comprise one or more subgroups selected from amyloid, sarcoid, and XRT. (337): The method of embodiment 334, wherein said storage subgroups comprise one or more subgroups selected from hemochromatosis, Fabry, and glycogen storage disease. (338): The method of embodiment 334, wherein said idiopathic/inherited subgroups comprise one or more subgroups selected from Trop I (beta myosin HC), Trop T (alpha cardiac actin), and desmin related subgroups. (339): The method of embodiment 334, wherein said congenital heart disease subgroups comprise one or more subgroups selected from pressure-overloaded RV, Tetralogy of Fallot, and pulmonic stenosis. (340): The method of any one of embodiments 241 to 332, wherein cardiovascular disease or a related condition is hypertrophic cardiomyopathy. (341): The method of any one of embodiments 241 to 332, wherein cardiovascular disease or a related condition is obstructive hypertrophic cardiomyopathy. (342): The method of any one of embodiments 241 to 332, wherein cardiovascular disease or a related condition is non-obstructive hypertrophic cardiomyopathy. (343): The method of any one of embodiments 241 to 332, wherein cardiovascular disease or a related condition is heart failure with preserved ejection fraction. (344): The method of any one of embodiments 241 to 332, wherein cardiovascular disease or a related condition is left ventricle stiffness. (345): A pharmaceutical composition comprising a compound or salt of any one of embodiments 1 to 224 and a pharmaceutically acceptable excipient. In certain aspects, the disclosure provides a compounds of Formula (I), (II), and (III), pharmaceutical compositions thereof as well as methods of use in the treatment of disease. In certain aspects, the disclosure provides a compounds of Formula (I), (II), (II') and (III), pharmaceutical compositions thereof as well as methods of use in the treatment of disease. In certain aspects, the disclosure provides a compounds of Formula (I), (II), and (III), pharmaceutical compositions thereof as well as methods of use in the treatment of disease. In certain aspects, the disclosure provides a compounds of Formula (I), (II), (II'-e) and (III), pharmaceutical compositions thereof as well as methods of use in the treatment of disease.

Additional Numbered Embodiments

Some additional numbered examples of embodiments (separate from the above numbered embodiments) follow. (346): A compound represented by Formula (Ia-e):

(Ia-e)

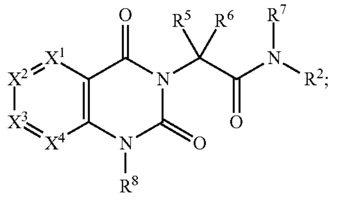

or a salt thereof, wherein: $R^2$ is selected from:

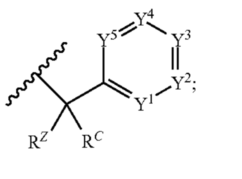

$X^1$ is selected from $C(R^{1a})$, N, and $N^+(—O^-)$; $X^2$ is selected from $C(R^{1b})$, N, and $N^+(—O^-)$; $X^3$ is selected from $C(R^{1c})$, N, and $N^+(—O^-)$; $X^4$ is selected from $C(R^{1d})$, N, and $N^+(—O^-)$; wherein no more than two of $X^1$, $X^2$, $X^3$, and $X^4$ are N; $Y^1$ is selected from $C(R^{9bA})$, N, and $N^+(—O^-)$; $Y^2$ is selected from $C(R^{9bB})$, N, and $N^+(—O^-)$; $Y^3$ is selected from $C(R^{9bC})$, N, and $N^+(—O^-)$; $Y^4$ is selected from $C(R^{9bD})$, N, and $N^+(—O^-)$; $Y^5$ is selected from $C(R^{9bE})$, N, and $N^+(—O^-)$; wherein at least one of $Y^1$, $Y^2$, $Y^3$, $Y^4$, and $Y^5$ is N; wherein no more than three of $Y^1Y^2$, $Y^3$, $Y^4$, and $Y^5$ are N; $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^Z$ is selected from: —CN, $—C(O)R^{10z}$, $—C(O)N(R^{10z})_2$, and $—C(O)OR^{10z}$; $C_{1-6}$ alkyl, $C_{2-6}$ alkenyl, and $C_{2-6}$ alkynyl, each of which is optionally substituted with one or more substituents independently selected from halogen, $—OR^{10z}$, $—SR^{10z}$, $—N(R^{10z})_2$, $—C(O)R^{10z}$, $—C(O)N(R^{10z})_2$, $—N(R^{10z})C(O)R^{10z}$, $—C(O)OR^{10z}$, $—OC(O)R^{10z}$, $—N(R^{10z})C(O)N(R^{10z})_2$, $—OC(O)N(R^{10z})_2$, $—N(R^{10z})C(O)OR^{10z}$, $S(O)R^{10z}$, $—S(O)_2R^{10z}$, $—NO_2$, =O, =S, $=N(R^{10z})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9z}$; $R^C$ is selected from: hydrogen; —CN, —$C(O)R^{10c}$, —$C(O)N(R^{10c})_2$, —$C(O)OR^{10c}$; $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9c}$; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9c}$; $R^5$ is selected from: hydrogen; halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, =O, =S, =$N(R^{10d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$; $R^6$ is selected from: hydrogen; halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, =O, =S, =$N(R^{10e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$N(R^{10e})C(O)N(R^{10e})_2$, —$OC(O)N(R^{10e})_2$, —$N(R^{10e})C(O)OR^{10e}$, —$C(O)OR^{10e}$, —$OC(O)R^{10e}$, —$S(O)R^{10e}$, —$S(O)_2R^{10e}$, —$NO_2$, =O, =S, =$N(R^{10e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$; or $R^6$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^{9e}$; $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9f}$; $R^8$ is selected from: hydrogen; —$C(O)R^{10g}$, —$C(O)N(R^{10g})_2$, —$C(O)OR^{10g}$, —$S(O)R^{10g}$, and —$S(O)_2R^{10g}$; $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{10g}$, —$S(O)R^{10g}$, —$S(O)_2R^{10g}$, —$NO_2$, =O, =S, =$N(R^{10g})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$; and $C_{3-10}$ carbocycle and 3- to 10-membered heterocycle, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9g}$; each $R^{9a}$ is independently selected from: halogen, —$OR^{10a}$, —$SR^{10a}$, —$N(R^{10a})_2$, —$C(O)R^{10a}$, —C(O)N ($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —NO$_2$, ═O, ═S, ═N($R^{10a}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —NO$_2$, ═O, ═S, ═N($R^{10a}$), —N$_3$, and —CN; $R^{9bA}$, $R^{9bB}$, $R^{9bC}$, $R^{9bD}$, and $R^{9bE}$ are each independently selected from: hydrogen; halogen, —NO$_2$, —N$_3$, —CN, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, and —S(O)$_2R^{10b}$; $C_{1-6}$ alkyl, $C_{2-6}$ alkenyl, and $C_{2-6}$ alkynyl, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —N($R^{10b}$)C(O)N($R^{10b}$)$_2$, —OC(O)N($R^{10b}$)$_2$, —N($R^{10b}$)C(O)O$R^{10b}$, —S(O)$R^{10b}$, —S(O)$_2R^{10b}$, —NO$_2$, ═O, ═S, ═N($R^{10b}$), —N$_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{10b}$, —S$R^{10b}$, —N($R^{10b}$)$_2$, —C(O)$R^{10b}$, —C(O)N($R^{10b}$)$_2$, —N($R^{10b}$)C(O)$R^{10b}$, —N($R^{10b}$)C(O)N($R^{10b}$)$_2$, —OC(O)N($R^{10b}$)$_2$, —N($R^{10b}$)C(O)O$R^{10b}$, —C(O)O$R^{10b}$, —OC(O)$R^{10b}$, —S(O)$R^{10b}$, —S(O)$_2R^{10b}$, —NO$_2$, ═O, ═S, ═N($R^{10b}$), —N$_3$, —CN, $C_{1-6}$ alkyl, $C_{2-6}$ alkenyl, and $C_{2-6}$ alkynyl; each $R^{9z}$ is independently selected from: halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2R^{10z}$, —NO$_2$, ═O, ═S, ═N($R^{10z}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2R^{10z}$, —NO$_2$, ═O, ═S, ═N($R^{10z}$), —N$_3$, and —CN; each $R^{9c}$ is independently selected from: halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$°—OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —NO$_2$, ═O, ═S, ═N($R^{10c}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10c}$, —S$R^{10c}$, —N($R^{10c}$)$_2$, —C(O)$R^{10c}$, —C(O)N($R^{10c}$)$_2$, —N($R^{10c}$)C(O)$R^{10c}$, —N($R^{10c}$)C(O)N($R^{10c}$)$_2$, —OC(O)N($R^{10c}$)$_2$, —N($R^{10c}$)C(O)O$R^{10c}$, —C(O)O$R^{10c}$, —OC(O)$R^{10c}$, —S(O)$R^{10c}$, —S(O)$_2R^{10c}$, —NO$_2$, ═O, ═S, ═N($R^{10c}$), —N$_3$, and —CN; each $R^{9d}$ is independently selected from: halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —NO$_2$, ═O, ═S, ═N($R^{10d}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —NO$_2$, ═O, ═S, ═N($R^{10d}$), —N$_3$, and —CN; each $R^{9e}$ is independently selected from: halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —NO$_2$, ═O, ═S, ═N($R^{10e}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —NO$_2$, ═O, ═S, ═N($R^{10e}$), —N$_3$, and —CN; each $R^{9f}$ is independently selected from: halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —N($R^{10f}$)C(O)N($R^{10f}$)$_2$, —OC(O)N($R^{10f}$)$_2$, —N($R^{10f}$)C(O)O$R^{10f}$, —C(O)O$R^{10f}$, —OC(O)$R^{10f}$, —S(O)$R^{10f}$, —S(O)$_2R^{10f}$, —NO$_2$, ═O, ═S, ═N($R^{10f}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —N($R^{10f}$)C(O)N($R^{10f}$)$_2$, —OC(O)N($R^{10f}$)$_2$, —N($R^{10f}$)C(O)O$R^{10f}$, —C(O)O$R^{10f}$, —OC(O)$R^{10f}$, —S(O)$R^{10f}$, —S(O)$_2R^{10f}$, —NO$_2$, ═O, ═S, ═N($R^{10f}$), —N$_3$, and —CN; each $R^{9g}$ is independently selected from: halogen, —O$R^{10g}$, —S$R^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —NO$_2$, ═O, ═S, ═N($R^{10g}$), —N$_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{10g}$, —S$R^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —NO$_2$, ═O, ═S, ═N($R^{10g}$), —N$_3$, and —CN; and each $R^{10a}$, $R^{10b}$, $R^{10z}$, $R^{10c}$, $R^{10d}$, $R^{10e}$, $R^{10f}$, and $R^{10g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —NO$_2$, —NH$_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —NO$_2$, —NH$_2$, ═O, ═S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein when $Y^1$ is N, $Y^2$ is C($R^{9bB}$), $Y^3$ is C($R^{9bC}$), $Y^4$ is C($R^{9bD}$), and $Y^5$ is C($R^{9bE}$); or when $Y^1$ is C($R^{9bA}$) $Y^2$ is C($R^{9bB}$), $Y^3$ is C($R^{9bC}$), $Y^4$ is C($R^{9bD}$), and $Y^5$ is N; then $R^7$ is selected from: hydrogen; —C(O)$R^{10f}$, —C(O)N($R^{10f}$)$_2$, —C(O)O$R^{10f}$, —S(O)$R^{10f}$, and —S(O)$_2R^{10f}$; $C_1$ alkyl substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, —N($R^{10f}$)C(O)N($R^{10f}$)$_2$, —OC(O)N($R^{10f}$)$_2$, —N($R^{10f}$)C(O)O$R^{10f}$, —S(O)$R^{10f}$, —S(O)$_2R^{10f}$, —NO$_2$, ═O, ═S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; $C_{2-6}$ alkyl optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—N(R^{10f})C(O)N(R^{10f})_2$, $—OC(O)N(R^{10f})_2$, $—N(R^{10f})C(O)OR^{10f}$, $—C(O)OR^{10f}$, $—OC(O)R^{10f}$, $—S(O)R^{10f}$, $—S(O)_2R^{10f}$, $—NO_2$, =O, =S, $=N(R^{10f})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9f}$; wherein when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^C$ is selected from: hydrogen; —CN, $—C(O)R^{10c}$, $—C(O)N(R^{10c})_2$, $—C(O)OR^{10c}$; $C_{1-6}$ alkyl, $C_{2-6}$ alkenyl, and $C_{2-6}$ alkynyl, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—C(O)OR^{10c}$, $—OC(O)R^{10c}$, $—N(R^{10c})C(O)N(R^{10c})_2$, $—OC(O)N(R^{10c})_2$, $—N(R^{10c})C(O)OR^{10c}$, $—S(O)R^{10c}$, $—S(O)_2R^{10c}$, $—NO_2$, =O, =S, $=N(R^{10c})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9c}$; and $C_{3-10}$ cycloalkyl and 3- to 10-membered heterocycle, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, $—S(O)R^{10c}$, $—S(O)_2R^{10c}$, $—NO_2$, =O, =S, $=N(R^{10c})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9c}$; and wherein when $Y^1$ is $C(R^{9bA})$, $Y^2$ is $C(R^{9bB})$, $Y^3$ is N, $Y^4$ is $C(R^{9bD})$, and $Y^5$ is $C(R^{9bE})$; then $R^7$ is selected from: hydrogen; $—C(O)R^{10f}$, $—C(O)N(R^{10f})_2$, $—C(O)OR^{10f}$, $—S(O)R^{10f}$, and $—S(O)_2R^{10f}$; $C_1$ alkyl substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; $C_{2-6}$ alkyl, $C_{2-6}$ alkenyl, and $C_{2-6}$ alkynyl, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—C(O)OR^{10f}$, $—OC(O)R^{10f}$, $—N(R^{10f})C(O)N(R^{10f})_2$, $—OC(O)N(R^{10f})_2$, $—N(R^{10f})C(O)OR^{10f}$, $—S(O)R^{10f}$, $—S(O)_2R^{10f}$, $—NO_2$, =O, =S, $=N(R^{10f})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^9$; and $C_{3-10}$ carbocycle and 3- to 10-membered heterocycle, each of which is optionally substituted with one or more substituents independently selected from halogen, $—OR^{10f}$, $—SR^{10f}$, $—N(R^{10f})_2$, $—C(O)R^{10f}$, $—C(O)N(R^{10f})_2$, $—N(R^{10f})C(O)R^{10f}$, $—N(R^{10f})C(O)N(R^{10f})_2$, $—OC(O)N(R^{10f})_2$, $—N(R^{10f})C(O)OR^{10f}$, $—C(O)OR^{10f}$, $—OC(O)R^{10f}$, $—S(O)R^{10f}$, $—S(O)_2R^{10f}$, $—NO_2$, =O, =S, $=N(R^{10f})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9f}$. (347): The compound or salt of embodiment 1, wherein no more than one of $X^1$, $X^2$, $X^3$, and $X^4$ is N. (348): The compound or salt of any one of embodiments 1 to embodiment 2, wherein no more than one of $Y^1$, $Y^2$, $Y^3$, $Y^4$, and $Y^5$ are N. (349): The compound or salt of any one of embodiments 1 to embodiment 3, wherein $X^1$ is selected from $C(R^{1a})$ and N, (350): The compound or salt of any one of embodiments 1 to embodiment 4, wherein $X^1$ is selected from $C(R^{1a})$, (351): The compound or salt of any one of embodiments 1 to embodiment 5, wherein $X^1$ is selected from C(H), C(F), and C(CN), and $C(CH_3)$. (352): The compound or salt of any one of embodiments 1 to embodiment 6, wherein $X^2$ is selected from $C(R^{1b})$ and N, (353): The compound or salt of any one of embodiments 1 to embodiment 7, wherein $X^2$ is selected from N, C(H), C(F), and C(CN). (354): The compound or salt of any one of embodiments 1 to embodiment 8, wherein $X^3$ is selected from C(H). (355): The compound or salt of any one of embodiments 1 to embodiment 9, wherein $X^4$ is selected from C(H). (356): The compound or salt of any one of embodiments 1 to 10, wherein $X^3$ and $X^4$ are C(H). (357): The compound or salt of any one of embodiments 1 to 11, wherein $R^{1a}$, $R^{1b}$, $R^{1c}$, and $R^{1d}$, are each independently selected from: hydrogen; halogen, $—NO_2$, $—N_3$, —CN, $—OR^{10a}$, $—SR^{10a}$, and $—N(R^{10a})_2$; $C_{1-6}$ alkyl optionally substituted with one or more substituents independently selected from halogen, $—OR^{10a}$, $—SR^{10a}$, $—N(R^{10a})_2$, $—NO_2$, =O, $—N_3$, and —CN. (358): The compound or salt of any one of embodiments 1 to 12, wherein $R^{1a}$, $R^{1b}R^{1c}$, and $R^{1d}$, are each independently selected from: hydrogen, fluoro, —CN, and $C_{1-6}$ alkyl. (359): The compound or salt of any one of embodiments 1 to 13, wherein $R^{1a}$, $R^{1b}$, $R^{1c}$, and $R^{1d}$, are each independently selected from: hydrogen and fluoro. (360): The compound or salt of any one of embodiments 1 to 14, wherein $R^Z$ is selected from: —CN, $—C(O)R^{10z}$, $—C(O)N(R^{10z})_2$, and $—C(O)OR^{10z}$; and $C_{1-6}$ alkyl optionally substituted with one or more substituents independently selected from halogen, $—OR^{10z}$, $—SR^{10z}$, $—N(R^{10z})_2$, =O, $—N_3$, —CN. (361): The compound or salt of any one of embodiments 1 to 15, wherein $R^Z$ is selected from $C_1$ alkyl. (362): The compound or salt of any one of embodiments 1 to 16, wherein $R^C$ is selected from: hydrogen; —CN, $—C(O)R^{10c}$, $—C(O)N(R^{10c})_2$, $—C(O)OR^{10c}$; $C_{1-6}$ alkyl, $C_{2-6}$ alkenyl, and $C_{2-6}$ alkynyl, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—C(O)OR^{10c}$, $—OC(O)R^{10c}$, $—N(R^{10c})C(O)N(R^{10c})_2$, $—OC(O)N(R^{10c})_2$, $—N(R^{10c})C(O)OR^{10c}$, $—S(O)R^{10c}$, $—S(O)_2R^{10c}$, $—NO_2$, =O, =S, $=N(R^{10c})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9c}$; and $C_{3-10}$ carbocycle and 3- to 10-membered heterocycle. (363): The compound or salt of any one of embodiments 1 to 17, wherein $R^C$ is selected from: hydrogen. (364): The compound or salt of any one of embodiments 1 to 18, wherein $R^5$ is selected from: hydrogen; halogen, —C(O)$R^{10d}$, —C(O)N($R^{10d}$)$_2$, —C(O)O$R^{10d}$, and —CN; $C_{1-6}$ alkyl, optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, =O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$. (365): The compound or salt of any one of embodiments 1 to 19, wherein $R^5$ is selected from: hydrogen and $C_{1-6}$ alkyl. (366): The compound or salt of any one of embodiments 1 to 20, wherein $R^5$ is selected from: hydrogen. (367): The compound or salt of any one of embodiments 1 to 21, wherein $R^6$ is selected from: hydrogen; halogen, —C(O)$R^{10e}$, —C(O)N($R^{10e}$)$_2$, —C(O)O$R^{10e}$, and —CN; $C_{1-6}$ alkyl, optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, =O, =S, =N($R^{10e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —O$R^{10}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —$NO_2$, =O, =S, =N($R^{10e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$. (368): The compound or salt of any one of embodiments 1 to 22, wherein $R^6$ is selected from: hydrogen and $C_{1-6}$ alkyl. (369): The compound or salt of any one of embodiments 1 to 23, wherein $R^6$ is selected from: hydrogen. (370): The compound or salt of any one of embodiments 1 to 24, wherein $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$. (371): The compound or salt of any one of embodiments 1 to 25, wherein $R^5$ is hydrogen, and $R^6$ is hydrogen. (372): The compound or salt of any one of embodiments 1 to 26, wherein $R^7$ is selected from: hydrogen; —C(O)$R^{10f}$, —C(O)N($R^{10f}$)$_2$, —C(O)O$R^{10f}$, —S(O)$R^{10f}$, and —S(O)$_2R^{10f}$; $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, =O, and —CN. (373): The compound or salt of any one of embodiments 1 to 27, wherein $R^7$ is selected from hydrogen. (374): The compound or salt of any one of embodiments 1 to 28, wherein $Y^1$ is selected from C(H) and N. (375): The compound or salt of any one of embodiments 1 to 29, wherein $Y^2$ is selected from C(H) and N. (376): The compound or salt of any one of embodiments 1 to 30, wherein $Y^3$ is selected from N, C(H), C(CN), C(F), C(Cl), and C(OH). (377): The compound or salt of any one of embodiments 1 to 31, wherein $Y^3$ is selected from C(CN). (378): The compound or salt of any one of embodiments 1 to 32, wherein $Y^4$ is selected from C(H) and N. (379): The compound or salt of any one of embodiments 1 to 33, wherein $Y^5$ is selected from N and C(H), C(F), C($CH_3$). (380): The compound or salt of any one of embodiments 1 to 34, wherein $Y^5$ is selected from C(H), and C(F). (381): The compound or salt of any one of embodiments 1 to 35, wherein $R^2$ is selected from

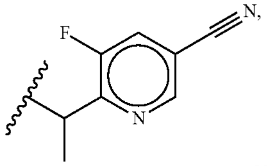, 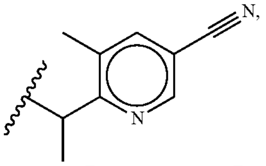, 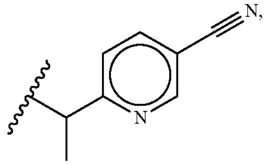, 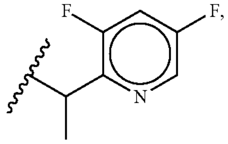, 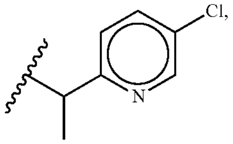, 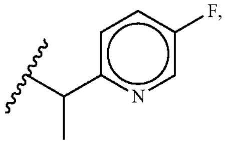, 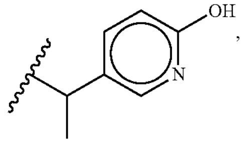, 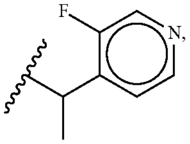, 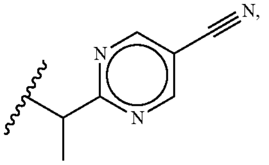, 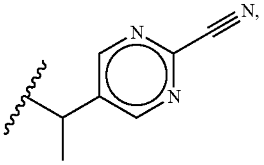, 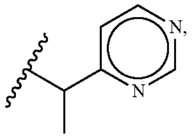, and 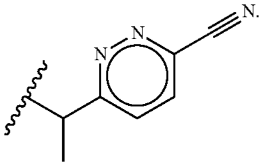.

(382): The compound or salt of any one of embodiments 1 to 36, wherein $R^8$ is selected from: hydrogen and $C_1$ alkyl. (383): The compound or salt of any one of embodiments 1 to 37, wherein $R^8$ is selected from: hydrogen. (384): The compound or salt of any one of embodiments 1 to 38, wherein each $R^{9a}$ is independently selected from: halogen, —O$R^{10a}$, S$R^{10a}$, —N($R^{10a}$)$_2$, =O, and —CN; and $C_{1-3}$ alkyl each of which is optionally substituted with one or more substituents independently selected from halogen, —O$R^{10a}$, —S$R^{10a}$, —N($R^{10a}$)$_2$, =O, and —CN. (385): The compound or salt of any one of embodiments 1 to 39, wherein $R^{9bA}$, $R^{9bB}$, $R^{9bC}$, $R^{9bD}$ and $R^{9bE}$ are each independently selected from: hydrogen; halogen, —CN, —$OR^{10b}$, —$SR^{10b}$, and —$N(R^{10b})_2$; and $C_{1-6}$ alkyl optionally substituted with one or more substituents independently selected from halogen, —$OR^{10b}$, —$SR^{10b}$, —$N(R^{10b})_2$, ═O, and —CN. (386): The compound or salt of any one of embodiments 1 to 40, wherein $R^{9bA}$, $R^{9bB}$, $R^{9bC}$, $R^{9bD}$, and $R^{9bE}$ are each independently selected from: hydrogen, fluoro, —CN, —OH, and $C_1$ alkyl. (387): The compound or salt of any one of embodiments 1 to 41, wherein each $R^{9z}$, $R^{9c}$, $R^{9e}$, $R^{9f}$, and $R^{9g-}$ is independently selected from: fluoro and —CN. (388): The compound or salt of any one of embodiments 1 to 42, wherein each $R^{10a}$, $R^{10b}$, $R^{10z}$, $R^{10c}$, $R^{10d}$, $R^{10e}$, $R^{10f}$, and $R^{10g}$ is independently selected from: hydrogen and $C_{1-6}$ alkyl. (389): The compound or salt of any one of embodiments 1 to 43, wherein each $R^{10a}$ is independently selected from: hydrogen. (390): The compound or salt of any one of embodiments 1 to 44, wherein when $Y^1$ is N; or when $Y^5$ is N; then $R^7$ is selected from hydrogen. (391): The compound or salt of any one of embodiments 1 to 45, wherein when $Y^3$ is N; then $R^C$ is selected from: hydrogen; and wherein when $Y^3$ is N; then $R^7$ is selected from: hydrogen. (392): The compound or salt of any one of embodiments 1 to 46, selected from: compound 1, 2, 11, 12, 5, 6, 97, 3, 4, 7, 8, 13, 14, 15, 16, 17, 18, 19, 20, 21, 22, 27, 28, 29, 30, 47, 105, 106, 98, 99, 100, 201, 202, 203, 204, 205, 206, 207, 208, 209, 210, 211, 212, 213, 214, and 215, or a salt of any one thereof.

(393): A compound of Formula (Ib-e):

(Ib-e)

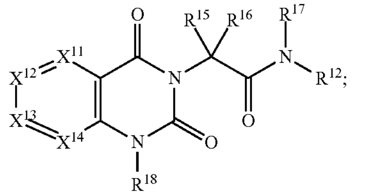

or a salt thereof, wherein: $R^{12}$ is selected from

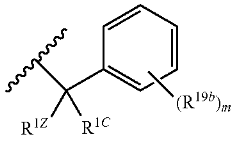

m is an integer selected from 1, 2, 3, 4, and 5; $X^{11}$ is selected from $C(R^{11a})$, N, and $N^+(—O^-)$; $X^{12}$ is selected from $C(R^{11b})$, N, and $N^+(—O^-)$; $X^{13}$ is selected from $C(R^{11c})$, N, and $N^+(—O^-)$; $X^{14}$ is selected from $C(R^{10d})$, N, and $N^+(—O^-)$; wherein at least one of $X^{11}$, $X^{12}$, $X^{13}$, and $X^{14}$ is N; wherein no more than two of $X^{11}$, $X^{12}$, $X^{13}$, and $X^{14}$ are N; $R^{11a}$, $R^{11b}$, $R^{11c}$, and $R^{11d}$ are each independently selected from: hydrogen; halogen, —$NO_2$, —$N_3$, —CN, —$OR^{110a}$, —$SR^{110a}$, —$N(R^{110a})_2$, —$C(O)R^{110a}$, —$C(O)N(R^{110a})_2$, —$N(R^{110a})C(O)R^{110a}$, —$N(R^{110a})C(O)N(R^{110a})_2$, —$OC(O)N(R^{110a})_2$, —$N(R^{110a})C(O)OR^{110a}$, —$C(O)OR^{110a}$, —$OC(O)R^{110a}$, —$S(O)R^{110a}$, and —$S(O)_2R^{110a}$; $C_{1-6}$ alkyl, $C_{2-6}$ alkenyl, and $C_{2-6}$ alkynyl, each of which is optionally substituted with one or more substituents independently selected from halogen, —$OR^{110a}$, —$SR^{110a}$, —$N(R^{110a})_2$, —$C(O)R^{110a}$, —$C(O)N(R^{110a})_2$, —$N(R^{110a})C(O)R^{110a}$, —$C(O)OR^{110a}$, —$OC(O)R^{110a}$, —$N(R^{110a})C(O)N(R^{110a})_2$, —$OC(O)N(R^{110a})_2$, —$N(R^{110a})C(O)OR^{110a}$, —$S(O)R^{110a}$, —$S(O)_2R^{110a}$, —$NO_2$, ═O, ═S, ═$N(R^{110a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19a}$; and $C_{3-10}$ carbocycle and 3- to 10-membered heterocycle, each of which is optionally substituted with one or more substituents independently selected from halogen, —$OR^{110a}$, —$SR^{110a}$, —$N(R^{110a})_2$, —$C(O)R^{110a}$, —$C(O)N(R^{110a})_2$, —$N(R^{110a})C(O)R^{110a}$, —$N(R^{110a})C(O)N(R^{110a})_2$, —$OC(O)N(R^{110a})_2$, —$N(R^{110a})C(O)OR^{110a}$, —$C(O)OR^{110a}$, —$OC(O)R^{110a}$, —$S(O)R^{110a}$, —$S(O)_2R^{110a}$, —$NO_2$, ═O, ═S, ═$N(R^{110a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19a}$; $R^{1Z}$ is selected from: —$C(O)R^{110z}$, —$C(O)N(R^{110z})_2$, —$C(O)OR^{110z}$, and —CN; $C_{1-6}$ alkyl, $C_{2-6}$ alkenyl, and $C_{2-6}$ alkynyl, each of which is optionally substituted with one or more substituents independently selected from halogen, —$OR^{110z}$, —$SR^{110z}$, —$N(R^{110z})_2$, —$C(O)R^{110z}$, —$C(O)N(R^{110z})_2$, —$N(R^{110z})C(O)R^{110z}$, —$C(O)OR^{110z}$, —$OC(O)R^{110z}$, —$N(R^{110z})C(O)N(R^{110z})_2$, —$OC(O)N(R^{110z})_2$, —$N(R^{110z})C(O)OR^{110z}$, —$S(O)R^{110z}$, —$S(O)_2R^{110z}$, —$NO_2$, ═O, ═S, ═$N(R^{110z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19z}$; and $C_{3-10}$ carbocycle and 3- to 10-membered heterocycle, each of which is optionally substituted with one or more substituents independently selected from halogen, —$OR^{110z}$, —$SR^{110z}$, —$N(R^{110z})_2$, —$C(O)R^{110z}$, —$C(O)N(R^{110z})_2$, —$N(R^{110z})C(O)R^{110z}$, —$N(R^{110z})C(O)N(R^{110z})_2$, —$OC(O)N(R^{110z})_2$, —$N(R^{110z})C(O)OR^{110z}$, —$C(O)OR^{110z}$, —$OC(O)R^{110z}$, —$S(O)R^{110z}$, —$S(O)_2R^{110z}$, —$NO_2$, ═O, ═S, ═$N(R^{110z})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19z}$; $R^{1C}$ is selected from: hydrogen; —$C(O)R^{110c}$, —$C(O)N(R^{110c})_2$, —$C(O)OR^{110c}$, and —CN; $C_{1-6}$ alkyl, $C_{2-6}$ alkenyl, and $C_{2-6}$ alkynyl, each of which is optionally substituted with one or more substituents independently selected from halogen, —$OR^{110c}$, —$SR^{110c}$, —$N(R^{110c})_2$, —$C(O)R^{110c}$, —$C(O)N(R^{110c})_2$, —$N(R^{110c})C(O)R^{110c}$, —$C(O)OR^{110c}$, —$OC(O)R^{110c}$, —$N(R^{110c})C(O)N(R^{110c})_2$, —$OC(O)N(R^{110c})_2$, —$N(R^{110c})C(O)OR^{110c}$, —$S(O)R^{110c}$, —$S(O)_2R^{110c}$, —$NO_2$, ═O, ═S, ═$N(R^{110c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19c}$; and $C_{3-10}$ carbocycle and 3- to 10-membered heterocycle, each of which is optionally substituted with one or more substituents independently selected from halogen, —$OR^{110c}$, —$SR^{110c}$, —$N(R^{110c})_2$, —$C(O)R^{110c}$, —$C(O)N(R^{110c})_2$, —$N(R^{110c})C(O)R^{110c}$, —$N(R^{110c})C(O)N(R^{110c})_2$, —$OC(O)N(R^{110c})_2$, —$N(R^{110c})C(O)OR^{110c}$, —$C(O)OR^{110c}$, —$OC(O)R^{110c}$, —$S(O)R^{110c}$, —$S(O)_2R^{110c}$, —$NO_2$, ═O, ═S, ═$N(R^{110c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19c}$; $R^{15}$ is selected from: hydrogen; halogen, —$OR^{110d}$, —$SR^{110d}$, —$N(R^{110d})_2$, —$C(O)R^{110d}$, —$C(O)N(R^{110d})_2$, —$N(R^{110d})C(O)R^{110d}$, —$C(O)OR^{110d}$, —$OC(O)R^{110d}$, —$N(R^{110d})C(O)N(R^{110d})_2$, —$OC(O)N(R^{110d})_2$, —$N(R^{110d})C(O)OR^{110d}$, —$S(O)R^{110d}$, —$S(O)_2R^{110d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{110d}$, —$SR^{110d}$, —$N(R^{110d})_2$, —$C(O)R^{110d}$, —$C(O)N(R^{110d})_2$, —$N(R^{110d})C$ (O)$R^{110d}$, —C(O)O$R^{110d}$, —OC(O)$R^{110d}$, —N($R^{110d}$)C(O)N($R^{110d}$)$_2$, —OC(O)N($R^{110d}$)$_2$, —N($R^{110d}$)C(O)O$R^{110d}$, —S(O)$R^{110d}$, —S(O)$_2R^{110d}$, —$NO_2$, =O, =S, =N($R^{110d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19d}$; and $C_{3-10}$ carbocycle and 3- to 10-membered heterocycle, each of which is optionally substituted with one or more substituents independently selected from halogen, —O$R^{110d}$, —S$R^{110d}$, —N($R^{110d}$)$_2$, —C(O)$R^{110d}$, —C(O)N($R^{110d}$)$_2$, —N($R^{110d}$)C(O)$R^{110d}$, —N($R^{110d}$)C(O)N($R^{110d}$)$_2$, —OC(O)N($R^{110d}$)$_2$, —N($R^{110d}$)C(O)O$R^{110d}$, —C(O)O$R^{110d}$, —OC(O)$R^{110d}$, —S(O)$R^{110d}$, —S(O)$_2R^{110d}$, —$NO_2$, =O, =S, =N($R^{110d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19d}$; or $R^{15}$ together with $R^{16}$ form a 3- to 10-membered heterocycle or $C_{3-10}$ carbocycle, wherein the 3- to 10-membered heterocycle or $C_{3-10}$ carbocycle is optionally substituted with one or more $R^{19d}$. $R^{16}$ is selected from: hydrogen; halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —C(O)O$R^{110e}$, —OC(O)$R^{110e}$, —N($R^{110e}$)C(O)N($R^{110e}$)$_2$, —OC(O)N($R^{110e}$)$_2$, —N($R^{110e}$)C(O)O$R^{110e}$, —S(O)$R^{110e}$, —S(O)$_2R^{110e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —C(O)O$R^{110e}$, —OC(O)$R^{110e}$, —N($R^{110e}$)C(O)N($R^{110e}$)$_2$, —OC(O)N($R^{110e}$)$_2$, —N($R^{110e}$)C(O)O$R^{110e}$, —S(O)$R^{110e}$, —S(O)$_2R^{110e}$, —$NO_2$, =O, =S, =N($R^{110e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19e}$; and $C_{3-10}$ carbocycle and 3- to 10-membered heterocycle, each of which is optionally substituted with one or more substituents independently selected from halogen, —O$R^{110e}$, —S$R^{110e}$, —N($R^{110e}$)$_2$, —C(O)$R^{110e}$, —C(O)N($R^{110e}$)$_2$, —N($R^{110e}$)C(O)$R^{110e}$, —N($R^{110e}$)C(O)N($R^{110e}$)$_2$, —OC(O)N($R^{110e}$)$_2$, —N($R^{110e}$)C(O)O$R^{110e}$, —C(O)O$R^{110e}$, —OC(O)$R^{110e}$, —S(O)$R^{110e}$, —S(O)$_2R^{110e}$, —$NO_2$, =O, =S, =N($R^{110e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19e}$; or $R^{16}$ together with $R^{15}$ form a 3- to 10-membered heterocycle or $C_{3-10}$ carbocycle, wherein the 3- to 10-membered heterocycle or $C_{3-10}$ carbocycle is optionally substituted with one or more $R^{19e}$; $R^{17}$ is selected from: hydrogen; —C(O)$R^{110f}$, —C(O)N($R^{110f}$)$_2$, —C(O)O$R^{110f}$, —S(O)$R^{110f}$, and —S(O)$_2R^{110f}$; $C_{1-6}$ alkyl optionally substituted with one or more substituents independently selected from halogen, —O$R^{110f}$, —S$R^{110f}$, —N($R^{110f}$)$_2$, —C(O)$R^{110f}$, —C(O)N($R^{110f}$)$_2$, —N($R^{110f}$)C(O)$R^{110f}$, —C(O)O$R^{110f}$, —OC(O)$R^{110f}$, —N($R^{110f}$)C(O)N($R^{110f}$)$_2$, —OC(O)N($R^{110f}$)$_2$, —N($R^{110f}$)C(O)O$R^{110f}$, —S(O)$R^{110f}$, —S(O)$_2R^{110f}$, —$NO_2$, =O, =S, =N($R^{110f}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19f}$; and $C_{3-10}$ carbocycle and 3- to 10-membered heterocycle, each of which is optionally substituted with one or more substituents independently selected from halogen, —O$R^{110f}$, —S$R^{110f}$, —N($R^{110f}$)$_2$, —C(O)$R^{110f}$, —C(O)N($R^{110f}$)$_2$, —N($R^{110f}$)C(O)$R^{110f}$, —N($R^{110f}$)C(O)N($R^{110f}$)$_2$, —OC(O)N($R^{110f}$)$_2$, —N($R^{110f}$)C(O)O$R^{110f}$, —C(O)O$R^{110f}$, —OC(O)$R^{110f}$, —S(O)$R^{110f}$, —S(O)$_2R^{110f}$, —$NO_2$, =O, =S, =N($R^{110f}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19f}$; $R^{18}$ is selected from: hydrogen; —C(O)$R^{110g}$, —C(O)N($R^{110g}$)$_2$, —C(O)O$R^{110g}$, —S(O)$R^{110g}$, and —S(O)$_2R^{110g}$; $C_{1-6}$ alkyl optionally substituted with one or more substituents independently selected from halogen, —O$R^{110g}$, —S$R^{110g}$, —N($R^{110g}$)$_2$, —C(O)$R^{110g}$, —C(O)N($R^{110g}$)$_2$, —N($R^{110g}$)C(O)$R^{110g}$, —C(O)O$R^{110g}$, —OC(O)$R^{110g}$, —N($R^{110g}$)C(O)N($R^{110g}$)$_2$, —OC(O)N($R^{110g}$)$_2$, —N($R^{110g}$)C(O)O$R^{110g}$, —S(O)$R^{110g}$, —S(O)$_2R^{110g}$, —$NO_2$, =O, =S, =N($R^{110g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{19g}$; and $C_{3-10}$ carbocycle and 3- to 10-membered heterocycle, each of which is optionally substituted with one or more substituents independently selected from halogen, —O$R^{110g}$, —S$R^{110g}$, —N($R^{110g}$)$_2$, —C(O)$R^{110g}$, —C(O)N($R^{110g}$)$_2$, —N($R^{110g}$)C(O)$R^{110g}$, —N($R^{110g}$)C(O)N($R^{110g}$)$_2$, —OC(O)N($R^{110g}$)$_2$, —N($R^{110g}$)C(O)O$R^{110g}$, —C(O)O$R^{110g}$, —OC(O)$R^{110g}$, —S(O)$R^{110g}$, —S(O)$_2R^{110g}$, —$NO_2$, =O, =S, =N($R^{110g}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{19g}$; each $R^{19a}$ is independently selected from: halogen, —O$R^{110a}$, —S$R^{110a}$, —N($R^{110a}$)$_2$, —C(O)$R^{110a}$, —C(O)N($R^{110a}$)$_2$, —N($R^{110a}$)C(O)$R^{110a}$, —N($R^{110a}$)C(O)N($R^{110a}$)$_2$, —OC(O)N($R^{110a}$)$_2$, —N($R^{110a}$)C(O)O$R^{110a}$, —C(O)O$R^{110a}$, —OC(O)$R^{110a}$, —S(O)$R^{110a}$, —S(O)$_2R^{110a}$, —$NO_2$, =O, =S, =N($R^{110a}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —O$R^{110a}$, —S$R^{110a}$, —N($R^{110a}$)$_2$, —C(O)$R^{110a}$, —C(O)N($R^{110a}$)$_2$, —N($R^{110a}$)C(O)$R^{110a}$, —N($R^{110a}$)C(O)N($R^{110a}$)$_2$, —OC(O)N($R^{110a}$)$_2$, —N($R^{110a}$)C(O)O$R^{110a}$, —C(O)O$R^{110a}$, —OC(O)$R^{110a}$, —S(O)$R^{110a}$, —S(O)$_2R^{110a}$, —$NO_2$, =O, =S, =N($R^{110a}$), —$N_3$, and —CN; each $R^{19b}$ is independently selected from: halogen, —$NO_2$, —$N_3$, —CN, —O$R^{110b}$, —S$R^{110b}$, —N($R^{110b}$)$_2$, —C(O)$R^{110b}$, —C(O)N($R^{110b}$)$_2$, —N($R^{110b}$)C(O)$R^{110b}$, —N($R^{110b}$)C(O)N($R^{110b}$)$_2$, —OC(O)N($R^{110b}$)$_2$, —N($R^{110b}$)C(O)O$R^{110b}$, —C(O)O$R^{110b}$, —OC(O)$R^{110b}$, —S(O)$R^{110b}$, and —S(O)$_2R^{110b}$; $C_{1-6}$ alkyl, $C_{2-6}$ alkenyl, and $C_{2-6}$ alkynyl, each of which is optionally substituted with one or more substituents independently selected from halogen, —O$R^{110b}$, —S$R^{110b}$, —N($R^{110b}$)$_2$, —C(O)$R^{110b}$, —C(O)N($R^{110b}$)$_2$, —N($R^{110b}$)C(O)$R^{110b}$, —C(O)O$R^{110b}$, —OC(O)$R^{110b}$, —N($R^{110b}$)C(O)N($R^{110b}$)$_2$, —OC(O)N($R^{110b}$)$_2$, —N($R^{110b}$)C(O)O$R^{110b}$, —S(O)$R^{110b}$, —S(O)$_2R^{110b}$, —$NO_2$, =O, =S, =N($R^{110b}$), —$N_3$, —CN, $C_{3-10}$ carbocycle and 3- to 10-membered heterocycle, wherein the $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —O$R^{110b}$, —S$R^{110b}$, —N($R^{110b}$)$_2$, —C(O)$R^{110b}$, —C(O)N($R^{110b}$)$_2$, —N($R^{110b}$)C(O)$R^{110b}$, —N($R^{110b}$)C(O)N($R^{110b}$)$_2$, —OC(O)N($R^{110b}$)$_2$, —N($R^{110b}$)C(O)O$R^{110b}$, —C(O)O$R^{110b}$, —OC(O)$R^{110b}$, —S(O)$R^{110b}$, —S(O)$_2R^{110b}$, —$NO_2$, =O, =S, =N($R^{110b}$), —$N_3$, —CN, $C_{1-6}$ alkyl, $C_{2-6}$ alkenyl, and $C_{2-6}$ alkynyl; each $R^{19z}$ is independently selected from: halogen, —O$R^{110z}$, —S$R^{110z}$, —N($R^{110z}$)$_2$, —C(O)$R^{110z}$, —C(O)N($R^{110z}$)$_2$, —N($R^{110z}$)C(O)$R^{110z}$, —N($R^{110z}$)C(O)N($R^{110z}$)$_2$—OC(O)N($R^{110z}$)$_2$, —N($R^{110z}$)C(O)O$R^{110z}$, —C(O)O$R^{110z}$, —OC(O)$R^{110z}$, —S(O)$R^{110z}$, —S(O)$_2R^{110z}$, —$NO_2$, =O, =S, =N($R^{110z}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —OR$^{110z}$, —SR$^{110z}$, —N(R$^{110z}$)$_2$, —C(O)R$^{110z}$, —C(O)N(R$^{110z}$)$_2$, —N(R$^{110z}$)C(O)R$^{110z}$, —N(R$^{110z}$)C(O)N(R$^{110z}$)$_2$—OC(O)N(R$^{110z}$)$_2$, —N(R$^{110z}$)C(O)OR$^{110z}$, —C(O)OR$^{110z}$, —OC(O)R$^{110z}$, —S(O)R$^{110z}$, —S(O)$_2$R$^{110z}$, —NO$_2$, =O, =S, =N(R$^{110z}$), —N$_3$, and —CN; each R$^{19c}$ is independently selected from: halogen, —OR$^{110c}$, —SR$^{110c}$, —N(R$^{110c}$)$_2$, —C(O)R$^{110c}$, —C(O)N(R$^{110c}$)$_2$, —N(R$^{110c}$)C(O)R$^{110c}$, —N(R$^{110c}$)C(O)N(R$^{110c}$)$_2$, —OC(O)N(R$^{110c}$)$_2$, —N(R$^{110c}$)C(O)OR$^{110c}$, —C(O)OR$^{110c}$, —OC(O)R$^{110c}$, —S(O)R$^{110c}$, —S(O)$_2$R$^{110c}$, —NO$_2$, =O, =S, =N(R$^{110c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110c}$, —SR$^{110c}$, —N(R$^{110c}$)$_2$, —C(O)R$^{110c}$, —C(O)N(R$^{110c}$)$_2$, —N(R$^{110c}$)C(O)R$^{110c}$, —N(R$^{110c}$)C(O)N(R$^{110c}$)$_2$, —OC(O)N(R$^{110c}$)$_2$, —N(R$^{110c}$)C(O)OR$^{110c}$, —C(O)OR$^{110c}$, —OC(O)R$^{110c}$, —S(O)R$^{110c}$, —S(O)$_2$R$^{110c}$, —NO$_2$, =O, =S, =N(R$^{110c}$), —N$_3$, and —CN; each R$^{19d}$ is independently selected from: halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —C(O)OR$^{110d}$, —OC(O)R$^{110d}$, —S(O)R$^{110d}$, —S(O)$_2$R$^{110d}$, —NO$_2$, =O, =S, =N(R$^{110d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110d}$, —SR$^{110d}$, —N(R$^{110d}$)$_2$, —C(O)R$^{110d}$, —C(O)N(R$^{110d}$)$_2$, —N(R$^{110d}$)C(O)R$^{110d}$, —N(R$^{110d}$)C(O)N(R$^{110d}$)$_2$, —OC(O)N(R$^{110d}$)$_2$, —N(R$^{110d}$)C(O)OR$^{110d}$, —C(O)OR$^{110d}$, —OC(O)R$^{110d}$, —S(O)R$^{110d}$, —S(O)$_2$R$^{110d}$, —NO$_2$, =O, =S, =N(R$^{110d}$), —N$_3$, and —CN; each R$^{19e}$ is independently selected from: halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —C(O)OR$^{110e}$, —OC(O)R$^{110e}$, —S(O)R$^{110e}$, —S(O)$_2$R$^{110e}$, —NO$_2$, =O, =S, =N(R$^{110e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110e}$, —SR$^{110e}$, —N(R$^{110e}$)$_2$, —C(O)R$^{110e}$, —C(O)N(R$^{110e}$)$_2$, —N(R$^{110e}$)C(O)R$^{110e}$, —N(R$^{110e}$)C(O)N(R$^{110e}$)$_2$, —OC(O)N(R$^{110e}$)$_2$, —N(R$^{110e}$)C(O)OR$^{110e}$, —C(O)OR$^{110e}$, —OC(O)R$^{110e}$, —S(O)R$^{110e}$, —S(O)$_2$R$^{110e}$, —NO$_2$, =O, =S, =N(R$^{110e}$), —N$_3$, and —CN; each R$^{19f}$ is independently selected from: halogen, —OR$^{110f}$, —SR$^{110f}$, —N(R$^{110f}$)$_2$, —C(O)R$^{110f}$, —C(O)N(R$^{110f}$)$_2$, —N(R$^{110f}$)C(O)R$^{110f}$, —N(R$^{110f}$)C(O)N(R$^{110f}$)$_2$, —OC(O)N(R$^{110f}$)$_2$, —N(R$^{110f}$)C(O)OR$^{110f}$, —C(O)OR$^{110f}$, —OC(O)R$^{110f}$, —S(O)R$^{110f}$, —S(O)$_2$R$^{110f}$, —NO$_2$, =O, =S, =N(R$^{110f}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110f}$, —SR$^{110f}$, —N(R$^{110f}$)$_2$, —C(O)R$^{110f}$, —C(O)N(R$^{110f}$)$_2$, —N(R$^{110f}$)C(O)R$^{110f}$, —N(R$^{110f}$)C(O)N(R$^{110f}$)$_2$, —OC(O)N(R$^{110f}$)$_2$, —N(R$^{110f}$)C(O)OR$^{110f}$, —C(O)OR$^{110f}$, —OC(O)R$^{110f}$, —S(O)R$^{110f}$, —S(O)$_2$R$^{110f}$, —NO$_2$, =O, =S, =N(R$^{110f}$), —N$_3$, and —CN; each R$^{19g}$ is independently selected from: halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —C(O)OR$^{110g}$, —OC(O)R$^{110g}$, —S(O)R$^{110g}$, —S(O)$_2$R$^{110g}$, —NO$_2$, =O, =S, =N(R$^{110g}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —C(O)OR$^{110g}$, —OC(O)R$^{110g}$, —S(O)R$^{110g}$, —S(O)$_2$R$^{110g}$, —NO$_2$, =O, =S, =N(R$^{110g}$), —N$_3$, and —CN; and each R$^{110a}$, R$^{110b}$, R$^{110c}$, R$^{110d}$, R$^{110e}$, R$^{110f}$, R$^{110g}$, R$^{110z}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; and wherein when X$^{14}$ is N, then R$^{18}$ is selected from: hydrogen; —C(O)R$^{110g}$, —C(O)N(R$^{110g}$)$_2$, —C(O)OR$^{110g}$, —S(O)R$^{110g}$, and —S(O)$_2$R$^{110g}$; C$_1$ alkyl substituted with one or more substituents independently selected from halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —C(O)OR$^{110g}$, —OC(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —S(O)R$^{110g}$, —S(O)$_2$R$^{110g}$, —NO$_2$, =O, =S, =N(R$^{110g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{199}$. C$_{2-6}$ alkyl optionally substituted with one or more substituents independently selected from halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —C(O)OR$^{110g}$, —OC(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —S(O)R$^{110g}$, —S(O)$_2$R$^{110g}$, —NO$_2$, =O, =S, =N(R$^{110g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{19g}$; and C$_{3-10}$ carbocycle and 3- to 10-membered heterocycle, each of which is optionally substituted with one or more substituents independently selected from halogen, —OR$^{110g}$, —SR$^{110g}$, —N(R$^{110g}$)$_2$, —C(O)R$^{110g}$, —C(O)N(R$^{110g}$)$_2$, —N(R$^{110g}$)C(O)R$^{110g}$, —N(R$^{110g}$)C(O)N(R$^{110g}$)$_2$, —OC(O)N(R$^{110g}$)$_2$, —N(R$^{110g}$)C(O)OR$^{110g}$, —C(O)OR$^{110g}$, —OC(O)R$^{110g}$, —S(O)R$^{110g}$, —S(O)$_2$R$^{110g}$, —NO$_2$, =O, =S, =N(R$^{110g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{19g}$. (394): The compound or salt of embodiment 48, wherein m is an integer selected from 1 and 2. (395): The compound or salt of embodiment 48 or embodiment 49, wherein no more than one of X$^{11}$ X$^{12}$, X$^{13}$, and X$^{14}$ is N. (396): The compound or salt of any one of embodiments 48 to embodiment 50, wherein X$^{11}$ is selected from C(H), C(OH), C(OCH$_3$), and N. (397): The compound or salt of any one of embodiments 48 to embodiment 51, wherein X$^{11}$ is selected from C(H) and N. (398): The compound or salt of any one of embodiments 48 to embodiment 52, wherein X$^{12}$ is selected from N, and C(H). (399): The compound or salt of any one of embodiments 48 to embodiment 53, wherein X$^{13}$ is selected from C(H). (400): The compound or salt of any one of embodiments 48 to embodiment 54, wherein X$^{13}$ is selected from C(H). (401): The compound or salt of any one of embodiments 48 to embodiment 55, wherein R$^{11a}$, R$^{11b}$, R$^{11c}$, and $R^{11d}$, are each independently selected from: hydrogen and —$OR^{110a}$. (402): The compound or salt of any one of embodiments 48 to embodiment 56, wherein $R^{11a}$, $R^{11b}$, $R^{11c}$, and $R^{11d}$, are each independently selected from: hydrogen, —OH, and —$OCH_3$. (403): The compound or salt of any one of embodiments 48 to embodiment 57, wherein $R^{11a}$, $R^{11b}$, $R^{11c}$, and $R^{11d}$, are each independently selected from: hydrogen. (404): The compound or salt of any one of embodiments 48 to embodiment 58, wherein $R^{Z}$ is selected from $C_1$ alkyl. (405): The compound or salt of any one of embodiments 48 to embodiment 59, wherein $R^{1C}$ is selected from: hydrogen. (406): The compound or salt of any one of embodiments 48 to embodiment 60, wherein $R^{15}$ is selected from: hydrogen and $C_{1-6}$ alkyl. (407): The compound or salt of any one of embodiments 48 to embodiment 61, wherein $R^{15}$ is selected from: hydrogen. (408): The compound or salt of any one of embodiments 48 to embodiment 62, wherein $R^{16}$ is selected from: hydrogen and $C_{1-6}$ alkyl. (409): The compound or salt of any one of embodiments 48 to embodiment 63, wherein $R^{16}$ is selected from: hydrogen. (410): The compound or salt of any one of embodiments 48 to embodiment 64, wherein $R^{17}$ is selected from hydrogen. (411): The compound or salt of any one of embodiments 48 to embodiment 65, wherein $R^{18}$ is selected from: hydrogen. (412): The compound or salt of any one of embodiments 48 to embodiment 66, wherein each $R^{19b}$ is independently selected from: halogen, —$NO_2$, —$N_3$, —CN, —$OR^{110b}$, —$SR^{110b}$, —$N(R^{110b})_2$, —$C(O)R^{110b}$, —$C(O)N(R^{110b})_2$, —$N(R^{110b})C(O)R^{110b}$, —$N(R^{110b})C(O)N(R^{110b})_2$, —$OC(O)N(R^{110b})_2$, —$N(R^{110b})C(O)OR^{110b}$, —$C(O)OR^{110b}$, —$OC(O)R^{110b}$, —$S(O)R^{110b}$, and —$S(O)_2R^{110b}$; $C_{1-6}$ alkyl optionally substituted with one or more substituents independently selected from halogen, —$OR^{110b}$, —$SR^{110b}$, —$N(R^{110b})_2$, =O, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{110b}$, —$SR^{110b}$, —$N(R^{110b})_2$, =O, —CN, $C_{1-6}$ alkyl. (413): The compound or salt of any one of embodiments 48 to embodiment 67, wherein each $R^{19b}$ is independently selected from: fluoro. (414): The compound or salt of any one of embodiments 48 to embodiment 68, wherein each $R^{110a}$, $R^{110b}$, $R^{110z}$, $R^{110c}$, $R^{110d}$, $R^{110e}$, $R^{110f}$, and $R^{110g}$ is independently selected from: hydrogen. (415): The compound or salt of any one of embodiments 48 to embodiment 69, wherein when $X^{14}$ is N, then $R^{18}$ is selected from: hydrogen. (416): The compound or salt of any one of embodiments 48 to embodiment 70, wherein $R^{12}$ is selected from

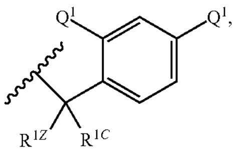

wherein $Q^1$ is selected from halogen, —CN, —OH, —$O(C_{1-6}$ alkyl), and —OH. (417): The compound or salt of any one of embodiments 48 to embodiment 72, wherein $R^{12}$ is selected from

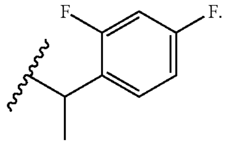 [SMILES: *C(C)c1ccc(F)cc1F]

(418) (e.g., compound 59, 65, 95, 96, 141, 301, 302, or 303, or a salt of any one thereof): The compound or salt of any one of embodiments 48 to embodiment 73, selected from: compounds: 59, 95, 96, and 96.

(419): A compound represented by Formula (IIa-e):

(IIa-e)

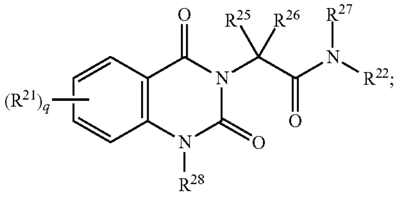

or a salt thereof, wherein $R^{22}$ is selected from:

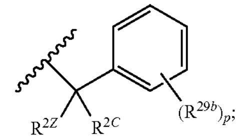

p is an integer selected from 1, 2, 3, 4, and 5; q is an integer selected from 1, 2, 3, and 4; each $R^{21}$ is independently selected from: halogen, —$NO_2$, —$N_3$, —CN, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, and —$S(O)_2R^{210a}$; $C_{1-6}$ alkyl, $C_{2-6}$ alkenyl, and $C_{2-6}$ alkynyl, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$C(O)OR^{210a}$, —$OC(O)R^{210a}$, —$N(R^{210a})C(O)N(R^{210a})_2$, —$OC(O)N(R^{210a})_2$, —$N(R^{210a})C(O)OR^{210a}$, —$S(O)R^{210a}$, —$S(O)_2R^{210a}$, —$NO_2$, =O, =S, =$N(R^{210a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29a}$; and $C_{3-10}$ carbocycle and 3- to 10-membered heterocycle, each of which is optionally substituted with one or more substituents independently selected from halogen, —$OR^{210a}$, —$SR^{210a}$, —$N(R^{210a})_2$, —$C(O)R^{210a}$, —$C(O)N(R^{210a})_2$, —$N(R^{210a})C(O)R^{210a}$, —$N(R^{210a})C(O)N(R^{210a})_2$, —$OC(O)N(R^{210a})_2$, —$N(R^{210a})C(O)OR^{210a}$, —$C(O)OR^{210a}$, —$OC(O)R^{210a}$, —$S(O)R^{210a}$, —$S(O)_2R^{210a}$, —$NO_2$, =O, =S, =$N(R^{210a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29a}$; $R^{2Z}$ is selected from: —$C(O)R^{210z}$, —$C(O)N(R^{210z})_2$, —$C(O)OR^{210z}$, and —CN; $C_{1-6}$ alkyl, $C_{2-6}$ alkenyl, and $C_{2-6}$ alkynyl, each of which is optionally substituted with one or more substituents independently selected from halogen, —$OR^{210z}$, —$SR^{210z}$, —$N(R^{210z})_2$, —$C(O)R^{210z}$, —$C(O)N(R^{210z})_2$, —$N(R^{210z})C(O)R^{210z}$, —$C(O)OR^{210z}$, —OC(O)$R^{210z}$, —N($R^{210z}$)C(O)N($R^{210z}$)$_2$, —OC(O)N($R^{210z}$)$_2$, —N($R^{210z}$)C(O)O$R^{210z}$, —S(O)$R^{210z}$, —S(O)$_2$$R^{210z}$, —NO$_2$, =O, =S, =N($R^{210z}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29z}$; and $C_{3-10}$ carbocycle and 3- to 10-membered heterocycle, each of which is optionally substituted with one or more substituents independently selected from halogen, —O$R^{210z}$, —S$R^{210z}$, —N($R^{210z}$)$_2$, —C(O)$R^{210z}$, —C(O)N($R^{210z}$)$_2$, —N($R^{210z}$)C(O)$R^{210z}$, —N($R^{210z}$)C(O)N($R^{210z}$)$_2$, —OC(O)N($R^{210z}$)$_2$, —N($R^{210z}$)C(O)O$R^{210z}$, —C(O)O$R^{210z}$, —OC(O)$R^{210z}$, —S(O)$R^{210z}$, —S(O)$_2$$R^{210z}$, —NO$_2$, =O, =S, =N($R^{210z}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29z}$; $R^{2C}$ is selected from: hydrogen; —C(O)$R^{210c}$, —C(O)N($R^{210c}$)$_2$, —C(O)O$R^{210c}$, and —CN; $C_{1-6}$ alkyl, $C_{2-6}$ alkenyl, and $C_{2-6}$ alkynyl, each of which is optionally substituted with one or more substituents independently selected from halogen, —O$R^{210c}$, —S$R^{210c}$, —N($R^{210c}$)$_2$, —C(O)$R^{210c}$, —C(O)N($R^{210c}$)$_2$, —N($R^{210c}$)C(O)$R^{210c}$, —C(O)O$R^{210c}$, —OC(O)$R^{210c}$, —N($R^{210c}$)C(O)N($R^{210c}$)$_2$, —OC(O)N($R^{210c}$)$_2$, —N($R^{210c}$)C(O)O$R^{210c}$, —S(O)$R^{210c}$, —S(O)$_2$$R^{210c}$, —NO$_2$, =O, =S, =N($R^{210c}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29c}$; and $C_{3-10}$ carbocycle and 3- to 10-membered heterocycle, each of which is optionally substituted with one or more substituents independently selected from halogen, —O$R^{210c}$, —S$R^{210c}$, —N($R^{210c}$)$_2$, —C(O)$R^{210c}$, —C(O)N($R^{210c}$)$_2$, —N($R^{210c}$)C(O)$R^{210c}$, —N($R^{210c}$)C(O)N($R^{210c}$)$_2$, —OC(O)N($R^{210c}$)$_2$, —N($R^{210c}$)C(O)O$R^{210c}$, —C(O)O$R^{210c}$, —OC(O)$R^{210c}$, —S(O)$R^{210c}$, —S(O)$_2$$R^{210c}$, —NO$_2$, =O, =S, =N($R^{210c}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29c}$; $R^{25}$ is selected from: hydrogen; halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210}$)$_2$, —OC(O)N($R^{210d}$)$_2$, —N($R^{210d}$)C(O)O$R^{210d}$, —S(O)$R^{210d}$, —S(O)$_2$$R^{210d}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —C(O)O$R^{210d}$, —OC(O)$R^{210d}$, —N($R^{210d}$)C(O)N($R^{210d}$)$_2$, —OC(O)N($R^{210d}$)$_2$, —N($R^{210d}$)C(O)O$R^{210d}$, —S(O)$R^{210d}$, —S(O)$_2$$R^{210d}$, —NO$_2$, =O, =S, =N($R^{210d}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29d}$; and $C_{3-10}$ carbocycle and 3- to 10-membered heterocycle, each of which is optionally substituted with one or more substituents independently selected from halogen, —O$R^{210d}$, —S$R^{210d}$, —N($R^{210d}$)$_2$, —C(O)$R^{210d}$, —C(O)N($R^{210d}$)$_2$, —N($R^{210d}$)C(O)$R^{210d}$, —N($R^{210d}$)C(O)N($R^{210d}$)$_2$, —OC(O)N($R^{210d}$)$_2$, —N($R^{210d}$)C(O)O$R^{210d}$, —C(O)O$R^{210d}$, —OC(O)$R^{210d}$, —S(O)$R^{210d}$, —S(O)$_2$$R^{210d}$, —NO$_2$, =O, =S, =N($R^{210d}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29d}$; or $R^{25}$ together with $R^{26}$ form a 3- to 10-membered heterocycle or $C_{3-10}$ carbocycle, wherein the 3- to 10-membered heterocycle or $C_{3-10}$ carbocycle is optionally substituted with one or more $R^{29d}$. $R^{26}$ is selected from:

hydrogen; halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2$$R^{210e}$, —NO$_2$, —N$_3$, and —CN; $C_{1-6}$ alkyl, $C_{2-6}$ alkenyl, and $C_{2-6}$ alkynyl, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —C(O)O$R^{210e}$, —OC(O)$R^{210e}$, —N($R^{210e}$)C(O)N($R^{210e}$)$_2$, —OC(O)N($R^{210e}$)$_2$, —N($R^{210e}$)C(O)O$R^{210e}$, —S(O)$R^{210e}$, —S(O)$_2$$R^{210e}$, —NO$_2$, =O, =S, =N($R^{210e}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29e}$; and $C_{3-10}$ carbocycle and 3- to 10-membered heterocycle, each of which is optionally substituted with one or more substituents independently selected from halogen, —O$R^{210e}$, —S$R^{210e}$, —N($R^{210e}$)$_2$, —C(O)$R^{210e}$, —C(O)N($R^{210e}$)$_2$, —N($R^{210e}$)C(O)$R^{210e}$, —N($R^{210e}$)C(O)N($R^{210e}$)$_2$, —OC(O)N($R^{210e}$)$_2$, —N($R^{210e}$)C(O)O$R^{210e}$, —C(O)O$R^{210e}$, —OC(O)$R^{210e}$, —S(O)$R^{210e}$, —S(O)$_2$$R^{210e}$, —NO$_2$, =O, =S, =N($R^{210e}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29e}$; or $R^{26}$ together with $R^{25}$ form a 3- to 10-membered heterocycle or $C_{3-10}$ carbocycle, wherein the 3- to 10-membered heterocycle or $C_{3-10}$ carbocycle is optionally substituted with one or more $R^{29e}$. $R^{27}$ is selected from: hydrogen; —C(O)$R^{210f}$, —C(O)N($R^{210f}$)$_2$, —C(O)O$R^{210f}$, —S(O)$R^{210f}$, and —S(O)$_2$$R^{210f}$; $C_{1-6}$ alkyl optionally substituted with one or more substituents independently selected from halogen, —O$R^{210f}$, —S$R^{210f}$, —N($R^{210f}$)$_2$, —C(O)$R^{210f}$, —C(O)N($R^{210f}$)$_2$, —N($R^{210f}$)C(O)$R^{210f}$, —C(O)O$R^{210f}$, —OC(O)$R^{210f}$, —N($R^{210f}$)C(O)N($R^{210f}$)$_2$, —OC(O)N($R^{210f}$)$_2$, —N($R^{210f}$)C(O)O$R^{210f}$, —S(O)$R^{210f}$, —S(O)$_2$$R^{210f}$, —NO$_2$, =O, =S, =N($R^{210f}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29f}$; and $C_{3-10}$ carbocycle and 3- to 10-membered heterocycle, each of which is optionally substituted with one or more substituents independently selected from halogen, —O$R^{210f}$, —S$R^{210f}$, —N($R^{210f}$)$_2$, —C(O)$R^{210f}$, —C(O)N($R^{210f}$)$_2$, —N($R^{210f}$)C(O)$R^{210f}$, —N($R^{210f}$)C(O)N($R^{210f}$)$_2$, —OC(O)N($R^{210f}$)$_2$, —N($R^{210f}$)C(O)O$R^{210f}$, —C(O)O$R^{210f}$, —OC(O)$R^{210f}$, —S(O)$R^{210f}$, —S(O)$_2$$R^{210f}$, —NO$_2$, =O, =S, =N($R^{210f}$), —N$_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{29f}$; $R^{28}$ is selected from: hydrogen; —C(O)$R^{210g}$, —C(O)N($R^{210g}$)$_2$, —C(O)O$R^{210g}$, —S(O)$R^{210g}$, and —S(O)$_2$$R^{210g}$; $C_{1-6}$ alkyl optionally substituted with one or more substituents independently selected from halogen, —O$R^{210g}$, —S$R^{210g}$, —N($R^{210g}$)$_2$, —C(O)$R^{210g}$, —C(O)N($R^{210g}$)$_2$, —N($R^{210g}$)C(O)$R^{210g}$, —C(O)O$R^{210g}$, —OC(O)$R^{210g}$, —N($R^{210g}$)C(O)N($R^{210g}$)$_2$, —OC(O)N($R^{210g}$)$_2$, —N($R^{210g}$)C(O)O$R^{210g}$, —S(O)$R^{210g}$, —S(O)$_2$$R^{210g}$, —NO$_2$, =O, =S, =N($R^{210g}$), —N$_3$, —CN, $C_{3-10}$ carbocycle and 3- to 10-membered heterocycle, wherein the $C_{3-10}$ carbocycle and 3- to 10-membered heterocycle are each optionally substituted with one or more $R^{29g}$; and $C_{3-10}$ carbocycle and 3- to 10-membered heterocycle, each of which is optionally substituted with one or more substituents independently selected from halogen, —O$R^{210g}$, —S$R^{210g}$, —N($R^{210g}$)$_2$, —C(O)$R^{210g}$, —C(O)N($R^{210g}$)$_2$, —N($R^{210g}$)C(O)$R^{210g}$, —N($R^{210g}$)C(O)N($R^{210g}$)$_2$, —OC(O)N($R^{210g}$)$_2$, —N($R^{210g}$)

C(O)OR$^{210g}$, —C(O)OR$^{210g}$, —OC(O)R$^{210g}$, —S(O)R$^{210g}$, —S(O)$_2$R$^{210g}$, —NO$_2$, =O, =S, =N(R$^{210g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{29g}$; each R$^{29a}$ is independently selected from: halogen, —OR$^{210a}$, —SR$^{210a}$, —N(R$^{210a}$)$_2$, —C(O)R$^{210a}$, —C(O)N(R$^{210a}$)$_2$, —N(R$^{210a}$)C(O)R$^{210a}$, —N(R$^{210a}$)C(O)N(R$^{210a}$)$_2$, —OC(O)N(R$^{210a}$)$_2$, —N(R$^{210a}$)C(O)OR$^{210a}$, —C(O)OR$^{210a}$, —OC(O)R$^{210a}$, —S(O)R$^{210a}$, —S(O)$_2$R$^{210a}$, —NO$_2$, =O, =S, =N(R$^{210a}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210a}$, —SR$^{210a}$, —N(R$^{210a}$)$_2$, —C(O)R$^{210a}$, —C(O)N(R$^{210a}$)$_2$, —N(R$^{210a}$)C(O)R$^{210a}$, —N(R$^{210a}$)C(O)N(R$^{210a}$)$_2$, —OC(O)N(R$^{210a}$)$_2$, —N(R$^{210a}$)C(O)OR$^{210a}$, —C(O)OR$^{210a}$, —OC(O)R$^{210a}$, —S(O)R$^{210a}$, —S(O)$_2$R$^{210a}$, —NO$_2$, =O, =S, =N(R$^{210a}$), —N$_3$, and —CN; each R$^{29b}$ is independently selected from: halogen, —NO$_2$, —N$_3$, —CN, —OR$^{210b}$, —SR$^{210b}$, —N(R$^{210b}$)$_2$, —C(O)R$^{210b}$, —C(O)N(R$^{210b}$)$_2$, —N(R$^{210b}$)C(O)R$^{210b}$, —N(R$^{210b}$)C(O)N(R$^{210b}$)$_2$, —OC(O)N(R$^{210b}$)$_2$, —N(R$^{210b}$)C(O)OR$^{210b}$, —C(O)OR$^{210b}$, —OC(O)R$^{210b}$, —S(O)R$^{210b}$, and —S(O)$_2$R$^{210b}$; C$_{1-6}$ alkyl, C$_{2-6}$ alkenyl, and C$_{2-6}$ alkynyl, each of which is optionally substituted with one or more substituents independently selected from halogen, —OR$^{210b}$, —SR$^{210b}$, —N(R$^{210b}$)$_2$, —C(O)R$^{210b}$, —C(O)N(R$^{210b}$)$_2$, —N(R$^{210b}$)C(O)R$^{210b}$, —C(O)OR$^{210b}$, —OC(O)R$^{210b}$, —N(R$^{210b}$)C(O)N(R$^{210b}$)$_2$, —OC(O)N(R$^{210b}$)$_2$, —N(R$^{210b}$)C(O)OR$^{210b}$, —S(O)R$^{210b}$, —S(O)$_2$R$^{210b}$, —NO$_2$, =O, =S, =N(R$^{210b}$), —N$_3$, —CN, C$_{3-10}$ carbocycle and 3- to 10-membered heterocycle; and C$_{3-10}$ carbocycle and 3- to 10-membered heterocycle, each of which is optionally substituted with one or more substituents independently selected from halogen, —OR$^{210b}$, —SR$^{210b}$, —N(R$^{210b}$)$_2$, —C(O)R$^{210b}$, —C(O)N(R$^{210b}$)$_2$, —N(R$^{210b}$)C(O)R$^{210b}$, —N(R$^{210b}$)C(O)N(R$^{210b}$)$_2$, —OC(O)N(R$^{210b}$)$_2$, —N(R$^{210b}$)C(O)OR$^{210b}$, —C(O)OR$^{210b}$, —OC(O)R$^{210b}$, —S(O)R$^{210b}$, —S(O)$_2$R$^{210b}$, —NO$_2$, =O, =S, =N(R$^{210b}$), —N$_3$, —CN, C$_{1-6}$ alkyl, C$_{2-6}$ alkenyl, and C$_{2-6}$ alkynyl; each R$^{29c}$ is independently selected from: halogen, —OR$^{210c}$, —SR$^{210c}$, —N(R$^{210c}$)$_2$, —C(O)R$^{210c}$, —C(O)N(R$^{210c}$)$_2$, —N(R$^{210c}$)C(O)R$^{210c}$, —N(R$^{210c}$)C(O)N(R$^{210c}$)$_2$, —OC(O)N(R$^{210c}$)$_2$, —N(R$^{210c}$)C(O)OR$^{210c}$, —C(O)OR$^{210c}$, —OC(O)R$^{210c}$, —S(O)R$^{210c}$, —S(O)$_2$R$^{210c}$, —NO$_2$, =O, =S, =N(R$^{210c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210c}$, —SR$^{210c}$, —N(R$^{210c}$)$_2$, —C(O)R$^{210c}$, —C(O)N(R$^{210c}$)$_2$, —N(R$^{210c}$)C(O)R$^{210c}$, —N(R$^{210c}$)C(O)N(R$^{210c}$)$_2$, —OC(O)N(R$^{210c}$)$_2$, —N(R$^{210c}$)C(O)OR$^{210c}$, —C(O)OR$^{210c}$, —OC(O)R$^{210c}$, —S(O)R$^{210c}$, —S(O)$_2$R$^{210c}$, —NO$_2$, =O, =S, =N(R$^{210c}$), —N$_3$, and —CN; each R$^{29d}$ is independently selected from: halogen, —OR$^{210d}$, —SR$^{210d}$N(R$^{210d}$)$_2$, —C(O)R$^{210d}$, —C(O)N(R$^{210d}$)$_2$, —N(R$^{210d}$)C(O)R$^{210d}$, —N(R$^{210d}$)C(O)N(R$^{210d}$)$_2$, —OC(O)N(R$^{210d}$)$_2$, —N(R$^{210d}$)C(O)OR$^{210d}$, —C(O)OR$^{210d}$, —OC(O)R$^{210d}$, —S(O)R$^{210d}$, —S(O)$_2$R$^{210d}$, —NO$_2$, =O, =S, =N(R$^{210d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210d}$, —SR$^{210d}$, —N(R$^{210d}$)$_2$, —C(O)R$^{210d}$, —C(O)N(R$^{210d}$)$_2$, —N(R$^{210d}$)C(O)R$^{210d}$, —N(R$^{210d}$)C(O)N(R$^{210d}$)$_2$, —OC(O)N(R$^{210d}$)$_2$, —N(R$^{210d}$)C(O)OR$^{210d}$, —C(O)OR$^{210d}$, —OC(O)R$^{210d}$, —S(O)R$^{210d}$, —S(O)$_2$R$^{210d}$, —NO$_2$, =O, =S, =N(R$^{210d}$), —N$_3$, and —CN; each R$^{29e}$ is independently selected from: halogen, —OR$^{210e}$, SR$^{210e}$, —N(R$^{210e}$)$_2$, —C(O)R$^{210e}$, —C(O)N(R$^{210e}$)$_2$, —N(R$^{210e}$)C(O)R$^{210e}$, —N(R$^{210e}$)C(O)N(R$^{210e}$)$_2$, —OC(O)N(R$^{210e}$)$_2$, —N(R$^{210e}$)C(O)OR$^{210e}$, —C(O)OR$^{210e}$, —OC(O)R$^{210e}$, —S(O)R$^{210e}$, —S(O)$_2$R$^{210e}$, —NO$_2$, =O, =S, =N(R$^{210e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210e}$, —SR$^{210e}$, —N(R$^{210e}$)$_2$, —C(O)R$^{210e}$, —C(O)N(R$^{210e}$)$_2$, —N(R$^{210e}$)C(O)R$^{210e}$, —N(R$^{210e}$)C(O)N(R$^{210e}$)$_2$, —OC(O)N(R$^{210e}$)$_2$, —N(R$^{210e}$)C(O)OR$^{210e}$, —C(O)OR$^{210e}$, —OC(O)R$^{210e}$, —S(O)R$^{210e}$, —S(O)$_2$R$^{210e}$, —NO$_2$, =O, =S, =N(R$^{210e}$), —N$_3$, and —CN; each R$^{29f}$ is independently selected from: halogen, —OR$^{210f}$, —SR$^{210f}$, —N(R$^{210f}$)$_2$, —C(O)R$^{210f}$, —C(O)N(R$^{210f}$)$_2$, —N(R$^{210f}$)C(O)R$^{210f}$, —N(R$^{210f}$)C(O)N(R$^{210f}$)$_2$, —OC(O)N(R$^{210f}$)$_2$, —N(R$^{210f}$)C(O)OR$^{210f}$, —C(O)OR$^{210f}$, —OC(O)R$^{210f}$, —S(O)R$^{210f}$, —S(O)$_2$R$^{210f}$, —NO$_2$, =O, =S, =N(R$^{210f}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210f}$, —SR$^{210f}$, —N(R$^{210f}$)$_2$, —C(O)R$^{210f}$, —C(O)N(R$^{210f}$)$_2$, —N(R$^{210f}$)C(O)R$^{210f}$, —N(R$^{210f}$)C(O)N(R$^{210f}$)$_2$, —OC(O)N(R$^{210f}$)$_2$, —N(R$^{210f}$)C(O)OR$^{210f}$, —C(O)OR$^{210f}$, —OC(O)R$^{210f}$, —S(O)R$^{210f}$, —S(O)$_2$R$^{210f}$, —NO$_2$, =O, =S, =N(R$^{210f}$), —N$_3$, and —CN; each R$^{29g}$ is independently selected from: halogen, —OR$^{210g}$, —SR$^{210g}$, —N(R$^{210g}$)$_2$, —C(O)R$^{210g}$, —C(O)N(R$^{210g}$)$_2$, —N(R$^{210g}$)C(O)R$^{210g}$, —N(R$^{210g}$)C(O)N(R$^{210g}$)$_2$, —OC(O)N(R$^{210g}$)$_2$, —N(R$^{210g}$)C(O)OR$^{210g}$, —C(O)OR$^{210g}$, —OC(O)R$^{210g}$, —S(O)R$^{210S}$, —S(O)$_2$R$^{210g}$, —NO$_2$, =O, =S, =N(R$^{210g}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210g}$, —SR$^{210g}$, —N(R$^{210g}$)$_2$, —C(O)R$^{210g}$, —C(O)N(R$^{210g}$)$_2$, —N(R$^{210g}$)C(O)R$^{210g}$, —N(R$^{210g}$)C(O)N(R$^{210g}$)$_2$, —OC(O)N(R$^{210g}$)$_2$, —N(R$^{210g}$)C(O)OR$^{210g}$, —C(O)OR$^{210g}$, —OC(O)R$^{210g}$, —S(O)R$^{210g}$, —S(O)$_2$R$^{210g}$, —NO$_2$, =O, =S, =N(R$^{210g}$), —N$_3$, and —CN; each R$^{29z}$ is independently selected from: halogen, —OR$^{210z}$, SR$^{210z}$, —N(R$^{210z}$)$_2$, —C(O)R$^{210z}$, —C(O)N(R$^{210z}$)$_2$, —N(R$^{210z}$)C(O)R$^{210z}$, —N(R$^{210z}$)C(O)N(R$^{210z}$)$_2$, —OC(O)N(R$^{210z}$)$_2$, —N(R$^{210z}$)C(O)OR$^{210z}$, —C(O)OR$^{210z}$, —OC(O)R$^{210z}$, —S(O)R$^{210z}$, —S(O)$_2$R$^{210z}$, —NO$_2$, =O, =S, =N(R$^{210z}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{210z}$, —SR$^{210z}$, —N(R$^{210z}$)$_2$, —C(O)R$^{210z}$, —C(O)N(R$^{210z}$)$_2$, —N(R$^{210z}$)C(O)R$^{210z}$, —N(R$^{210z}$)C(O)N(R$^{210z}$)$_2$, —OC(O)N(R$^{210z}$)$_2$, —N(R$^{210z}$)C(O)OR$^{210z}$, —C(O)OR$^{210z}$, —OC(O)R$^{210z}$, —S(O)R$^{210z}$, —S(O)$_2$R$^{210z}$, —NO$_2$, =O, =S, =N(R$^{210z}$), —N$_3$, and —CN; and each R$^{210a}$, R$^{210b}$, R$^{210c}$, R$^{210d}$, R$^{210e}$, R$^{210f}$, R$^{210g}$ and R$^{210z}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl. (420): The compound or salt of embodiment 74, wherein p is an integer selected from 1 and 2. (421): The compound or salt of embodiment 74 or embodiment 75, wherein q is an integer selected from 1 and 2. (422): The compound or salt of any one of embodiments 74 to 76, wherein each $R^{21}$ is independently selected from: halogen, —CN, —$OR^{210a}$, and $C_{1-6}$ alkyl optionally substituted with one or more substituents independently selected from fluoro and —CN. (423): The compound or salt of any one of embodiments 74 to 77, wherein each $R^{21}$ is independently selected from: fluoro, chloro, —OH, —$O(CH_3)$, —$CF_3$, and $C_1$ alkyl. (424): The compound or salt of any one of embodiments 74 to 78, wherein $R^{2Z}$ is selected from $C_1$ alkyl. (425): The compound or salt of any one of embodiments 74 to 79, wherein $R^{2C}$ is selected from: hydrogen. (426): The compound or salt of any one of embodiments 74 to 80, wherein $R^{25}$ is selected from hydrogen. (427): The compound or salt of any one of embodiments 74 to 81, wherein $R^{26}$ is selected from: hydrogen. (428): The compound or salt of any one of embodiments 74 to 82, wherein $R^{25}$ is hydrogen, and $R^{26}$ is hydrogen. (429): The compound or salt of any one of embodiments 74 to 83, wherein $R^{27}$ is selected from hydrogen. (430): The compound or salt of any one of embodiments 74 to 84, wherein $R^{22}$ is selected from The compound or salt of any one of embodiments 1 to 177, wherein $R^{12}$ is

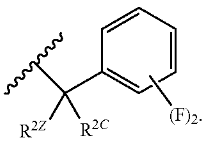

(431): The compound or salt of any one of emb 74 to 85, wherein $R^{22}$ is

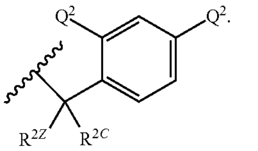

wherein $Q^2$ is selected from halogen, —CN, —OH, —$O(C_{1-6}$ alkyl), and —OH. (432): The compound or salt of any one of embodiments 74 to 86, wherein $R^{22}$ is selected from

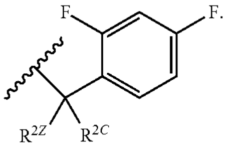

(433): The compound or salt of any one of embodiments 74 to 87, wherein $R^{22}$ is selected from

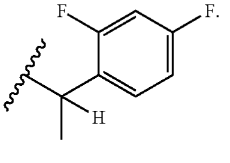 [SMILES: *C(C)c1ccc(F)cc1F]

(434): The compound or salt of any one of embodiments 74 to 88, wherein $R^{28}$ is selected from: hydrogen. (435): The compound or salt of any one of embodiments 74 to 89, wherein each $R^{210a}$, $R^{210b}$, $R^{210z}$, $R^{210c}$, $R^{210c}$, $R^{210d}$, $R^{210e}$, $R^{210f}$ and $R^{210g}$ is independently selected from: hydrogen. (436): The compound or salt of any one of embodiments 74 to 90, selected from: compound 33, 34, 35, 36, 37, 38, 39, 40, 41, 51, 69, 72, 73, 104, 136, 142, 143, 154, 155, 401, 402, 403, 404, 405, 406, 407, and 408,or a salt of any one thereof.

(437): A compound represented by Formula (IIb-e):

(IIb-e)

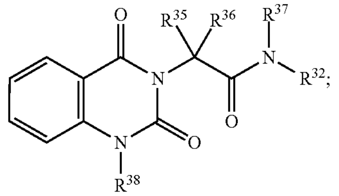

or a salt thereof, wherein: $R^{32}$ is selected from

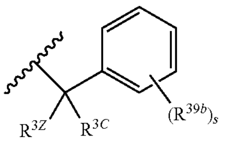

s is an integer selected from 2, 3, 4, and 5; $R^{3Z}$ is selected from: —$C(O)R^{310z}$, —$C(O)N(R^{310z})_2$, —$C(O)OR^{310z}$, and —CN; $C_{1-6}$ alkyl, $C_{2-6}$ alkenyl, and $C_{2-6}$ alkynyl, each of which is optionally substituted with one or more substituents independently selected from halogen, —$OR^{310z}$, —$SR^{310z}$, —$N(R^{310z})_2$, —$C(O)R^{310z}$, —$C(O)N(R^{310z})_2$, —$N(R^{310z})C(O)R^{310z}$, —$C(O)OR^{310z}$, —$OC(O)R^{310z}$, —$N(R^{310z})C(O)N(R^{310z})_2$, —$OC(O)N(R^{310z})_2$, —$N(R^{310z})C(O)OR^{310z}$, —$S(O)R^{310z}$, —$S(O)_2R^{310z}$, —$NO_2$, =O, =S, =$N(R^{310z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39z}$; and $C_{3-10}$ carbocycle and 3- to 10-membered heterocycle, each of which is optionally substituted with one or more substituents independently selected from halogen, —$OR^{310z}$, —$SR^{310z}$, —$N(R^{310z})_2$, —$C(O)R^{310z}$, —$C(O)N(R^{310z})_2$, —$N(R^{310z})C(O)R^{310z}$, —$N(R^{310z})C(O)N(R^{310z})_2$, —$OC(O)N(R^{310z})_2$, —$N(R^{310z})C(O)OR^{310z}$, —$C(O)OR^{310z}$, —$OC(O)R^{310z}$, —$S(O)R^{310z}$, —$S(O)_2R^{310z}$, —$NO_2$, =O, =S, =$N(R^{310z})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{39z}$; $R^{3C}$ is selected from: hydrogen; —$C(O)R^{310c}$, —$C(O)N(R^{310c})_2$, —$C(O)OR^{310c}$, and —CN; $C_{1-2}$ alkyl optionally substituted with one or more substituents independently selected from halogen, —$OR^{310c}$, —$SR^{310c}$, —$N(R^{310c})_2$, —$C(O)R^{310c}$, —$C(O)N(R^{310c})_2$, —$N(R^{310c})C(O)R^{310c}$, —$C(O)OR^{310c}$, —$OC(O)R^{310c}$, —$N(R^{310c})C(O)N(R^{310c})_2$, —$OC(O)N(R^{310c})_2$, —$N(R^{310c})C(O)OR^{310c}$, —$S(O)R^{310c}$, —$S(O)_2R^{310c}$, —$NO_2$, =S, =$N(R^{310c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{39c}$ $C_{3-6}$ alkyl, $C_{2-6}$ alkenyl, and $C_{2-6}$ alkynyl, each of which is optionally substituted with one or more substituents independently selected from halogen, —OR$^{310c}$, —SR$^{310c}$, —N(R$^{310c}$)$_2$, —C(O)R$^{310c}$, —C(O)N(R$^{310c}$)$_2$, —N(R$^{310c}$)C(O)R$^{310c}$, —C(O)OR$^{310c}$, —OC(O)R$^{310c}$, —N(R$^{310c}$)C(O)N(R$^{310c}$)$_2$, —OC(O)N(R$^{310c}$)$_2$, —N(R$^{310c}$)C(O)OR$^{310c}$, —S(O)R$^{310c}$, —S(O)$_2$R$^{310c}$, —NO$_2$, =O, =S, =N(R$^{310c}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{39c}$; and C$_{3-10}$ carbocycle and 3- to 10-membered heterocycle, each of which is optionally substituted with one or more substituents independently selected from halogen, —OR$^{310c}$, —SR$^{310c}$, —N(R$^{310c}$)$_2$, —C(O)R$^{310c}$, —C(O)N(R$^{310c}$)$_2$, —N(R$^{310c}$)C(O)R$^{310c}$, —N(R$^{310c}$)C(O)N(R$^{310c}$)$_2$, —OC(O)N(R$^{310c}$)$_2$, —N(R$^{310c}$)C(O)OR$^{310c}$, —C(O)OR$^{310c}$, —OC(O)R$^{310c}$, —S(O)R$^{310c}$, —S(O)$_2$R$^{310c}$, —NO$_2$, =O, =S, =N(R$^{310c}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{39c}$; R$^{35}$ is selected from: hydrogen; halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —C(O)OR$^{310d}$, —OC(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —S(O)R$^{310d}$, —S(O)$_2$R$^{310d}$, —NO$_2$, —N$_3$, and —CN; C$_{1-6}$ alkyl, C$_{2-6}$ alkenyl, and C$_{2-6}$ alkynyl, each of which is optionally substituted with one or more substituents independently selected from halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —C(O)OR$^{310d}$, —OC(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —S(O)R$^{310d}$, —S(O)$_2$R$^{310d}$, —NO$_2$, =O, =S, =N(R$^{310d}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{39d}$; and C$_{3-10}$ carbocycle and 3- to 10-membered heterocycle, each of which is optionally substituted with one or more substituents independently selected from halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —C(O)OR$^{310d}$, —OC(O)R$^{310d}$, —S(O)R$^{310d}$, —S(O)$_2$R$^{310d}$, —NO$_2$, =O, =S, =N(R$^{310d}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{39d}$; or R$^{35}$ together with R$^{36}$ form a 3- to 10-membered heterocycle or C$_{3-10}$ carbocycle, wherein the 3- to 10-membered heterocycle or C$_{3-10}$ carbocycle is optionally substituted with one or more R$^{39d}$; R$^{36}$ is selected from: hydrogen; halogen, —OR$^{310e}$, —SR$^{310e}$, —N(R$^{310e}$)$_2$, —C(O)R$^{310e}$, —C(O)N(R$^{310e}$)$_2$, —N(R$^{310e}$)C(O)R$^{310e}$, —C(O)OR$^{310e}$, —OC(O)R$^{310}$, —N(R$^{310e}$)C(O)N(R$^{310e}$)$_2$, —OC(O)N(R$^{310e}$)$_2$, —N(R$^{310e}$)C(O)OR$^{310e}$, —S(O)R$^{310e}$, —S(O)$_2$R$^{310e}$, —NO$_2$, —N$_3$, and —CN; C$_{1-6}$ alkyl, C$_{2-6}$ alkenyl, and C$_{2-6}$ alkynyl, each of which is optionally substituted with one or more substituents independently selected from halogen, —OR$^{310e}$, —SR$^{310e}$, —N(R$^{310e}$)$_2$, —C(O)R$^{310e}$, —C(O)N(R$^{310e}$)$_2$, —N(R$^{310e}$)C(O)R$^{310e}$, —C(O)OR$^{310e}$, —OC(O)R$^{310e}$, —N(R$^{310e}$)C(O)N(R$^{310e}$)$_2$, —OC(O)N(R$^{310e}$)$_2$, —N(R$^{310e}$)C(O)OR$^{310e}$, —S(O)R$^{310e}$, —S(O)$_2$R$^{310e}$, —NO$_2$, =O, =S, =N(R$^{310e}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{39e}$; and C$_{3-10}$ carbocycle and 3- to 10-membered heterocycle, each of which is optionally substituted with one or more substituents independently selected from halogen, —OR$^{310e}$, —SR$^{310e}$, —N(R$^{310e}$)$_2$, —C(O)R$^{310e}$, —C(O)N(R$^{310e}$)$_2$, —N(R$^{310e}$)C(O)R$^{310e}$, —N(R$^{310e}$)C(O)N(R$^{310e}$)$_2$, —OC(O)N(R$^{310e}$)$_2$, —N(R$^{310e}$)C(O)OR$^{310e}$, —C(O)OR$^{310e}$, —OC(O)R$^{310e}$, —S(O)R$^{310e}$, —S(O)$_2$R$^{310e}$, —NO$_2$, =O, =S, =N(R$^{310e}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{39e}$; or R$^{36}$ together with R$^{35}$ form a 3- to 10-membered heterocycle or C$_{3-10}$ carbocycle, wherein the 3- to 10-membered heterocycle or C$_{3-10}$ carbocycle is optionally substituted with one or more R$^{39e}$. R$^{37}$ is selected from: hydrogen; —C(O)R$^{310f}$, —C(O)N(R$^{310f}$)$_2$, —C(O)OR$^{310f}$, —S(O)R$^{310f}$, and —S(O)$_2$R$^{310f}$; C$_{1-6}$ alkyl optionally substituted with one or more substituents independently selected from halogen, —OR$^{310f}$, —SR$^{310f}$, —N(R$^{310f}$)$_2$, —C(O)R$^{310f}$, —C(O)N(R$^{310f}$)$_2$, —N(R$^{310f}$)C(O)R$^{310f}$, —C(O)OR$^{310f}$, —OC(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —S(O)R$^{310f}$, —S(O)$_2$R$^{310f}$, —NO$_2$, =O, =S, =N(R$^{310f}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{39f}$; and C$_{3-10}$ carbocycle and 3- to 10-membered heterocycle, each of which is optionally substituted with one or more substituents independently selected from halogen, —OR$^{310f}$, —SR$^{310f}$, —N(R$^{310f}$)$_2$, —C(O)R$^{310f}$, —C(O)N(R$^{310f}$)$_2$, —N(R$^{310f}$)C(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —C(O)OR$^{310f}$, —OC(O)R$^{310f}$, —S(O)R$^{310f}$, —S(O)$_2$R$^{310f}$, —NO$_2$, =O, =S, =N(R$^{310f}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{39f}$; R$^{38}$ is selected from: hydrogen; —C(O)R$^{310g}$, —C(O)N(R$^{310g}$)$_2$, —C(O)OR$^{310g}$, —S(O)R$^{310g}$, and —S(O)$_2$R$^{310g}$; C$_{1-6}$ alkyl optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —C(O)OR$^{310g}$, —OC(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —S(O)R$^{310g}$, —S(O)$_2$R$^{310g}$, —NO$_2$, =O, =S, =N(R$^{310g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{39g}$; and C$_{3-10}$ carbocycle and 3- to 10-membered heterocycle, each of which is optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —C(O)OR$^{310g}$, —OC(O)R$^{310g}$, —S(O)R$^{310g}$, —S(O)$_2$R$^{310g}$, —NO$_2$, =O, =S, =N(R$^{310g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{39g}$; each R$^{39z}$ is independently selected from: halogen, —OR$^{310z}$, —SR$^{310z}$, —N(R$^{310z}$)$_2$, —C(O)R$^{310z}$, —C(O)N(R$^{310z}$)$_2$, —N(R$^{310z}$)C(O)R$^{310z}$, —N(R$^{310z}$)C(O)N(R$^{310z}$)$_2$, —OC(O)N(R$^{310z}$)$_2$, —N(R$^{310z}$)C(O)OR$^{310z}$, —C(O)OR$^{310z}$, —OC(O)R$^{310z}$, —S(O)R$^{310z}$, —S(O)$_2$R$^{310z}$, —NO$_2$, =O, =S, =N(R$^{310z}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310z}$, —SR$^{310z}$, —N(R$^{310z}$)$_2$, —C(O)R$^{310z}$, —C(O)N(R$^{310z}$)$_2$, —N(R$^{310z}$)C(O)R$^{310z}$, —N(R$^{310z}$)C(O)N(R$^{310z}$)$_2$, —OC(O)N(R$^{310z}$)$_2$, —N(R$^{310z}$)C(O)OR$^{310z}$, —C(O)OR$^{310z}$, —OC(O)R$^{310z}$, —S(O)R$^{310z}$, —S(O)$_2$R$^{310z}$, —NO$_2$, =O, =S, =N(R$^{310z}$), —N$_3$, and —CN; each R$^{39b}$ is independently selected from: halogen, —NO$_2$, —N$_3$, —CN, —O(C$_{4-6}$ alkyl), —O(C$_{1-6}$ haloalkyl), —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$ and —S(O)$_2$R$^{310b}$; C$_1$ alkyl substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, —CN, and C$_{3-10}$ carbocycle and 3- to 10-membered heterocycle; C$_{2-6}$ alkyl, C$_{2-6}$ alkenyl, and C$_{2-6}$ alkynyl, each of which is optionally substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, and —CN; and C$_{3-10}$ carbocycle and 3- to 10-membered heterocycle, each of which is optionally substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, —S(O)$_2$R$^{310b}$, —NO$_2$, =O, =S, =N(R$^{310b}$), —N$_3$, —CN, C$_{1-6}$ alkyl, C$_{2-6}$ alkenyl, and C$_{2-6}$ alkynyl; each R$^{39c}$ is independently selected from: halogen, —OR$^{310c}$, —SR$^{310c}$, —N(R$^{310c}$)$_2$, —C(O)R$^{310c}$, —C(O)N(R$^{310c}$)$_2$, —N(R$^{310c}$)C(O)R$^{310c}$, —N(R$^{310c}$)C(O)N(R$^{310c}$)$_2$, —OC(O)N(R$^{310c}$)$_2$, —N(R$^{310c}$)C(O)OR$^{310c}$, —C(O)OR$^{310c}$, —OC(O)R$^{310c}$, —S(O)R$^{310c}$, —S(O)$_2$R$^{310c}$, —NO$_2$, =O, =S, =N(R$^{310c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310c}$, —SR$^{310c}$, —N(R$^{310c}$)$_2$, —C(O)R$^{310c}$, —C(O)N(R$^{310c}$)$_2$, —N(R$^{310c}$)C(O)R$^{310c}$, —N(R$^{310c}$)C(O)N(R$^{310c}$)$_2$, —OC(O)N(R$^{310c}$)$_2$, —N(R$^{310c}$)C(O)OR$^{310c}$, —C(O)OR$^{310c}$, —OC(O)R$^{310c}$, —S(O)R$^{310c}$, —S(O)$_2$R$^{310c}$, —NO$_2$, =O, =S, =N(R$^{310c}$), —N$_3$, and —CN; each R$^{39d}$ is independently selected from: halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —C(O)OR$^{310d}$, —OC(O)R$^{310d}$, —S(O)R$^{310d}$, —S(O)$_2$R$^{310d}$, —NO$_2$, =O, =S, =N(R$^{310d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310d}$, —SR$^{310d}$, —N(R$^{310d}$)$_2$, —C(O)R$^{310d}$, —C(O)N(R$^{310d}$)$_2$, —N(R$^{310d}$)C(O)R$^{310d}$, —N(R$^{310d}$)C(O)N(R$^{310d}$)$_2$, —OC(O)N(R$^{310d}$)$_2$, —N(R$^{310d}$)C(O)OR$^{310d}$, —C(O)OR$^{310d}$, OC(O)R$^{310d}$, —S(O)R$^{310d}$, —S(O)$_2$R$^{310d}$, —NO$_2$, =O, =S, =N(R$^{310d}$), —N$_3$, and —CN; each R$^{39e}$ is independently selected from: halogen, —OR$^{310e}$, SR$^{310e}$, —N(R$^{310e}$)$_2$, —C(O)R$^{310e}$, —C(O)N(R$^{310e}$)$_2$, —N(R$^{310e}$)C(O)R$^{310e}$, —N(R$^{310e}$)C(O)N(R$^{310e}$)$_2$, —OC(O)N(R$^{310e}$)$_2$, —N(R$^{310e}$)C(O)OR$^{310e}$, —C(O)OR$^{310e}$, —OC(O)R$^{310e}$, —S(O)R$^{310e}$, —S(O)$_2$R$^{310e}$, —NO$_2$, =O, =S, =N(R$^{310e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310e}$, —SR$^{310e}$, —N(R$^{310e}$)$_2$, —C(O)R$^{310e}$, —C(O)N(R$^{310e}$)$_2$, —N(R$^{310e}$)C(O)R$^{310e}$, —N(R$^{310e}$)C(O)N(R$^{310e}$)$_2$, —OC(O)N(R$^{310e}$)$_2$, —N(R$^{310e}$)C(O)OR$^{310e}$, —C(O)OR$^{310e}$, —OC(O)R$^{310e}$, —S(O)R$^{310e}$, —S(O)$_2$R$^{310e}$, —NO$_2$, =O, =S, =N(R$^{310e}$), —N$_3$, and —CN; each R$^{39f}$ is independently selected from: halogen, —OR$^{310f}$, —SR$^{310f}$, —N(R$^{310f}$)$_2$, —C(O)R$^{310f}$, —C(O)N(R$^{310f}$)$_2$, —N(R$^{310f}$)C(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —C(O)OR$^{310f}$, —OC(O)R$^{310f}$, —S(O)R$^{310f}$, —S(O)$_2$R$^{310f}$, —NO$_2$, =O, =S, =N(R$^{310f}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310f}$, —SR$^{310f}$, —N(R$^{310f}$)$_2$, —C(O)R$^{310f}$, —C(O)N(R$^{310f}$)$_2$, —N(R$^{310f}$)C(O)R$^{310f}$, —N(R$^{310f}$)C(O)N(R$^{310f}$)$_2$, —OC(O)N(R$^{310f}$)$_2$, —N(R$^{310f}$)C(O)OR$^{310f}$, —C(O)OR$^{310f}$, —OC(O)R$^{310f}$, —S(O)R$^{310f}$, —S(O)$_2$R$^{310f}$, —NO$_2$, =O, =S, =N(R$^{310f}$, —N$_3$, and —CN; each R$^{39g}$ is independently selected from: halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —C(O)OR$^{310g}$, —OC(O)R$^{310g}$, —S(O)R$^{310g}$, —S(O)$_2$R$^{310g}$, —NO$_2$, =O, =S, =N(R$^{310g}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —C(O)OR$^{310g}$, —OC(O)R$^{310g}$, —S(O)R$^{310g}$, —S(O)$_2$R$^{310g}$, —NO$_2$, =O, =S, =N(R$^{310g}$), —N$_3$, and —CN; and each R$^{310z}$, R$^{310b}$, R$^{310c}$, R$^{310d}$, R$^{310e}$, R$^{310f}$, and R$^{310g}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; wherein when s is 3, then each R$^{39b}$ is independently selected from: fluoro, bromo, iodo, —NO$_2$, —N$_3$, —CN, —O(C$_{4-6}$ alkyl), —O(C$_{1-6}$ haloalkyl), —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, and —S(O)$_2$R$^{310b}$; C$_1$ alkyl substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, —CN, and C$_{3-10}$ carbocycle and 3- to 10-membered heterocycle; C$_{2-6}$ alkyl, C$_{2-6}$ alkenyl, and C$_{2-6}$ alkynyl, each of which is optionally substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, and —CN; and C$_{3-10}$ carbocycle and 3- to 10-membered heterocycle, each of which is optionally substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, —S(O)$_2$R$^{310b}$, —NO$_2$, =O, =S, =N(R$^{310b}$), —N$_3$, —CN, C$_{1-6}$ alkyl, C$_{2-6}$ alkenyl, and C$_{2-6}$ alkynyl; wherein when R$^{37}$ is —CH$_3$, then R$^2$ is selected from

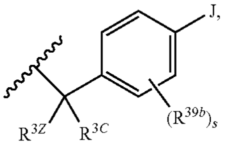

wherein J is selected from halogen, —NO$_2$, —N$_3$, —CN, —O(C$_{4-6}$ alkyl), —O(C$_{1-6}$ haloalkyl), —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, and —S(O)$_2$R$^{310b}$; C$_1$ alkyl substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, —CN, and C$_{3-10}$ carbocycle and 3- to 10-membered heterocycle; C$_{2-6}$ alkyl, C$_{2-6}$ alkenyl, and C$_{2-6}$ alkynyl, each of which is optionally substituted with one or more substituents independently selected from halogen, —OR$^{310b}$, —SR$^{310b}$, —N(R$^{310b}$)$_2$, —C(O)R$^{310b}$, C(O)N(R$^{310b}$)$_2$, —N(R$^{310b}$)C(O)R$^{310b}$, —C(O)OR$^{310b}$, —OC(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —S(O)R$^{310b}$, —S(O)$_2$R$^{310b}$, —NO$_2$, =O, =S, =N(R$^{310b}$), —N$_3$, and —CN; and C$_{3-10}$ carbocycle and 3- to 10-membered heterocycle, each of which is optionally substituted with one or more substituents independently selected from halogen, —OR$^{310b}$, —SR$^{310b}$, —N(R$^{310b}$)$_2$, —C(O)R$^{310b}$, —C(O)N(R$^{310b}$)$_2$, —N(R$^{310b}$)C(O)R$^{310b}$, —N(R$^{310b}$)C(O)N(R$^{310b}$)$_2$, —OC(O)N(R$^{310b}$)$_2$, —N(R$^{310b}$)C(O)OR$^{310b}$, —C(O)OR$^{310b}$, —OC(O)R$^{310b}$, —S(O)R$^{310b}$, —S(O)$_2$R$^{310b}$, —NO$_2$, =O, =S, =N(R$^{310b}$), —N$_3$, —CN, C$_{1-6}$ alkyl, C$_{2-6}$ alkenyl, and C$_{2-6}$ alkynyl; wherein when R$^2$ is

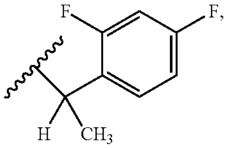

and R$^{37}$ is H, and R$^{35}$ is H, and R$^{36}$ is H; then R$^{38}$ is selected from —C(O)R$^{310g}$, —C(O)N(R$^{310g}$)$_2$, —C(O)OR$^{310g}$, —S(O)R$^{310g}$, and —S(O)$_2$R$^{310g}$; C$_{1-6}$ alkyl optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —C(O)OR$^{310g}$, —OC(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —S(O)R$^{310g}$, —S(O)$_2$R$^{310g}$, —NO$_2$, =O, =S, =N(R$^{310g}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{39g}$; and C$_{3-10}$ carbocycle and 3- to 10-membered heterocycle, each of which is optionally substituted with one or more substituents independently selected from halogen, —OR$^{310g}$, —SR$^{310g}$, —N(R$^{310g}$)$_2$, —C(O)R$^{310g}$, —C(O)N(R$^{310g}$)$_2$, —N(R$^{310g}$)C(O)R$^{310g}$, —N(R$^{310g}$)C(O)N(R$^{310g}$)$_2$, —OC(O)N(R$^{310g}$)$_2$, —N(R$^{310g}$)C(O)OR$^{310g}$, —C(O)OR$^{310g}$, —OC(O)R$^{310g}$, —S(O)R$^{310g}$, —S(O)$_2$R$^{310g}$, —NO$_2$, =O, =S, =N(R$^{310g}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{39g}$. (438): The compound or salt of embodiment 92, wherein when s is 3; then each R$^{39b}$ is independently selected from: fluoro and —CN. (439): The compound or salt of embodiment 92 or embodiment 93, wherein when s is 3; then each R$^{39b}$ is independently selected from; and fluoro. (440): The compound or salt of any one of embodiments 92 to 94, wherein when R$^{37}$ is —CH$_3$; then R$^2$ is selected from

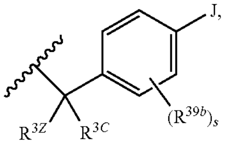

wherein J is selected from fluoro and —CN. (441): The compound or salt of any one of embodiments 92 to 95, wherein when R$^{37}$ is —CH$_3$; then R$^2$ is selected from

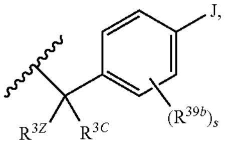

wherein J is selected from fluoro. (442): The compound or salt of any one of embodiments 92 to 96, wherein when R$^2$ is

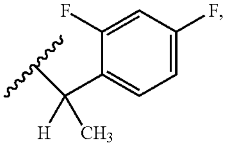 [SMILES: *C(C)c1ccc(F)cc1F]

and R$^{37}$ is H, and R$^{35}$ is H, and R$^{36}$ is H; then R$^8$ is selected from C$_{1-6}$ alkyl. (443): The compound or salt of any one of embodiments 92 to 97, wherein s is an integer selected from 2. (444): The compound or salt of any one of embodiments 92 to 98, wherein R$^{3Z}$ is selected from: methyl. (445): The compound or salt of any one of embodiments 92 to 99, wherein R$^{3C}$ is selected from: hydrogen. (446): The compound or salt of any one of embodiments 92 to 100, wherein R$^{35}$ is selected from: hydrogen. (447): The compound or salt of any one of embodiments 92 to 101, wherein R$^{36}$ is selected from: hydrogen. (448): The compound or salt of any one of embodiments 92 to 102, wherein R$^{35}$ is hydrogen, and R$^{36}$ is hydrogen. (449): The compound or salt of any one of embodiments 92 to 103, wherein R$^{37}$ is selected from hydrogen. (450): The compound or salt of any one of embodiments 92 to 104, wherein R$^{32}$ is selected from The compound or salt of any one of embodiments 1 to 177, wherein R$^{12}$ is selected from

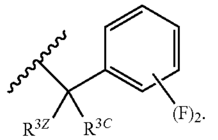

(451): The compound or salt of any one of embodiments 92 to 105, wherein $R^{32}$ is selected from

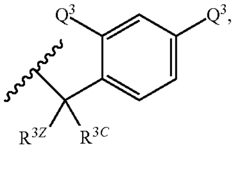

wherein $Q^3$ is selected from halogen, —CN, —OH, —O($C_{1-6}$ alkyl), and —OH. (452): The compound or salt of any one of embodiments 92 to 106, wherein $R^{32}$ is selected from

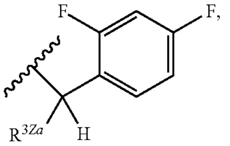

wherein $R^{3Za}$ is selected from methyl, ethyl, isopropyl, isobutyl, and $CH_2OH$. (453): The compound or salt of any one of embodiments 92 to 107, wherein $R^{32}$ is selected from

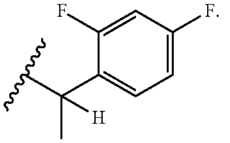 [SMILES: *C(C)c1ccc(F)cc1F]

(454): The compound or salt of any one of embodiments 92 to 108, wherein $R^{38}$ is selected from: hydrogen. (455): The compound or salt of any one of embodiments 92 to 109, wherein each $R^{39b}$ is independently selected from: halogen, —$NO_2$, —CN, —O($C_{1-6}$ haloalkyl), —$SR^{310b}$, and —$N(R^{310b})_2$; $C_1$ alkyl substituted with one or more substituents independently selected from halogen, —$OR^{310b}$, —$SR^{310b}$, —$N(R^{310b})_2$, ═O, —CN; and $C_{2-6}$ alkyl optionally substituted with one or more substituents independently selected from halogen, —$OR^{310b}$, —$SR^{310b}$, —$N(R^{310b})_2$, ═O, and —CN. (456): The compound or salt of any one of embodiments 92 to 110, wherein each $R^{39b}$ is independently selected from: fluoro, and —CN. (457): The compound or salt of any one of embodiments 92 to 111, wherein each $R^{39b}$ is independently selected from: fluoro. (458): The compound or salt of any one of embodiments 1 to 112, selected from compound 31, 32, 42, 50, 87, 101, 102, 166, 167, 169, 501, 502, 504, 506, 507, 508, 509, 510, 511, 512, 513, 514, 517, 517, 519, 520, 521, 522, 523, 524, 525, 527, 528, 529, 530, 531, 532, 533, 534, and 535.

(459): A compound represented by Formula (Ic-e):

(Ic-e)

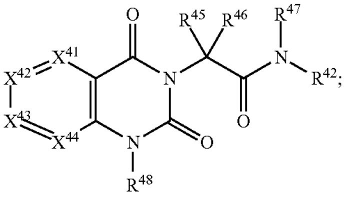

or a salt thereof, wherein: $R^{42}$ is selected from:

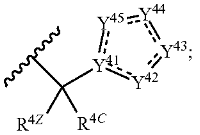

each ---- is independently selected from a single bond and a double bond; $X^{41}$ is selected from $C(R^{41a})$, N, and $N^+$(—$O^-$); $X^{42}$ is selected from $C(R^{41b})$, N, and $N^+$(—$O^-$); $X^{43}$ is selected from $C(R^{41c})$, N, and $N^+$(—$O^-$); $X^{44}$ is selected from $C(R^{41d})$, N, and $N^+$(—$O^-$); wherein no more than two of $X^{41}$, $X^{42}$, $X^{43}$, and $X^{44}$ are N; $Y^{41}$ is selected from C, $C(R^{49bA})$, and N; $Y^{42}$ is selected from $C(R^{49bB})$, $C(R^{49bB})_2$, N, $N^+$(—$O^-$), —$N(R^{49bB})$, O, and S; $Y^{43}$ is selected from $C(R^{49bC})$, $C(R^{49bC})_2$, N, N(—O—), —$N(R^{49bC})$, O, and S; $Y^{44}$ is selected from $C(R^{49bD})$, $C(R^{49bD})_2$, N, $N^+$(—$O^-$), —$N(R^{49bD})$ and S; $Y^{45}$ is selected from $C(R^{49bE})$, $C(R^{49bE})_2$, N, $N^+$(—$O^-$), —$N(R^{49bE})$, O, and S; wherein at least one of $Y^{41}$, $Y^{42}$, $Y^{43}$, $Y^{44}$, and $Y^{45}$ is N; and no more than three of $Y^{41}$, $Y^{42}$, $Y^{43}$, $Y^{44}$, and $Y^{45}$ are N; $R^{41a}$, $R^{41b}$, $R^{41c}$, and $R^{41d}$ are each independently selected from: hydrogen; halogen, —$NO_2$, —$N_3$, —CN, —OR 410a —$SR^{410a}$, —$N(R^{410a})_2$, —$C(O)R^{410a}$, —$C(O)N(R^{410a})_2$, —$N(R^{410a})C(O)R^{410a}$, —$N(R^{410a})C(O)N(R^{410a})_2$, —$OC(O)N(R^{410a})_2$, —$N(R^{410a})C(O)OR^{410a}$, —$C(O)OR^{410}$a —$OC(O)R^{410a}$, —$S(O)R^{410a}$, and —$S(O)_2R^{410a}$; $C_{1-6}$ alkyl, $C_{2-6}$ alkenyl, and $C_{2-6}$ alkynyl, each of which is optionally substituted with one or more substituents independently selected from halogen, —$OR^{410a}$, —$SR^{410a}$, —$N(R^{410a})_2$, —$C(O)R^{410a}$, —$C(O)N(R^{410a})_2$, —$N(R^{410a})C(O)R^{410a}$, —$C(O)OR^{410a}$, —$OC(O)R^{410a}$, —$N(R^{410a})C(O)N(R^{410a})_2$, —$OC(O)N(R^{410a})_2$, —$N(R^{410a})C(O)OR^{410a}$, —$S(O)R^{410a}$, —$S(O)_2R^{410a}$, —$NO_2$, ═O, ═S, ═$N(R^{410a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49a}$; and $C_{3-10}$ carbocycle and 3- to 10-membered heterocycle, each of which is optionally substituted with one or more substituents independently selected from halogen, —$OR^{410a}$, —$SR^{410a}$, —$N(R^{410a})_2$, —$C(O)R^{410a}$, —$C(O)N(R^{410a})_2$, —$N(R^{410a})C(O)R^{410a}$, —$N(R^{410a})C(O)N(R^{410a})_2$, —$OC(O)N(R^{410a})_2$, —$N(R^{410a})C(O)OR^{410a}$, —$C(O)OR^{410a}$, —$OC(O)R^{410a}$, —$S(O)R^{410a}$, —$S(O)_2R^{410a}$, —$NO_2$, ═O, ═S, ═$N(R^{410a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49a}$; $R^{4Z}$ is selected from: hydrogen; —$C(O)R^{10z}$, —$C(O)N(R^{10z})_2$, —$C(O)OR^{10z}$, and —CN; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —N($R^{10z}$)C(O)N($R^{10z}$)$_2$, —OC(O)N($R^{10z}$)$_2$, —N($R^{10z}$)C(O)O$R^{10z}$, —S(O)$R^{10z}$, —S(O)$_2R^{10z}$, —$NO_2$, =O, =S, =N($R^{10z}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —O$R^{10z}$, —S$R^{10z}$, —N($R^{10z}$)$_2$, —C(O)$R^{10z}$, —C(O)N($R^{10z}$)$_2$, —N($R^{10z}$)C(O)$R^{10z}$, —N($R^{10z}$)C(O)N($R^{10z}$)$_2$, —OC(O)N($R^{10z}$)$_2$, —N($R^{10z}$)C(O)O$R^{10z}$, —C(O)O$R^{10z}$, —OC(O)$R^{10z}$, —S(O)$R^{10z}$, —S(O)$_2R^{10z}$, —$NO_2$, =O, =S, =N($R^{10z}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9z}$; $R^{4C}$ is selected from: hydrogen; —C(O)$R^{410c}$, —C(O)N($R^{410c}$)$_2$, —C(O)O$R^{410c}$, and —CN; $C_{1-6}$ alkyl, $C_{2-6}$ alkenyl, and $C_{2-6}$ alkynyl, each of which is optionally substituted with one or more substituents independently selected from halogen, —O$R^{410c}$, —S$R^{410c}$, —N($R^{410c}$)$_2$, —C(O)$R^{410c}$, —C(O)N($R^{410c}$)$_2$, —N($R^{410c}$)C(O)$R^{410c}$, —C(O)O$R^{410c}$, —OC(O)$R^{410c}$, —N($R^{410c}$)C(O)N($R^{410c}$)$_2$, —OC(O)N($R^{410c}$)$_2$, —N($R^{410c}$)C(O)O$R^{410c}$, —S(O)$R^{410c}$, —S(O)$_2R^{410c}$, —$NO_2$, =O, =S, =N($R^{410c}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49c}$; and $C_{3-10}$ carbocycle and 3- to 10-membered heterocycle, each of which is optionally substituted with one or more substituents independently selected from halogen, —O$R^{410c}$, —S$R^{410c}$, —N($R^{410c}$)$_2$, —C(O)$R^{410c}$, —C(O)N($R^{410c}$)$_2$, —N($R^{410c}$)C(O)$R^{410c}$, —N($R^{410c}$)C(O)N($R^{410c}$)$_2$, —OC(O)N($R^{410c}$)$_2$, —N($R^{410c}$)C(O)O$R^{410c}$, —C(O)O$R^{410c}$, —OC(O)$R^{410c}$, —S(O)$R^{410c}$, —S(O)$_2R^{410c}$, —$NO_2$, =O, =S, =N($R^{410c}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49c}$; $R^{45}$ is selected from: hydrogen; halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —OC(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2R^{410d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —C(O)O$R^{410d}$, —C(O)$R^{410d}$, —N($R^{410d}$)C(O)N($R^{410d}$)$_2$, —OC(O)N($R^{410d}$)$_2$, —N($R^{410d}$)C(O)O$R^{410d}$, —S(O)$R^{410d}$, —S(O)$_2R^{410d}$, —$NO_2$, =O, =S, =N($R^{410d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49d}$; and $C_{3-10}$ carbocycle and 3- to 10-membered heterocycle, each of which is optionally substituted with one or more substituents independently selected from halogen, —O$R^{410d}$, —S$R^{410d}$, —N($R^{410d}$)$_2$, —C(O)$R^{410d}$, —C(O)N($R^{410d}$)$_2$, —N($R^{410d}$)C(O)$R^{410d}$, —N($R^{410d}$)C(O)N($R^{410d}$)$_2$, —OC(O)N($R^{410d}$)$_2$, —N($R^{410d}$)C(O)O$R^{410d}$, —C(O)O$R^{410d}$, —OC(O)$R^{410d}$, —S(O)$R^{410d}$, —S(O)$_2R^{410d}$, —$NO_2$, =O, =S, =N($R^{410d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49d}$; or $R^{45}$ together with $R^{46}$ form a 3- to 10-membered heterocycle or $C_{3-10}$ carbocycle, wherein the 3- to 10-membered heterocycle or $C_{3-10}$ carbocycle is optionally substituted with one or more $R^{49d}$. $R^{46}$ is selected from: hydrogen; halogen, —O$R^{410e}$, —S$R^{410e}$, —N($R^{410e}$)$_2$, —C(O)$R^{410e}$, —C(O)N($R^{410e}$)$_2$, —N($R^{410e}$)C(O)$R^{410e}$, —C(O)O$R^{410e}$, —OC(O)$R^{410e}$, —N($R^{410e}$)C(O)N($R^{410e}$)$_2$, —OC(O)N($R^{410e}$)$_2$, —N($R^{410e}$)C(O)O$R^{410e}$, —S(O)$R^{410e}$, —S(O)$_2R^{410e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —O$R^{410e}$, —S$R^{410e}$, —N($R^{410e}$)$_2$, —C(O)$R^{410e}$, —C(O)N($R^{410e}$)$_2$, —N($R^{410e}$)C(O)$R^{410e}$, —C(O)O$R^{410e}$, —OC(O)$R^{410e}$, —N($R^{410e}$)C(O)N($R^{410e}$)$_2$, —OC(O)N($R^{410e}$)$_2$, —N($R^{410e}$)C(O)O$R^{410e}$, —S(O)$R^{410e}$, —S(O)$_2R^{410e}$, —$NO_2$, =O, =S, =N($R^{410e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49e}$; and $C_{3-10}$ carbocycle and 3- to 10-membered heterocycle, each of which is optionally substituted with one or more substituents independently selected from halogen, —O$R^{410e}$, —S$R^{410e}$, —N($R^{410e}$)$_2$, —C(O)$R^{410e}$, —C(O)N($R^{410e}$)$_2$, —N($R^{410e}$)C(O)$R^{410e}$, —N($R^{410e}$)C(O)N($R^{410e}$)$_2$, —OC(O)N($R^{410e}$)$_2$, —N($R^{410e}$)C(O)O$R^{410e}$, —C(O)O$R^{410e}$, —OC(O)$R^{410e}$, —S(O)$R^{410e}$, —S(O)$_2R^{410e}$, —$NO_2$, =O, =S, =N($R^{410e}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49e}$; or $R^{46}$ together with $R^{45}$ form a 3- to 10-membered heterocycle or $C_{3-10}$ carbocycle, wherein the 3- to 10-membered heterocycle or $C_{3-10}$ carbocycle is optionally substituted with one or more $R^{49e}$. $R^{47}$ is selected from: hydrogen; —C(O)$R^{410f}$, —C(O)N($R^{410f}$)$_2$, —C(O)O$R^{410f}$, —S(O)$R^{410f}$, and —S(O)$_2R^{410f}$; $C_{1-6}$ alkyl optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —C(O)O$R^{410f}$, —OC(O)$R^{410f}$, —N($R^{410f}$)C(O)N($R^{410f}$)$_2$, —OC(O)N($R^{410f}$)$_2$, —N($R^{410f}$)C(O)O$R^{410f}$, —S(O)$R^{410f}$, —S(O)$_2R^{410f}$, —$NO_2$, =O, =S, =N($R^{410f}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49f}$; and $C_{3-10}$ carbocycle and 3- to 10-membered heterocycle, each of which is optionally substituted with one or more substituents independently selected from halogen, —O$R^{410f}$, —S$R^{410f}$, —N($R^{410f}$)$_2$, —C(O)$R^{410f}$, —C(O)N($R^{410f}$)$_2$, —N($R^{410f}$)C(O)$R^{410f}$, —N($R^{410f}$)C(O)N($R^{410f}$)$_2$, —OC(O)N($R^{410f}$)$_2$, —N($R^{410f}$)C(O)O$R^{410f}$, —C(O)O$R^{410f}$, —OC(O)$R^{410f}$, —S(O)$R^{410f}$, —S(O)$_2R^{410f}$, —$NO_2$, =O, =S, =N($R^{410f}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49f}$; $R^{48}$ is selected from: hydrogen; —C(O)$R^{410g}$, —C(O)N($R^{410g}$)$_2$, —C(O)O$R^{410g}$, —S(O)$R^{410g}$, and —S(O)$_2R^{410g}$; $C_{1-6}$ alkyl optionally substituted with one or more substituents independently selected from halogen, —O$R^{410g}$, —S$R^{410g}$, —N($R^{410g}$)$_2$, —C(O)$R^{410g}$, —C(O)N($R^{410g}$)$_2$, —N($R^{410g}$)C(O)$R^{410g}$, —C(O)O$R^{410g}$, —OC(O)$R^{410g}$, —N($R^{410g}$)C(O)N($R^{410g}$)$_2$, —OC(O)N($R^{410g}$)$_2$, —N($R^{410g}$)C(O)O$R^{410g}$, —S(O)$R^{410g}$, —S(O)$_2R^{410g}$, —$NO_2$, =O, =S, =N($R^{410g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{49g}$; and $C_{3-10}$ carbocycle and 3- to 10-membered heterocycle, each of which is optionally substituted with one or more substituents independently selected from halogen, —O$R^{410g}$, —S$R^{410g}$, —N($R^{410g}$)$_2$, —C(O)$R^{410g}$, —C(O)N($R^{410g}$)$_2$, —N($R^{410g}$)C(O)$R^{410g}$, —N($R^{410g}$)C(O)N($R^{410g}$)$_2$, —OC(O)N($R^{410g}$)$_2$, —N($R^{410g}$)C(O)O$R^{410g}$, —C(O)O$R^{410g}$, —OC(O)$R^{410g}$, —S(O)$R^{410g}$, —$S(O)_2R^{410g}$, —$NO_2$, =O, =S, =$N(R^{410g})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{49g}$; wherein when $R^{4Z}$ is hydrogen, and $R^{4C}$ is hydrogen; then: $Y^{42}$ is selected from $C(R^{14b})$, N, $N^+(—O^-)$, and $N(C_{1-6}$ alkyl); and $Y^{45}$ is selected from $C(R^{14b})$, N, $N^+(—O^-)$, and $N(C_{1-6}$ alkyl); each $R^{49a}$ is independently selected from: halogen, —$OR^{410a}$, —$SR^{410a}$, —$N(R^{410a})_2$, —$C(O)R^{410a}$, —$C(O)N(R^{410a})_2$, —$N(R^{410a})C(O)R^{410a}$, —$N(R^{410a})C(O)N(R^{410a})_2$, —$OC(O)N(R^{410a})_2$, —$N(R^{410a})C(O)OR^{410a}$, —$C(O)OR^{410a}$, —$OC(O)R^{410a}$, —$S(O)R^{410a}$, —$S(O)_2R^{410a}$, —$NO_2$, =O, =S, =$N(R^{410a})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410a}$, —$SR^{410a}$, —$N(R^{410a})_2$, —$C(O)R^{410a}$, —$C(O)N(R^{410a})_2$, —$N(R^{410a})C(O)R^{410a}$, —$N(R^{410a})C(O)N(R^{410a})_2$, —$OC(O)N(R^{410a})_2$, —$N(R^{410a})C(O)OR^{410a}$, —$C(O)OR^{410a}$, —$OC(O)R^{410a}$, —$S(O)R^{410a}$, —$S(O)_2R^{410a}$, —$NO_2$, =O, =S, =$N(R^{410a})$, —$N_3$, and —CN; each $R^{49bA}$, $R^{49bB}$, $R^{49bC}$, $R^{49bD}$, and $R^{49bE}$ is independently selected from: hydrogen; halogen, —$NO_2$, —$N_3$, —CN, —$OR^{410b}$, —$SR^{410b}$, —$N(R^{410b})_2$, —$C(O)R^{410b}$, —$C(O)N(R^{410b})_2$, —$N(R^{410b})C(O)R^{410b}$, —$N(R^{410b})C(O)N(R^{410b})_2$, —$OC(O)N(R^{410b})_2$, —$N(R^{410b})C(O)OR^{410b}$, —$C(O)OR^{410b}$, —$OC(O)R^{410b}$, —$S(O)R^{410b}$, and —$S(O)_2R^{410b}$; $C_{1-6}$ alkyl, $C_{2-6}$ alkenyl, and $C_{2-6}$ alkynyl, each of which is optionally substituted with one or more substituents independently selected from halogen, —$OR^{410b}$, —$SR^{410b}$, —$N(R^{410b})_2$, —$C(O)R^{410b}$, —$C(O)N(R^{410})_2$, —$N(R^{410b})C(O)R^{410b}$, —$C(O)OR^{410b}$, —$OC(O)R^{410b}$, —$N(R^{410b})C(O)N(R^{410b})_2$, —$OC(O)N(R^{410b})_2$, —$N(R^{410b})C(O)OR^{410b}$, —$S(O)R^{410b}$, —$S(O)_2R^{410b}$, —$NO_2$, =O, =S, =$N(R^{410b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{410b}$, —$SR^{410b}$, —$N(R^{410b})_2$, —$C(O)R^{410b}$, —$C(O)N(R^{410b})_2$, —$N(R^{410b})C(O)R^{410b}$, —$N(R^{410b})C(O)N(R^{410b})_2$, —$OC(O)N(R^{410b})_2$, —$N(R^{410b})C(O)OR^{410b}$, —$C(O)OR^{410b}$, —$OC(O)R^{410b}$, —$S(O)R^{410b}$, —$S(O)_2R^{410b}$, —$NO_2$, =O, =S, =$N(R^{410b})$, —$N_3$, —CN, $C_{1-6}$ alkyl, $C_{2-6}$ alkenyl, and $C_{2-6}$ alkynyl; each $R^{49z}$ is independently selected from: halogen, —$OR^{410z}$, —$SR^{410z}$, —$N(R^{410z})_2$, —$C(O)R^{410z}$, —$C(O)N(R^{410z})_2$, —$N(R^{410z})C(O)R^{410z}$, —$N(R^{410z})C(O)N(R^{410z})_2$, —$OC(O)N(R^{410z})_2$, —$N(R^{410z})C(O)OR^{410z}$, —$C(O)OR^{410z}$, —$OC(O)R^{410z}$, —$S(O)R^{410z}$, —$S(O)_2R^{410z}$, —$NO_2$, =O, =S, =$N(R^{410z})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410z}$, —$SR^{410z}$, —$N(R^{410z})_2$, —$C(O)R^{410z}$, —$C(O)N(R^{410z})_2$, —$N(R^{410z})C(O)R^{410z}$, —$N(R^{410z})C(O)N(R^{410z})_2$, —$OC(O)N(R^{410z})_2$, —$N(R^{410z})C(O)OR^{410z}$, —$C(O)OR^{410z}$, —$OC(O)R^{410z}$, —$S(O)R^{410z}$, —$S(O)_2R^{410z}$, —$NO_2$, =O, =S, =$N(R^{410z})$, —$N_3$, and —CN; each $R^{49c}$ is independently selected from: halogen, —$OR^{410c}$, —$SR^{410c}$, —$N(R^{410c})_2$, —$C(O)R^{410c}$, —$C(O)N(R^{410c})_2$, —$N(R^{410c})C(O)R^{410c}$, —$N(R^{410c})C(O)N(R^{410c})_2$, —$OC(O)N(R^{410c})_2$, —$N(R^{410c})C(O)OR^{410c}$, —$C(O)OR^{410c}$, —$OC(O)R^{410c}$, —$S(O)R^{410c}$, —$S(O)_2R^{410c}$, —$NO_2$, =O, =S, =$N(R^{410c})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410c}$, —$SR^{410c}$, —$N(R^{410c})_2$, —$C(O)R^{410c}$, —$C(O)N(R^{410c})_2$, —$N(R^{410c})C(O)R^{410c}$, —$N(R^{410c})C(O)N(R^{410c})_2$, —$OC(O)N(R^{410c})_2$, —$N(R^{410c})C(O)OR^{410c}$, —$C(O)OR^{410c}$, —$OC(O)R^{410c}$, —$S(O)R^{410c}$, —$S(O)_2R^{410c}$, —$NO_2$, =O, =S, =$N(R^{410c})$, —$N_3$, and —CN; each $R^{49d}$ is independently selected from: halogen, —$OR^{410d}$, —$SR^{410d}$, —$N(R^{410d})_2$, —$C(O)R^{410d}$, —$C(O)N(R^{410d})_2$, —$N(R^{410d})C(O)R^{410d}$, —$N(R^{410d})C(O)N(R^{410d})_2$, —$OC(O)N(R^{410d})_2$, —$N(R^{410d})C(O)OR^{410d}$, —$C(O)OR^{410d}$, —$OC(O)R^{410d}$, —$S(O)R^{410d}$, —$S(O)_2R^{410d}$, —$NO_2$, =O, =S, =$N(R^{410d})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410d}$, —$SR^{410d}$, —$N(R^{410d})_2$, —$C(O)R^{410d}$, —$C(O)N(R^{410d})_2$, —$N(R^{410d})C(O)R^{410d}$, —$N(R^{410d})C(O)N(R^{410d})_2$, —$OC(O)N(R^{410d})_2$, —$N(R^{410d})C(O)OR^{410d}$, —$C(O)OR^{410d}$, —$OC(O)R^{410d}$, —$S(O)R^{410d}$, —$S(O)_2R^{410d}$, —$NO_2$, =O, =S, =$N(R^{410d})$, —$N_3$, and —CN; each $R^{49e}$ is independently selected from: halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410e}$, —$SR^{410e}$, —$N(R^{410e})_2$, —$C(O)R^{410e}$, —$C(O)N(R^{410e})_2$, —$N(R^{410e})C(O)R^{410e}$, —$N(R^{410e})C(O)N(R^{410e})_2$, —$OC(O)N(R^{410e})_2$, —$N(R^{410e})C(O)OR^{410e}$, —$C(O)OR^{410e}$, —$OC(O)R^{410e}$, —$S(O)R^{410e}$, —$S(O)_2R^{410e}$, —$NO_2$, =O, =S, =$N(R^{410e})$, —$N_3$, and —CN; each $R^{49f}$ is independently selected from: halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$N(R^{410f})C(O)N(R^{410f})_2$, —$OC(O)N(R^{410f})_2$, —$N(R^{410f})C(O)OR^{410f}$, —$C(O)OR^{410f}$, —$OC(O)R^{410f}$, —$S(O)R^{410f}$, —$S(O)_2R^{410f}$, —$NO_2$, =O, =S, =$N(R^{410f})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410f}$, —$SR^{410f}$, —$N(R^{410f})_2$, —$C(O)R^{410f}$, —$C(O)N(R^{410f})_2$, —$N(R^{410f})C(O)R^{410f}$, —$N(R^{410f})C(O)N(R^{410f})_2$, —$OC(O)N(R^{410f})_2$, —$N(R^{410f})C(O)OR^{410f}$, —$C(O)OR^{410f}$, —$OC(O)R^{410f}$, —$S(O)R^{410f}$, —$S(O)_2R^{410f}$, —$NO_2$, =O, =S, =$N(R^{410f})$, —$N_3$, and —CN; each $R^{49g}$ is independently selected from: halogen, —$OR^{410g}$, —$SR^{410g}$, —$N(R^{410g})_2$, —$C(O)R^{410g}$, —$C(O)N(R^{410g})_2$, —$N(R^{410g})C(O)R^{410g}$, —$N(R^{410g})C(O)N(R^{410g})_2$, —$OC(O)N(R^{410g})_2$, —$N(R^{410g})C(O)OR^{410g}$, —$C(O)OR^{410g}$, —$OC(O)R^{410g}$, —$S(O)R^{410g}$, —$S(O)_2R^{410g}$, —$NO_2$, =O, =S, =$N(R^{410g})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{410g}$, —$SR^{410g}$, —$N(R^{410g})_2$, —$C(O)R^{410g}$, —$C(O)N(R^{410g})_2$, —$N(R^{410g})C(O)R^{410g}$, —$N(R^{410g})C(O)N(R^{410g})_2$, —$OC(O)N(R^{410g})_2$, —$N(R^{410g})C(O)OR^{410g}$, —$C(O)OR^{410g}$, —$OC(O)R^{410g}$, —$S(O)R^{410g}$, —$S(O)_2R^{410g}$, —$NO_2$, =O, =S, =$N(R^{410g})$, —$N_3$, and —CN; and each $R^{410a}$, $R^{410b}$, $R^{410c}$, $R^{410d}$, $R^{410e}$, $R^{410f}$, $R^{410g}$ is independently selected from: hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl. (460): The compound or salt of embodiment 114, wherein two of ---- are selected from double bond. (461): The compound or salt of embodiment 114 or embodiment 115, wherein no more than one of $X^{41}$, $X^{42}$, $X^{43}$, and $X^{44}$ is N. (462): The compound or salt of any one of embodiments 114 to embodiment 116, wherein no more than one of $Y^{41}$, $Y^{42}$, $Y^{43}$, $Y^{44}$, and $Y^{45}$ are N. (463): The compound or salt of any one of embodiments 114 to embodiment 117, wherein $X^{41}$, $X^{42}$, $X^{43}$, and $X^{44}$ are each independently selected from N, C(H), C(F), and C(CN). (464): The compound or salt of any one of embodiments 114 to 118, wherein $X^{43}$ and $X^{44}$ are C(H). (465): The compound or salt of any one of embodiments 114 to 119, wherein $R^{41a}$, $R^{41b}$, $R^{41c}$, and $R^{41d}$, are each independently selected from: hydrogen, fluoro, —CN, and $C_{1-6}$ alkyl. (466): The compound or salt of any one of embodiments 114 to 120, wherein $R^{4Z}$ is selected from $C_1$ alkyl. (467): The compound or salt of any one of embodiments 114 to 121, wherein $R^{4C}$ is selected from: hydrogen. (468): The compound or salt of any one of embodiments 114 to 122, wherein $R^{45}$ is selected from: hydrogen. (469): The compound or salt of any one of embodiments 114 to 123, wherein $R^{46}$ is selected from: hydrogen. (470): The compound or salt of any one of embodiments 114 to 124, wherein $R^{45}$ is hydrogen, and $R^{46}$ is hydrogen. (471): The compound or salt of any one of embodiments 114 to 125, wherein $R^{47}$ is selected from hydrogen. (472): The compound or salt of any one of embodiments 114 to 126, wherein $Y^{41}$ is selected from C and N. (473): The compound or salt of any one of embodiments 114 to 127, wherein $Y^{41}$ is selected from C. (474): The compound or salt of any one of embodiments 114 to 128, wherein $Y^{42}$, $Y^{43}$, $Y^{44}$, and $Y^{45}$ are each independently selected from C(H), C(CN), C(F), C(Cl), N, O, and S. (475): The compound or salt of any one of embodiments 114 to 129, wherein $Y^{42}$, $Y^{43}$, $Y^{44}$, and $Y^{45}$ are each independently selected from C(H), C(CN), C(F), C(Cl), and N. (476): The compound or salt of any one of embodiments 114 to 130, wherein $R^{48}$ is selected from: hydrogen. (477): The compound or salt of any one of embodiments 114 to 131, wherein $R^{9bA}$, $R^{9bB}$, $R^{9bC}$, $R^{9bD}$, and $R^{9bE}$ are each independently selected from: hydrogen, halogen, —CN, —$OR^{410b}$, —$SR^{410b}$, and —$N(R^{410b})_2$, and $C_{1-6}$ alkyl. (478): The compound or salt of any one of embodiments 114 to 132, wherein $R^{9bA}$, $R^{9bB}$, $R^{9bC}$, $R^{9bD}$, and $R^{9bE}$ are each independently selected from: hydrogen, halogen, —CN, —$OR^{410b}$, and $C_{1-6}$ alkyl. (479): The compound or salt of any one of embodiments 114 to 133, wherein each $R^{410a}$, $R^{410b}$, $R^{410z}$, $R^{410c}$, $R^{410d}$, $R^{410e}$, $R^{410f}$, and $R^{410g}$ is independently selected from: hydrogen. (480): The compound or salt of any one of embodiments 114 to 134, wherein when $R^{4Z}$ is hydrogen, and $R^{4C}$ is hydrogen; then: $Y^{42}$ is selected from C(F), C(CN) and N; and $Y^{45}$ is selected from C(F), C(CN), and N. (481): The compound or salt of any one of embodiments 114 to 135, wherein $R^{42}$ is selected from

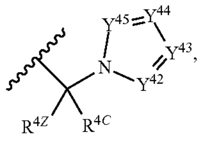

wherein $Y^{42}$ is selected from $C(R^{49bB})$, N, and $N^+(—O^-)$; $Y^{43}$ is selected from $C(R^{49bC})$, N, and $N^+(—O^-)$; $Y^{44}$ is selected from $C(R^{49bD})$, N, and $N^+(—O^-)$; and $Y^{45}$ is selected from $C(R^{49bE})$, N, and $N^+(—O^-)$. (482): The compound or salt of any one of embodiments 114 to 136, wherein $R^{42}$ is selected from

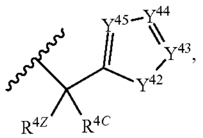

wherein $Y^{42}$ is selected from $C(R^{49bB})_2$, —$N(R^{49bB})$, —$N(R^{49bB})(—O^-)$ O, and S; $Y^{43}$ is selected from $C(R^{49bC})$, N, and $N^+(—O^-)$; $Y^{44}$ is selected from $C(R^{49bD})$, N, and $N^+(—O^-)$; and $Y^{45}$ is selected from $C(R^{49bE})$, N, and $N^+(—O^-)$. (483): The compound or salt of any one of embodiments 114 to 137, wherein $R^{42}$ is selected from

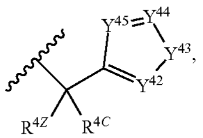

wherein $Y^{42}$ is selected from $C(R^{49bB})$, N, and $N^+(—O^-)$; $Y^{43}$ is selected from $C(R^{49bC})_2$, —$N(R^{49bC})$, $N^+(R^{49bC})(—O^-)$, O, and S; $Y^{44}$ is selected from $C(R^{49bD})$, N, and $N^+(—O^-)$; and $Y^{45}$ is selected from $C(R^{49bE})$, N, and $N^+(—O^-)$. (484): The compound or salt of any one of embodiments 114 to 138, wherein $R^{42}$ is selected from

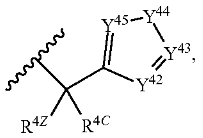

wherein $Y^{42}$ is selected from $C(R^{49bB})$, N, and $N^+(—O^-)$; $Y^{43}$ is selected from $C(R^{49bC})$, N, and $N^+(—O^-)$; $Y^{44}$ is selected from $C(R^{49bD})_2$, —$N(R^{49bD})$, $N^+(R^{49bD})(—O^-)$, and S; and $Y^{45}$ is selected from $C(R^{49bE})$, N, and $N^+(—O^-)$; or $R^{42}$ is selected from:

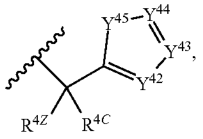

wherein $Y^{42}$ is selected from $C(R^{49bB})$, N, and $N^+(—O^-)$; $Y^{43}$ is selected from $C(R^{49bC})$, N, and $N^+(—O^-)$; $Y^{44}$ is selected from $C(R^{49bD})$, N, and $N^+(—O^-)$; and $Y^{45}$ is selected from $C(R^{49bE})_2$, —$N(R^{49bE})$, —$N(R^{49bE})(—O^-)$, O, and S. (485): The compound or salt of any one of embodiments 114 to 139, wherein $R^{42}$ is selected from:

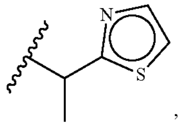
,
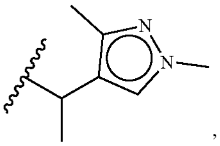
,
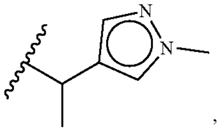
,
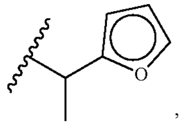
, and
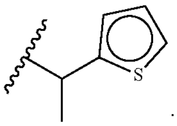
.

(486): A compound represented by Formula (Id-e):

(Id-e)

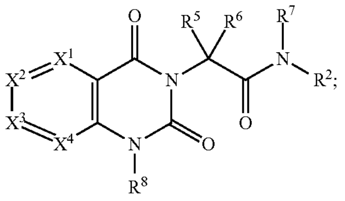

or a salt thereof, wherein: $R^2$ is selected from:

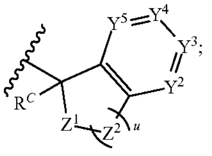

u is an integer selected from 0, 1, 2, and 3; $Z^1$ is selected from: —$C(R^Z)_2$—, —$N(R^Z)$—, —O—, and —S—; each $Z^2$ is independently selected from: —$C(R^Z)_2$—, —$N(R^Z)$—, —O—, and —S—; $X^1$ is selected from $C(R^{1a})$, N, and $N^+(—O^-)$; $X^2$ is selected from $C(R^{1b})$, N, and $N^+(—O^-)$; $X^3$ is selected from $C(R^{1c})$, N, and $N^+(—O^-)$; $X^4$ is selected from $C(R^{1d})$ N, and $N^+(—O^-)$; wherein no more than two of $X^1$, $X^2$, $X^3$, and $X^4$ are N; $Y^2$ is selected from $C(R^{9bB})$ N, and $N^+(—O^-)$; $Y^3$ is selected from $C(R^{9b}c)$, N, and $N^+(—O^-)$; $Y^4$ is selected from $C(R^{9bD})$, N, and $N^+(—O^-)$; $Y^5$ is selected from $C(R^{9bE})$, N, and $N^+(—O^-)$; wherein at least one of $Y^2$, $Y^3$, $Y^4$, and $Y^5$ is N; wherein no more than three of $Y^2$, $Y^3$, $Y^4$, and $Y^5$ are N; $R^{1a}$, $R^{1b}$, $R^{1c}$, and $R^{1d}$, are each independently selected from: hydrogen; halogen, —$NO_2$, —$N_3$, —CN, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, and —$S(O)_2R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$C(O)OR^{10a}$, —$OC(O)R^{10a}$, —$N(R^{10a})C(O)N(R^{10a})_2$, —$OC(O)N(R^{10a})_2$, —$N(R^{10a})C(O)OR^{10a}$, —$S(O)R^{10a}$, —$S(O)_2R^{10a}$, —$NO_2$, =O, =S, =$N(R^{10a})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; each $R^Z$ is independently selected from: hydrogen; —CN, —$C(O)R^{10z}$, —$C(O)N(R^{10z})_2$, and —$C(O)OR^{10z}$; $C_{1-6}$ alkyl, $C_{2-6}$ alkenyl, and $C_{2-6}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$C(O)OR^{10z}$, —$OC(O)R^{10z}$, —$N(R^{10z})C(O)N(R^{10z})_2$, —$OC(O)N(R^{10z})_2$, —$N(R^{10z})C(O)OR^{10z}$, —$S(O)R^{10z}$, —$S(O)_2R^{10z}$, —$NO_2$, =O, =S, =$N(R^{10z})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9z}$; and $C_{3-10}$ carbocycle and 3- to 10-membered heterocycle, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9z}$; $R^C$ is selected from: hydrogen; —CN, —$C(O)R^{10c}$, —$C(O)N(R^{10c})_2$, —$C(O)OR^{10c}$; $C_{1-6}$ alkyl, $C_{2-6}$ alkenyl, and $C_{2-6}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$C(O)OR^{10c}$, —$OC(O)R^{10c}$, —$N(R^{10c})C(O)N(R^{10c})_2$, —$OC(O)N(R^{10c})_2$, —$N(R^{10c})C(O)OR^{10c}$, —$S(O)R^{10c}$, —$S(O)_2R^{10c}$, —$NO_2$, =O, =S, =$N(R^{10c})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9c}$; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9c}$; $R^5$ is selected from: hydrogen; halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$C(O)OR^{10d}$, —$OC(O)R^{10d}$, —$N(R^{10d})C(O)N(R^{10d})_2$, —$OC(O)N(R^{10d})_2$, —$N(R^{10d})C(O)OR^{10d}$, —$S(O)R^{10d}$, —$S(O)_2R^{10d}$, —$NO_2$, =O, =S, =$N(R^{10d})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9d}$; and $C_{3-10}$ carbocycle and 3- to 10-membered heterocycle, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9d}$; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9d}$; $R^6$ is selected from: hydrogen; halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, —$N_3$, and —CN; $C_{1-6}$ alkyl, $C_{2-6}$ alkenyl, and $C_{2-6}$ alkynyl, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$C(O)OR^{10e}$, —$OC(O)R^{10e}$, —$N(R^{10e})C(O)N(R^{10e})_2$, —$OC(O)N(R^{10e})_2$, —$N(R^{10e})C(O)OR^{10e}$, —$S(O)R^{10e}$, —$S(O)_2R^{10e}$, —$NO_2$, =O, =S, =$N(R^{10e})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9e}$; and $C_{3-10}$ carbocycle and 3- to 10-membered heterocycle, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$N(R^{10e})C(O)N(R^{10e})_2$, —$OC(O)N(R^{10e})_2$, —$N(R^{10e})C(O)OR^{10e}$, —$C(O)OR^{10e}$, —$OC(O)R^{10e}$, —$S(O)R^{10e}$, —$S(O)_2R^{10c}$, —$NO_2$, =O, =S, =$N(R^{10e})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9e}$; or $R^6$ together with $R^5$ form a 3- to 10-membered heterocycle or $C_{3-10}$ carbocycle, wherein the 3- to 10-membered heterocycle or $C_{3-10}$ carbocycle is optionally substituted with one or more $R^{9e}$; $R^7$ is selected from: hydrogen; —$C(O)R^{10f}$, —$C(O)N(R^{10f})_2$, —$C(O)OR^{10f}$, —$S(O)R^{10f}$, and —$S(O)_2R^{10f}$; $C_{1-6}$ alkyl optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$C(O)OR^{10f}$, —$OC(O)R^{10f}$, —$N(R^{10f})C(O)N(R^{10f})_2$, —$OC(O)N(R^{10f})_2$, —$N(R^{10f})C(O)OR^{10f}$, —$S(O)R^{10f}$, —$S(O)_2R^{10f}$, —$NO_2$, =O, =S, =$N(R^{10f})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9f}$; and $C_{3-10}$ carbocycle and 3- to 10-membered heterocycle, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9f}$; $R^8$ is selected from: hydrogen; —$C(O)R^{10g}$, —$C(O)N(R^{10g})_2$, —$C(O)OR^{10g}$, —$S(O)R^{10g}$, and —$S(O)_2R^{10g}$; $C_{1-6}$ alkyl optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$C(O)OR^{10g}$, —$OC(O)R^{10g}$, —$N(R^{10g})C(O)N(R^{10g})_2$, —$OC(O)N(R^{10g})_2$, —$N(R^{10g})C(O)OR^{109}$, —$S(O)R^{109}$, —$S(O)_2R^{10g}$, —$NO_2$, =O, =S, =$N(R^{10g})$, —$N_3$, —CN, $C_{3-10}$ carbocycle and 3- to 10-membered heterocycle, wherein the $C_{3-10}$ carbocycle and 3- to 10-membered heterocycle are each optionally substituted with one or more $R^{9g}$; and $C_{3-10}$ carbocycle and 3- to 10-membered heterocycle, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9g}$; each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, and —CN; $R^{9bB}$, $R^{9bC}$, $R^{9bD}$, and $R^{9bE}$ are each independently selected from: hydrogen; halogen, —$NO_2$, —$N_3$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$; $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —$N_3$, —CN, $C_{1-6}$ alkyl, $C_{2-6}$ alkenyl, and $C_{2-6}$ alkynyl; each $R^{9z}$ is independently selected from: halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, and —CN; each $R^{9c}$ is independently selected from: halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{10c}$, —SR$^{10c}$, —N(R$^{10c}$)$_2$, —C(O)R$^{10c}$, —C(O)N(R$^{10c}$)$_2$, —N(R$^{10c}$)C(O)R$^{10c}$, —N(R$^{10c}$)C(O)N(R$^{10c}$)$_2$, —OC(O)N(R$^{10c}$)$_2$, —N(R$^{10c}$)C(O)OR$^{10c}$, —C(O)OR$^{10c}$, —OC(O)R$^{10c}$, —S(O)R$^{10c}$, —S(O)$_2$R$^{10c}$, —NO$_2$, =O, =S, =N(R$^{10c}$), —N$_3$, and —CN; each R$^{9d}$ is independently selected from: halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, =O, =S, =N(R$^{10d}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{10d}$, —SR$^{10d}$, —N(R$^{10d}$)$_2$, —C(O)R$^{10d}$, —C(O)N(R$^{10d}$)$_2$, —N(R$^{10d}$)C(O)R$^{10d}$, —N(R$^{10d}$)C(O)N(R$^{10d}$)$_2$, —OC(O)N(R$^{10d}$)$_2$, —N(R$^{10d}$)C(O)OR$^{10d}$, —C(O)OR$^{10d}$, —OC(O)R$^{10d}$, —S(O)R$^{10d}$, —S(O)$_2$R$^{10d}$, —NO$_2$, =O, =S, =N(R$^{10d}$), —N$_3$, and —CN; each R$^{9e}$ is independently selected from: halogen, —OR$^{10e}$, —SR$^{10e}$, —N(R$^{10e}$)$_2$, —C(O)R$^{10e}$, —C(O)N(R$^{10e}$)$_2$, —N(R$^{10e}$)C(O)R$^{10e}$, —N(R$^{10e}$)C(O)N(R$^{10e}$)$_2$, —OC(O)N(R$^{10e}$)$_2$, —N(R$^{10e}$)C(O)OR$^{10e}$, —C(O)OR$^{10e}$, —OC(O)R$^{10e}$, —S(O)R$^{10e}$, —S(O)$_2$R$^{10e}$, —NO$_2$, =O, =S, =N(R$^{10e}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{10e}$, —SR$^{10e}$, —N(R$^{10e}$)$_2$, —C(O)R$^{10e}$, —C(O)N(R$^{10e}$)$_2$, —N(R$^{10e}$)C(O)R$^{10e}$, —N(R$^{10e}$)C(O)N(R$^{10e}$)$_2$, —OC(O)N(R$^{10e}$)$_2$, —N(R$^{10e}$)C(O)OR$^{10e}$, —C(O)OR$^{10e}$, —OC(O)R$^{10e}$, —S(O)R$^{10e}$, —S(O)$_2$R$^{10e}$, —NO$_2$, =O, =S, =N(R$^{10e}$), —N$_3$, and —CN; each R$^{9f}$ is independently selected from: halogen, —OR$^{10f}$, —SR$^{10f}$, —N(R$^{10f}$)$_2$, —C(O)R$^{10f}$, —C(O)N(R$^{10f}$)$_2$, —N(R$^{10f}$)C(O)R$^{10f}$, —N(R$^{10f}$)C(O)N(R$^{10f}$)$_2$, —OC(O)N(R$^{10f}$)$_2$, —N(R$^{10f}$)C(O)OR$^{10f}$, —C(O)OR$^{10f}$, —OC(O)R$^{10f}$, —S(O)R$^{10f}$, —S(O)$_2$R$^{10f}$, —NO$_2$, =O, =S, =N(R$^{10f}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{10f}$, —SR$^{10f}$, —N(R$^{10f}$)$_2$, —C(O)R$^{10f}$, —C(O)N(R$^{10f}$)$_2$, —N(R$^{10f}$)C(O)R$^{10f}$, —N(R$^{10f}$)C(O)N(R$^{10f}$)$_2$, —OC(O)N(R$^{10f}$)$_2$, —N(R$^{10f}$)C(O)OR$^{10f}$, —C(O)OR$^{10f}$, —OC(O)R$^{10f}$, —S(O)R$^{10f}$, —S(O)$_2$R$^{10f}$, —NO$_2$, =O, =S, =N(R$^{10f}$), —N$_3$, and —CN; each R$^{9g}$ is independently selected from: halogen, —OR$^{10g}$, —SR$^{10g}$, —N(R$^{10g}$)$_2$, —C(O)R$^{10g}$, —C(O)N(R$^{10g}$)$_2$, —N(R$^{10g}$)C(O)R$^{10g}$, —N(R$^{10g}$)C(O)N(R$^{10g}$)$_2$, —OC(O)N(R$^{10g}$)$_2$, —N(R$^{10g}$)C(O)OR$^{10g}$, —C(O)OR$^{10g}$, —OC(O)R$^{10g}$, —S(O)R$^{10g}$, —S(O)$_2$R$^{10g}$, —NO$_2$, =O, =S, =N(R$^{10g}$), —N$_3$, and —CN; and C$_{1-3}$ alkyl, C$_{2-3}$ alkenyl, and C$_{2-3}$ alkynyl, each of which is optionally substituted with one or more substituents independently selected from halogen, —OR$^{10g}$, —SR$^{10g}$, —N(R$^{10g}$)$_2$, —C(O)R$^{10g}$, —C(O)N(R$^{10g}$)$_2$, —N(R$^{10g}$)C(O)R$^{10g}$, —N(R$^{10g}$)C(O)N(R$^{10g}$)$_2$, —OC(O)N(R$^{10g}$)$_2$, —N(R$^{10g}$)C(O)OR$^{10g}$, —C(O)OR$^{10g}$, —OC(O)R$^{10g}$, —S(O)R$^{10g}$, —S(O)$_2$R$^{10g}$, —NO$_2$, =O, =S, =N(R$^{10g}$), —N$_3$, and —CN; and each R$^{10a}$, R$^{10b}$, R$^{10z}$, R$^{10c}$, R$^{10d}$, R$^{10e}$, R$^{10f}$, and R$^{10g}$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl; wherein when X$^1$ is selected from C(R$^{1a}$), X$^2$ is selected from C(R$^{1b}$), X$^3$ is selected from C(R$^{1c}$), and X$^4$ is selected from C(R$^{1d}$); then R$^{9bC}$ is selected from: halogen, —NO$_2$, —N$_3$, —CN, —OH, —O(C$_{2-6}$ alkyl), —O(C$_{1-6}$ haloalkyl), —SR$^{10b}$, —NH(C$_{1-6}$ alkyl), —N(C$_{1-6}$ alkyl)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, and —S(O)$_2$R$^{10b}$; C$_{1-6}$ alkyl, C$_{2-6}$ alkenyl, and C$_{2-6}$ alkynyl, each of which is optionally substituted with one or more substituents independently selected from halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —C(O)OR$^{10b}$, —OC(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —S(O)R$^{10b}$, —S(O)$_2$R$^{10b}$, —NO$_2$, =O, =S, =N(R$^{10b}$), —N$_3$, —CN, C$_{3-10}$ carbocycle and 3- to 10-membered heterocycle; and C$_{3-10}$ carbocycle and 3- to 10-membered heterocycle, each of which is optionally substituted with one or more substituents independently selected from halogen, —OR$^{10b}$, —SR$^{10b}$, —N(R$^{10b}$)$_2$, —C(O)R$^{10b}$, —C(O)N(R$^{10b}$)$_2$, —N(R$^{10b}$)C(O)R$^{10b}$, —N(R$^{10b}$)C(O)N(R$^{10b}$)$_2$, —OC(O)N(R$^{10b}$)$_2$, —N(R$^{10b}$)C(O)OR$^{10b}$, —C(O)OR$^{10b}$, —OC(O)R$^{10b}$, —S(O)R$^{10b}$, —S(O)$_2$R$^{10b}$, —NO$_2$, =O, =S, =N(R$^{10b}$), —N$_3$, —CN, C$_{1-6}$ alkyl, C$_{2-6}$ alkenyl, and C$_{2-6}$ alkynyl; wherein when R$^7$ is —CH$_3$, and R$^8$ is —CH$_3$, and R$^4$ is N, then R$^{1c}$ is selected from hydrogen; halogen, —NO$_2$, —N$_3$, —CN, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, and —S(O)$_2$R$^{10a}$; C$_{1-6}$ alkyl, C$_{2-6}$ alkenyl, and C$_{2-6}$ alkynyl, each of which is optionally substituted with one or more substituents independently selected from chloro, bromo, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —C(O)OR$^{10a}$, —OC(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —S(O)R$^{10a}$, —S(O)$_2$R$^{10a}$, —NO$_2$, =O, =S, =N(R$^{10a}$), —N$_3$, —CN, C$_{3-10}$ carbocycle and 3- to 10-membered heterocycle, wherein the C$_{3-10}$ carbocycle and 3- to 10-membered heterocycle are each optionally substituted with one or more R$^{9a}$; C$_{1-6}$ alkyl substituted with one —F or two —F; and C$_{3-10}$ carbocycle and 3- to 10-membered heterocycle, each of which is optionally substituted with one or more substituents independently selected from halogen, —OR$^{10a}$, —SR$^{10a}$, —N(R$^{10a}$)$_2$, —C(O)R$^{10a}$, —C(O)N(R$^{10a}$)$_2$, —N(R$^{10a}$)C(O)R$^{10a}$, —N(R$^{10a}$)C(O)N(R$^{10a}$)$_2$, —OC(O)N(R$^{10a}$)$_2$, —N(R$^{10a}$)C(O)OR$^{10a}$, —C(O)OR$^{10a}$, —OC(O)R$^{10a}$, —S(O)R$^{10a}$, —S(O)$_2$R$^{10a}$, —NO$_2$, =O, =S, =N(R$^{10a}$), —N$_3$, —CN, C$_{1-6}$ alkyl, C$_{2-6}$ alkenyl, and C$_{2-6}$ alkynyl, wherein C$_{1-6}$ alkyl, C$_{2-6}$ alkenyl, and C$_{2-6}$ alkynyl are each optionally substituted with one or more R$^{9a}$. (487): The compound or salt of embodiment 141, wherein X$^3$ and X$^4$ are C(H). (488): The compound or salt of any one of embodiments 141 to embodiment 142, wherein R$^{1a}$, R$^{1b}$, R$^{1c}$, and R$^{1d}$, are each independently selected from: hydrogen, fluoro, and C$_1$ alkyl. (489): The compound or salt of any one of embodiments 141 to embodiment 143, wherein each $R^Z$ is independently selected from hydrogen. (490): The compound or salt of any one of embodiments 141 to embodiment 144, wherein $R^C$ is selected from: hydrogen. (491): The compound or salt of any one of embodiments 141 to embodiment 145, wherein $R^5$ is hydrogen, and $R^6$ is hydrogen. (492): The compound or salt of any one of embodiments 141 to embodiment 146, wherein $R^7$ and $R^8$ are each independently selected from hydrogen. (493): The compound or salt of any one of embodiments 141 to embodiment 147, wherein $R^2$ is selected from

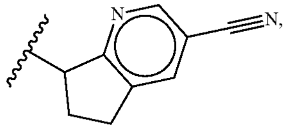
,
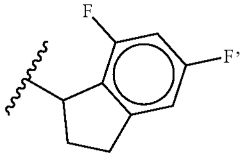
,
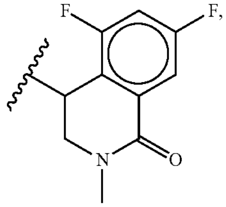
,
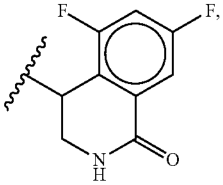
,
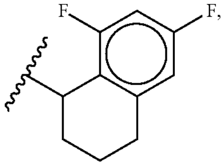
, and
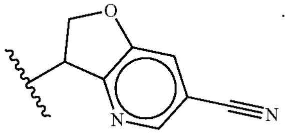
.

(494): The compound or salt of any one of embodiments 141 to embodiment 148, wherein $R^{9bB}$, $R^{9bC}$, $R^{9bD}$, and $R^{9bE}$ are each independently selected from: hydrogen, fluoro, and —CN. (495): The compound or salt of any one of embodiments 141 to embodiment 149, selected from Compound 9, 10, 44, 48, 43, 46, 57, 701, and 702, or a salt thereof.

(496): A method of treating cardiovascular disease or a related condition comprising administering to a subject in need thereof a compound or salt of any one of embodiments 1 to 150. (497): A method of treating diastolic dysfunction or a related condition comprising administering to a subject in need thereof a compound or salt of any one of embodiments 1 to 150. (498): A method of treating a condition selected from hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina; the method comprising administering to a subject in need thereof a compound or salt of any one of embodiments 1 to 150. (499): The method of embodiment 153, wherein said heart failure with preserved ejection fraction (HFpEF) comprises one or more disorders selected from disorders of relaxation and disorders of chamber stiffness (diabetic HFpEF). (500): The method of embodiment 153, wherein said left ventricular (LV) hypertrophy is malignant left ventricular (LV) hypertrophy. (501):

The method of embodiment 153, wherein said restrictive cardiomyopathy comprises one or more subgroups selected from inflammatory subgroups, infiltrative subgroups, storage subgroups, idiopathic/inherited subgroups, congenital heart disease subgroups. (502): The method of embodiment 156, wherein said inflammatory subgroups comprise one or more subgroups selected from Loefllers and EMF. (503): The method of embodiment 156, wherein said inflammatory subgroups comprise one or more subgroups selected from amyloid, sarcoid, and XRT. (504): The method of embodiment 156, wherein said storage subgroups comprise one or more subgroups selected from hemochromatosis, Fabry, and glycogen storage disease. (505): The method of embodiment 156, wherein said idiopathic/inherited subgroups comprise one or more subgroups selected from Trop I (beta myosin HC), Trop T (alpha cardiac actin), and desmin related subgroups. (506): The method of embodiment 156, wherein said congenital heart disease subgroups comprise one or more subgroups selected from pressure-overloaded RV, Tetralogy of Fallot, and pulmonic stenosis. (507): A method of treating hypertrophic cardiomyopathy or a related condition comprising administering to a subject in need thereof a compound or salt of any one of embodiments 1 to 150. (508): A method of treating obstructive hypertrophic cardiomyopathy comprising administering to a subject in need thereof a compound or salt of any one of embodiments 1 to 150. (509): A method of treating non-obstructive hypertrophic cardiomyopathy comprising administering to a subject in need thereof a compound or salt of any one of embodiments 1 to 150. (510): A method of treating heart failure with preserved ejection fraction comprising administering to a subject in need thereof a compound or salt of any one of embodiments 1 to 150. (511): A method of treating left ventricle stiffness comprising administering to a subject in need thereof a compound or salt of any one of embodiments 1 to 150. (512): A pharmaceutical composition comprising a compound or salt of any one of embodiments 1 to 150 and a pharmaceutically acceptable excipient.

(513): A method of treating a cardiovascular disease or a related condition comprising administering to a subject in need thereof a compound or salt of Formula (IIIa-e):

(IIIa-e)

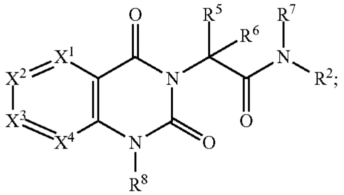

or a salt thereof, wherein $X^1$, $X^2$, $X^3$, and $X^4$ are each independently selected from $C(R^1)$, N, and $N^+(—O^-)$; each $R^1$ is independently selected from: hydrogen; halogen, $—NO_2$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$; $C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$; $R^2$ is selected from: $C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9b}$; $R^5$ and $R^6$ are each independently selected from: hydrogen, halogen, —$OR^{10c}$, —$SR^{10c}$, —$N(R^{10c})_2$, —$NO_2$, and —CN; $C_{1-6}$ alkyl, $C_{2-6}$ alkenyl, and $C_{2-6}$ alkynyl, any of which is optionally substituted at each occurrence with one or more substituents independently selected from halogen, —$OR^{10c}$, —$SR^{10c}$, —$N(R^{10c})_2$, —$NO_2$, —CN, and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; and $C_{3-10}$ carbocycle and 3- to 10-membered heterocycle, each of which is optionally substituted with one or more substituents independently selected from halogen, —$OR^{10c}$, —$SR^{10c}$, —$N(R^{10c})_2$, —$NO_2$, and —CN; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more $R^{9c}$; $R^7$ is selected from: hydrogen and $C_{1-6}$ alkyl optionally substituted with one or more substituents independently selected from halogen, —$OR^{10d}$, —$SR^{10d}$, —$N(R^{10d})_2$, —$NO_2$, and —CN; $R^8$ is selected from: hydrogen; and $C_1$ alkyl optionally substituted with one or more substituents independently selected from halogen, —$OR^{10e}$, —$SR^{10e}$, —$N(R^{10e})_2$, —$NO_2$, —CN, and 3- to 10-membered heterocycle, wherein each 3- to 10-membered heterocycle is optionally substituted with one or more substituents independently selected from halogen, —$OR^{10e}$, —$SR^{10e}$, —$N(R^{10e})_2$, —$NO_2$, and —CN; $C_{2-6}$ alkyl optionally substituted with one or more substituents independently selected from halogen, —$OR^{10e}$, —$SR^{10e}$, —$N(R^{10e})_2$, —$NO_2$, —CN, $C_{3-10}$ carbocycle, and 3- to 10-membered heterocycle, wherein each $C_{3-10}$ carbocycle and 3- to 10-membered heterocycle are optionally substituted with one or more substituents independently selected from halogen, —$OR^{10e}$, —$SR^{10e}$, —$N(R^{10e})_2$—$NO_2$, and —CN; each $R^{9a}$ is independently selected from: halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, and —CN; each $R^{9b}$ is independently selected from: halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, and —CN; each $R^{9c}$ is independently selected from: halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, and —CN; each $R^{10a}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10b}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10c}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10d}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; each $R^{10c}$ is independently selected from: hydrogen; and $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{3-10}$ carbocycle, 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —N($C_{1-6}$ alkyl)$_2$, —NH($C_{1-6}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl; wherein when $R^2$ is phenyl, benzyl, cyclohexyl, $C_{1-6}$ alkyl substituted with =O, methyl, or —$CH_2$(4-pyridyl); then at least one of $X^1$, $X^2$, $X^3$, and $X^4$ is N; or each $R^1$ is independently selected from halogen, —$NO_2$, —CN, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, and —S(O)$_2$$R^{10a}$; $C_{1-6}$ alkyl, $C_{2-6}$ alkenyl, and $C_{2-6}$ alkynyl, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —C(O)O$R^{10a}$, —OC(O)$R^{10a}$, —N($R^{10a}$)C(O)N($R^{10a}$)$_2$, —OC(O)N($R^{10a}$)$_2$, —N($R^{10a}$)C(O)O$R^{10a}$, —S(O)$R^{10a}$, —S(O)$_2$$R^{10a}$, —$NO_2$, =O, =S, =N($R^{10a}$), —CN, $C_{3-10}$ carbocycle and 3- to 10-membered heterocycle, wherein the $C_{3-10}$ carbocycle and 3- to 10-membered heterocycle are each optionally substituted with one or more $R^{9a}$; and $C_{3-10}$ carbocycle and 3- to 10-membered heterocycle, each of which is optionally substituted with one or more substituents independently selected from halogen, —$OR^{10a}$, —$SR^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2$$R^{10a}$, —$NO_2$, =O, =S, =N($R^{10a}$), —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more $R^{9a}$. (514): The method of embodiment 168, wherein $X^1$, $X^2$, $X^3$, and $X^4$ are each independently selected from C($R^1$) and N. (515): The method of embodiment 168 or 169, wherein one of $X^1$, $X^2$, $X^3$, or $X^4$ is N. (516): The method of embodiment 168 or 169, wherein $X^1$, $X^2$, $X^3$, and $X^4$ are each independently selected from C($R^1$). (517): The method of any one of embodiments 168 to 171, wherein each $R^1$ is independently selected from: hydrogen; halogen, —CN, —$OR^{10a}$, —$SR^{10a}$, —N($R^{10a}$)$_2$; and $C_{1-6}$ alkyl optionally substituted with —F and —CN. (518): The method of any one of embodiments 168 to 172, wherein each $R^1$ is independently selected from: hydrogen; fluoro, chloro, —CN, —OH, —O($CH_3$), and $C_{1-6}$ alkyl. (519): The method of any one of embodiments 168 to 173, wherein each $R^1$ is independently selected from: hydrogen, fluoro, and —CN. (520): The method of any one of embodiments 168 to 174, wherein $R^2$ is selected from $C_{1-6}$ alkyl, optionally substituted with one or more substituents independently selected from halogen, —$OR^{10b}$, —$SR^{10b}$, —N($R^{10b}$)$_2$, —C(O)$R^{10b}$, —C(O)N($R^{10b}$)$_2$, —N($R^{10b}$)C(O)$R^{10b}$, —C(O)O$R^{10b}$, —OC(O)$R^{10b}$, —$NO_2$, =O, —CN, $C_{3-10}$ carbocycle and 3- to 10-membered heterocycle, wherein the $C_{3-10}$ carbocycle and 3- to 10-membered heterocycle are each optionally substituted with one or more $R^{9b}$. (521): The method of any one of embodiments 168 to 175, wherein $R^2$ is selected from $C_2$ alkyl substituted with one or more substituents independently selected from $C_{3-10}$ carbocycle and 3- to 10-membered heterocycle, wherein the $C_{3-10}$ carbocycle and 3- to 10-membered heterocycle are each optionally substituted with one or more substituents independently selected from chloro, fluoro, —CN, —$CH_3$, and —OH. (522): The method of any one of embodiments 168 to 176, wherein $R^2$ is a substituent represented by the following:

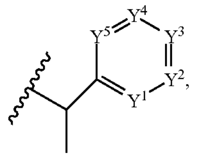

wherein $Y^1$, $Y^2$, $Y^3$, $Y^4$, and $Y^5$ are each independently selected from N, C(H), C(F), C(CN), C($CH_3$), C(Cl), and C(OH). (523): The method of any one of embodiments 168 to 177, wherein $R^2$ is selected from

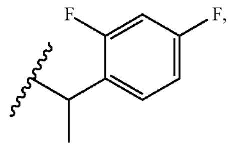
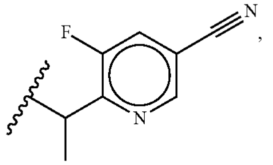
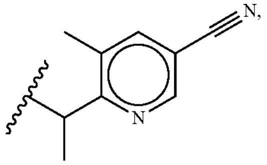
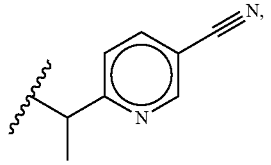
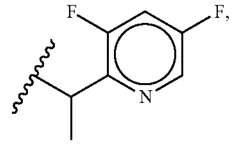
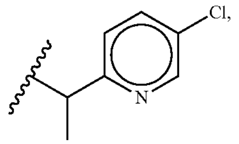

-continued

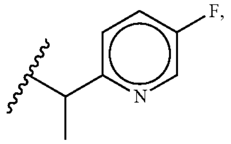

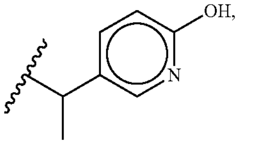

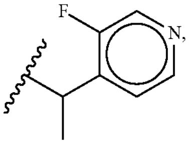

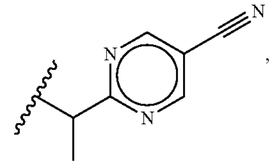

,

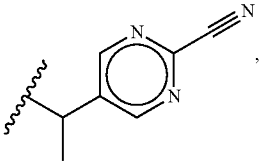

,

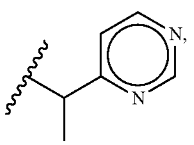

and

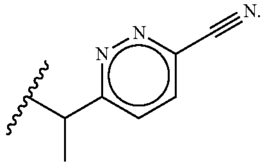

(524): The method of any one of embodiments 168 to 178, wherein $R^5$ and $R^6$ are each independently selected from: hydrogen and $C_{1-6}$ alkyl optionally substituted with one or more $C_{3-10}$ carbocycle. (525): The method of any one of embodiments 168 to 179, wherein $R^5$ and $R^6$ are each independently selected from: hydrogen, methyl, benzyl, and isobutyl. (526): The method of any one of embodiments 168 to 180, wherein $R^7$ is selected from hydrogen. (527): The method of any one of embodiments 168 to 181, wherein $R^8$ is selected from hydrogen. (528): The method of any one of embodiments 168 to 182, wherein each $R^{10a}$, $R^{10b}$, $R^{10c}$, $R^{10d}$, and $R^{10e}$ is hydrogen. (529): The method of any one of embodiments 168 to 183, wherein the compound or salt is selected from compounds: 166, 167, and 169, or a salt thereof. (530): The method of any one of embodiments 168 to 183, wherein the compound or salt is selected from: compounds 97, 105, 98, 99, 100, 213, 214, 215, 95, 96, 301, 303, 142, 405, 406, 408, 42, 508, 509, 510, 513, 514, 515, 516, 517, 518, 519, 520, 522, 523, 525, 526, 527, 528, 529, 530, 531, 532, 533, 534, 535, 601, 602, 603, 604, 605, 606, 43, 703, 701, 13, 155, 22, 72, 208, 136, 39, 8, 9, 210, 21, 6, 73, 104, 206, 154, 36, 7, 503, 35, 30, 12, 38, 4, 18, 40, 167, 20, 702, 48, 17, 3015, 51, 16, 203, 37, 1, 14, 57, 41, 169, 34, 29, 501, 141, 204, 101, 102, 2, 11, 5, 3, 15, 19, 27, 28, 47, 106, 201, 202, 205, 207, 209, 211, 212, 59, 65, 302, 33, 69, 143, 401, 402, 403, 404, 407, 31, 32, 49, 50, 70, 71, 87, 166, 502, 504, 505, 506, 507, 511, 512, 521, 524, 10, 44, 46, and 55, or a salt thereof (531): The method of any one of embodiments 168 to 185, wherein the cardiovascular disease or a related condition is selected from: hypertrophic cardiomyopathy (HCM); heart failure with preserved ejection fraction (HFpEF); heart failure with mid ranged ejection fraction disorders of relaxation; disorders of chamber stiffness (diabetic HFpEF); dilated cardiomyopathy (DCM); ischemic cardiomyopathy; cardiac transplant allograft vasculopathy; restrictive cardiomyopathy; valvular heart disease (e.g., aortic stenosis—including elderly post AVR/TAVR and congenital forms); left ventricular (LV) hypertrophy; right ventricular (RV) hypertrophy; acute myocardial infarction; acute revascularization; ischemia; and angina. (532): The method of embodiment 186, wherein said heart failure with preserved ejection fraction (HFpEF) comprises one or more disorders selected from disorders of relaxation and disorders of chamber stiffness (diabetic HFpEF). (533): The method of embodiment 186, wherein said left ventricular (LV) hypertrophy is malignant left ventricular (LV) hypertrophy. (534): The method of embodiment 186, wherein said restrictive cardiomyopathy comprises one or more subgroups selected from inflammatory subgroups, infiltrative subgroups, storage subgroups, idiopathic/inherited subgroups, congenital heart disease subgroups. (535): The method of embodiment 189, wherein said inflammatory subgroups comprise one or more subgroups selected from Loefilers and EMF. (536): The method of embodiment 189, wherein said inflammatory subgroups comprise one or more subgroups selected from amyloid, sarcoid, and XRT. (537): The method of embodiment 189, wherein said storage subgroups comprise one or more subgroups selected from hemochromatosis, Fabry, and glycogen storage disease. (538): The method of embodiment 189, wherein said idiopathic/inherited subgroups comprise one or more subgroups selected from Trop I (beta myosin HC), Trop T (alpha cardiac actin), and desmin related subgroups. (539): The method of embodiment 189, wherein said congenital heart disease subgroups comprise one or more subgroups selected from pressure-overloaded RV, Tetralogy of Fallot, and pulmonic stenosis. (540): The method of any one of embodiments 168 to 186, wherein the cardiovascular disease or a related condition is hypertrophic cardiomyopathy. (541): The method of any one of embodiments 168 to 186, wherein the cardiovascular disease or a related condition is obstructive hypertrophic cardiomyopathy. (542): The method of any one of embodiments 168 to 186, wherein the cardiovascular disease or a related condition is non-obstructive hypertrophic cardiomyopathy. (543): The method of any one of embodiments 168 to 186, wherein the cardiovascular disease or a related condition is heart failure with preserved ejection fraction. (544): The method of any one of embodiments 168 to 186, wherein the cardiovascular disease or a related condition is left ventricle stiffness.

(545): A pharmaceutical composition comprising the compound or salt of any one of embodiments 1 to 167 and a pharmaceutically acceptable excipient.

What is claimed is:

1. A compound represented by Formula (Ia):

(Ia)

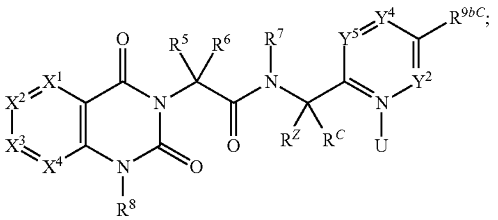

or a salt thereof, wherein:

$X^1$ is selected from $C(R^{1a})$, N, and $N^+(—O^-)$;

$X^2$ is selected from $C(R^{1b})$, N, and $N^+(—O^-)$;

$X^3$ is selected from $C(R^{1c})$, N, and $N^+(—O^-)$;

$X^4$ is selected from $C(R^{1d})$, N, and $N^+(—O^-)$;

wherein no more than two of $X^1$, $X^2$, $X^3$, and $X^4$ are N or $N^+(—O^-)$;

U is absent or selected from $—O^-$;

$Y^2$ is selected from $C(R^{9bB})$, N, and $N^+(—O^-)$;
$Y^4$ is selected from $C(R^{9bD})$, N, and $N^+(—O^-)$;
$Y^5$ is selected from $C(R^{9bE})$, N, and $N^+(—O^-)$;
wherein no more than two of $Y^2$, $Y^4$, and $Y^5$ are N or $N^+(—O^-)$;
$R^{1a}$, $R^{1b}$, and $R^{1c}$ are each independently selected from:
hydrogen;
halogen, $—NO_2$, $—N_3$, —CN, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;
$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2R^{10a}$, $—NO_2$, =O, =S, $=N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; and
$C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$;
$R^{1d}$ is selected from:
hydrogen;
$NO_2$, $—N_3$, —CN, $—OR^{10a}$, $—SR^{10a}—N(R^{10a})_2$, $—C(O)R^{10a}-C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, and $—S(O)_2R^{10a}$;
$C_{1-6}$ alkyl, $C_{2-6}$ alkenyl, and $C_{2-6}$ alkynyl, each of which is optionally substituted with one or more substituents independently selected from halogen, $—OR^{10a}$, $—SR^{10a}$ $N(R^{10a})_2$, $—C(O)R^{10a}$, $—C(O)N(R^{10a})_2$, $—N(R^{10a})C(O)R^{10a}$, $—C(O)OR^{10a}$, $—OC(O)R^{10a}$, $—N(R^{10a})C(O)N(R^{10a})_2$, $—OC(O)N(R^{10a})_2$, $—N(R^{10a})C(O)OR^{10a}$, $—S(O)R^{10a}$, $—S(O)_2$ $R^{10a}$, $—NO_2$, —O, =S, $—N(R^{10a})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9a}$; and
$C_{3-10}$ carbocycle and 3- to 10-membered heterocycle, each of which is optionally substituted with one or more substituents independently selected from halogen, $—OR^{10a}$, $—SR^{10a}$, $—N(R^{10a})_2$, $—C(O)R^{10a}$, $—C(O)N(R^{10a})_2$, $—N(R^{10a})C(O)R^{10a}$, $—N(R^{10a})C(O)N(R^{10a})_2$, $—OC(O)N(R^{10a})_2$, $—N(R^{10a})C(O)OR^{10a}$, $—C(O)OR^{10a}$, $—OC(O)R^{10a}$, $—S(O)R^{10a}$, $—S(O)_2R^{10a}$, $—NO_2$, =O, =S, $=N(R^{10a})$, $—N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9a}$;
$R^Z$ is selected from:
CN, $—C(O)R^{10z}$, $—C(O)N(R^{10z})_2$, and $—C(O)OR^{10z}$;
$C_{1-6}$ alkyl, $C_{2-6}$ alkenyl, and $C_{2-6}$ alkynyl, each of which is optionally substituted with one or more substituents independently selected from halogen, $—OR^{10z}—SR^{10z}$, $—N(R^{10z})_2$, $—C(O)R^{10z}$, $—C(O)N(R^{10z})_2$, $-N(R^{10z})C(O)R^{10z}$, $—C(O)OR^{10z}$, $—OC(O)R^{10z}$, $—N(R^{10z})C(O)N(R^{10z})_2$, $—OC(O)N(R^{10z})_2$, $—N(R^{10z})C(O)OR^{10z}$, $—S(O)R^{10z}$, $—S(O)_2R^{10z}$, $—NO_2$, =O, =S, $=N(R^{10z})$, $—N_3$, —CN, $C_{3-10}$ carbocycle, and 3- to 10-membered heterocycle, wherein the $C_{3-10}$ carbocycle and 3- to 10-membered heterocycle are each optionally substituted with one or more substituents independently selected from $R^{9z}$; and
$C_{3-10}$ carbocycle and 3- to 10-membered heterocycle, each of which is optionally substituted with one or more substituents independently selected from halogen, $—OR^{10z}$, $—SR^{10z}$, $—N(R^{10z})_2$, $—C(O)R^{10z}$, $—C(O)N(R^{10z})_2$, $—N(R^{10z})C(O)R^{10z}$, $—N(R^{10z})C(O)N(R^{10z})_2$, $—OC(O)N(R^{10z})_2$, $—N(R^{10z})C(O)OR^{10z}$, $—C(O)OR^{10z}$, $—OC(O)R^{10z}$, $—S(O)R^{10z}$, $—S(O)_2R^{10z}$, $—NO_2$, =O, =S, $=N(R^{10z})$, $—N_3$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{9z}$;
$R^C$ is selected from:
hydrogen;
CN, $—C(O)R^{10c}$, $—C(O)N(R^{10c})_2$, and $—C(O)OR^{10c}$;
$C_{1-6}$ alkyl, $C_{2-6}$ alkenyl, and $C_{2-6}$ alkynyl, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—C(O)OR^{10c}$, $—OC(O)R^{10c}$, $—N(R^{10c})C(O)N(R^{10c})_2$, $—OC(O)N(R^{10c})_2$, $—N(R^{10c})C(O)OR^{10c}$, $—S(O)R^{10c}$, $—S(O)_2R^{10c}$, $—NO_2$, =O, =S, $=N(R^{10c})$, $—N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9c}$; and
$C_{3-10}$ carbocycle and 3- to 10-membered heterocycle, each of which is optionally substituted with one or more substituents independently selected from halogen, $—OR^{10c}$, $—SR^{10c}$, $—N(R^{10c})_2$, $—C(O)R^{10c}$, $—C(O)N(R^{10c})_2$, $—N(R^{10c})C(O)R^{10c}$, $—N(R^{10c})C(O)N(R^{10c})_2$, $—OC(O)N(R^{10c})_2$, $—N(R^{10c})C(O)OR^{10c}$, $—C(O)OR^{10c}$, $—OC(O)R^{10c}$, $—S(O)R^{10c}$, $—S(O)_2R^{10c}$, $—NO_2$, =O, =S, $=N(R^{10c})$, $—N_3$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{9c}$; or
$R^Z$ together with $R^C$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9c}$;
$R^5$ is selected from:
hydrogen;
halogen, $—OR^{10d}$, $—SR^{10d}$, $—N(R^{10d})_2$, $—C(O)R^{10d}$, $—C(O)N(R^{10d})_2$, $—N(R^{10d})C(O)R^{10d}$, —C(O)

$OR^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2R^{10d}$, —$NO_2$, —$N_3$, and —CN;

$C_{1-6}$ alkyl, $C_{2-6}$ alkenyl, and $C_{2-6}$ alkynyl, each of which is optionally substituted with one or more substituents independently selected from halogen, —O$R^{10d}$, —S$R^{10d}$, N($R^{10d}$)$_2$, —C(O)$R^{10d}$, —C(O)N($R^{10d}$)$_2$, —N($R^{10d}$)C(O)$R^{10d}$, —C(O)O$R^{10d}$, —OC(O)$R^{10d}$, —N($R^{10d}$)C(O)N($R^{10d}$)$_2$, —OC(O)N($R^{10d}$)$_2$, —N($R^{10d}$)C(O)O$R^{10d}$, —S(O)$R^{10d}$, —S(O)$_2$ $R^{10d}$, —$NO_2$, -O, =S, =N($R^{10d}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9d}$; and $C_{3-10}$ carbocycle and 3- to 10-membered heterocycle, each of which is optionally substituted with one or more substituents independently selected from halogen, —O$R^{10d}$, —S$R^{10d}$, —N($R^{10d}$)$_2$, —C(O)$R^{10d}$, —C(O)N($R^{10d}$)$_2$, —N($R^{10d}$)C(O)$R^{10d}$, —N($R^{10d}$)C(O)N($R^{10d}$)$_2$, —OC(O)N($R^{10d}$)$_2$, —N($R^{10d}$)C(O)O$R^{10d}$, —C(O)O$R^{10d}$, —OC(O)$R^{10d}$, —S(O)$R^{10d}$, —S(O)$_2R^{10d}$, —$NO_2$, =O, =S, =N($R^{10d}$), —$N_3$, —CN, $C_{1-6}$ alkyl, $C_{2-6}$ alkenyl, and $C_{2-6}$ alkynyl, wherein $C_{1-6}$ alkyl, $C_{2-6}$ alkenyl, and $C_{2-6}$ alkynyl are each optionally substituted with one or more substituents independently selected from $R^{9d}$; or $R^5$ together with $R^6$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9d}$;

$R^6$ is selected from:

hydrogen;

halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, —$N_3$, and —CN;

$C_{1-6}$ alkyl, $C_{2-6}$ alkenyl, and $C_{2-6}$ alkynyl, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —C(O)O$R^{10e}$, —OC(O)$R^{10e}$, —N($R^{10e}$)C(O)N($R^{10e}$)$_2$, —OC(O)N($R^{10e}$)$_2$, —N($R^{10e}$)C(O)O$R^{10e}$, —S(O)$R^{10e}$, —S(O)$_2R^{10e}$, —$NO_2$, -O, =S, =N($R^{10e}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9e}$; and $C_{3-10}$ carbocycle and 3- to 10-membered heterocycle, each of which is optionally substituted with one or more substituents independently selected from halogen, —O$R^{10e}$, —S$R^{10e}$, —N($R^{10e}$)$_2$, —C(O)$R^{10e}$, —C(O)N($R^{10e}$)$_2$, —N($R^{10e}$)C(O)$R^{10e}$, —N($R^{10e}$)C(O)N($R^{10e}$)$_2$, —OC(O)N($R^{10e}$)$_2$, —N($R^{10e}$)C(O)O$R^{10e}$, —C(O)O$R^{10e}$, —OC(O)$R^{10e}$, —S(O)$R^{10e}$, —S(O)$_2R^{10e}$, —$NO_2$, =O, =S, =N($R^{10e}$), —$N_3$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{9e}$; or $R^6$ together with $R^5$ form a 3- to 10-membered heterocycle or $C_{3-10}$ carbocycle, wherein the 3- to 10-membered heterocycle or $C_{3-10}$ carbocycle is optionally substituted with one or more substituents independently selected from $R^{9e}$;

$R^7$ is selected from:

hydrogen;

C(O)$R^{10f}$, —C(O)N($R^{10f}$)$_2$, —C(O)O$R^{10f}$, —S(O)$R^{10f}$, and —S(O)$_2R^{10f}$, $C_{1-6}$ alkyl optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —C(O)O$R^{10f}$, —OC(O)$R^{10f}$, —N($R^{10f}$)C(O)N($R^{10f}$)$_2$, —OC(O)N($R^{10f}$)$_2$, —N($R^{10f}$)C(O)O$R^{10f}$, —S(O)$R^{10f}$, —S(O)$_2R^{10f}$, —$NO_2$, =O, =S, =N($R^{10f}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9f}$; and $C_{3-10}$ carbocycle and 3- to 10-membered heterocycle, each of which is optionally substituted with one or more substituents independently selected from halogen, —O$R^{10f}$, —S$R^{10f}$, —N($R^{10f}$)$_2$, —C(O)$R^{10f}$, —C(O)N($R^{10f}$)$_2$, —N($R^{10f}$)C(O)$R^{10f}$, —N($R^{10f}$)C(O)N($R^{10f}$)$_2$, —OC(O)N($R^{10f}$)$_2$, —N($R^{10f}$)C(O)O$R^{10f}$, —C(O)O$R^{10f}$, —OC(O)$R^{10f}$, —S(O)$R^{10f}$, —S(O)$_2R^{10f}$, —$NO_2$, =O, =S, —N($R^{10f}$), —$N_3$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{9f}$;

$R^8$ is selected from:

hydrogen;

C(O)$R^{10g}$, —C(O)N($R^{10g}$)$_2$, —C(O)O$R^{10g}$, —S(O)$R^{10g}$, and —S(O)$_2R^{10g}$;

$C_{1-6}$ alkyl optionally substituted with one or more substituents independently selected from halogen, —O$R^{10g}$, —S$R^{10g}$, —N($R^{10g}$)$_2$, —C(O)$R^{10g}$, —C(O)N($R^{10g}$)$_2$, —N($R^{10g}$)C(O)$R^{10g}$, —C(O)O$R^{10g}$, —OC(O)$R^{10g}$, —N($R^{10g}$)C(O)N($R^{10g}$)$_2$, —OC(O)N($R^{10g}$)$_2$, —N($R^{10g}$)C(O)O$R^{10g}$, —S(O)$R^{10g}$, —S(O)$_2R^{10g}$, —$NO_2$, =O, =S, =N($R^{10g}$), —$N_3$, —CN, $C_{3-10}$ carbocycle and 3- to 10-membered heterocycle, wherein the $C_{3-10}$ carbocycle and 3- to 10-membered heterocycle are each optionally substituted with one or more substituents independently selected from $R^{9g}$; and $C_{3-10}$ carbocycle and 3- to 10-membered heterocycle, each of which is optionally substituted with one or more substituents independently selected from halogen, —O$R^{10g}$, —S$R^{10g}$, —N($R^{10g}$)$_2$, —C(O)$R^{10g}$, —C(O)N($R^{10g}$)$_2$, —N($R^{10g}$)C(O)$R^{10g}$, —N($R^{10g}$)C(O)N($R^{10g}$)$_2$, —OC(O)N($R^{10g}$)$_2$, —N($R^{10g}$)C(O)O$R^{10g}$, —C(O)O$R^{10g}$, —OC(O)$R^{10g}$, —S(O)$R^{10g}$, —S(O)$_2R^{10g}$, —$NO_2$, =O, =S, =N($R^{10g}$), —$N_3$, —CN, $C_{1-6}$ alkyl, $C_{2-6}$ alkenyl, and $C_{2-6}$ alkynyl, wherein the $C_{1-6}$ alkyl, $C_{2-6}$ alkenyl, and $C_{2-6}$ alkynyl are each optionally substituted with one or more substituents independently selected from $R^{9g}$;

each $R^{9a}$ is independently selected from:

halogen, —O$R^{10a}$, —S$R^{10a}$, —N($R^{10a}$)$_2$, —C(O)$R^{10a}$, —C(O)N($R^{10a}$)$_2$, —N($R^{10a}$)C(O)$R^{10a}$, —N($R^{10a}$)C(O)N($R^{10a}$)$_2$, —OC(O)N($R^{10a}$)$_2$, —N($R^{10a}$)C(O)O$R^{10a}$, —C(O)O$R^{10a}$, —OC(O)$R^{10a}$, —S(O)$R^{10a}$, —S(O)$_2R^{10a}$, —$NO_2$, -O, =S, =N($R^{10a}$), —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10a}$, —$SR^{10a}$, —$N(R^{10a})_2$, —$C(O)R^{10a}$, —$C(O)N(R^{10a})_2$, —$N(R^{10a})C(O)R^{10a}$, —$N(R^{10a})C(O)N(R^{10a})_2$, —$OC(O)N(R^{10a})_2$, —$N(R^{10a})C(O)OR^{10a}$, —$C(O)OR^{10a}$, —$OC(O)R^{10a}$, —$S(O)R^{10a}$, —$S(O)_2R^{10a}$, —$NO_2$, =O, =S, =$N(R^{10a})$, —$N_3$, and —CN;

$R^{9bB}$, $R^{9bD}$, and $R^{9bE}$ are each independently selected from:

hydrogen;

halogen, —$NO_2$, —$N_3$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2R^{10b}$, —$NO_2$, =O, =S, =$N(R^{10b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, =O, =S, =$N(R^{10b})$, —$N_3$, —CN, $C_{1-6}$ alkyl, $C_{2-6}$ alkenyl, and $C_{2-6}$ alkynyl;

$R^{9bC}$ is selected from:

halogen, —$NO_2$, —$N_3$, —CN, —$OR^{10b}$, —$SR^{10b}$, —$N(R^{10b})_2$, —$C(O)R^{10b}$, —$C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, $C(O)OR^{10b}$, —$OC(O)R^{10b}$, —$S(O)R^{10b}$, and —$S(O)_2R^{10b}$;

$C_{1-6}$ alkyl, $C_{2-6}$ alkenyl, and $C_{2-6}$ alkynyl, each of which is optionally substituted with one or more substituents independently selected from halogen, —$OR^{10b}$, —$SR^{10b}$, —$N(R^{10b})_2$, —$C(O)R^{10b}$, $C(O)N(R^{10b})_2$, —$N(R^{10b})C(O)R^{10b}$, $C(O)OR^{10b}$, —$OC(O)R^{10b}$, —$N(R^{10b})C(O)N(R^{10b})_2$, —$OC(O)N(R^{10b})_2$, —$N(R^{10b})C(O)OR^{10b}$, —$S(O)R^{10b}$, —$S(O)_2$ $R^{10b}$, —$NO_2$, =O, =S, =$N(R^{10b})$, —$N_3$, —CN, $C_{3-10}$ carbocycle and 3- to 10-membered heterocycle; and $C_{3-10}$ carbocycle and 3- to 10-membered heterocycle, each of which is optionally substituted with one or more substituents independently selected from halogen, —$OR^{10b}$, —$SR^{10b}$, —$N(R^{10b})_2$, —$C(O)R^{10b}$, $C(O)N(R^{10b})_2$, —$N(R^{10b})C(O)R^{10b}$, —$N(R^{10b})C(O)N(R^{10b})_2$, —$OC(O)N(R^{10b})_2$, —$N(R^{10b})C(O)OR^{10b}$, —$C(O)OR^{10b}$, —$OC(O)R^{10b}$, —$S(O)R^{10b}$, —$S(O)_2R^{10b}$, —$NO_2$, —O, =S, =$N(R^{10b})$, —$N_3$, —CN, $C_{1-6}$ alkyl, $C_{2-6}$ alkenyl, and $C_{2-6}$ alkynyl;

each $R^{9z}$ is independently selected from:

halogen, —$OR^{10z}$, —$SR^{10z}$, —$N(R^{10z})^2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10z}$, —$SR^{10z}$, —$N(R^{10z})_2$, —$C(O)R^{10z}$, —$C(O)N(R^{10z})_2$, —$N(R^{10z})C(O)R^{10z}$, —$N(R^{10z})C(O)N(R^{10z})_2$, —$OC(O)N(R^{10z})_2$, —$N(R^{10z})C(O)OR^{10z}$, —$C(O)OR^{10z}$, —$OC(O)R^{10z}$, —$S(O)R^{10z}$, —$S(O)_2R^{10z}$, —$NO_2$, =O, =S, =$N(R^{10z})$, —$N_3$, and —CN;

each $R^{9c}$ is independently selected from:

halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10c}$, —$SR^{10c}$, —$N(R^{10c})_2$, —$C(O)R^{10c}$, —$C(O)N(R^{10c})_2$, —$N(R^{10c})C(O)R^{10c}$, —$N(R^{10c})C(O)N(R^{10c})_2$, —$OC(O)N(R^{10c})_2$, —$N(R^{10c})C(O)OR^{10c}$, —$C(O)OR^{10c}$, —$OC(O)R^{10c}$, —$S(O)R^{10c}$, —$S(O)_2R^{10c}$, —$NO_2$, =O, =S, =$N(R^{10c})$, —$N_3$, and —CN;

each $R^{9d}$ is independently selected from:

halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10d}$, —$SR^{10d}$, —$N(R^{10d})_2$, —$C(O)R^{10d}$, —$C(O)N(R^{10d})_2$, —$N(R^{10d})C(O)R^{10d}$, —$N(R^{10d})C(O)N(R^{10d})_2$, —$OC(O)N(R^{10d})_2$, —$N(R^{10d})C(O)OR^{10d}$, —$C(O)OR^{10d}$, —$OC(O)R^{10d}$, —$S(O)R^{10d}$, —$S(O)_2R^{10d}$, —$NO_2$, =O, =S, =$N(R^{10d})$, —$N_3$, and —CN;

each $R^{9e}$ is independently selected from:

halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$N(R^{10e})C(O)N(R^{10e})_2$, —$OC(O)N(R^{10e})_2$, —$N(R^{10e})C(O)OR^{10e}$, —$C(O)OR^{10e}$, —$OC(O)R^{10e}$, —$S(O)R^{10e}$, —$S(O)_2R^{10e}$, —$NO_2$, =O, =S, =$N(R^{10e})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10e}$, —$SR^{10e}$, —$N(R^{10e})_2$, —$C(O)R^{10e}$, —$C(O)N(R^{10e})_2$, —$N(R^{10e})C(O)R^{10e}$, —$N(R^{10e})C(O)N(R^{10e})_2$, —$OC(O)N(R^{10e})_2$, —$N(R^{10e})C(O)OR^{10e}$, —$C(O)OR^{10e}$, —$OC(O)R^{10e}$, —$S(O)R^{10e}$, —$S(O)_2R^{10e}$, —$NO_2$, =O, =S, =$N(R^{10e})$, —$N_3$, and —CN;

each $R^{9f}$ is independently selected from:

halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10f}$, —$SR^{10f}$, —$N(R^{10f})_2$, —$C(O)R^{10f}$, —$C(O)N(R^{10f})_2$, —$N(R^{10f})C(O)R^{10f}$, —$N(R^{10f})C(O)N(R^{10f})_2$, —$OC(O)N(R^{10f})_2$, —$N(R^{10f})C(O)OR^{10f}$, —$C(O)OR^{10f}$, —$OC(O)R^{10f}$, —$S(O)R^{10f}$, —$S(O)_2R^{10f}$, —$NO_2$, =O, =S, =$N(R^{10f})$, —$N_3$, and —CN;

each $R^{9g}$ is independently selected from:

halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, and —CN; and $C_{1-3}$ alkyl, $C_{2-3}$ alkenyl, and $C_{2-3}$ alkynyl, each of which is optionally substituted with one or more substituents independently selected from halogen, —$OR^{10g}$, —$SR^{10g}$, —$N(R^{10g})_2$, —$C(O)R^{10g}$, —$C(O)N(R^{10g})_2$, —$N(R^{10g})C(O)R^{10g}$, —$N(R^{10g})C(O)N(R^{10g})_2$, —$OC(O)N(R^{10g})_2$, —$N(R^{10g})C(O)OR^{10g}$, —$C(O)OR^{10g}$, —$OC(O)R^{10g}$, —$S(O)R^{10g}$, —$S(O)_2R^{10g}$, —$NO_2$, =O, =S, =$N(R^{10g})$, —$N_3$, and —CN; and each $R^{10a}$, $R^{10b}$, $R^{10z}$, $R^{10c}$, $R^{10d}$, $R^{10e}$, $R^{10f}$, and $R^{10g}$ is independently selected from: hydrogen;

$C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}\text{ alkyl})_2$, —$NH(C_{1-6}\text{ alkyl})$, $C_{3-10}$ carbocycle, and 3- to 10-membered heterocycle; and $C_{3-10}$ carbocycle and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}\text{ alkyl})_2$, —$NH(C_{1-6}\text{ alkyl})$, $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

2. The compound or salt of claim 1, wherein:
$X^1$ is selected from $C(R^{1a})$;
$X^2$ is selected from $C(R^{1b})$;
$X^3$ is selected from $C(R^{1c})$;
$X^4$ is selected from $(R^{1d})$; and
no more than one of $Y^2$, $Y^4$, and $Y^5$ is N or $N^+(O^-)$.

3. The compound or salt of claim 1, wherein
$X^1$ is selected from C(H), C(F), and C(CN), and $C(CH_3)$;
$X^2$ is selected from N, C(H), C(F), $C(CH_3)$, and C(CN);
$X^3$ is C(H); and
$X^4$ is CH).

4. The compound or salt of claim 1, wherein $R^{1a}$, $R^{1b}$, and $R^{1c}$ are each independently selected from:
hydrogen;
halogen, —$NO_2$, —CN, —$OR^{10a}$, —$SR^{10a}$, and —$N(R^{10a})_2$; and
$C_{1-6}$ alkyl optionally substituted with one or more substituents independently selected from halogen, —$OR^{10a}$, —$SR^{10a}$, —$N(R^{10a})_2$, —$NO_2$, =O, and —CN.

5. The compound or salt of claim 1, wherein $R^{1a}$, $R^{1b}$, and $R^{1c}$ are each independently selected from: hydrogen, halogen, —CN, and $C_{1-6}$ alkyl.

6. The compound or salt of claim 1, wherein $R^Z$ is selected from $C_{1-6}$ alkyl optionally substituted with one or more substituents independently selected from halogen and —OH.

7. The compound or salt of claim 1, wherein $R^Z$ is selected from —$CH_3$, and $R^C$ is selected from hydrogen.

8. The compound or salt of claim 1, wherein $R^5$ together with $R^6$ form a cyclopropyl.

9. The compound or salt of claim 1, wherein $R^5$ is hydrogen, and $R^6$ is hydrogen.

10. The compound or salt of claim 1, wherein $R^7$ is hydrogen.

11. The compound or salt of claim 1, wherein $R^7$ is hydrogen, and $R^8$ is hydrogen.

12. The compound or salt of claim 1, wherein:
$Y^2$ is selected from C(H), C(F), $C(CH_3)$, and N;
$R^{9bC}$ is selected from —CN, C—F, C—Cl, and C—OH;
$Y^4$ is selected from C(H), C(F), $C(CH_3)$, and N; and
$Y^5$ is selected from N, C(H), C(F), and $C(CH_3)$.

13. The compound or salt of claim 1, wherein $R^{9bC}$ is selected from C—CN.

14. The compound or salt of claim 1, wherein:
$Y^2$ is $C(R^{9bB})$, $Y^4$ is $C(R^{9bD})$, and $Y^5$ is $C(R^{9bE})$; or
$Y^2$ is $C(R^{9bB})$, $Y^4$ is $C(R^{9bD})$, and $Y^5$ is N; or
$Y^2$ is N, $Y^4$ is $C(R^{9bD})$, and $Y^5$ is $C(R^{9bE})$.

15. The compound or salt of claim 1, wherein $R^{9bB}$, $R^{9bD}$, and $R^{9bE}$ are each independently selected from: hydrogen; halogen, —CN, —$OR^{10b}$, —$SR^{10b}$, and —$N(R^{10b})_2$; and $C_{1-6}$ alkyl optionally substituted with one or more substituents independently selected from halogen, —$OR^{10b}$, —$SR^{10b}$, —$N(R^{10b})_2$, =O, and —CN.

16. The compound or salt of claim 1, wherein $R^{9bB}$, $R^{9bD}$, and $R^{9bE}$ are each independently selected from: hydrogen, fluoro, —CN, —OH, and $C_1$ alkyl.

17. The compound or salt of claim 1, wherein each $R^{9a}$, $R^{9z}$, $R^{9c}$, $R^{9e}$, $R^{9f}$, and $R^{9g}$ is independently selected from: fluoro and —CN; and each $R^{10a}$, $R^{10b}$, $R^{10z}$, $R^{10c}$, $R^{10d}$, $R^{10e}$, $R^{10f}$, and $R^{10g}$ is independently selected from: hydrogen and $C_{1-6}$ alkyl.

18. The compound or salt of claim 1, wherein:
$R^8$ is hydrogen.

19. The compound or salt of claim 1, wherein $R^{1d}$ is selected from:
hydrogen;
$NO_2$, —CN, —$OR^{10a}$, —$SR^{10a}$, and —$N(R^{10a})_2$; and
$C_{1-6}$ alkyl optionally substituted with one or more substituents independently selected from halogen, —$OR^{10a}$, —$SR^{10a}$, —$N(R^{10a})_2$, —$NO_2$, =O, and —CN.

20. The compound or salt of claim 1, wherein $R^{1d}$ is selected from: hydrogen, —CN, and $C_{1-6}$ alkyl.

21. The compound or salt of claim 1, wherein U is absent.

22. The compound of claim 1, wherein the compound is

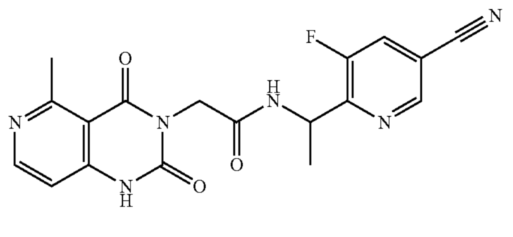 [SMILES: Cc1nccc2[nH]c(=O)n(CC(=O)NC(C)c3ncc(C#N)cc3F)c(=O)c12]

or a salt thereof.

23. The compound of claim 1, wherein the compound is

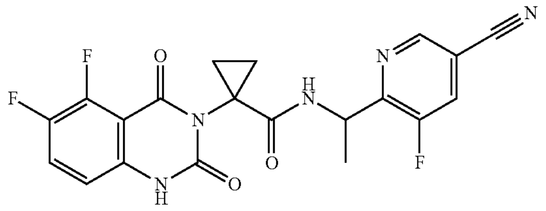 [SMILES: CC(NC(=O)C1(n2c(=O)[nH]c3ccc(F)c(F)c3c2=O)CC1)c1ncc(C#N)cc1F]

or a salt thereof.

24. The compound of claim 1, wherein the compound is

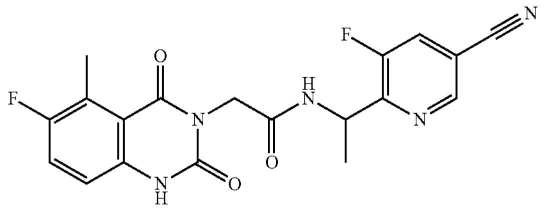 [SMILES: Cc1c(F)ccc2[nH]c(=O)n(CC(=O)NC(C)c3ncc(C#N)cc3F)c(=O)c12]

or a salt thereof.

25. The compound of claim 1, wherein the compound is

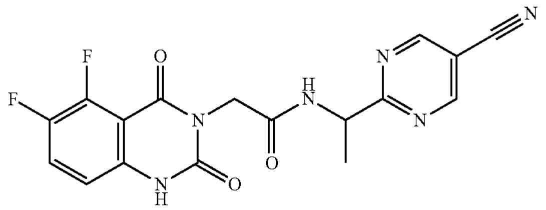 [SMILES: CC(NC(=O)Cn1c(=O)[nH]c2ccc(F)c(F)c2c1=O)c1ncc(C#N)cn1]

or a salt thereof.

26. The compound of claim 1, wherein the compound is

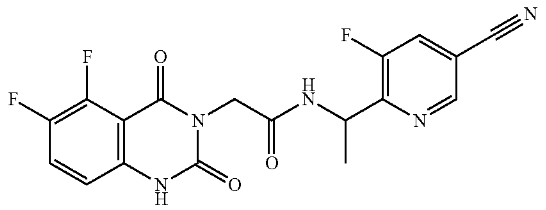 [SMILES: CC(NC(=O)Cn1c(=O)[nH]c2ccc(F)c(F)c2c1=O)c1ncc(C#N)cc1F]

or a salt thereof.

27. The compound of claim 1, wherein the compound is

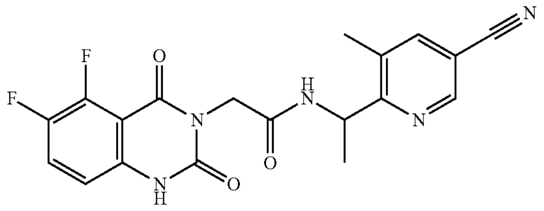 [SMILES: Cc1cc(C#N)cnc1C(C)NC(=O)Cn1c(=O)[nH]c2ccc(F)c(F)c2c1=O]

or a salt thereof.

28. The compound of claim 1, wherein the compound is

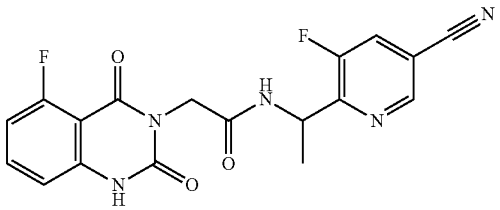 [SMILES: CC(NC(=O)Cn1c(=O)[nH]c2cccc(F)c2c1=O)c1ncc(C#N)cc1F]

or a salt thereof.

29. The compound of claim 1, wherein the compound is

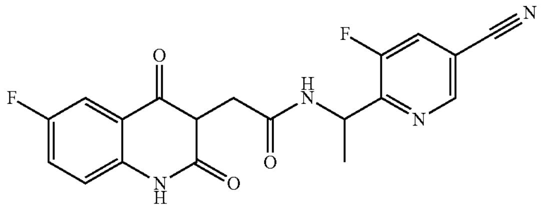 [SMILES: CC(NC(=O)CC1C(=O)Nc2ccc(F)cc2C1=O)c1ncc(C#N)cc1F]

or a salt thereof.

30. A pharmaceutical composition comprising the compound or salt of claim 1 and a pharmaceutically acceptable excipient.

* * * * *